United States Patent
Li et al.

(10) Patent No.: US 11,555,018 B2
(45) Date of Patent: Jan. 17, 2023

(54) ORGANIC COMPOUND BASED ON TRIAZINE AND BENZOXAZOLE AND APPLICATION THEREOF IN ORGANIC ELECTROLUMINESCENT DEVICE

(71) Applicant: JIANGSU SUNERA TECHNOLOGY CO., LTD., Wuxi (CN)

(72) Inventors: Chong Li, Wuxi (CN); Xiao Cai, Wuxi (CN); Zhaochao Zhang, Wuxi (CN); Yujia Pang, Wuxi (CN)

(73) Assignee: JIANGSU SUNERA TECHNOLOGY CO., LTD., Wuxi (CN)

( * ) Notice: Subject to any disclaimer, the term of this patent is extended or adjusted under 35 U.S.C. 154(b) by 305 days.

(21) Appl. No.: 16/772,161

(22) PCT Filed: Nov. 13, 2018

(86) PCT No.: PCT/CN2018/115169
§ 371 (c)(1),
(2) Date: Jun. 12, 2020

(87) PCT Pub. No.: WO2019/114478
PCT Pub. Date: Jun. 20, 2019

(65) Prior Publication Data
US 2021/0070717 A1    Mar. 11, 2021

(30) Foreign Application Priority Data

Dec. 14, 2017  (CN) .......................... 201711340861.4
Jun. 7, 2018   (CN) .......................... 201810580722.7
Aug. 2, 2018   (CN) .......................... 201810868403.6

(51) Int. Cl.
H01L 51/50      (2006.01)
C07D 251/04     (2006.01)
(Continued)

(52) U.S. Cl.
CPC ......... *C07D 251/04* (2013.01); *C07D 498/00* (2013.01); *H01L 51/008* (2013.01);
(Continued)

(58) Field of Classification Search
None
See application file for complete search history.

(56) References Cited

U.S. PATENT DOCUMENTS

2015/0318487 A1    11/2015   Ito et al.

FOREIGN PATENT DOCUMENTS

CN    101255172 A    9/2008
CN    104835921 A    8/2015
(Continued)

*Primary Examiner* — Gregory D Clark
(74) *Attorney, Agent, or Firm* — Bayramoglu Law Offices LLC

(57) ABSTRACT

Disclosed are an organic compound based on triazine and benzoxazole and an application thereof in an OLED device. The compound of the present application has a relatively high glass transition temperature and molecular thermal stability, is low in absorption and high in refractive index in the field of visible light, and is capable of effectively improving the light extraction efficiency of an OLED device when applied to a capping layer of the OLED device; with a deep HOMO energy level and high electronic mobility, the compound of the present application can be used as the hole blocking layer or the electron transport layer material, so that the recombination degree of the hole and the electron in the light-emitting layer can be improved, and thus the light-emitting efficiency of the OLED device can be enhanced and the service life of the OLED device can be prolonged.

10 Claims, 2 Drawing Sheets

(51) Int. Cl.
*C07D 498/00* (2006.01)
*H01L 51/00* (2006.01)

(52) U.S. Cl.
CPC ...... *H01L 51/0067* (2013.01); *H01L 51/0069* (2013.01); *H01L 51/0072* (2013.01); *H01L 51/0073* (2013.01); *H01L 51/0074* (2013.01); *H01L 51/506* (2013.01); *H01L 51/5072* (2013.01)

(56) References Cited

FOREIGN PATENT DOCUMENTS

| KR | 20170116927 A | | 10/2017 | |
|----|---------------|---|---------|---|
| WO | 2010126270 A1 | | 11/2010 | |
| WO | WO 2010126270 | * | 11/2010 | ............. C09K 11/06 |

* cited by examiner

ORGANIC COMPOUND BASED ON TRIAZINE AND BENZOXAZOLE AND APPLICATION THEREOF IN ORGANIC ELECTROLUMINESCENT DEVICE

CROSS REFERENCE TO THE RELATED APPLICATIONS

This application is the national phase entry of International Application No. PCT/CN2018/115169, filed on Nov. 13, 2018, which is based upon and claims priority to Chinese Patent Application No. 201810868403.6, filed on Aug. 2, 2018, which is based upon and claims priority to Chinese Patent Application No. 201810580722.7, filed on Jun. 7, 2018, which is based upon and claims priority to Patent Application No. 201711340861.4, filed on Dec. 14, 2017, the entire contents of which are incorporated herein by reference.

TECHNICAL FIELD

The present application relates to the field of semiconductor technology, and in particular, to an organic compound based on triazine and benzoxazole and an application thereof in an organic electroluminescent device.

BACKGROUND

Organic electroluminescent (OLED, Organic Light Emission Diodes) device technology can be used to fabricate not only a novel display product but also a novel lighting product. It is expected to replace the existing liquid crystal display and fluorescent lamp lighting, and has a promising application prospect. The OLED light-emitting device is of a sandwich structure, and includes an electrode material film layer and organic functional materials sandwiched between different electrode film layers, and various functional materials are overlapped with one another according to purposes so as to together form an OLED light-emitting device. Positive and negative charges in the organic functional material film layer are acted by the electric field and then combined in the light-emitting layer when the OLED light-emitting device serves as a current device and a voltage is applied to electrodes at two ends of the OLED light-emitting device, that is, the OLED electroluminescence is generated.

Currently, the OLED display technology has been applied in the fields of smart phones, tablet computers and the like, and will be further applied in the fields of large size devices such as TVs. However, the huge gap between the external quantum efficiency and the internal quantum efficiency of an OLED has greatly restricted the development of OLED. Therefore, how to improve the light extraction efficiency of an OLED device has become a heat-point in research. Total reflection may occur at the interface between the ITO film and the glass substrate and the interface between the glass substrate and the air, and the light emitted to the forward outer space of the OLED device accounts for about 20% of the total amount of the light emitted from organic material film, and the remaining about 80% of the light is mainly limited in the organic material film, the ITO film and the glass substrate in a guided wave form. The relatively low light extraction efficiency of conventional OLED devices (about 20%) severely restricts the development and application of OLED devices. How to reduce the total reflection effect in the OLED device and improve the ratio of the light coupling to the forward outer space of the device (light extraction efficiency) attract considerable attention.

At present, an important method for improving the external quantum efficiency of the OLED is to form structures, such as wrinkles, photonic crystals, micro lens arrays (MLA) or surface capping layers on the light-emitting surface of the substrate. The first two structures will affect the radiation spectrum angle distribution of the OLED and the third structure is complex in fabrication process, the use of the surface capping layer is simple in process, and has a luminous efficiency improved by more than 30%, and thus has gained great attention. According to the optical principle, when light is transmitted through a substance having a refractive index of $n_1$ to a substance having a refractive index of $n_2$ ($n_1 > n_2$), the light can be incident to the substance having a refractive index of $n_2$ only when the incident angle is less than $\arcsin(n_2/n_1)$, and the absorptivity B can be calculated by the following formula:

$$B = \frac{1 - \sqrt{1 - \left(\frac{n_2}{n_1}\right)^2}}{2}$$

Let $n_1 = n_{general\ OLED\ organic\ material} = 1.70$, $n_2 = n_{glass} = 1.46$, then $2B = 0.49$. Assuming that light propagating outwards is totally reflected by the metal electrodes, only 51% of the light can be waveguided by high-refractive-index organic film and ITO layer, and the transmittance of light emitted from the glass substrate to the air also can be calculated. Therefore, when light emitted from the organic layer is emitted to outside of the device, only about 17% of the light is visible. Accordingly, aiming at the current situation that the light extraction efficiency of the existing OLED device is low, it is necessary to add a capping layer (CPL), that is, light extraction materials, to the device structure, and the refractive index of the surface capping layer material should be as high as possible, according to the optical absorption and refraction principles.

Current research on improving the performance of the OLED light-emitting device includes: reducing the driving voltage of the device, improving the light-emitting efficiency of the device, prolonging service life of the device and etc. In order to continuously improve the performance of the OLED device, not only the innovation from the structure and manufacturing process of OLED devices, but also the continuous research and innovation of OLED optoelectronic functional materials are needed to create OLED functional materials with higher performances.

SUMMARY

In view of the problems existing in the prior art, the applicant provides an organic compound based on triazine and benzoxazole and an application thereof in an organic electroluminescent device. The compound of the present application contains a structure of triazine and benzoxazole, has a relatively high glass transition temperature and molecular thermal stability, is low in absorption and high in refractive index in the field of visible light, and is capable of effectively improving the light extraction efficiency of an OLED device when applied to a CPL layer of the OLED device; with a deep HOMO energy level and a wide forbidden band (Eg) energy level, the triazine and benzoxazole can be used as the hole blocking layer or the electron transport layer material, for blocking holes from transmitting from the light-emitting layer to the electron layer, so that the recombination degree of the hole and the electron in the light-emitting layer can be improved, thus the light-emitting efficiency of the OLED device can be enhanced and the service life of the OLED device can be prolonged.

The technical solutions of the present application are as follows:

An organic compound based on triazine and benzoxazole, wherein the structure of the organic compound is represented by the following formula (1):

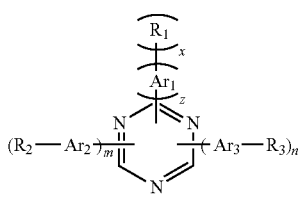

formula (1)

wherein, x represents 1 or 2; z represents 1 or 2; m and n independently represent 0, 1 or 2; and m+n+z=3;

In the formula (1), $Ar_1$, $Ar_2$, and $Ar_3$ each independently represent substituted or unsubstituted arylene with 6 to 60 carbon atoms or substituted or unsubstituted 5 to 60-membered heteroarylene with one or more heteroatoms; the heteroatom is nitrogen atom, oxygen atom or sulfur atom; $Ar_1$, $Ar_2$, and $Ar_3$ each further independently represent a single bond; $Ar_1$, $Ar_2$, and $Ar_3$ are identical or different;

$R_1$ represents hydrogen atom, substituted or unsubstituted aryl with 6 to 60 carbon atoms, substituted or unsubstituted 5 to 60-membered heteroary with one or more heteroatoms, or

the heteroatom is nitrogen atom, oxygen atom, or sulfur atom;

$Q_1$ and $Q_2$ each independently represent substituted or unsubstituted aryl with 6 to 60 carbon atoms, or substituted or unsubstituted 5 to 60-membered heteroary with one or more heteroatoms; the heteroatom is nitrogen atom, oxygen atom, or sulfur atom;

$R_2$ represents a structure represented by the following formula (2) or formula (3):

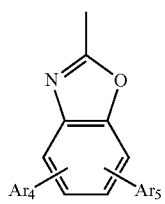

formula (2)

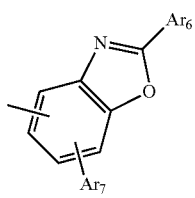

formula (3)

$R_3$ represents a structure represented by the following formula (4) or formula (5):

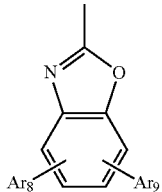

formula (4)

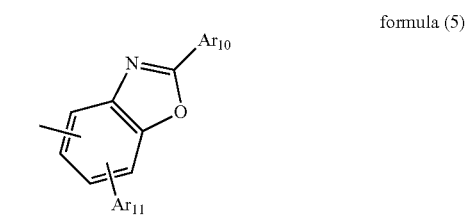

formula (5)

wherein $Ar_4$, $Ar_5$, $Ar_6$, $Ar_7$, $Ar_8$, $Ar_9$, $Ar_{10}$ and $Ar_{11}$ each independently represent hydrogen atom, linear or branched alkyl with 1 to 10 carbon atoms, substituted or unsubstituted aryl with 6 to 60 carbon atoms, or substituted or unsubstituted 5- to 60-membered heteroary with one or more heteroatoms; the heteroatom is nitrogen atom, oxygen atom, or sulfur atom;

preferably, wherein $Ar_1$, $Ar_2$, and $Ar_3$ each independently represent phenylene substituted or unsubstituted by halogen atoms, protium atoms, deuterium atoms, tritium atoms, linear or branched alkyl with 1 to 10 carbon atoms; naphthylene substituted or unsubstituted by halogen atoms, protium atoms, deuterium atoms, tritium atoms, or linear or branched alkyl with 1 to 10 carbon atoms; biphenylene substituted or unsubstituted by halogen atoms, protium atoms, deuterium atoms, tritium atoms, or linear or branched alkyl with 1 to 10 carbon atoms; pyridinylene substituted or unsubstituted by halogen atoms, protium atoms, deuterium atoms, tritium atoms, or linear or branched alkyl with 1 to 10 carbon atoms; carbazolylene; furanylene; pyrimidinylene; pyrazinylene; pyridazinylene; dibenzofuranylene; 9,9-dimethylfluorenylene; or N-phenylcarbazolylene; quinolylene; or isoquinolylene or naphthyridinylene; $R_1$, $Ar_4$, $Ar_5$, $Ar_6$, $Ar_7$, $Ar_8$, $Ar_9$, $Ar_{10}$, $Ar_{11}$ and $Q_1$ and $Q_2$ each independently represent phenyl substituted or unsubstituted by halogen atoms, protium atoms, deuterium atoms, tritium atoms, linear or branched alkyl with 1 to 10 carbon atoms; naphthyl substituted or unsubstituted by halogen atoms, protium atoms, deuterium atoms, tritium atoms, linear or branched alkyl with 1 to 10 carbon atoms; biphenyl substituted or unsubstituted by halogen atoms, protium atoms, deuterium atoms, tritium atoms, linear or branched alkyl with 1 to 10 carbon atoms; pyridinyl substituted or unsubstituted by halogen atoms, protium atoms, deuterium atoms, tritium atoms, linear or branched alkyl with 1 to 10 carbon atoms; carbazolyl; furanyl; pyrimidinyl; pyrazinyl; pyridazinyl; dibenzofuranyl; 9,9-dimethylfluorenyl; N-phenylcarbazolyl; quinolinyl; or isoquinolinyl or naphthyridinyl.

Preferably, when z represents 1, $—Ar_1—(R_1)_x$ contains at least one heteroatom, and the heteroatom is nitrogen atom, oxygen atom, or sulfur atom.

The structural formula of the organic compound is any one of (I)-(VII):
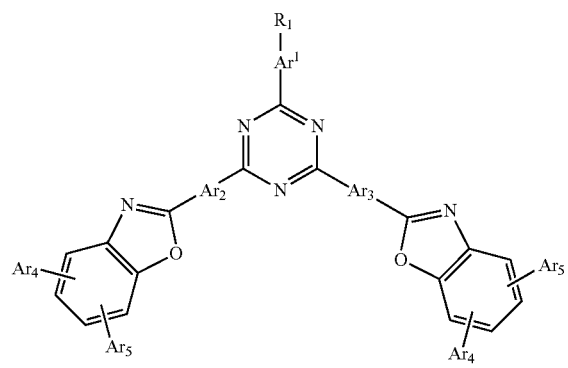
(I)
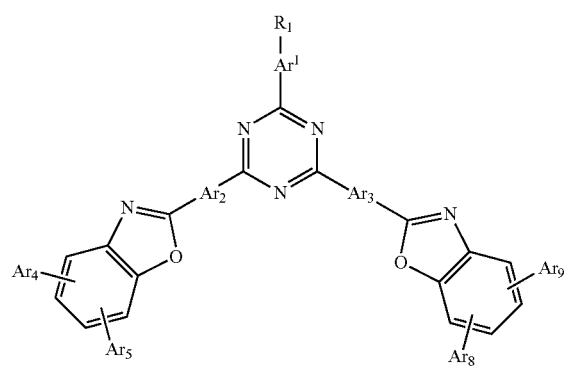
(II)
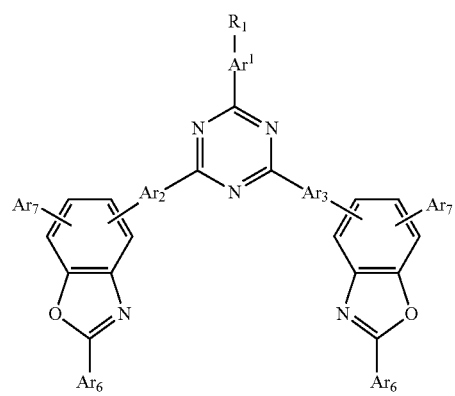
(III)
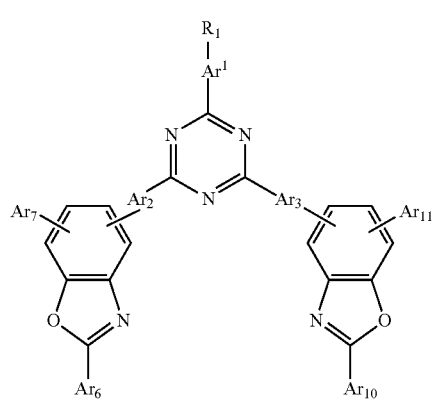
(IV)
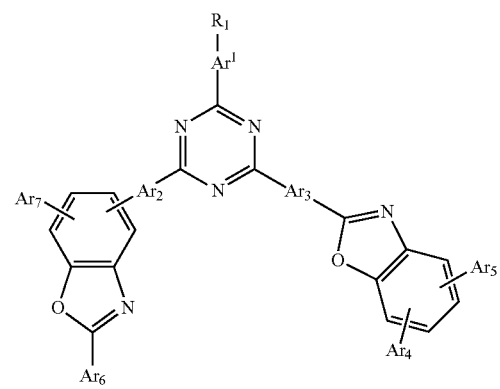
(V)
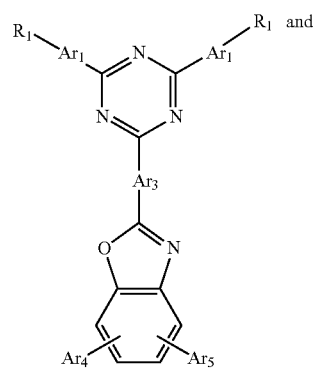
(VI)
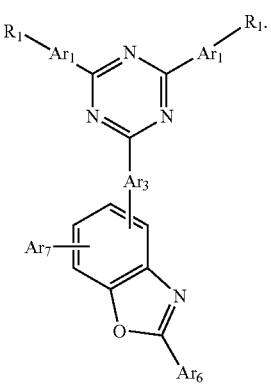
(VII)
$R_1$ in formula (1) represents one of
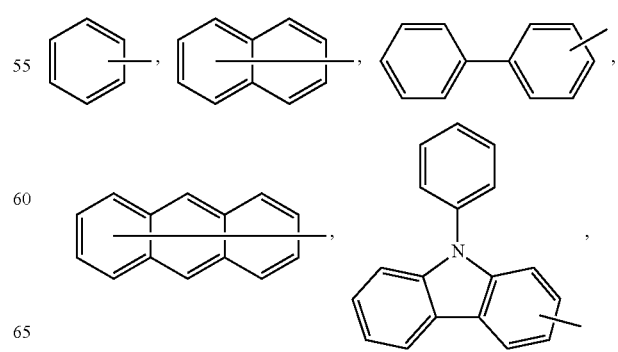

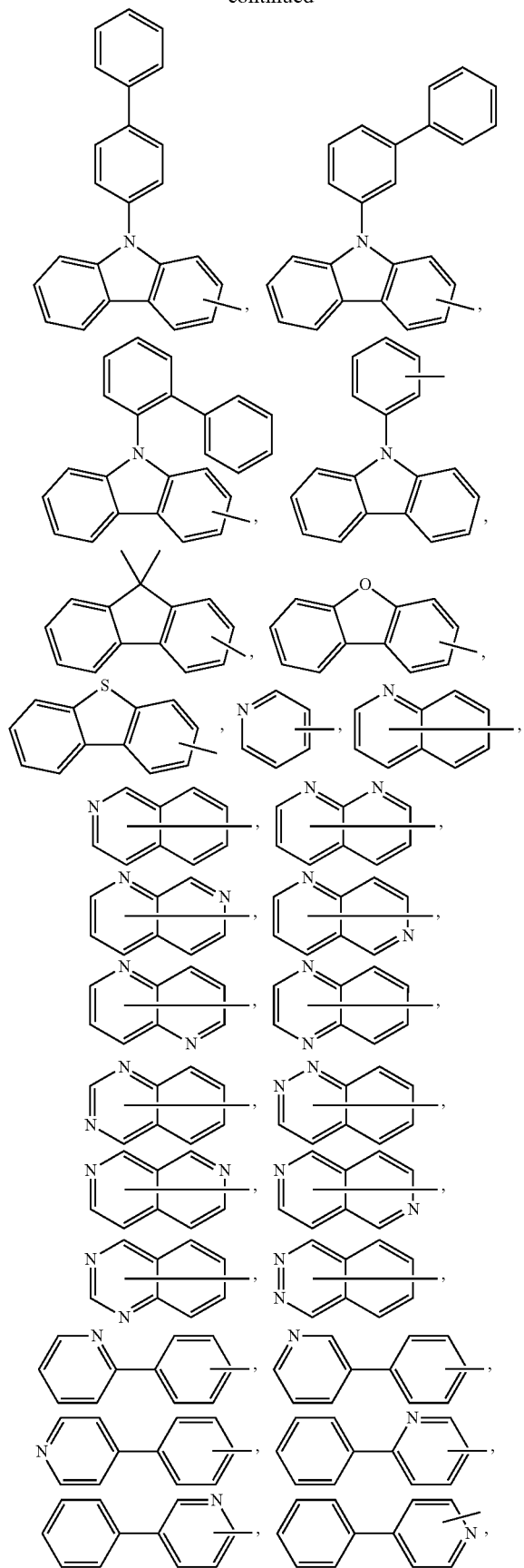
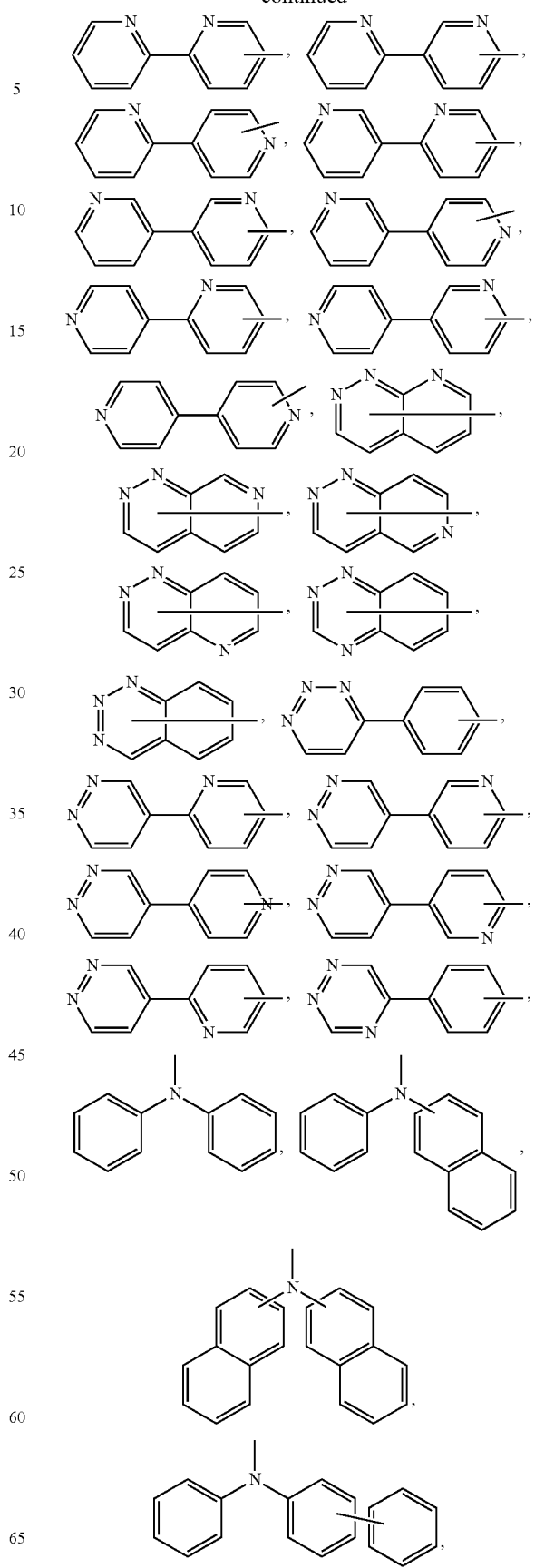

-continued
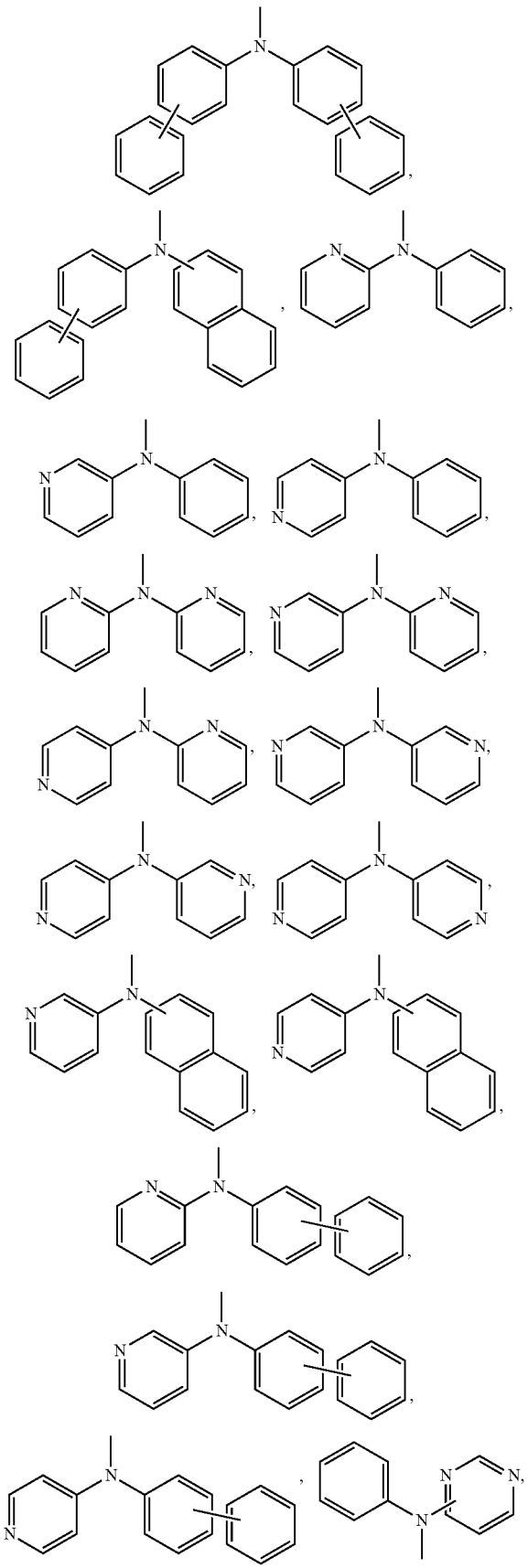
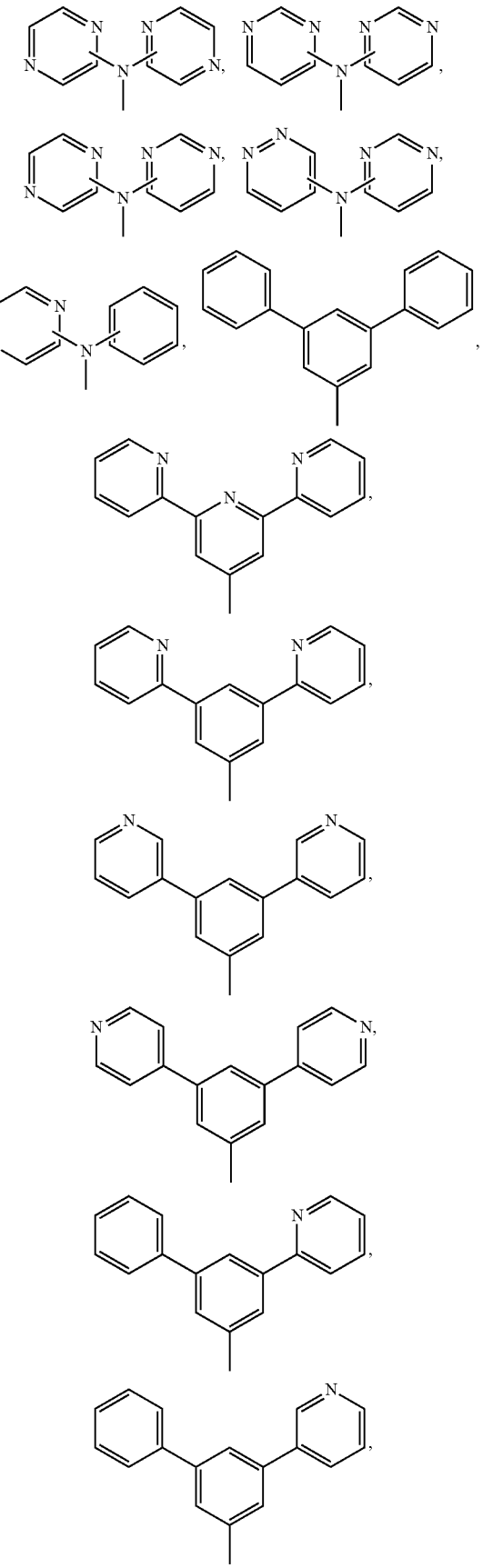

-continued
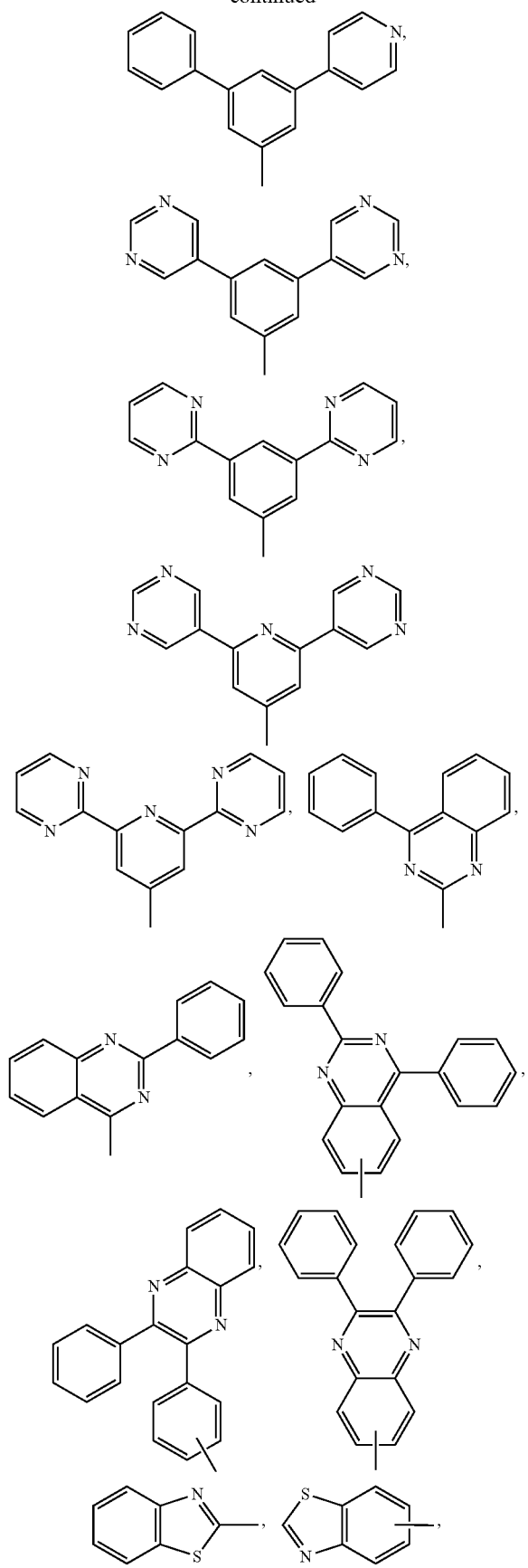
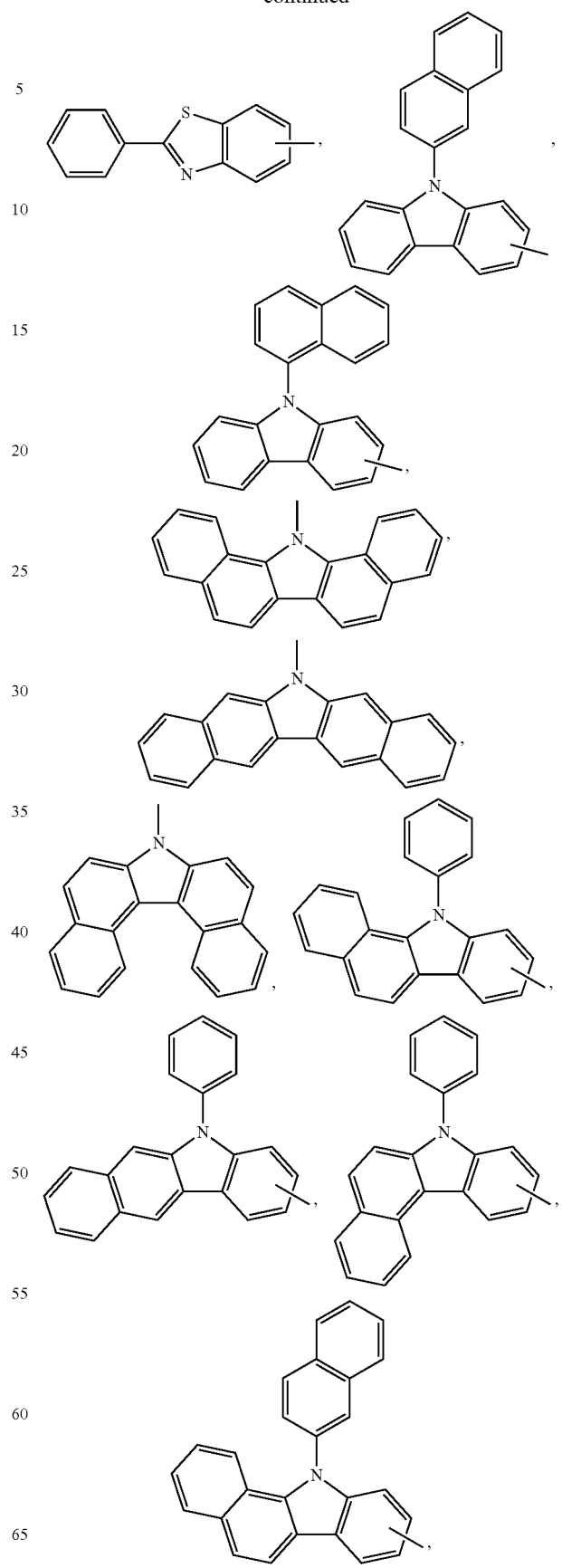

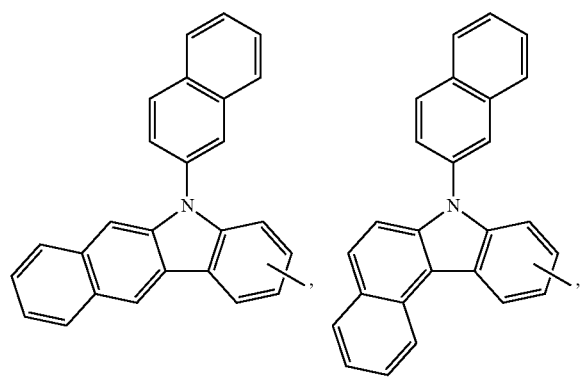
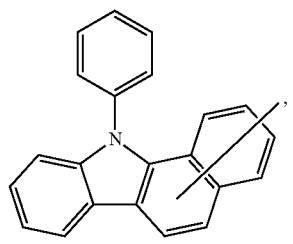
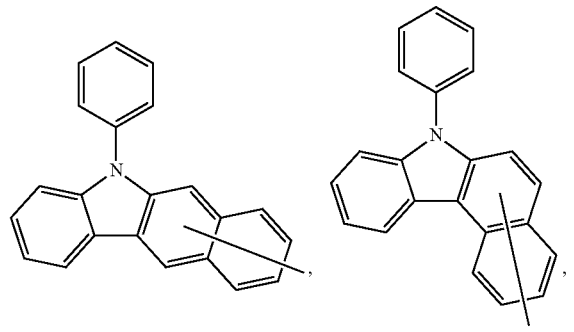
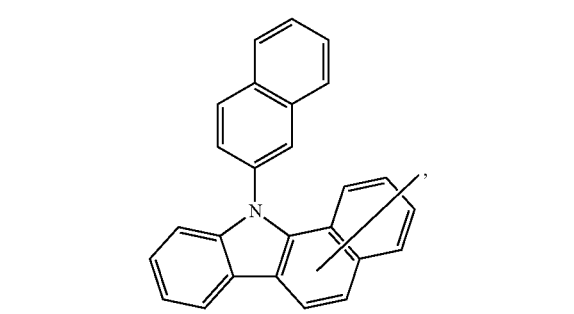
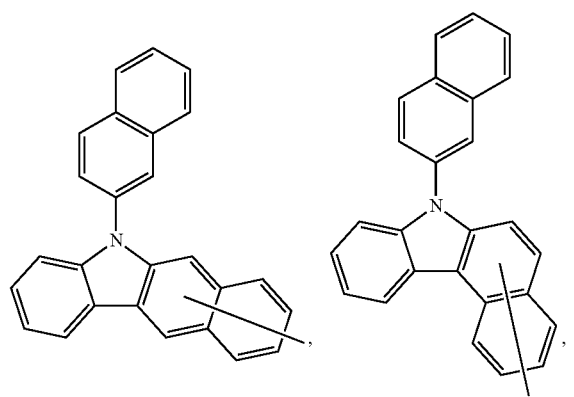
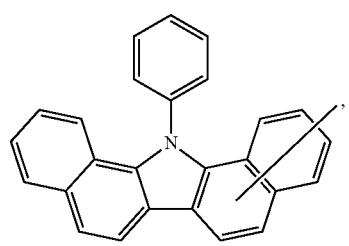
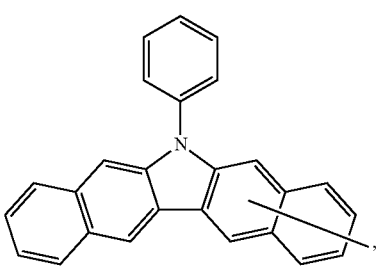
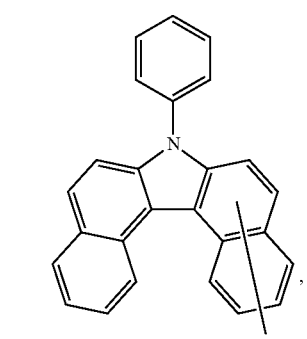
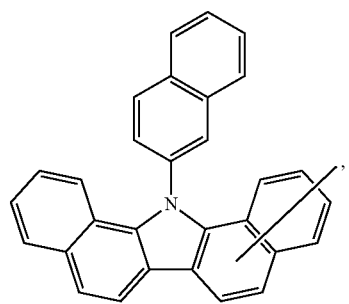
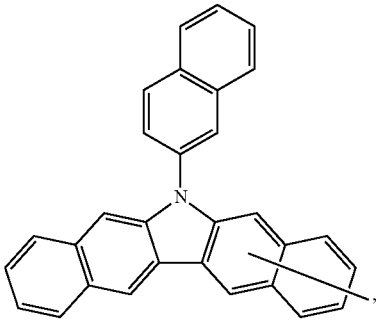

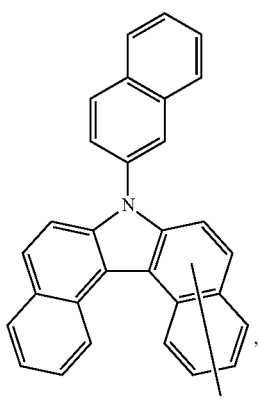
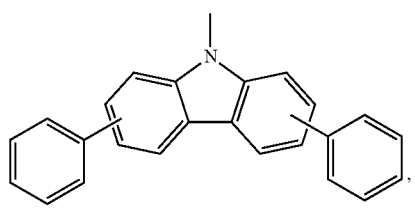
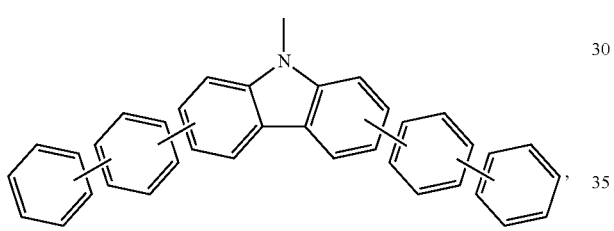
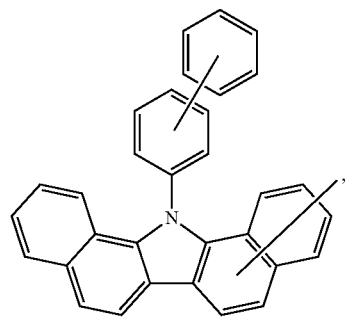
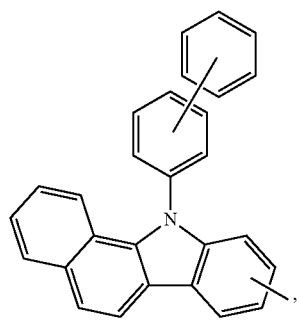
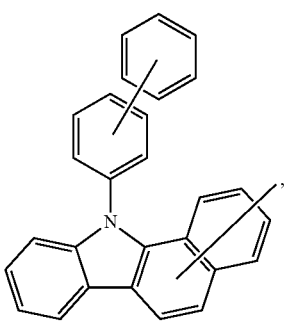
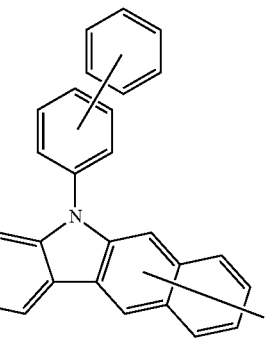
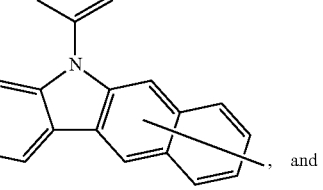
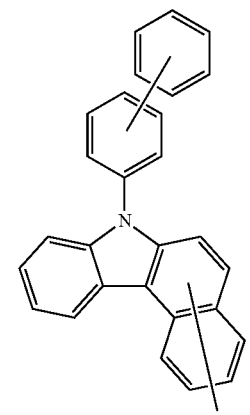
, and
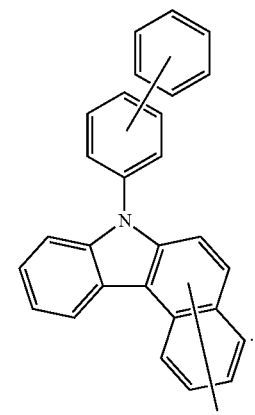

The particular structural formula of the organic compound is preferably any one of:
(1)
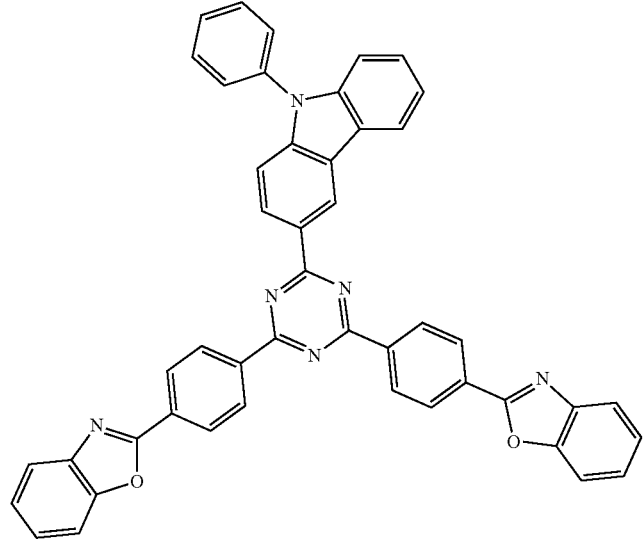
(2)
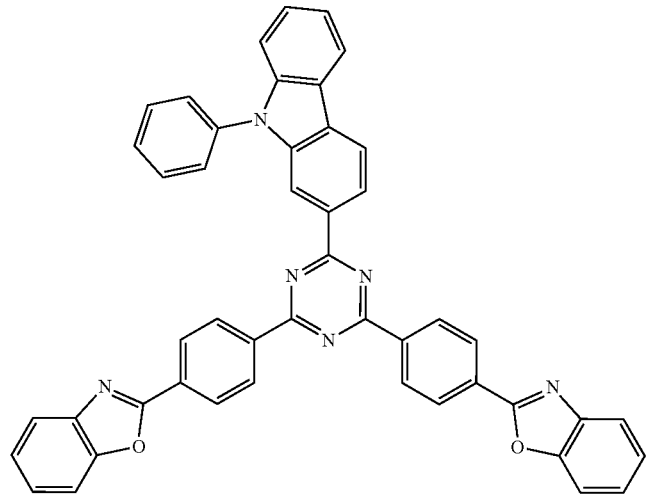
(3)
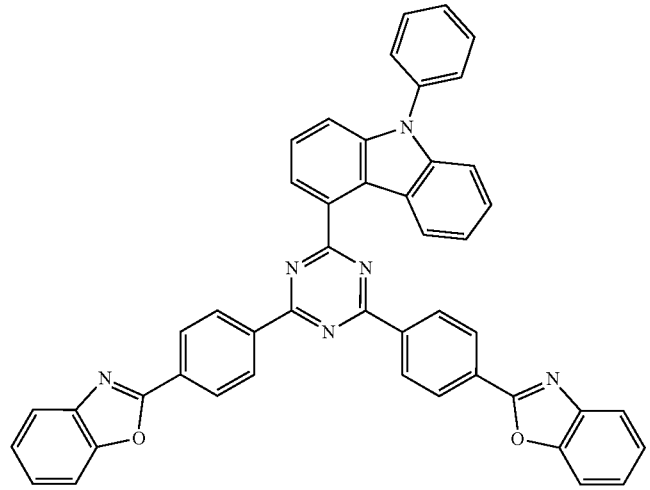

-continued
(4)
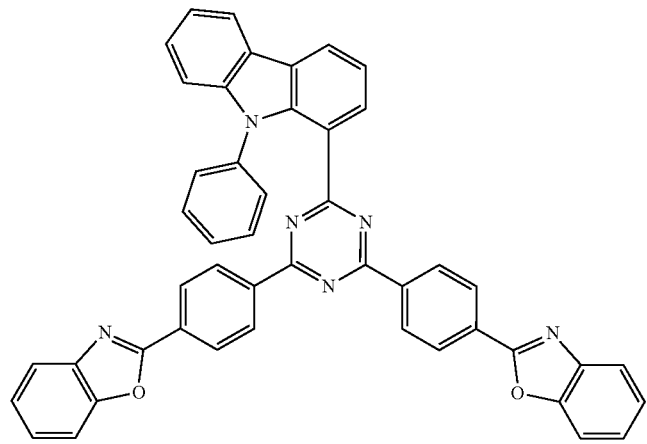
(5)
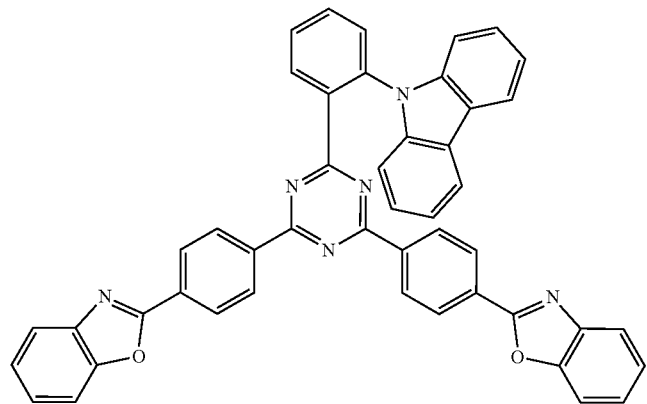
(6)
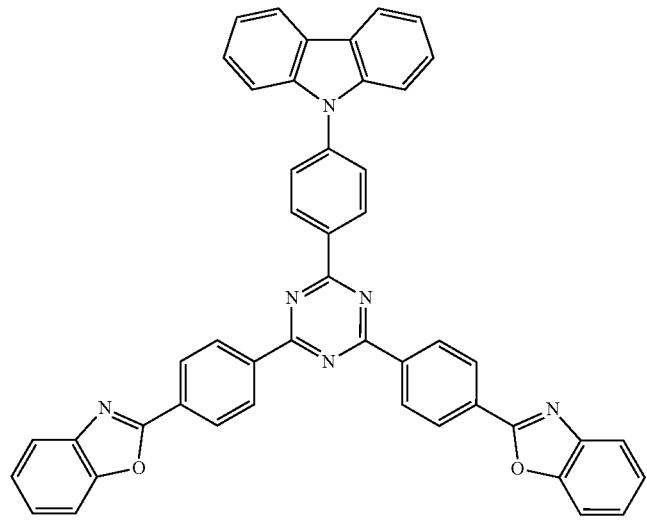

-continued
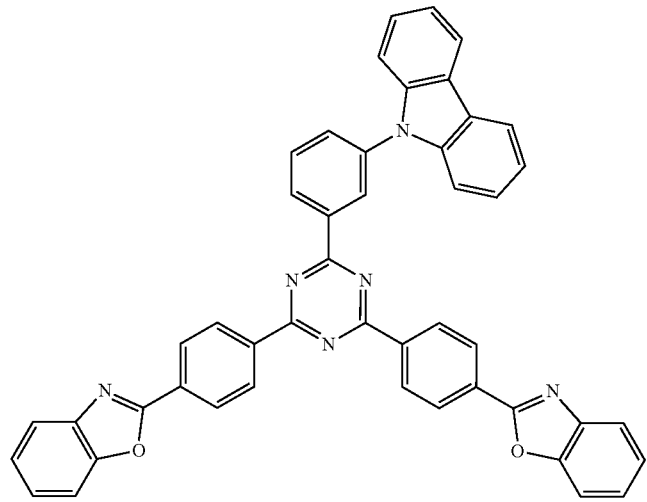
(7)
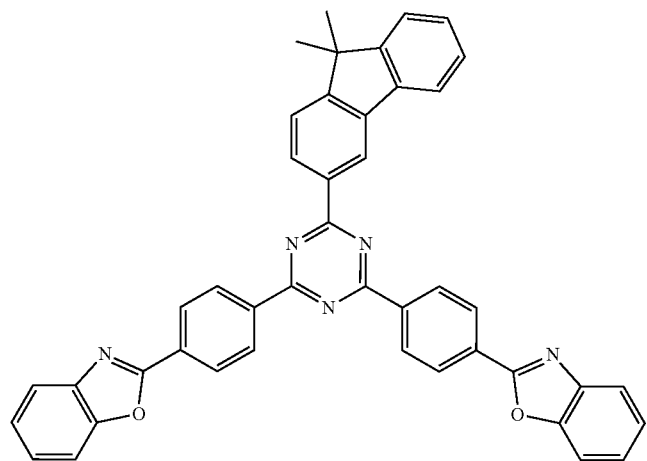
(8)
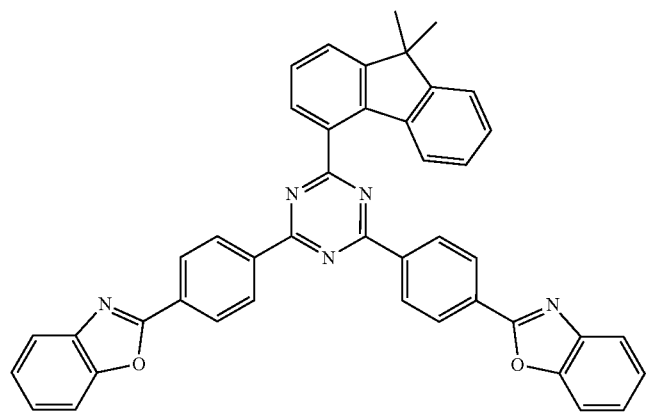
(9)

-continued
(10)
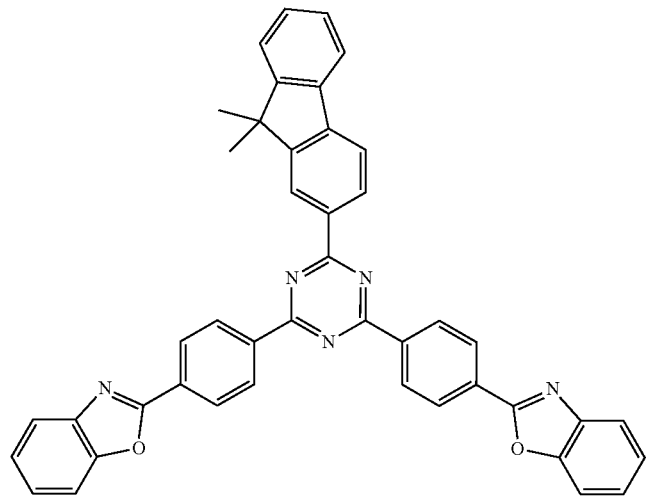
(11)
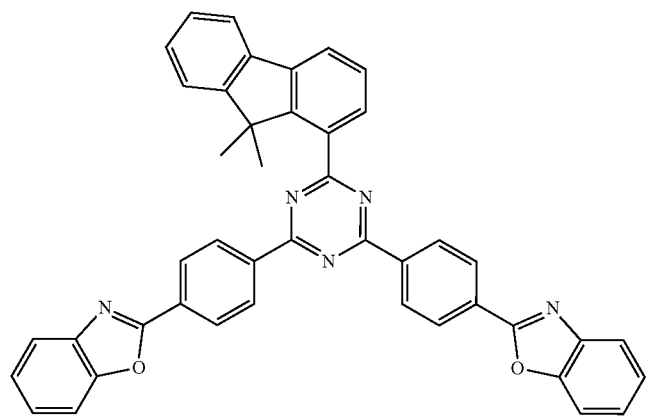
(12)
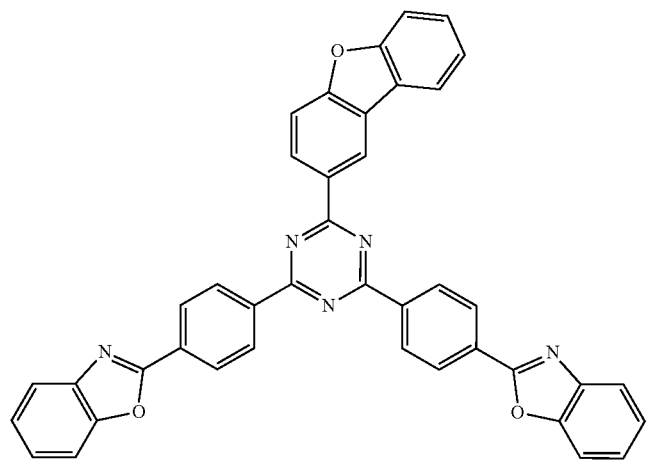

-continued
(13)
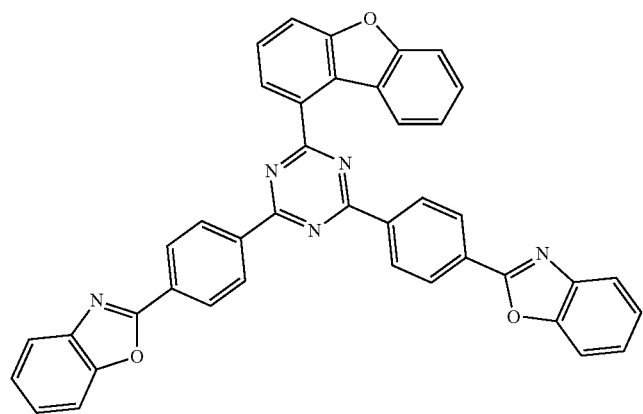
(14)
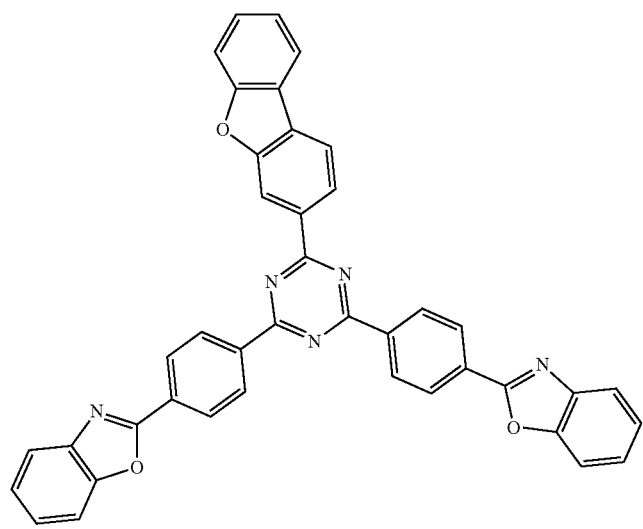
(15)
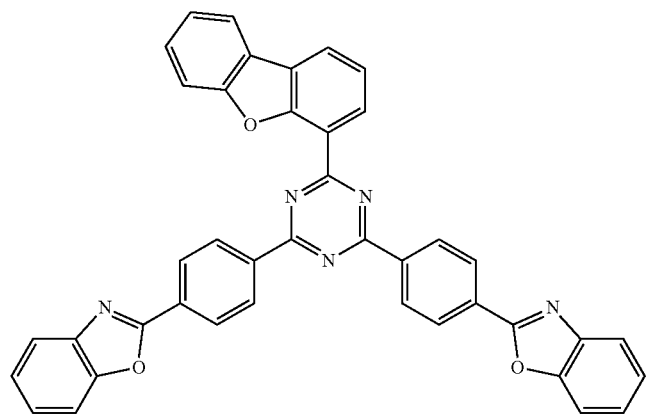

-continued
(16)
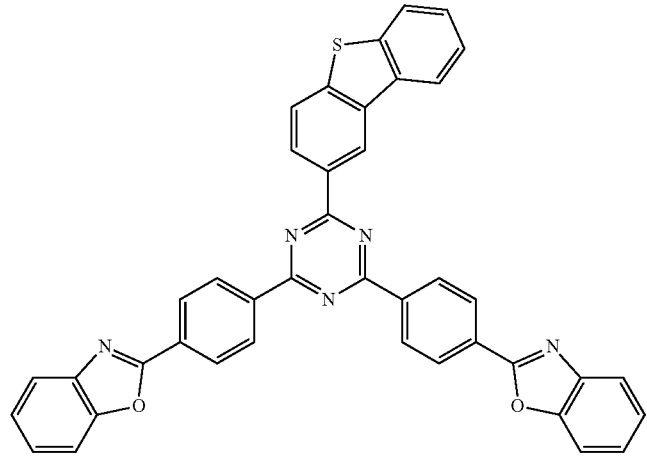
(17)
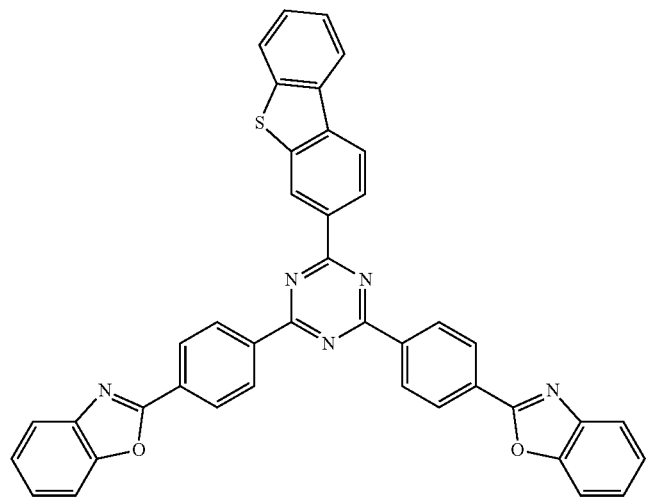
(18)
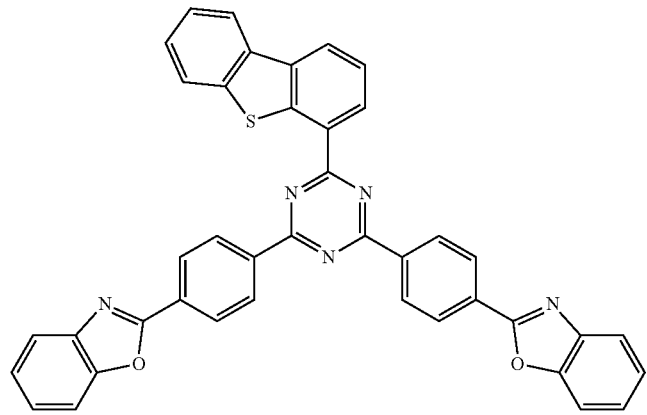

-continued
(19)
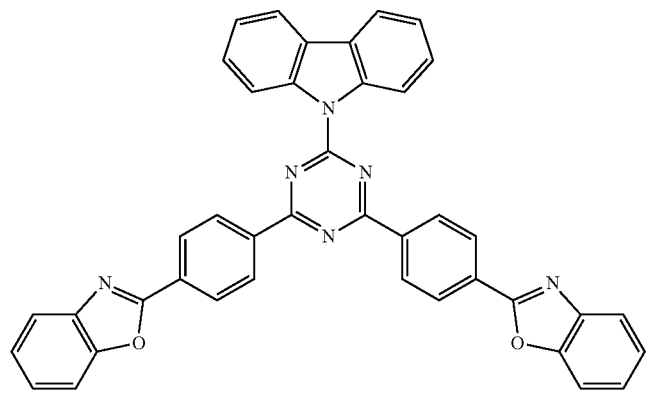
(20)
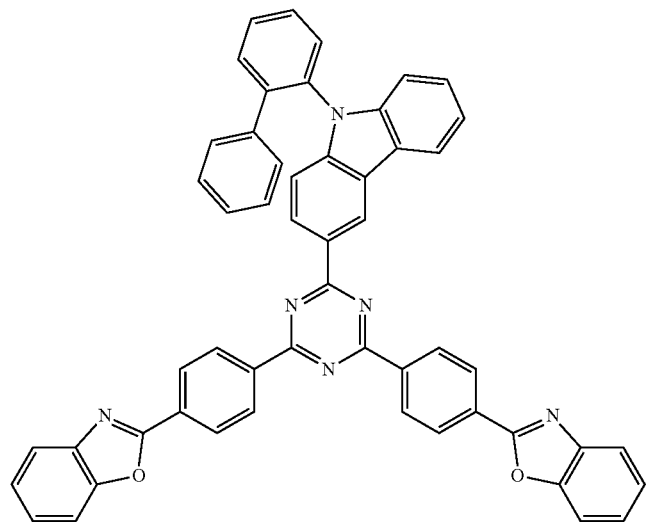
(21)
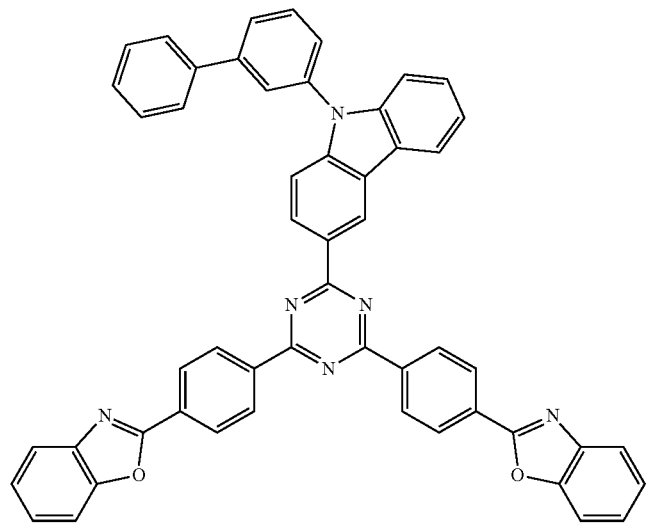

-continued
(22)
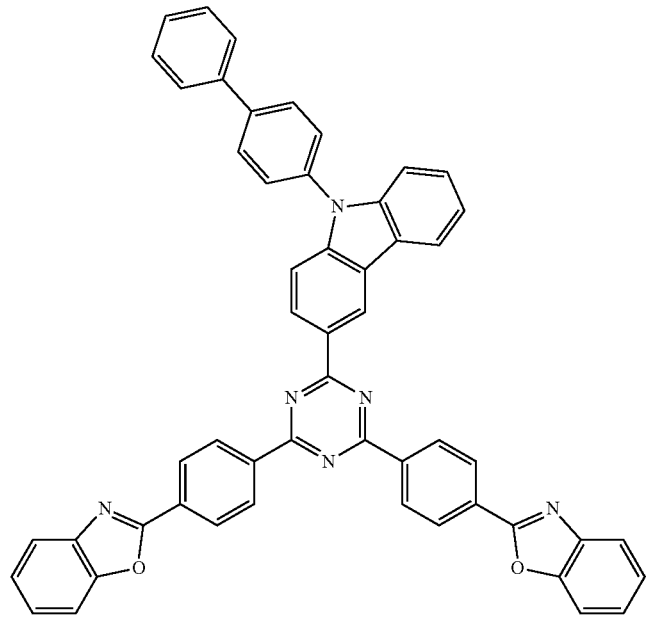
(28)
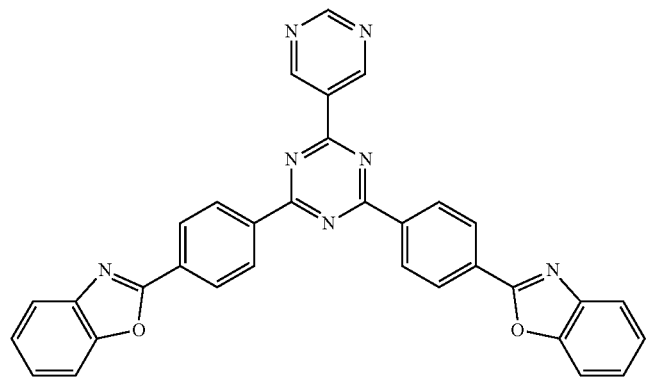
(29)
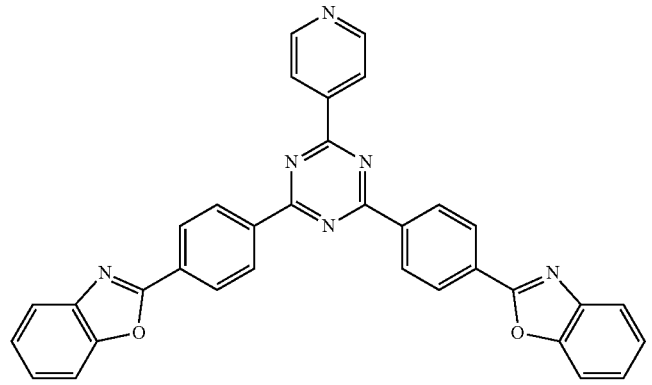

-continued
(30)
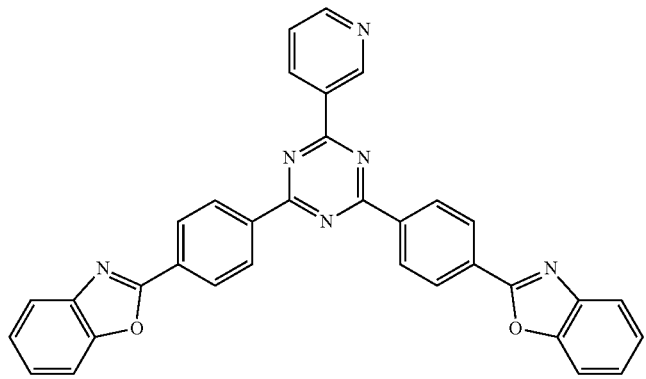
(31)
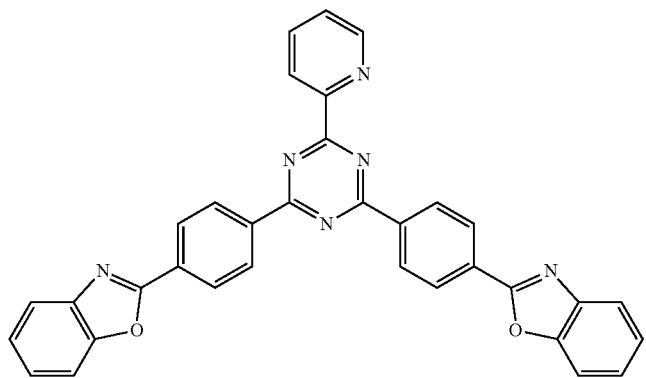
(35)
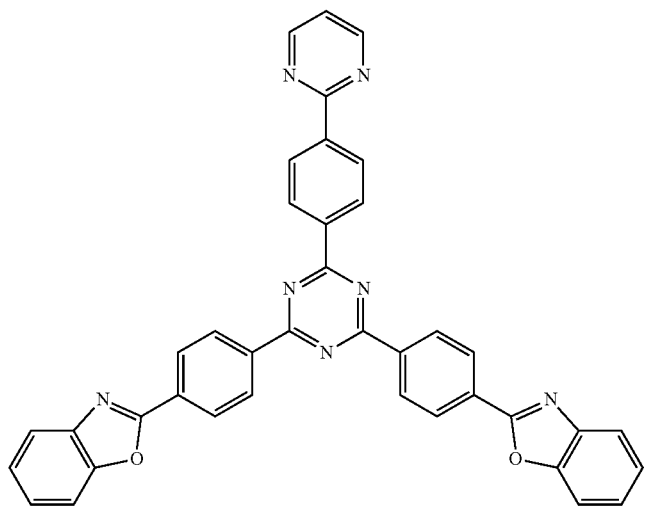

(36)
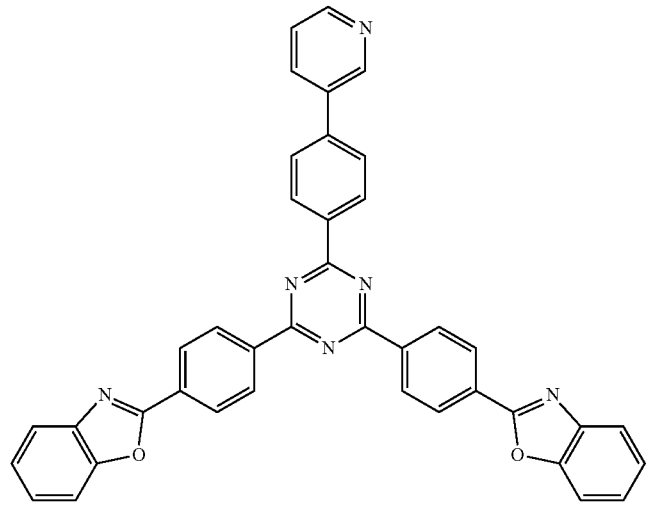
(37)
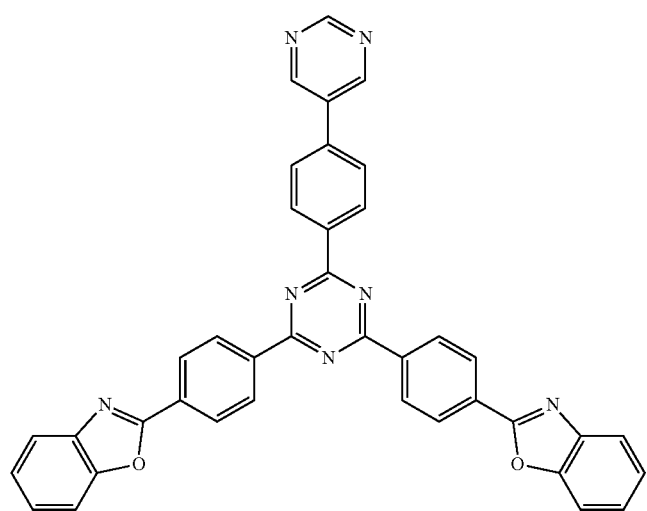
(38)
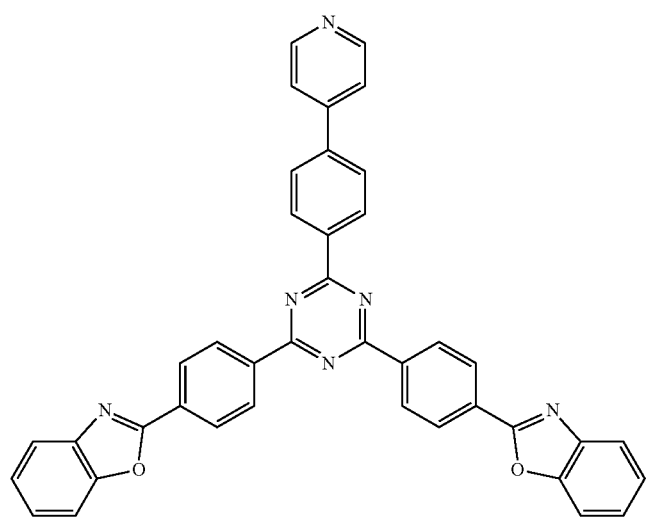

-continued
(39)
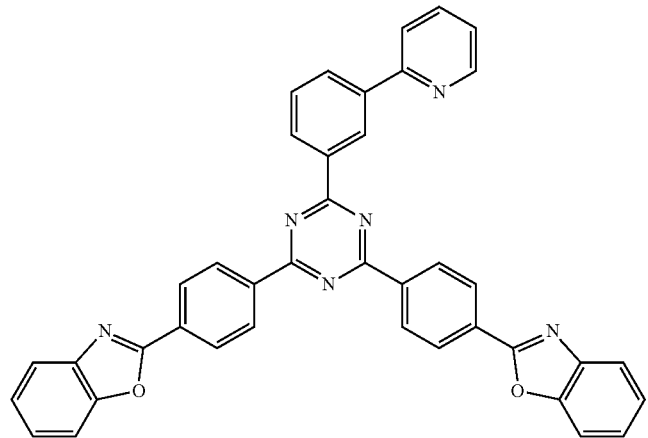
(40)
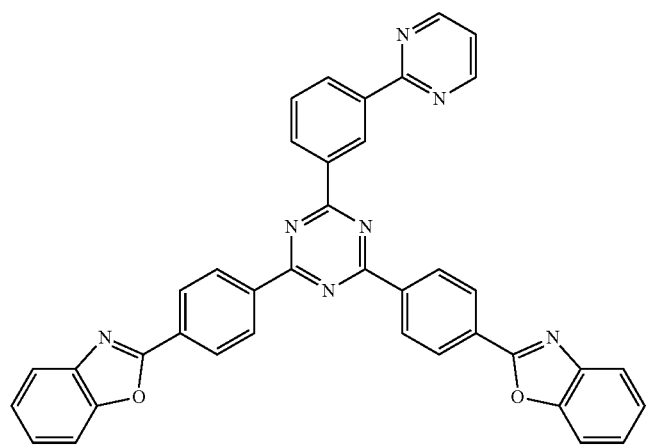
(41)
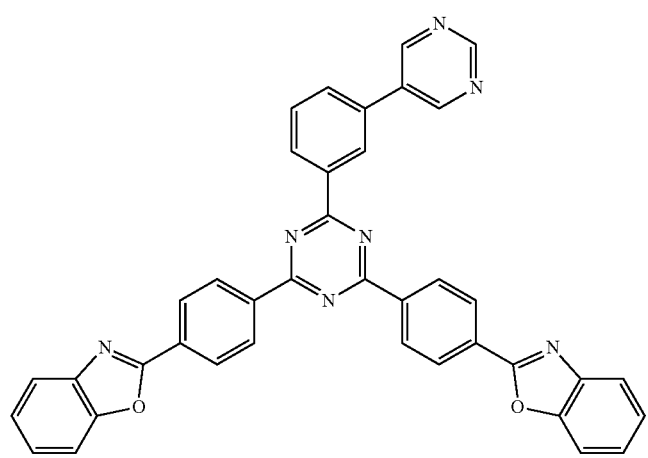

-continued
(42)
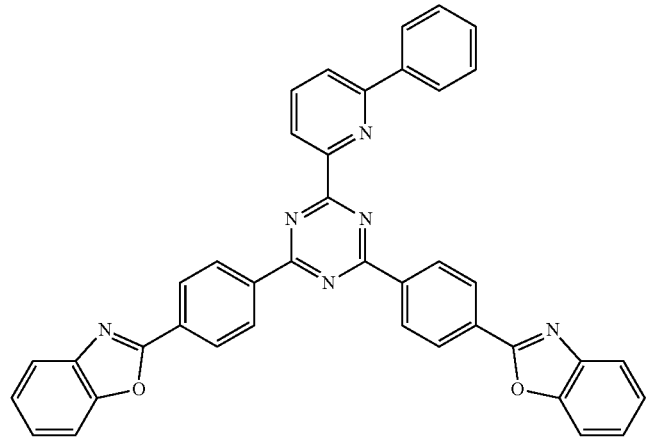
(43)
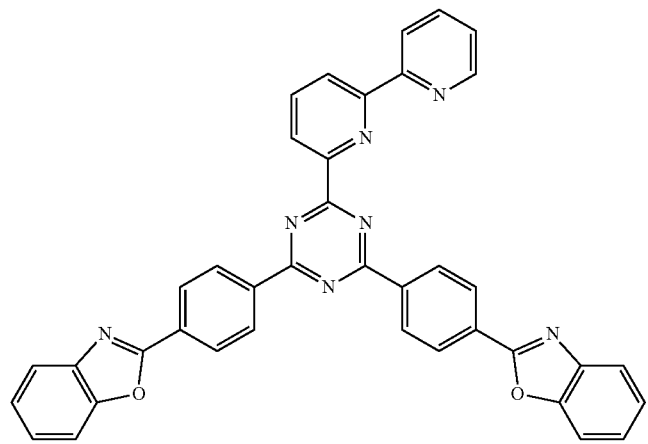
(44)
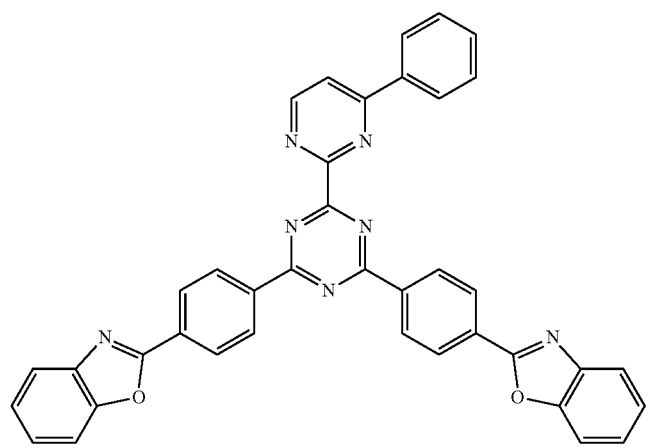

-continued
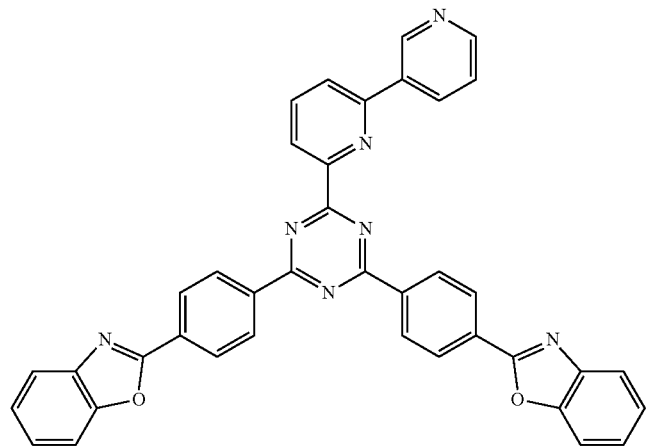
(45)
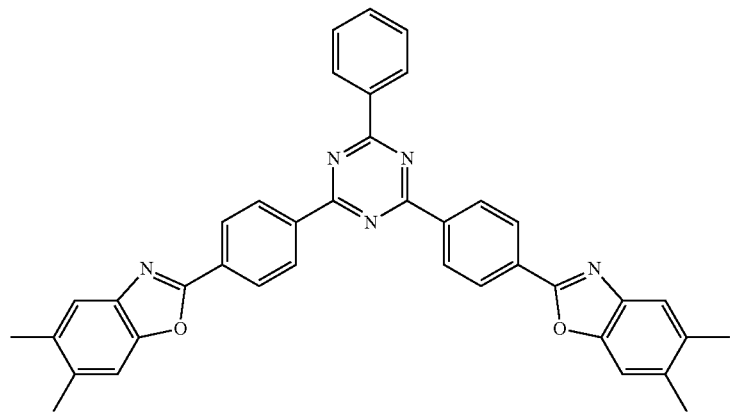
(46)
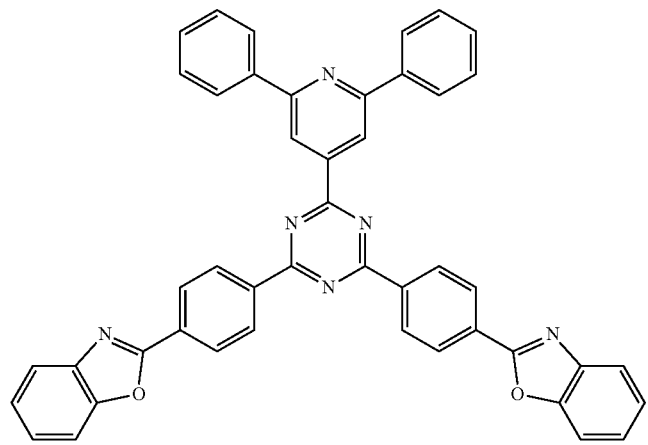
(47)

-continued
(48)
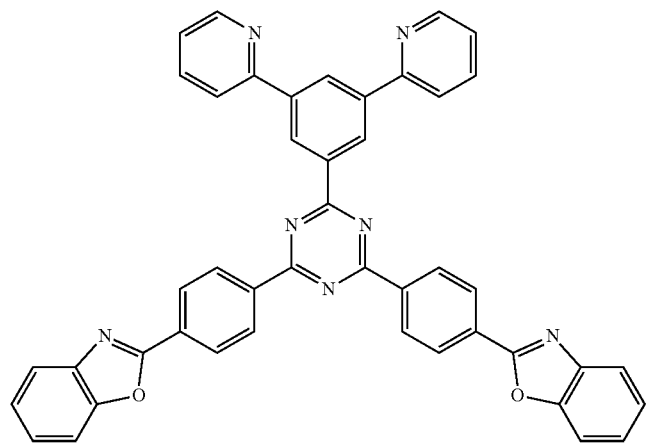
(49)
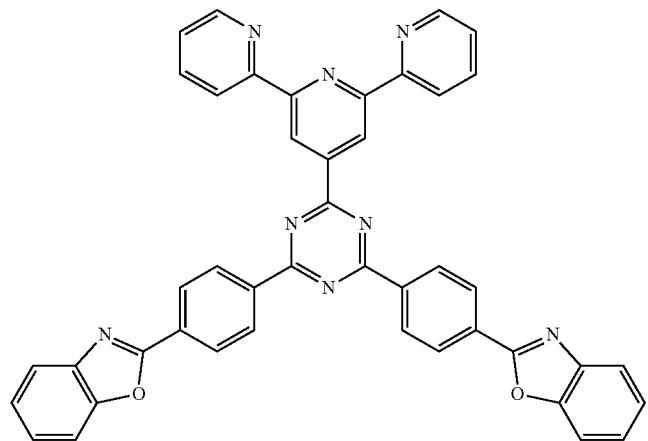
(50)
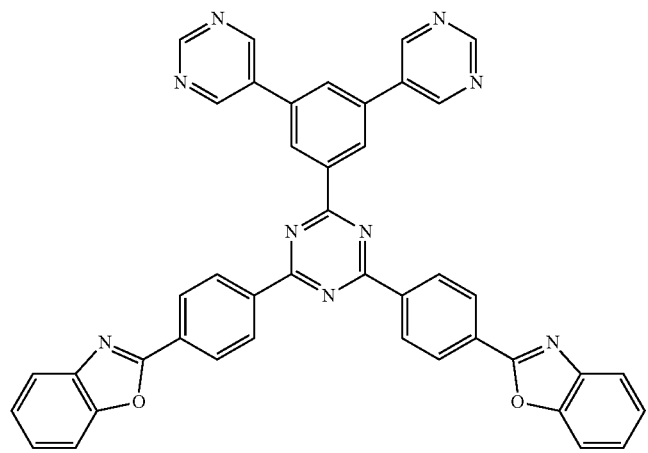

(51)
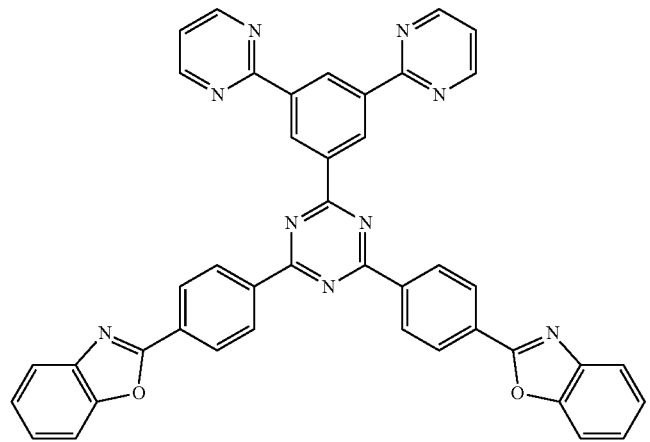
(52)
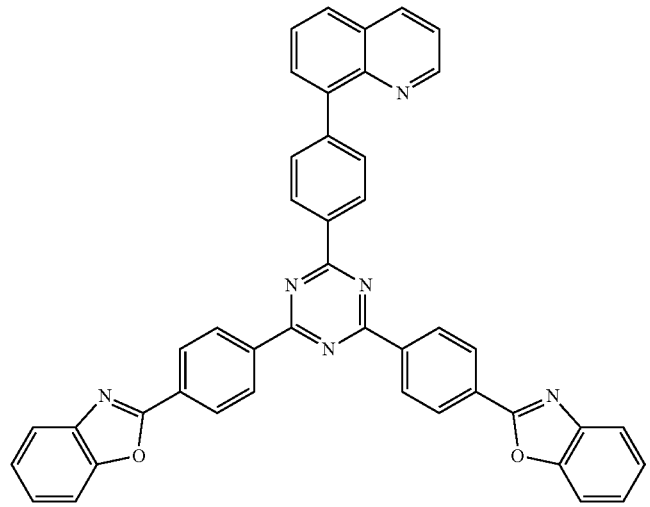
(53)
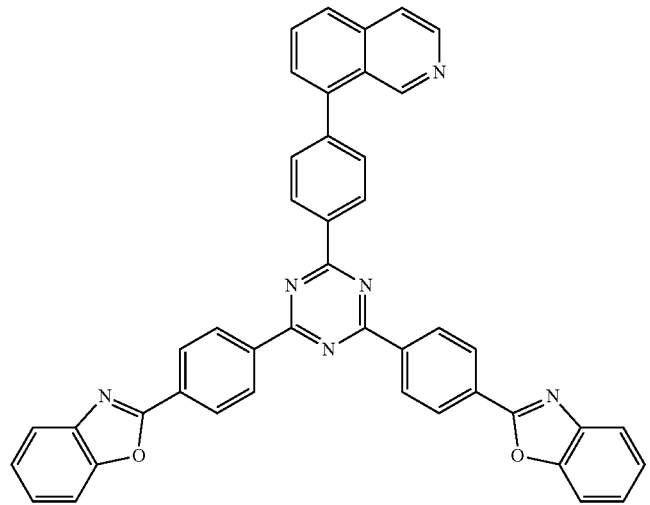

-continued
(54)
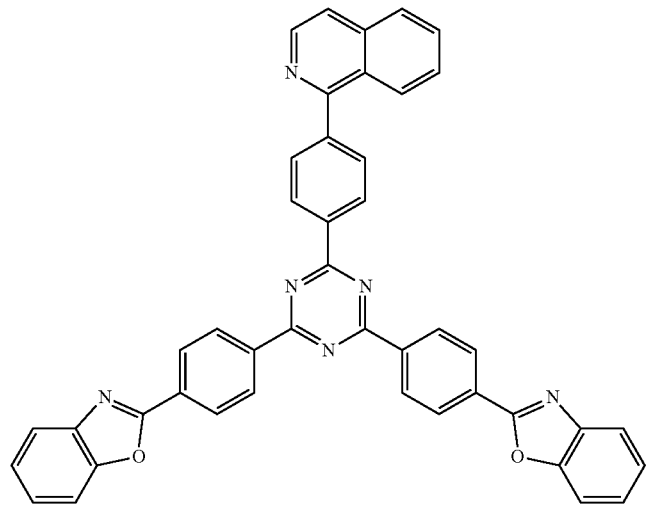
(55)
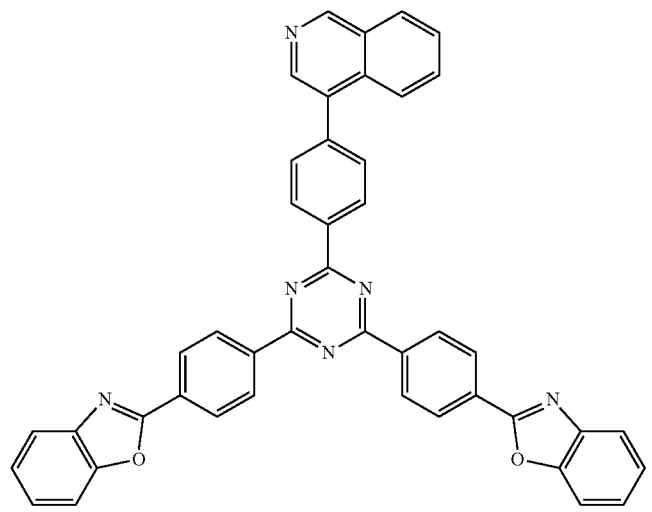
(56)
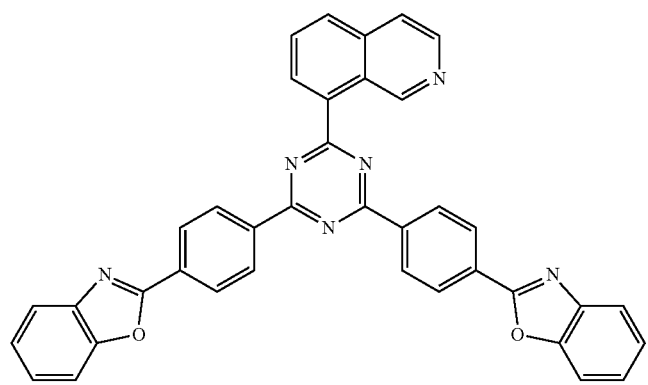

(57)
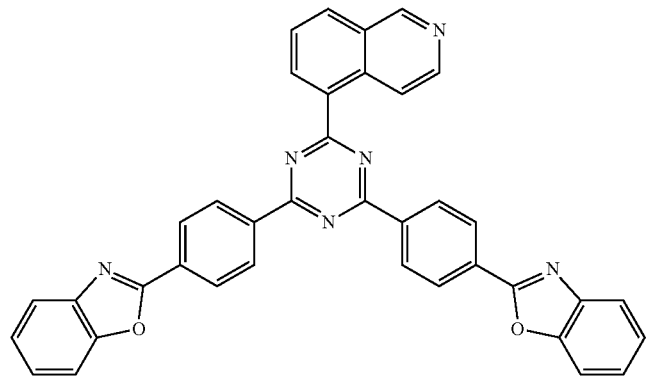
(58)
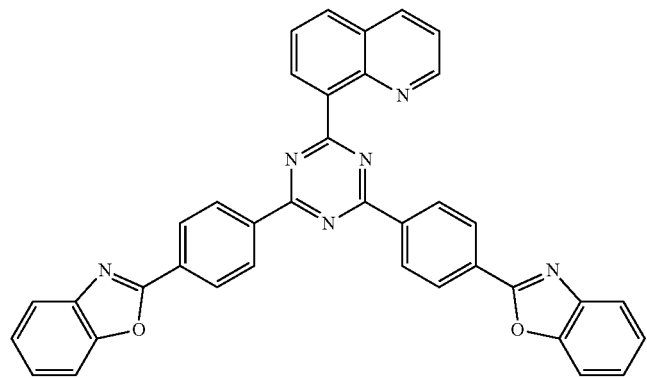
(59)
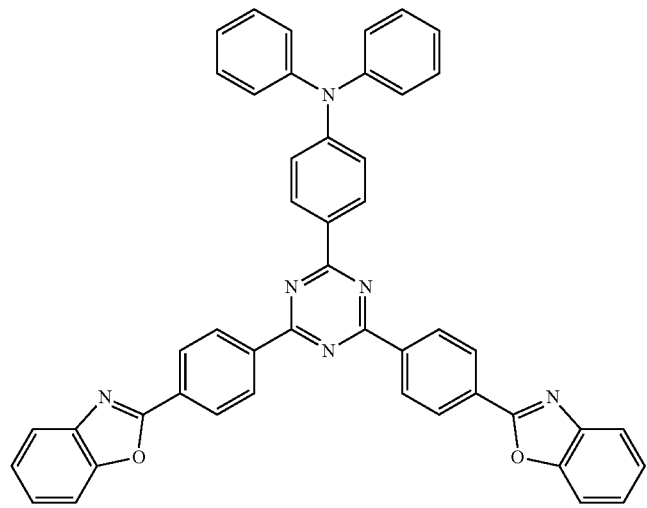

-continued
(60)
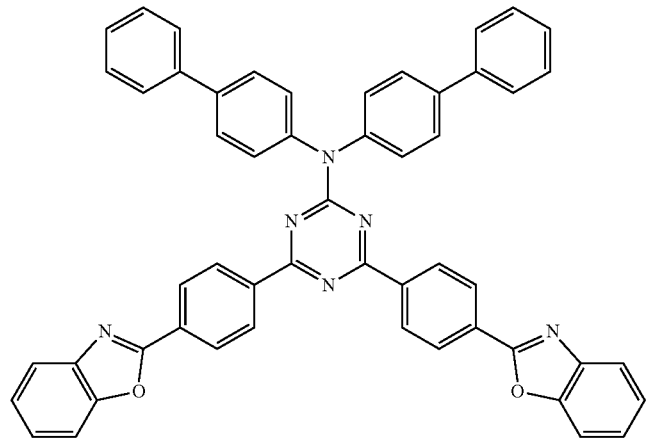
(61)
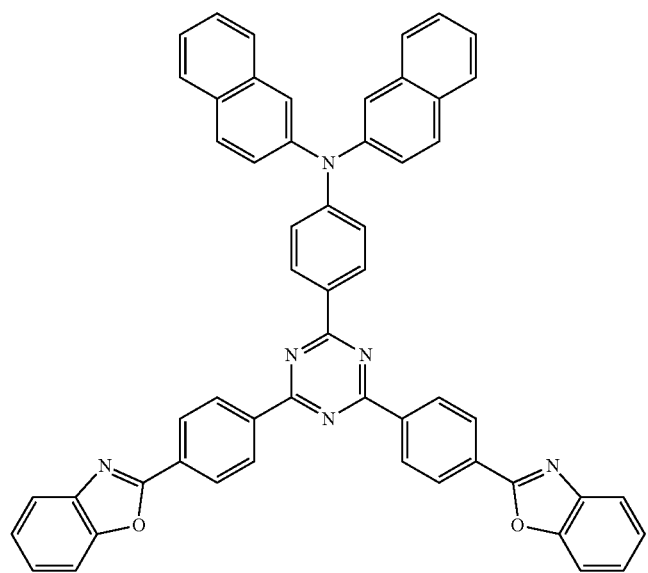
(62)
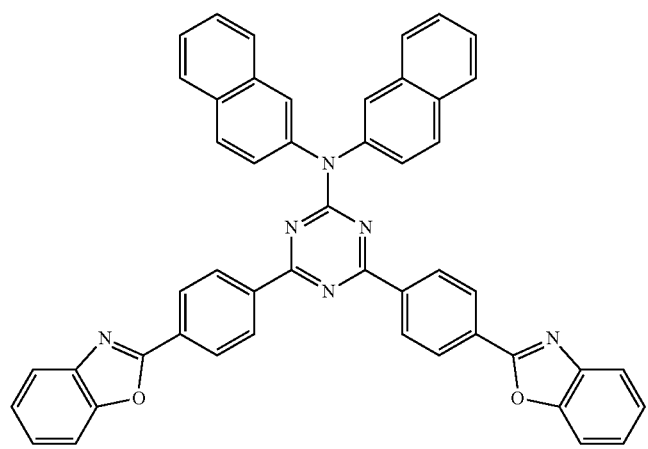

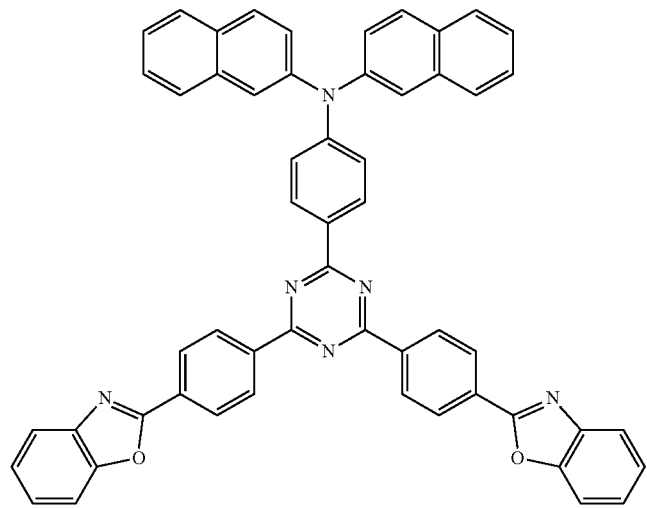
(63)
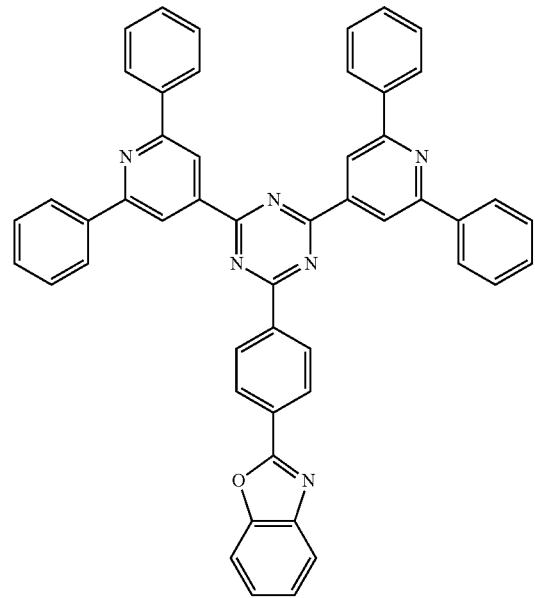
(65)

(66)
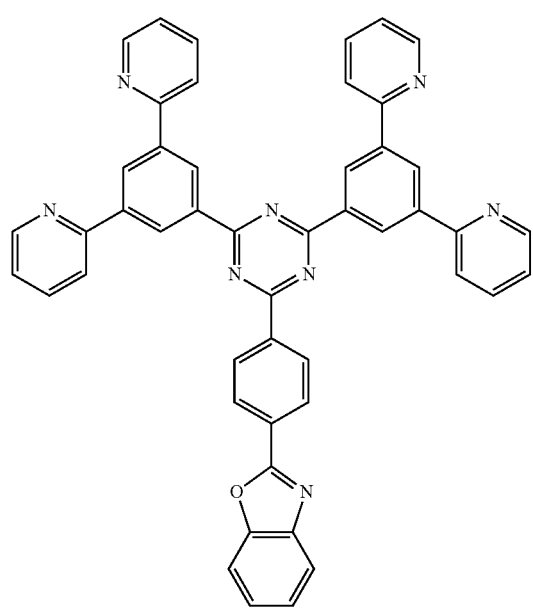
(67)
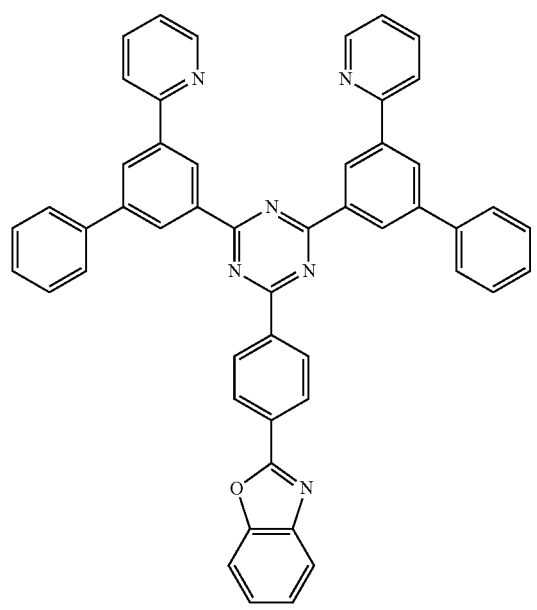

-continued
(68)
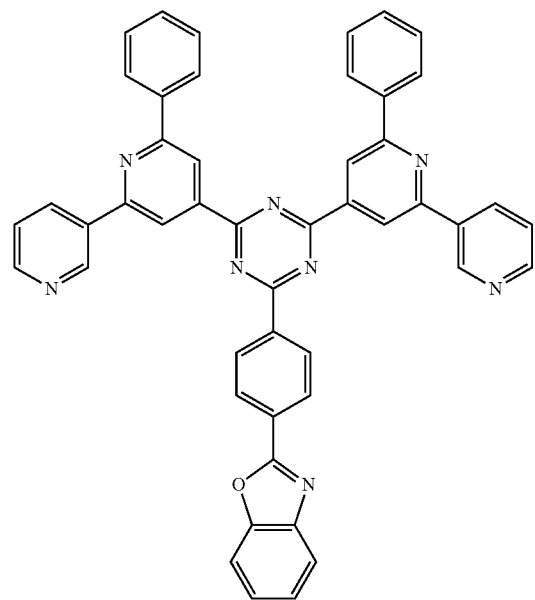
(69)
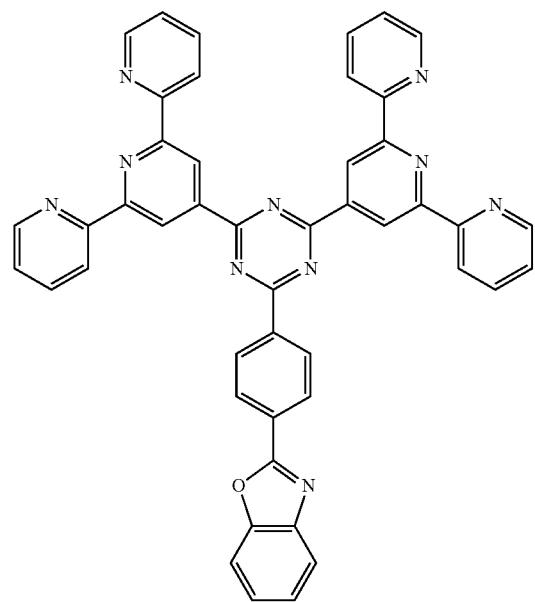

-continued
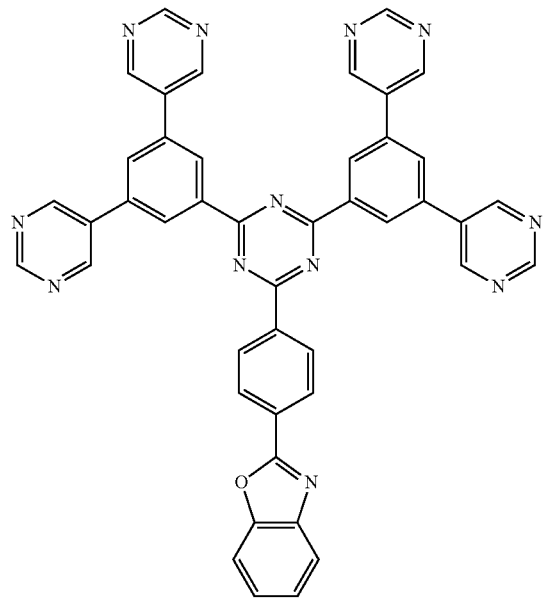
(70)
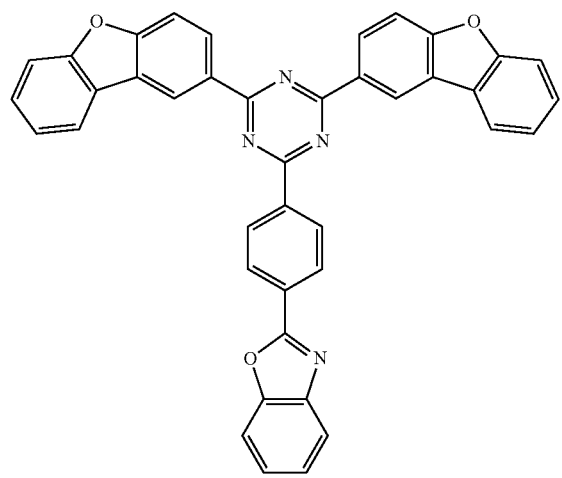
(71)
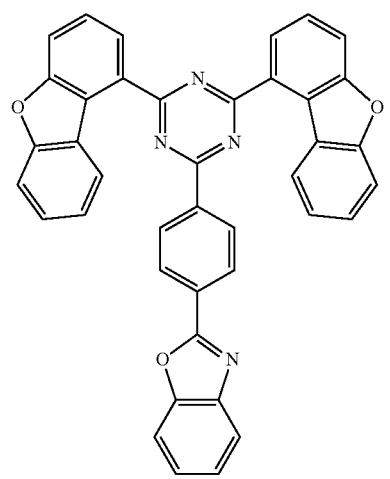
(72)

-continued
(73)
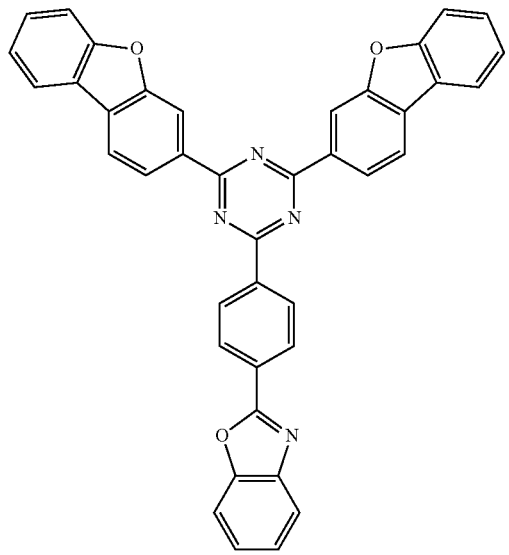
(74)
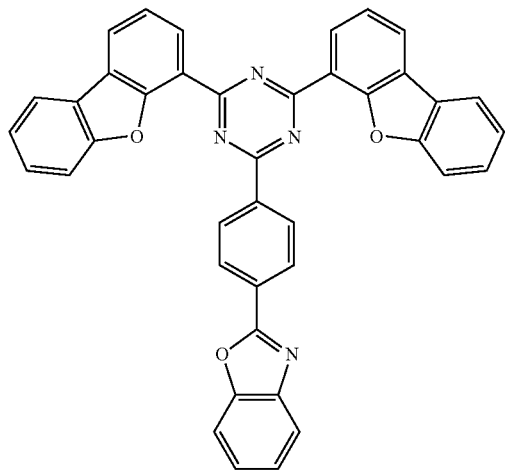
(75)
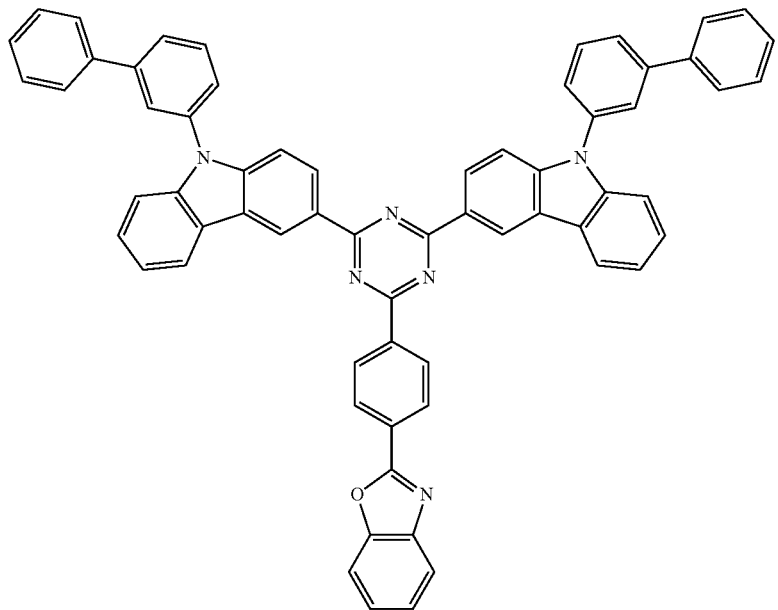

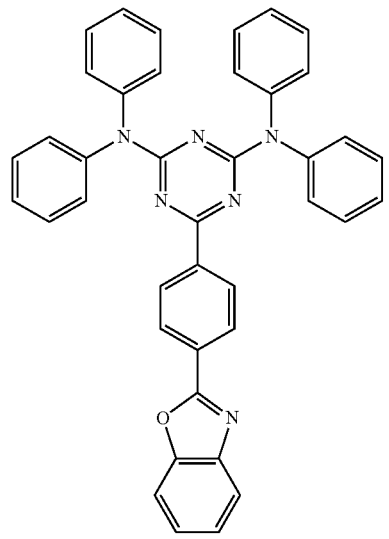
(76)
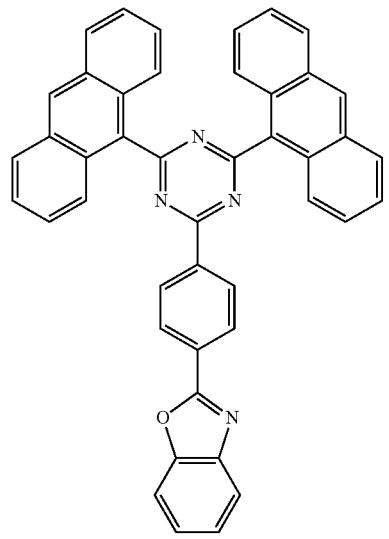
(77)
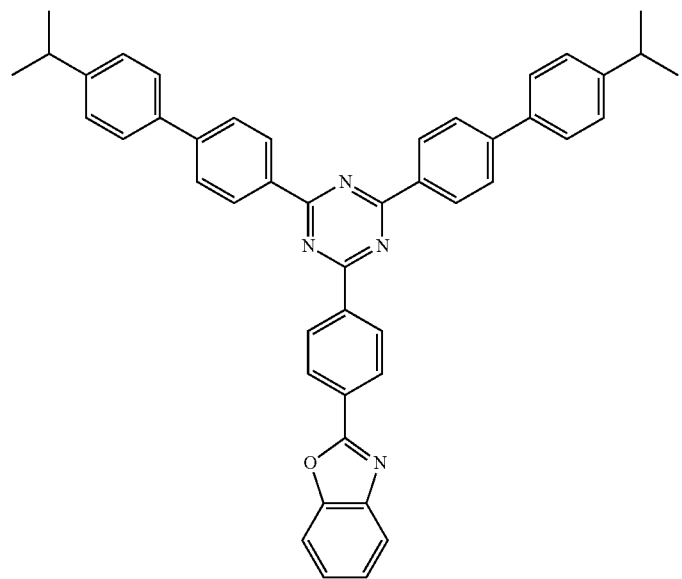
(78)

-continued
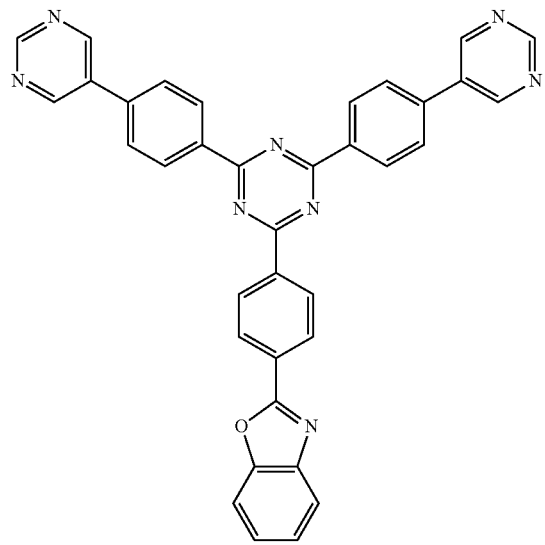
(79)
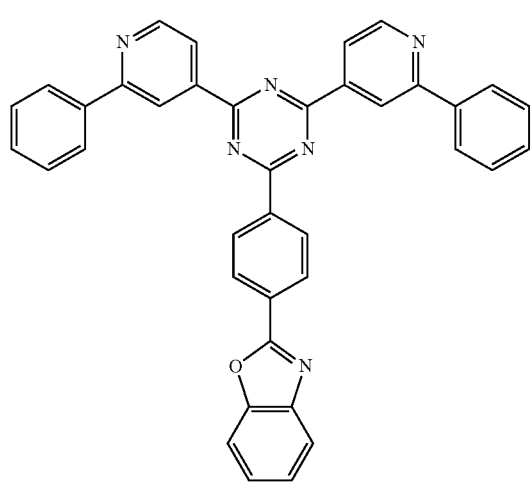
(80)
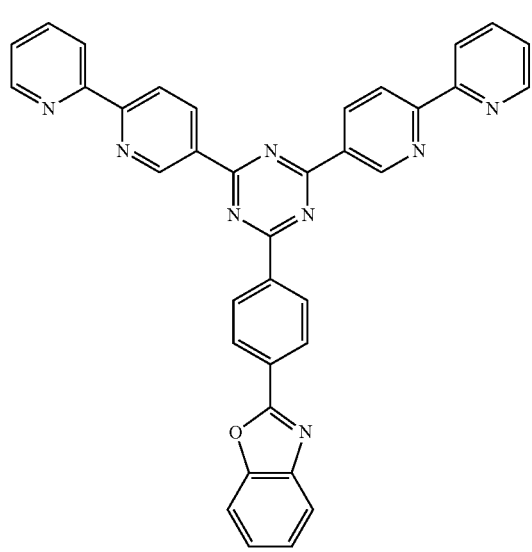
(81)

-continued
(82)
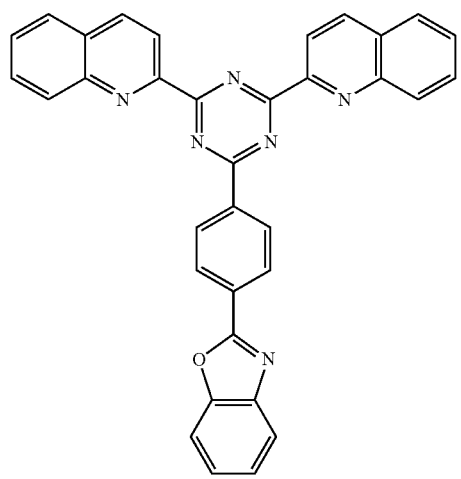
(85)
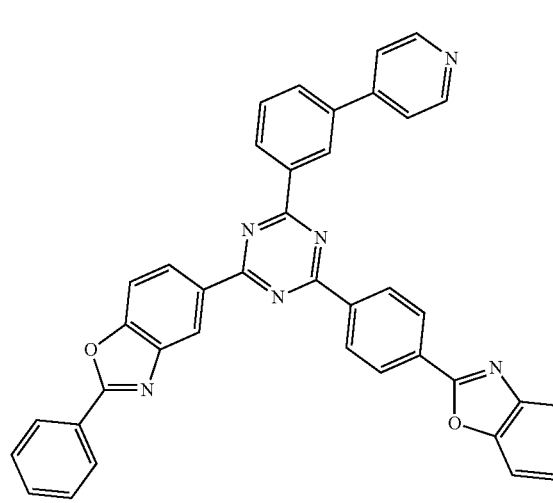
(86)
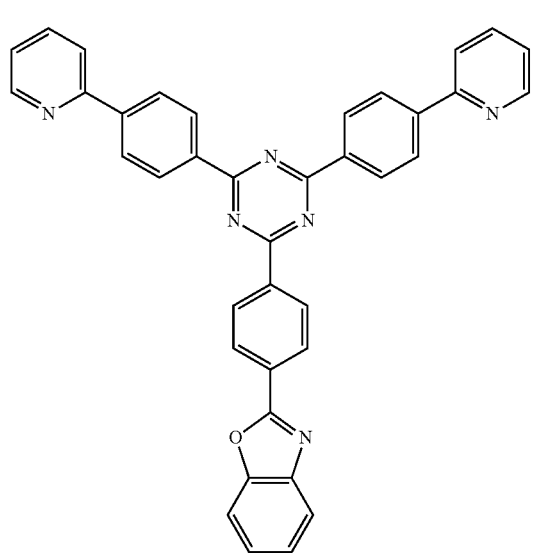

-continued
(87)
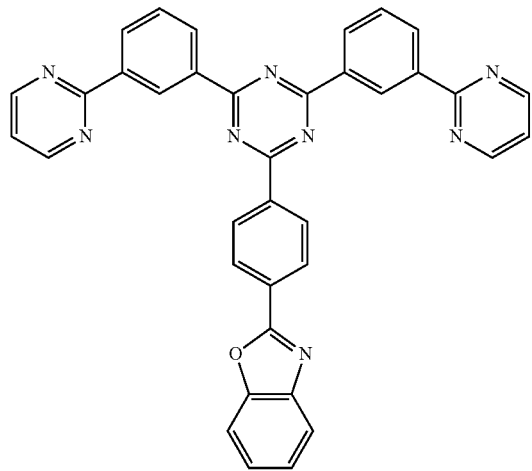
(88)
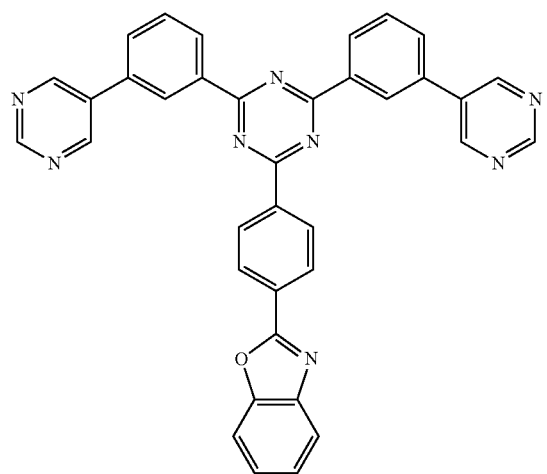
(89)
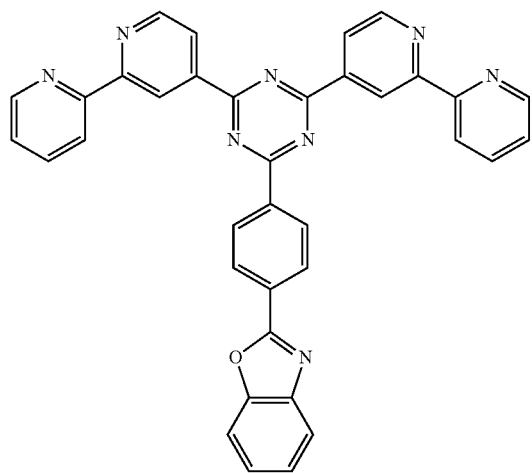

-continued
(90)
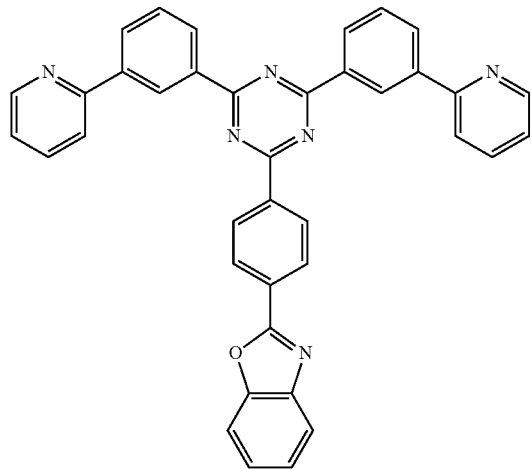
(91)
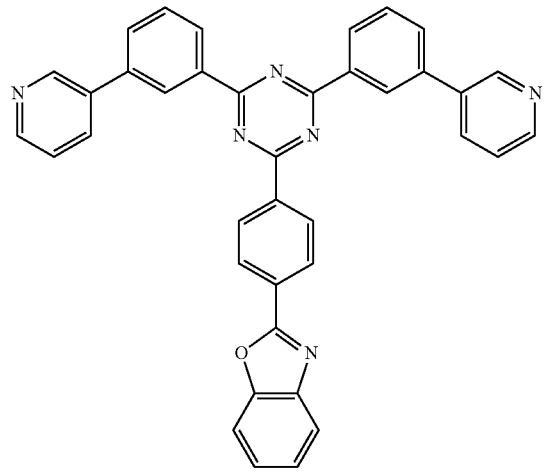
(92)
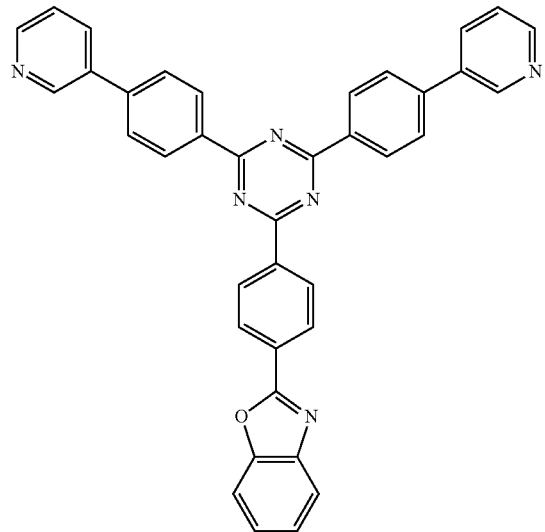

-continued
(93)
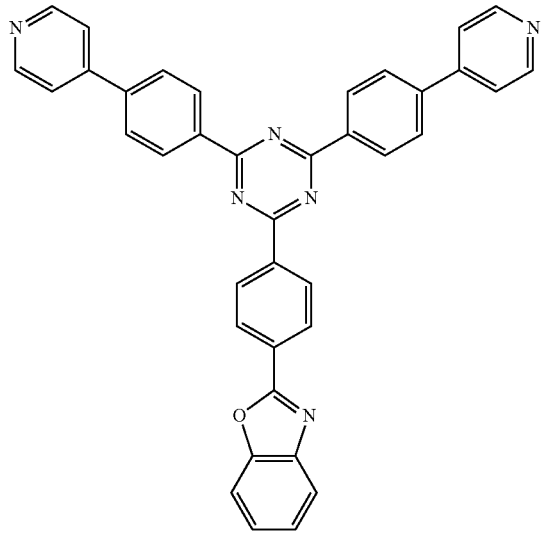
(94)
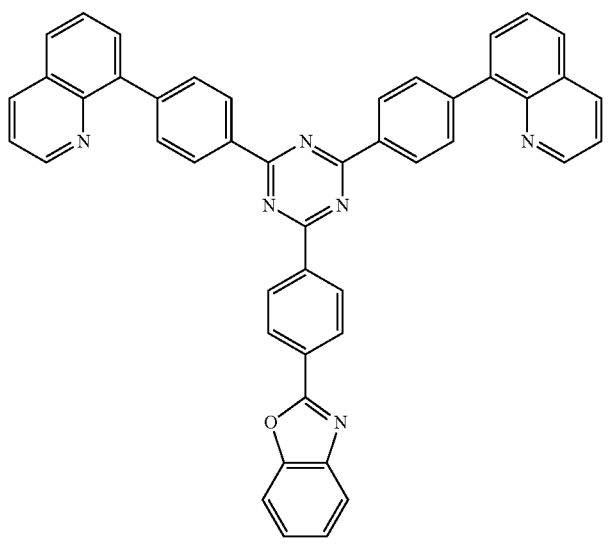
(95)
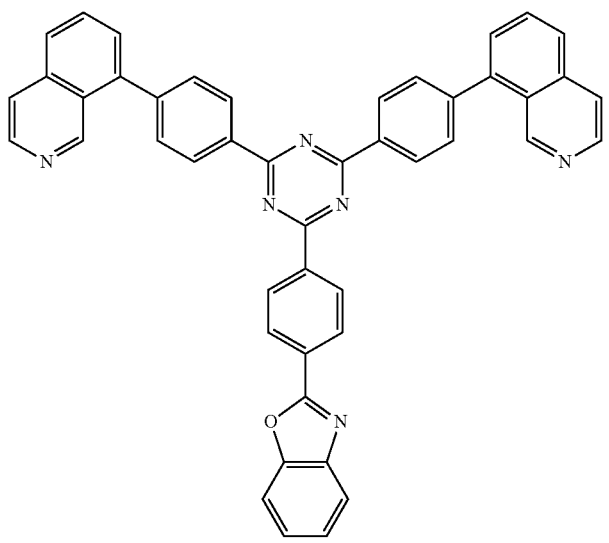

-continued
(96)
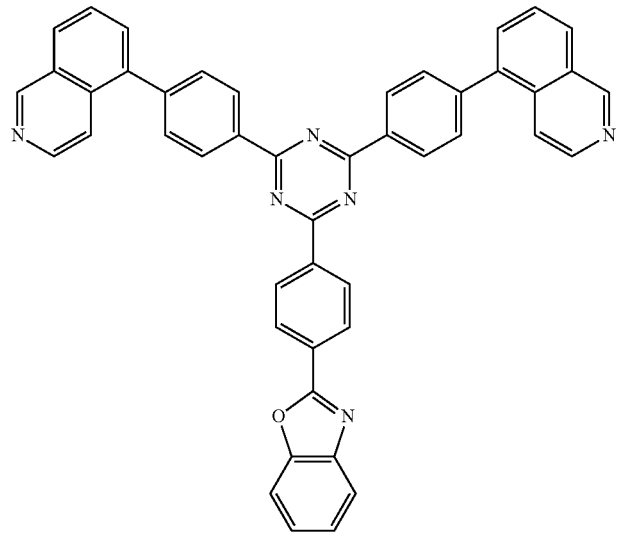
(97)
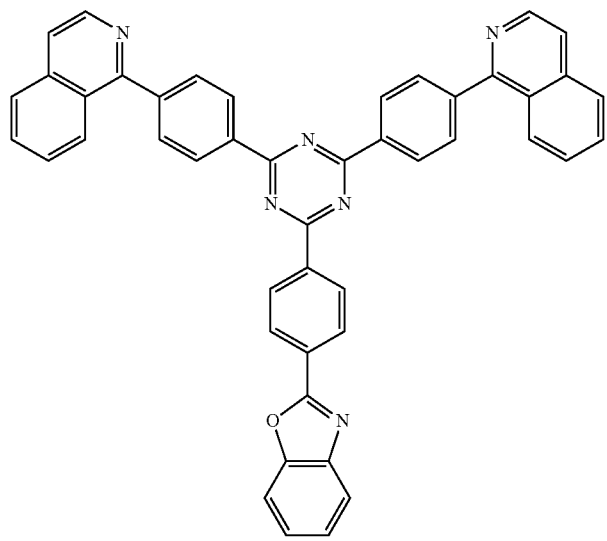
(98)
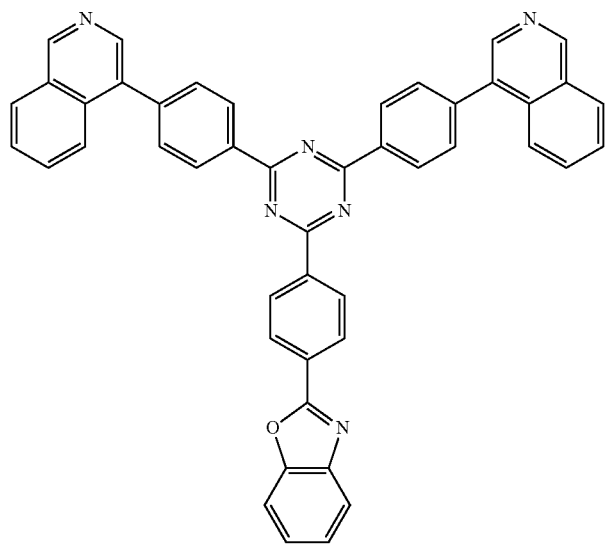

-continued
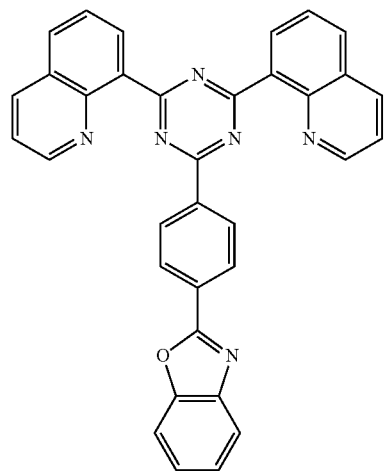
(99)
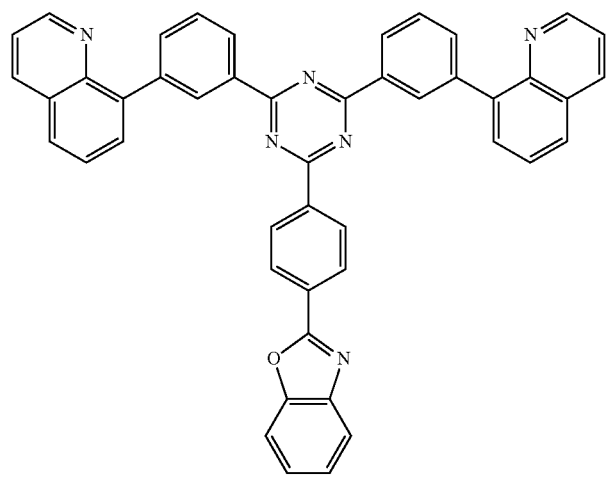
(100)
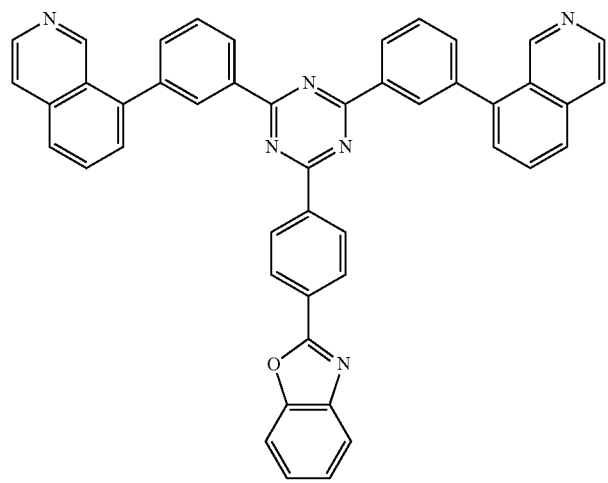
(101)

-continued
(102)
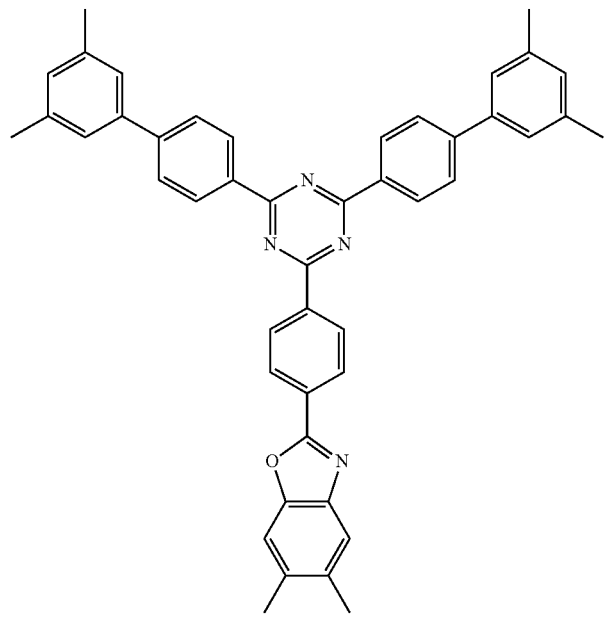
(103)
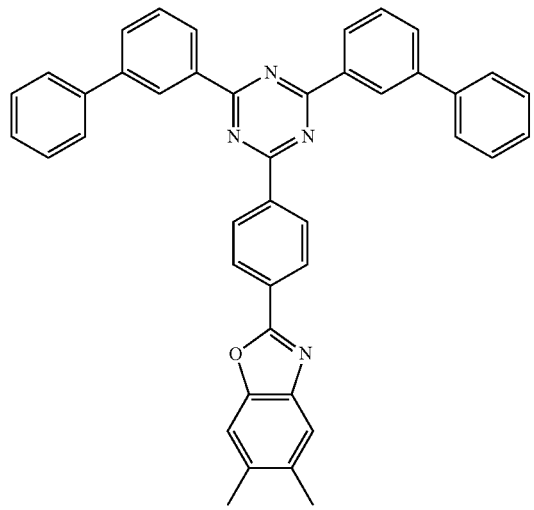
(104)
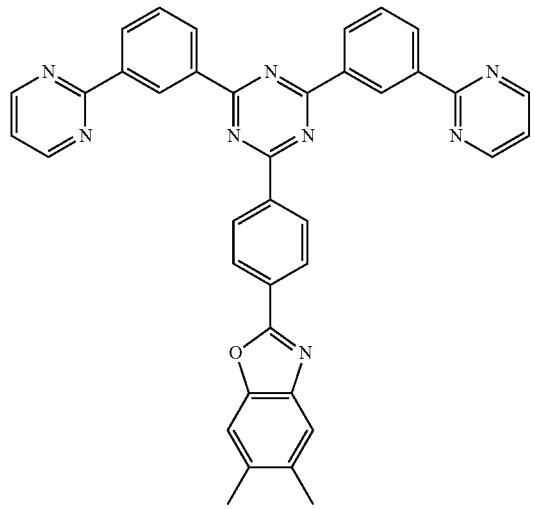

-continued
(105)
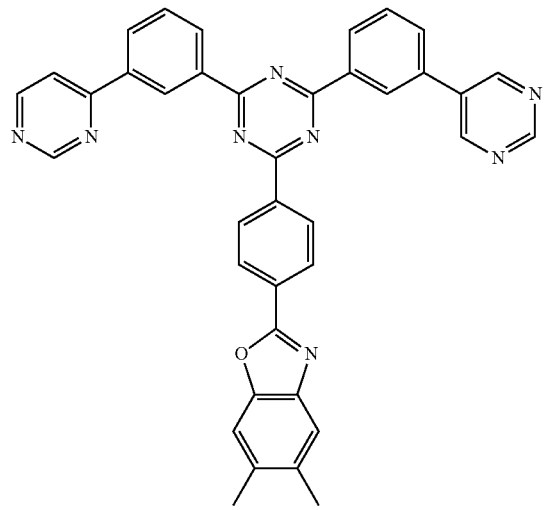
(106)
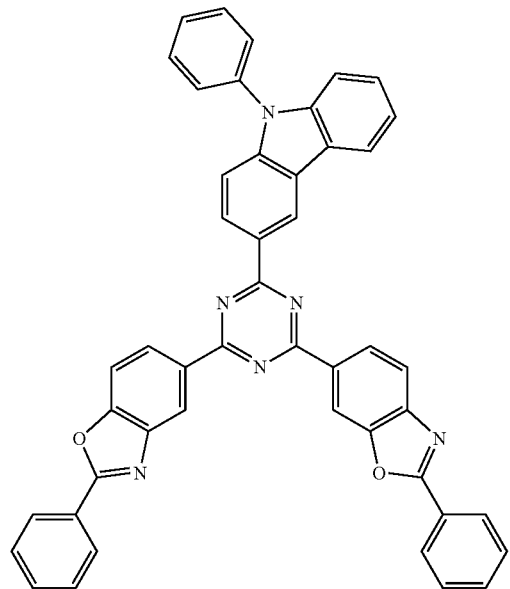
(107)
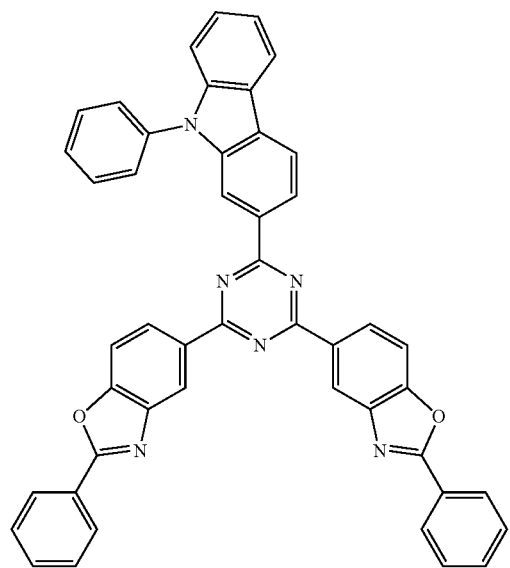

-continued
(108)
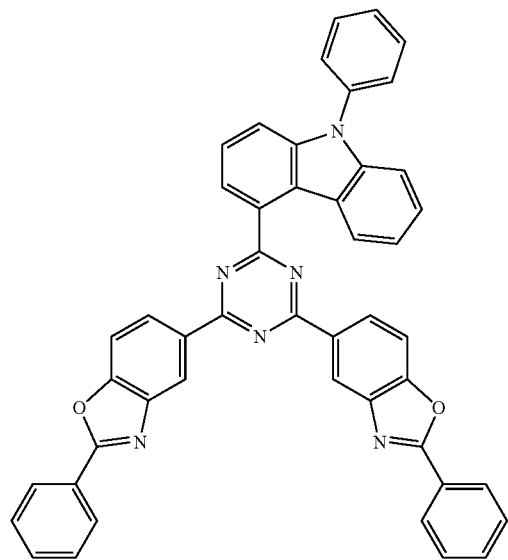
(109)
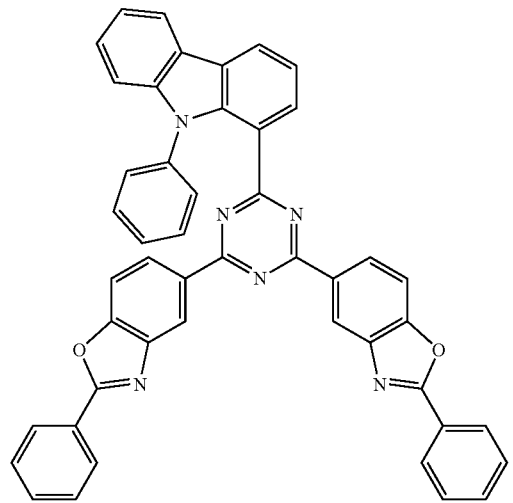
(110)
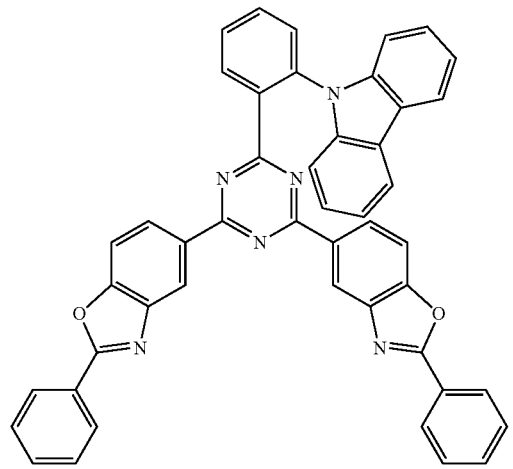

(111)
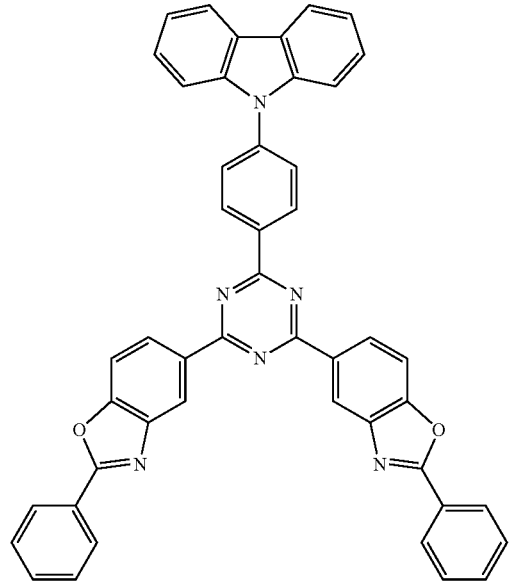
(112)
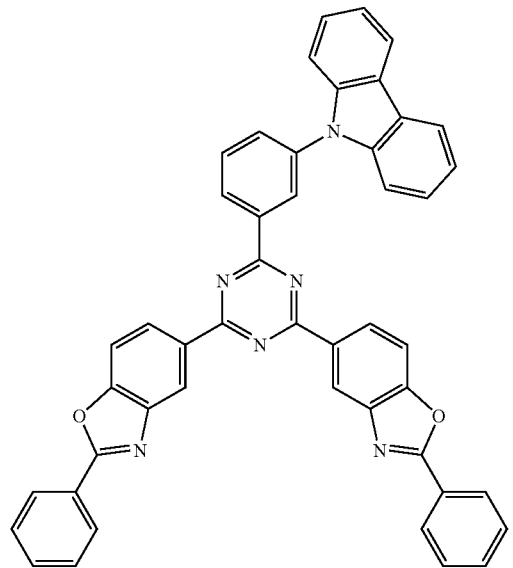

-continued
(113)
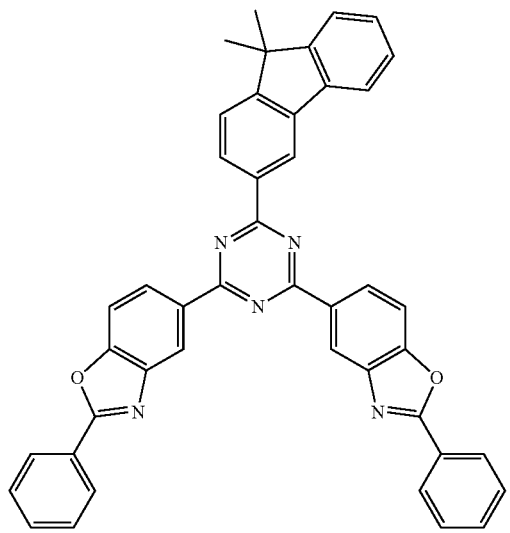
(114)
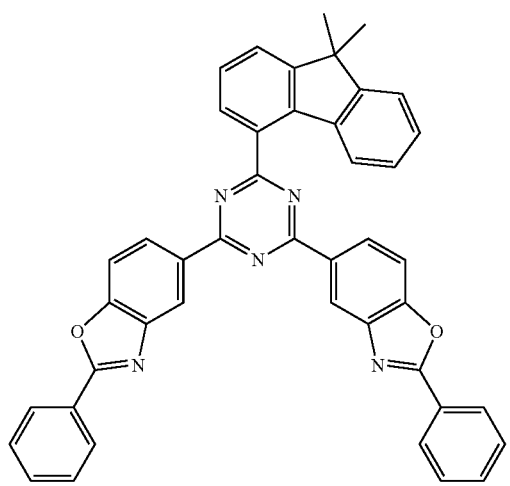
(115)
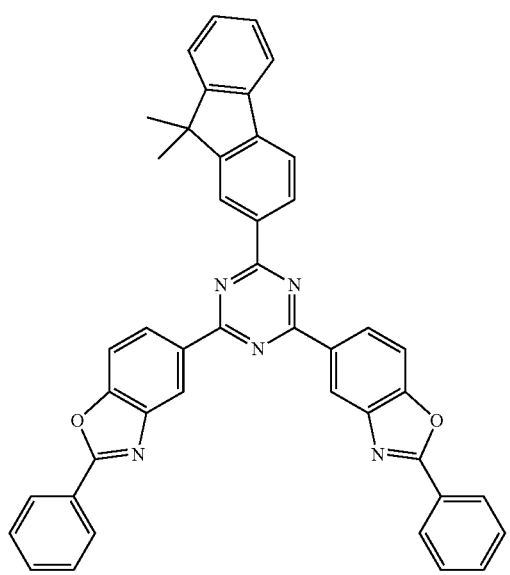

-continued
(116)
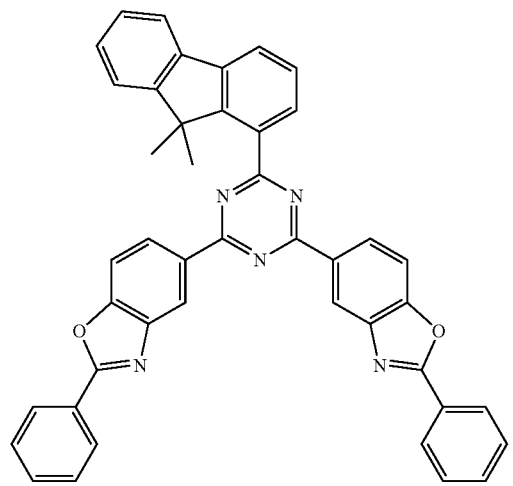
(117)
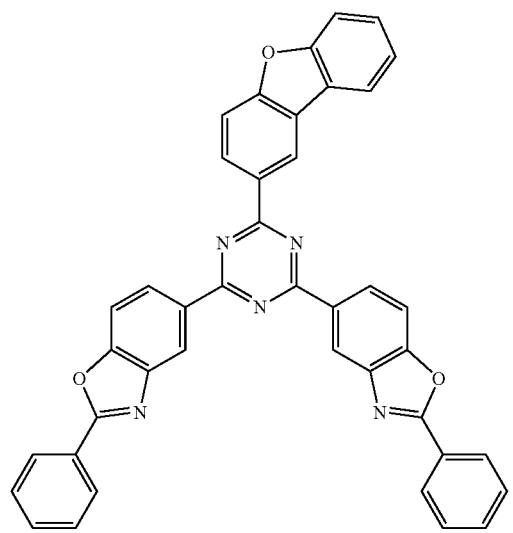
(118)
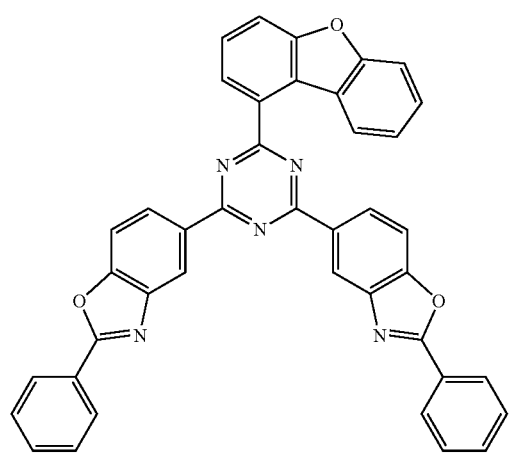

-continued
(119)
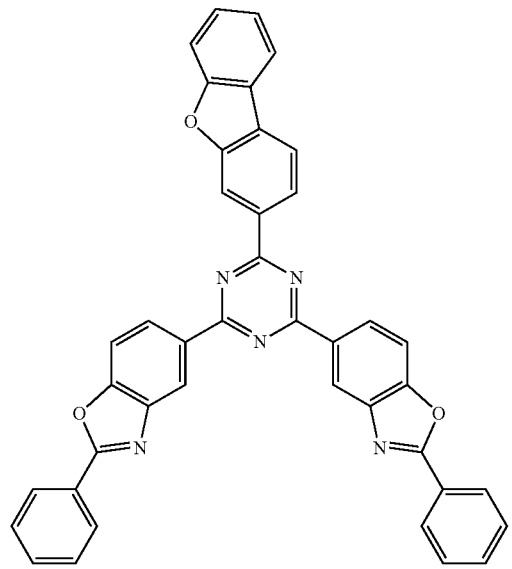
(120)
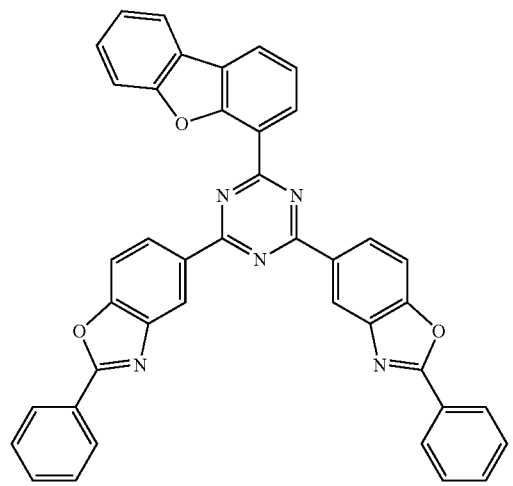
(121)
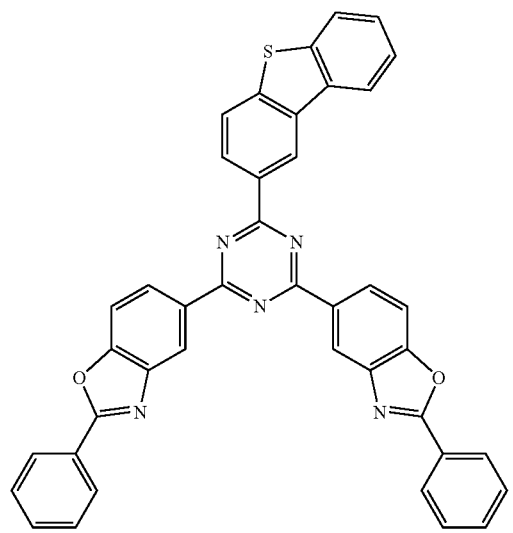

-continued
(122)
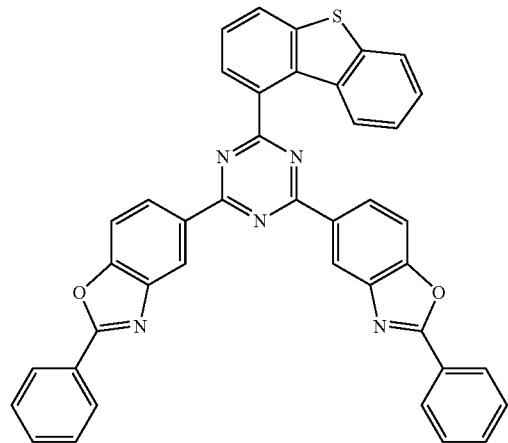
(123)
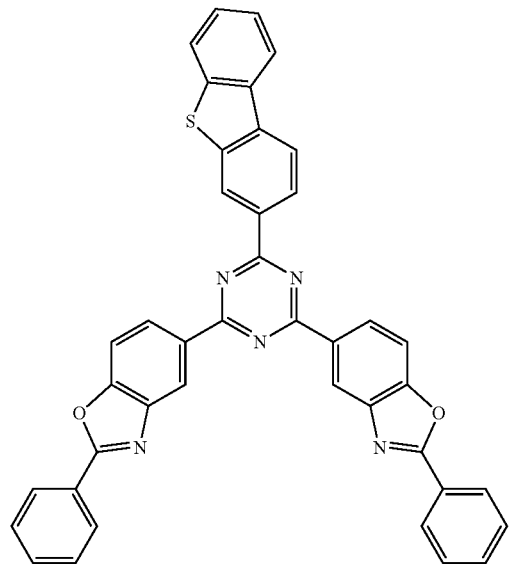
(124)
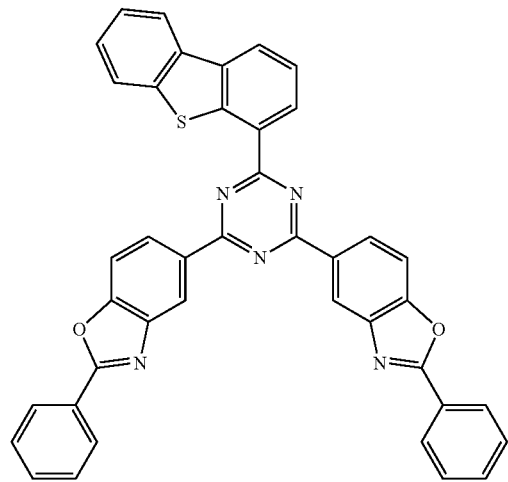

-continued
(125)
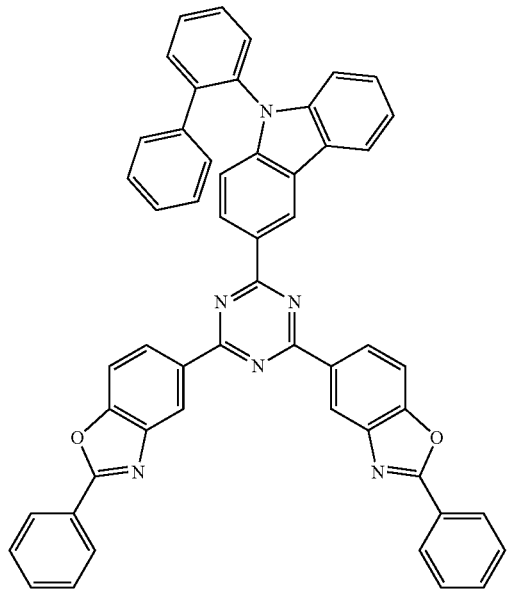
(129)
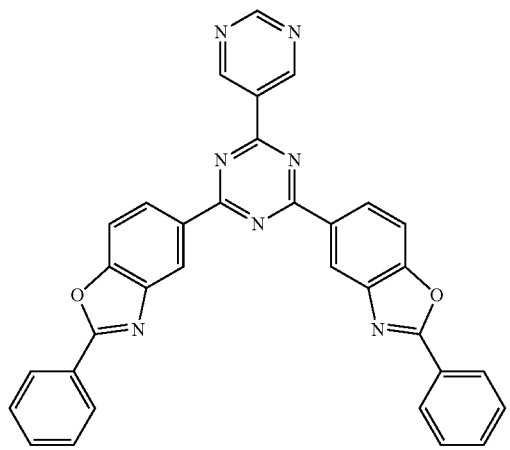
(130)
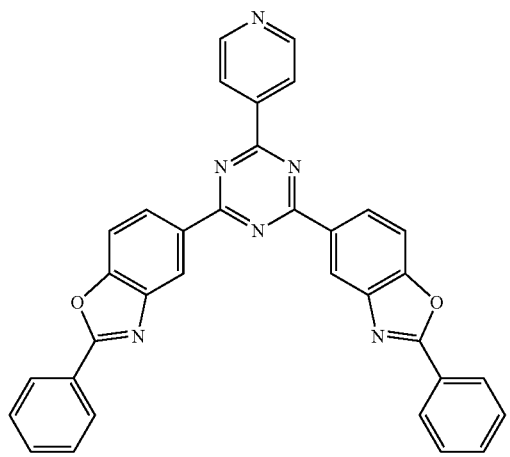

-continued
(131)
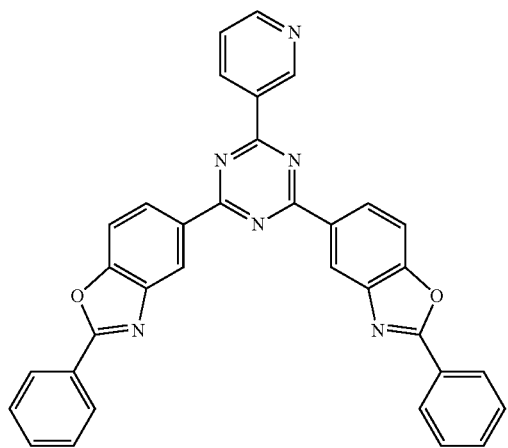
(132)
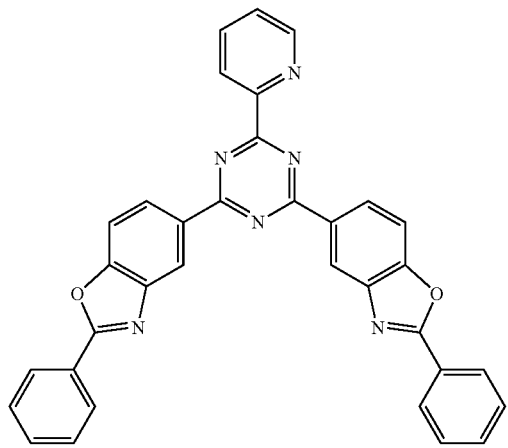
(135)
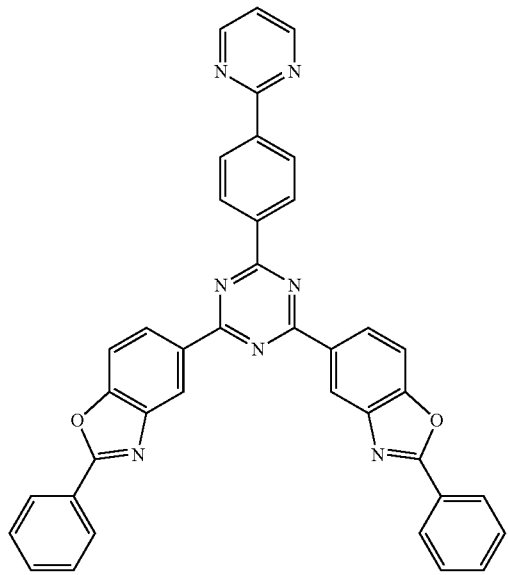

(137)
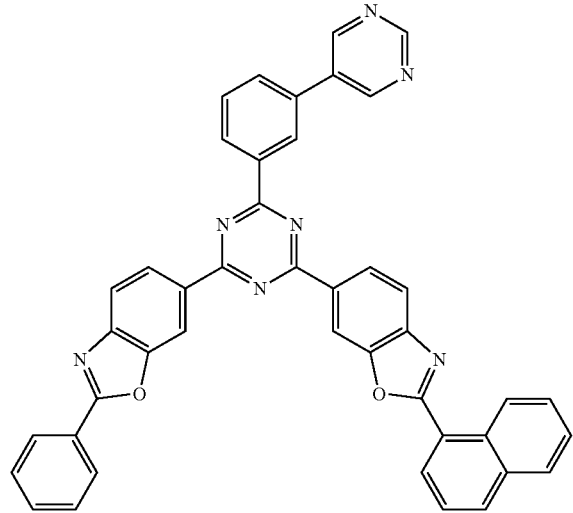
(138)
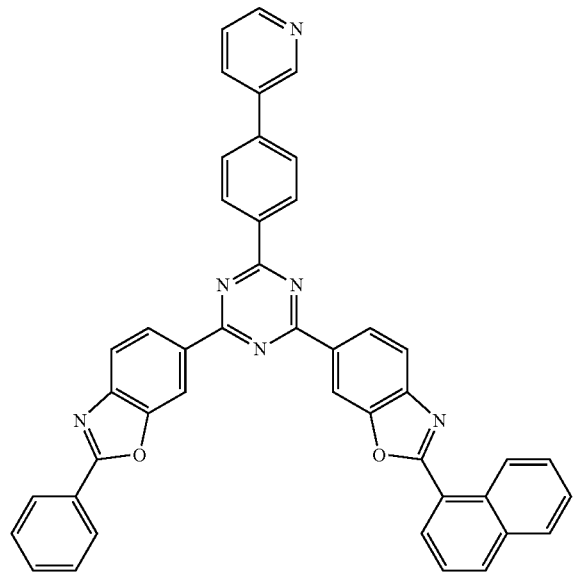

-continued
(139)
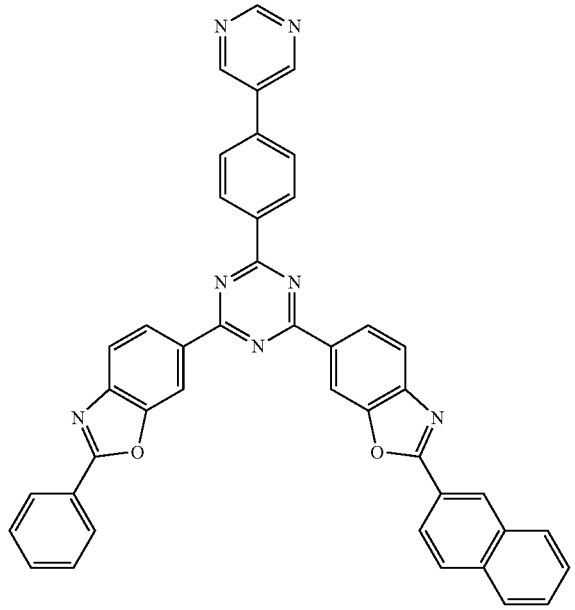
(140)
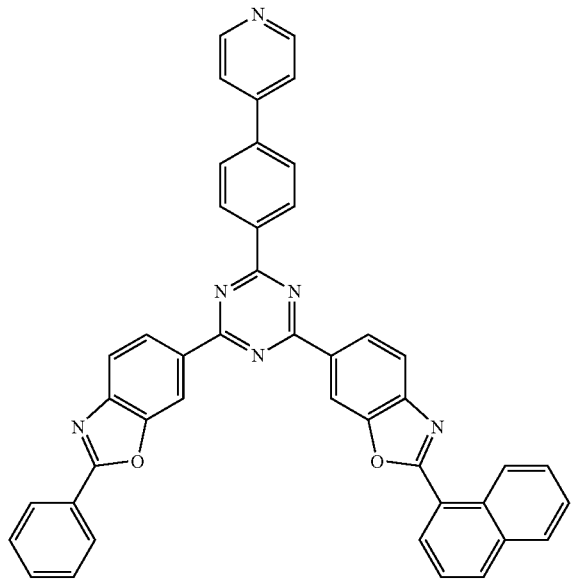

-continued
(141)
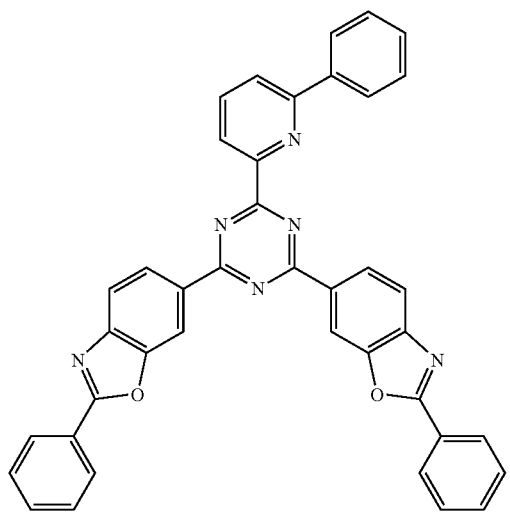
(142)
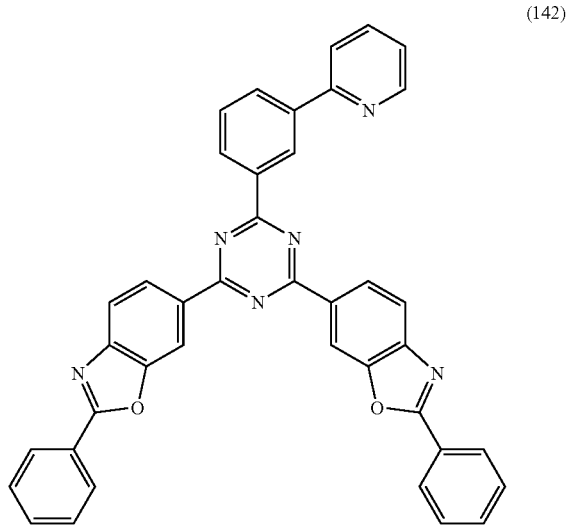
(143)
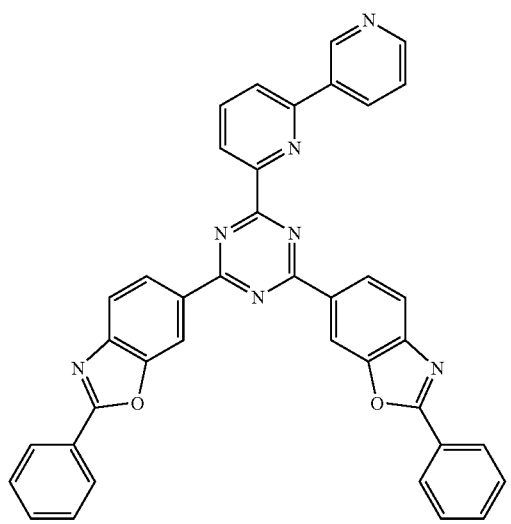

-continued
(144)
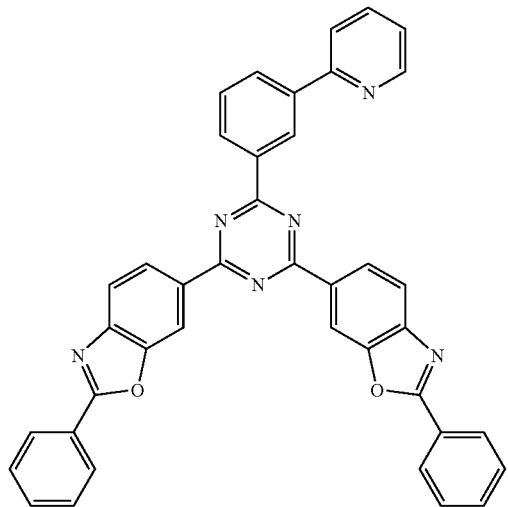
(148)
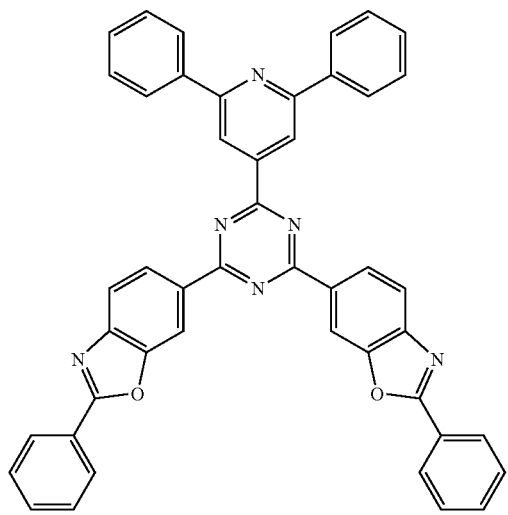
(149)
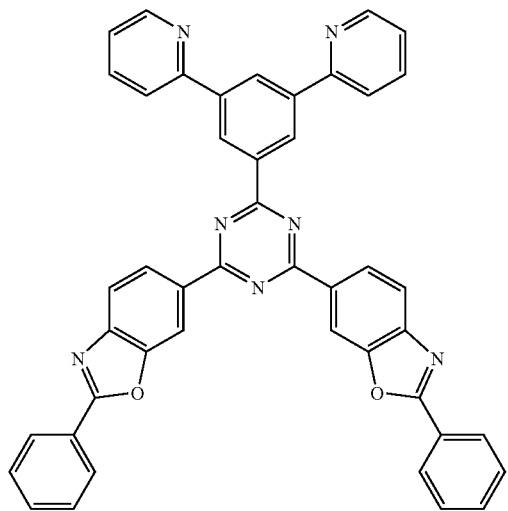

-continued
(150)
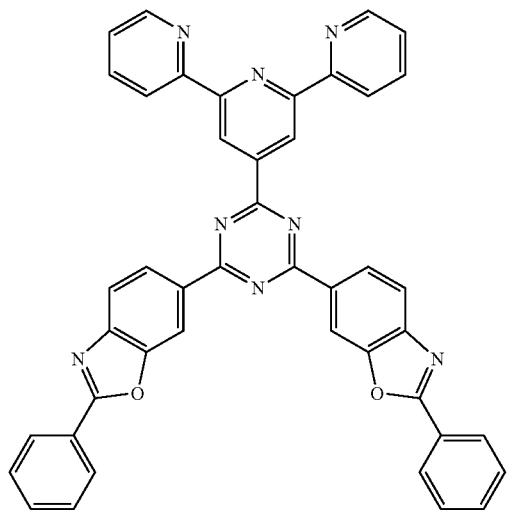
(151)
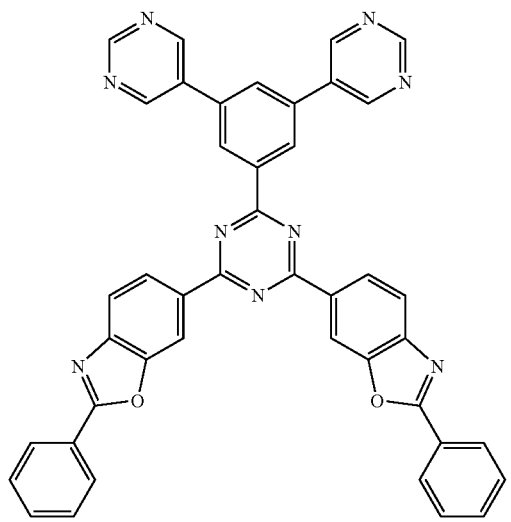
(152)
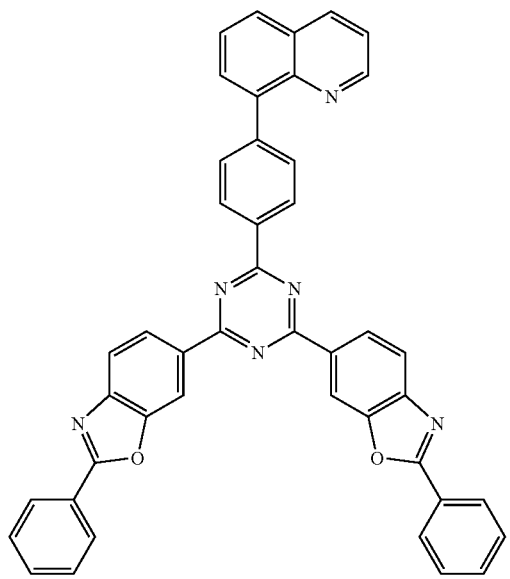

(153)
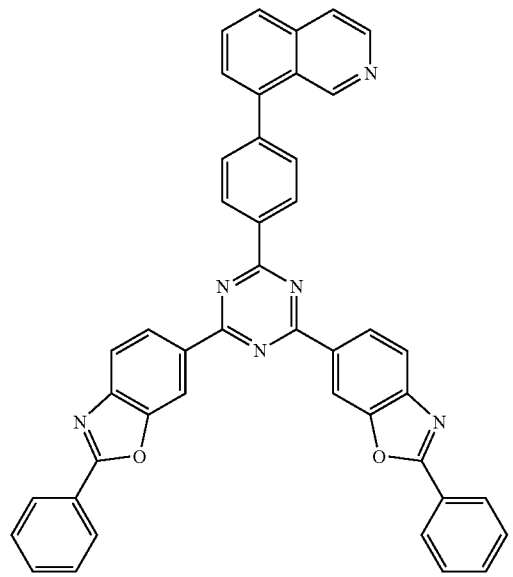
(154)
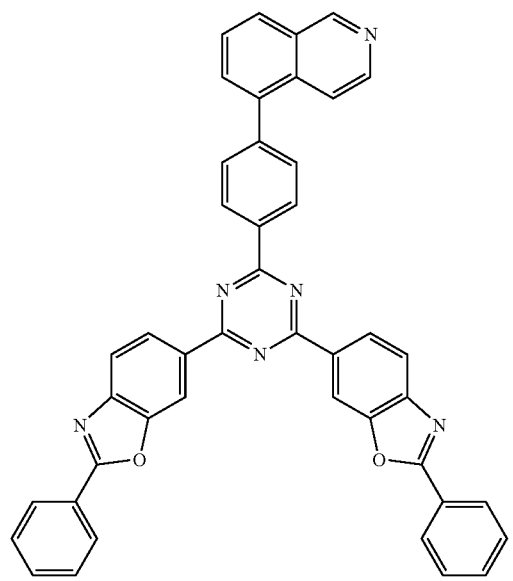

-continued
(155)
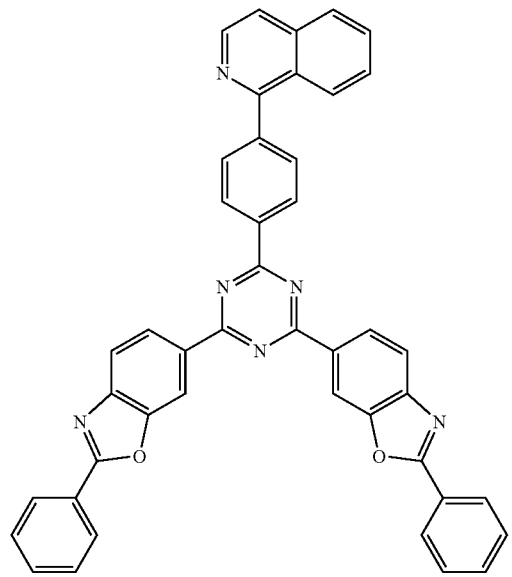
(156)
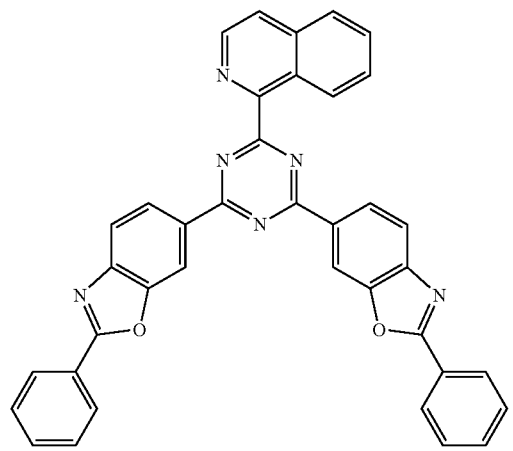
(157)
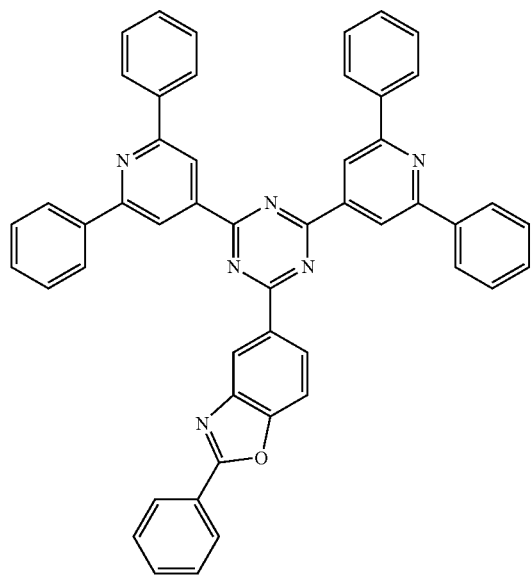

(158)
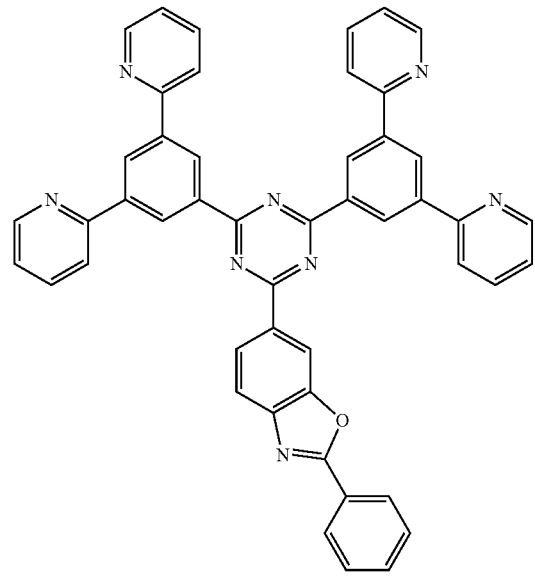
(159)
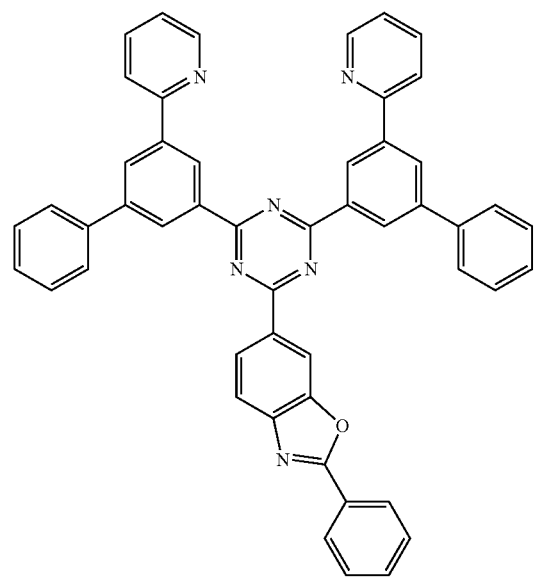

-continued
(160)
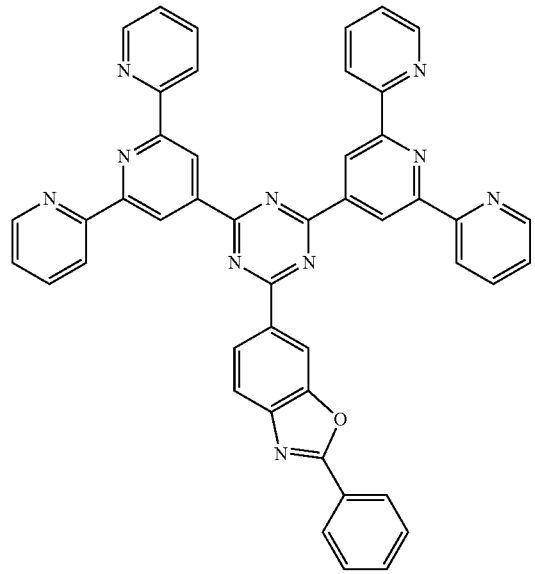
(161)
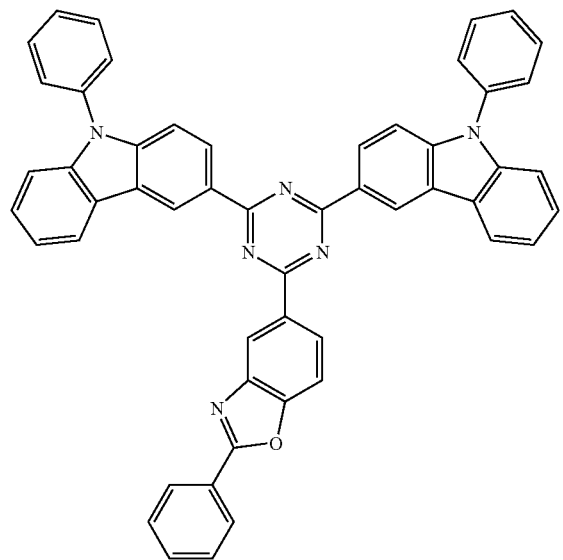
(162)
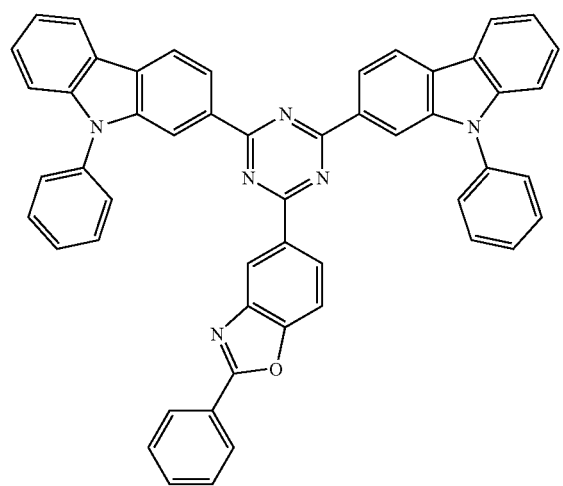

-continued
(163)
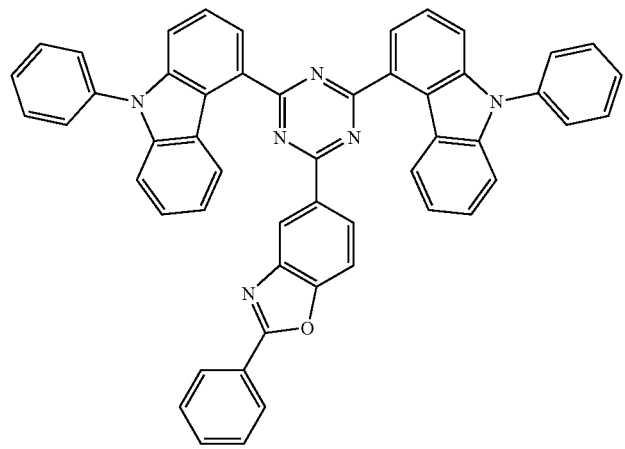
(164)
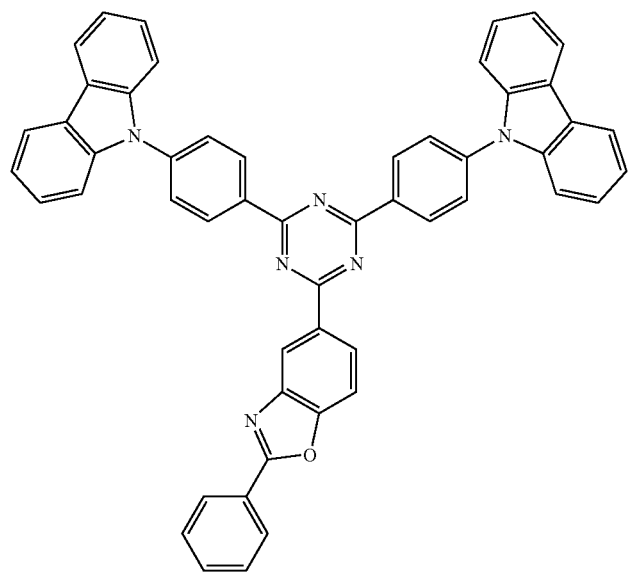
(165)
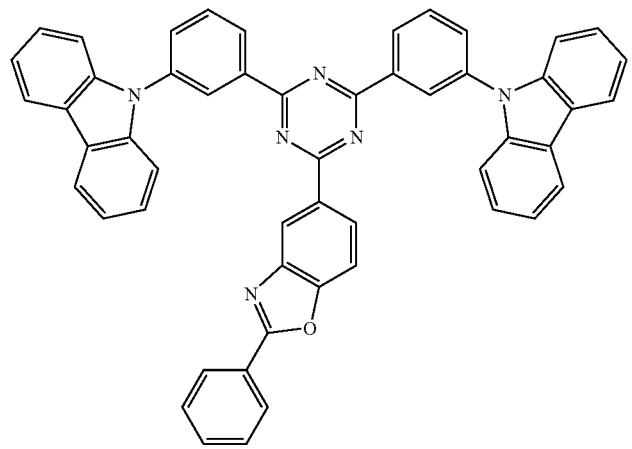

-continued
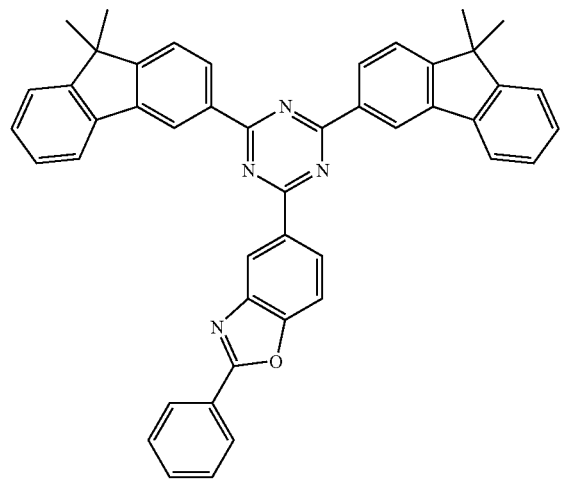
(166)
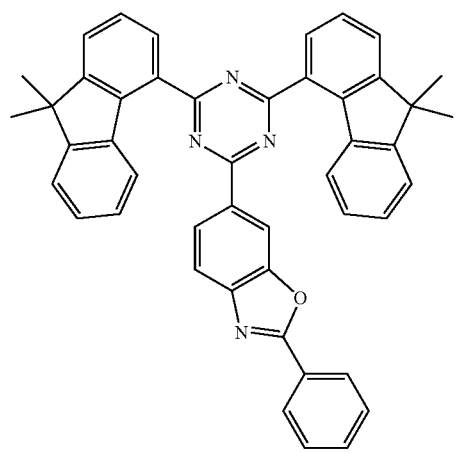
(167)
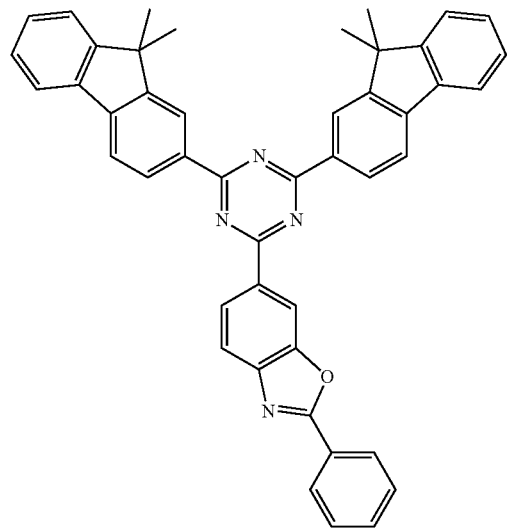
(168)

-continued
(169)
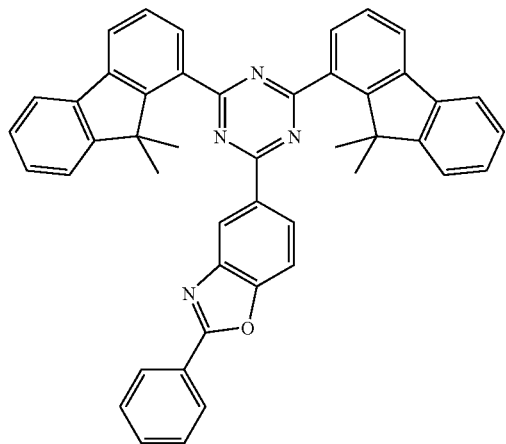
(170)
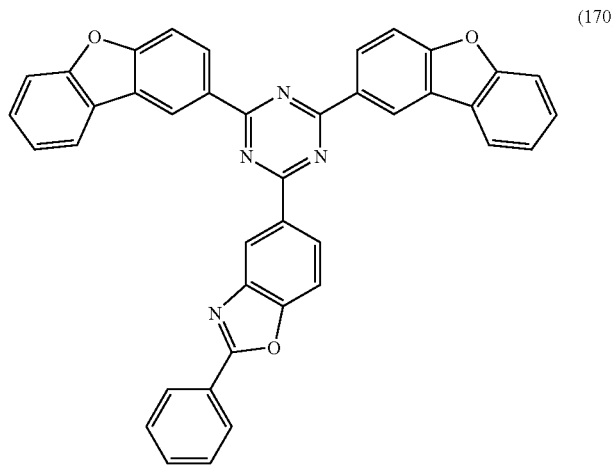
(171)
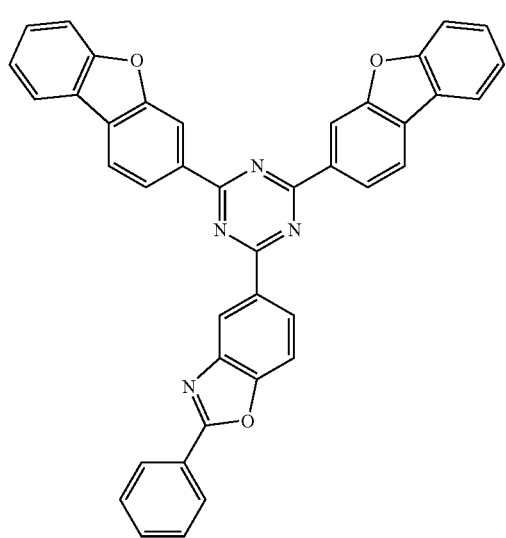

-continued
(172)
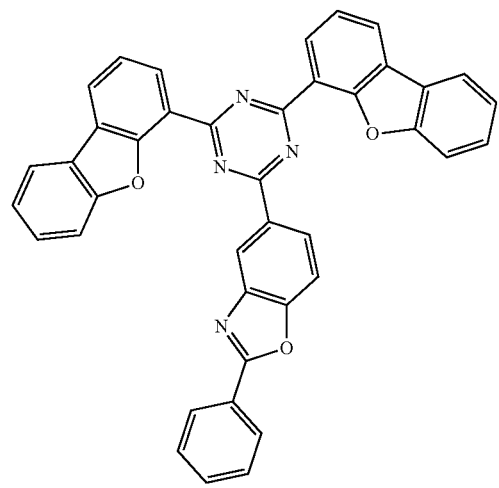
(173)
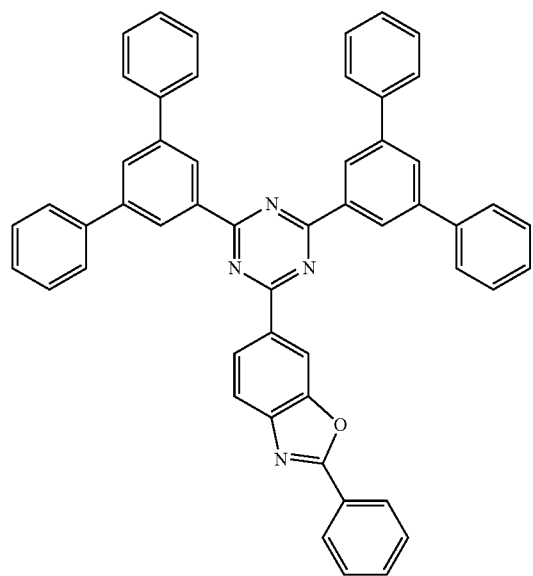
(174)
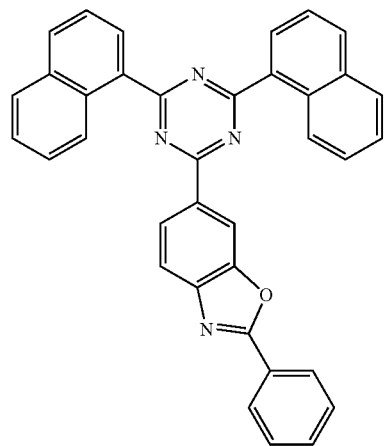

-continued
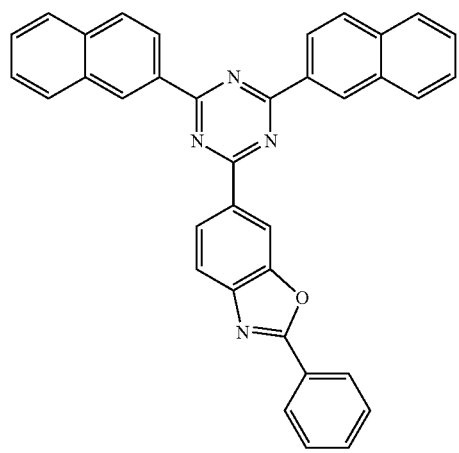
(175)
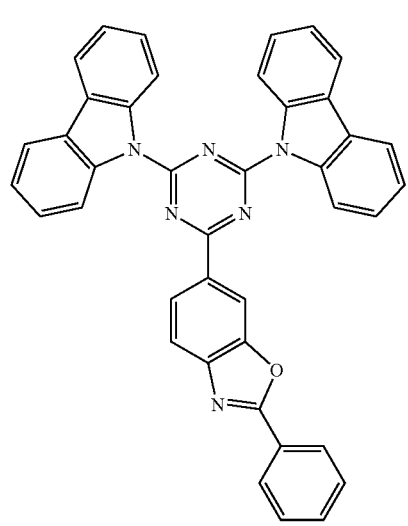
(176)
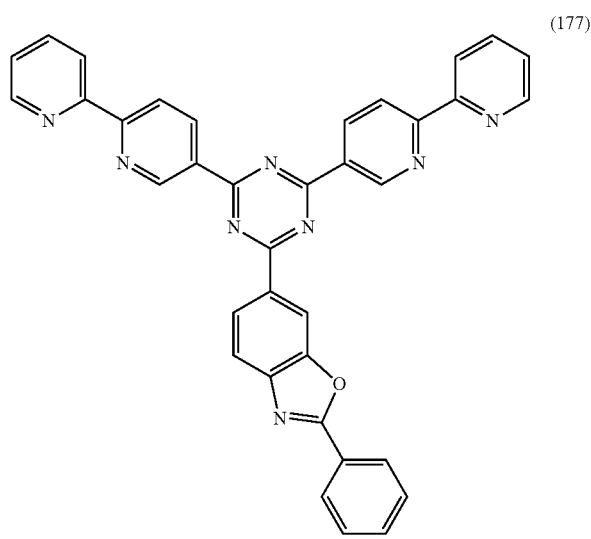
(177)

-continued
(178)
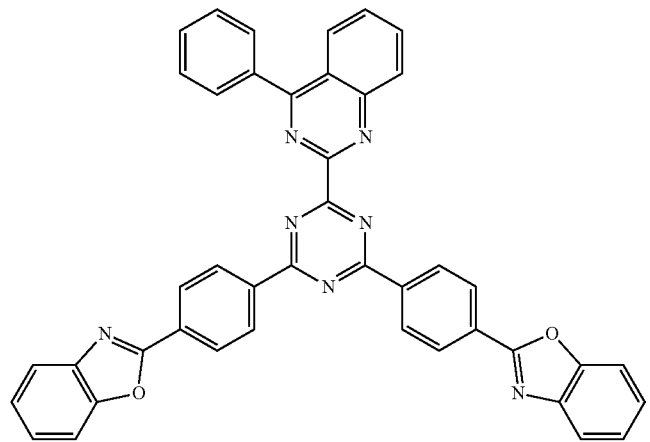
(179)
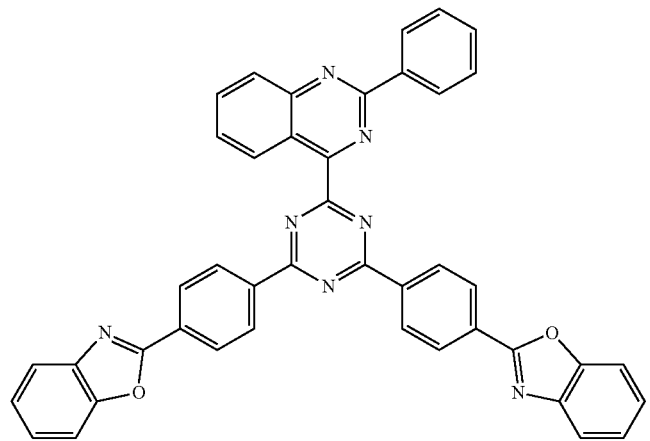
(180)
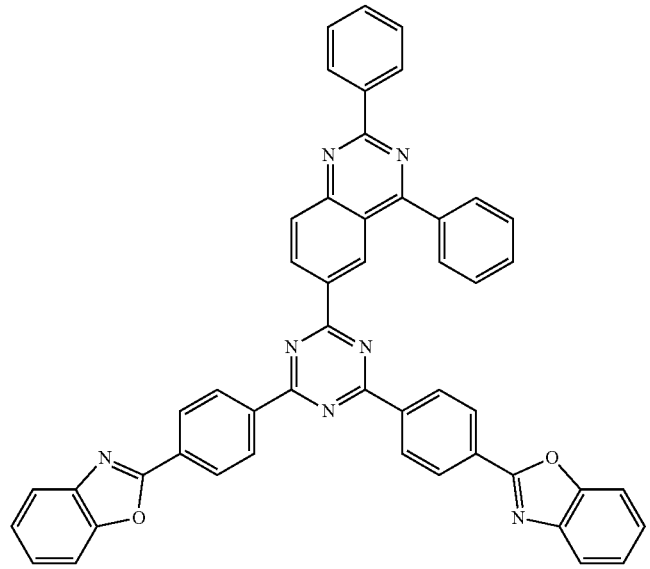

-continued
(181)
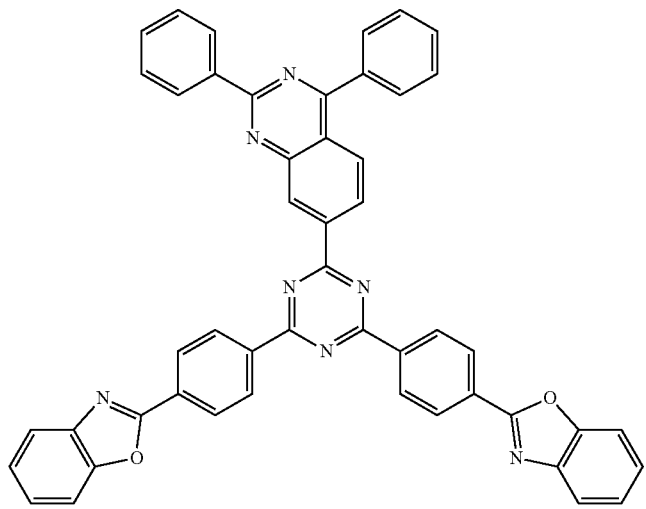
(182)
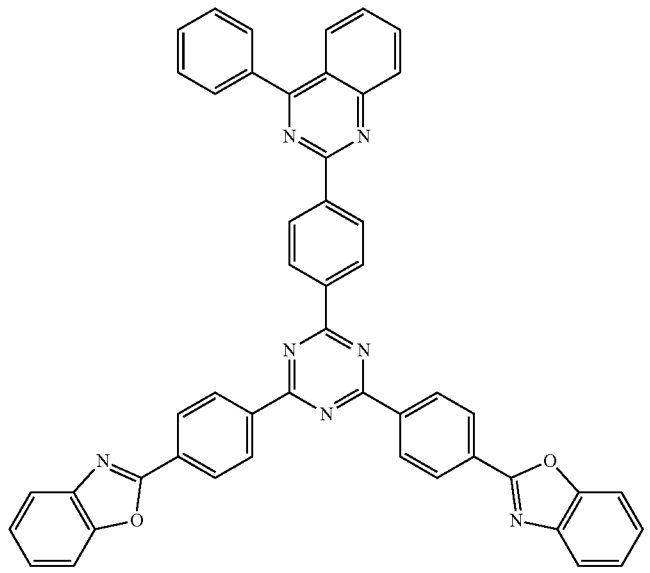
(183)
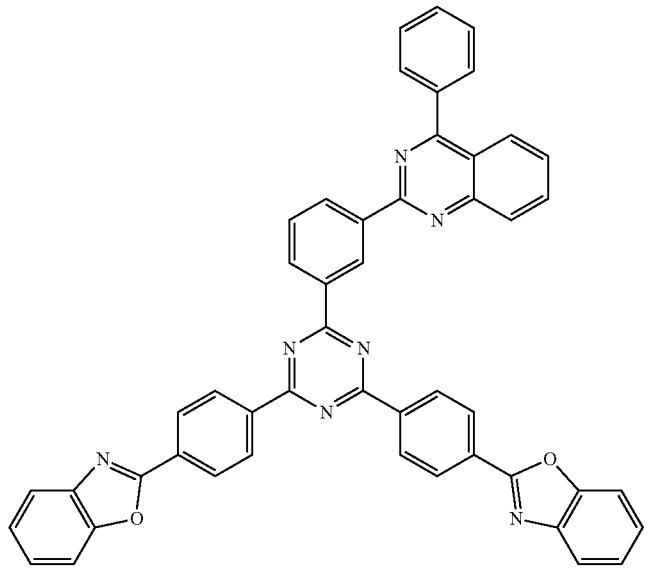

(184)
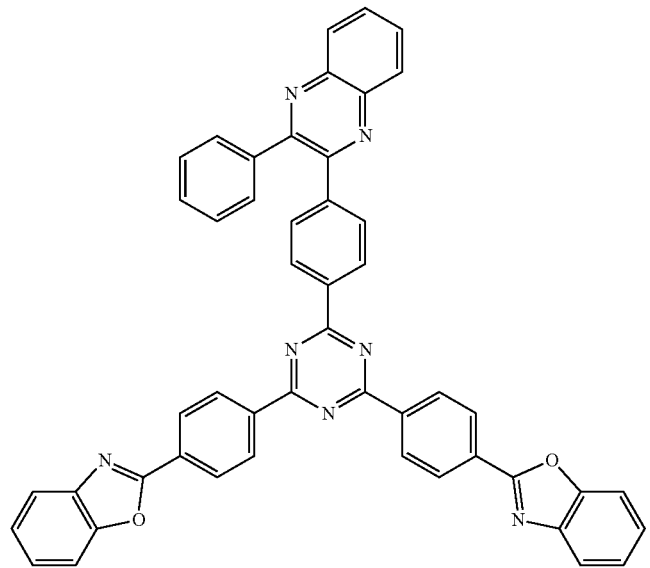
(185)
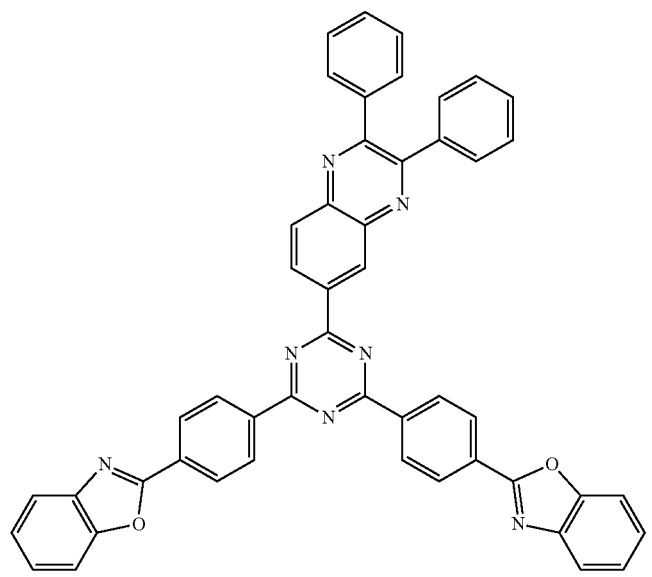
(186)
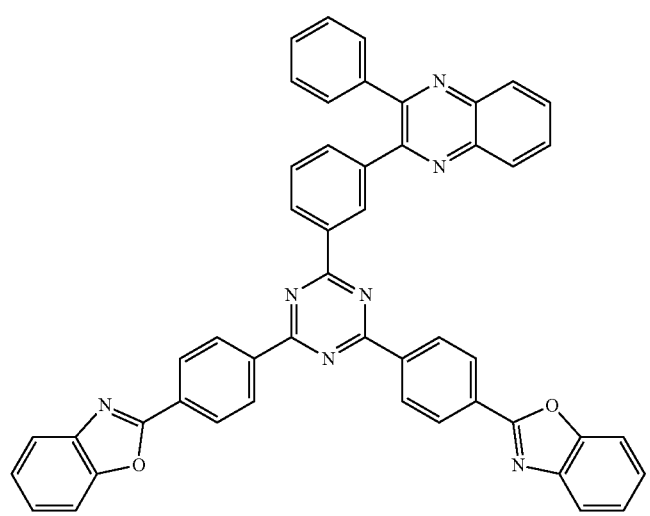

-continued
(187)
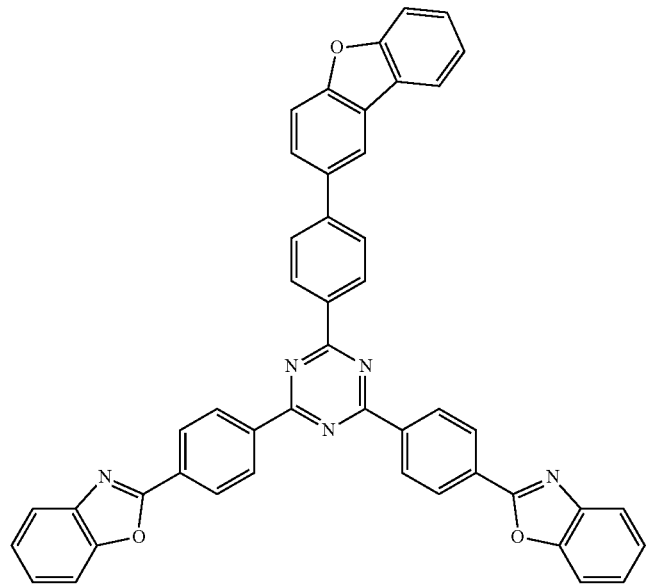
(188)
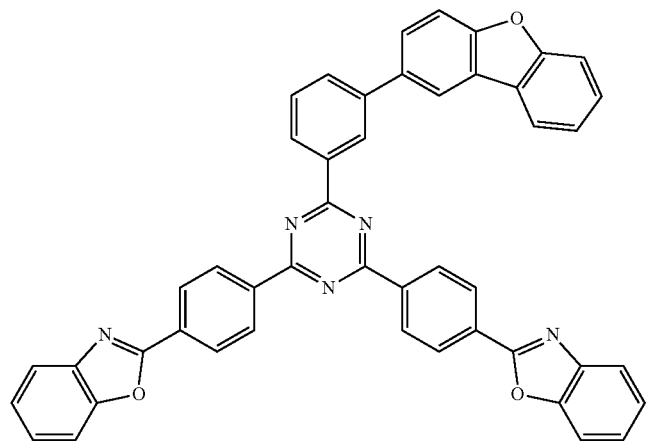
(189)
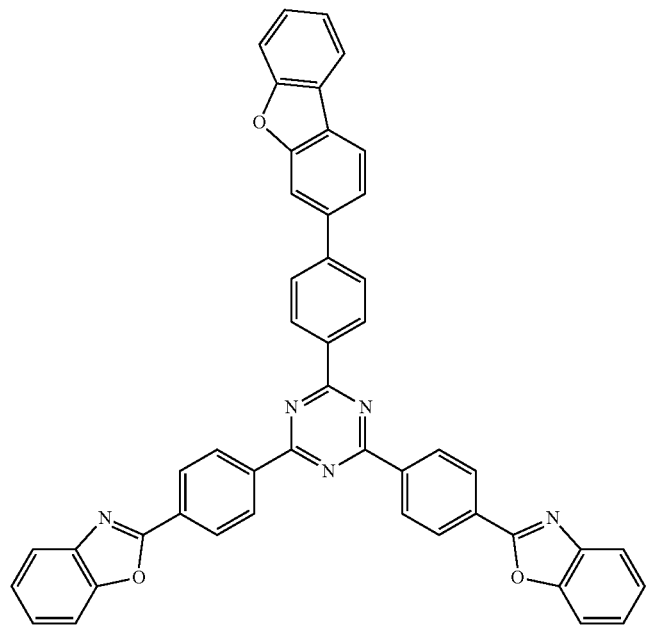

-continued
(190)
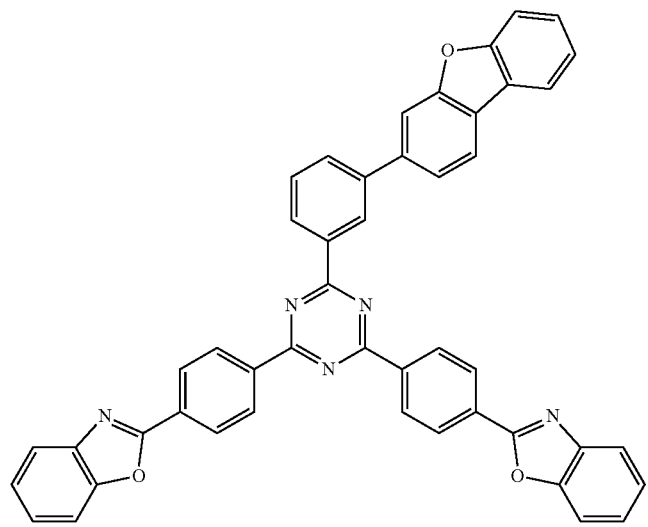
(191)
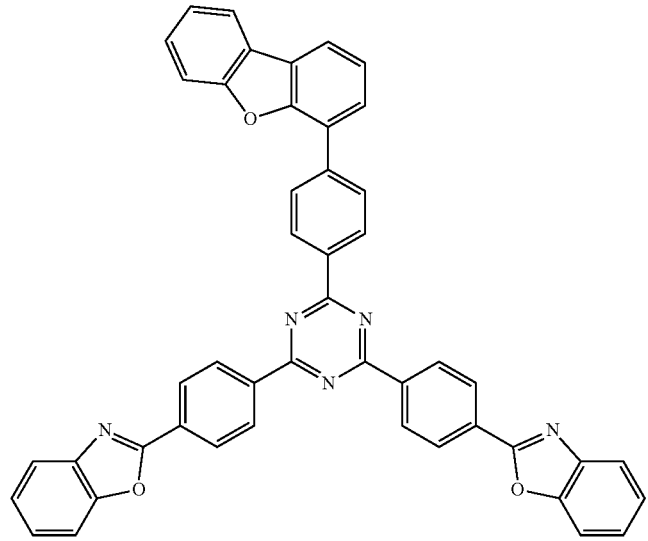
(192)
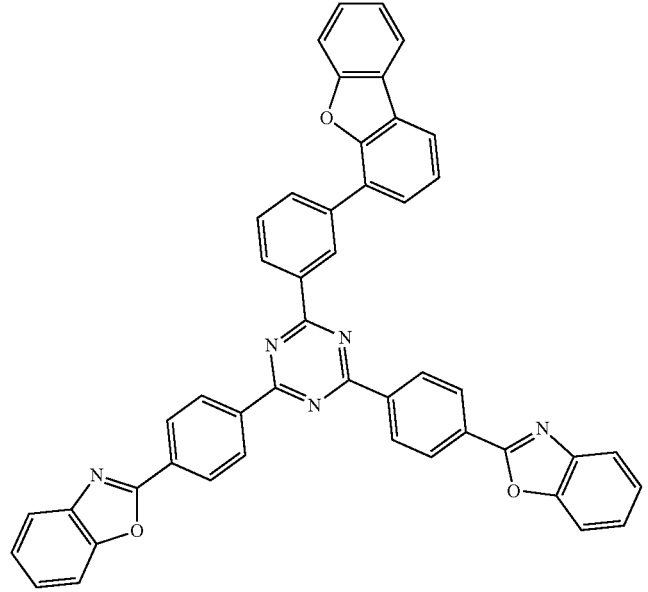

-continued
(193)
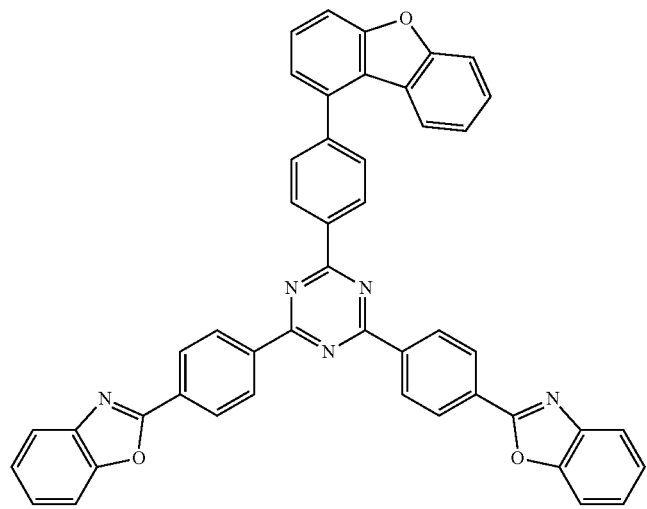
(194)
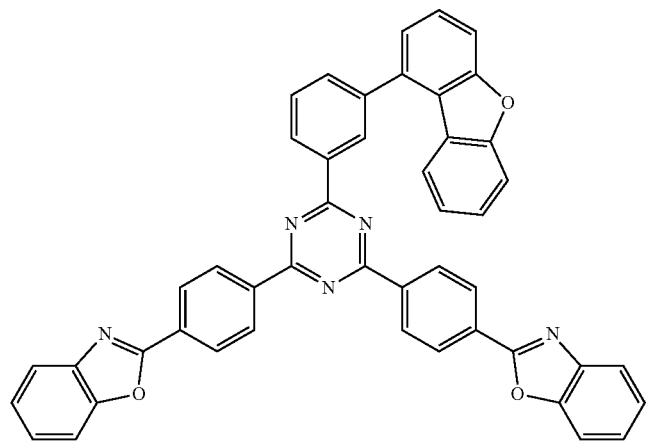
(195)
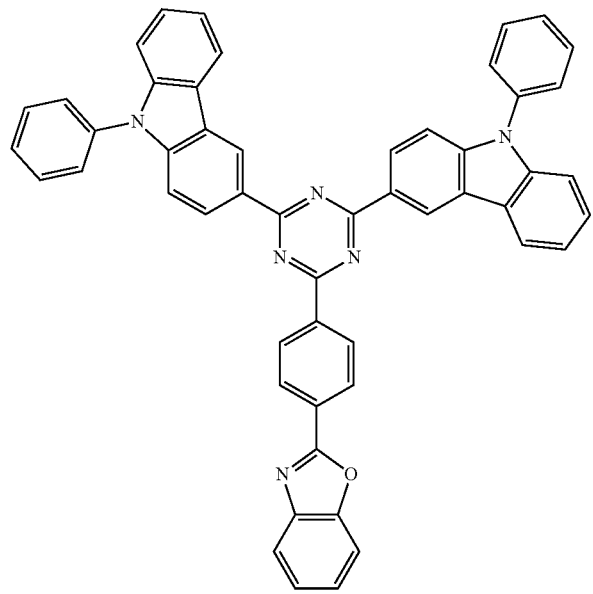

-continued
(196)
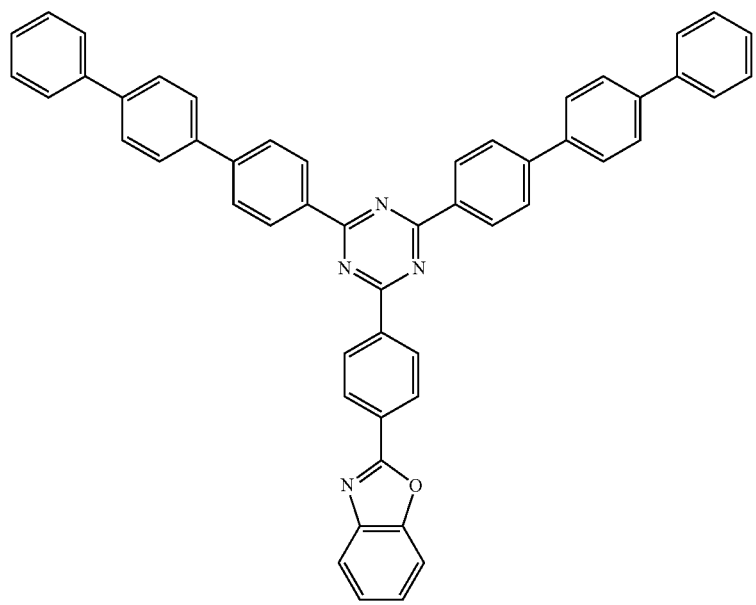
(197)
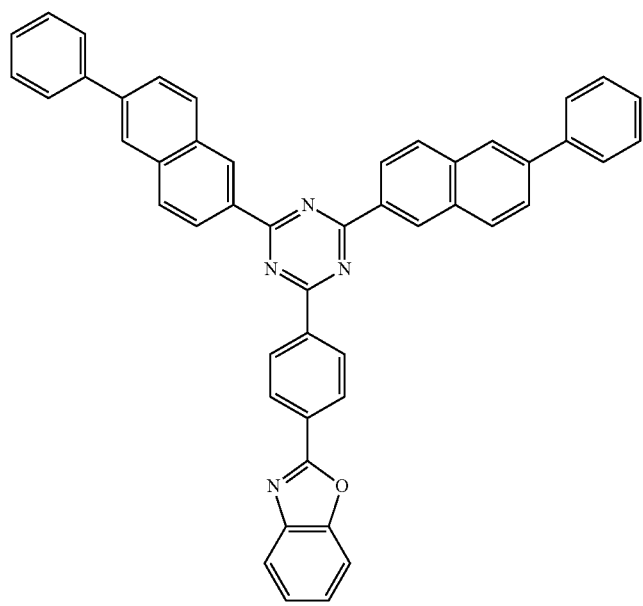
(198)
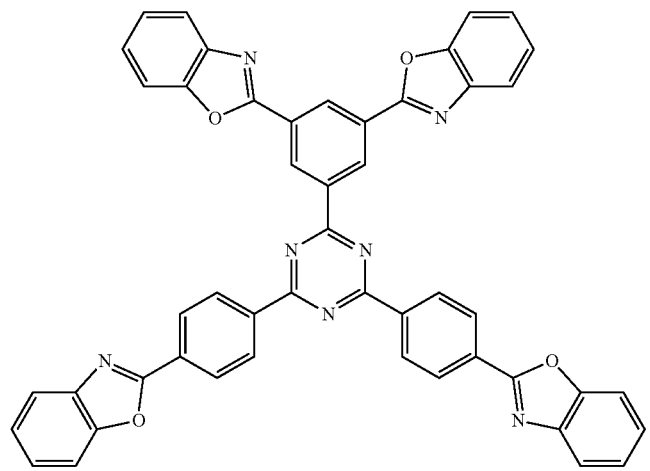

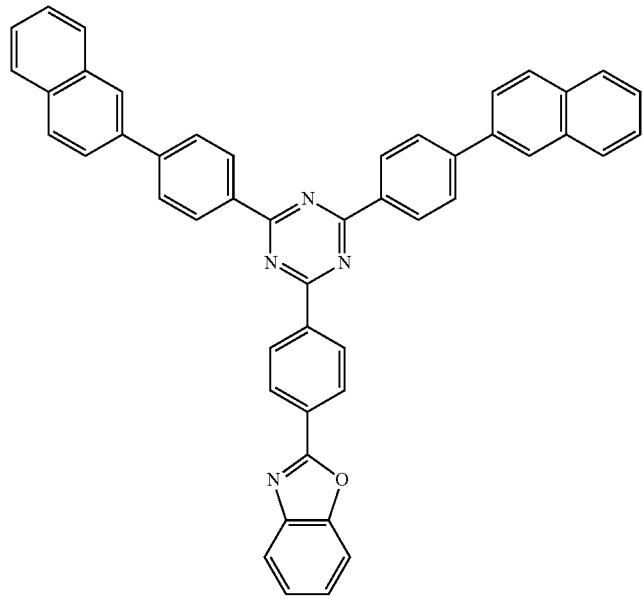
(199)
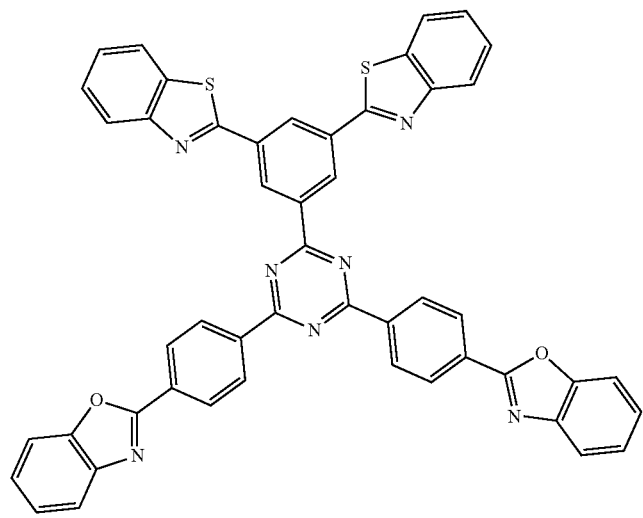
(200)
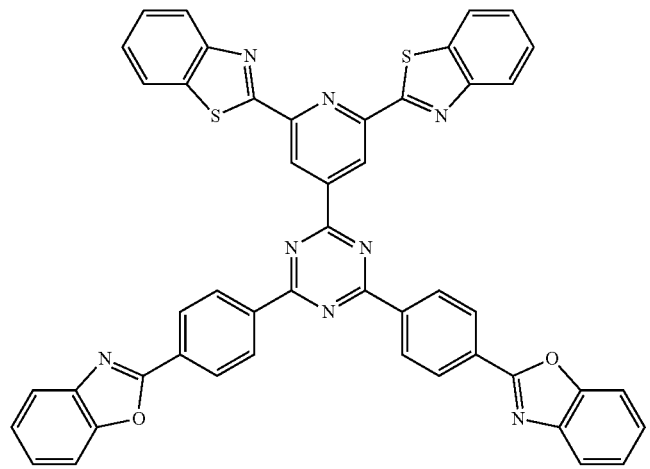
(201)

-continued
(202)
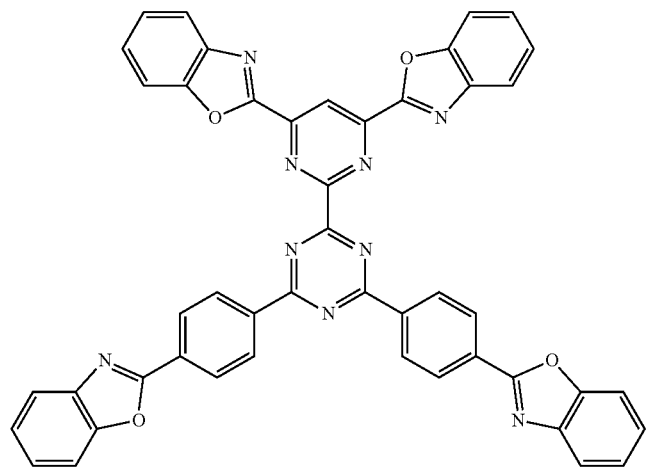
(203)
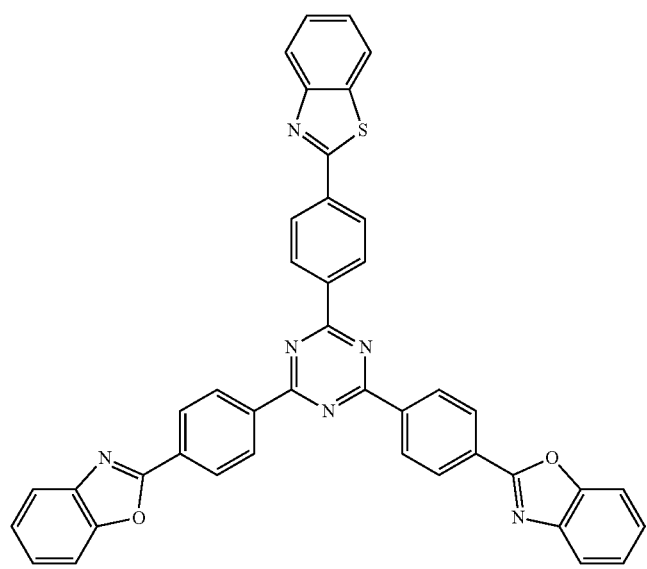
(204)
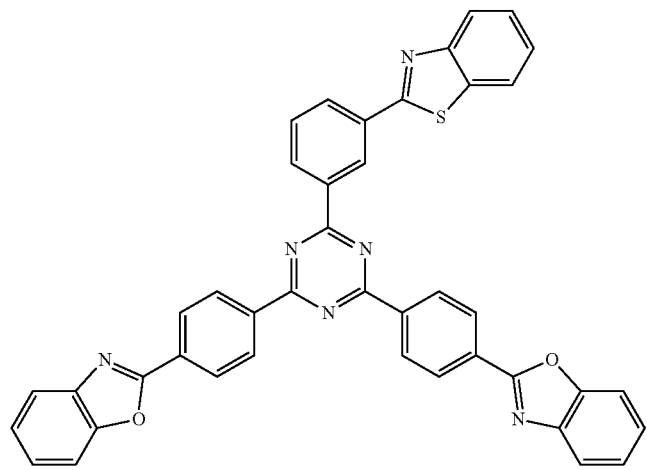

-continued
(205)
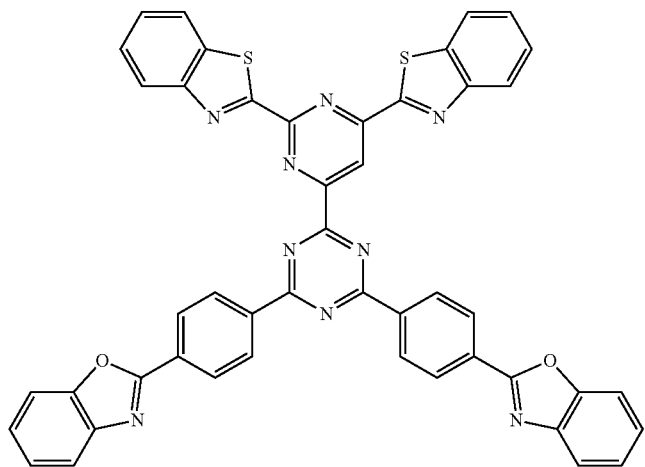
(206)
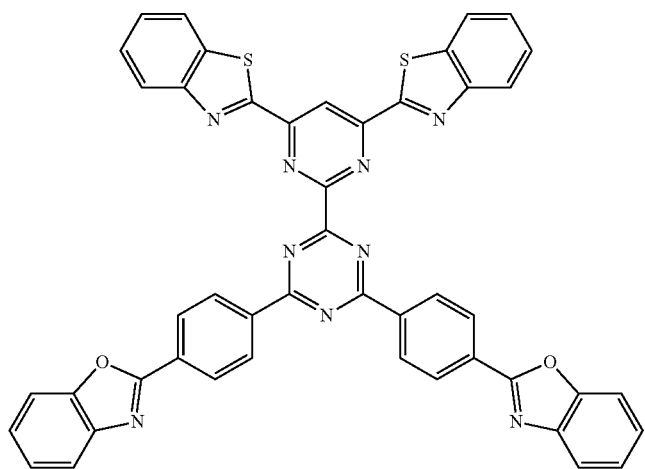
(207)
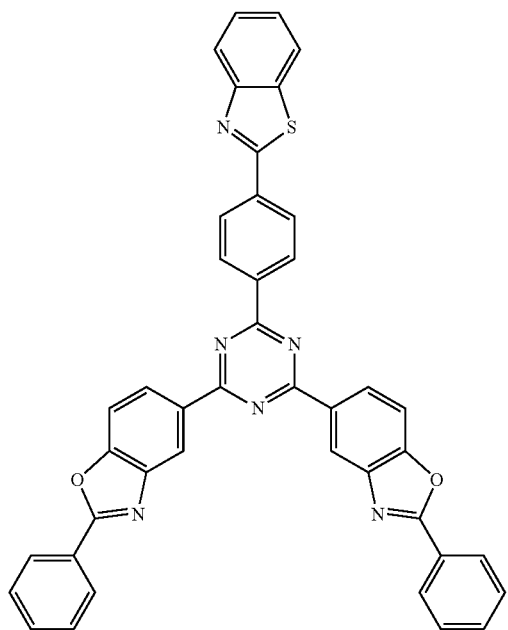

-continued
(208)
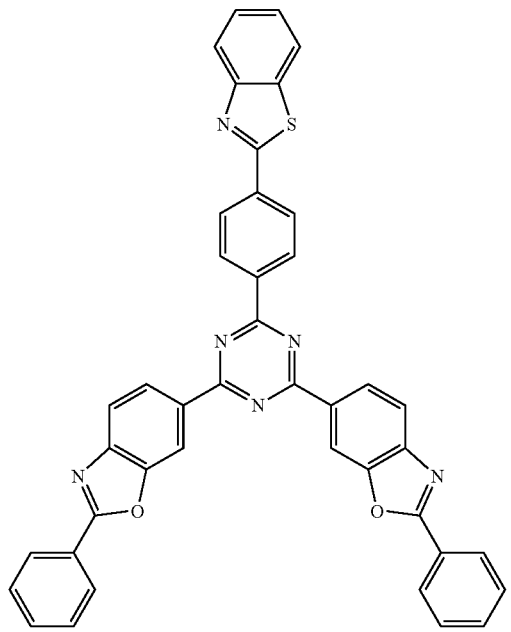
(209)
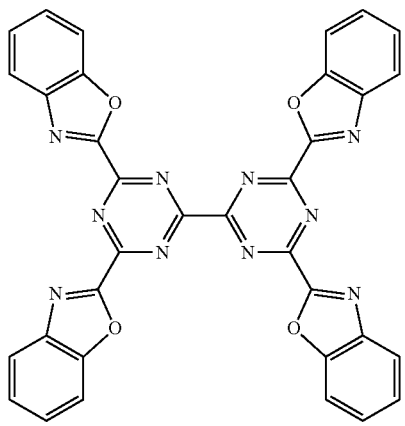
(210)
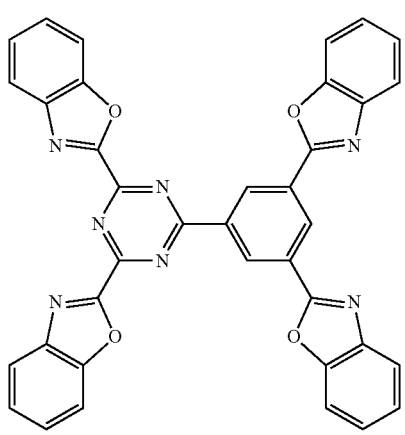

-continued
(211)
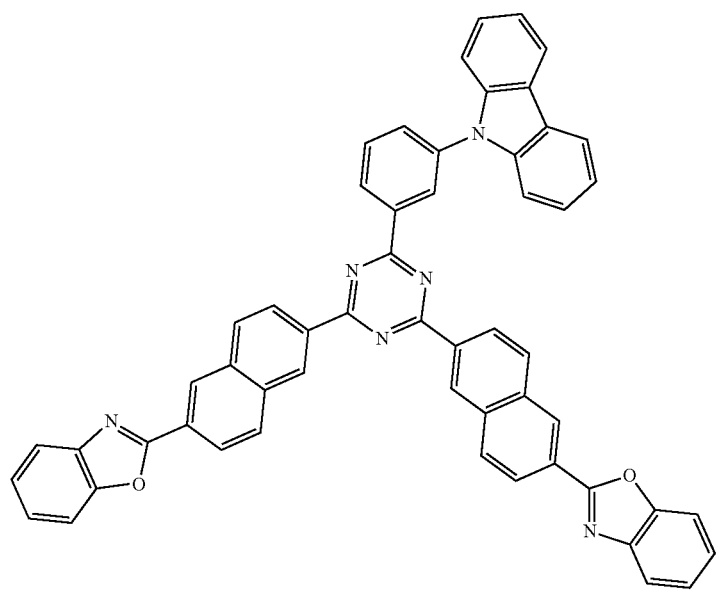
(212)
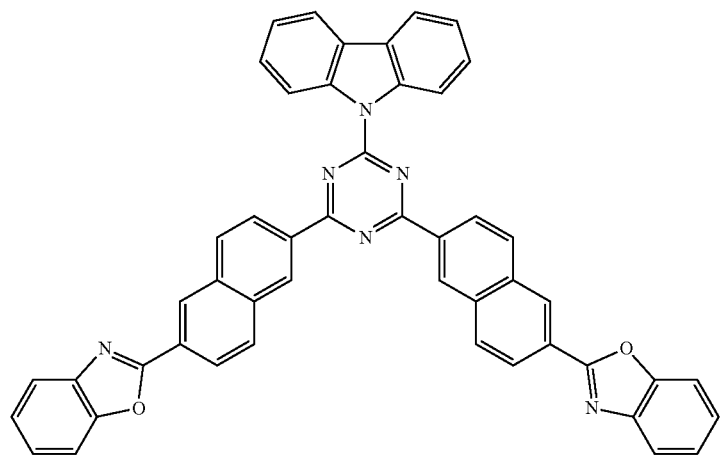
(213)
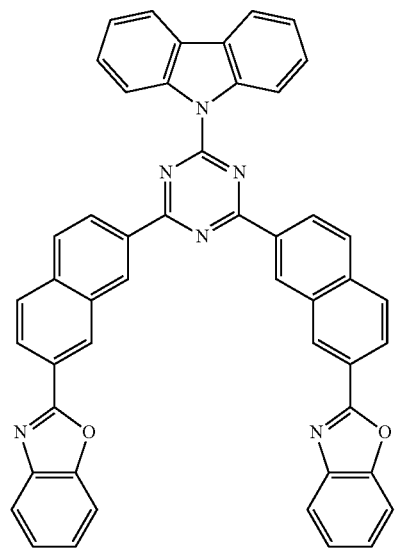

-continued
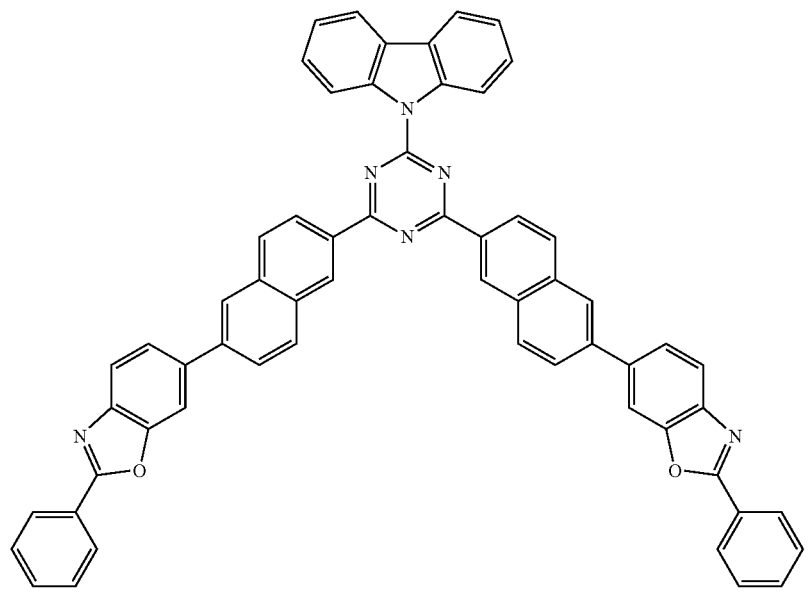
(214)
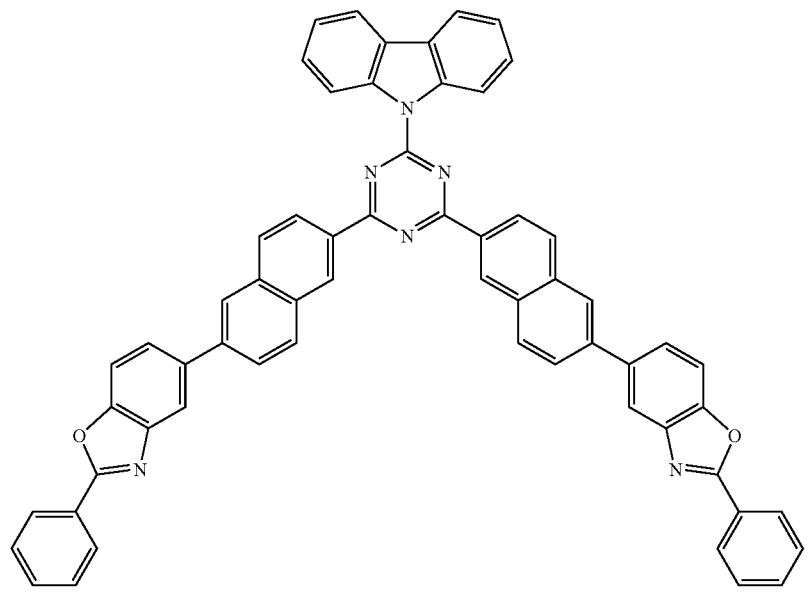
(215)

-continued
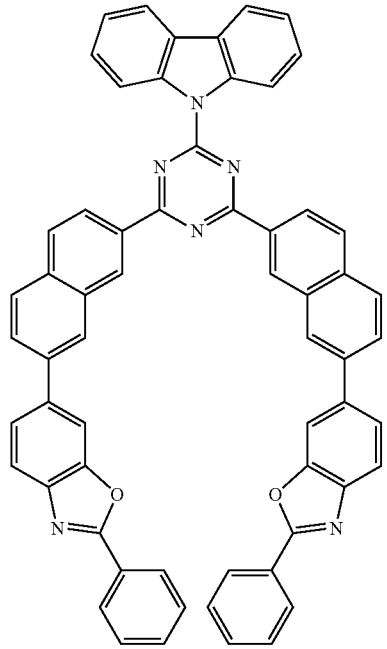
(216)
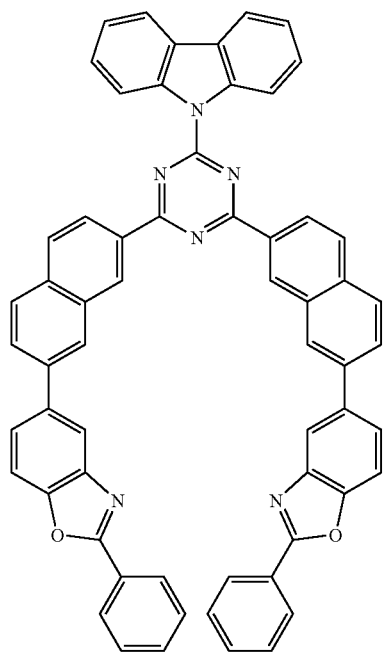
(217)

(218)
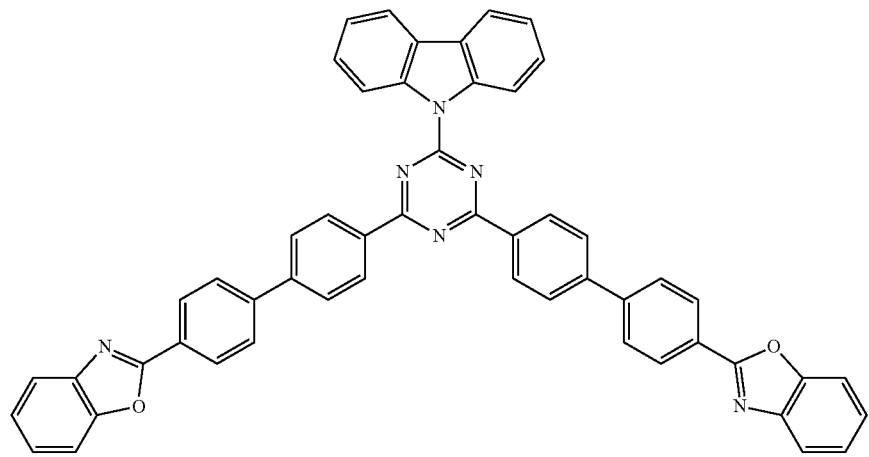
(219)
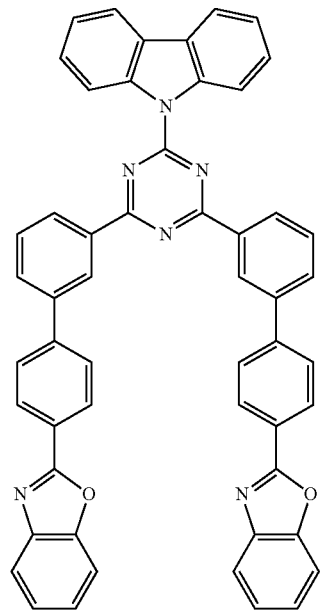
(220)
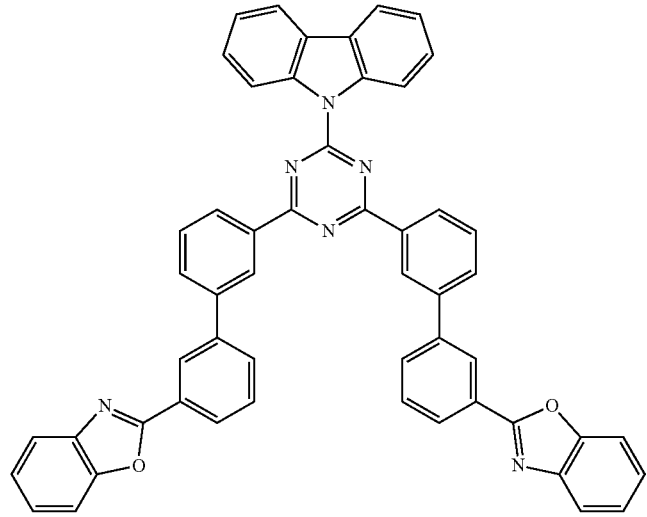

-continued
(221)
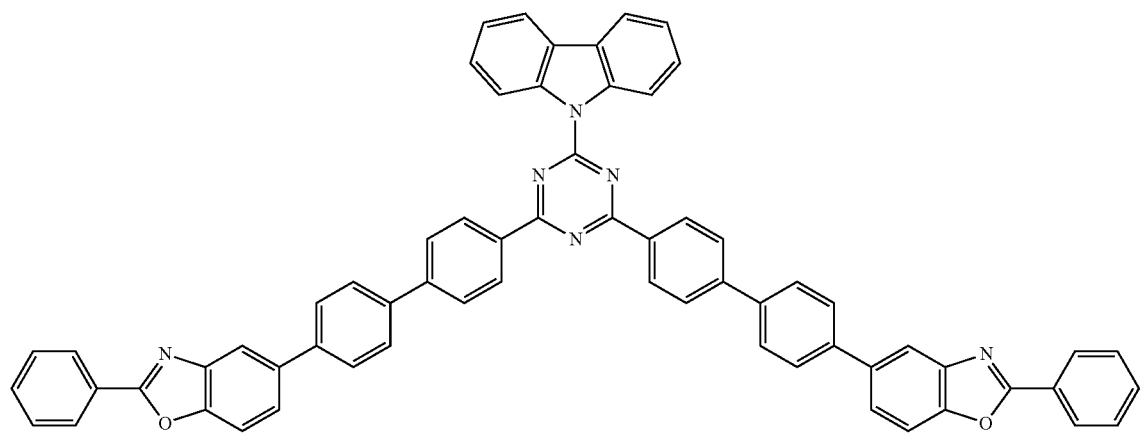
(222)
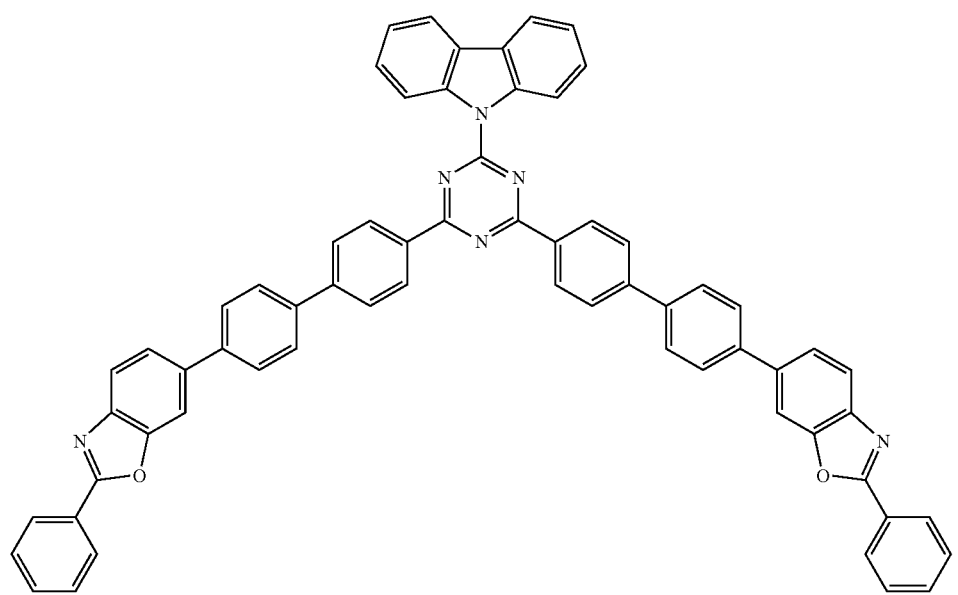
(223)
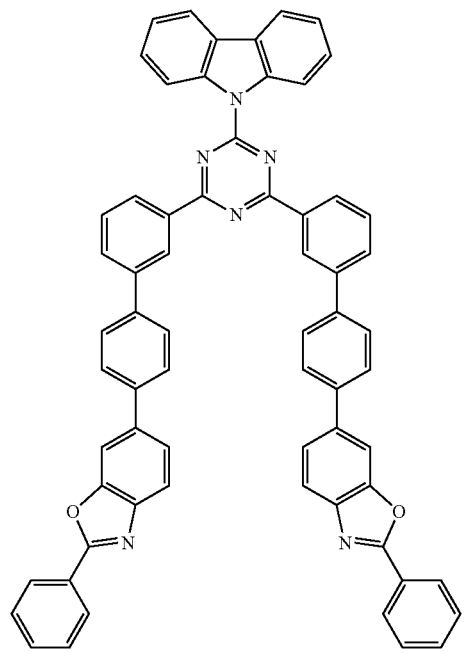

(224)
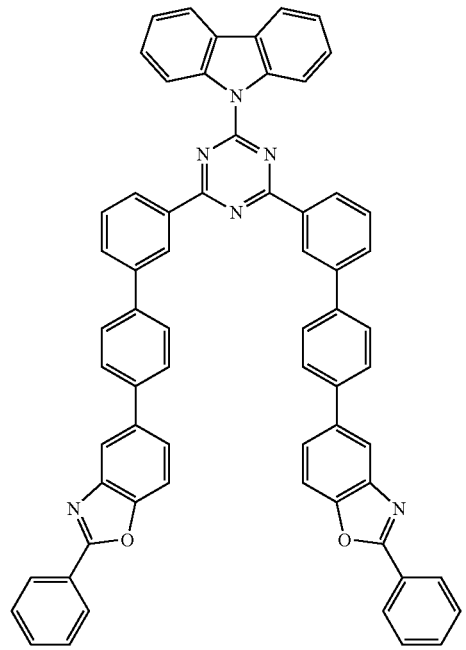
(225)
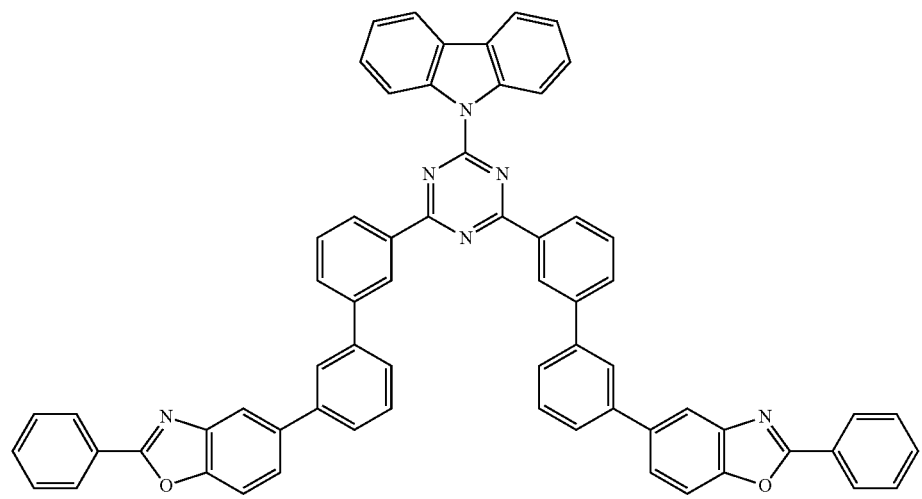

(226)
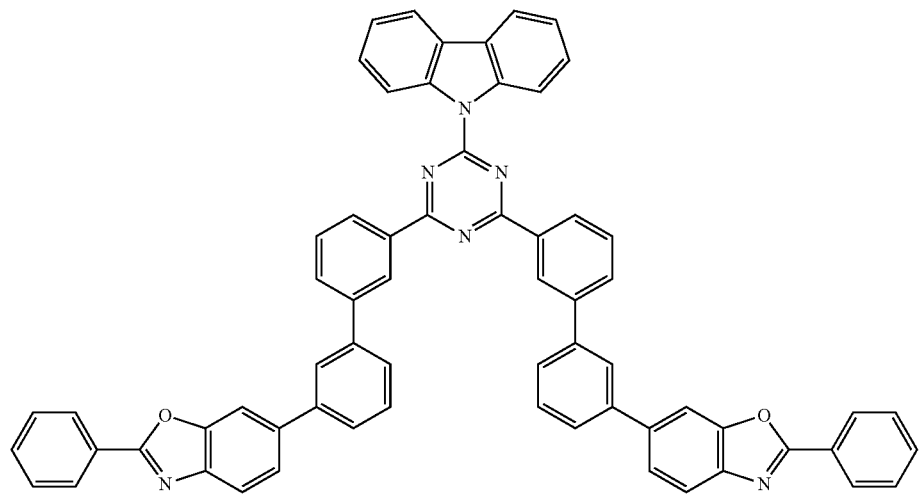
(227)
(228)
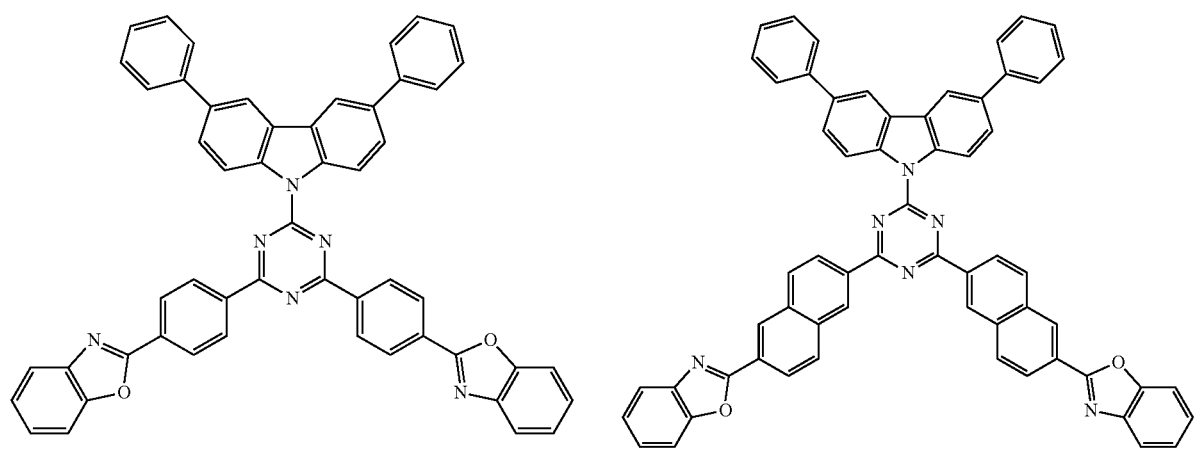
(229)
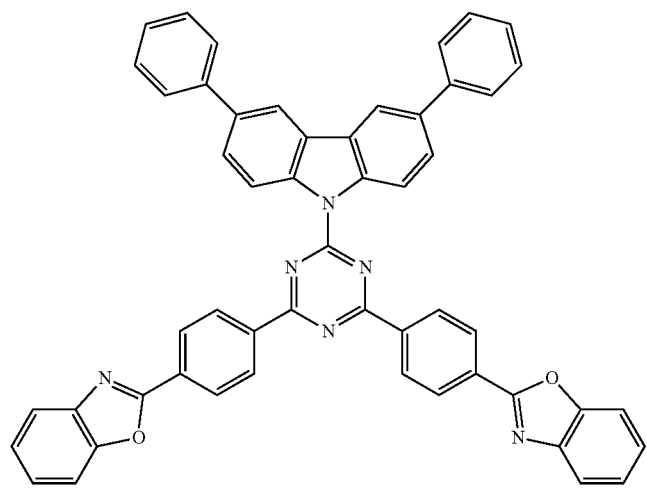

-continued
(230)
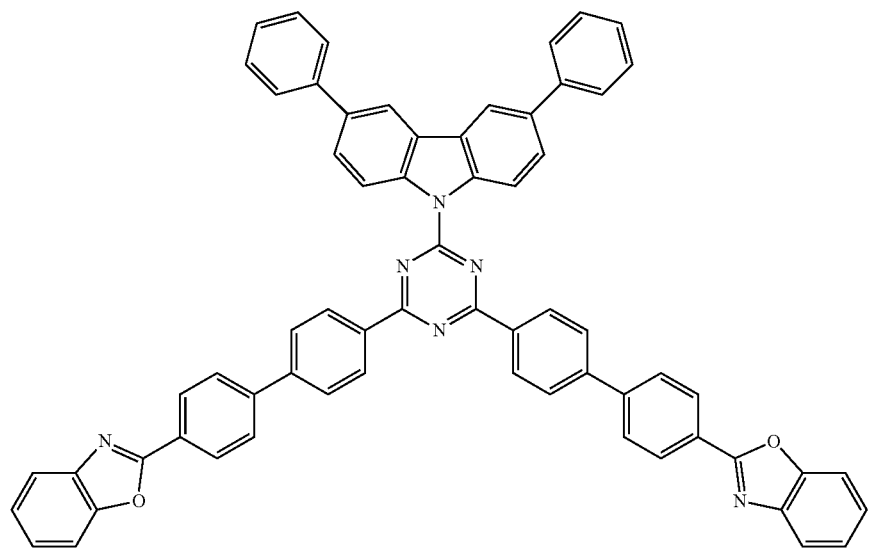
(231) (232)
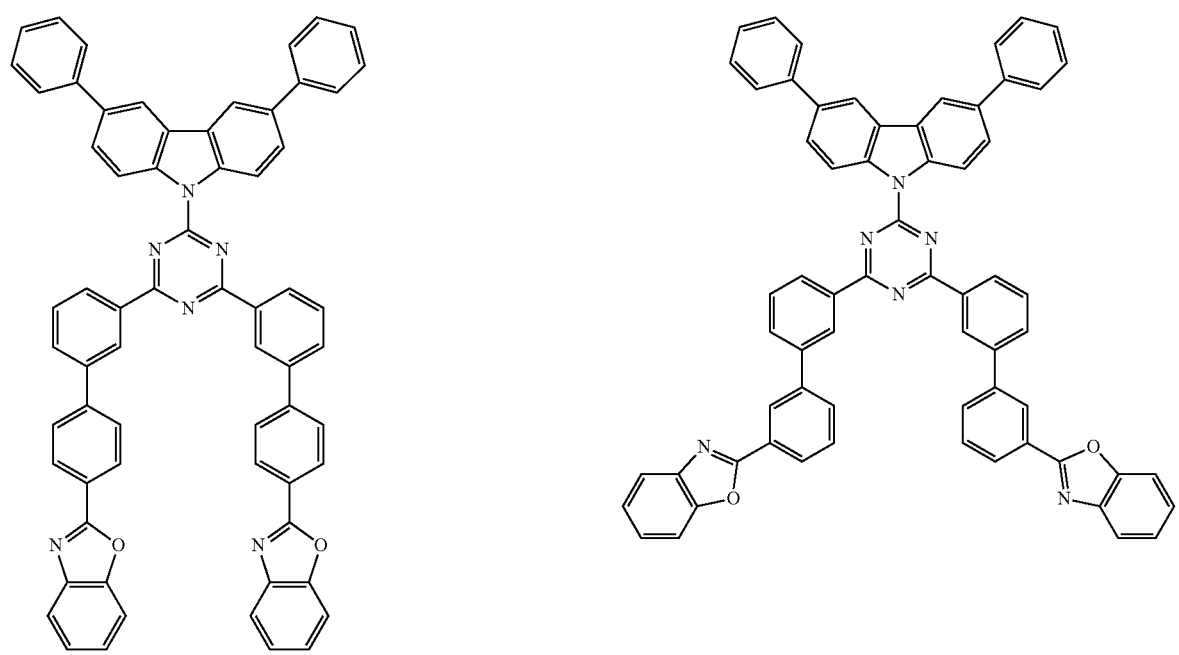
(233) (234)
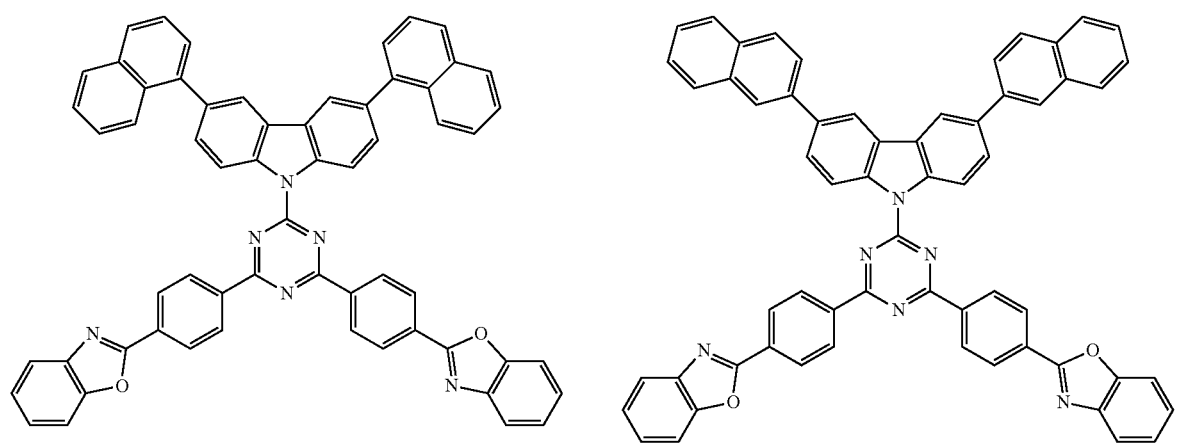

(235)
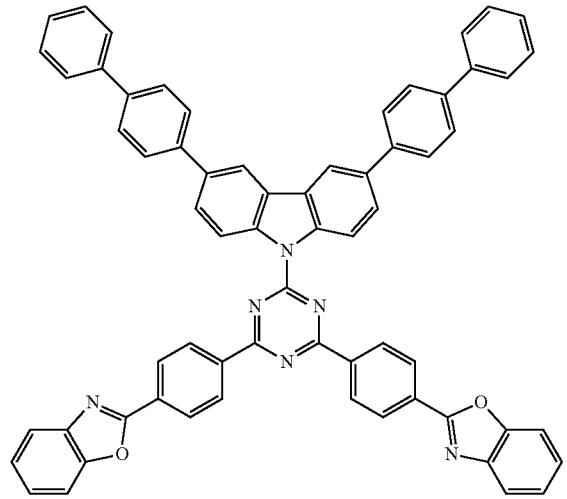
(236)
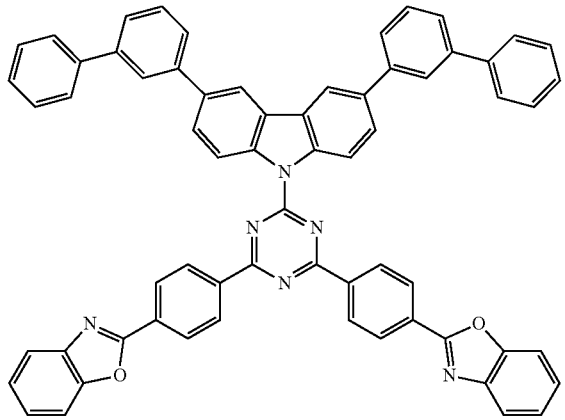
(237)
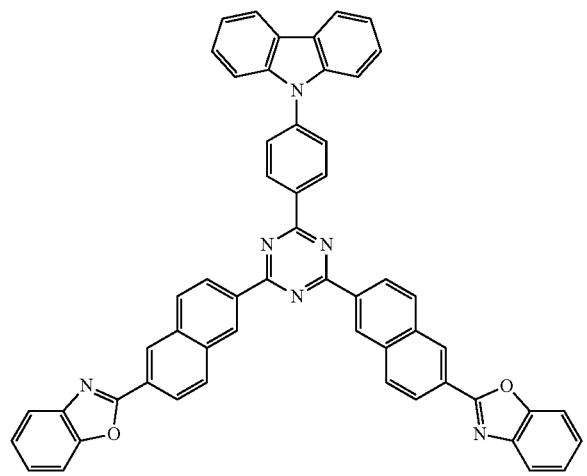
(238)
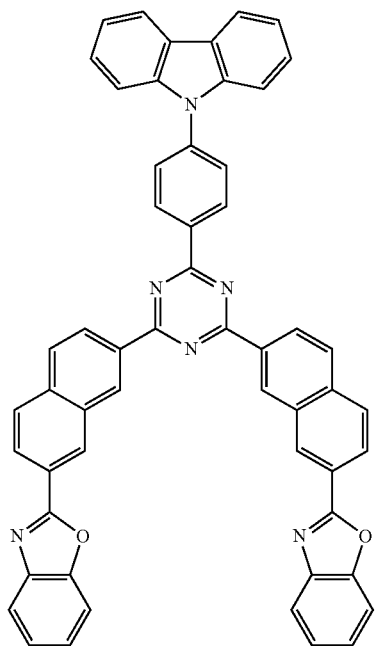

-continued
(239)
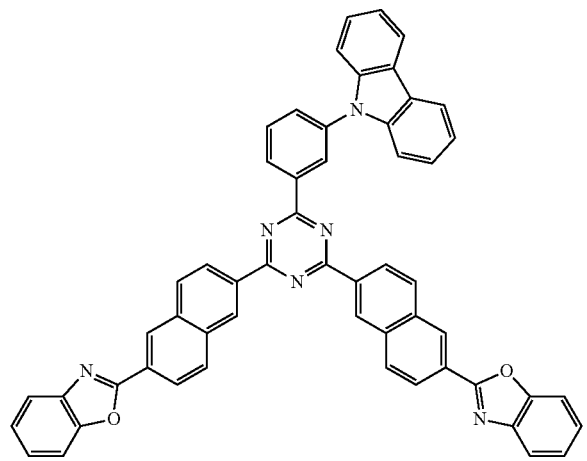
(240)
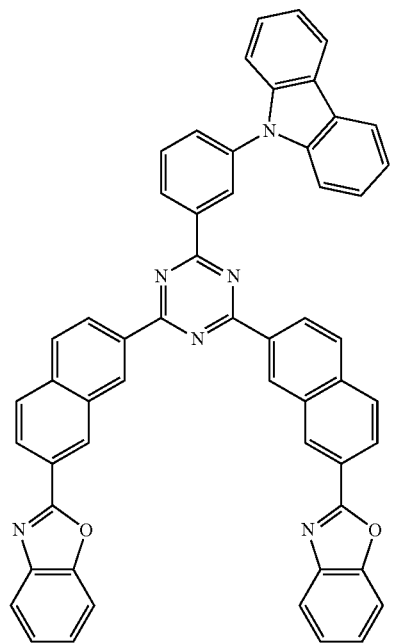
(241)
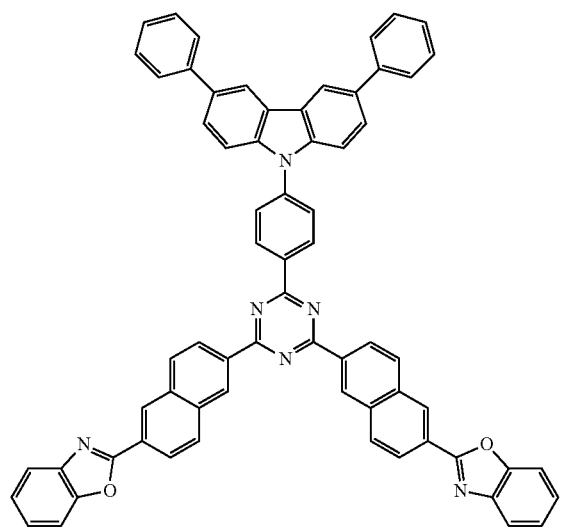
(242)
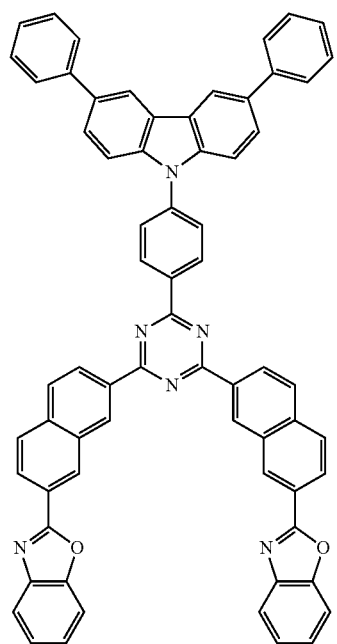

-continued
(243)
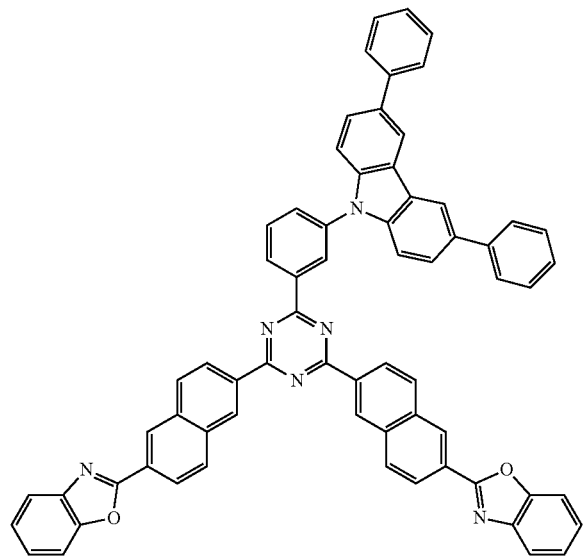
(244)
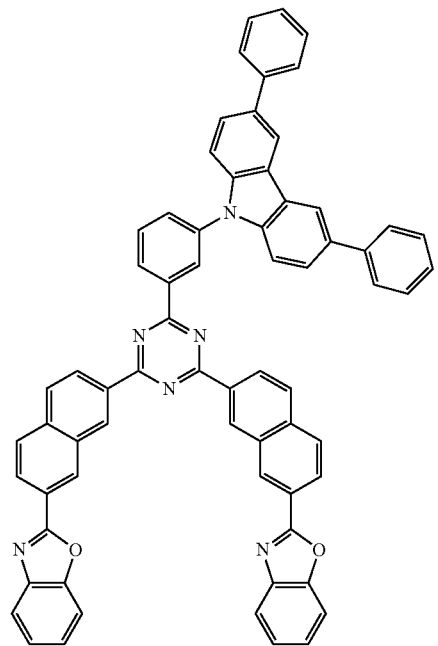
(245)
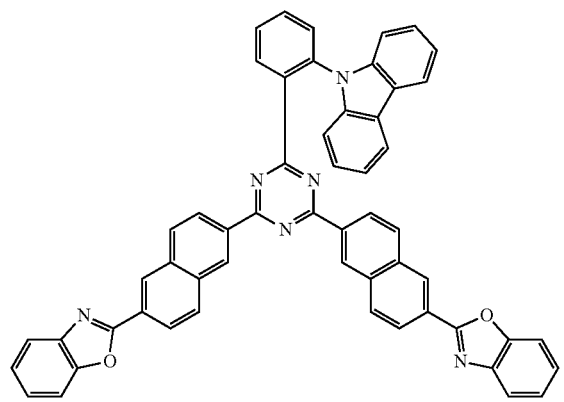
(246)
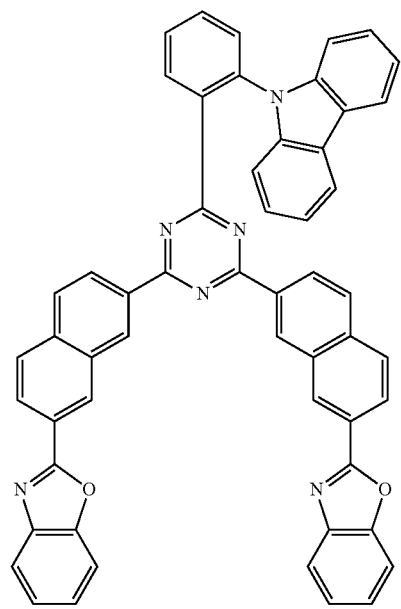

-continued
(247)
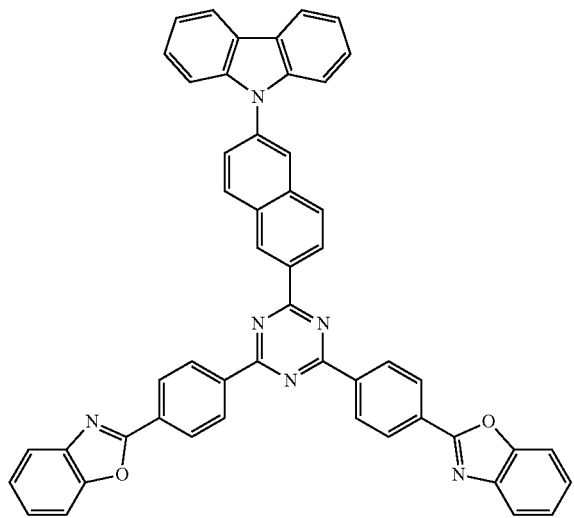
(248)
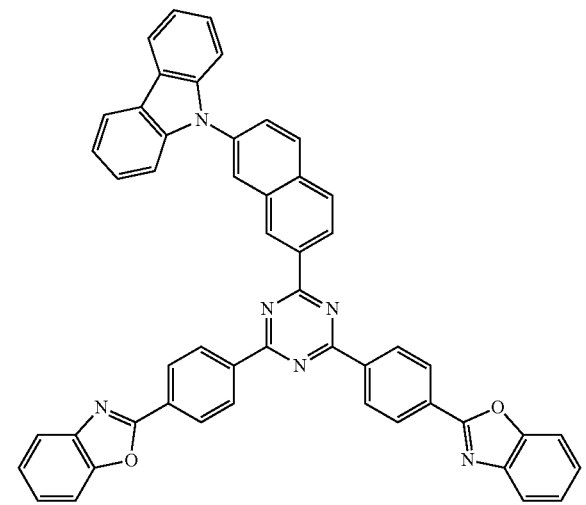
(249)
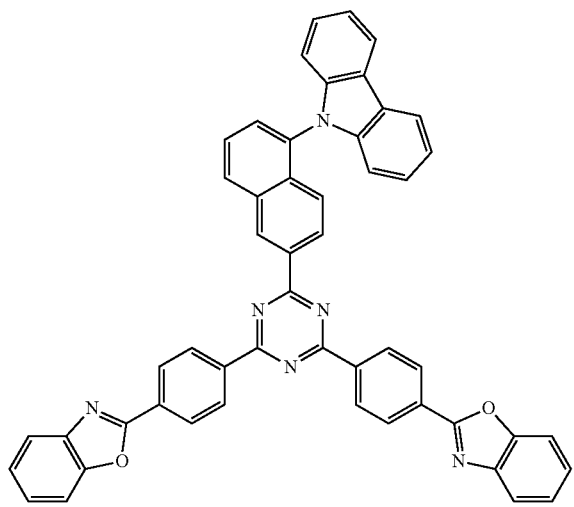
(250)
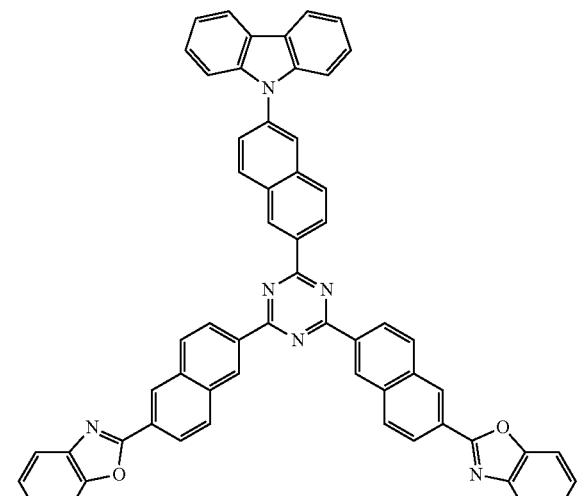
(251)
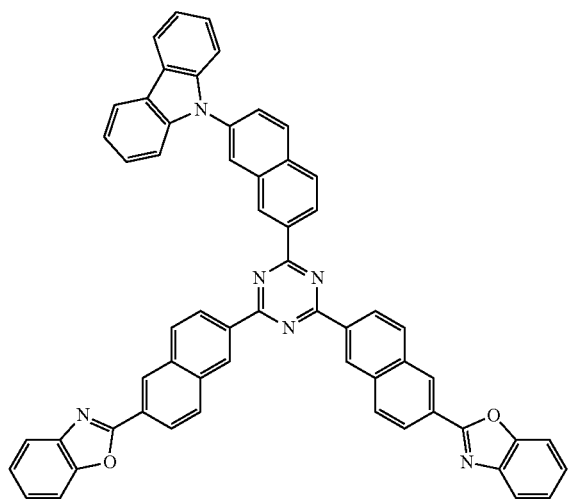
(252)
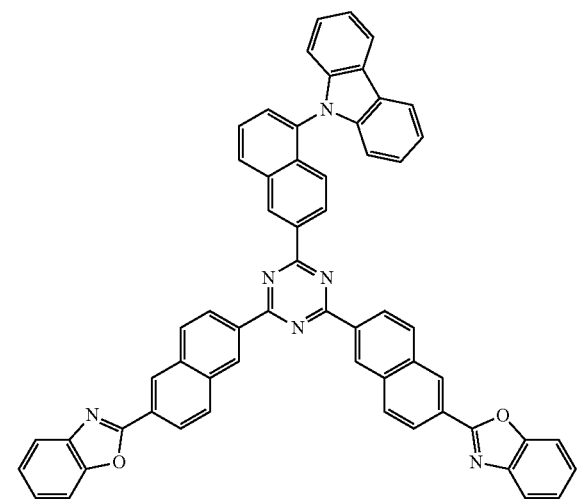

(253)
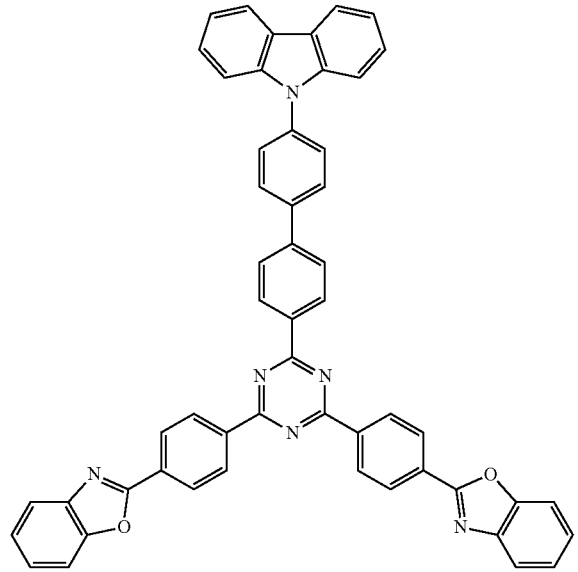
(254)
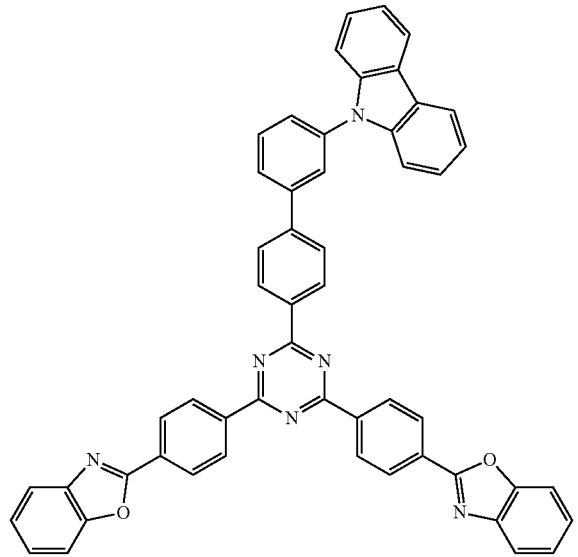
(255)
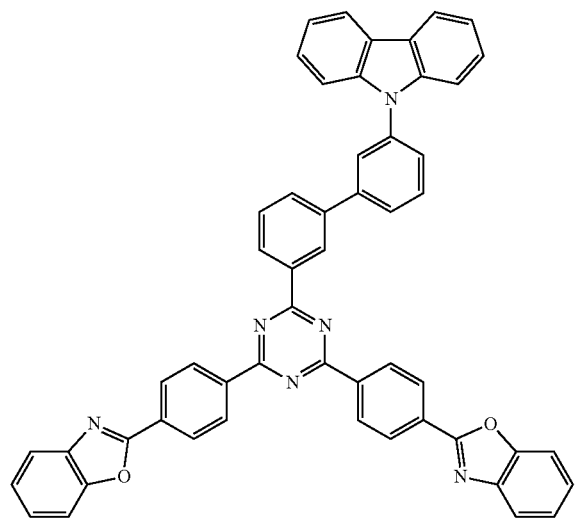
(256)
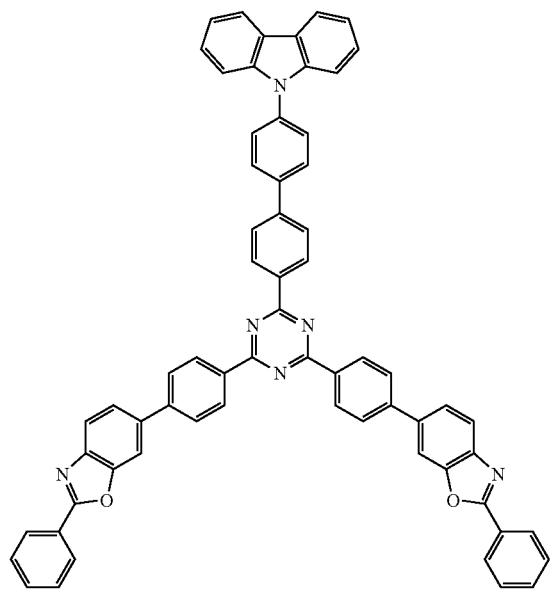

(257)
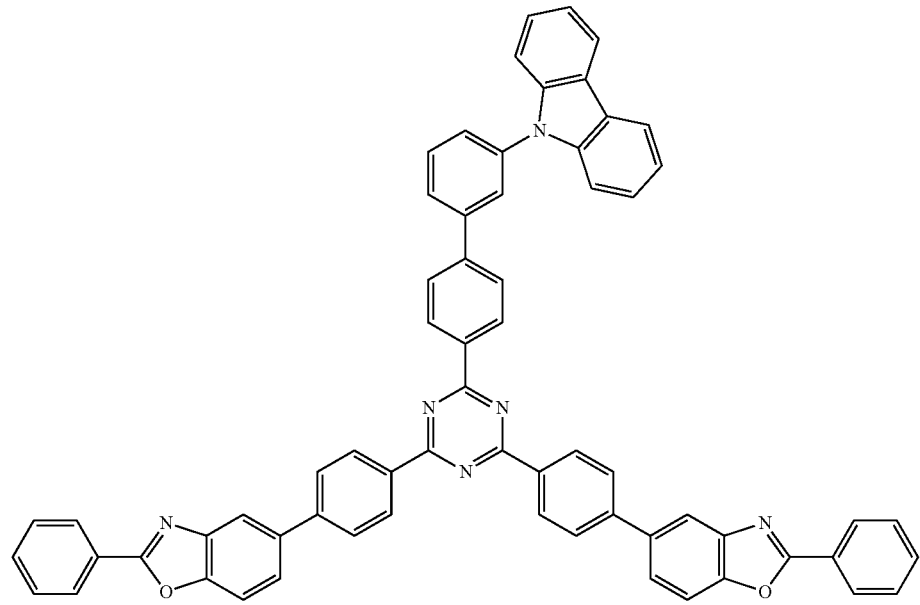
(258)
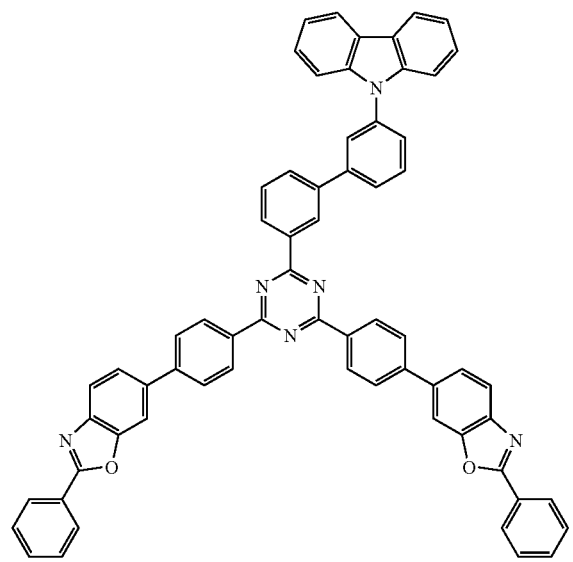
(259)
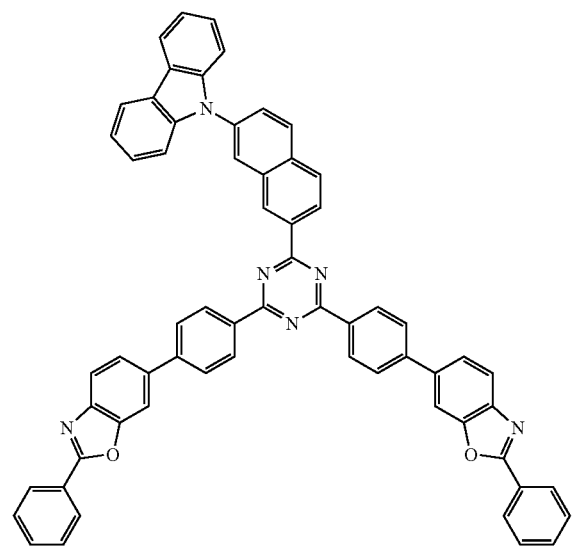

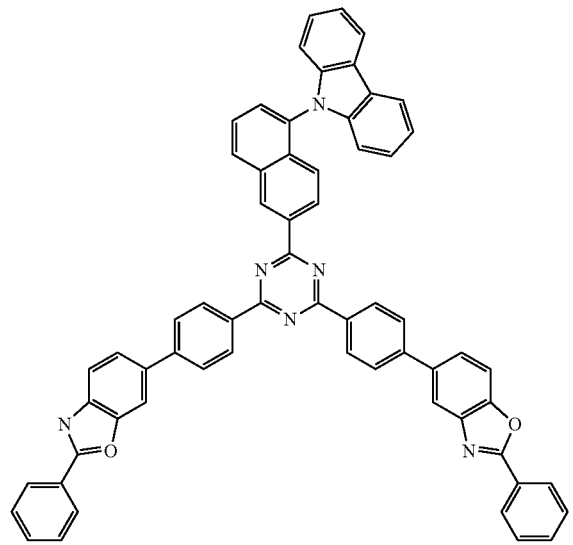
(260)
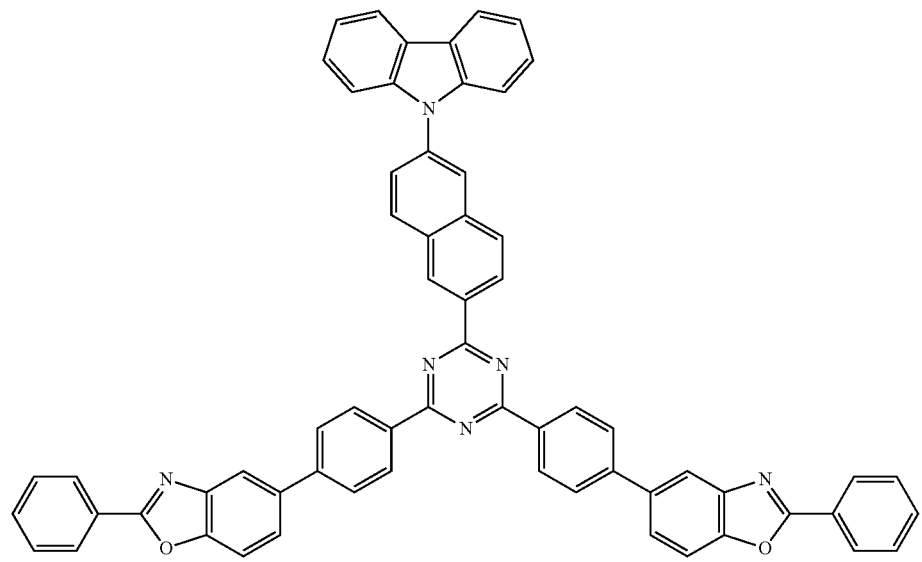
(261)

(262)
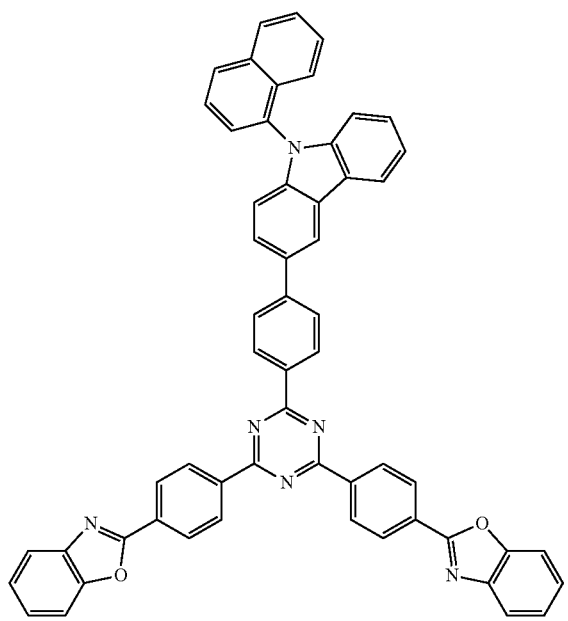
(263)
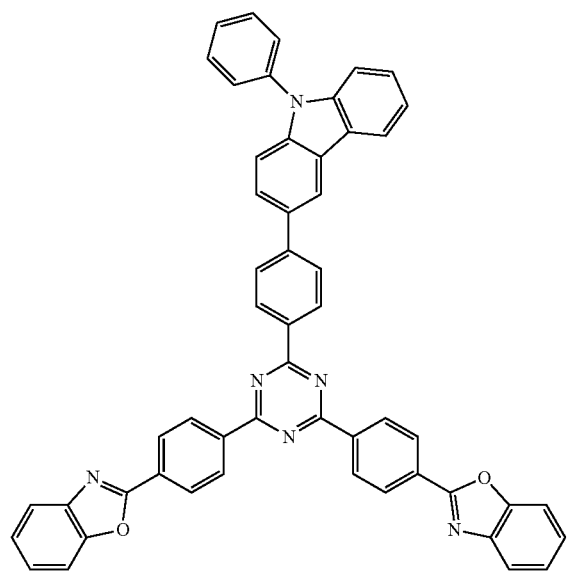
(264)
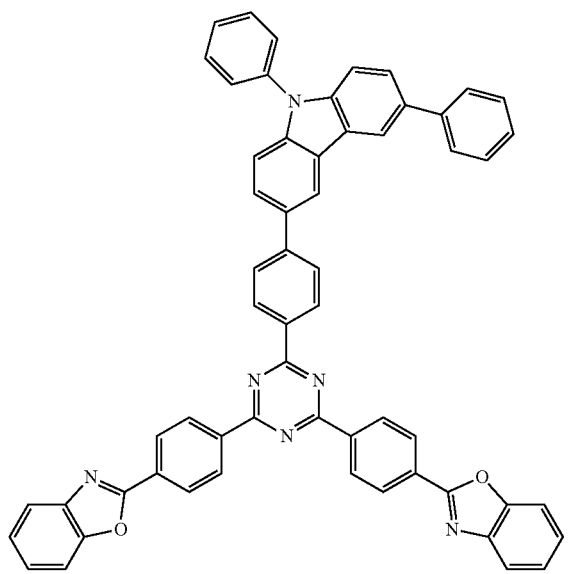
(265)
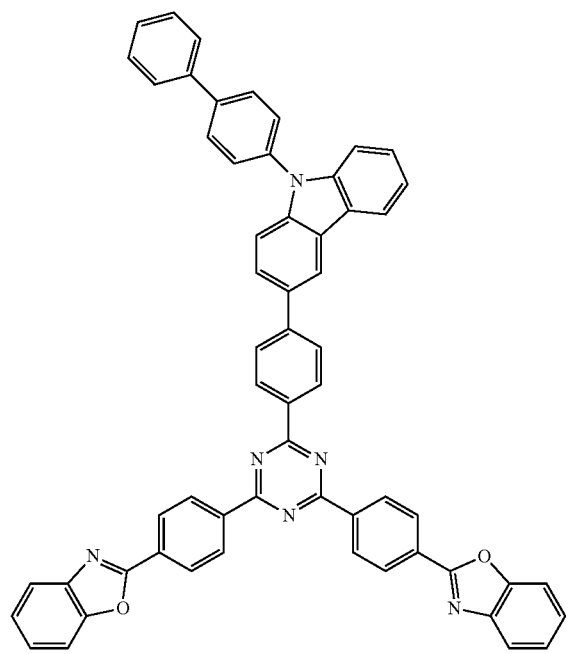

-continued
(266)
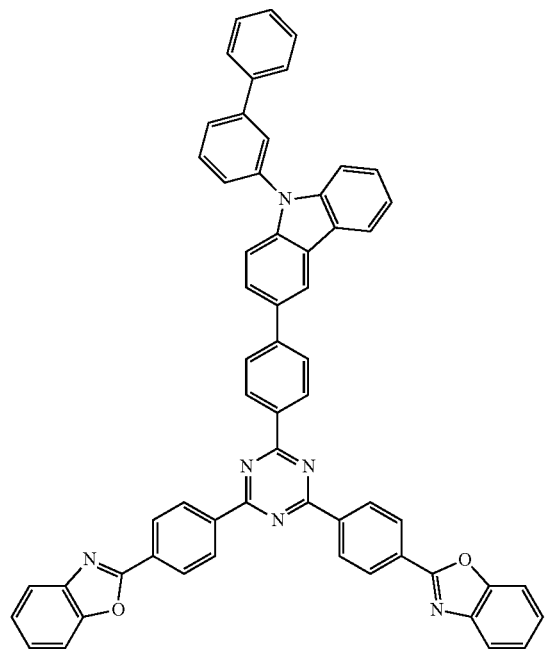
(267)
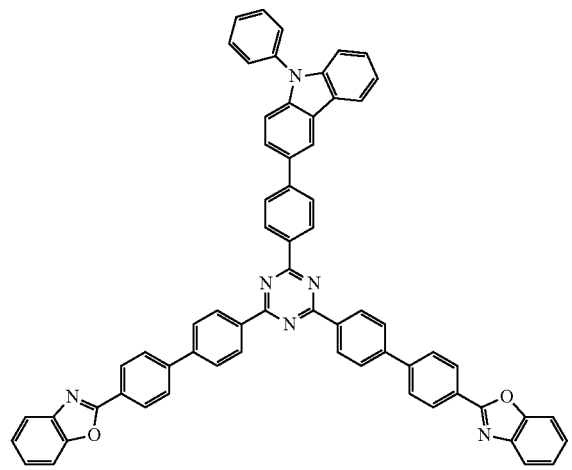
(268)
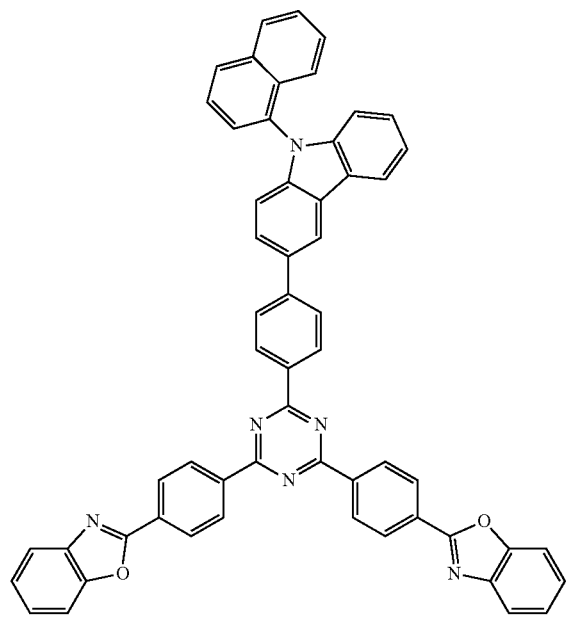
(269)
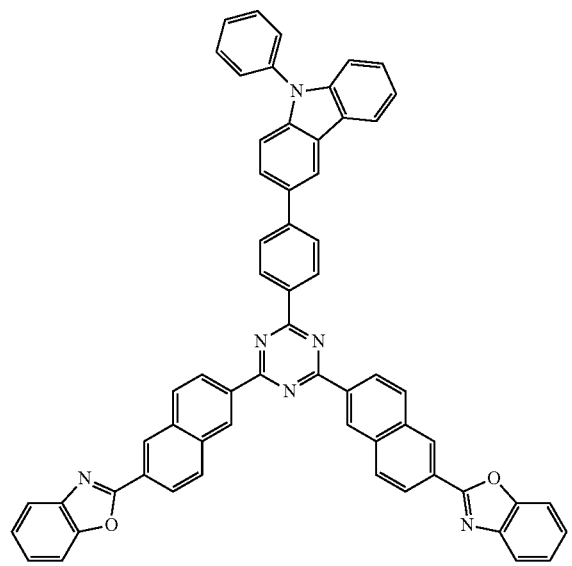

(270)
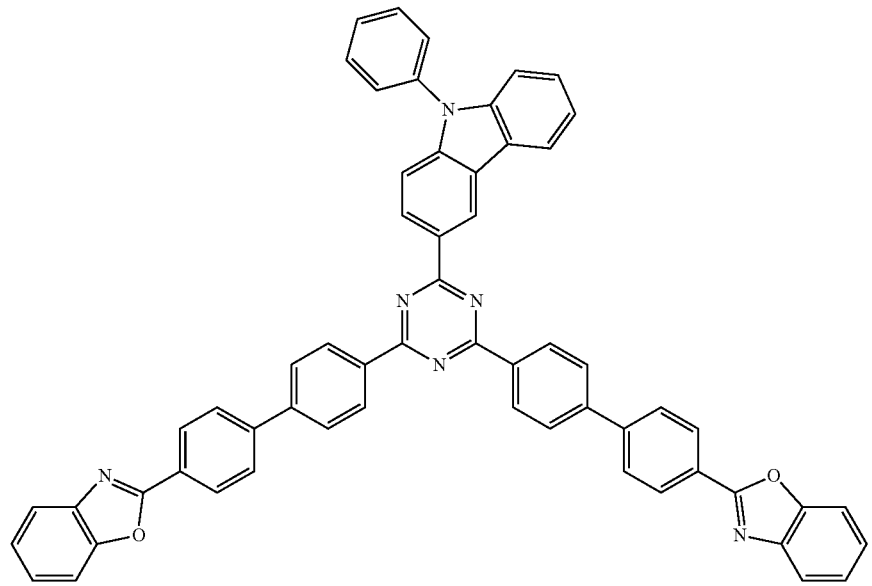
(271)
(272)
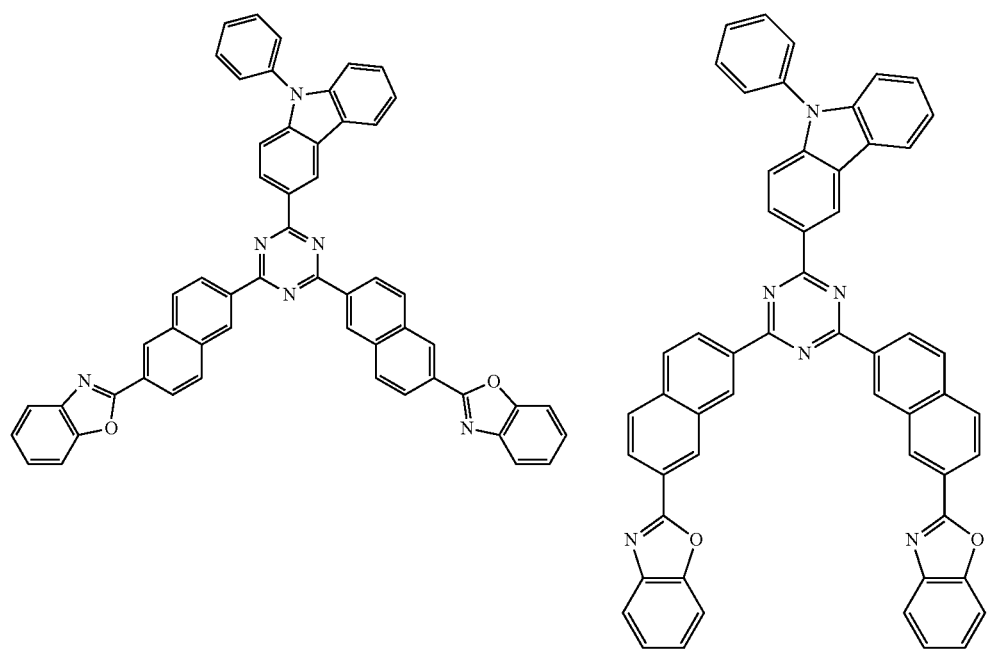

(273)
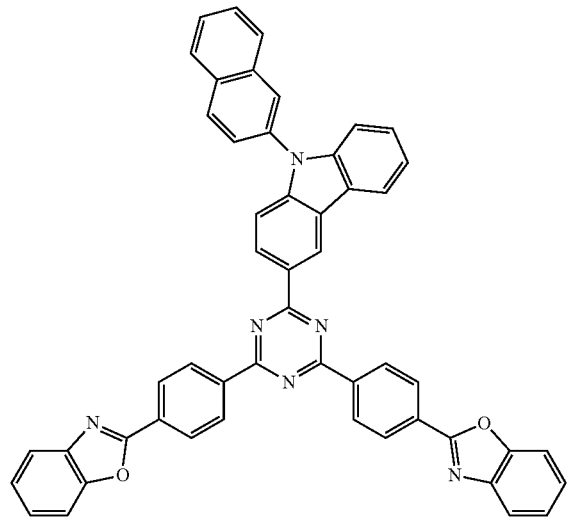
(274)
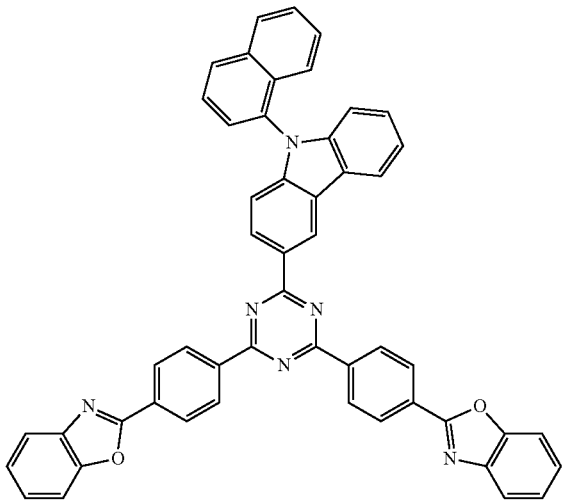
(275)
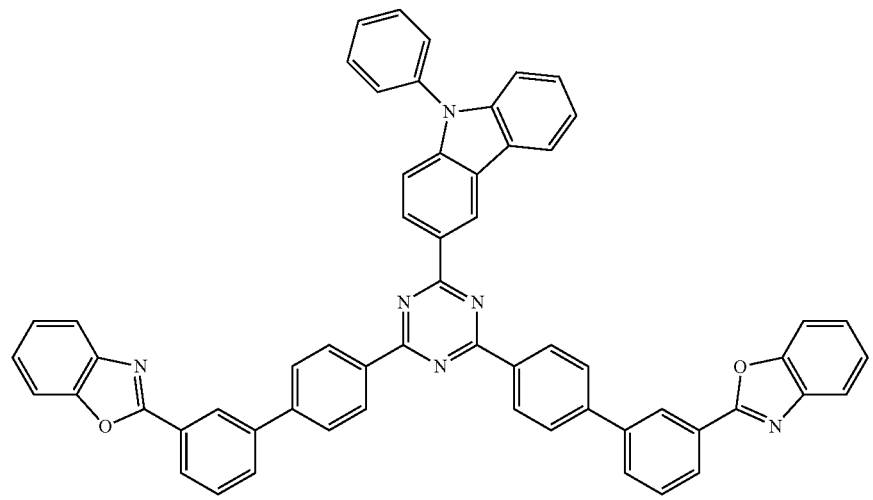

(276)
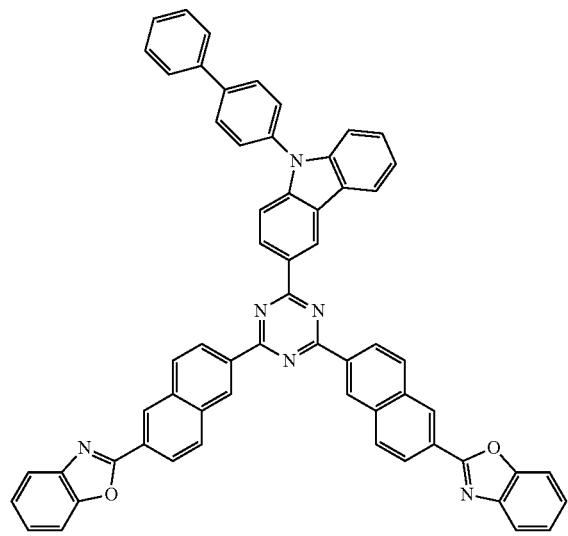
(277)
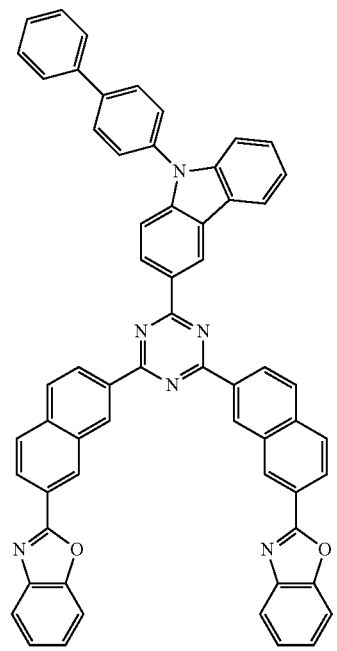
(278)
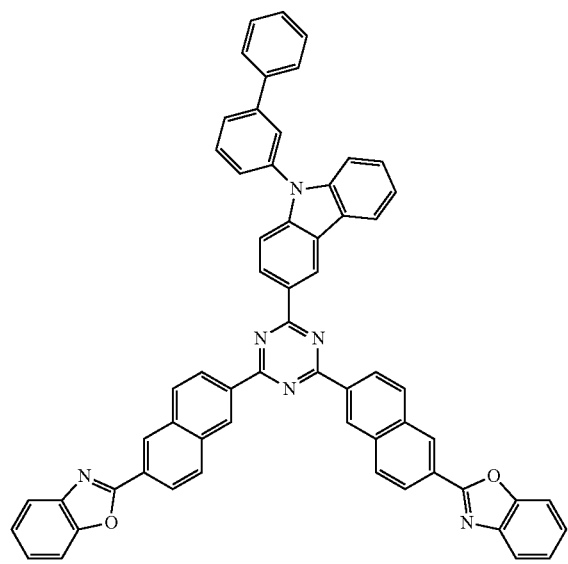
(279)
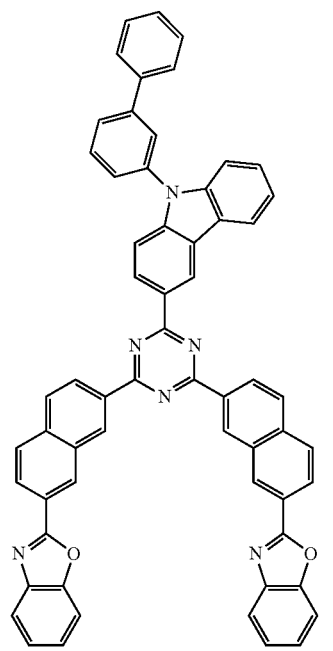

-continued
(280)
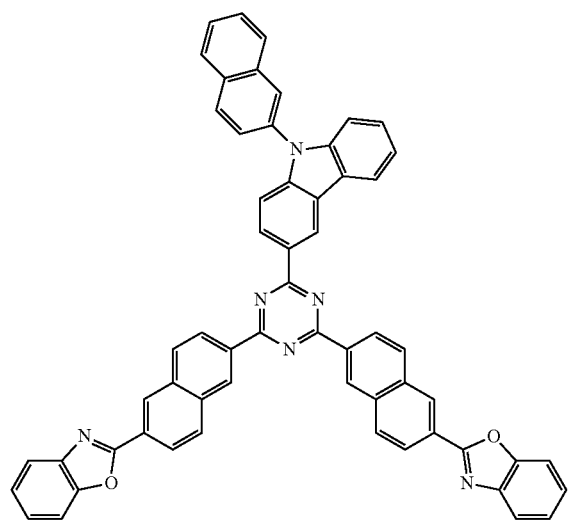
(281)
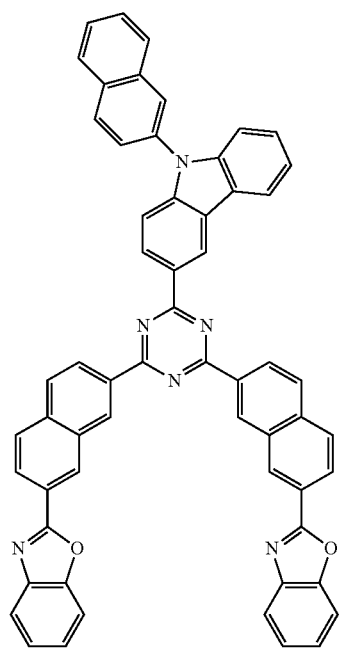
(282)
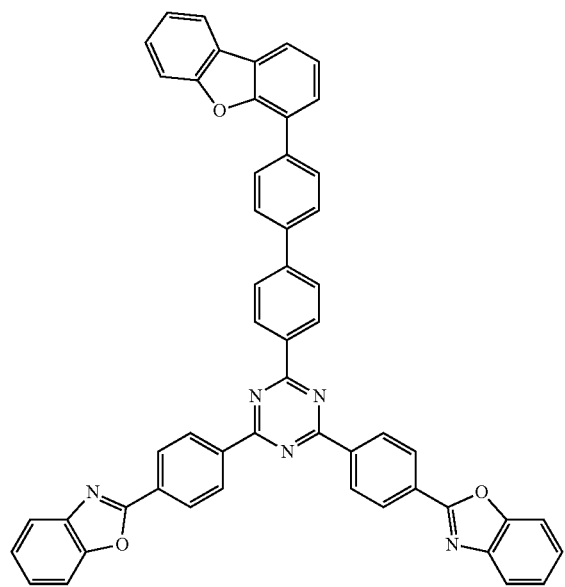
(283)
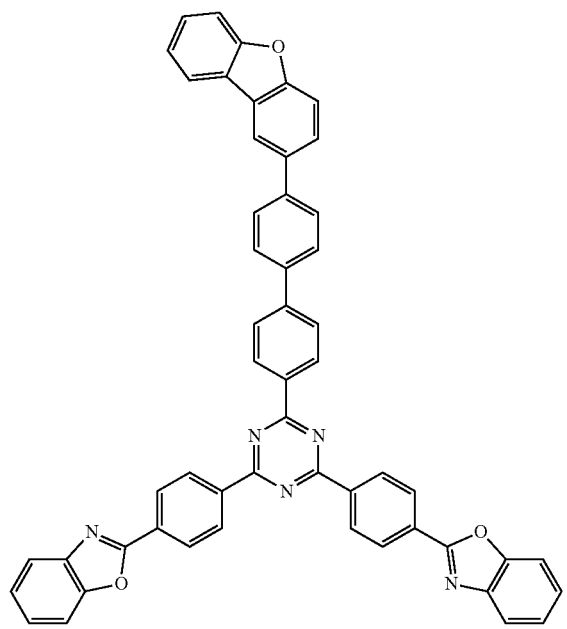

(284)
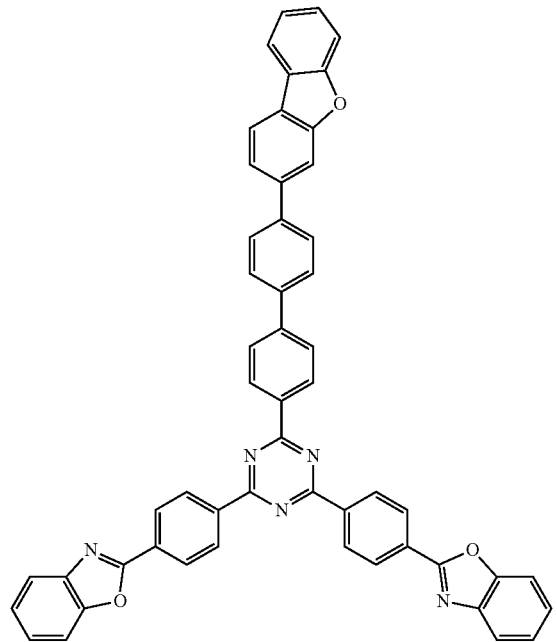
(285)
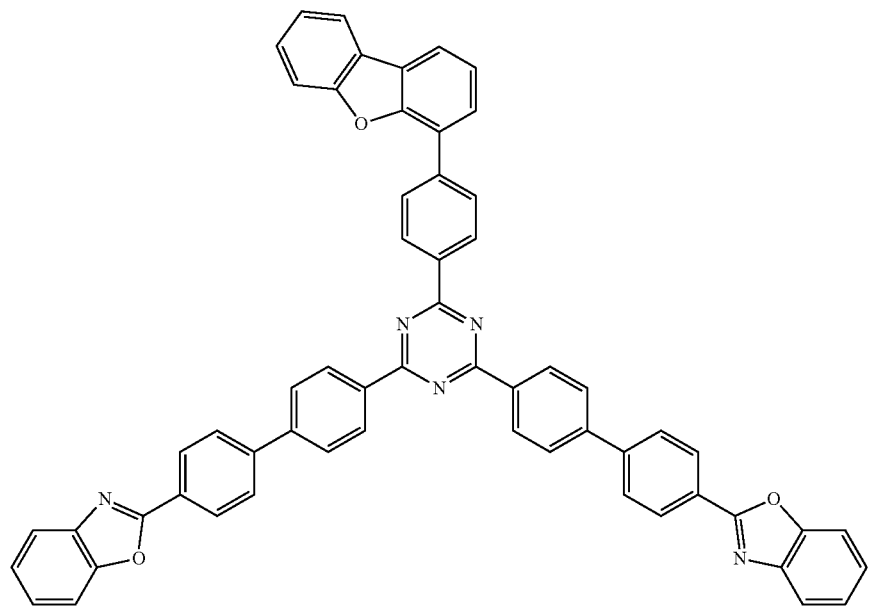

(286)
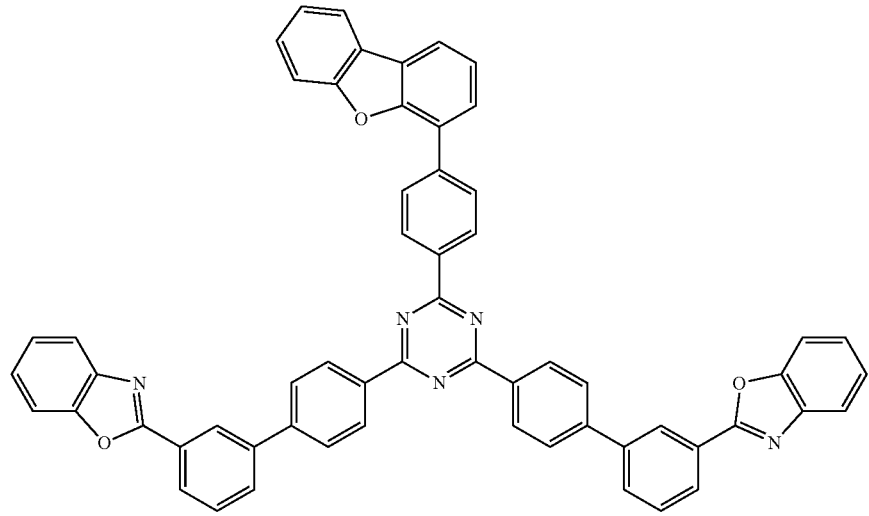
(287)
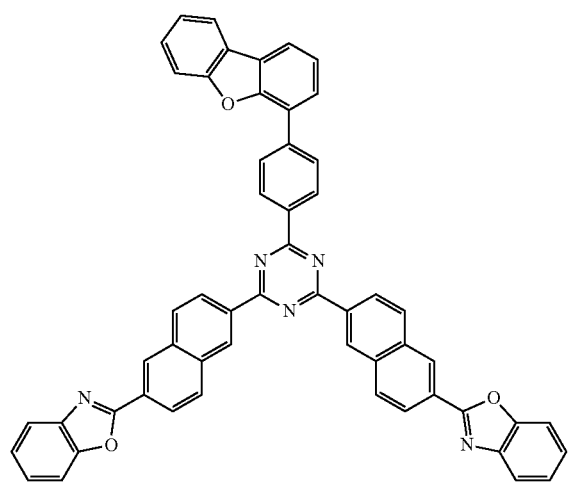
(288)
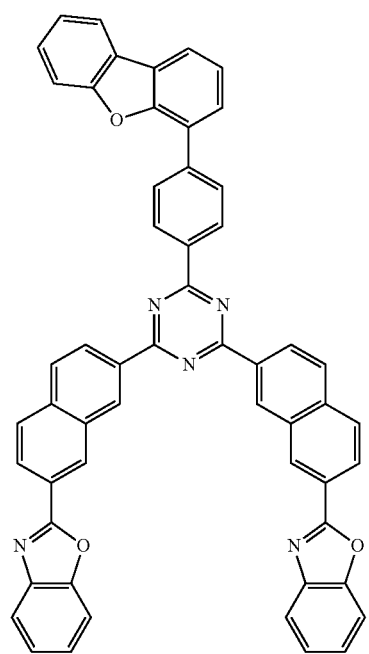

(289)
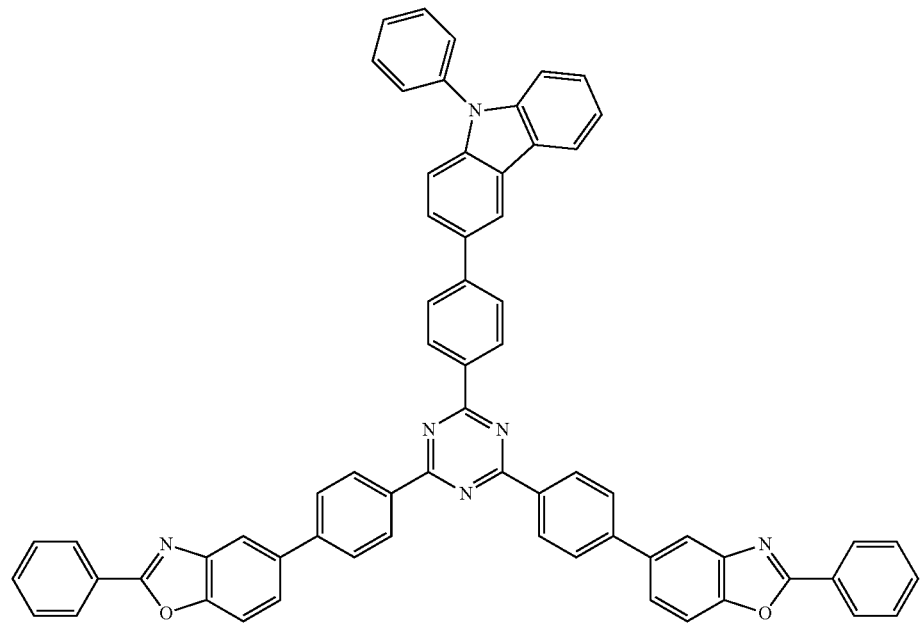
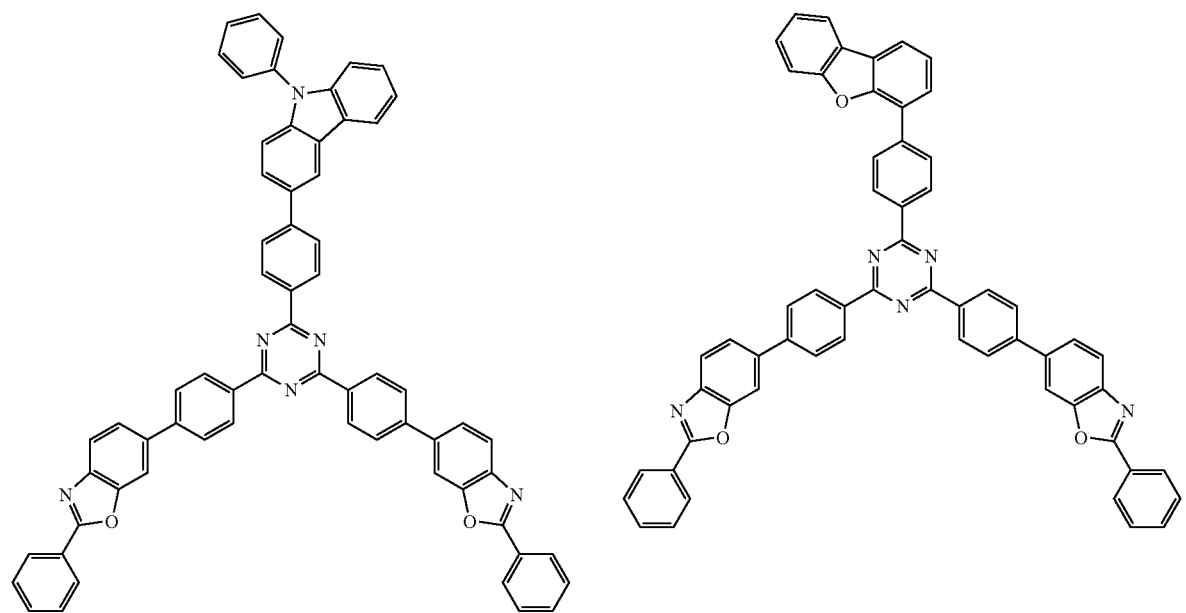

(292)
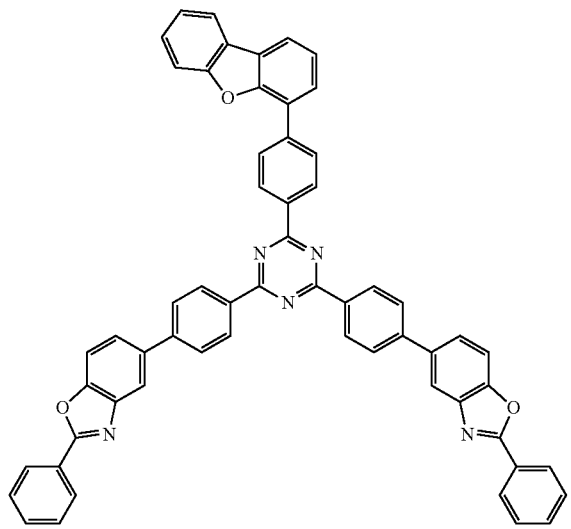
(293)
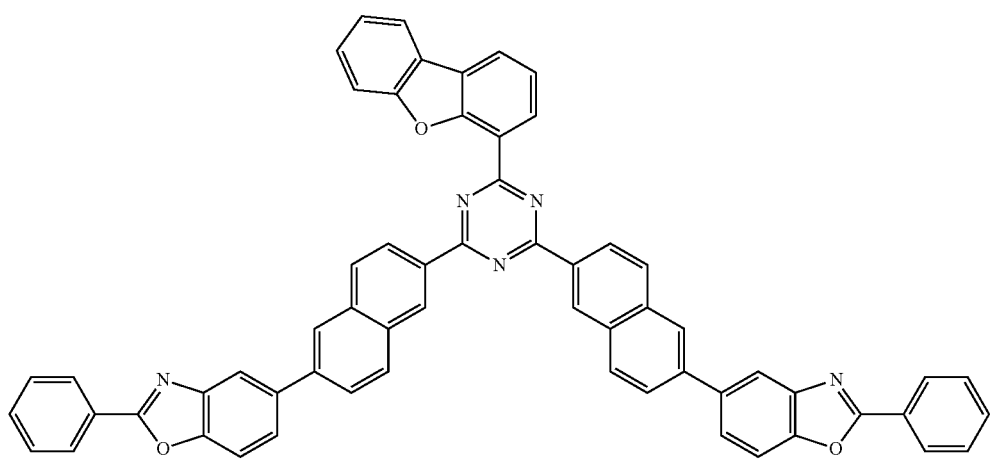
(294)
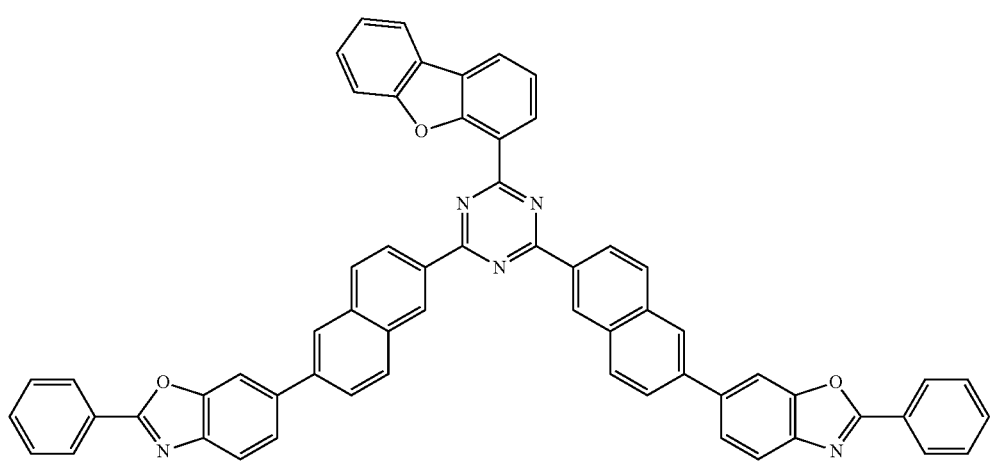

-continued
(295)
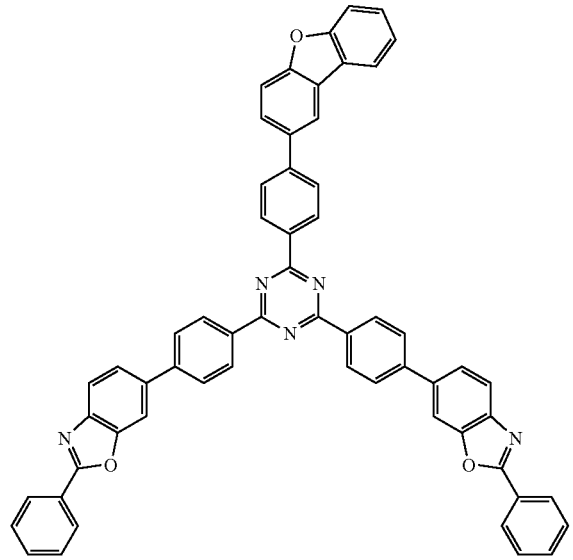
(296)
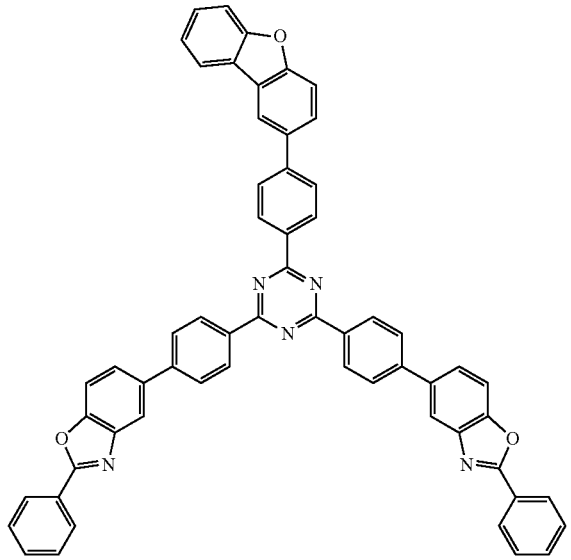
(297)
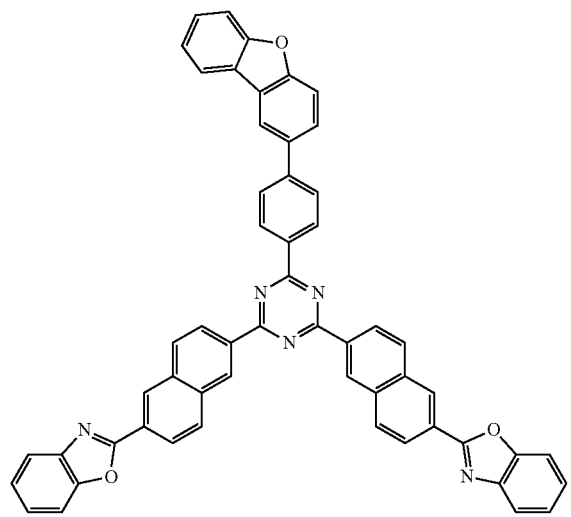
(298)
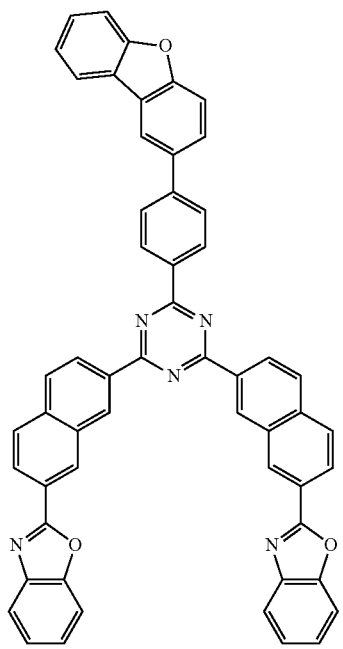

201
202
-continued
(299)
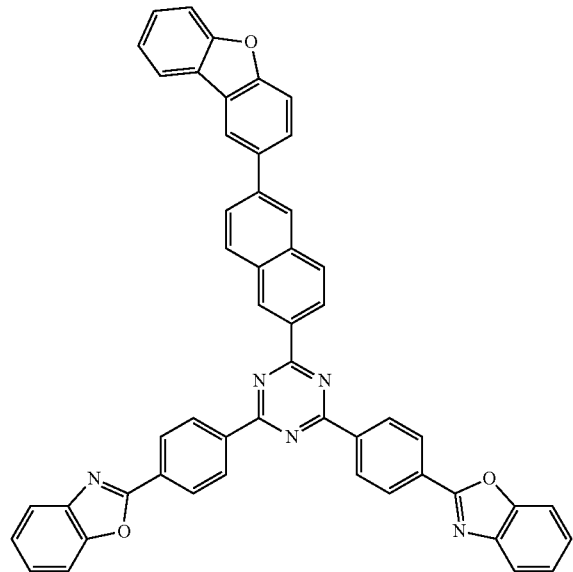
(300)
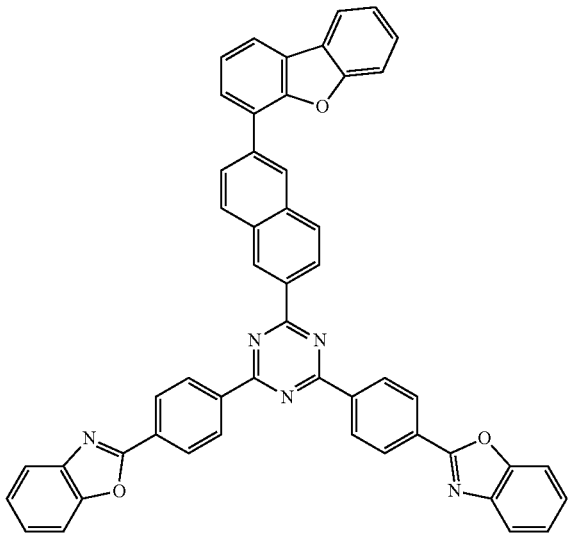
(301)
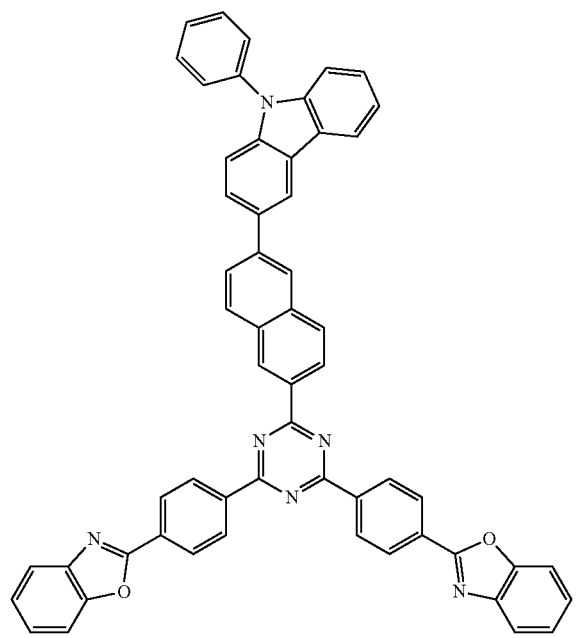
(302)
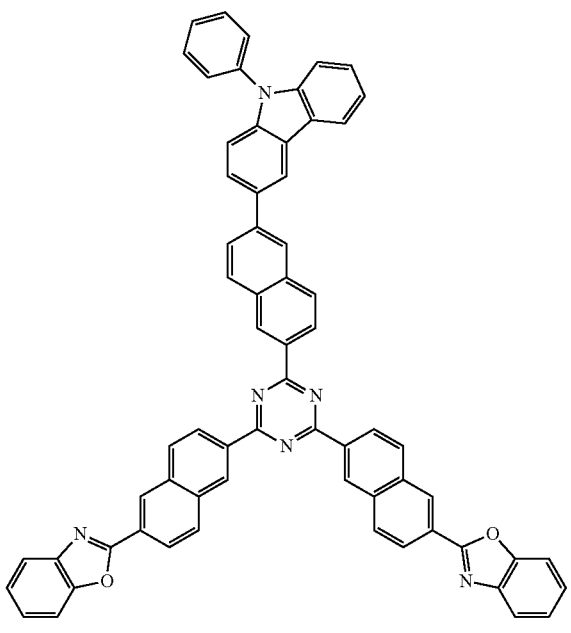

-continued
(303)
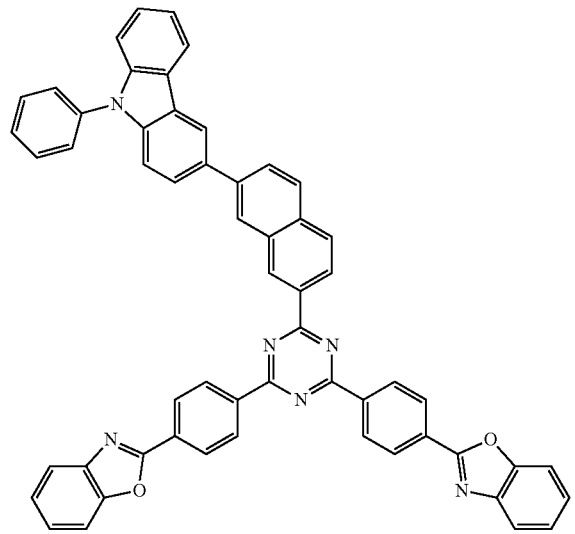
(304)
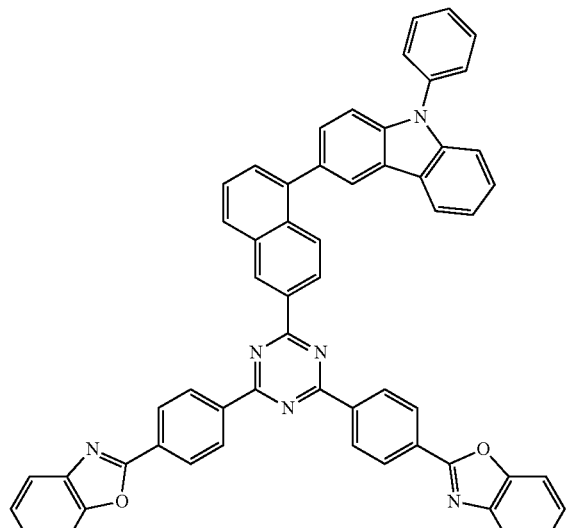
(305)
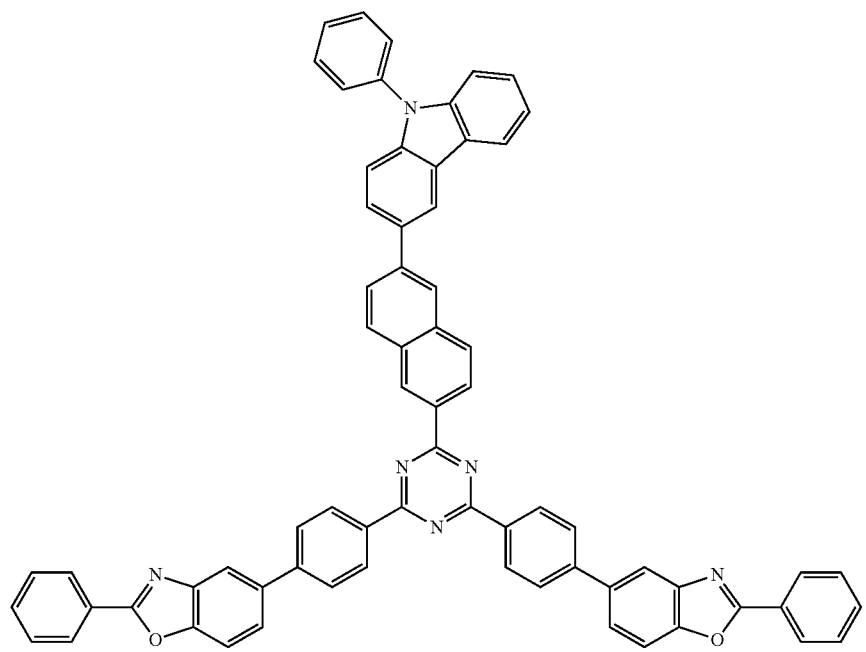
(306)
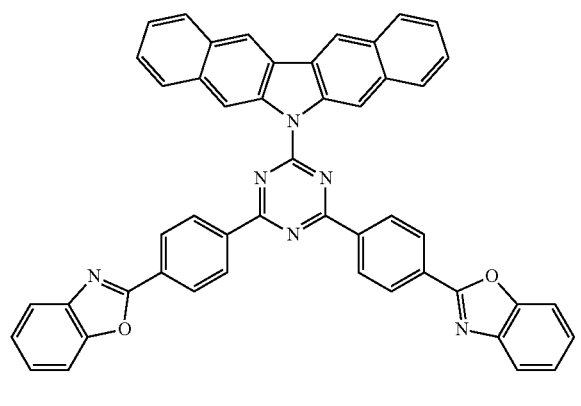
(307)
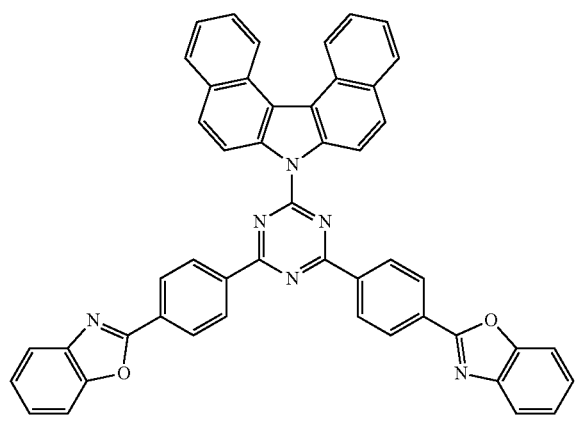

-continued
(308)
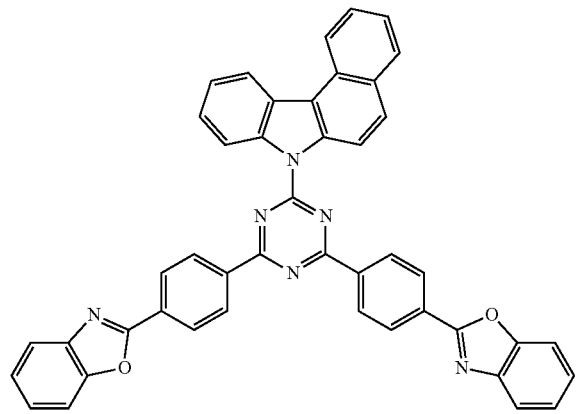
(309)
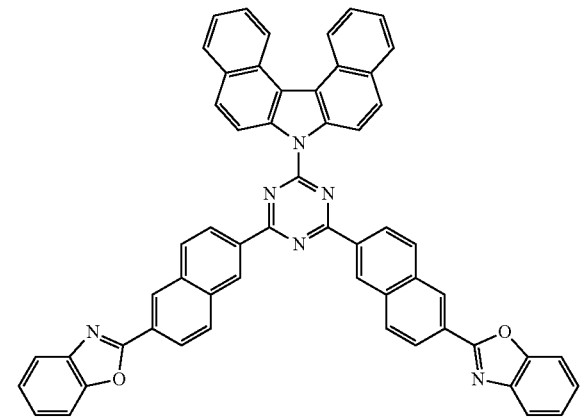
(310)
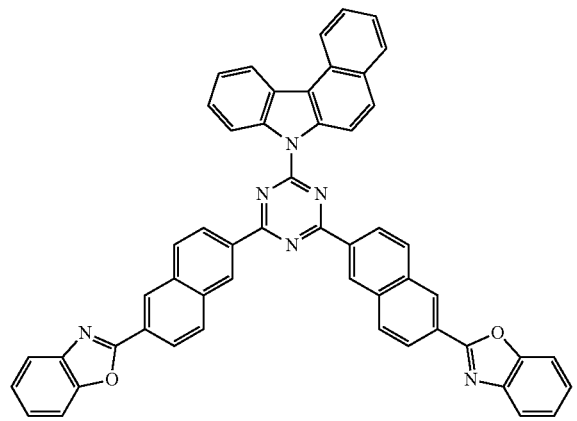
(311)
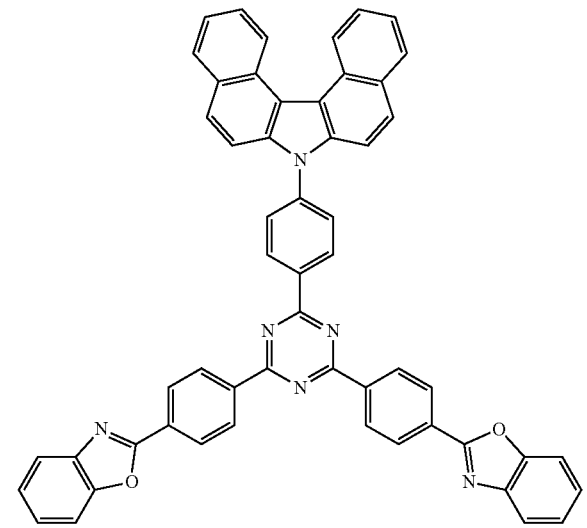
(312)
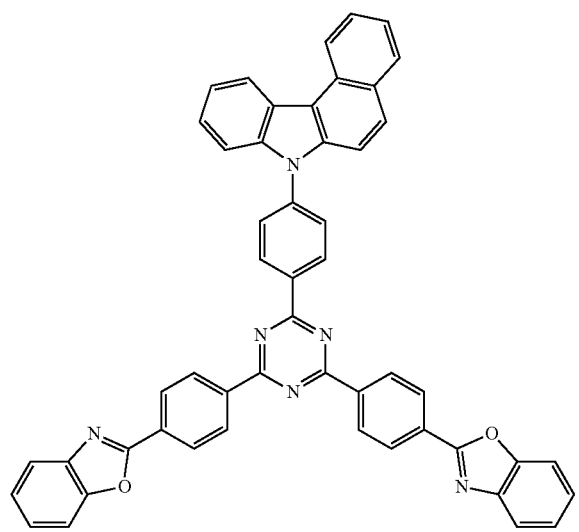
(313)
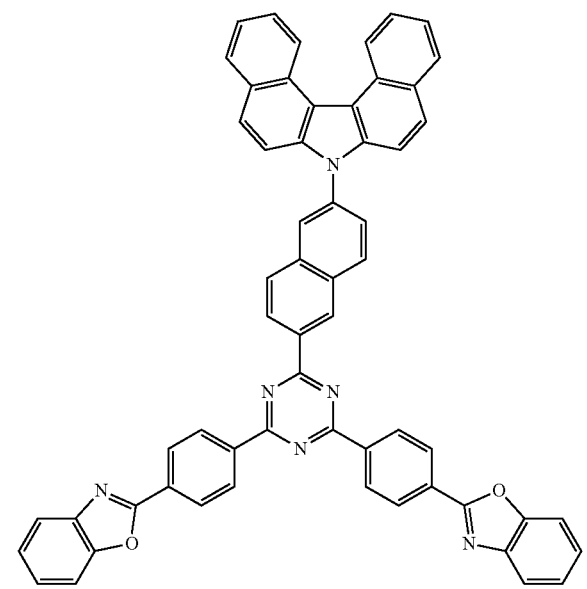

(314)
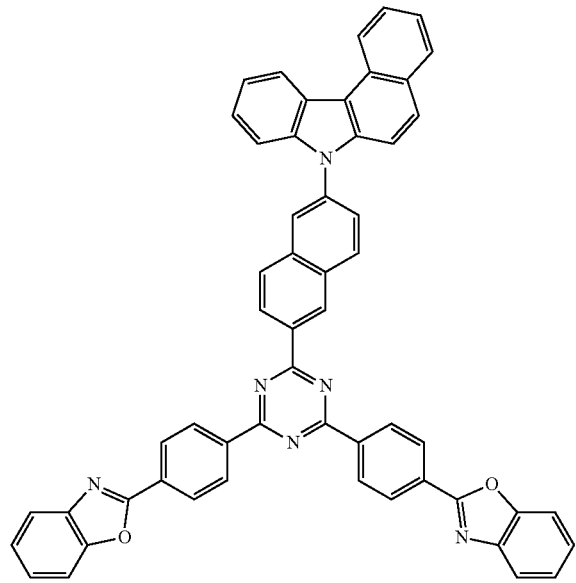
(315)
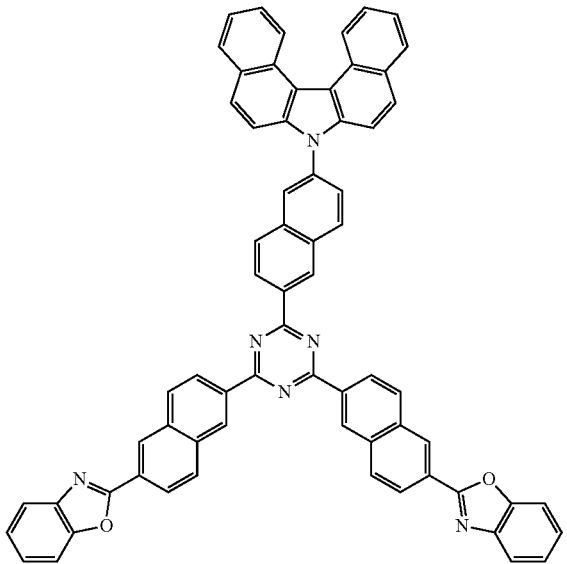
(316)
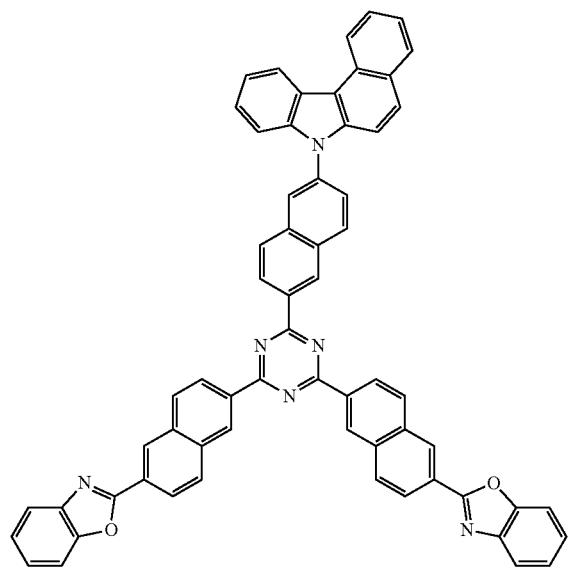
(317)
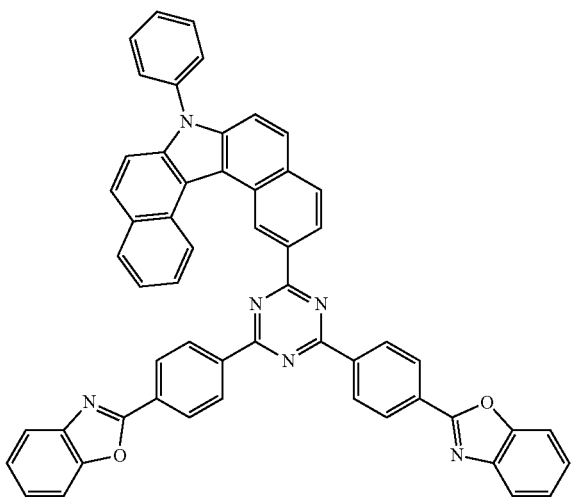

(318)
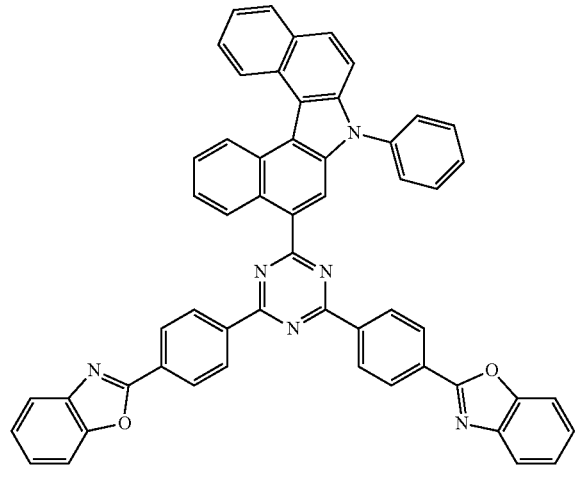
(319)
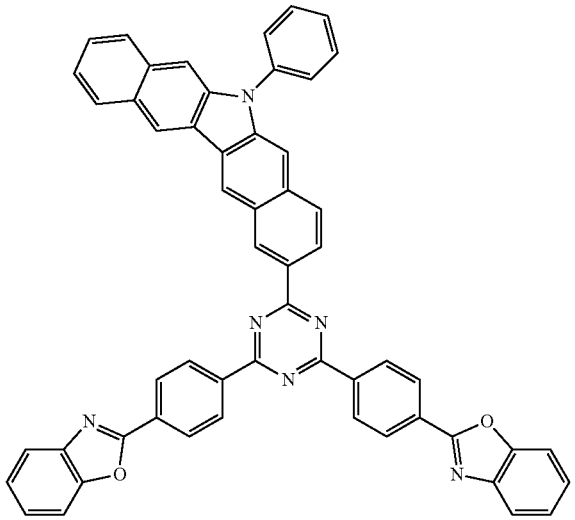
(320)
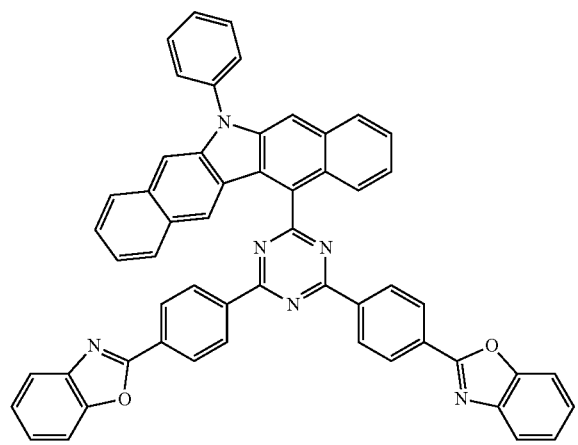
(321)
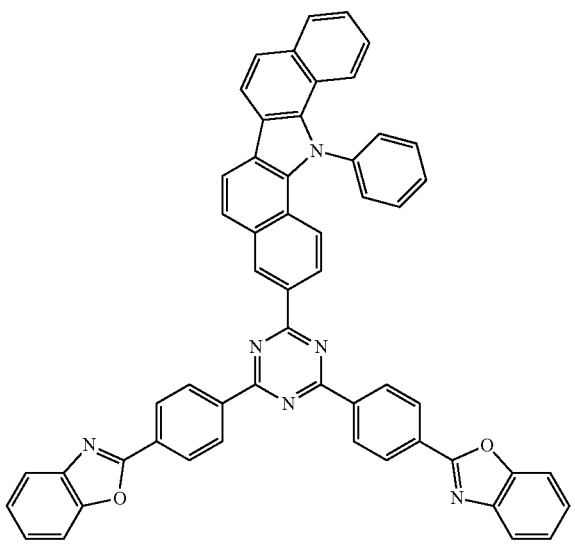

211
(322)
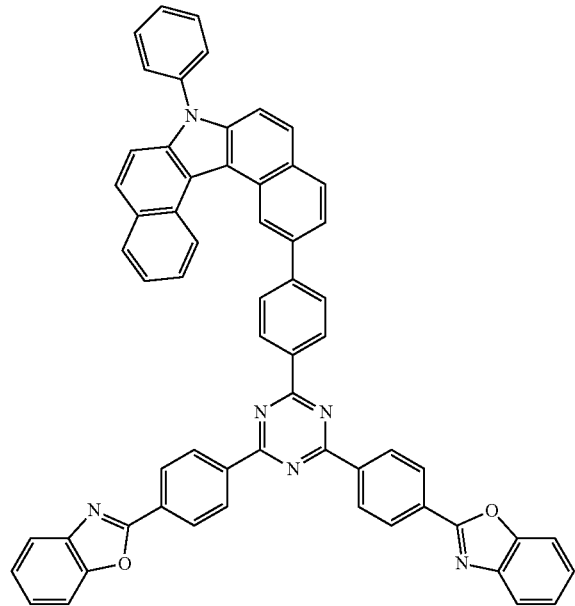
212
-continued
(323)
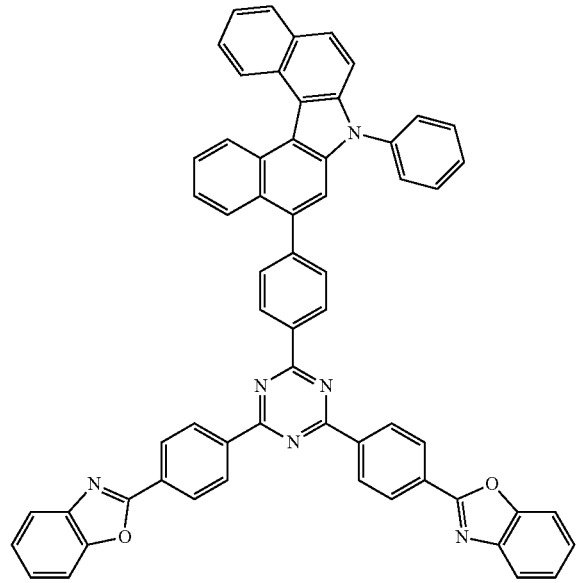
(324)
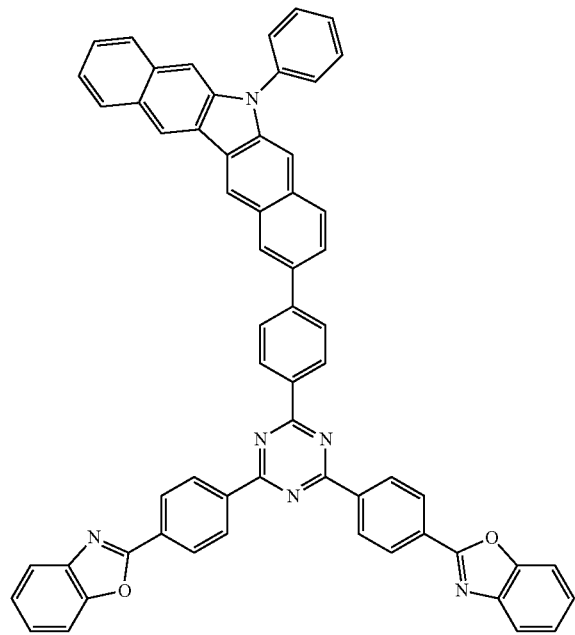
(325)
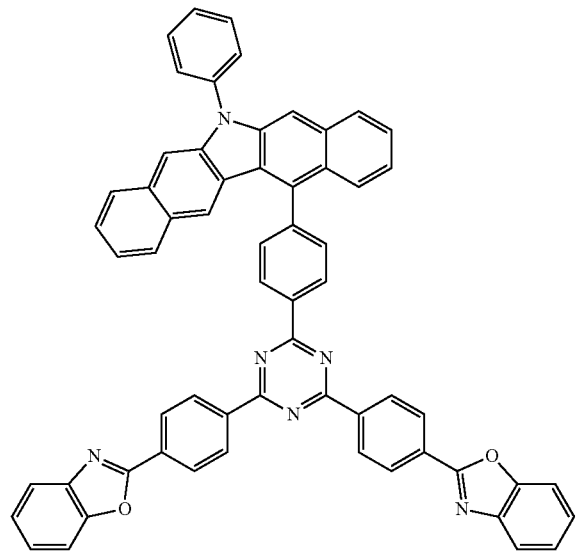

-continued
(326)
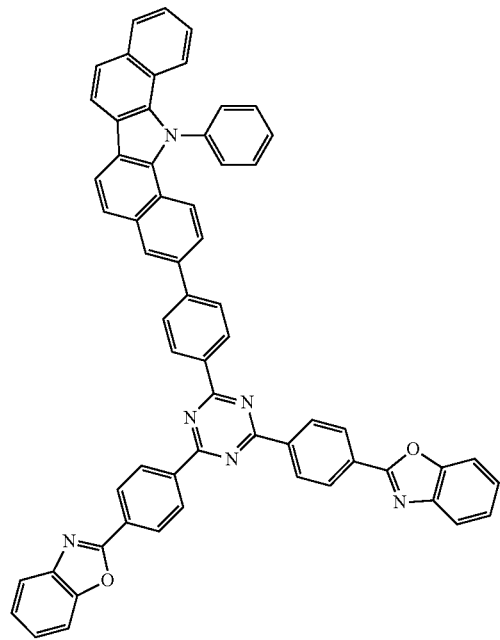
(327)
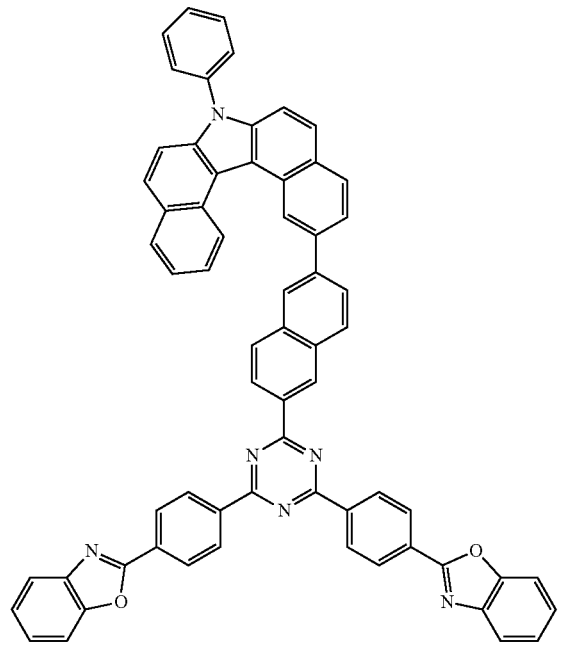
(328)
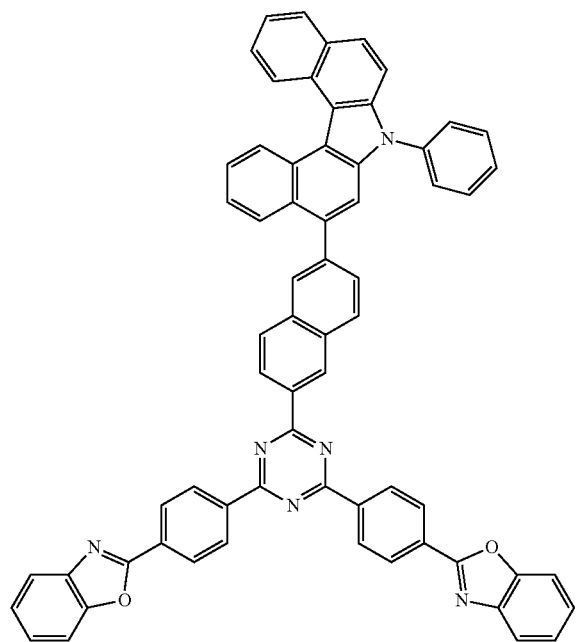
(329)
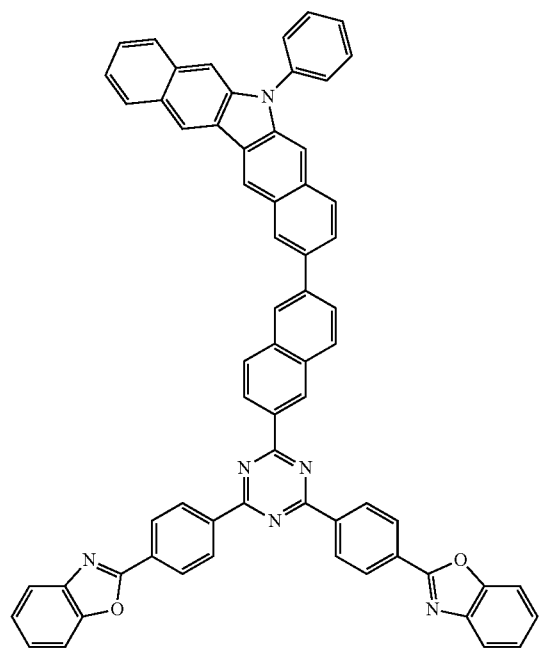

215
216
-continued
(330)
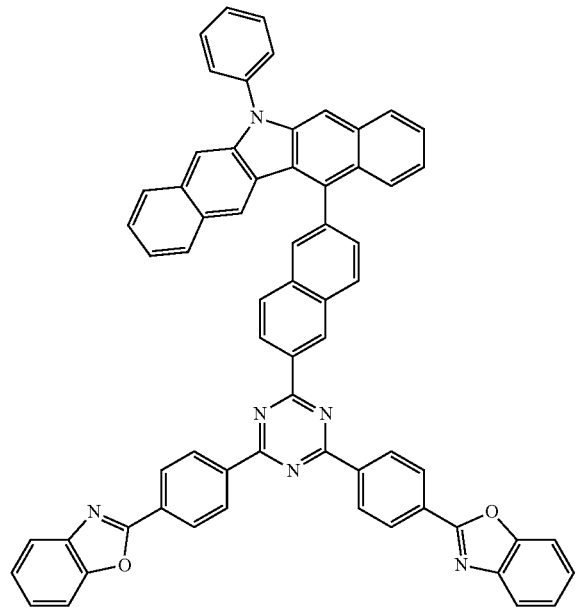
(331)
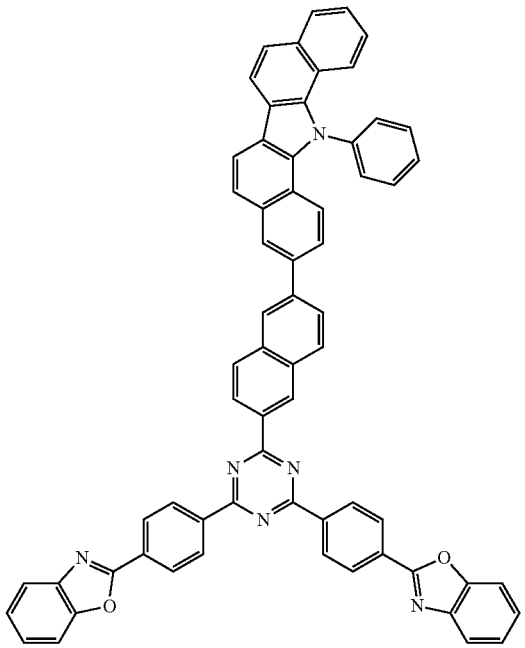
(332)
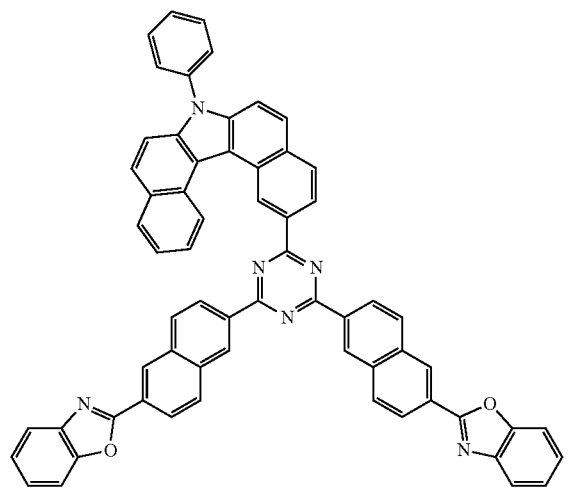
(333)
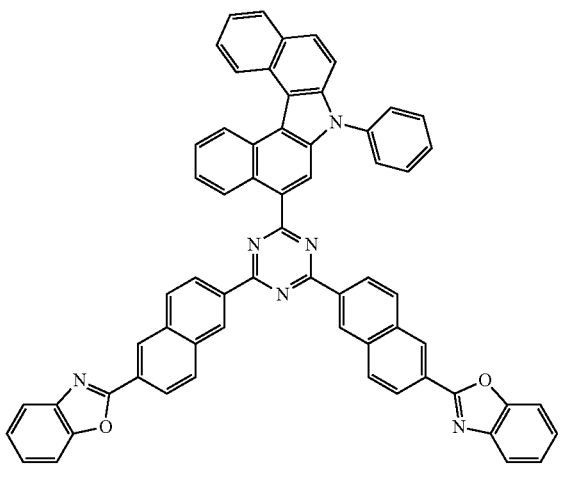

(334)
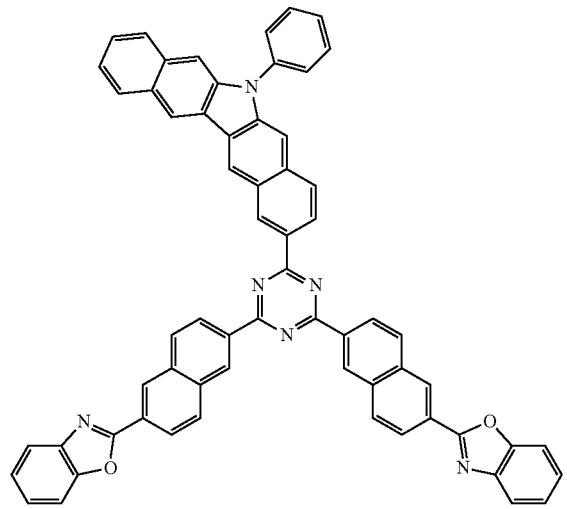
(335)
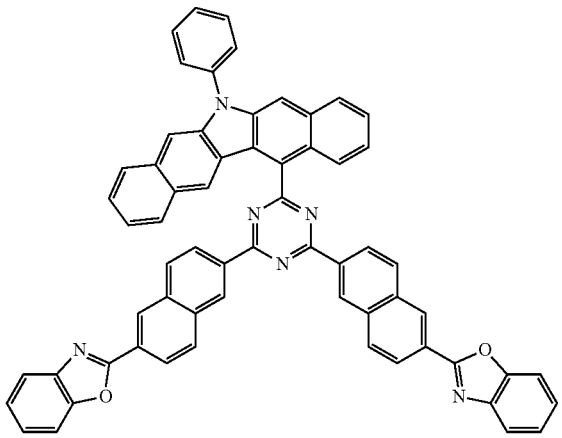
(336)
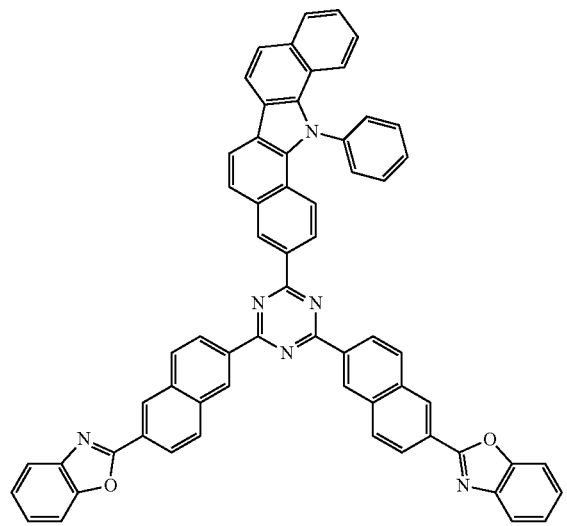
(337)
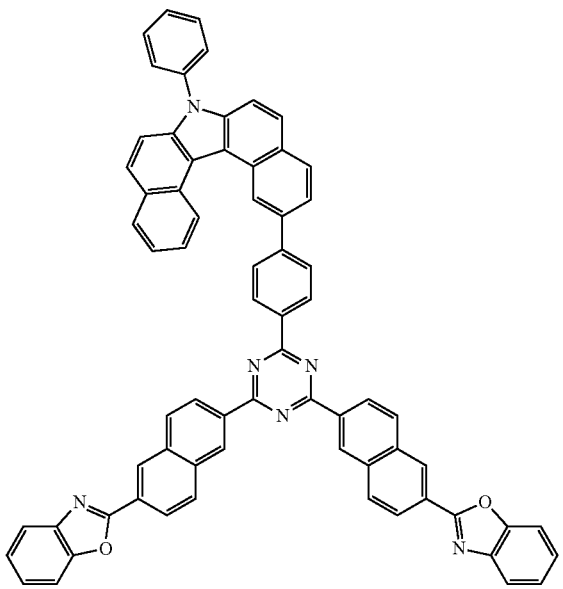

-continued
(338)
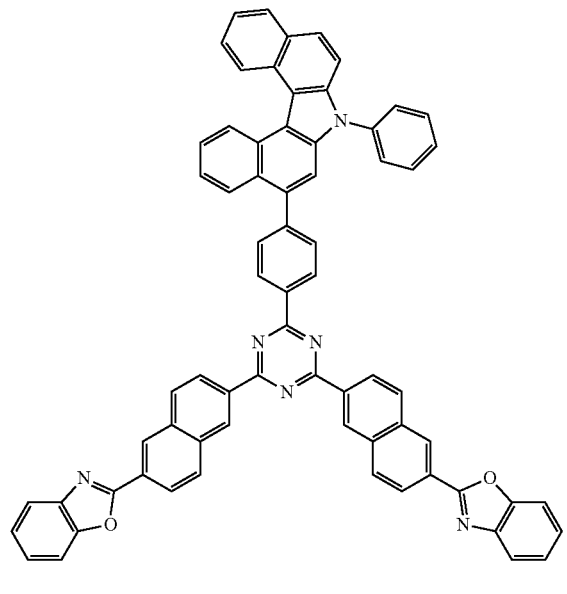
(339)
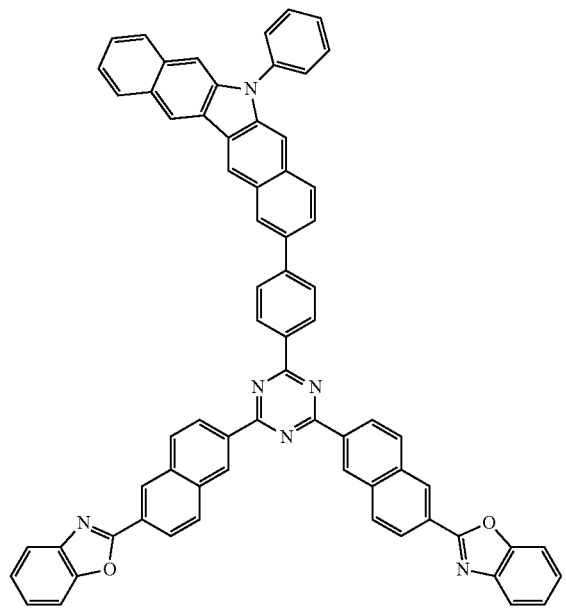
(340)
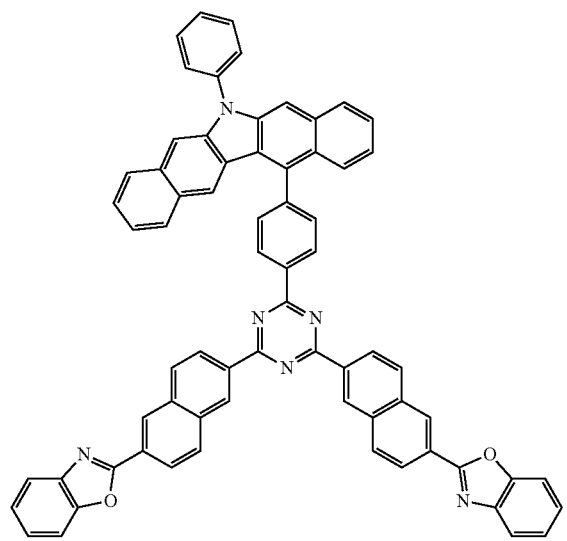
(341)
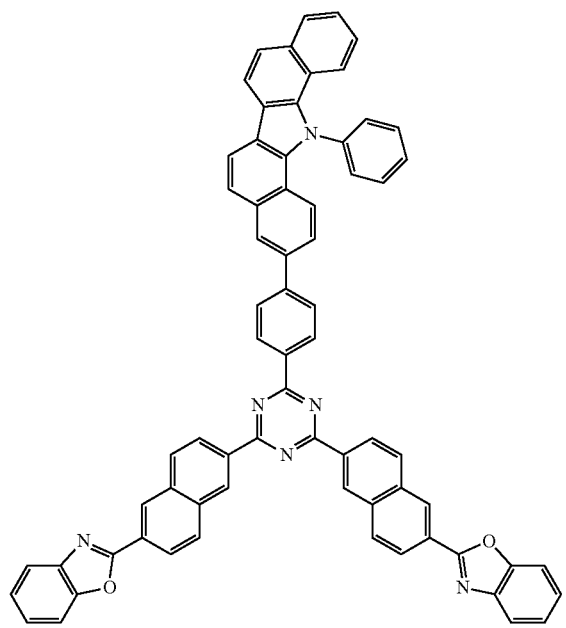

221 222
-continued
(342)
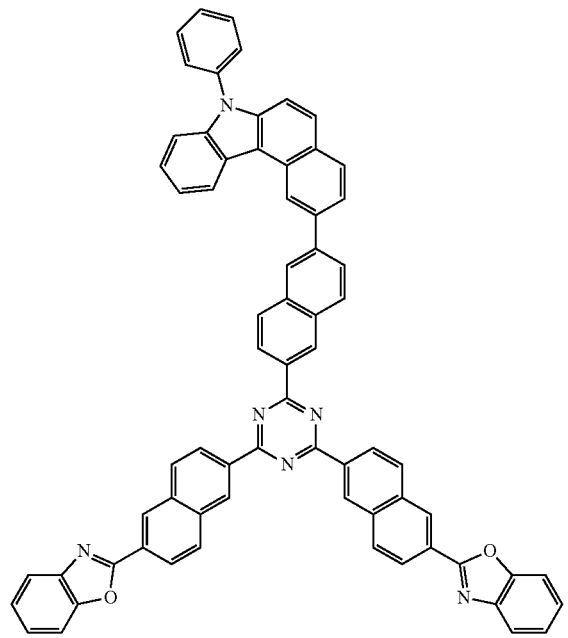
(343)
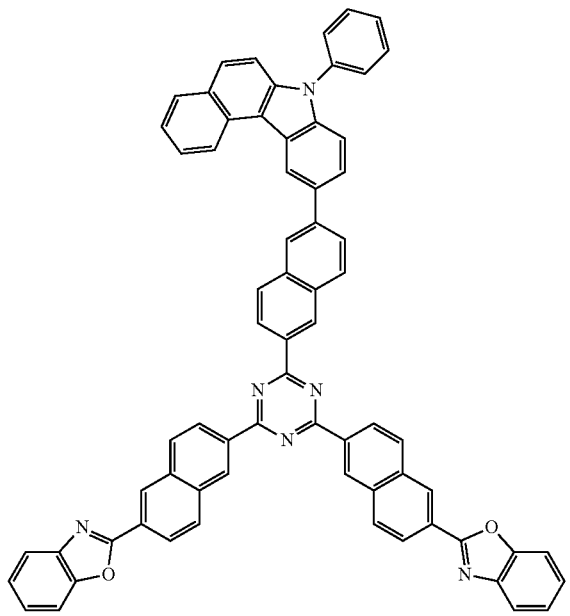
(344)
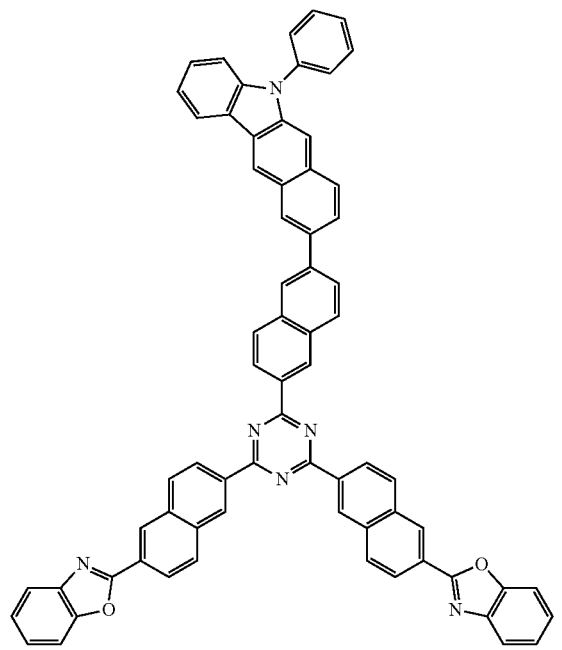
(345)
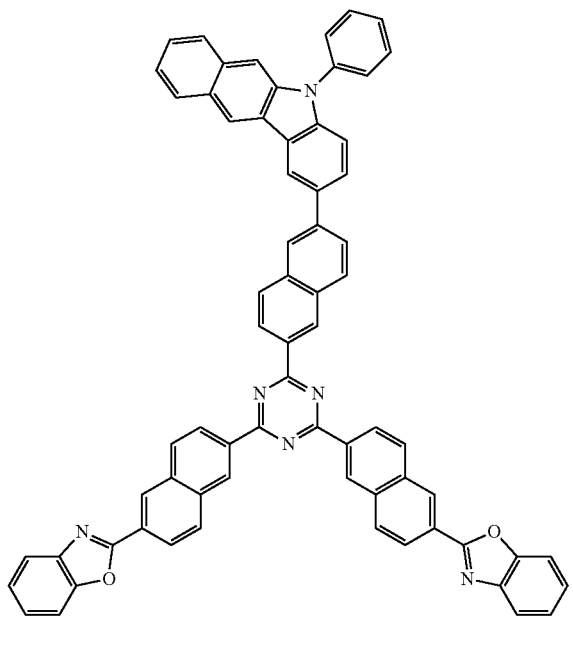

-continued
(346)
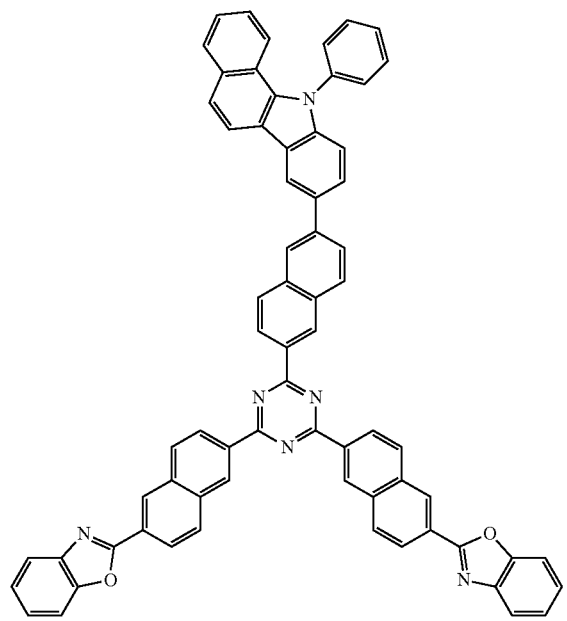
(347)
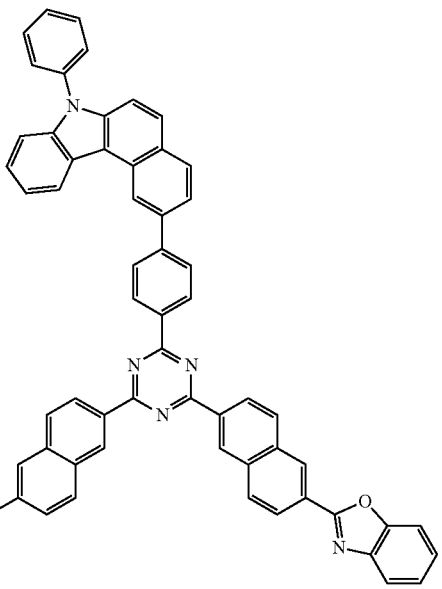
(348)
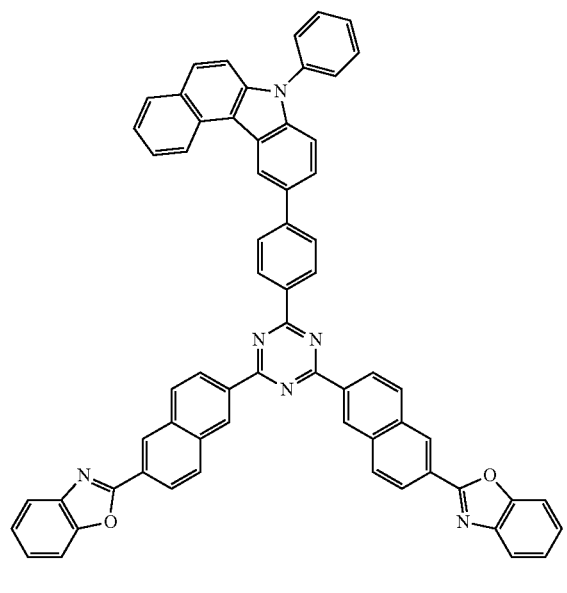
(349)
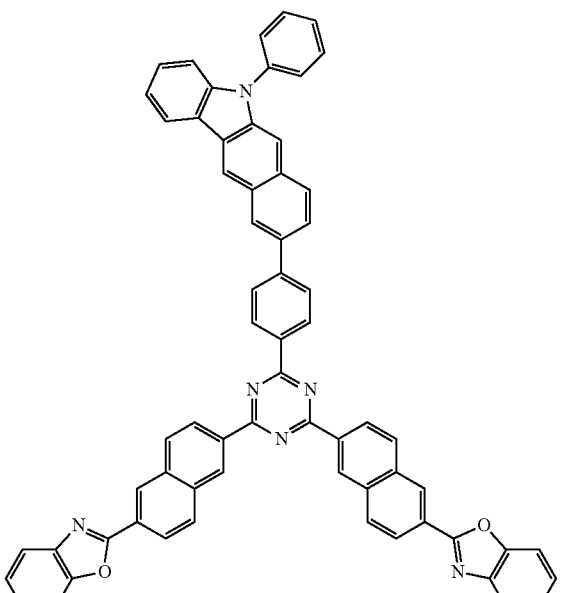

-continued
(350)
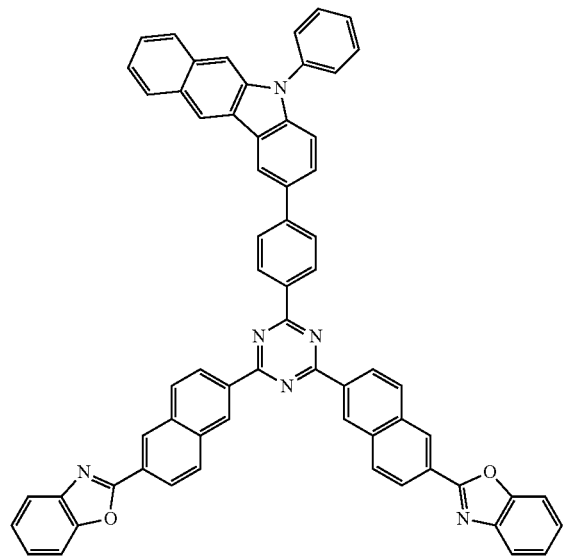
(351)
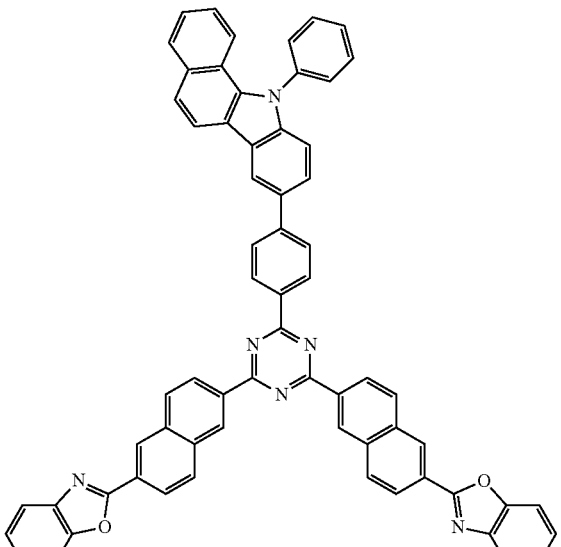
(352)
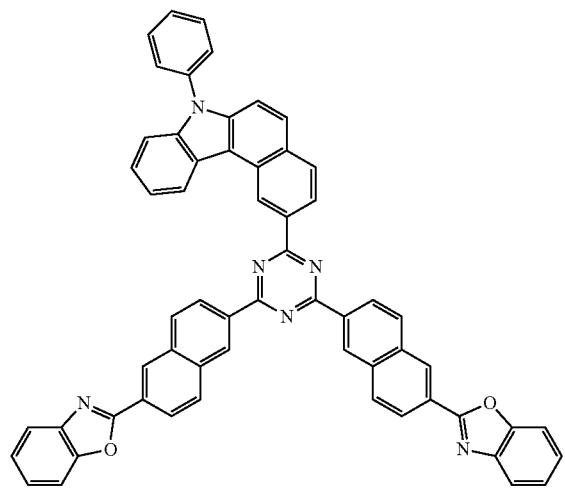
(353)
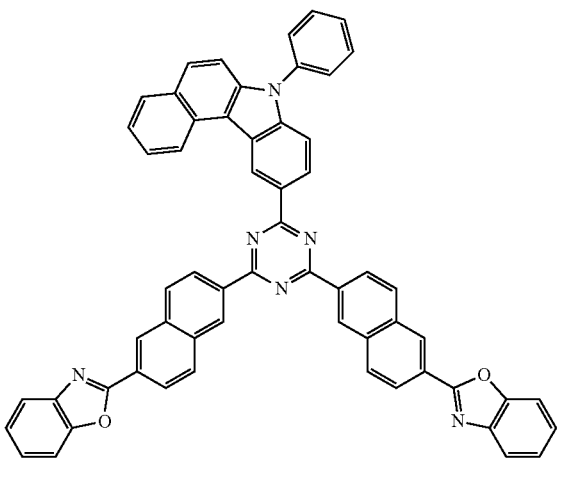
(354)
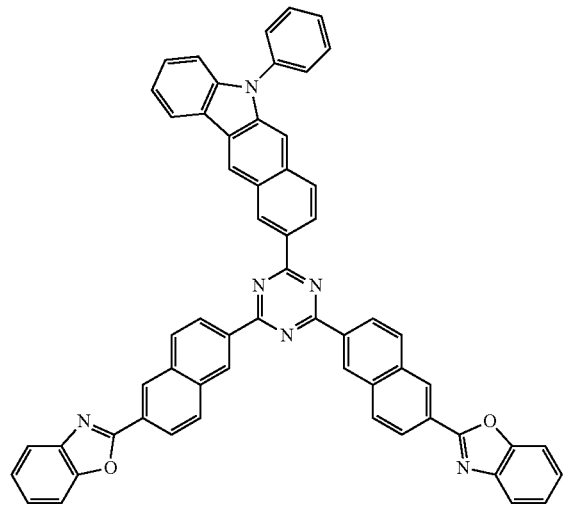
(355)
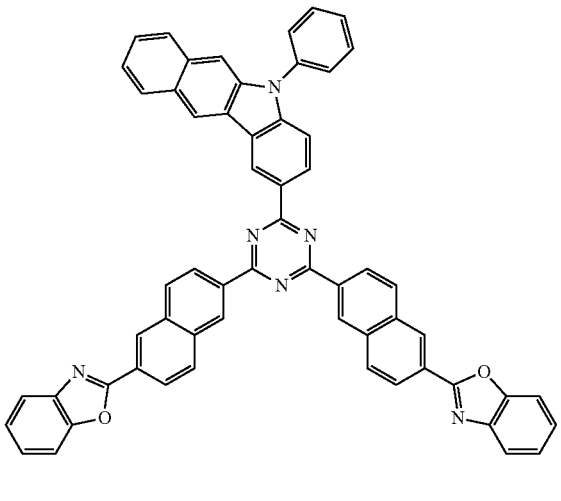

-continued
(356)
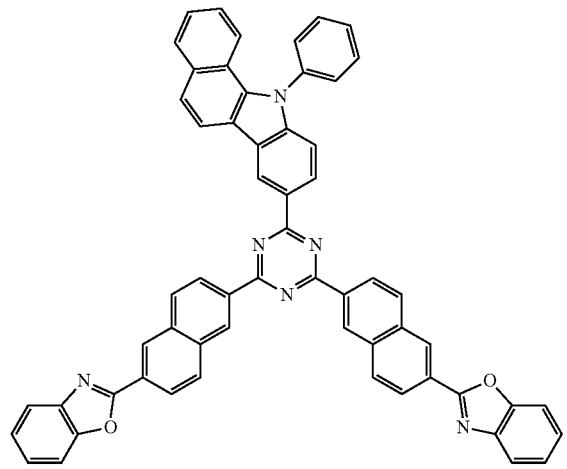
(357)
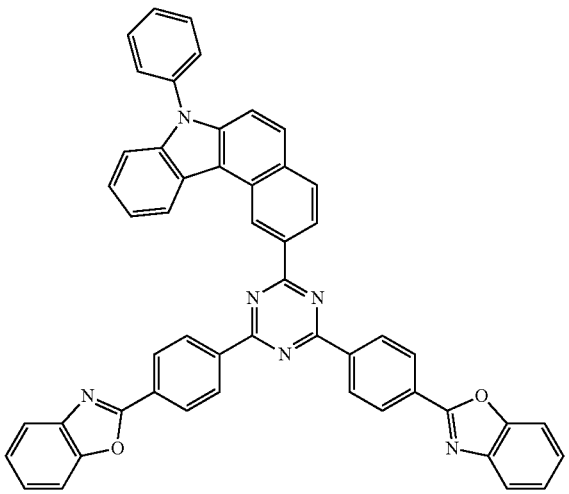
(358)
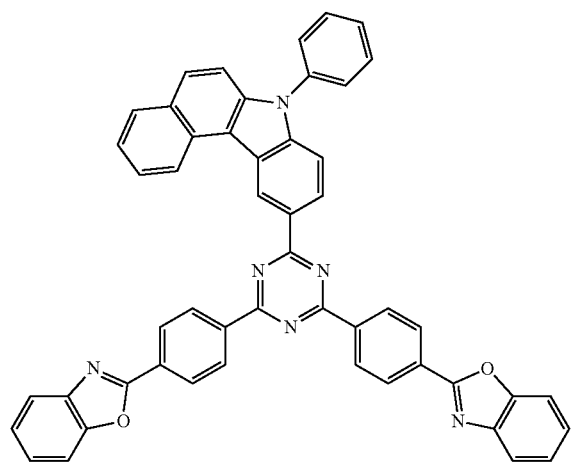
(359)
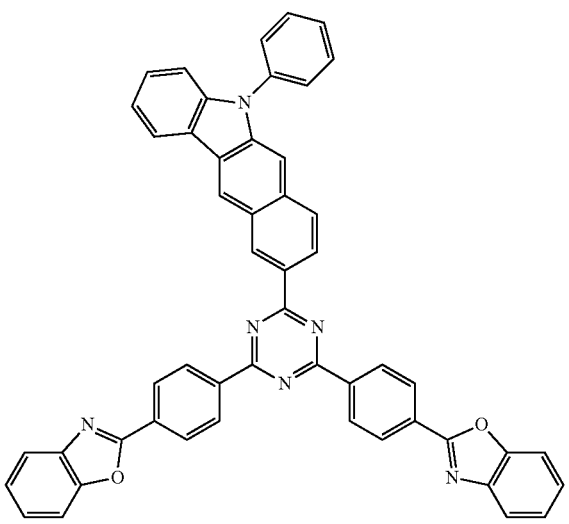
(360)
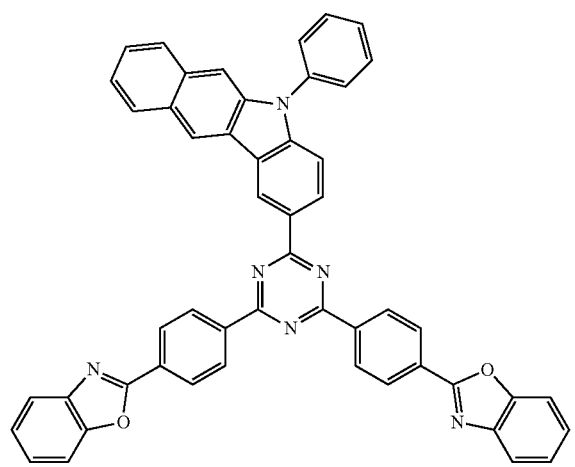
(361)
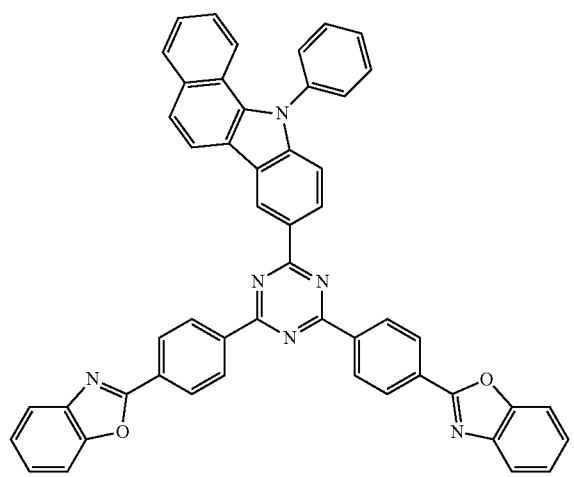

(362)
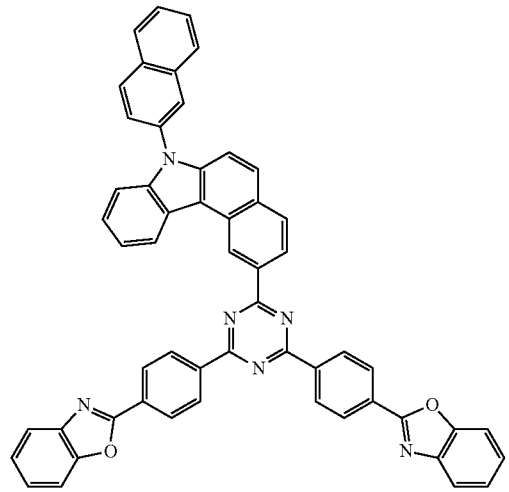
(363)
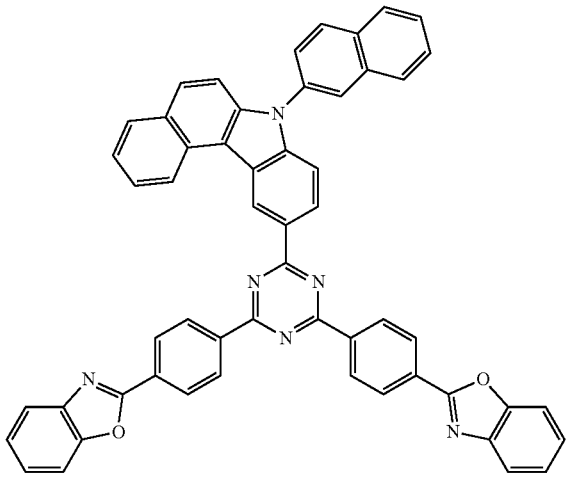
(364)
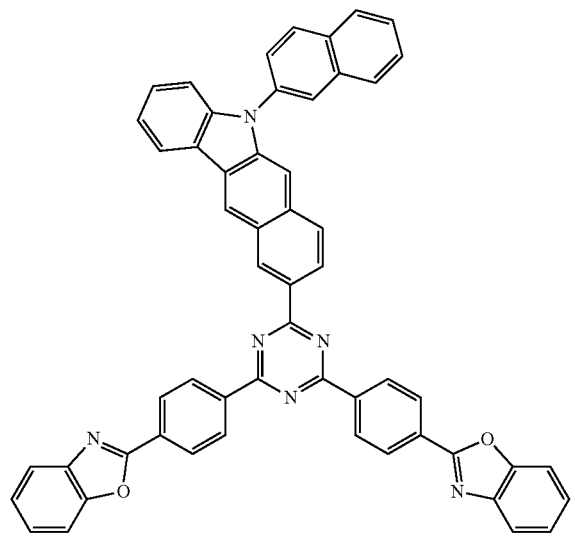
(365)
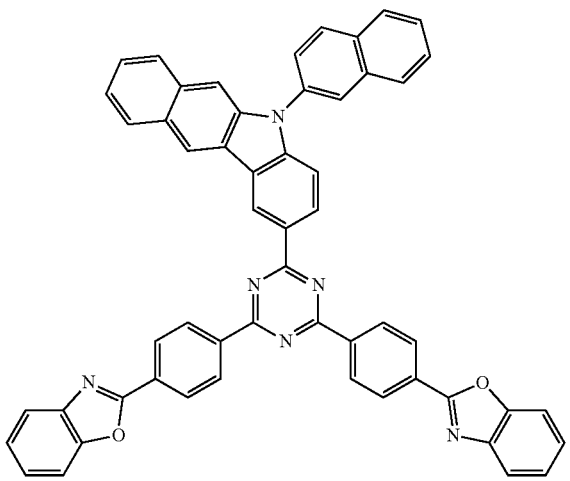

(366)
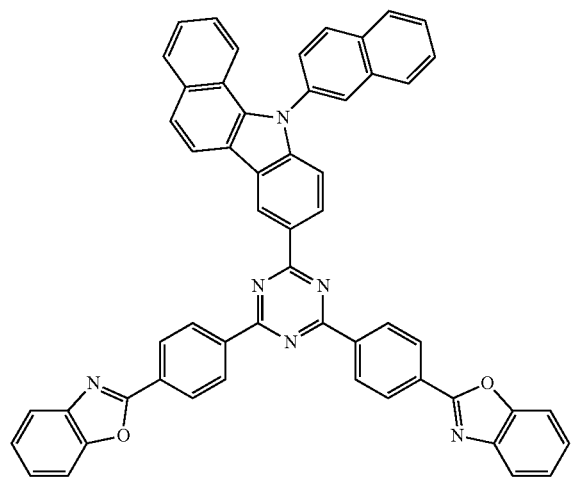
(367)
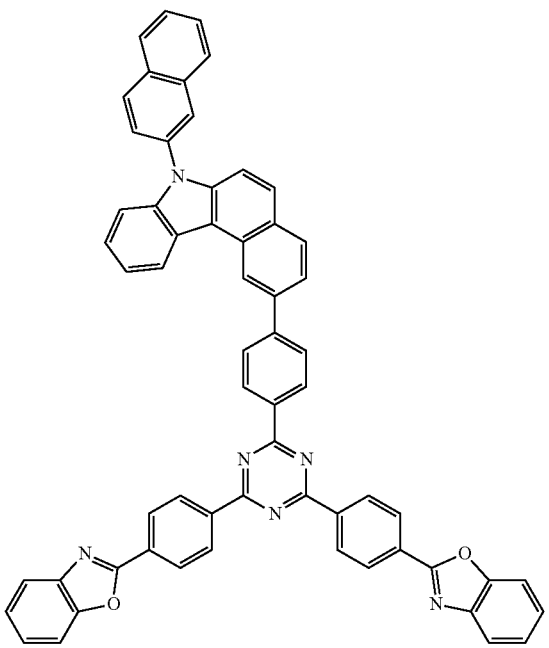
(368)
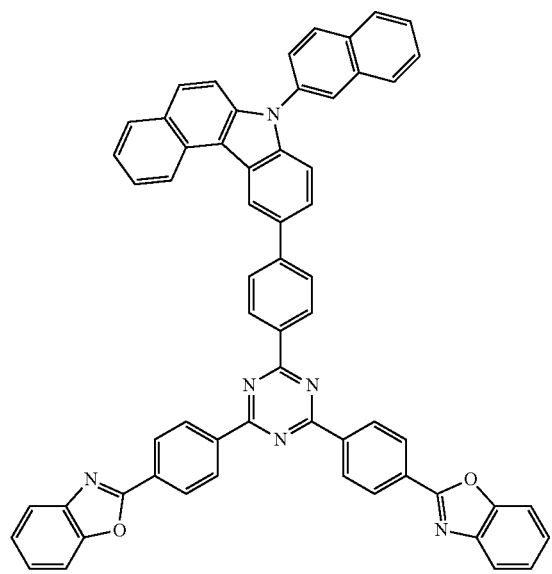
(369)
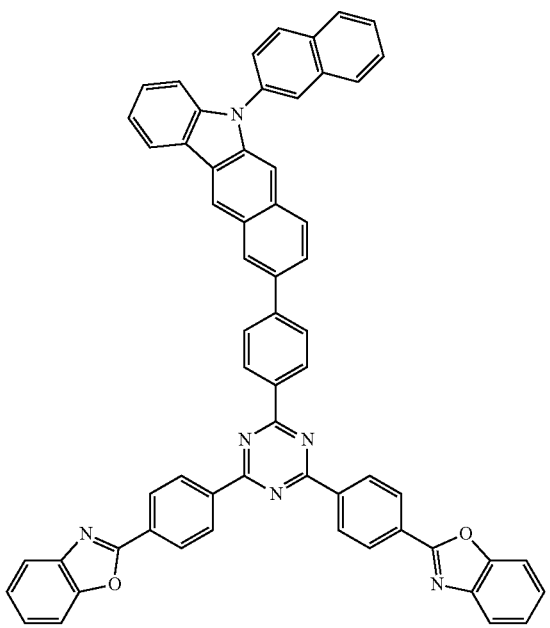

-continued
(370)
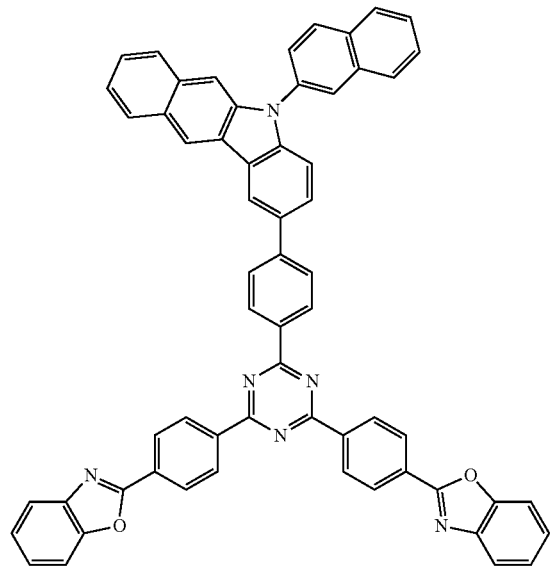
(371)
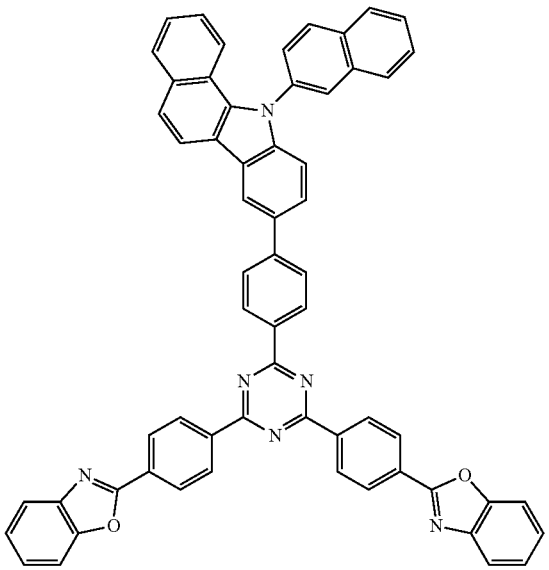
(372)
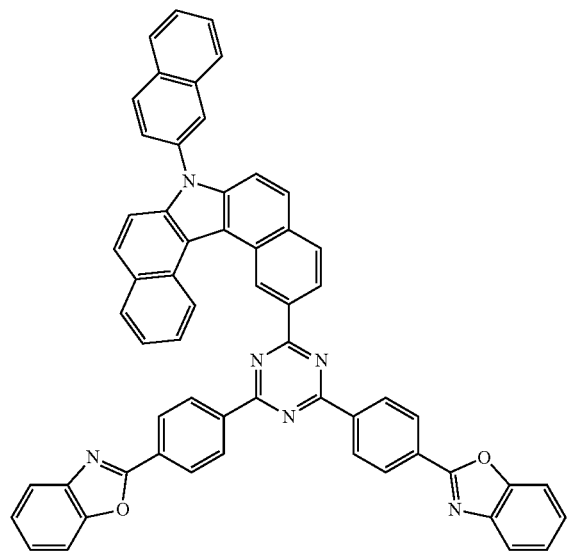
(373)
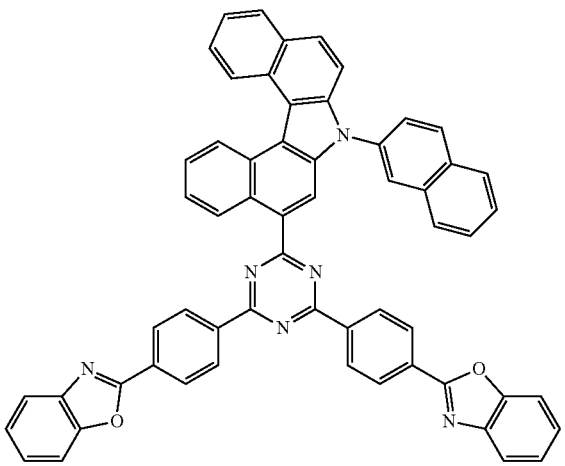

-continued
(374)
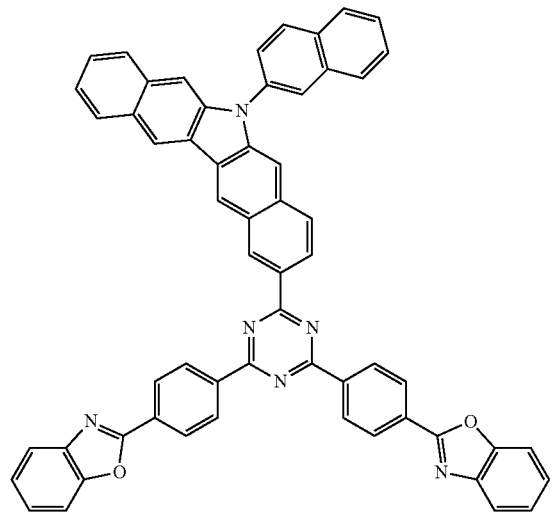
(375)
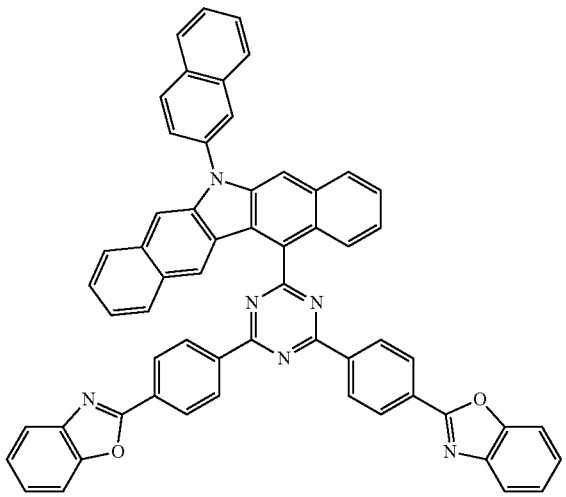
(376)
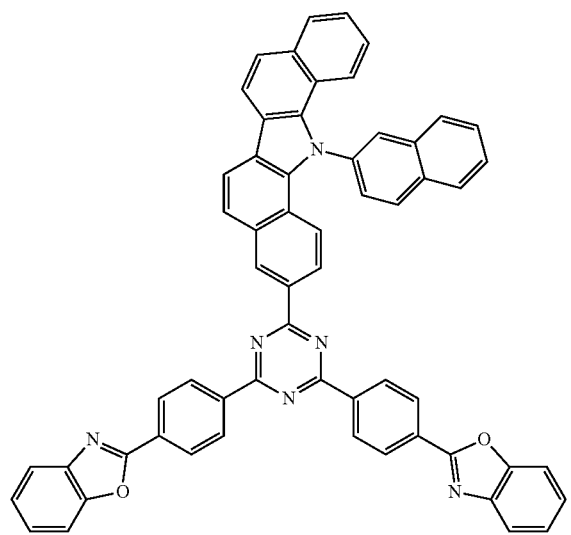
(377)
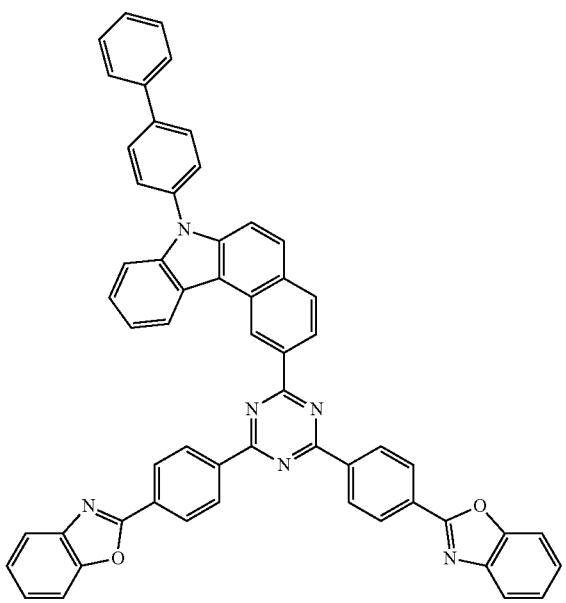

(378)
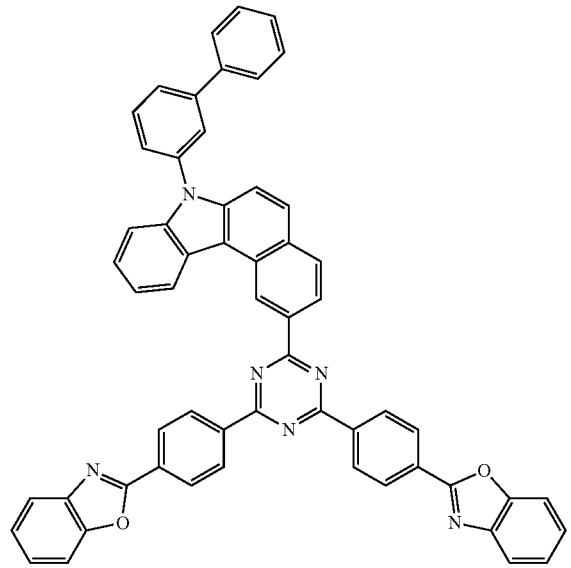
(379)
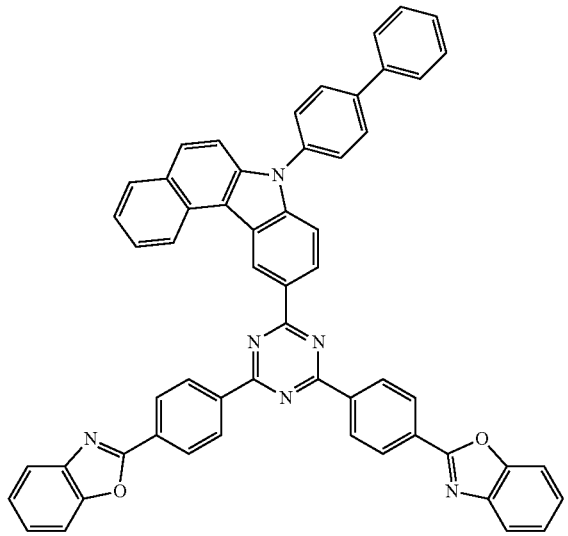
(380)
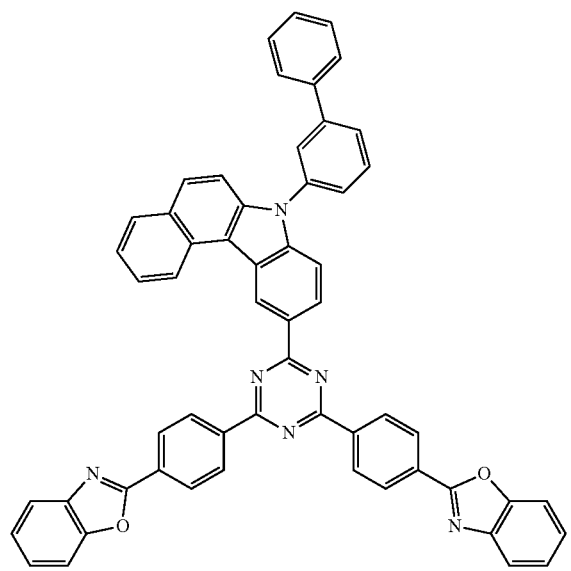
(381)
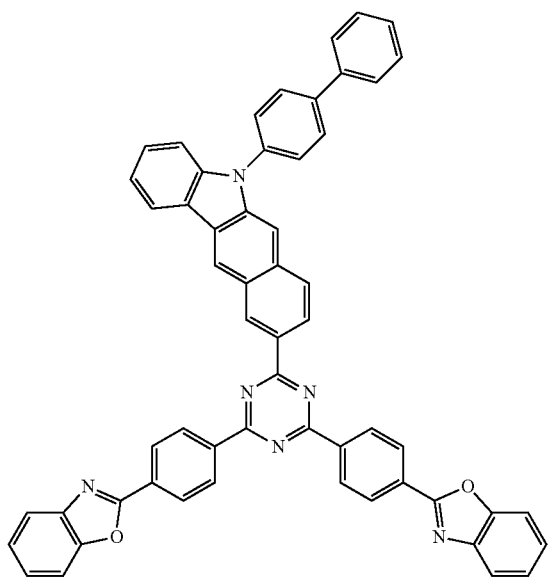

(382)
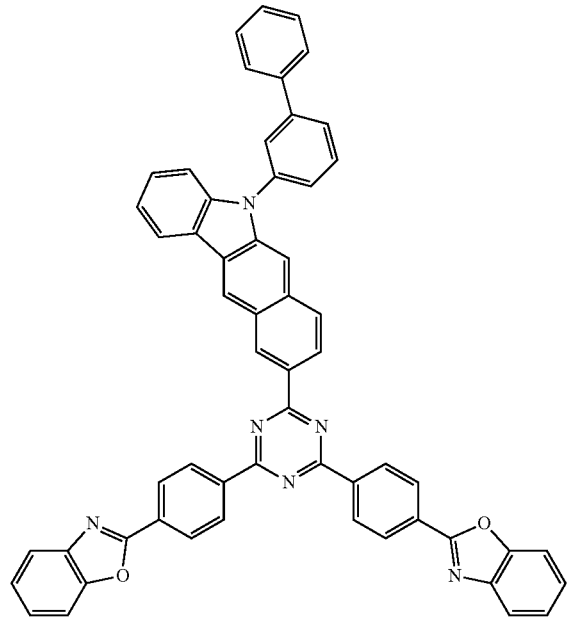
(383)
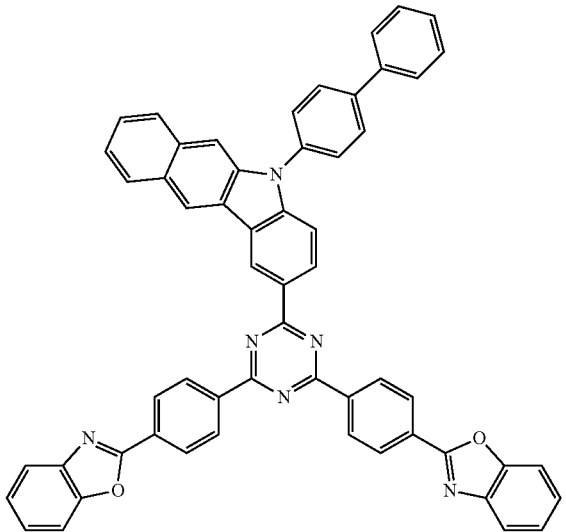
(384)
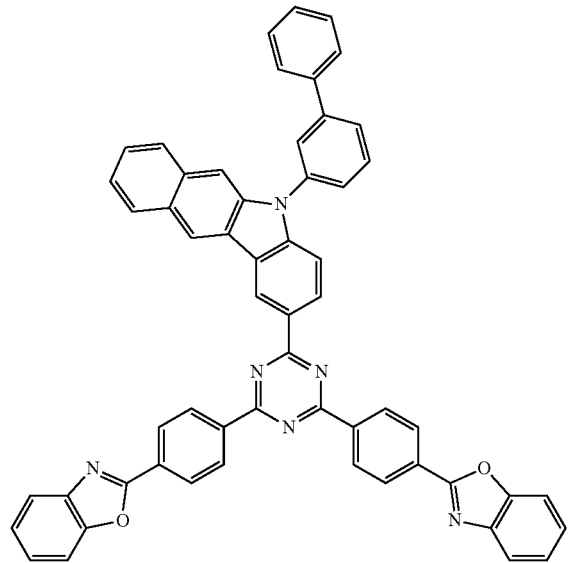
(385)
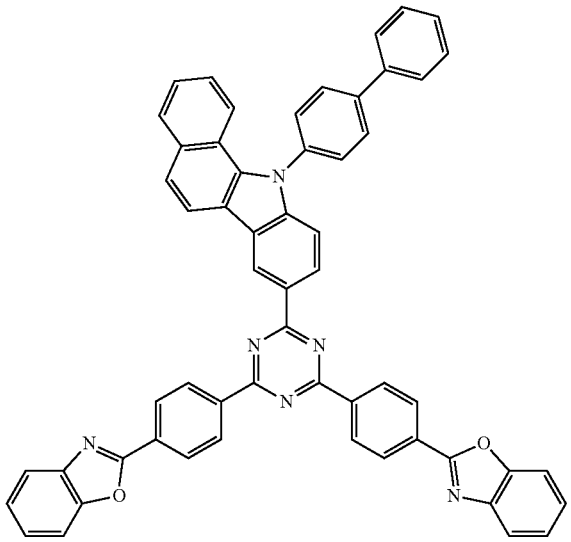

(386)
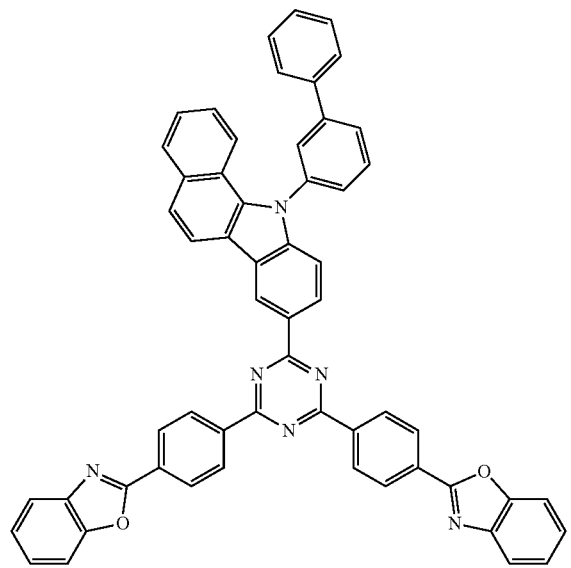
(387)
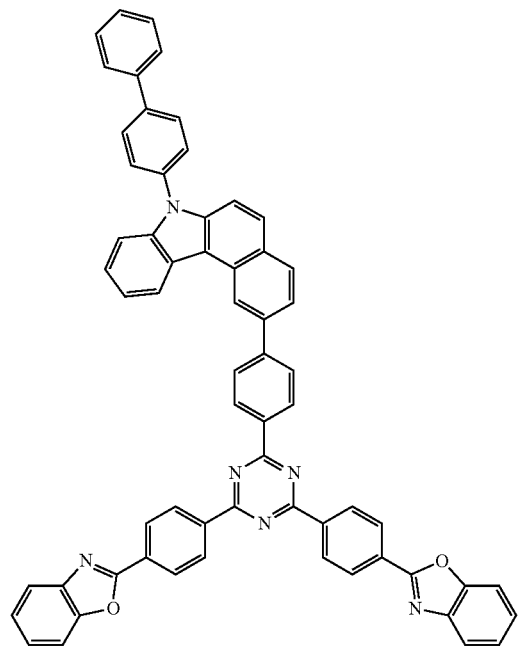
(388)
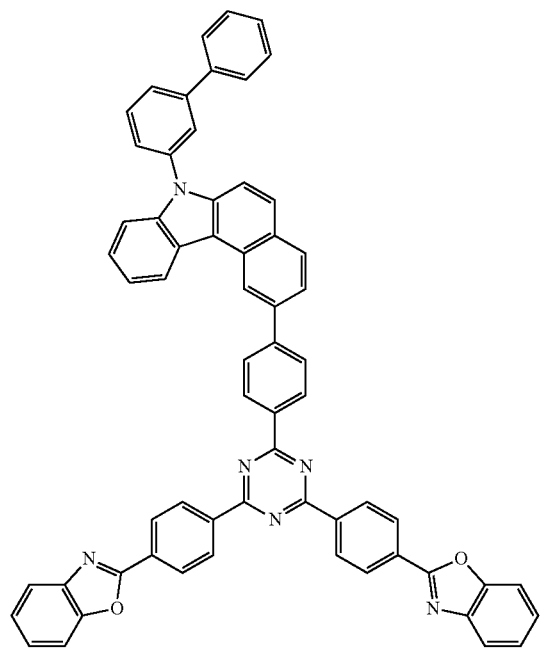
(389)
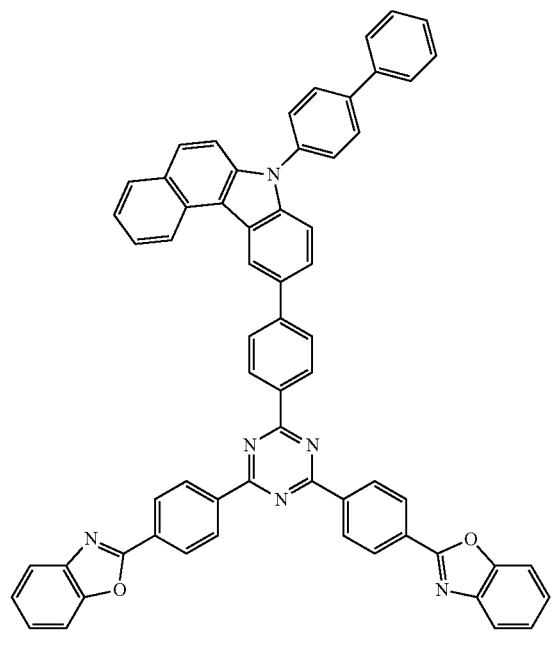

-continued
(390)
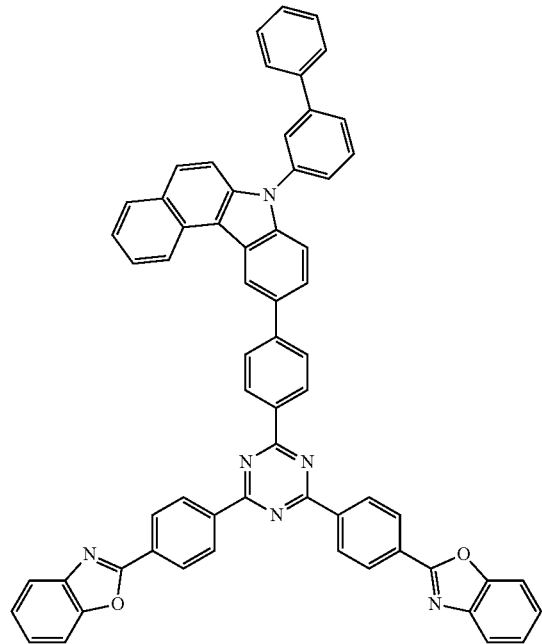
(391)
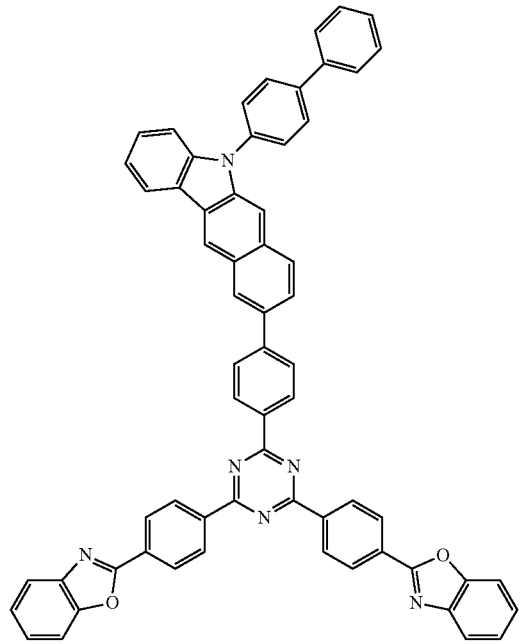
(392)
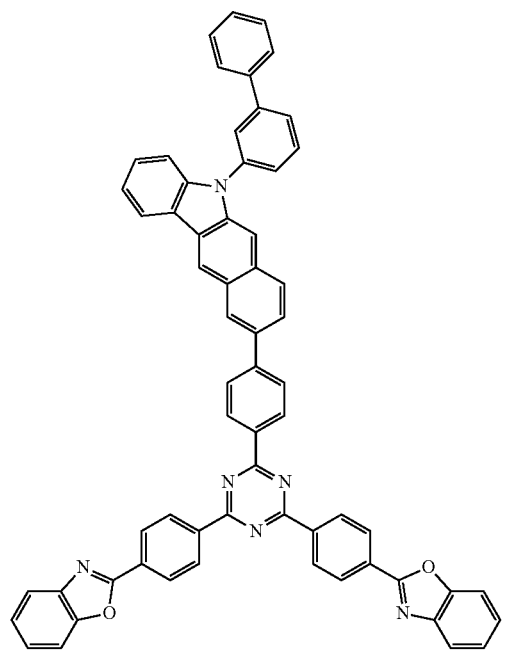
(393)
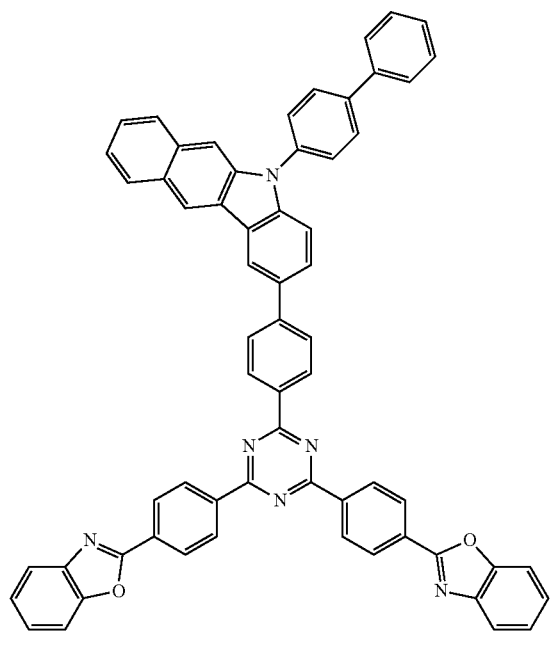

-continued
(394)
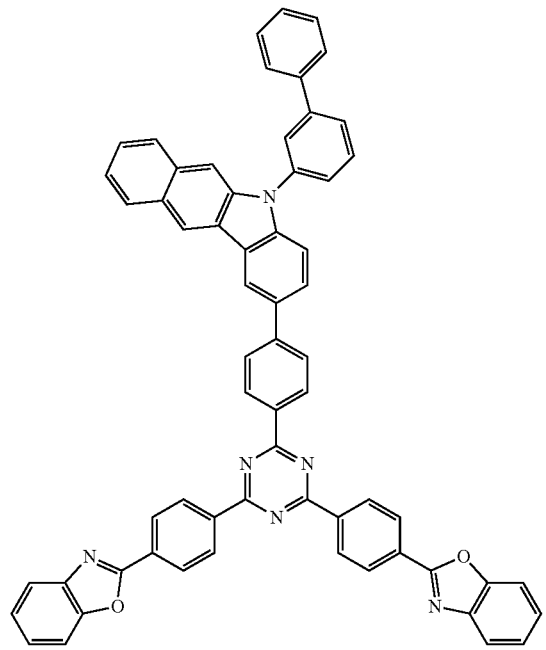
(395)
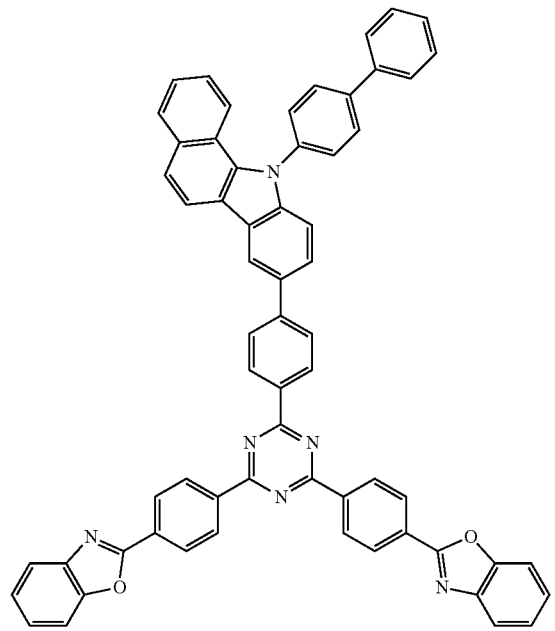
(396)
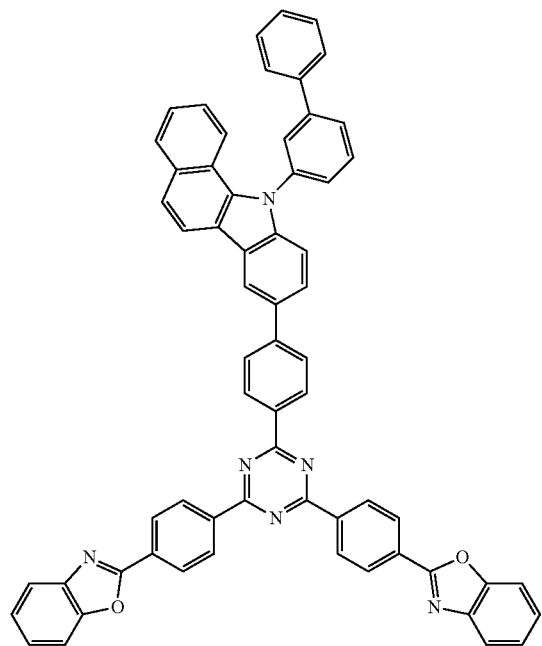
(397)
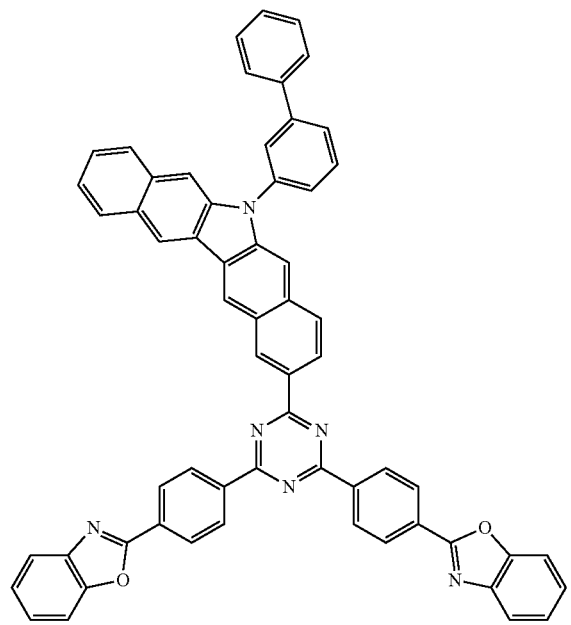

247
248
-continued
(398)
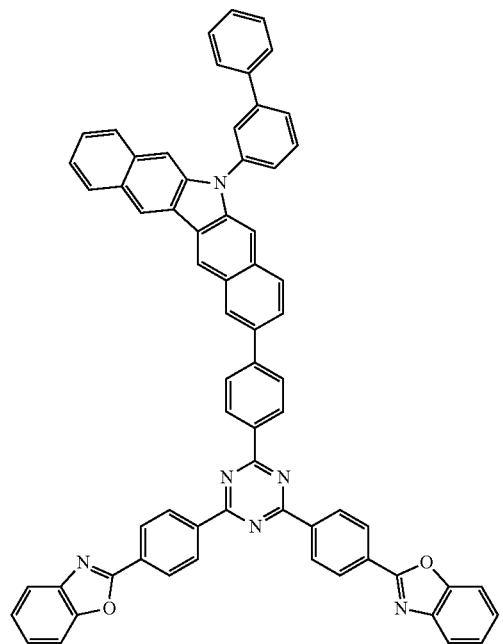
(399)
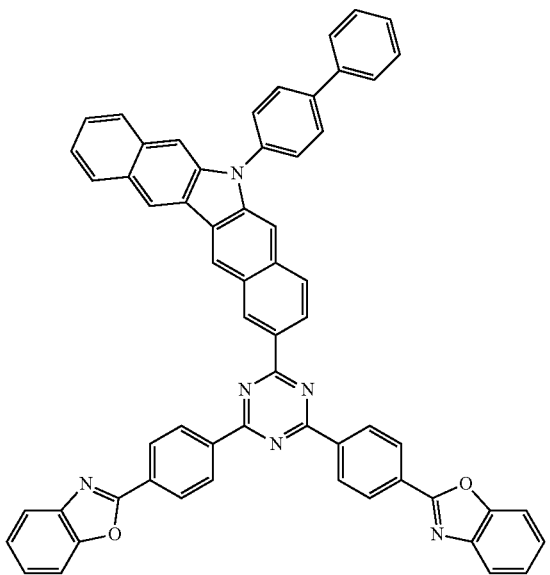
(400)
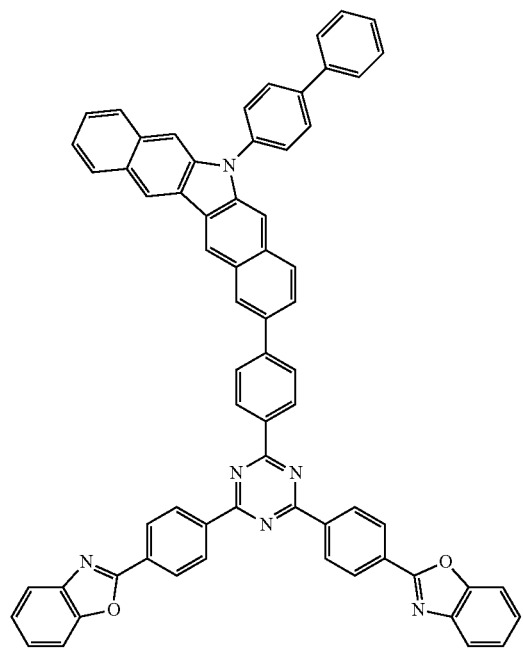
(401)
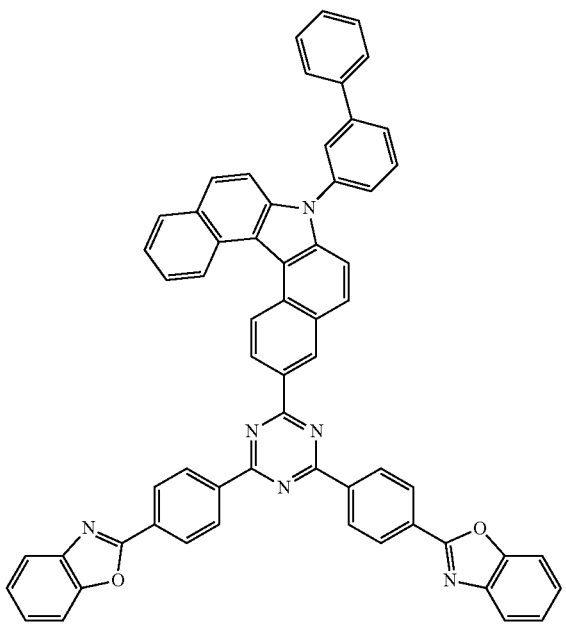

-continued
(402)
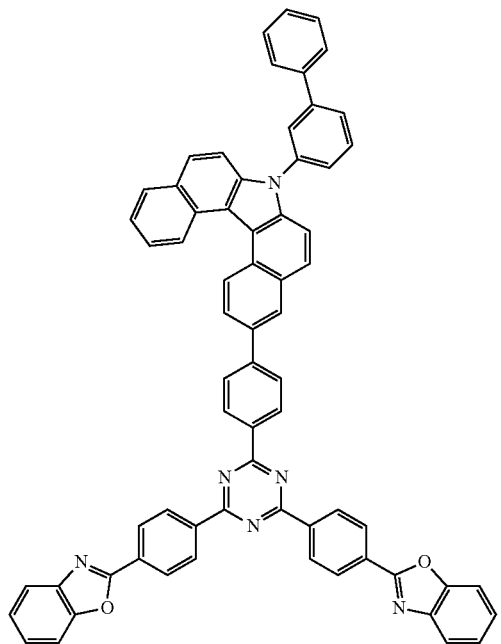
(403)
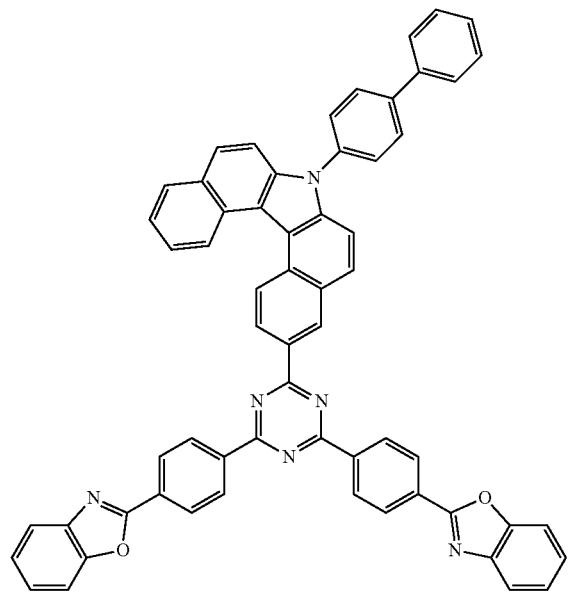
(404)
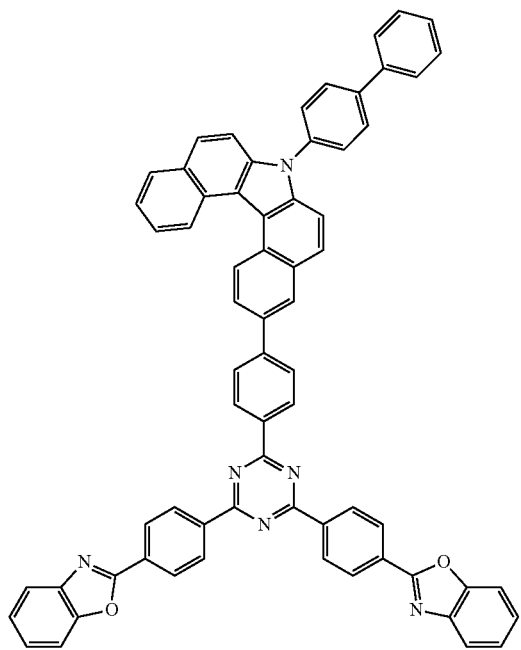
(405)
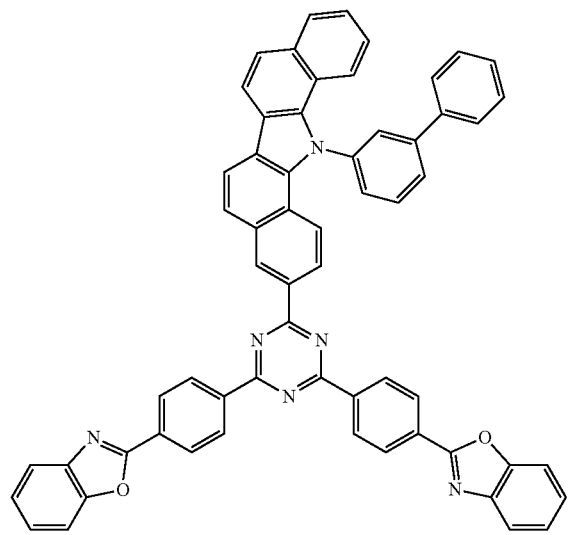

-continued
(406)
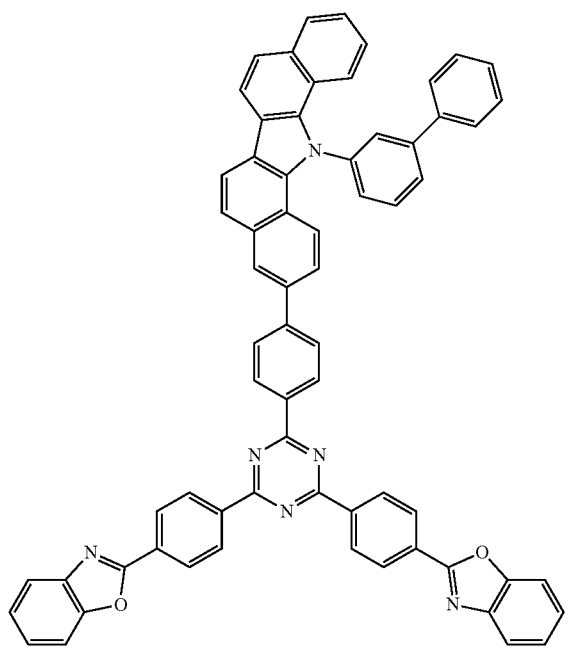
(407)
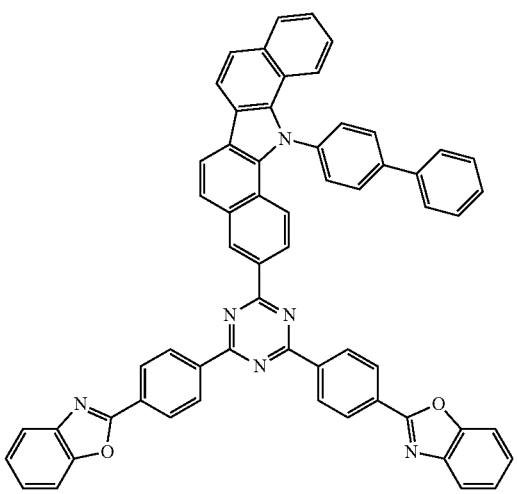
and
(408)
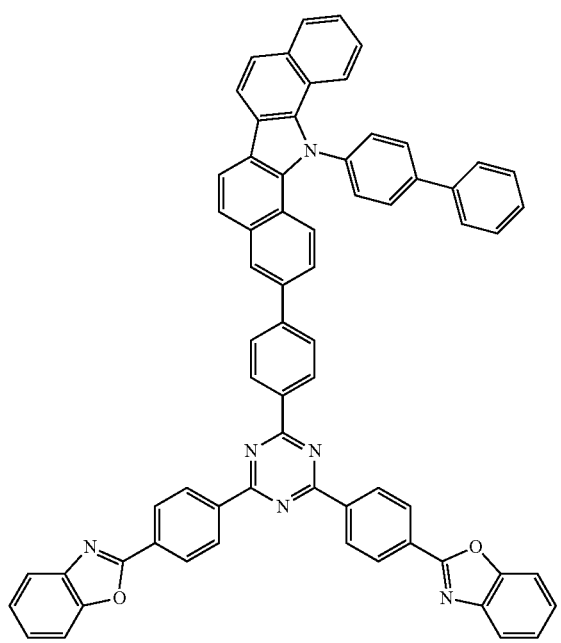
A preparation method of the organic compound, wherein reaction occurring in the preparation process follows an equation as follows:
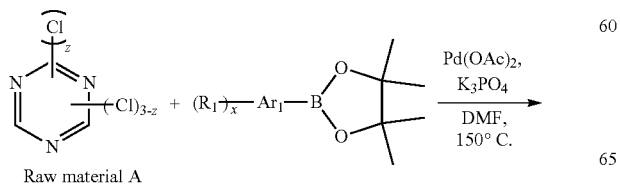
Raw material A
-continued
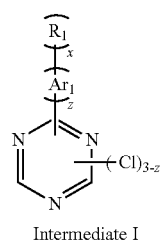
Intermediate I (1) in a nitrogen atmosphere, weighing and dissolving raw material A in DMF, then, adding

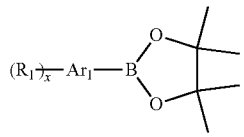

and palladium acetate, stirring the mixture and then adding an aqueous solution of potassium phosphate, heating and refluxing a mixed solution containing the above reactants for 5-15 hours at 120° C. to 150° C.; after completion of the reaction, cooling, adding water, filtering the mixture and drying in a vacuum oven, and purifying the resulting residue using a silica gel column to obtain a compound Intermediate I, wherein the molar ratio of raw material A to

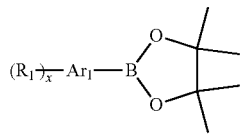

is 1:1.0-3, the molar ratio of palladium acetate to raw material A is 0.001-0.04:1, the molar ratio of potassium phosphate to raw material A is 1.0-4.0:1, and the dosage ratio of raw material A to DMF is 1 g:10-30 ml;

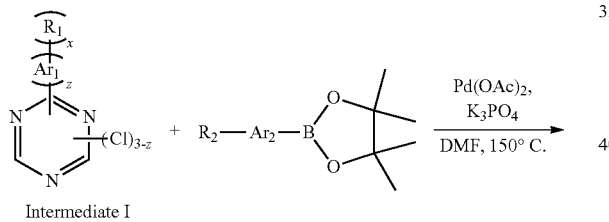

Intermediate I

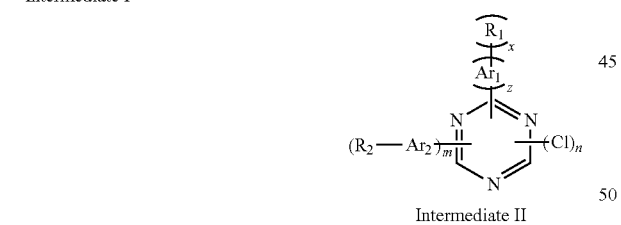

Intermediate II (2) in a nitrogen atmosphere, weighing and dissolving the Intermediate I in DMF, then, adding

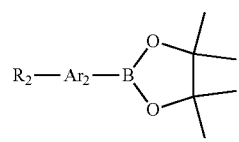

and palladium acetate, stirring the mixture and then adding an aqueous solution of potassium phosphate, heating and refluxing a mixed solution containing the above reactants for 10-24 hours at 120° C. to 150° C.; after completion of the reaction, cooling, adding water, filtering the mixture and drying in a vacuum oven, and purifying the resulting residue using a silica gel column to obtain a compound Intermediate II, wherein the molar ratio of Intermediate I to

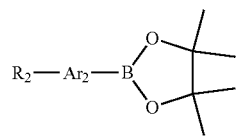

is 1:1.0-3, the molar ratio of palladium acetate to Intermediate I is 0.001-0.04:1, the molar ratio of potassium phosphate to Intermediate I is 1.0-4.0:1, and the dosage ratio of Intermediate I to DMF is 1 g:10-40 ml;

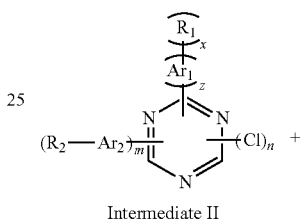

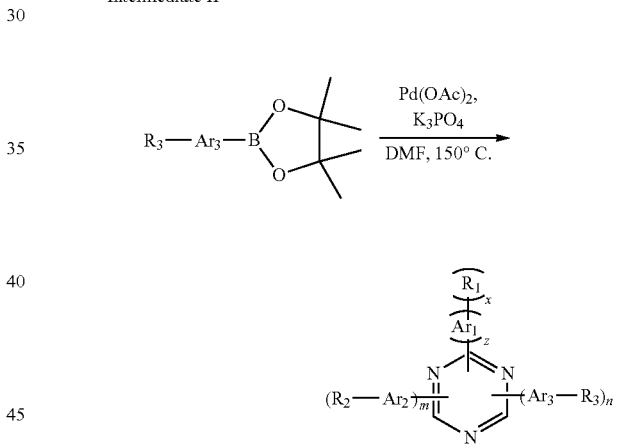

(3) in a nitrogen atmosphere, weighing and dissolving the Intermediate II in DMF, then, adding

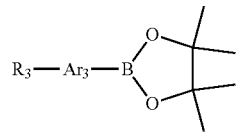

and palladium acetate, stirring the mixture and then adding an aqueous solution of potassium phosphate, heating and refluxing a mixed solution containing the above reactants for 10-24 hours at 120° C. to 150° C.; after completion of the reaction, cooling, adding water, filtering the mixture and drying in a vacuum oven, and purifying the resulting residue using a silica gel column to obtain a target compound, wherein the molar ratio of Intermediate II to

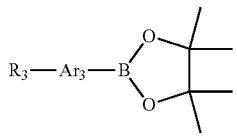

is 1:1.0-3, the molar ratio of palladium acetate to Intermediate II is 0.001-0.04:1, the molar ratio of potassium phosphate to Intermediate II is 1.0-4.0:1, and the dosage ratio of Intermediate II to DMF is 1 g:15-50 ml;

An application method of the organic compound based on triazine and benzoxazole in preparing an organic electroluminescent device.

An organic electroluminescent device containing the organic compound, wherein the organic electroluminescent device includes at least one functional layer containing the organic compound based on triazine and benzoxazole.

An organic electroluminescent device containing the organic compound, wherein the organic electroluminescent device includes a hole block layer or an electron transport layer, wherein, the hole block layer or the electron transport layer contains the organic compound based on triazine and benzoxazole.

An organic electroluminescent device containing the organic compound, wherein the organic electroluminescent device includes a capping layer, wherein the capping layer contains the organic compound based on triazine and benzoxazole.

A lighting or display element, including the organic electroluminescent device.

The present application achieves the following beneficial effects:

The structure of the organic compound of the present application contains two rigid groups of triazine and benzoxazole, and the structural stability of the material is improved; in spatial structure, the material of the present application contains strong electronic triazine and benzoxazole groups and the three groups are crossed and separated from each other to prevent the groups from rotating freely, so that the material has a higher density and achieves a higher refractive index; moreover, based on this, the material of the present application also has a very high Tg temperature; in addition, the evaporation temperature of the material is generally less than 350° C. in a vacuum state, ensuring that the material does not decompose during the long-time evaporation in the mass production process, and reducing the influence on the deformation of the evaporation MASK due to the heat radiation of the evaporation temperature.

The material of the present application is applied to the CPL layer of the OLED device, does not participate in the electron and hole transmission of the device, but is subjected to very high requirements on thermal stability, film crystallinity and light transmission (high refractive index). As described above, the triazine and benzoxazole are rigid groups, so that the stability of the material is improved; the high Tg temperature ensures that the material does not crystallize in the film state; the low evaporation temperature is the premise that the material can be applied to mass production; the high refractive index is the most major factor that the material of the present application can be applied to a CPL layer. The organic compound based on triazine and benzoxazole has a refractive index n≥2.1 between 430 nm and 470 nm in the blue light region.

With a deep HOMO energy level and a high electron mobility, the material of the present application can effectively block holes/energy from transmitting from a light-emitting layer to the electron layer, so that the recombination efficiency of the hole and the electron in the light-emitting layer can be improved, and thus the light-emitting efficiency of the OLED device can be enhanced and the service life of the OLED device can be prolonged. The prcan effectively improve the light extraction efficiency of the OLED device when applied to the CPL layer of the OLED device. To sum up, the compound of the present application has a good application effect and industrialization prospect in an OLED light-emitting device.

wherein, 1, an OLED device substrate, 2, an anode layer, 3, a hole injection layer, 4, a hole transport layer, 5, a light-emitting layer, 6, a hole block layer or an electron transport layer, 7, an electron injection layer, 8, a cathode layer, and 9, a CPL layer.

Figure 2:
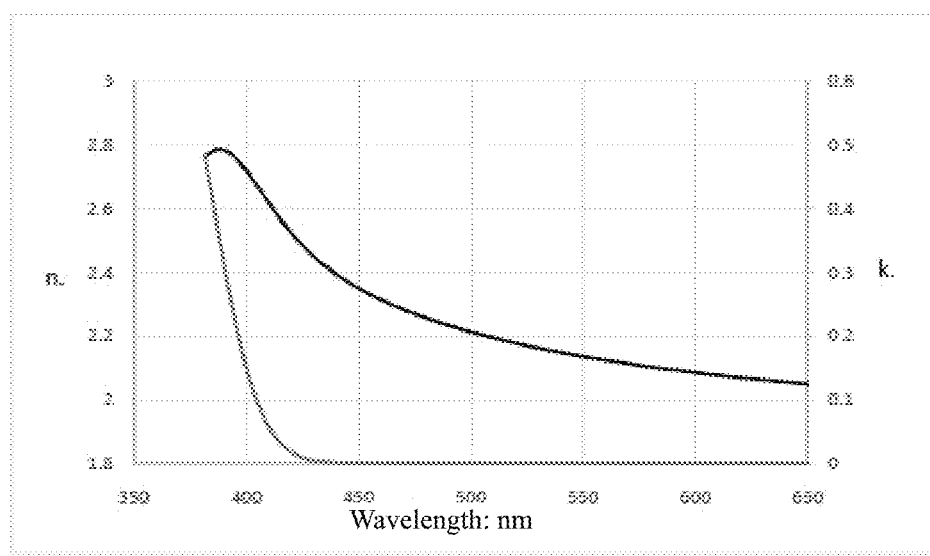
Figure 3:
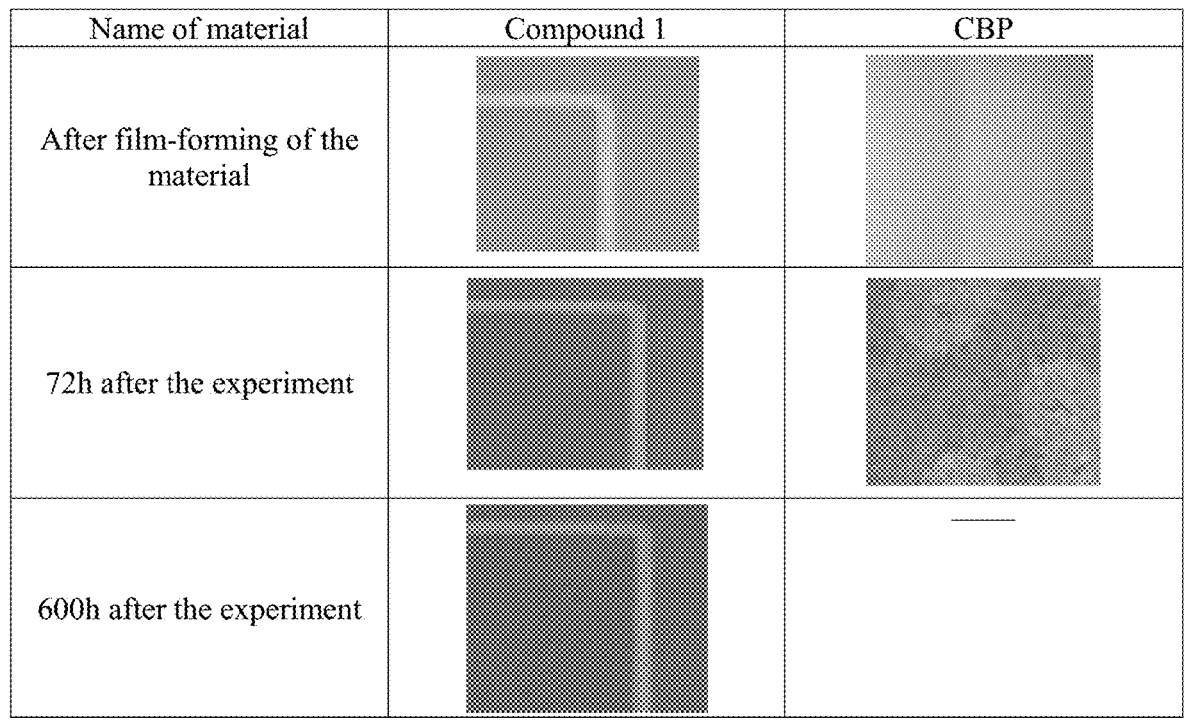
Figure 4:
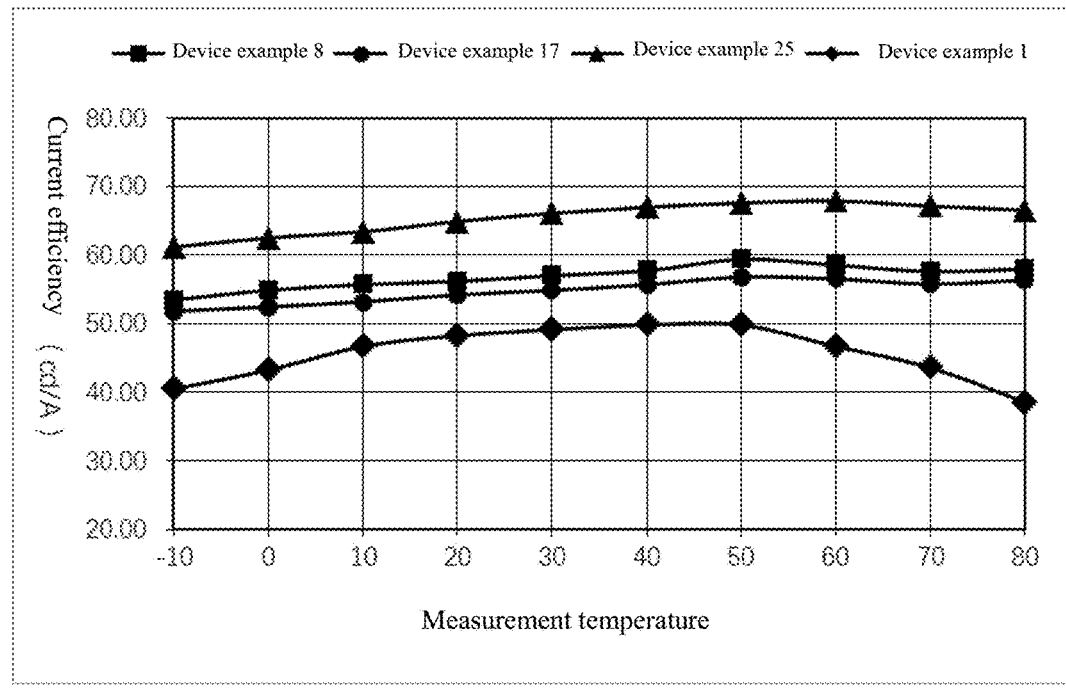

FIG. 2 is a refractive index test graph of compound 8;

FIG. 3 is a comparative diagram of film accelerated experiments between compound 1 and the known material CBP; and FIG. 4 is the efficiency curve of the device measured at different temperatures.

DETAILED DESCRIPTION OF THE EMBODIMENTS

Example 1: Synthesis of Intermediate A

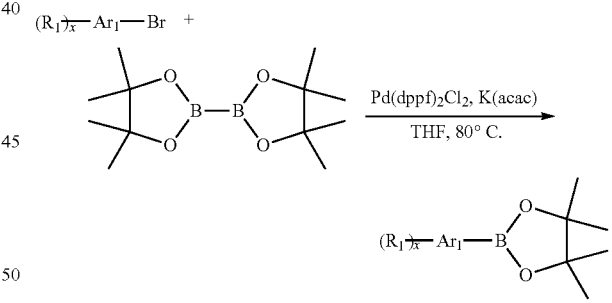

In a nitrogen atmosphere,

bromide was weighed and dissolved in tetrahydrofuran (THF), then, bis (pinacolyl) diboron, (1,1'-bis (diphenylphosphino) ferrocene) dichloropalladium (II) and potassium acetate were added, the mixture was stirred and mixed to be uniform, and the mixed solution containing the above reactants was heated and refluxed for 5-10 hours at a reaction temperature of 70 to 90° C.; after completion of the reaction, the reaction solution was added with water and cooled and then the mixture was filtered and dried in a vacuum oven. The resulting residue was separated and purified using a silica gel column to obtain a boronic acid pinacol ester of

the molar ratio of

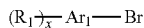

to bis (pinacolyl) diboron is 1:1.0-3, the molar ratio of Pd(dppf)$_2$Cl$_2$ to

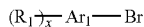

is 0.001-0.04:1, the molar ratio of potassium acetate to

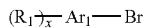

is 1.0-4.0:1, and the dosage ratio of

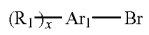

to THF is 1 g:10-30 ml.

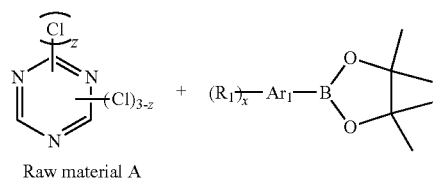
Raw material A

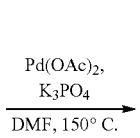

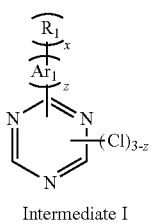
Intermediate I

In a nitrogen atmosphere, raw material A was weighed and dissolved in N, N-dimethylformamide (DMF), then,

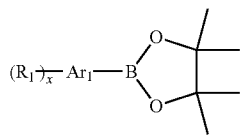

and palladium acetate were added, the mixture was stirred, an aqueous solution of potassium phosphate was then added, and the mixed solution containing the above reactants was heated and refluxed for 5-15 hours at a reaction temperature of 120° C. to 150° C.; after completion of the reaction, the reaction solution was cooled and added with water, the mixture was filtered and dried in a vacuum oven, and the resulting residue was purified using a silica gel column to obtain a compound Intermediate I;

The molar ratio of material A to

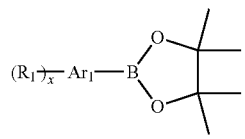

is 1:1.0-3, the molar ratio of Pd(OAc)$_2$ to material A is 0.001-0.04:1, the molar ratio of K$_3$PO$_4$ to material A is 1.0-4.0:1, and the dosage ratio of DMF to material A is 1 g:10-30 ml;

Taking the synthesis of Intermediate A1 as an example:

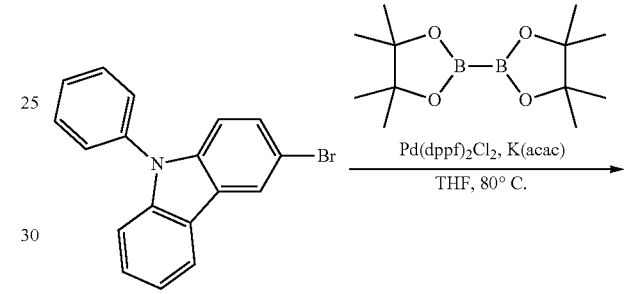
Intermediate D1

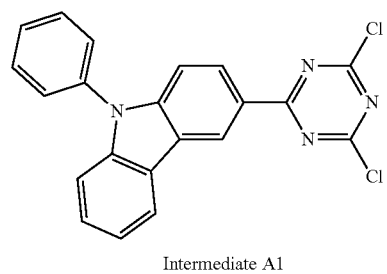
Intermediate A1

(1) In a 250 ml three-necked flask, nitrogen gas was introduced, 0.02 mol of an Intermediate 3-bromo-9-phenyl-9H-carbazole was added to and dissolved in 100 ml of THF, 0.024 mol of bis (pinacolyl) diboron, 0.0002 mol of (1,1'-bis (diphenylphosphino) ferrocene) dichloropalladium (II) and 0.05 mol of potassium acetate were added, the mixture was stirred, the mixed solution of the above reactants was heated and refluxed for 5 hours at a reaction temperature of 80° C.; after completion of the reaction, the reaction solution was cooled and added with 100 ml of water, and the mixture was filtered and dried in a vacuum oven. The resulting residue was separated and purified using a silica gel column to obtain an Intermediate D1. The purity of the product by HPLC was 99.8%, and the yield was 90.5%.

Elemental analysis structure (molecular formula $C_{24}H_{24}BNO_2$): theoretical values: C, 78.06; H, 6.55; B, 2.93; N, 3.79; O, 8.67; test values: C, 78.09; H, 6.56; B, 2.91; N, 3.76; O, 8.68. ESI-MS(m/z)(M$^+$): the theoretical value is 369.19, and the test value is 369.27.

(2) In a 250 ml three-necked flask, nitrogen gas was introduced, 0.02 mol of raw material 2,4,6-trichloro-1,3,5-triazine, 150 ml of DMF, 0.024 mol of Intermediate D1, and 0.0002 mol of palladium acetate were added, the mixture was stirred, 0.03 mol of the aqueous solution of $K_3PO_4$ was added, and the mixed solution was heated to 130° C. and refluxed for 10 hours, sampled and spotted until completion of the reaction. The mixed solution was cooled naturally and added with water, and the mixture was filtered and dried in a vacuum dryer; the resulting residue was purified using a silica gel column to obtain a compound Intermediate A1. The purity of the product by HPLC was 99.6%, and the yield was 73.3%.

Elemental analysis structure (molecular formula $C_{21}H_2Cl_2N_4$): theoretical values: C, 64.47; H, 3.09; Cl, 18.12; N, 14.32; test values: C, 64.45; H, 3.07; Cl, 18.16; N, 14.34. ESI-MS(m/z)(M$^+$): the theoretical value is 390.04, and the test value is 390.13. Taking the synthesis of Intermediate A12 as an example:

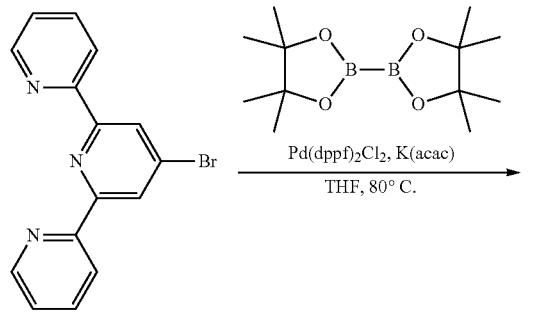

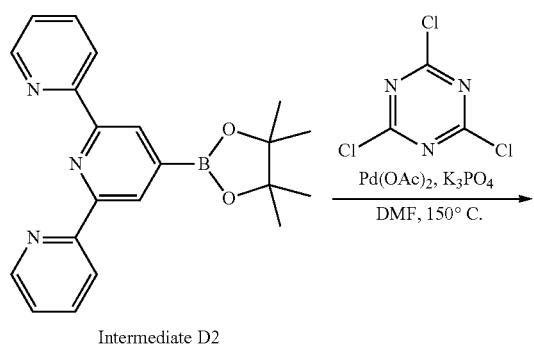

Intermediate D2

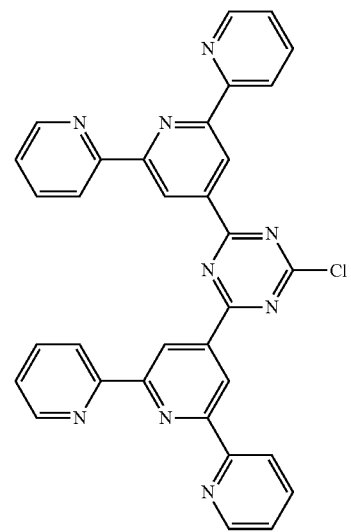

Intermediate A12

(1) In a 250 ml three-necked flask, nitrogen gas was introduced, 0.02 mol of an Intermediate 4'-bromo-2,2':6',2'-terpyridine was added to and dissolved in 100 ml of THF, 0.024 mol of bis (pinacolyl) diboron, 0.0002 mol of (1,1'-bis (diphenylphosphino) ferrocene) dichloropalladium (II) and 0.05 mol of potassium acetate were added, the mixture was stirred, the mixed solution of the above reactants was heated and refluxed for 5 hours at a reaction temperature of 80° C.; after completion of the reaction, the reaction solution was cooled and added with 100 ml of water, and the mixture was filtered and dried in a vacuum oven. The resulting residue was separated and purified using a silica gel column to obtain an Intermediate D2. The purity of the product by HPLC was 99.8%, and the yield was 88.5%.

Elemental analysis structure (molecular formula $C_{21}H_{22}BN_3O_2$): theoretical values: C, 70.21; H, 6.17; B, 3.00; N, 11.70; O, 8.91; test values: C, 70.23; H, 6.14; B, 3.01; N, 11.70; O, 8.92. ESI-MS(m/z)(M$^+$): the theoretical value is 359.18, and the test value is 359.24.

(2) In a 250 ml three-necked flask, nitrogen gas was introduced, 0.02 mol of raw material 2,4,6-trichloro-1,3,5-triazine, 150 ml of DMF, 0.048 mol of Intermediate D2, and 0.0002 mol of palladium acetate were added, the mixture was stirred, 0.03 mol of the aqueous solution of $K_3PO_4$ was added, and the mixed solution was heated to 130° C. and refluxed for 10 hours, sampled and spotted until completion of the reaction. The mixed solution was cooled naturally and added with water, and the mixture was filtered and dried in a vacuum dryer; the resulting residue was purified using a silica gel column to obtain a compound Intermediate A12. The purity of the product by HPLC was 99.5%, and the yield was 78.3%.

Elemental analysis structure (molecular formula $C_{33}H_2ClN_9$): theoretical values: C, 68.57; H, 3.49; Cl, 6.13; N, 21.81; test values: C, 68.55; H, 3.47; Cl, 6.15; N, 21.84. ESI-MS(m/z)(M⁺): the theoretical value is 577.15, and the test value is 577.23. Taking the synthesis of Intermediate A20 as an example:

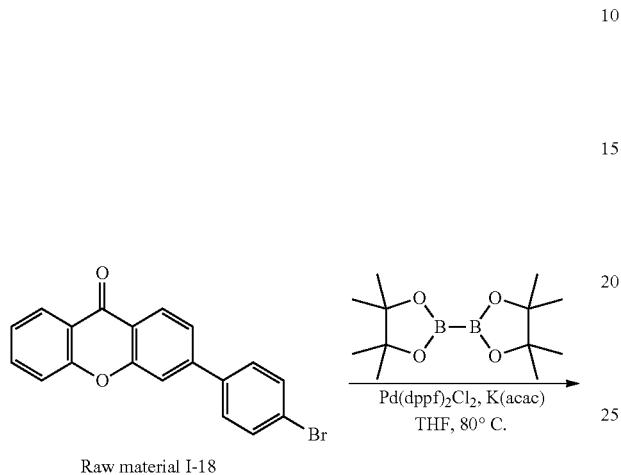

Raw material I-18

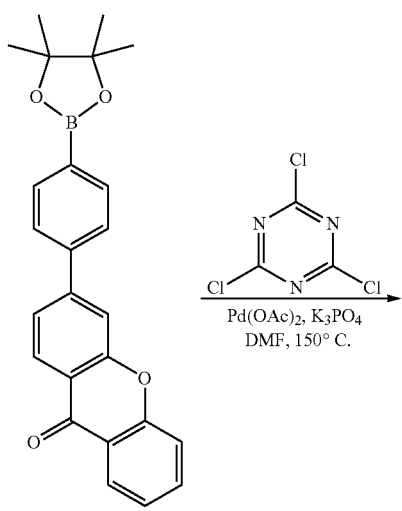

Intermediate D3

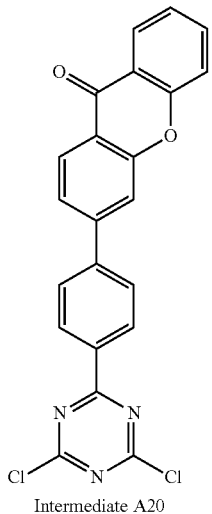

Intermediate A20

(1) In a 250 ml three-necked flask, nitrogen gas was introduced, 0.02 mol of raw material I-18 was added to and dissolved in 100 ml of THF, 0.024 mol of bis (pinacolyl) diboron, 0.0002 mol of (1,1'-bis (diphenylphosphino) ferrocene) dichloropalladium (II) and 0.05 mol of potassium acetate were added, the mixture was stirred, the mixed solution of the above reactants was heated and refluxed for 5 hours at a reaction temperature of 80° C.; after completion of the reaction, the reaction solution was cooled and added with 100 ml of water, and the mixture was filtered and dried in a vacuum oven. The resulting residue was separated and purified using a silica gel column to obtain an Intermediate D3. The purity of the product by HPLC was 99.4%, and the yield was 88.7%.

Elemental analysis structure (molecular formula $C_{25}H_{23}BO_4$): theoretical values: C, 75.40; H, 5.82; B, 2.71; O, 16.07; test values: C, 75.41; H, 5.85; B, 2.69; O, 16.05. ESI-MS(m/z)(M⁺): the theoretical value is 398.17, and the test value is 398.34.

(2) In a 250 ml three-necked flask, nitrogen gas was introduced, 0.02 mol of raw material 2,4,6-trichloro-1,3,5-triazine, 150 ml of DMF, 0.024 mol of Intermediate D3, and 0.0002 mol of palladium acetate were added, the mixture was stirred, 0.03 mol of the aqueous solution of $K_3PO_4$ was added, and the mixed solution was heated to 130° C. and refluxed for 12 hours, sampled and spotted until completion of the reaction. The mixed solution was cooled naturally and added with water, and the mixture was filtered and dried in a vacuum dryer; the resulting residue was purified using a silica gel column to obtain a compound Intermediate A20. The purity of the product by HPLC was 99.2%, and the yield was 70.5%.

Elemental analysis structure (molecular formula $C_{22}H_{11}Cl_2N_3O_2$): theoretical values: C, 62.88; H, 2.64; Cl, 16.87; N, 10.00; test values: C, 62.86; H, 2.67; Cl, 16.85; N, 10.02. ESI-MS(m/z)(M⁺): the theoretical value is 419.02, and the test value is 419.33.

Intermediate A was prepared by the synthesis method of Intermediates A1, A12 and A20. The specific structures are shown in Table 1.

TABLE 1

| Raw material I | Raw material II | Intermediate A |
|---|---|---|
| 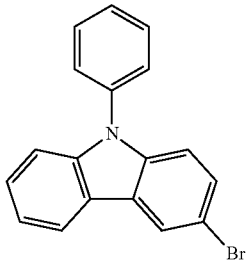<br>Raw material I-1 | 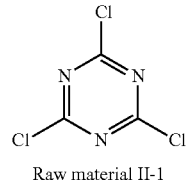<br>Raw material II-1 | 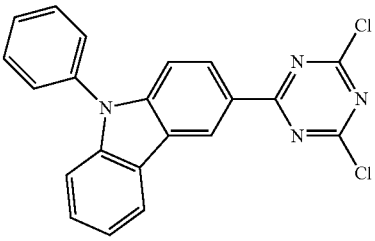<br>Intermediate A1 |
| 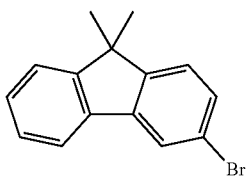<br>Raw material I-2 | 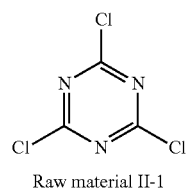<br>Raw material II-1 | 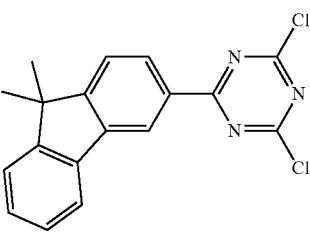<br>Intermediate A2 |
| 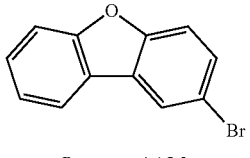<br>Raw material I-3 | 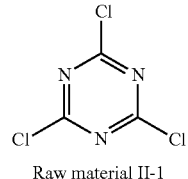<br>Raw material II-1 | 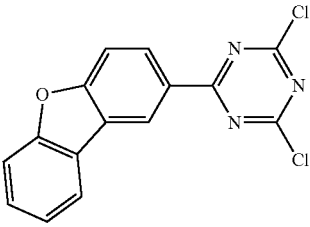<br>Intermediate A3 |
| 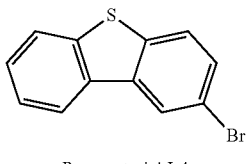<br>Raw material I-4 | 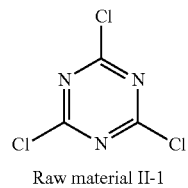<br>Raw material II-1 | 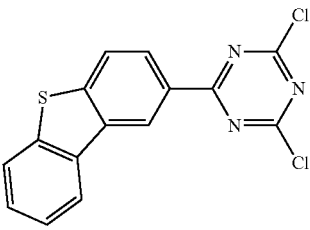<br>Intermediate A4 |
| 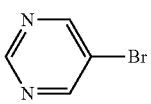<br>Raw material I-5 | 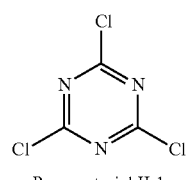<br>Raw material II-1 | 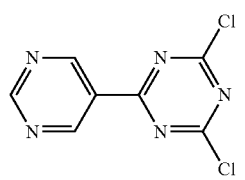<br>Intermediate A5 |
| 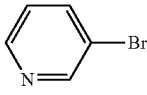<br>Raw material I-6 | 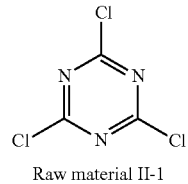<br>Raw material II-1 | 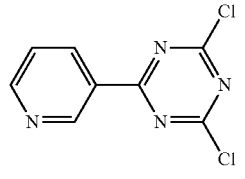<br>Intermediate A6 |

TABLE 1-continued
| Raw material I | Raw material II | Intermediate A |
|---|---|---|
| 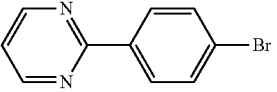<br>Raw material I-7 | 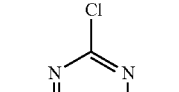<br>Raw material II-1 | 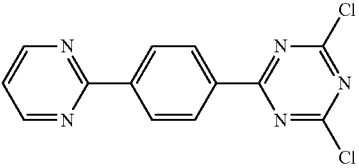<br>Intermediate A7 |
| 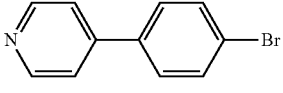<br>Raw material I-8 | 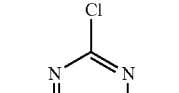<br>Raw material II-1 | 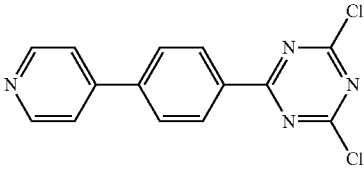<br>Intermediate A8 |
| 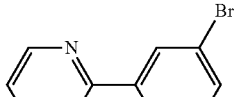<br>Raw material I-9 | 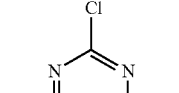<br>Raw material II-1 | 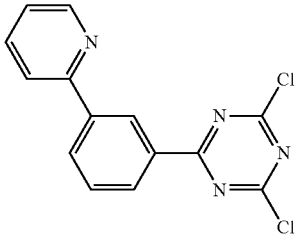<br>Intermediate A9 |
| 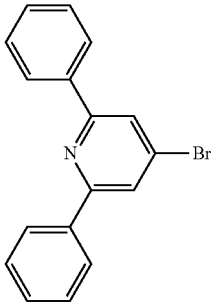<br>Raw material I-10 | 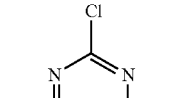<br>Raw material II-1 | 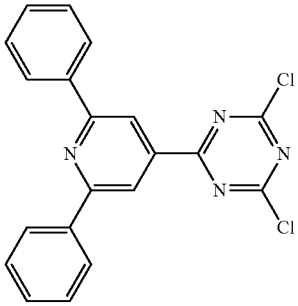<br>Intermediate A10 |
| 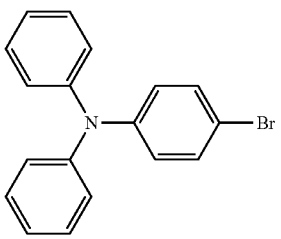<br>Raw material I-11 | 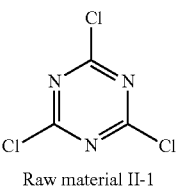<br>Raw material II-1 | 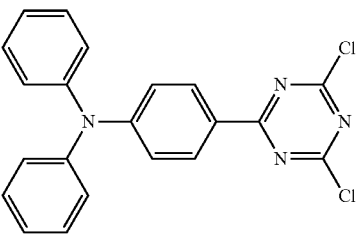<br>Intermediate A11 |

TABLE 1-continued
| Raw material I | Raw material II | Intermediate A |
|---|---|---|
| 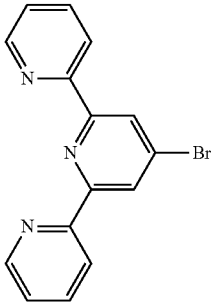<br>Raw material I-12 | 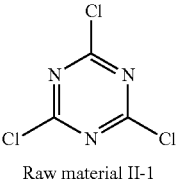<br>Raw material II-1 | 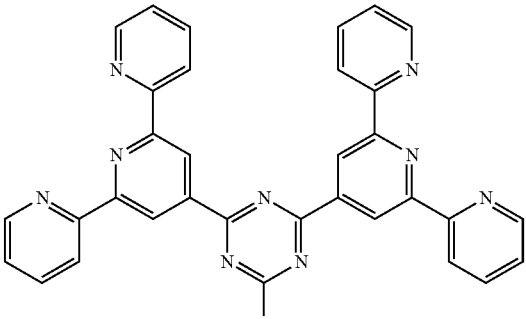<br>Intermediate A12 |
| 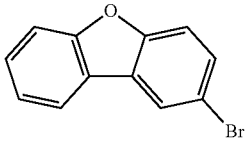<br>Raw material I-3 | 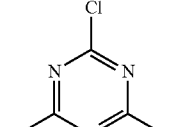<br>Raw material II-1 | 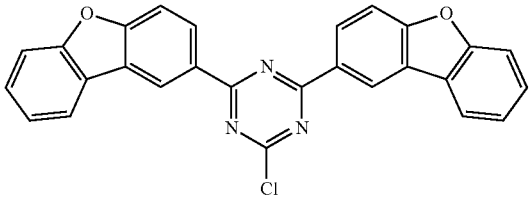<br>Intermediate A13 |
| 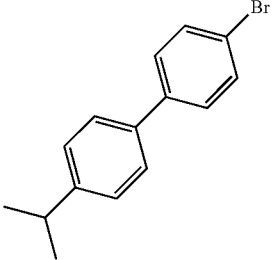<br>Raw material I-13 | 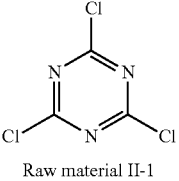<br>Raw material II-1 | 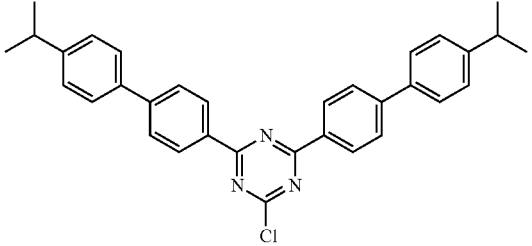<br>Intermediate A14 |
| 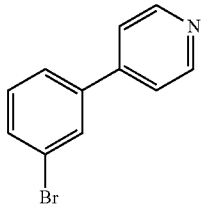<br>Raw material I-14 | 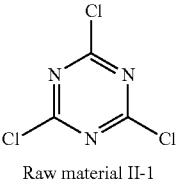<br>Raw material II-1 | 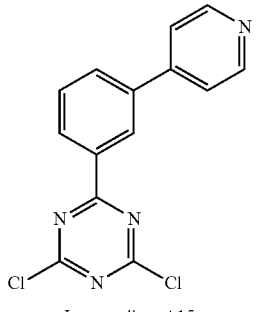<br>Intermediate A15 |
| 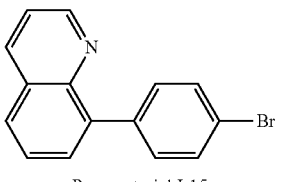<br>Raw material I-15 | 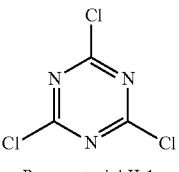<br>Raw material II-1 | 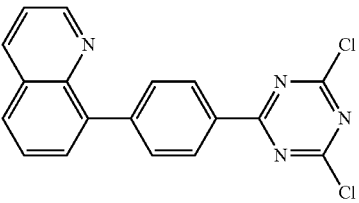<br>Intermediate A16 |

TABLE 1-continued
| Raw material I | Raw material II | Intermediate A |
|---|---|---|
| 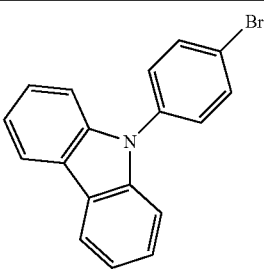<br>Raw material I-16 | 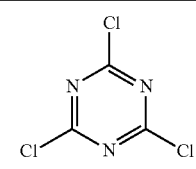<br>Raw material II-1 | 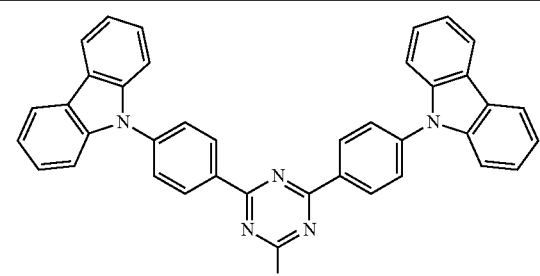<br>Intermediate A17 |
| 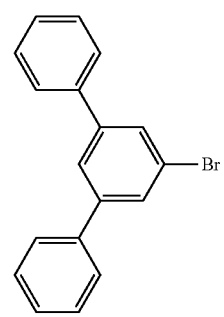<br>Raw material I-7 | 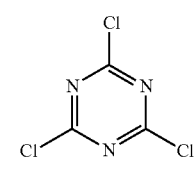<br>Raw material II-1 | 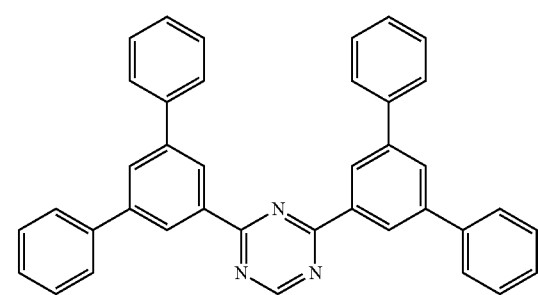<br>Intermediate A18 |
| 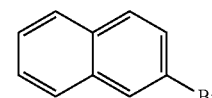<br>Raw material I-5 | 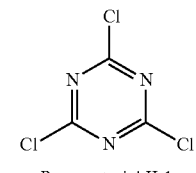<br>Raw material II-1 | 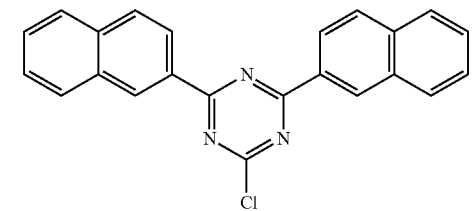<br>Intermediate A19 |
| 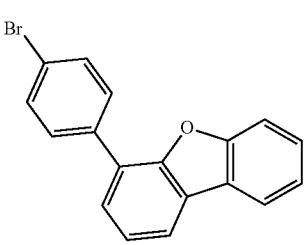<br>Raw material I-18 | 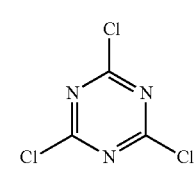<br>Raw material II-1 | 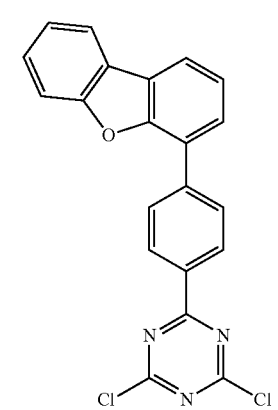<br>Intermediate A20 |

TABLE 1-continued
| Raw material I | Raw material II | Intermediate A |
|---|---|---|
| 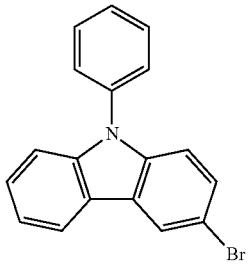<br>Raw material I-1 | 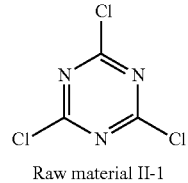<br>Raw material II-1 | 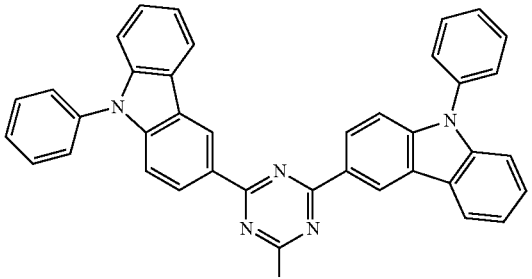<br>Intermediate A21 |
| 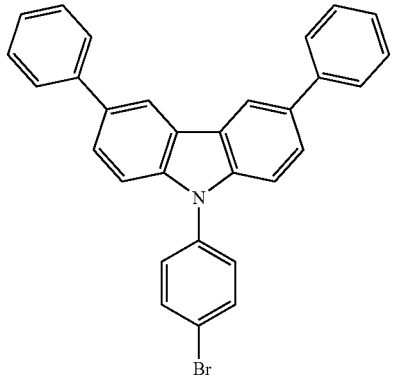<br>Raw material I-19 | 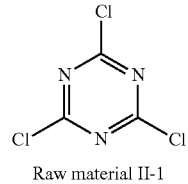<br>Raw material II-1 | 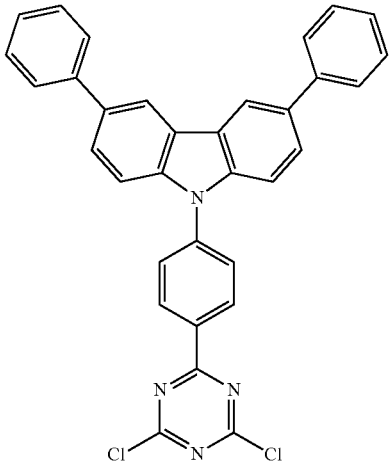<br>Intermediate A22 |
| 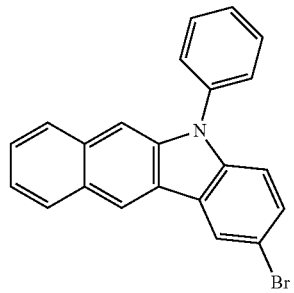<br>Raw material I-20 | 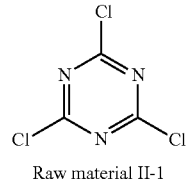<br>Raw material II-1 | 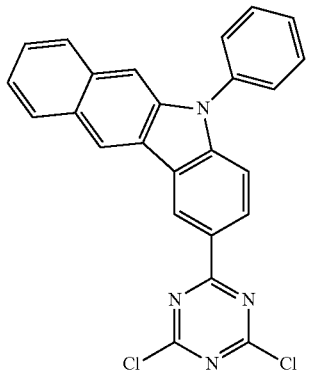<br>Intermediate A23 |

Example 2: Synthesis of Compound 1

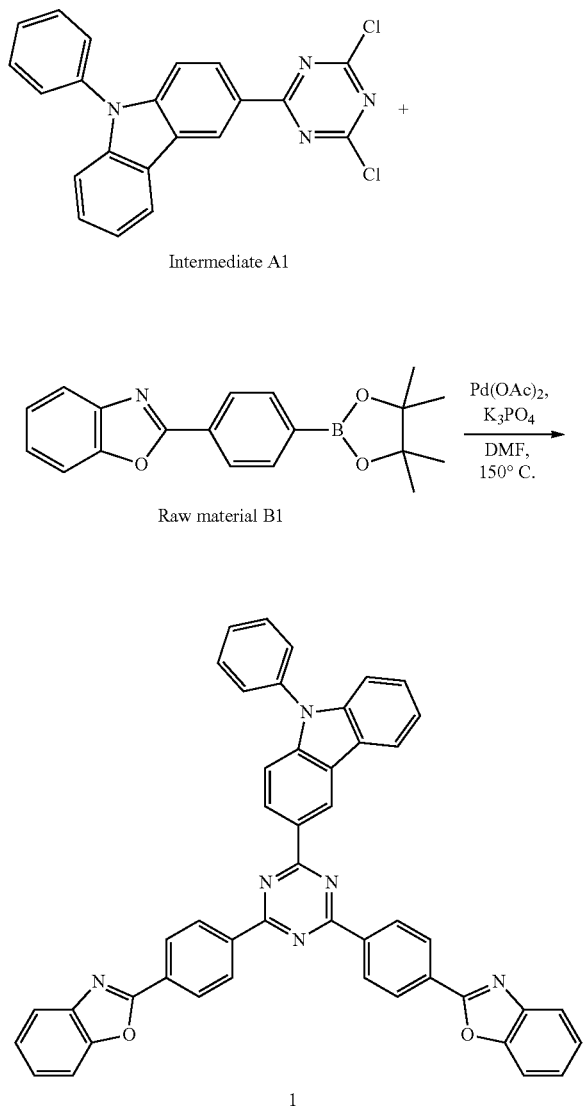

In a 250 ml three-necked flask, nitrogen gas was introduced, 0.01 mol of Intermediate A1, 150 ml of DMF, 0.03 mol of raw material B1, and 0.0002 mol of palladium acetate were added, the mixture was stirred, 0.02 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target product; the purity of the target product by HPLC was 99.2%, and the yield was 53.6%.

Elemental analysis structure (molecular formula $C_{47}H_{28}N_6O_2$): theoretical values: C, 79.65; H, 3.98; N, 11.86; O, 4.51; test values: C, 79.62; H, 3.99; N, 11.87; O, 4.52. ESI-MS(m/z)(M$^+$): the theoretical value is 708.23, and the test value is 708.31.

Example 3: Synthesis of Compound 8

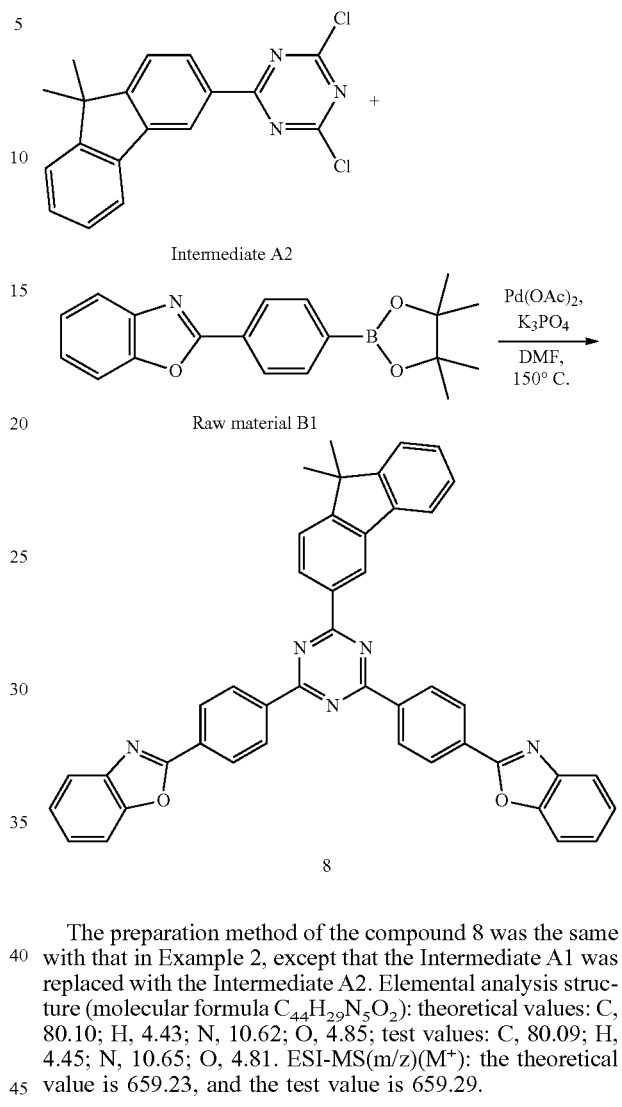

The preparation method of the compound 8 was the same with that in Example 2, except that the Intermediate A1 was replaced with the Intermediate A2. Elemental analysis structure (molecular formula $C_{44}H_{29}N_5O_2$): theoretical values: C, 80.10; H, 4.43; N, 10.62; O, 4.85; test values: C, 80.09; H, 4.45; N, 10.65; O, 4.81. ESI-MS(m/z)(M$^+$): the theoretical value is 659.23, and the test value is 659.29.

Example 4: Synthesis of Compound 12

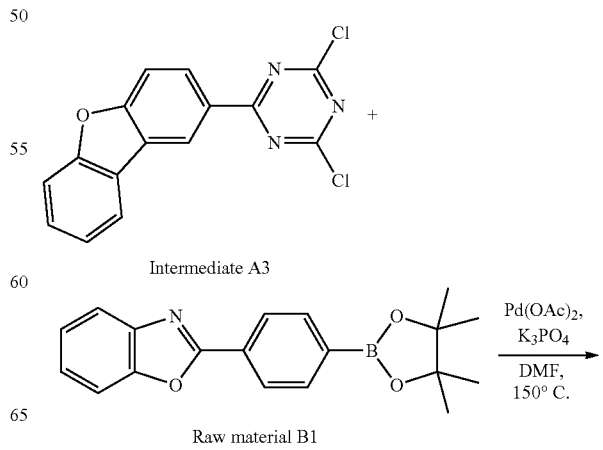

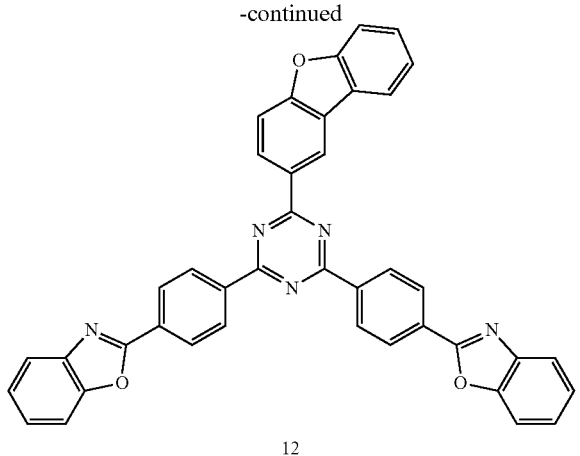

12

The preparation method of the compound 12 was the same with that in Example 2, except that the Intermediate A1 was replaced with the Intermediate A3. Elemental analysis structure (molecular formula $C_{41}H_{23}N_5O_3$): theoretical values: C, 77.71; H, 3.66; N, 11.05; O, 7.57; test values: C, 77.73; H, 3.69; N, 11.02; O, 7.56. ESI-MS(m/z)(M⁺): the theoretical value is 633.18, and the test value is 633.24.

Example 5: Synthesis of Compound 16

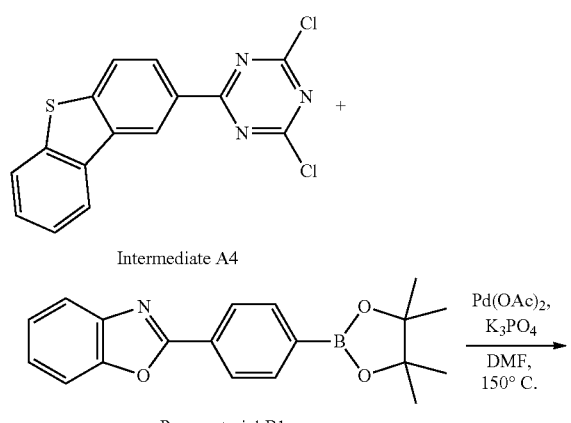

16

The preparation method of the compound 16 was the same with that in Example 2, except that the Intermediate A1 was replaced with the Intermediate A4. Elemental analysis structure (molecular formula $C_{41}H_{23}N_5O_2S$): theoretical values: C, 75.79; H, 3.57; N, 10.78; S, 4.93; O, 4.92; test values: C, 75.81; H, 3.59; N, 10.73; S, 4.96; O, 4.91. ESI-MS(m/z)(M⁺): the theoretical value is 649.16, and the test value is 649.23.

Example 6: Synthesis of Compound 28

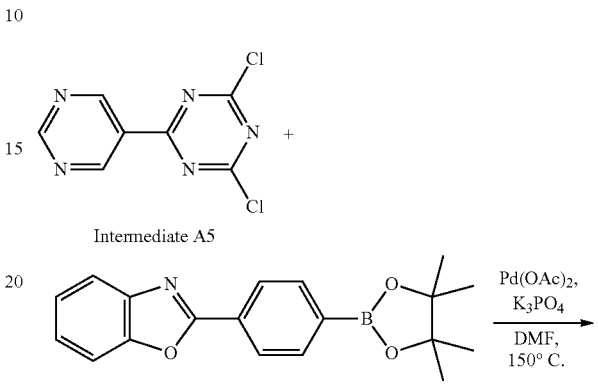

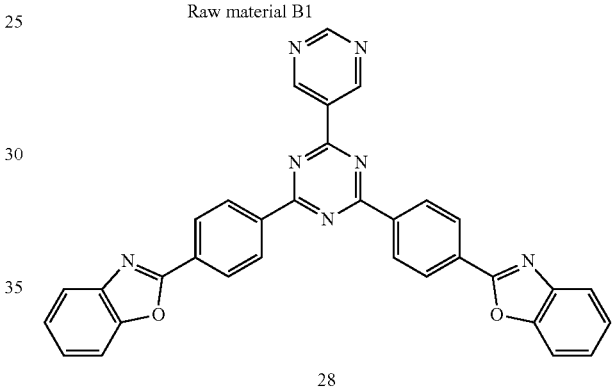

28

The preparation method of the compound 28 was the same with that in Example 3, except that the Intermediate A1 was replaced with the Intermediate A5. Elemental analysis structure (molecular formula $C_{33}H_{19}N_7O_2$): theoretical values: C, 72.65; H, 3.51; N, 17.97; O, 5.87; test values: C, 72.63; H, 3.52; N, 17.96; O, 5.89. ESI-MS(m/z)(M⁺): the theoretical value is 545.16, and the test value is 545.37.

Example 7: Synthesis of Compound 30

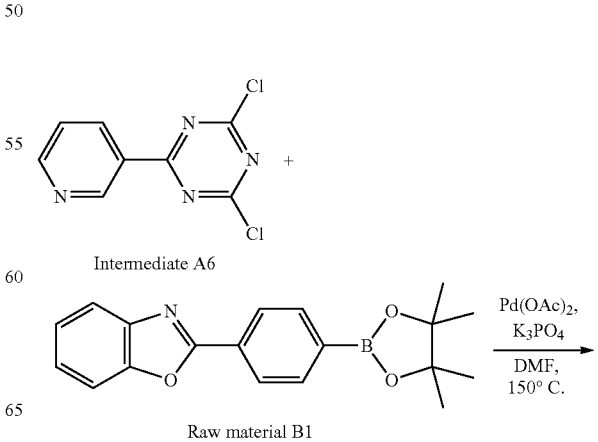

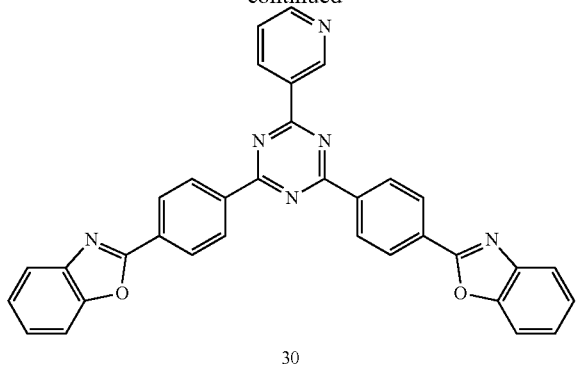

30

The preparation method of the compound 30 was the same with that in Example 2, except that the Intermediate A1 was replaced with the Intermediate A6. Elemental analysis structure (molecular formula $C_{34}H_{20}N_6O_2$): theoretical values: C, 74.99; H, 3.70; N, 15.43; O, 5.88; test values: C, 74.96; H, 3.73; N, 15.41; O, 5.90. ESI-MS(m/z)(M$^+$): the theoretical value is 544.16, and the test value is 544.24.

Example 8: Synthesis of Compound 35

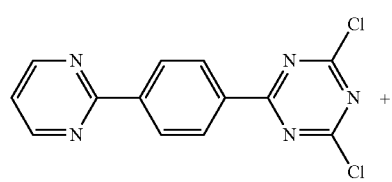

Intermediate A7

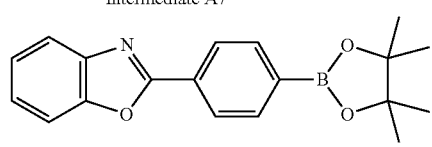

Raw material B1

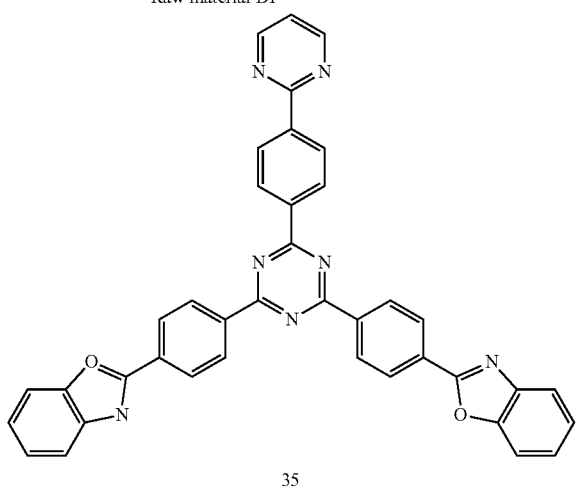

35

The preparation method of the compound 35 was the same with that in Example 2, except that the Intermediate A1 was replaced with the Intermediate A7. Elemental analysis structure (molecular formula $C_{39}H_{23}N_7O_2$): theoretical values: C, 75.35; H, 3.73; N, 15.77; O, 5.15; test values: C, 75.34; H, 3.75; N, 15.76; O, 5.15. ESI-MS(m/z)(M$^+$): the theoretical value is 621.19, and the test value is 621.33.

Example 9: Synthesis of Compound 38

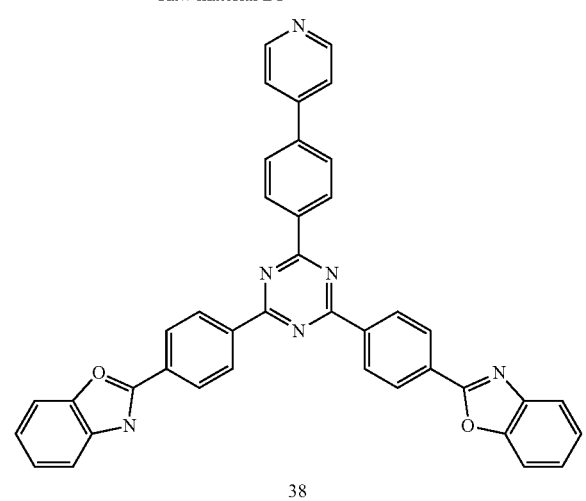

38

The preparation method of the compound 38 was the same with that in Example 2, except that the Intermediate A1 was replaced with the Intermediate A8. Elemental analysis structure (molecular formula $C_{40}H_{24}N_6O_2$): theoretical values: C, 77.41; H, 3.90; N, 13.54; O, 5.16; test values: C, 77.39; H, 3.93; N, 13.52; O, 5.16. ESI-MS(m/z)(M$^+$): the theoretical value is 620.20, and the test value is 620.47.

Example 10: Synthesis of Compound 39

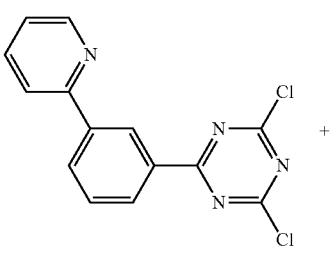

Intermediate A9

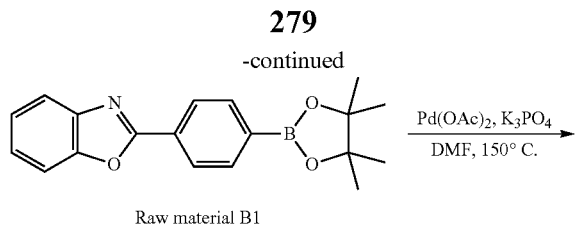

Raw material B1

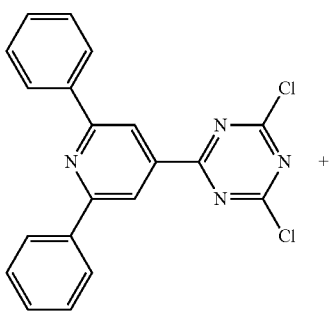

39

The preparation method of the compound 39 was the same with that in Example 2, except that the Intermediate A1 was replaced with the Intermediate A8. Elemental analysis structure (molecular formula $C_{40}H_{24}N_6O_2$): theoretical values: C, 77.41; H, 3.90; N, 13.54; O, 5.16; test values: C, 77.45; H, 3.87; N, 13.51; O, 5.17. ESI-MS(m/z)(M⁺): the theoretical value is 620.20, and the test value is 620.31.

Example 11: Synthesis of Compound 47

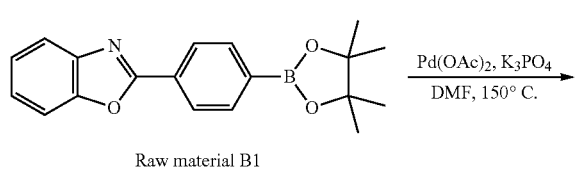

Intermediate A10

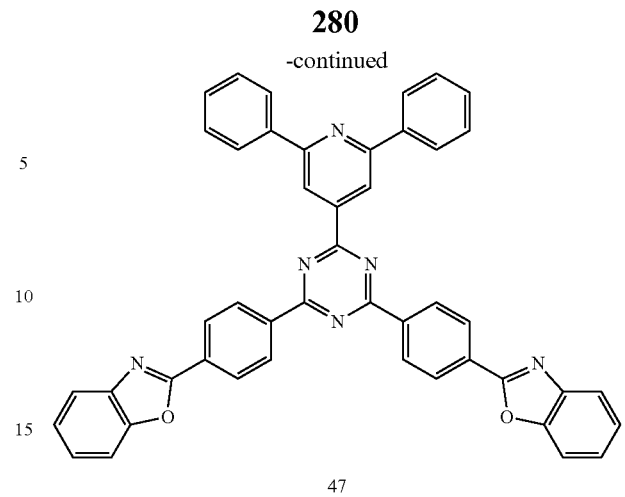

47

The preparation method of the compound 47 was the same with that in Example 2, except that the Intermediate A1 was replaced with the Intermediate A10. Elemental analysis structure (molecular formula $C_{46}H_{28}N_6O_2$): theoretical values: C, 79.30; H, 4.05; N, 12.06; O, 4.59; test values: C, 79.33; H, 4.02; N, 12.03; O, 4.62. ESI-MS(m/z)(M⁺): the theoretical value is 695.23, and the test value is 695.32.

Example 12: Synthesis of Compound 59

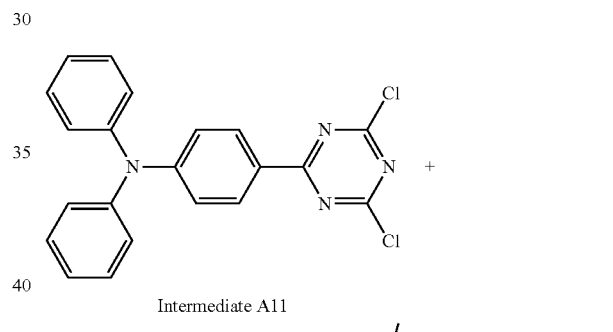

Intermediate A11

Raw material B1

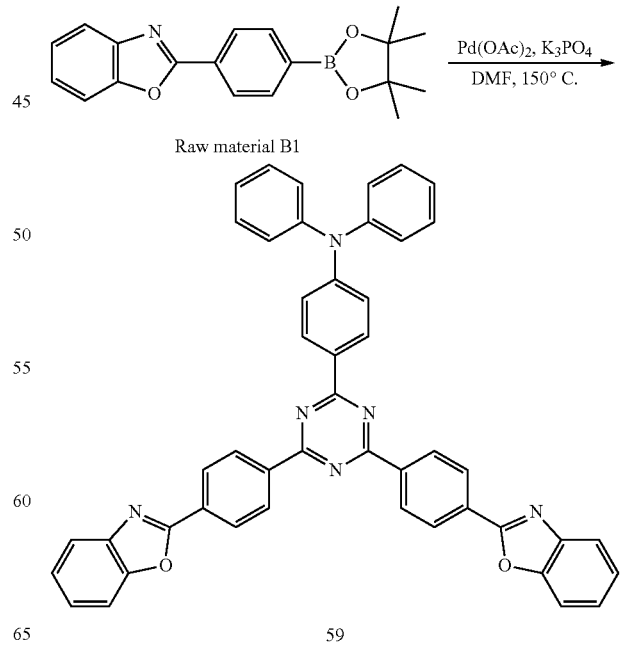

59

The preparation method of the compound 59 was the same with that in Example 2, except that the Intermediate A1 was replaced with the Intermediate A11. Elemental analysis structure (molecular formula $C_{47}H_{30}N_6O_2$): theoretical values: C, 79.42; H, 4.25; N, 11.82; O, 4.50; test values: C, 79.44; H, 4.22; N, 11.83; O, 4.51. ESI-MS(m/z)(M⁺): the theoretical value is 710.24, and the test value is 710.33.

Example 13: Synthesis of Compound 69

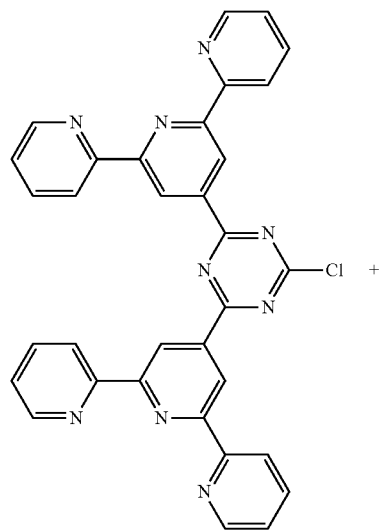
Intermediate A12

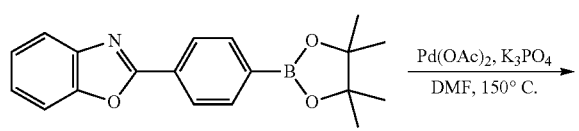
Raw material B1

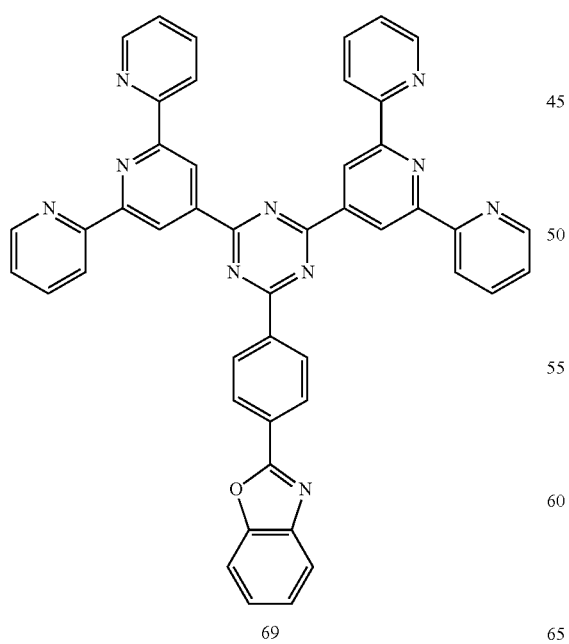
69

In a 250 ml three-necked flask, nitrogen gas was introduced, 0.01 mol of Intermediate A12, 150 ml of DMF, 0.012 mol of raw material B1, and 0.0001 mol of palladium acetate were added, the mixture was stirred, 0.012 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target product; the purity of the target product by HPLC was 99.4%, and the yield was 60.8%.

Elemental analysis structure (molecular formula $C_{46}H_{28}N_{10}O$: theoretical values: C, 74.99; H, 3.83; N, 19.01; O, 2.17; test values: C, 74.95; H, 3.85; N, 19.04; O, 2.16. ESI-MS(m/z)(M⁺): the theoretical value is 736.24, and the test value is 736.33.

Example 14: Synthesis of Compound 71

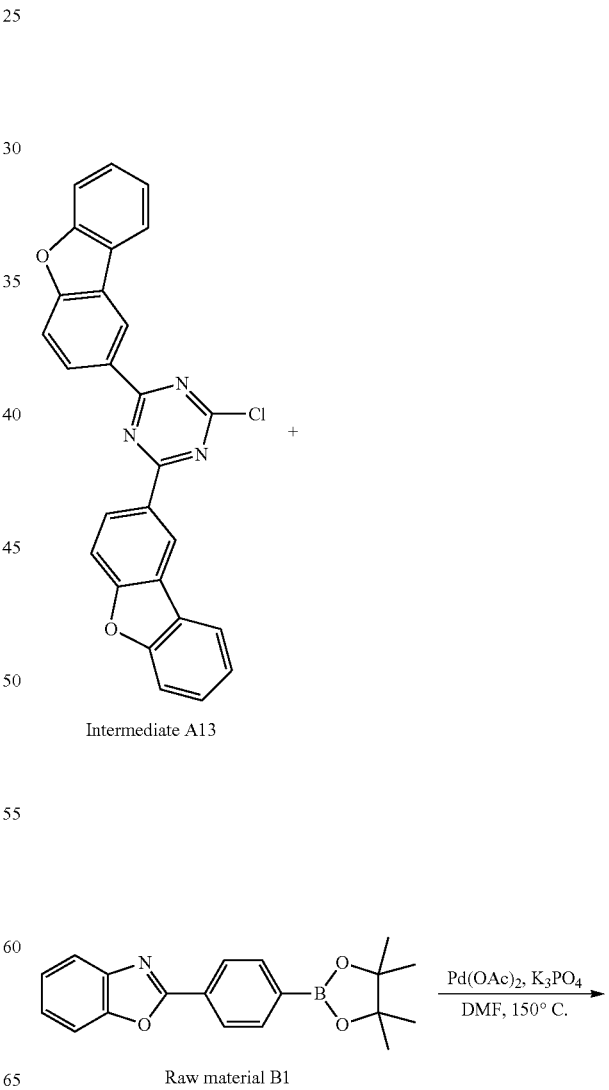

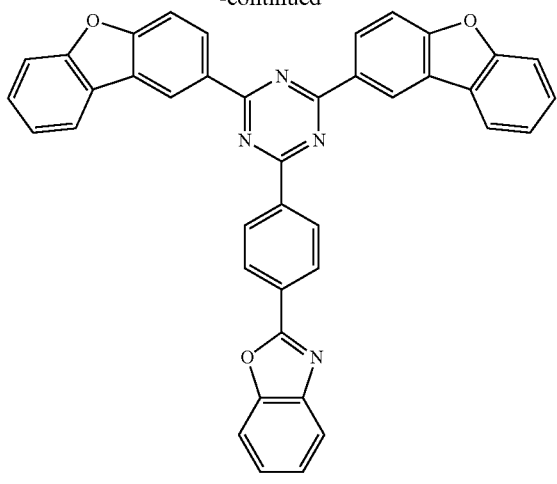

71

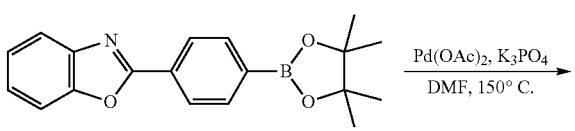

Raw material B1

The preparation method of the compound 71 was the same with that in Example 13, except that the Intermediate A12 was replaced with the Intermediate A13. Elemental analysis structure (molecular formula $C_{40}H_{22}N_4O_3$): theoretical values: C, 79.20; H, 3.66; N, 9.24; O, 7.91; test values: C, 79.21; H, 3.68; N, 9.22; O, 7.89. ESI-MS(m/z) ($M^+$): the theoretical value is 606.17, and the test value is 606.23.

Example 15: Synthesis of Compound 78

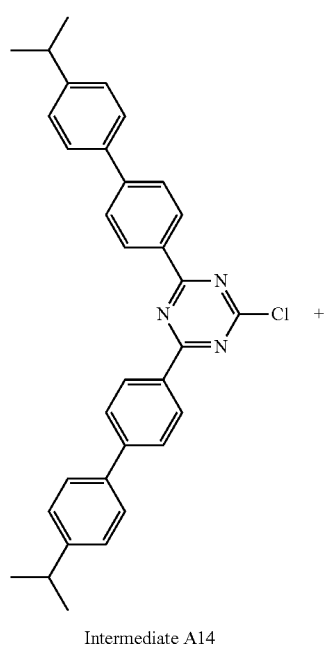

Intermediate A14

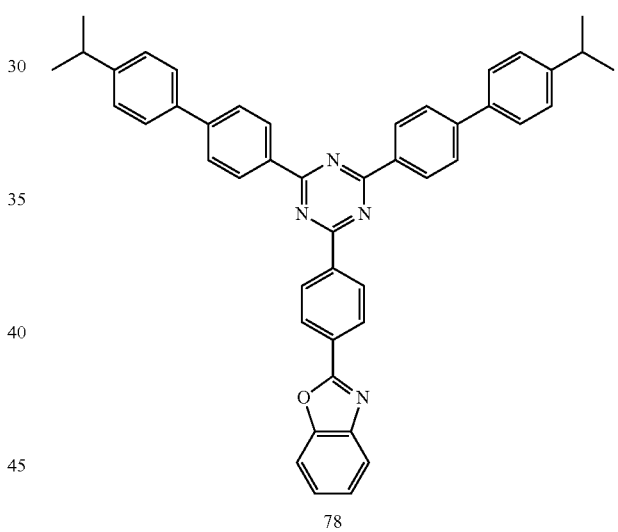

78

The preparation method of the compound 78 was the same with that in Example 13, except that the Intermediate A12 was replaced with the Intermediate A14. Elemental analysis structure (molecular formula $C_{46}H_{28}N_4O$): theoretical values: C, 83.35; H, 5.78; N, 8.45; O, 2.41; test values: C, 83.38; H, 5.74; N, 8.43; O, 2.45. ESI-MS(m/z) ($M^+$): the theoretical value is 662.30, and the test value is 662.45.

Example 16: Synthesis of Compound 85

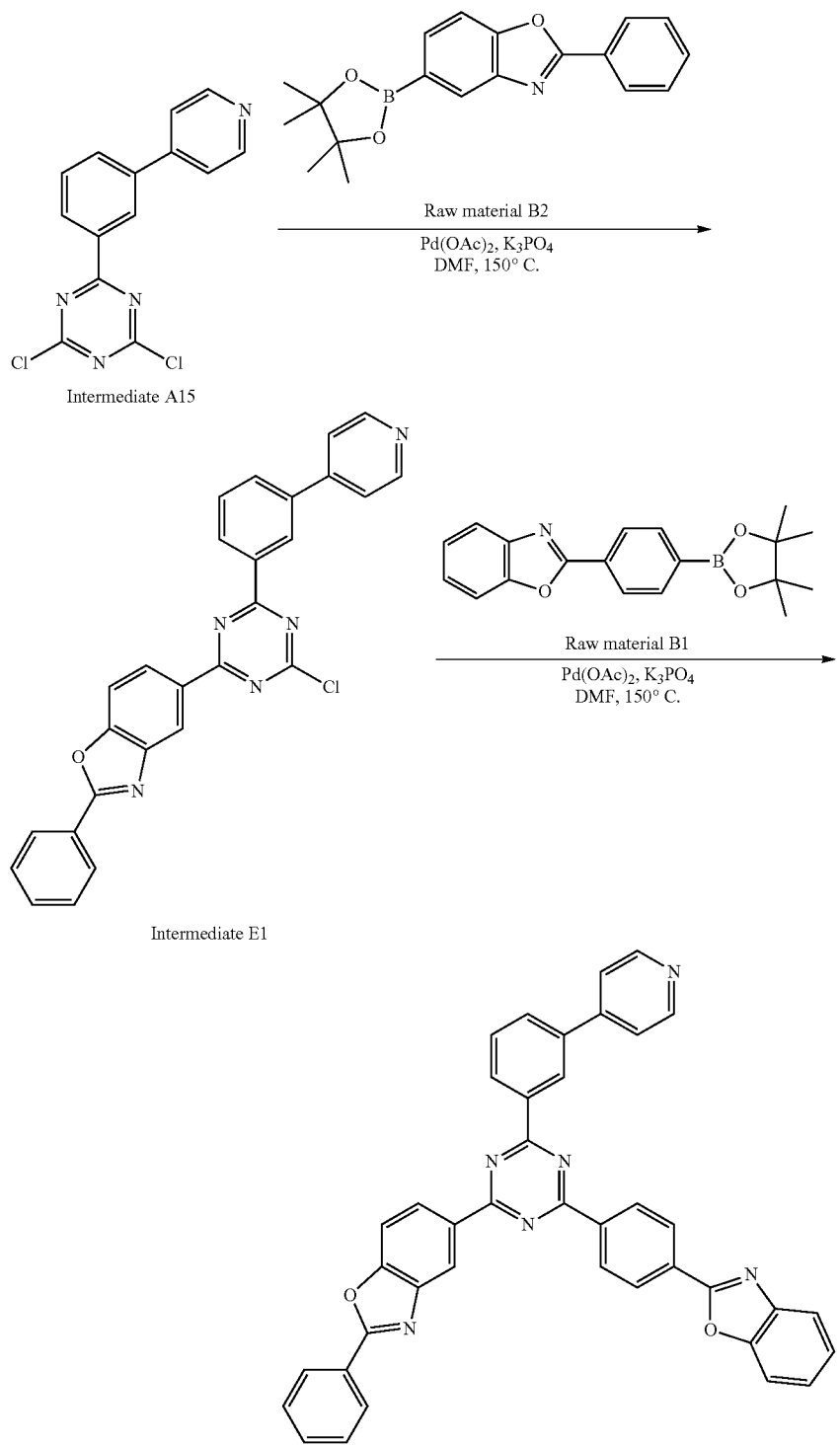

In a 250 ml three-necked flask, nitrogen gas was introduced, 0.01 mol of Intermediate A15, 150 ml of DMF, 0.015 mol of raw material B2, and 0.0001 mol of palladium acetate were added, the mixture was stirred, 0.01 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain an Intermediate E1; the purity of the product by HPLC was 99.1%, and the yield was 70.3%.

Elemental analysis structure (molecular formula $C_{27}H_{16}ClN_5O$): theoretical values: C, 70.21; H, 3.49; Cl, 7.67; N, 15.16; O, 3.46; test values: C, 70.23; H, 3.45; Cl, 7.70; N, 15.17; O, 3.45. ESI-MS(m/z)(M⁺): the theoretical value is 461.10, and the test value is 461.37.

In a 250 ml three-necked flask, nitrogen gas was introduced, 0.01 mol of Intermediate E1, 150 ml of DMF, 0.015 mol of intermediate B1, and 0.0001 mol of palladium acetate were added, the mixture was stirred, 0.01 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target product; the purity of the target product by HPLC was 99.3%, and the yield was 58.7%.

Elemental analysis structure (molecular formula $C_{40}H_{24}N_6O_2$): theoretical values: C, 77.41; H, 3.90; N, 13.54; O, 5.16; test values: C, 77.45; H, 3.88; N, 13.52; O, 5.15. ESI-MS(m/z)(M⁺): the theoretical value is 620.20, and the test value is 620.27.

Example 17: Synthesis of Compound 153

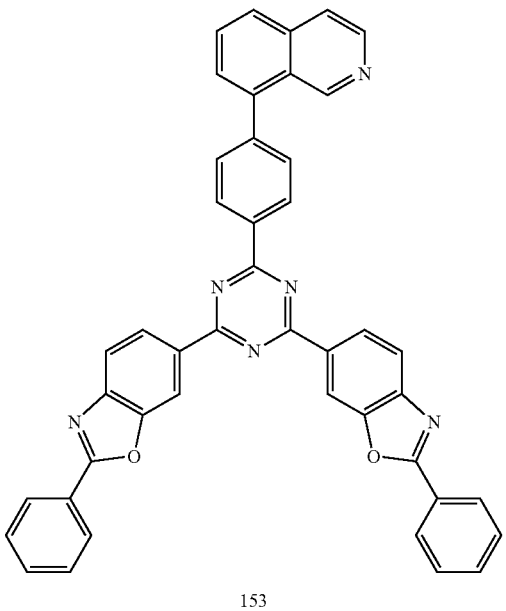

153

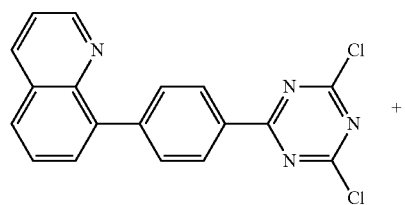

Intermediate A16

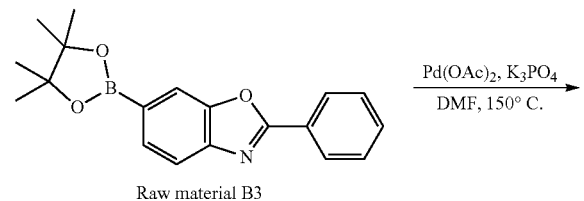

Raw material B3

In a 250 ml three-necked flask, nitrogen gas was introduced, 0.01 mol of Intermediate A16, 150 ml of DMF, 0.028 mol of raw material B3, and 0.0002 mol of palladium acetate were added, the mixture was stirred, 0.02 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target product; the purity of the target product by HPLC was 99.2%, and the yield was 53.6%.

Elemental analysis structure (molecular formula $C_{44}H_{26}N_6O_2$): theoretical values: C, 78.79; H, 3.91; N, 12.53; O, 4.77; test values: C, 78.77; H, 3.94; N, 12.51; O, 4.78. ESI-MS(m/z)(M⁺): the theoretical value is 670.21, and the test value is 670.35.

Example 18: Synthesis of Compound 164

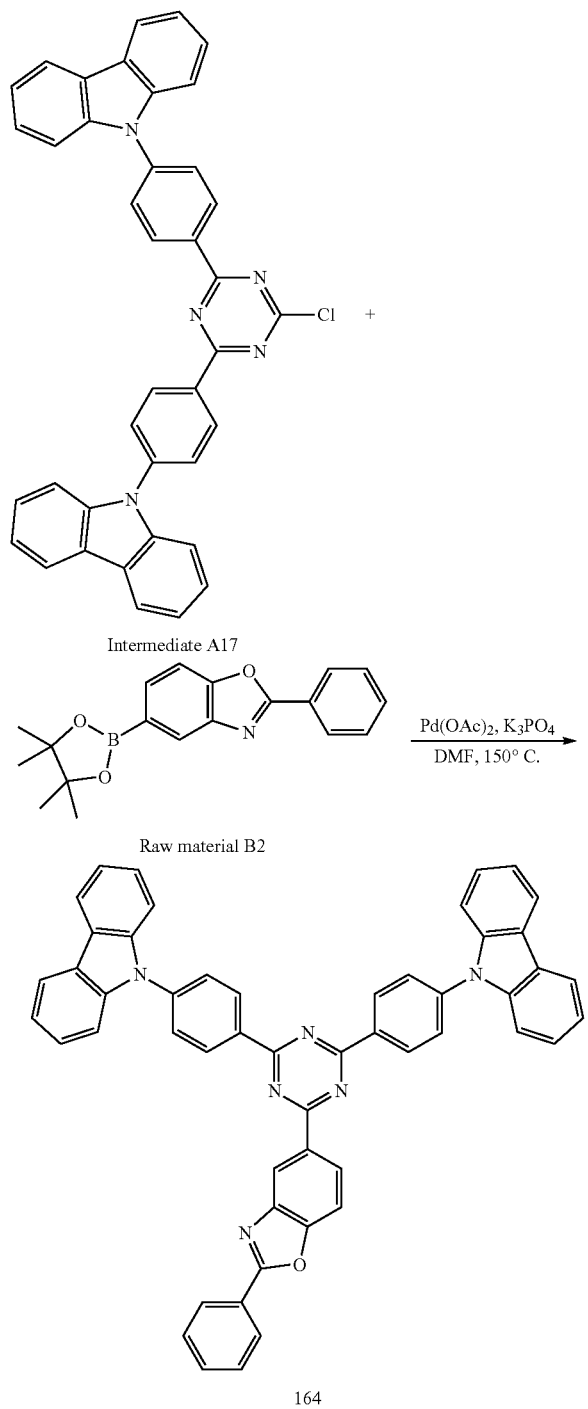

Example 19: Synthesis of Compound 173

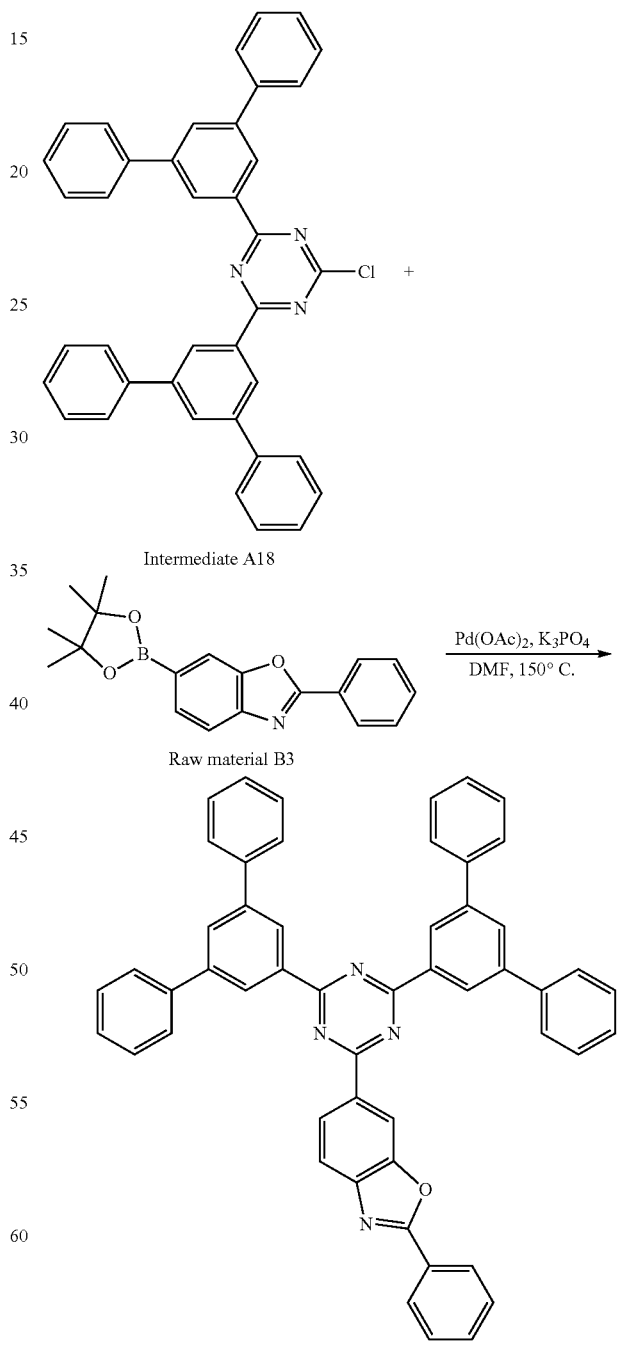

anhydrous sodium sulfate, and filtered, the filtrate was rotarily evaporated, and purified using a silica gel column to obtain a target product; the purity of the target product by HPLC was 99.1%, and the yield was 59.6%.

Elemental analysis structure (molecular formula $C_{52}H_{32}N_6O$): theoretical values: C, 82.52; H, 4.26; N, 11.10; O, 2.11; test values: C, 82.53; H, 4.27; N, 11.07; O, 2.13. ESI-MS(m/z)(M$^+$): the theoretical value is 756.26, and the test value is 756.34.

In a 250 ml three-necked flask, nitrogen gas was introduced, 0.01 mol of Intermediate A17, 150 ml of DMF, 0.015 mol of raw material B2, and 0.0001 mol of palladium acetate were added, the mixture was stirred, 0.01 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over The preparation method of the compound 173 was the same with that in Example 13, except that the Intermediate A12 was replaced with the Intermediate A18. Elemental analysis structure (molecular formula $C_{52}H_{34}N_4O$): theoretical values: C, 85.46; H, 4.69; N, 7.67; O, 2.19; test values: C, 85.42; H, 4.67; N, 7.70; O, 2.21. ESI-MS(m/z) (M$^+$): the theoretical value is 730.27, and the test value is 730.35.

Example 20: Synthesis of Compound 175

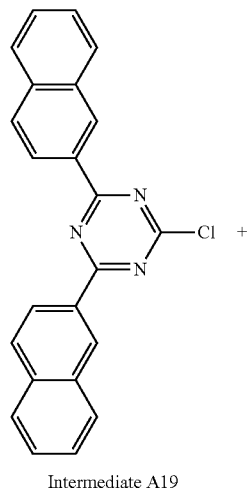

Intermediate A19

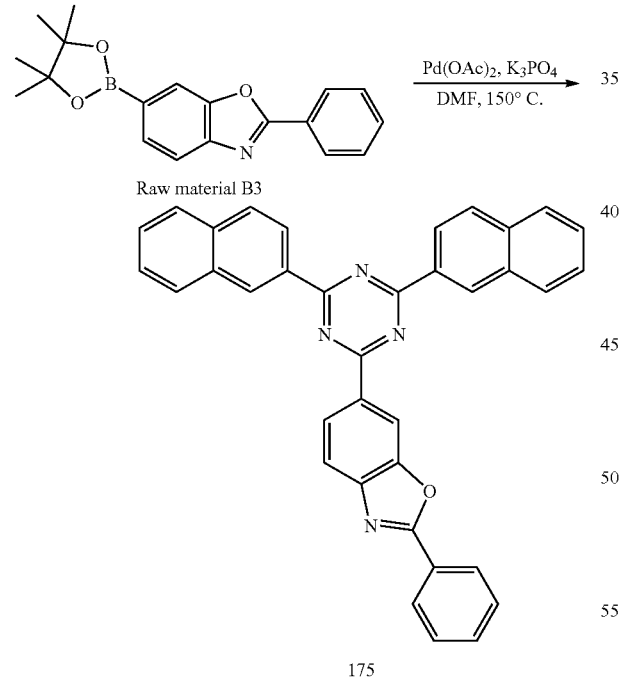

175

Example 21: Synthesis of Compound 191

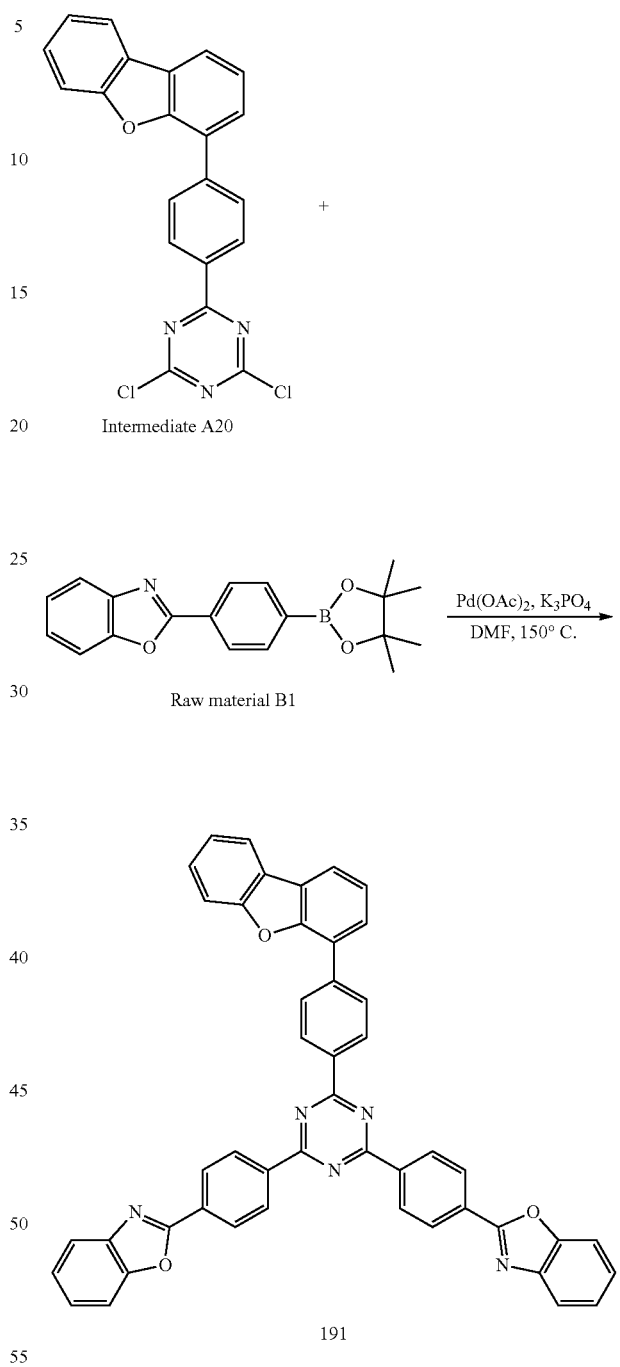

The preparation method of the compound 175 was the same with that in Example 13, except that the Intermediate A12 was replaced with the Intermediate A19. Elemental analysis structure (molecular formula $C_{36}H_{22}N_4O$): theoretical values: C, 82.11; H, 4.21; N, 10.64; O, 3.04; test values: C, 82.13; H, 4.23; N, 10.63; O, 3.01. ESI-MS(m/z) (M$^+$): the theoretical value is 526.18, and the test value is 526.23.

The preparation method of the compound 191 was the same with that in Example 2, except that the Intermediate A1 was replaced with the Intermediate A20. Elemental analysis structure (molecular formula $C_{47}H_{27}N_5O_3$): theoretical values: C, 79.54; H, 3.83; N, 9.87; O, 6.76; test values: C, 79.57; H, 3.81; N, 9.86; O, 6.76. ESI-MS(m/z)(M$^+$): the theoretical value is 709.21, and the test value is 709.43.

Example 22: Synthesis of Compound 195

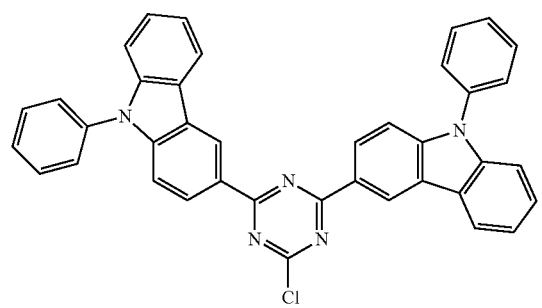

Intermediate A21

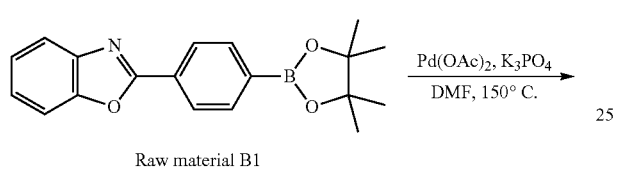

Raw material B1

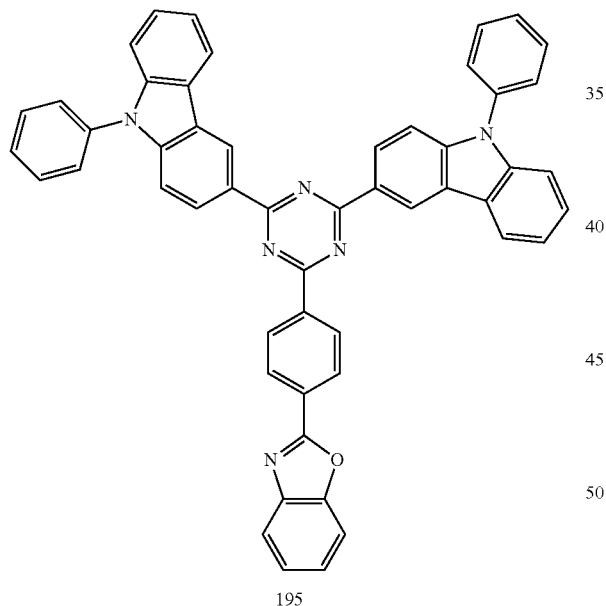

195

Example 23: Synthesis of Compound 227

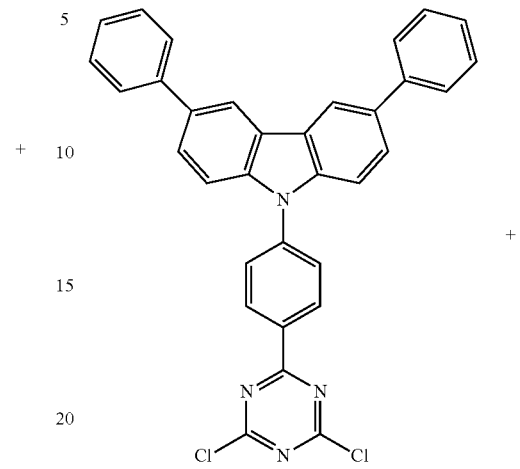

Intermediate A22

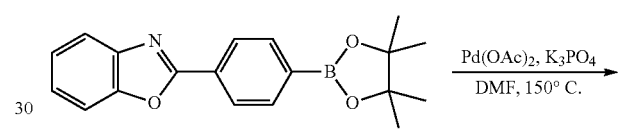

Raw material B1

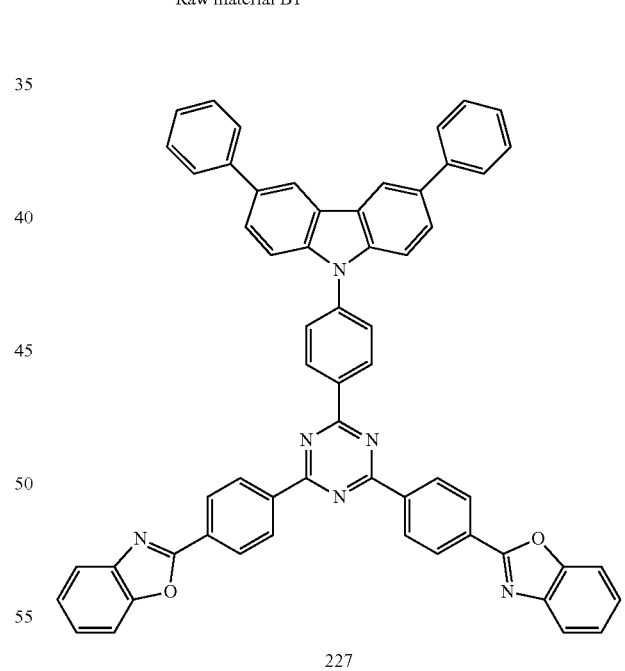

227

The preparation method of the compound 195 was the same with that in Example 13, except that the Intermediate A12 was replaced with the Intermediate A21. Elemental analysis structure (molecular formula $C_{52}H_{23}N_6O$): theoretical values: C, 82.52; H, 4.26; N, 11.10; O, 2.11; test values: C, 82.53; H, 4.27; N, 11.13; O, 2.07. ESI-MS(m/z) (W): the theoretical value is 756.26, and the test value is 756.37.

The preparation method of the compound 227 was the same with that in Example 2, except that the Intermediate A1 was replaced with the Intermediate A22. Elemental analysis structure (molecular formula $C_{59}H_{36}N_6O_2$): theoretical values: C, 82.31; H, 4.21; N, 9.76; O, 3.72. test values: C, 82.33; H, 4.20; N, 9.77; O, 3.70. ESI-MS(m/z)($M^+$): the theoretical value is 860.29, and the test value is 860.46.

Example 24: Synthesis of Compound 270

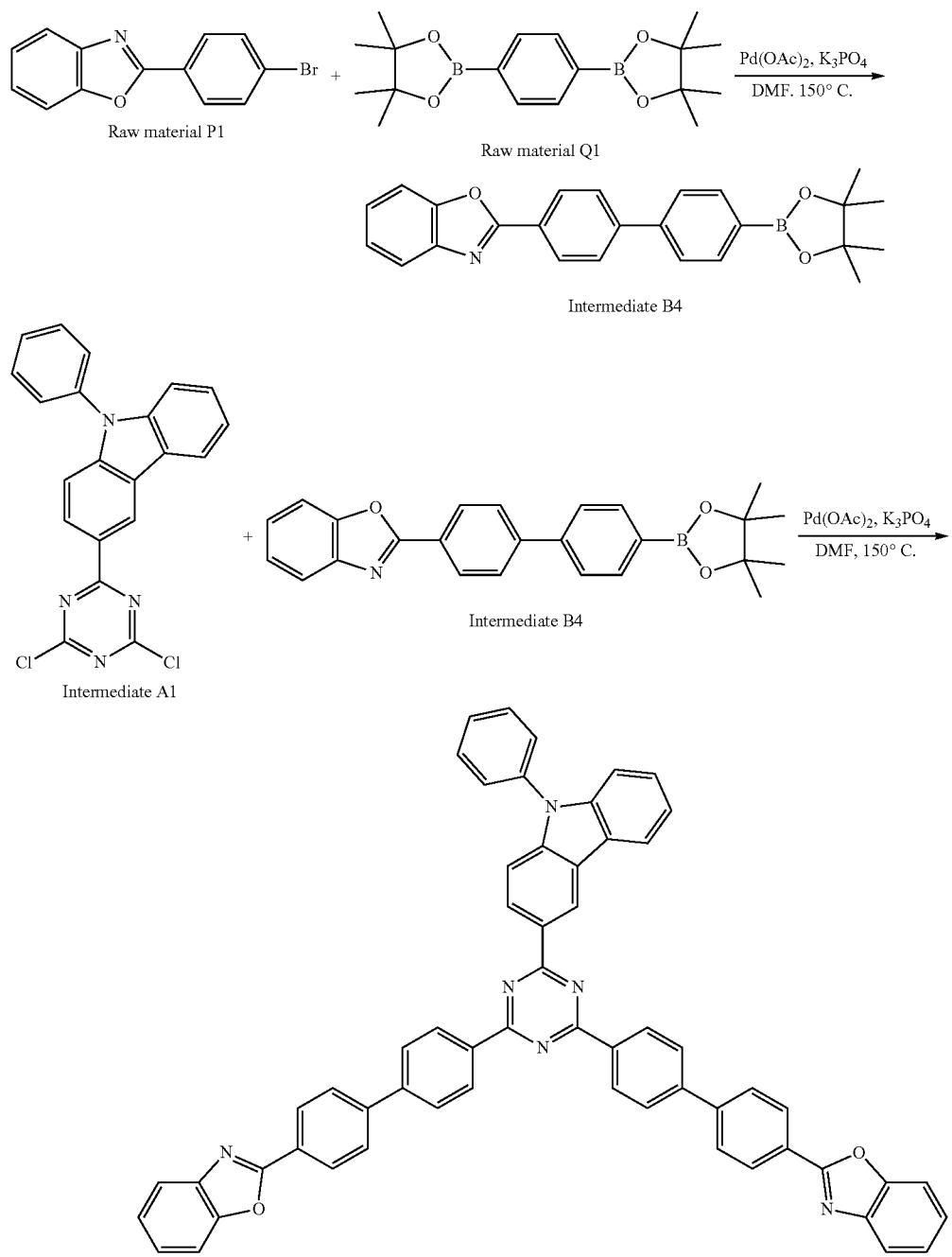

In a 250 ml three-necked flask, nitrogen gas was introduced, 0.01 mol of raw material P1, 150 ml of DMF, 0.012 mol of raw material $Q_1$, and 0.0001 mol of palladium acetate were added, the mixture was stirred, 0.012 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain an Intermediate B4; the purity of the product by HPLC was 99.3%, and the yield was 70.8%.

In a 250 ml three-necked flask, nitrogen gas was introduced, 0.01 mol of Intermediate A1, 150 ml of DMF, 0.03 mol of Intermediate B4, and 0.0002 mol of palladium acetate were added, the mixture was stirred, 0.02 mol of the aqueous solution of $K_3PO_4$ was added, and the mixed solution was heated to 150° C. and refluxed for 24 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target product; the purity of the target product by HPLC was 99.1%, and the yield was 51.3%.

Elemental analysis structure (molecular formula $C_{59}H_{36}N_6O_2$): theoretical values: C, 82.31; H, 4.21; N, 9.76; O, 3.72; test values: C, 82.34; H, 4.19; N, 9.78; O, 3.69. ESI-MS(m/z)(M$^+$): the theoretical value is 860.29, and the test value is 860.47.

Example 25: Synthesis of Compound 360

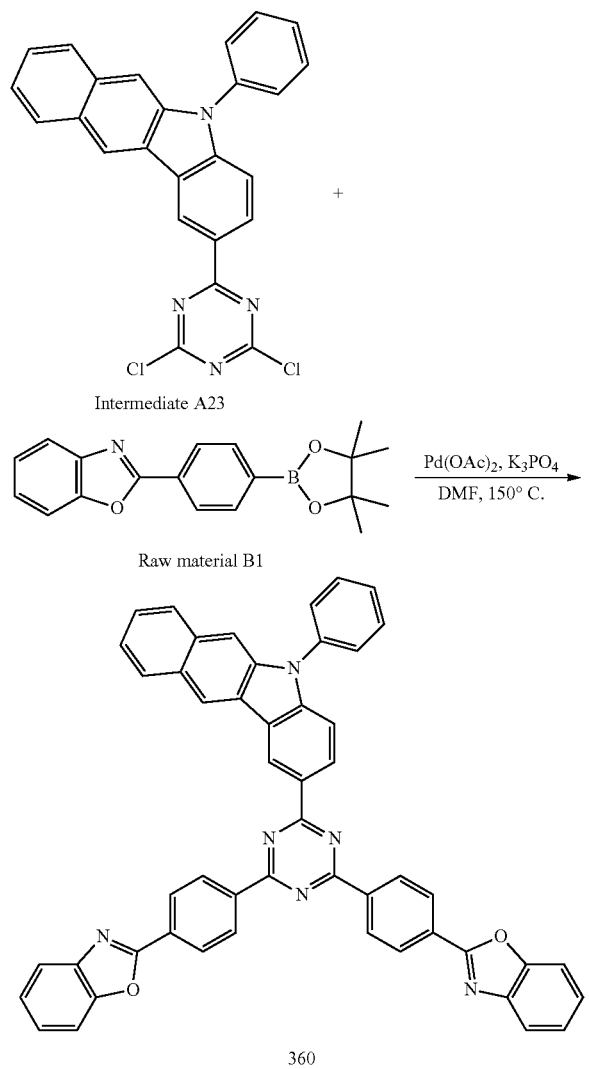

The preparation method of the compound 360 was the same with that in Example 2, except that the Intermediate A1 was replaced with the Intermediate A23. Elemental analysis structure (molecular formula $C_{51}H_{30}N_6O_2$): theoretical values: C, 80.72; H, 3.99; N, 11.08; O, 4.22; test values: C, 80.73; H, 4.01; N, 11.06; O, 4.20. ESI-MS(m/z)(M$^+$): the theoretical value is 758.24, and the test value is 758.47.

The organic compound of the present application is used as a CPL layer material in a light-emitting device, and has a high Tg temperature (glass transition temperature) and a high refractive index. Thermal property tests and refractive index tests were performed on the compounds of the present application and the existing materials, respectively, and the results were as shown in Table 2. Particularly, the refractive index test graph of the compound 8 was as shown in FIG. 2.

TABLE 2

| Compound | Tg (° C.) | Refractive index n@450 nm | n@600 nm |
|---|---|---|---|
| Compound 1 | 157 | 2.387 | 2.053 |
| Compound 8 | 159 | 2.305 | 2.041 |
| Compound 12 | 155 | 2.308 | 2.025 |
| Compound 16 | 161 | 2.377 | 2.066 |
| Compound 28 | 163 | 2.356 | 2.078 |
| Compound 30 | 159 | 2.337 | 2.067 |
| Compound 35 | 155 | 2.378 | 2.043 |
| Compound 38 | 163 | 2.306 | 2.011 |
| Compound 39 | 158 | 2.349 | 2.006 |
| Compound 47 | 156 | 2.388 | 2.012 |
| Compound 59 | 158 | 2.378 | 2.098 |
| Compound 69 | 158 | 2.306 | 2.086 |
| Compound 71 | 155 | 2.342 | 2.056 |
| Compound 78 | 154 | 2.387 | 2.087 |
| Compound 85 | 157 | 2.397 | 2.076 |
| Compound 153 | 153 | 2.378 | 2.005 |
| Compound 164 | 155 | 2.391 | 2.056 |
| Compound 173 | 158 | 2.305 | 2.088 |
| Compound 175 | 152 | 2.314 | 2.076 |
| Compound 191 | 157 | 7.335 | 2.068 |
| Compound 195 | 154 | 2.372 | 2.064 |
| Compound 227 | 155 | 2.346 | 2.074 |
| Compound 270 | 157 | 2.354 | 2.068 |
| Compound 360 | 162 | 2.343 | 2.065 |
| CBP | — | 1.881 | 1.789 |
| Alq3 | 149 | 1.775 | 1.728 |
| TPBi | 121 | 1.797 | 1.734 |

Note:
the glass transition temperature (Tg) was determined by differential scanning calorimetry (DSC, DSC204F1 Differential Scanning Calorimeter, NETZSCH, Germany) at a heating rate of 10° C./min; the refractive index was measured using an ellipsometer in an (J. A.Woollam Co., USA, Model: ALPHA-SE), and the tests were conducted atmospheric environment.

As can be seen from Table 2, compared to the currently-used materials, such as CBP, Alq3 and TPBi, the organic compound of the present application has a relatively high glass transition temperature and a high refractive index, and meanwhile, since there are rigid groups of triazine and benzoxazole, the thermal stability of the material can be guaranteed. Therefore, the organic material with triazine and benzoxazole as the core of the present application can effectively improve the light extraction efficiency of a device and ensure a long service life of the OLED device when applied to the CPL layer of the OLED device.

Hereinafter, the application effect of the OLED material synthesized in the invention in the device will be described in detail through Device examples 1 to 27 and Device comparative example 1. Compared to Device example 1, Device examples 2 to 27 and Device comparative example 1 of the present application have identical device fabricating processes, adopt the same substrate materials and electrode materials, and maintain consistency in film thickness of the electrode material, except that Device examples 2 to 23 replace the CPL layer material in the device; Device examples 24 to 27 replace the hole block layer or the electron transport layer material, and performance test results of the device in each example are as shown in Table 3.

Figure 1:
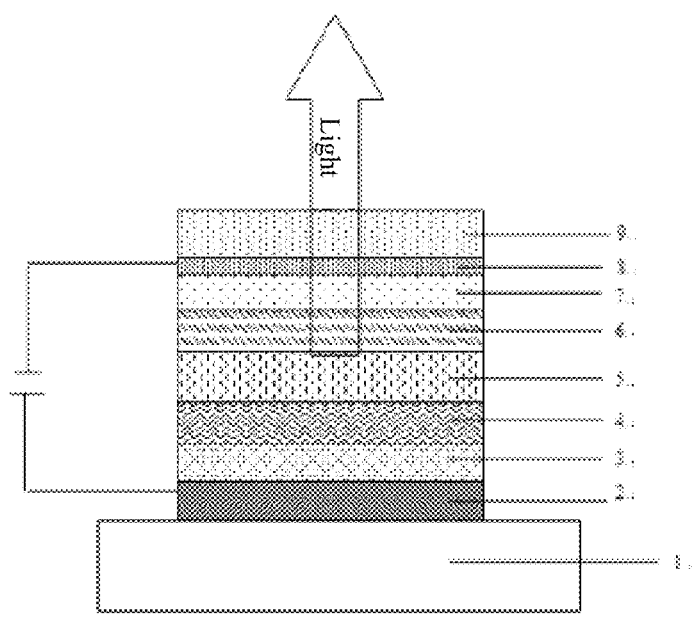
FIG. 1 is a schematic structural diagram when materials set forth in the present application are applied to an OLED device.

Device example 1: as shown in FIG. 1, an electroluminescent device was prepared by the steps of:

a) cleaning an ITO anode layer 2 on a transparent OLED device substrate 1, cleaning in deionized water, acetone and alcohol each for 15 minutes, and then treating in a plasma cleaner for 2 minutes; b) vapor-depositing a hole injection layer material HAT-CN with a thickness of 10 nm on the ITO anode layer 2 by vacuum vapor deposition, wherein, this layer functions as a hole injection layer 3; c) vapor-depositing a hole transport layer material NPB with a thickness of 80 nm on the hole injection layer 3 by vacuum vapor deposition, wherein, this layer functions as a hole transport layer 4; d) vapor-depositing a light-emitting layer 5 with a thickness of 30 nm on the hole transport layer 4, wherein, CBP functions as a host material, Ir(ppy)$_3$ functions as a doping material, and a mass ratio of Ir(ppy)$_3$ to CBP is 1:9; e) vapor-depositing an electron transport material TPBI with a thickness of 40 nm on the light-emitting layer 5 by vacuum vapor deposition, wherein, this organic material layer is used as a hole block or electron transport layer 6; f) vapor-depositing an electron injection layer LiF with a thickness of 1 nm by vacuum vapor deposition on the hole block or electron transport layer 6, wherein, this layer functions as an electron injection layer 7; g) vapor-depositing a cathode Mg:Ag/Ag layer on the electron injection layer 7 by vacuum vapor deposition, Mg:Ag (at a doping ratio of 9:1) layer has a thickness of 15 nm, the Ag layer has a thickness of 3 nm, and this layer is a cathode layer 8; and h) vapor-depositing CPL material compound 1 with a thickness of 50 nm by vacuum vapor deposition on the cathode layer 8, wherein, this organic material layer is used as a CPL layer 9. After the fabrication of the electroluminescent device was completed according to the above steps, the current efficiency and the service life of the device were measured, and the results are as shown in Table 3. Molecular structural formulas of related materials are as shown below:

HAT-CN

NPB

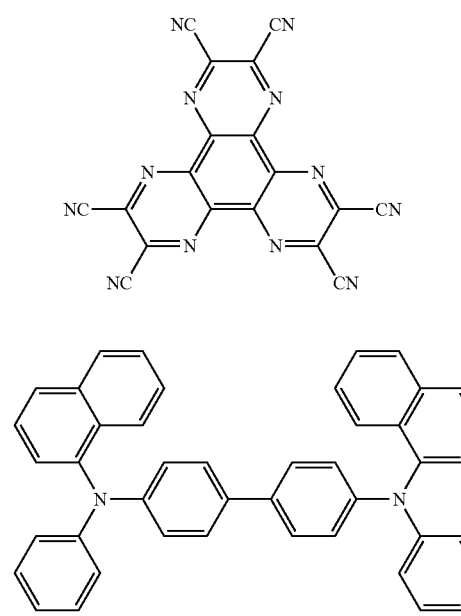

CBP

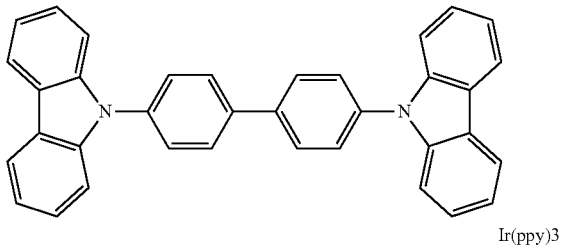

Ir(ppy)3

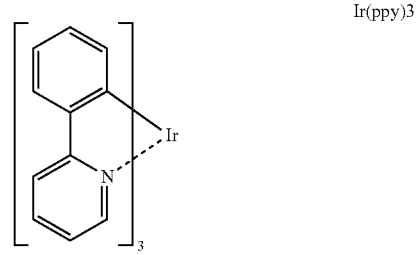

TPBI

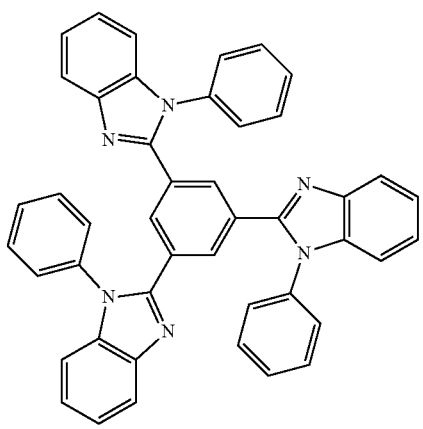

Alq3

Device example 2: CPL layer material of the electroluminescent device was changed to Compound 8 of the present application. Device example 3: CPL layer material of the electroluminescent device was changed to Compound 12 of the present application. Device example 4: CPL layer material of the electroluminescent device was changed to Compound 16 of the present application. Device example 5: CPL layer material of the electroluminescent device was changed to Compound 28 of the present application. Device example 6: CPL layer material of the electroluminescent device was changed to Compound 30 of the present application. Device example 7: CPL layer material of the electroluminescent device was changed to Compound 35 of the present application. Device example 8: CPL layer material of the electroluminescent device was changed to Compound 38 of the present application. Device example 9: CPL layer material of the electroluminescent device was changed to Compound 39 of the present application. Device example 10: CPL layer material of the electroluminescent device was changed to Compound 47 of the present application. Device example 11: CPL layer material of the electroluminescent device was changed to Compound 59 of the present application. Device example 12: CPL layer material of the electroluminescent device was changed to Compound 69 of the present application. Device example 13: CPL layer material of the electroluminescent device was changed to Compound 71 of the present application. Device example 14: CPL layer material of the electroluminescent device was changed to Compound 78 of the present application. Device example 15: CPL layer material of the electroluminescent device was changed to Compound 85 of the present application. Device example 16: CPL layer material of the electroluminescent device was changed to Compound 153 of the present application. Device example 17: CPL layer material of the electroluminescent device was changed to Compound 164 of the present application. Device example 18: CPL layer material of the electroluminescent device was changed to Compound 173 of the present application. Device example 19: CPL layer material of the electroluminescent device was changed to Compound 175 of the present application. Device example 20: CPL layer material of the electroluminescent device was changed to Compound 191 of the present application. Device example 21: CPL layer material of the electroluminescent device was changed to Compound 227 of the present application. Device example 22: CPL layer material of the electroluminescent device was changed to Compound 270 of the present application. Device example 23: CPL layer material of the electroluminescent device was changed to Compound 360 of the present application. Device example 24: the hole block layer or the electron transport layer material of the electroluminescent device was changed to Compound 35 of the present application, and CPL layer material of the electroluminescent device was changed to a known material Alq3. Device example 25: the hole block layer or the electron transport layer material of the electroluminescent device was changed to Compound 39 of the present application, and CPL layer material of the electroluminescent device was changed to a known material Alq3. Device example 26: the hole block layer or the electron transport layer material of the electroluminescent device was changed to Compound 69 of the present application, and CPL layer material of the electroluminescent device was changed to a known material Alq3. Device example 27: the hole block layer or the electron transport layer material of the electroluminescent device was changed to Compound 195 of the present application, and CPL layer material of the electroluminescent device was changed to a known material Alq3. Device comparative example 1: CPL layer material of the electroluminescent device was changed to a known material Alq3. The measured data of the electroluminescent device obtained is as shown in Table 3.

TABLE 3

| No. | @10 mA/cm² | | Color |
| | Current efficiency (cd/A) | Brightness (cd/m2) | |
| --- | --- | --- | --- |
| Device example 1 | 55.93 | 5597.50 | Green light |
| Device example 2 | 56.23 | 5622.74 | Green light |
| Device example 3 | 56.28 | 5627.78 | Green light |
| Device example 4 | 55.76 | 5575.71 | Green light |
| Device example 5 | 55.40 | 5540.43 | Green light |
| Device example 6 | 55.09 | 5508.52 | Green light |
| Device example 7 | 55.77 | 5577.39 | Green light |
| Device example 8 | 56.24 | 5624.42 | Green light |
| Device example 9 | 55.29 | 5528.68 | Green light |
| Device example 10 | 55.94 | 5594.18 | Green light |
| Device example 11 | 55.77 | 5577.39 | Green light |
| Device example 12 | 56.24 | 5624.42 | Green light |
| Device example 13 | 55.17 | 5516.92 | Green light |
| Device example 14 | 55.93 | 5592.50 | Green light |
| Device example 15 | 56.09 | 5609.30 | Green light |
| Device example 16 | 55.77 | 5577.39 | Green light |
| Device example 17 | 54.19 | 5599.22 | Green light |
| Device example 18 | 54.55 | 5454.77 | Green light |
| Device example 19 | 54.70 | 5469.89 | Green light |
| Device example 70 | 55.43 | 5573.61 | Green light |
| Device example 21 | 56.08 | 5523 | Green light |
| Device example 22 | 55.73 | 5507 | Green light |
| Device example 23 | 54.96 | 5379 | Green light |
| Device example 24 | 63.42 | 6488.52 | Green light |
| Device example 25 | 64.88 | 6179.91 | Green light |
| Device example 26 | 61.79 | 6342.77 | Green light |
| Device example 27 | 62.62 | 6327.49 | Green light |
| Device comparative example 1 | 48.34 | 4834 | Green light |

As can be seen from results in Table 3, after the organic compound with triazine and benzoxazole as the core of the present application was applied to fabrication of the OLED light-emitting device, the light extraction efficiency was improved significantly when compared with that in device comparative example 1, both brightness and efficiency of the device were improved under the same current density; since brightness and efficiency had been improved, the power consumption of the OLED device under constant brightness was relatively reduced, and the service life of the OLED device was prolonged.

In order to illustrate the phase-state crystallization stability of the material film of the present application, the material compound 1 of the present application and a known material CBP were subjected to film accelerated crystallization experiments: the compound 1 and the CBP were vapor-deposited on the alkali-free glass by vacuum vapor deposition, respectively, and packaged in a glove-box (content of water and oxygen <0.1 ppm), the packaged samples were placed under double 85 (temperature 85° C., humidity 85%) conditions, and observed periodically with microscope (LEICA, DM8000M, 5*10 magnification) for the crystalline state of the material film. The experimental results were as shown in Table 4, and surface morphologies of the materials were as shown in FIG. 3:

TABLE 4

| Name of material | Compound 1 | CBP |
|---|---|---|
| After film-forming of the material. | The surface is smooth, flat, uniform | The surface is smooth, flat, uniform |
| 72 h after the experiment | The surface is smooth, flat, uniform, with no crystallization | The surface forms several dispersed circular crystallization surfaces |
| 600 h after the experiment | The surface is smooth, flat, uniform, with no crystallization | The surface is cracked |

The above experiment shows that the film crystallization stability of the material disclosed in the invention is far higher than that of known materials, and has beneficial effects on the service life after being applied to an OLED device.

Further, the efficiency of the OLED device prepared by using the material of the present application is relatively stable when operating at a low temperature. Device examples 8, 17 and 25 and Device comparative example 1 were tested for efficiency in the range of −10° C. to 80° C. The results are shown in Table 5 and the FIG. 4.

TABLE 5

| Current efficiency | Temperature (° C.) | | | | | | | | | |
|---|---|---|---|---|---|---|---|---|---|---|
| (cd/A) | −10 | 0 | 10 | 20 | 30 | 40 | 50 | 60 | 70 | 80 |
| Device example 8 | 53.52 | 54.94 | 55.77 | 56.24 | 57.07 | 57.78 | 59.43 | 58.60 | 57.66 | 58.01 |
| Device example 17 | 51.76 | 52.41 | 53.16 | 54.19 | 54.85 | 55.69 | 56.81 | 56.53 | 55.78 | 56.34 |
| Device example 25 | 61.17 | 62.50 | 63.40 | 64.88 | 66.07 | 66.96 | 67.55 | 67.85 | 67.11 | 66.51 |
| Device comparative example 1 | 40.57 | 43.33 | 46.79 | 48.34 | 49.20 | 49.89 | 49.89 | 46.79 | 43.68 | 38.67 |

As can be seen from the results in Table 5 and FIG. 4, Device examples 8, 17 and 25 disclose device structures using both the material of the present application and known materials. Compared with Device comparative example 1, these Device examples have higher low-temperature efficiency, and also have the efficiency increased steadily during the temperature rise.

To sum up, the embodiments mentioned above are merely preferred embodiments of the present application and not intended to limit the present application. Any of modifications, equivalent substitutions and improvements, etc., made within the spirit and principle of the invention shall be covered in the protection scope of the present application.

What is claimed is:

1. An organic electroluminescent device comprising a capping layer, wherein the capping layer comprises an organic compound based on triazine and benzoxazole, and wherein a structure of the organic compound is represented by the following formula (1):

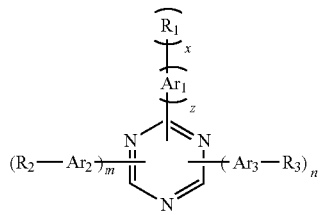

formula (1)

wherein, x represents 1 or 2; z represents 1 or 2; m and n independently represent 0, 1 or 2; and m+n+z=3;

In the formula (1), $Ar_1$, $Ar_2$, and $Ar_3$ each independently represent substituted or unsubstituted arylene with 6 to 60 carbon atoms or substituted or unsubstituted 5 to 60-membered heteroarylene with one or more heteroatoms; the heteroatom is nitrogen atom, oxygen atom or sulfur atom; $Ar_1$, $Ar_2$, and $Ar_3$ each further independently represent a single bond; $Ar_1$, $Ar_2$, and $Ar_3$ are identical or different;

$R_1$ represents hydrogen atom, substituted or unsubstituted aryl with 6 to 60 carbon atoms, substituted or unsubstituted 5 to 60-membered heteroary with one or more heteroatoms, or

the heteroatom is nitrogen atom, oxygen atom, or sulfur atom;

$Q_1$ and $Q_2$ each independently represent substituted or unsubstituted aryl with 6 to 60 carbon atoms, or substituted or unsubstituted 5 to 60-membered heteroary with one or more heteroatoms; the heteroatom is nitrogen atom, oxygen atom, or sulfur atom;

$R_2$ represents a structure represented by the following formula (2) or formula (3):

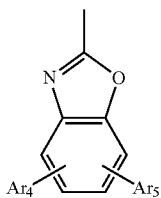

formula (2)

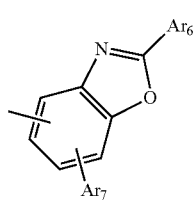

formula (3)

$R_3$ represents a structure represented by the following formula (4) or formula (5):

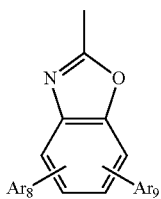

formula (4)

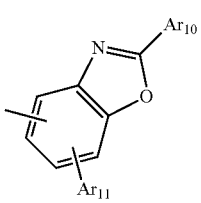

formula (5)

wherein $Ar_4$, $Ar_5$, $Ar_6$, $Ar_7$, $Ar_8$, $Ar_9$, $Ar_{10}$ and $Ar_{11}$ each independently represent hydrogen atom, substituted or unsubstituted aryl with 6 to 60 carbon atom, linear or branched alkyl with 1 to 10 carbon atoms, or substituted or unsubstituted 5- to 60-membered heteroary with one or more heteroatoms; the heteroatom is nitrogen atom, oxygen atom, or sulfur atom.

2. The organic electroluminescent device according to claim 1, wherein $Ar_1$, $Ar_2$, and $Ar_3$ each independently represent phenylene substituted or unsubstituted by halogen atoms, protium atoms, deuterium atoms, tritiutn atoms, linear or branched alkyl with 1 to 10 carbon atoms; naphthylene substituted or unsubstituted by halogen atoms, protium atoms, deuterium atoms, tritium atoms, or linear or branched alkyl with 1 to 10 carbon atoms; biphenylene substituted or unsubstituted by halogen atoms, protium atoms, deuterium atoms, tritium atoms, or linear or branched alkyl with 1 to 10 carbon atoms; pyridinylene substituted or unsubstituted by halogen atoms, protium atoms, deuterium atoms, tritium atoms, or linear or branched alkyl with 1 to 10 carbon atoms; carbazolylene; furanylene; pyrimidinylene; pyrazinylene; pyridazinylene; dibenzofuranylene; 9,9-ditnethylfluorenylene, or N-phenylcarbazolylene; quinolylene; or isoquinolylene or naphthyridinylene; $R_1$, $Ar_4$, $Ar_5$, $Ar_6$, $Ar_7$, $Ar_8$, $Ar_9$, $Ar_{10}$, $Ar_{11}$ and $Q_1$ and $Q_2$ each independently represent phenyl substituted or unsubstituted by halogen atoms, protium atoms, deuterium atoms, tritium atoms, linear or branched alkyl with 1 to 10 carbon atoms; naphthyl substituted or unsubstituted by halogen atoms, protium atoms, deuterium atoms, tritium atoms, linear or branched alkyl with 1 to 10 carbon atoms; biphenyl substituted or unsubstituted by halogen atoms, protium atoms, deuterium atoms, tritium atoms, linear or branched alkyl with 1 to 10 carbon atoms; pyridinyl substituted or unsubstituted by halogen atoms, protium atoms, deuterium atoms, tritium atoms, linear or branched alkyl with 1 to 10 carbon atoms; carbazolyl; furanyl; pyrimidinyl; pyrazinyl; pyridazinyl; dibenzofuranyl; 9,9-dimethylfluorenyl; N-phenylcarbazolyl; quinolinyl; or isoquinolinyl or naphthyridinyl.

3. The organic electroluminescent device according to claim 1, wherein, when z represents 1, $-Ar_1-(R_1)_x$ contains at least one heteroatom, and the heteroatom is nitrogen atom, oxygen atom, or sulfur atom.

4. The organic electroluminescent device according to claim 1, wherein the structure of the organic compound is represented as any one of the following formulas (I)-(VII):

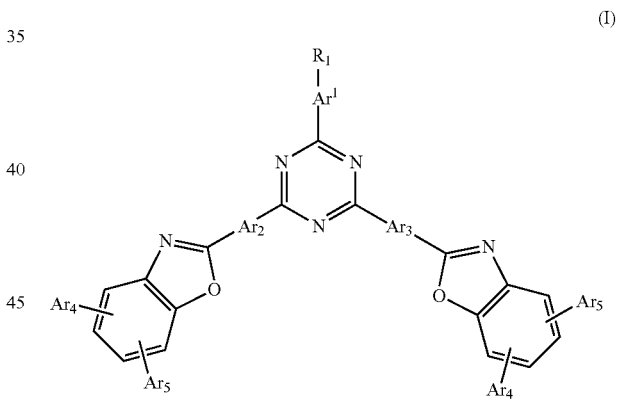

(I)

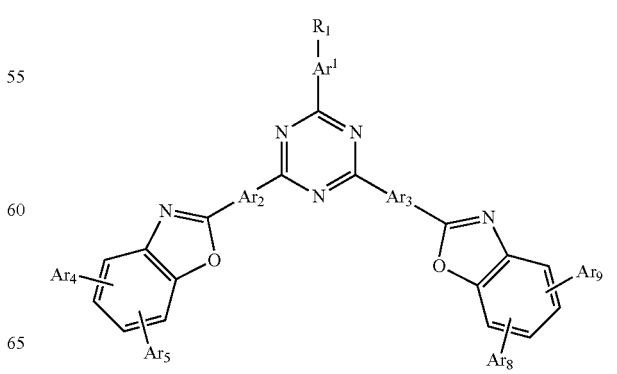

(II)

(III)
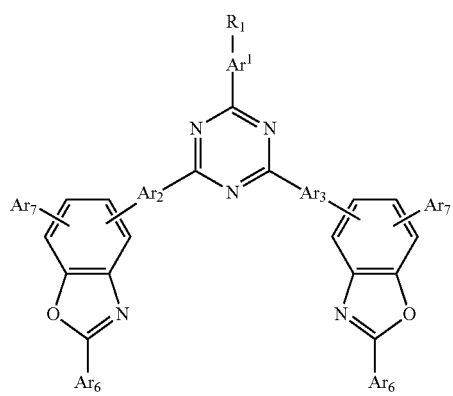
(IV)
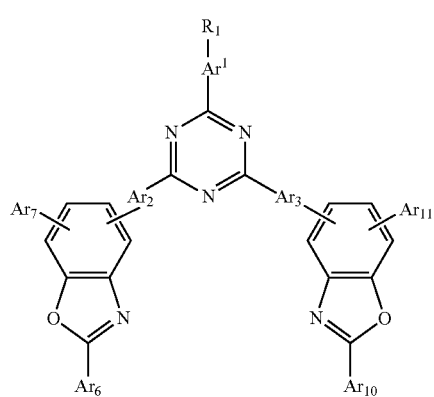
(V)
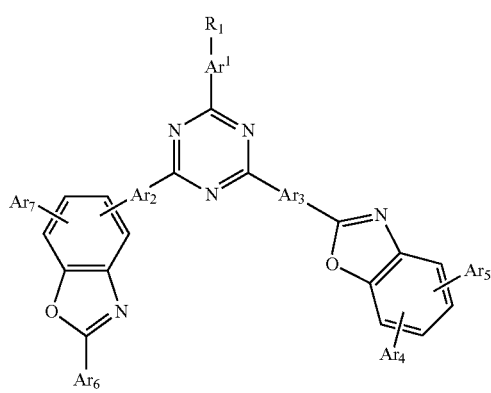
(VI)
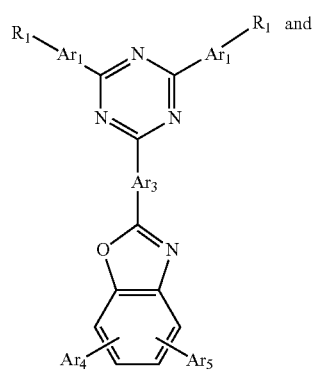
(VII)
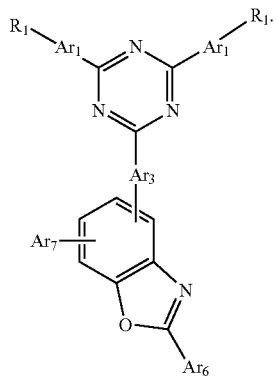
5. The organic electroluminescent device according to claim 1, wherein $R_1$ in formula (1) represents any one of:
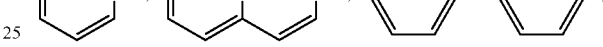
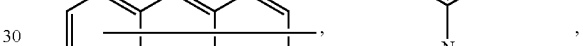
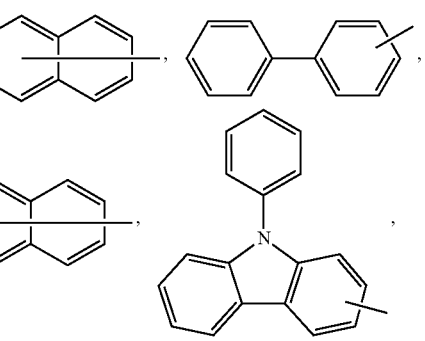
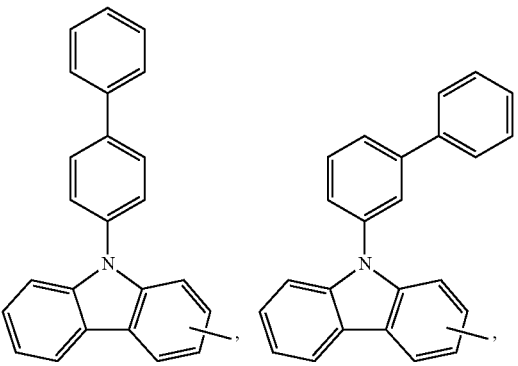
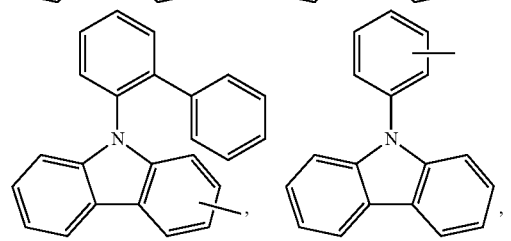
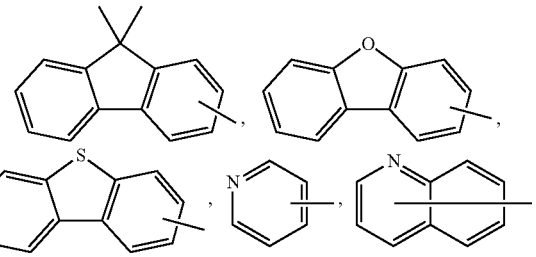

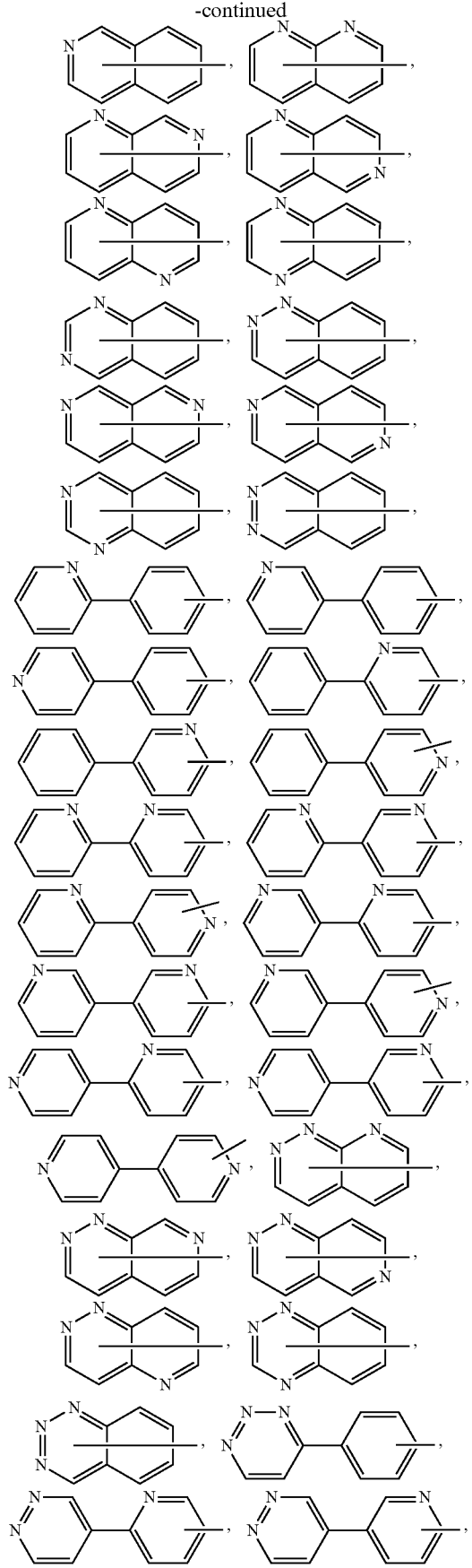
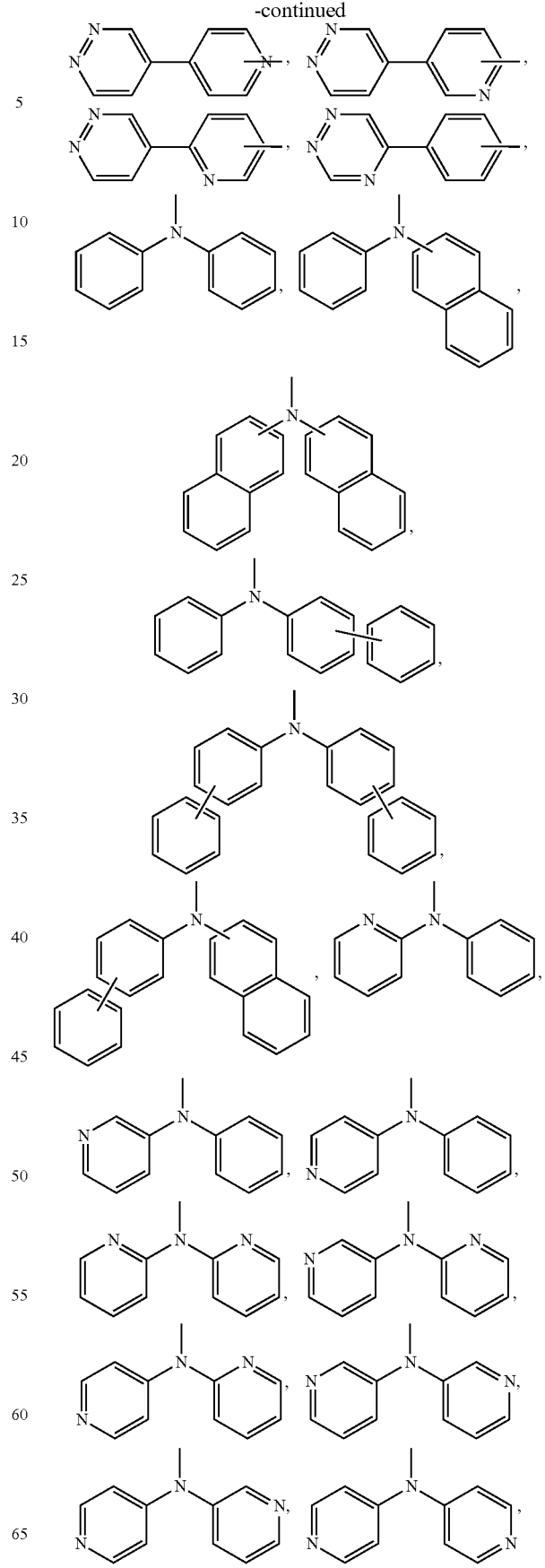

311
-continued
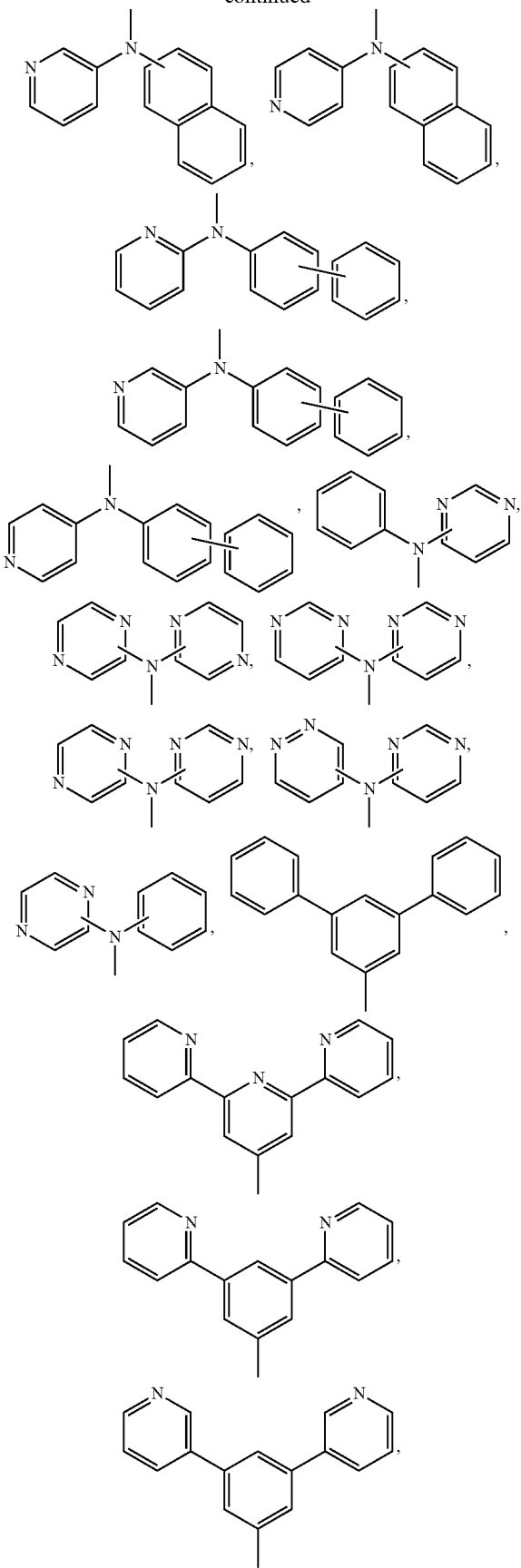
312
-continued
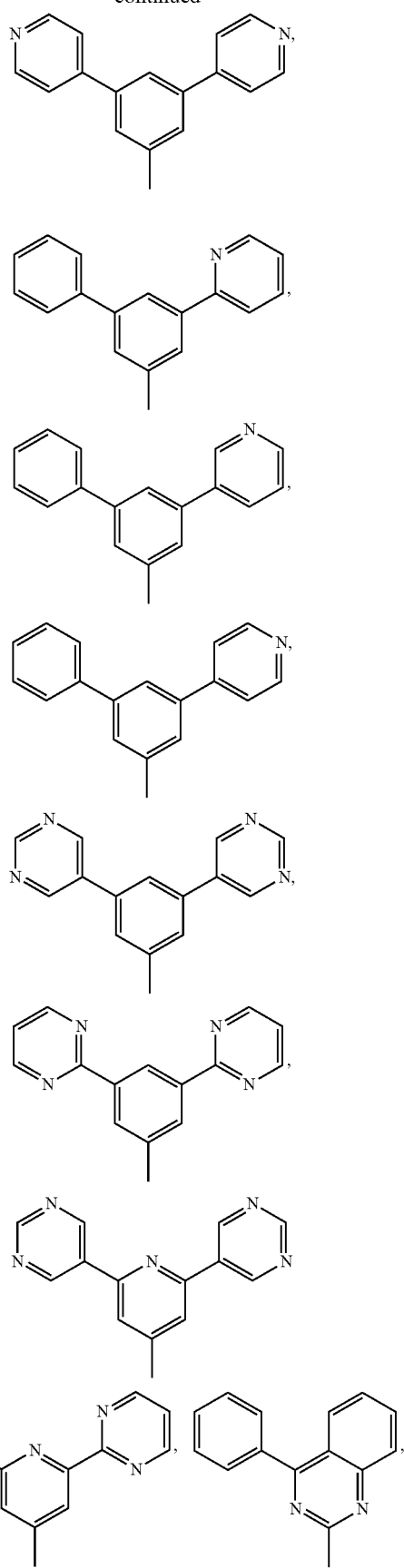

313
-continued
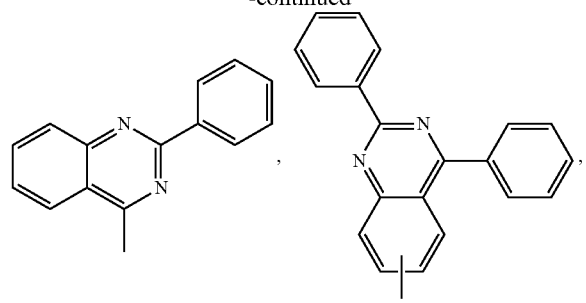
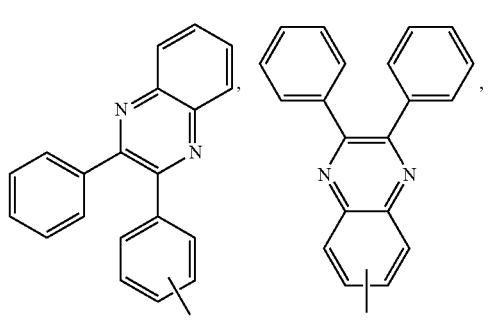
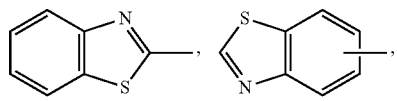
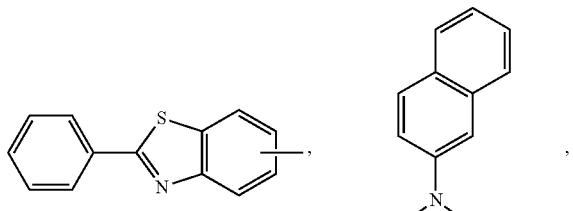
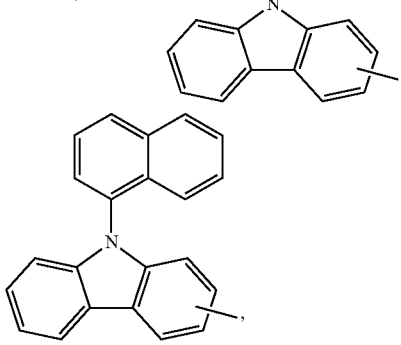
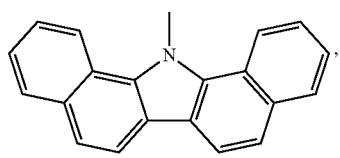
314
-continued
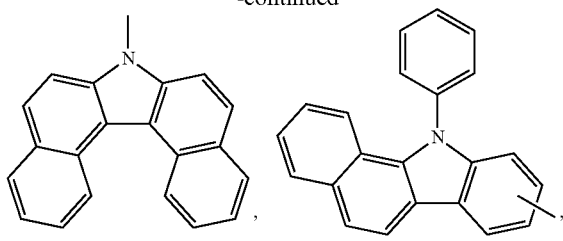
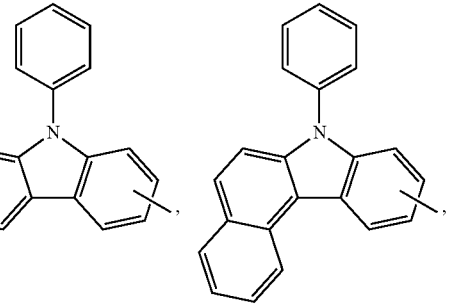
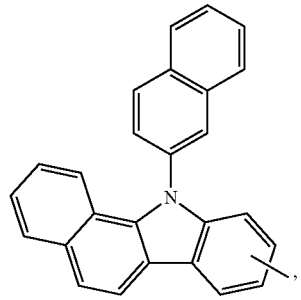
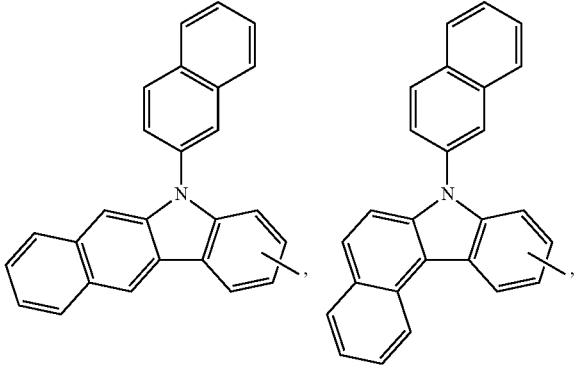
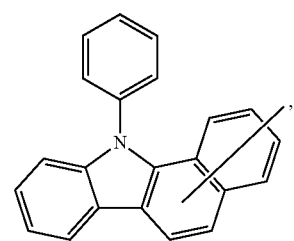

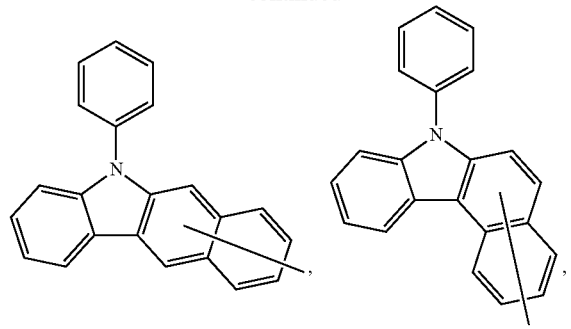
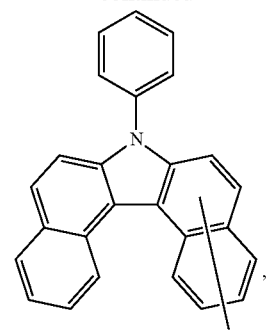
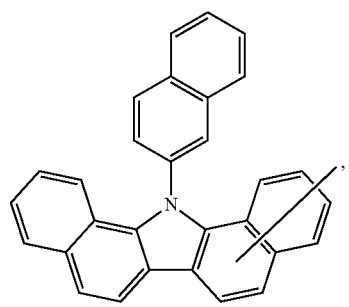
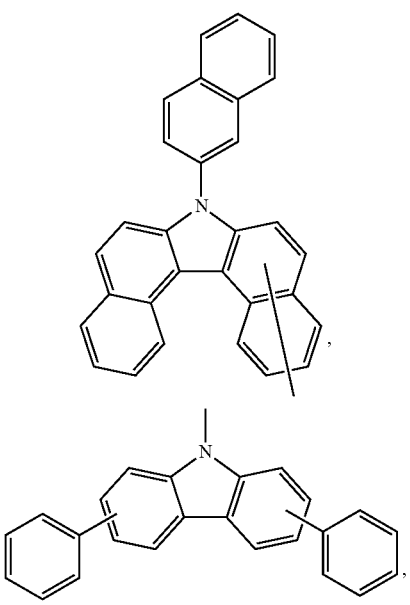

317
-continued
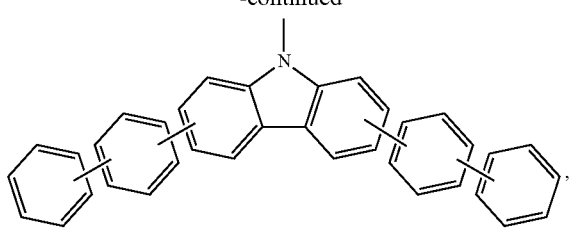,
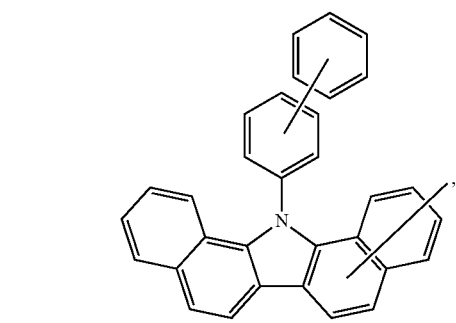,
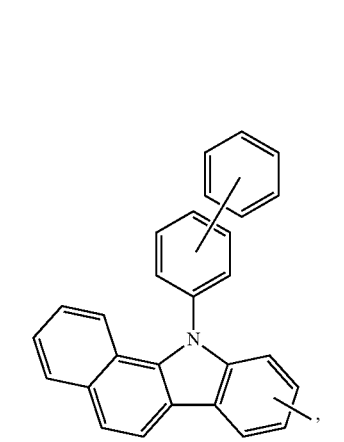,
, 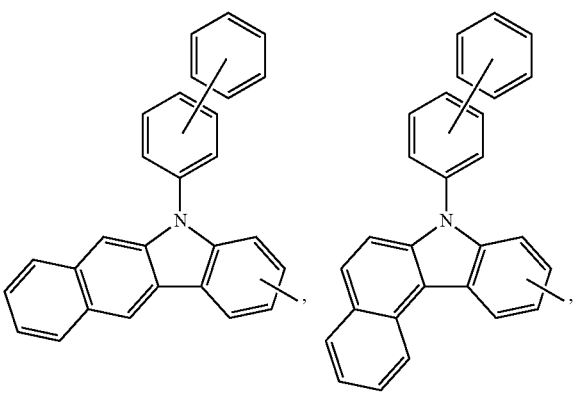,
318
-continued
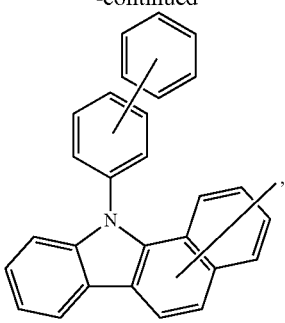,
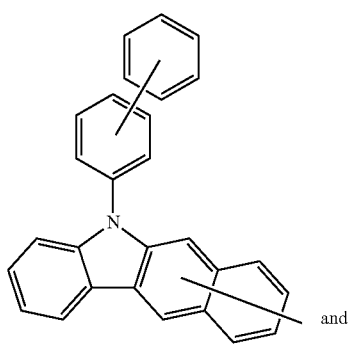, and
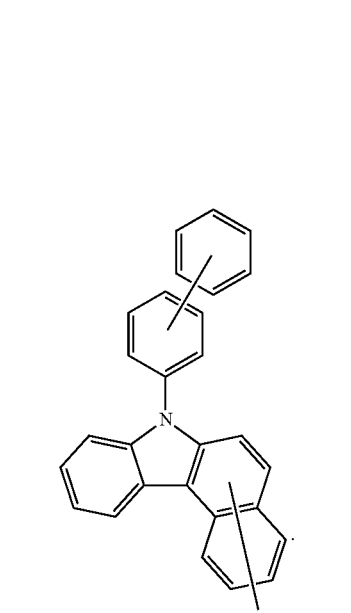,
6. The organic electroluminescent device according to claim 1, wherein a particular structural formula of the organic compound is any one of:

319 320
(1)
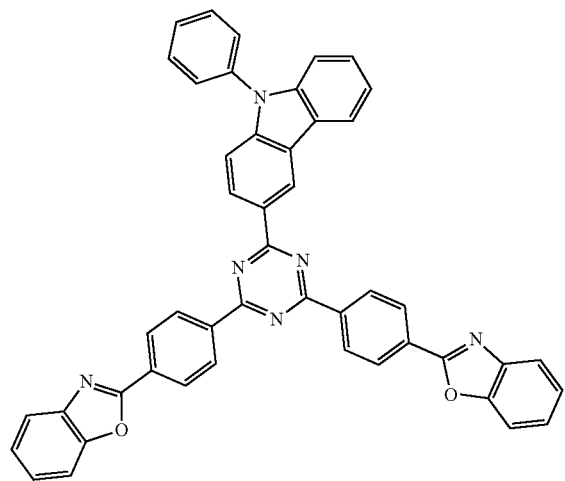
(2)
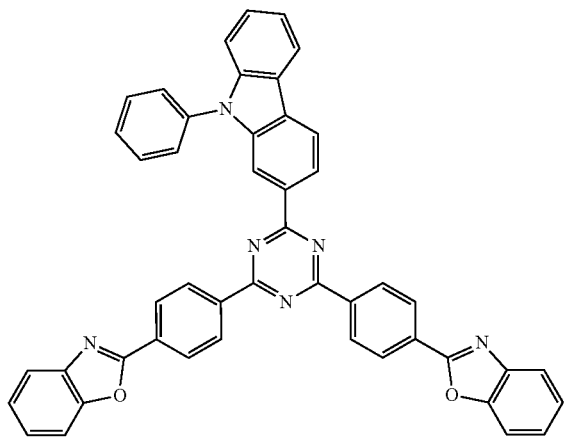
(3)
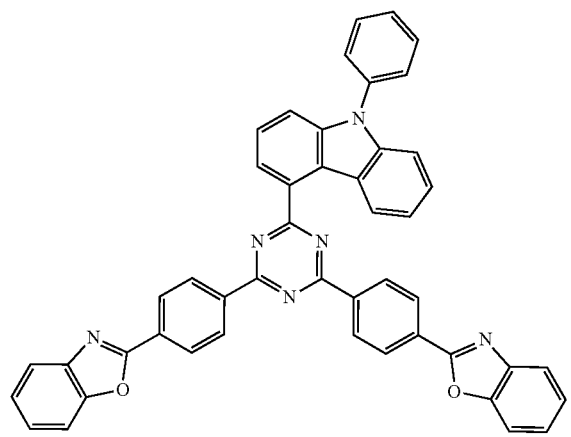
(4)
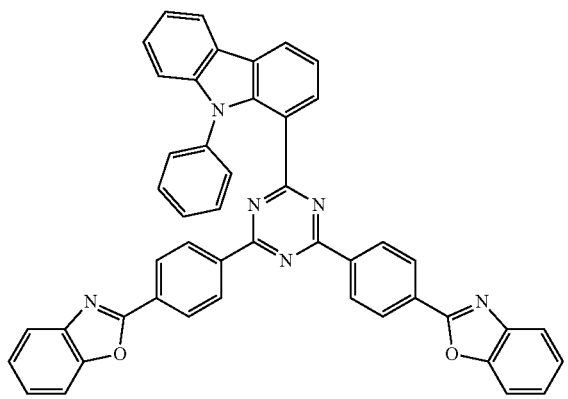
(5)
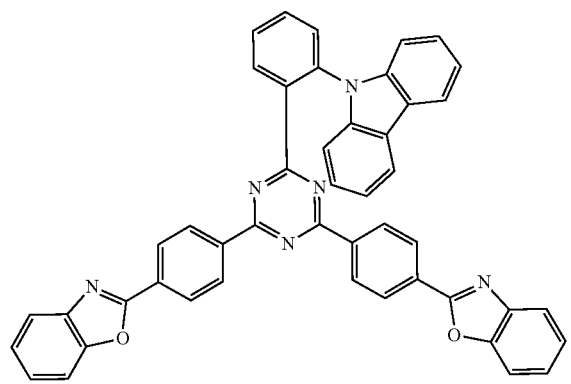
(6)
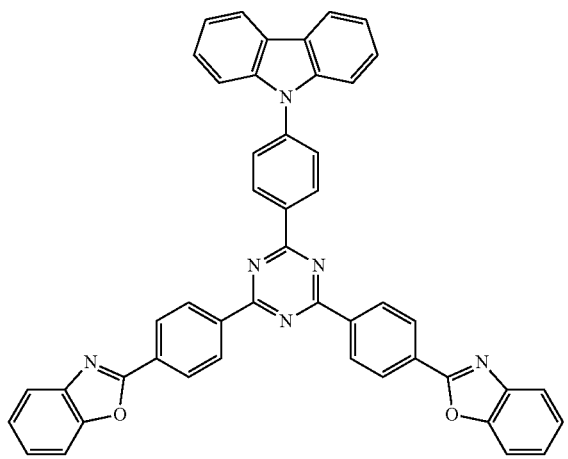

-continued
(7)
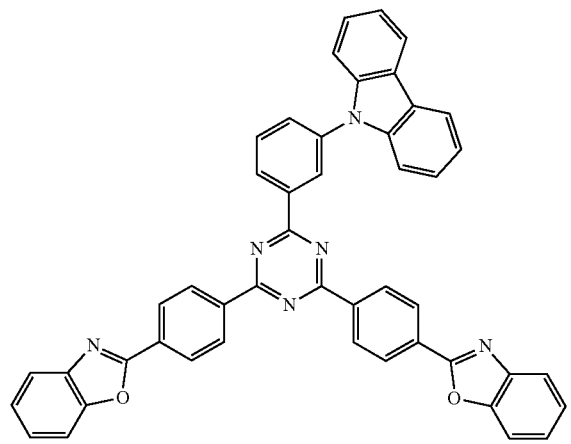
(8)
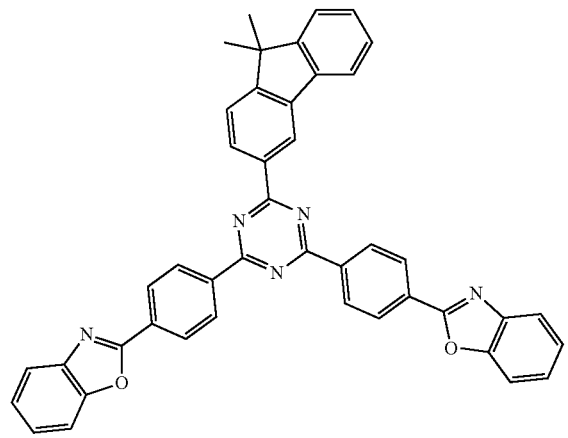
(9)
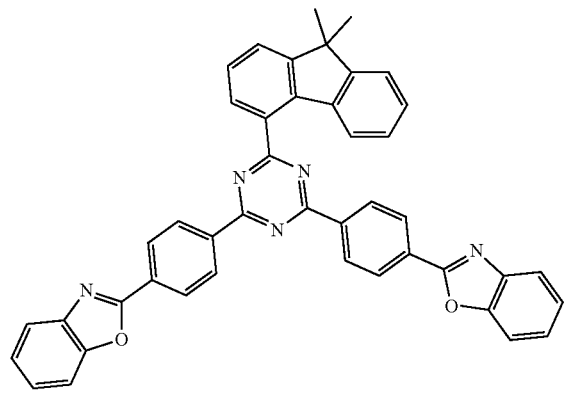
(10)
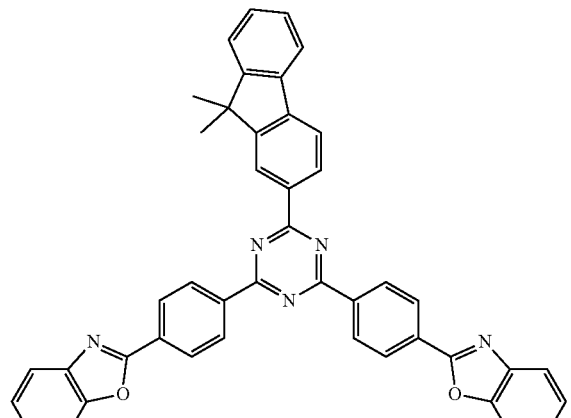
(11)
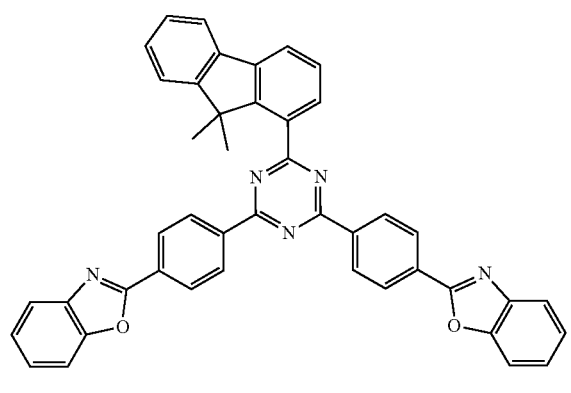
(12)
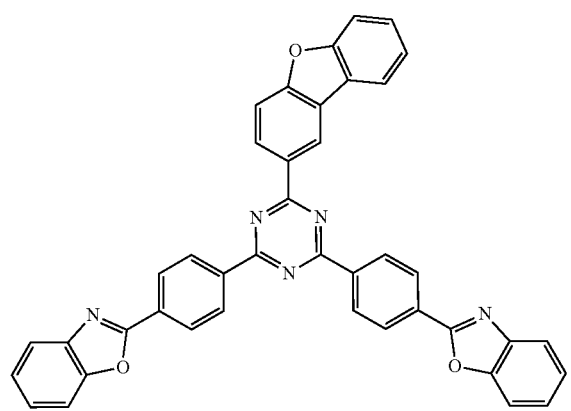

-continued
(13)
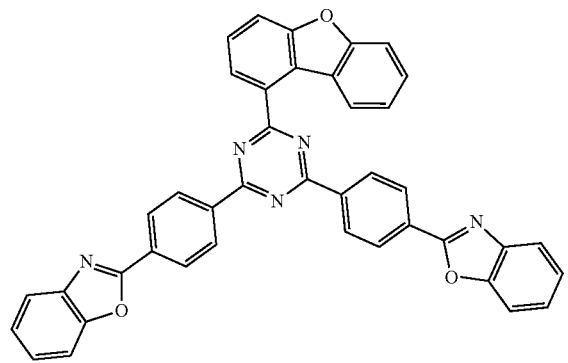
(14)
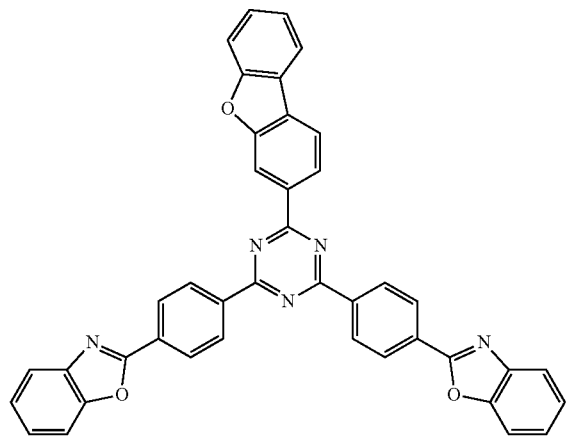
(15)
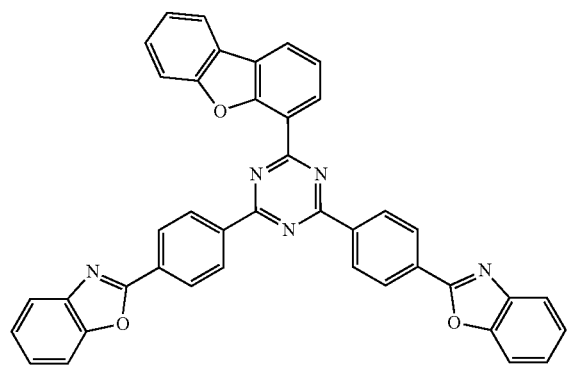
(16)
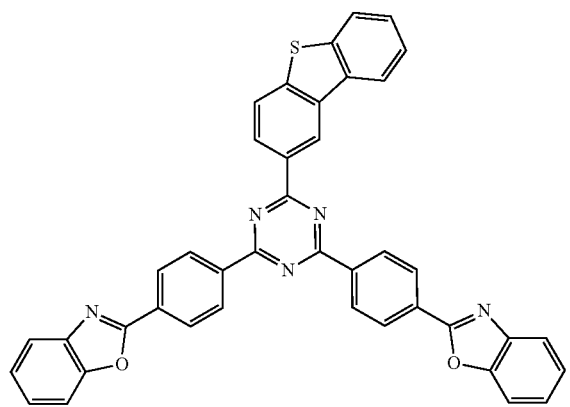
(17)
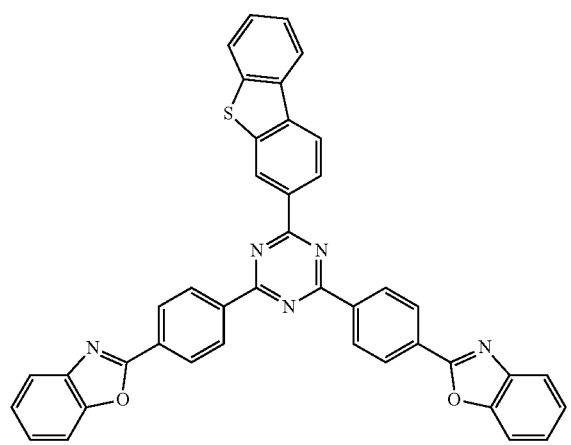
(18)
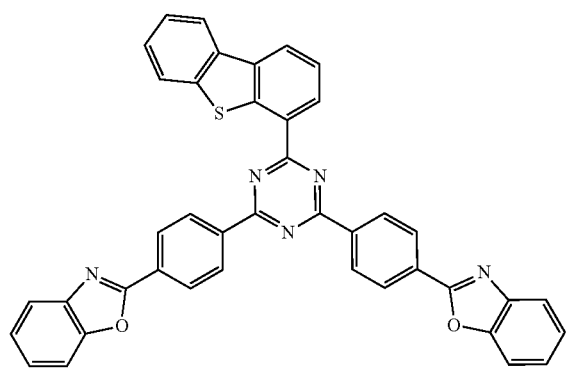

-continued
(19)
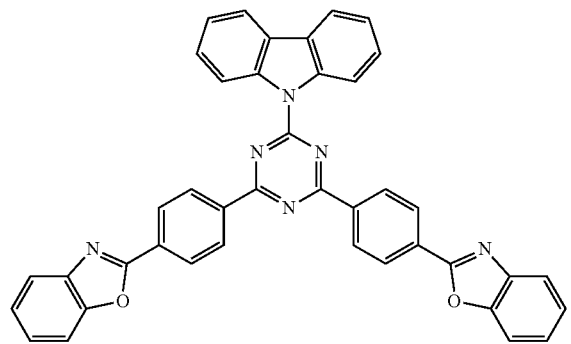
(20)
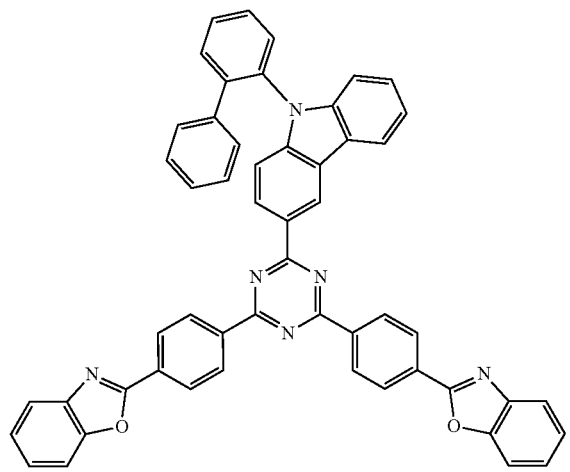
(21)
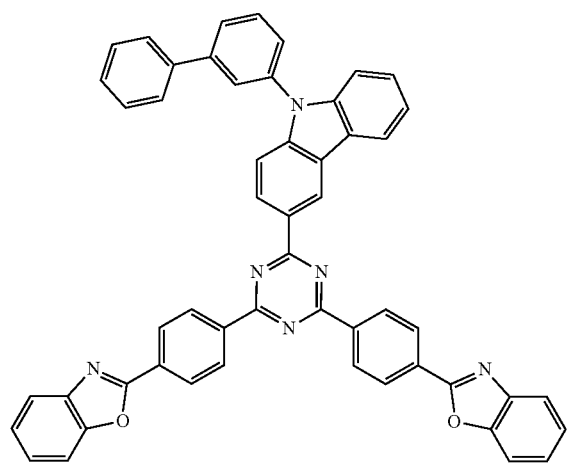
(22)
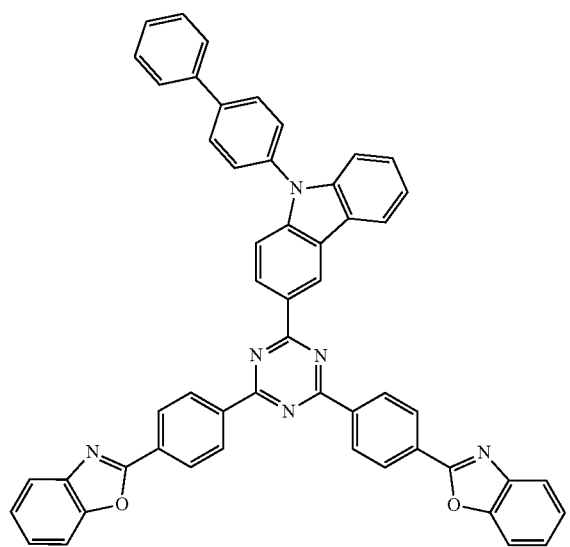
(28)
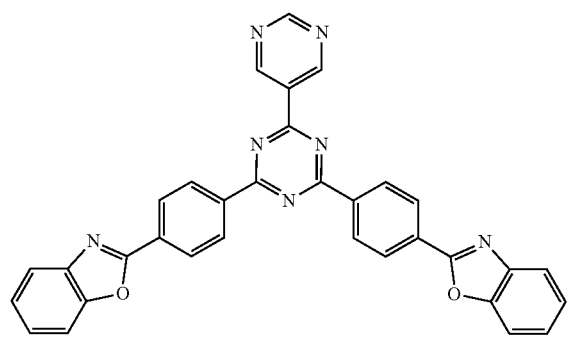
(29)
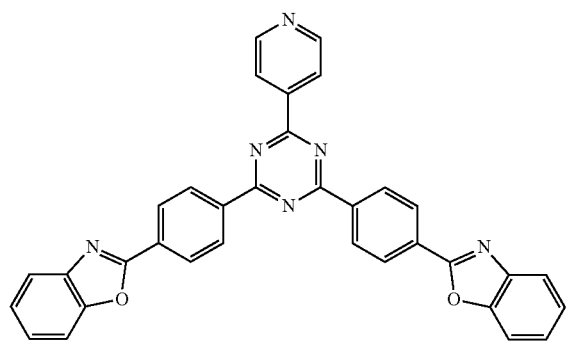

-continued
(30)
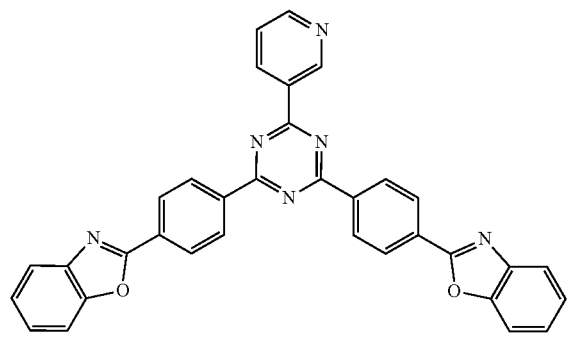
(31)
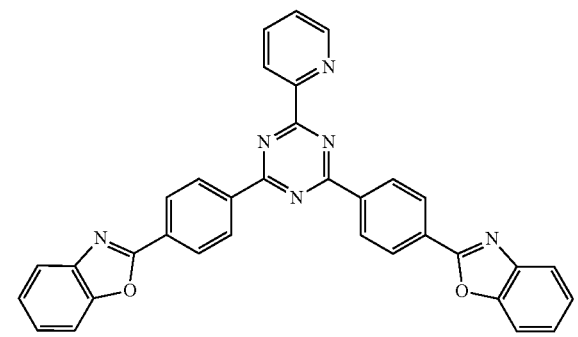
(35)
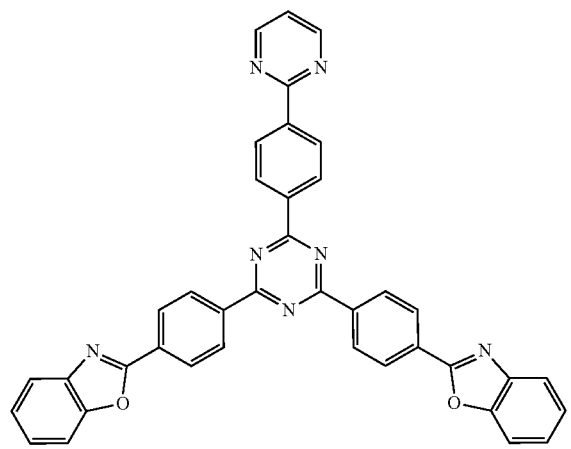
(36)
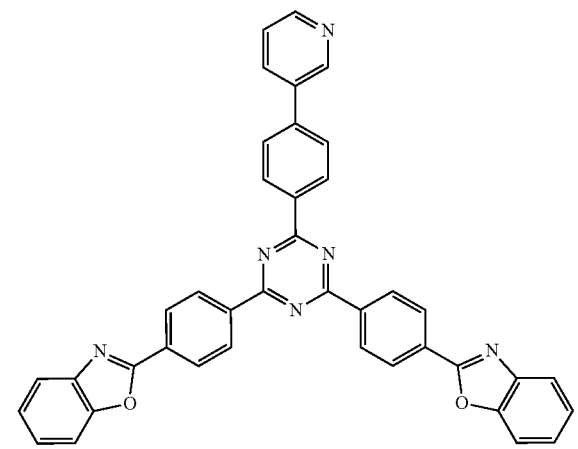
(37)
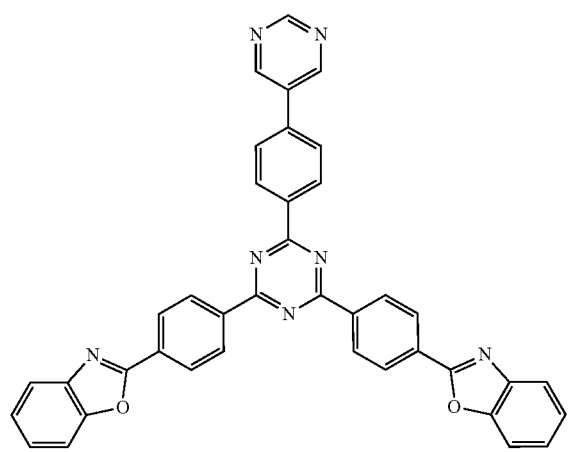
(38)
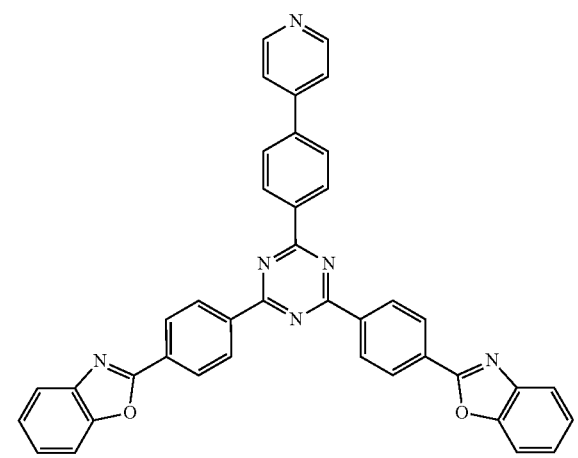

-continued
(39)
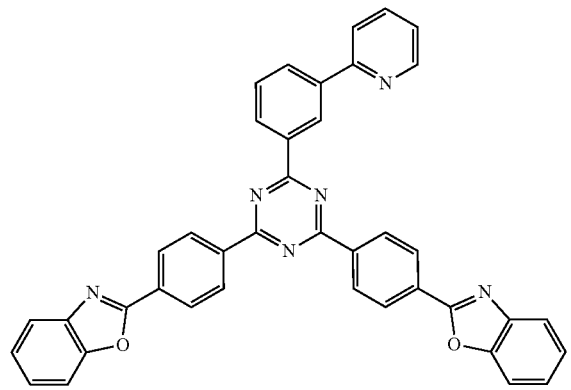
(40)
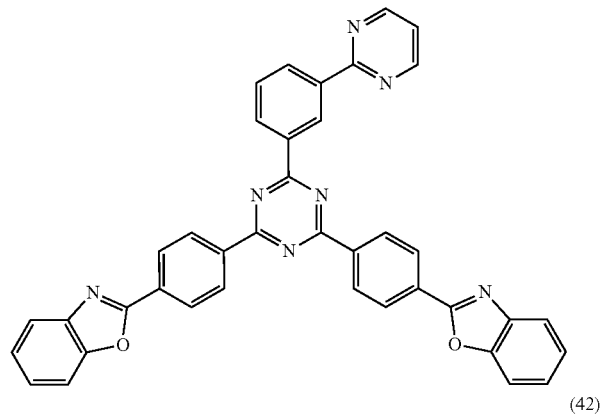
(41)
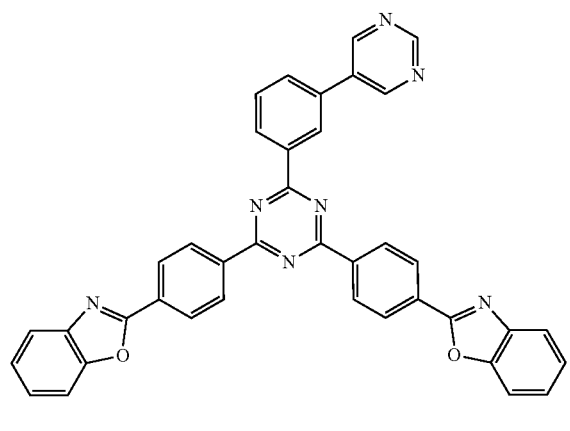
(42)
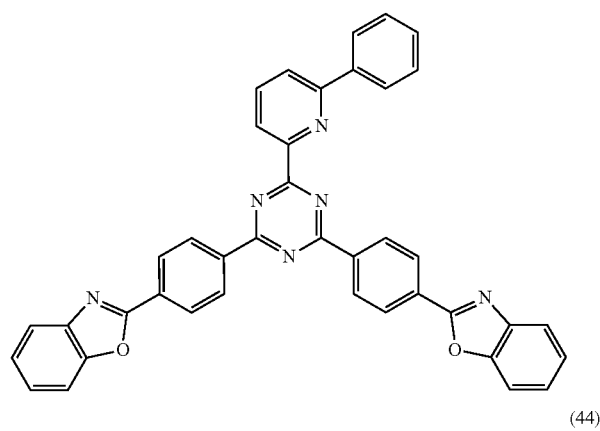
(43)
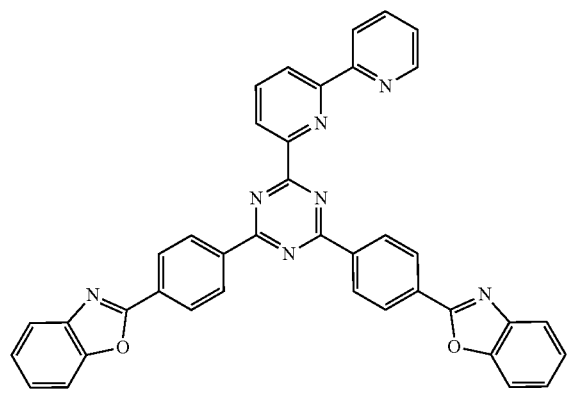
(44)
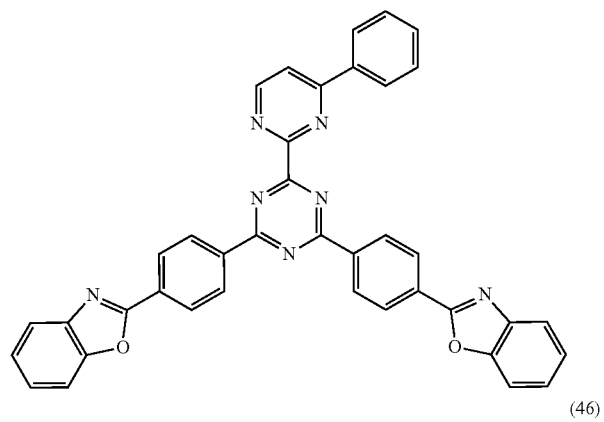
(45)
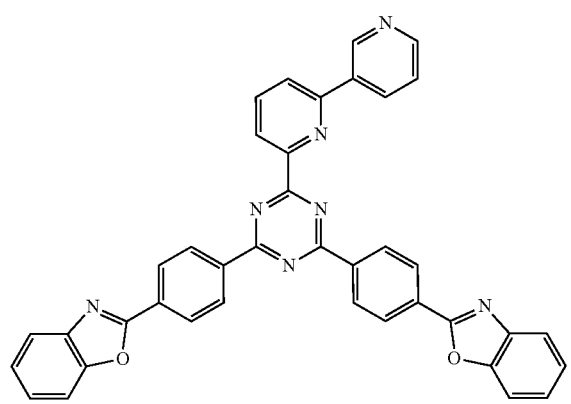
(46)
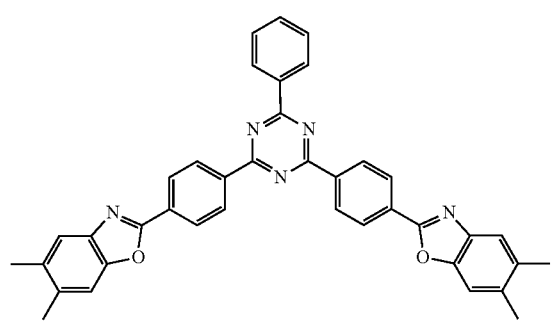

-continued
(47)
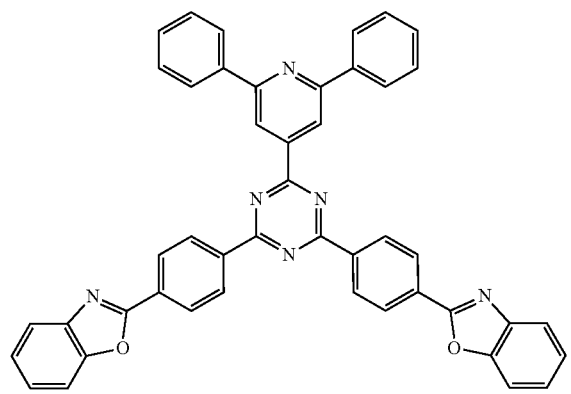
(48)
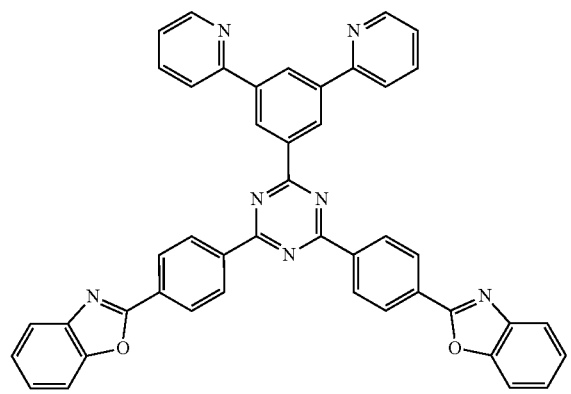
(49)
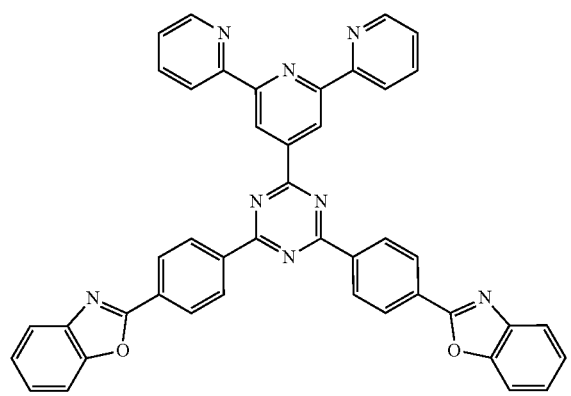
(50)
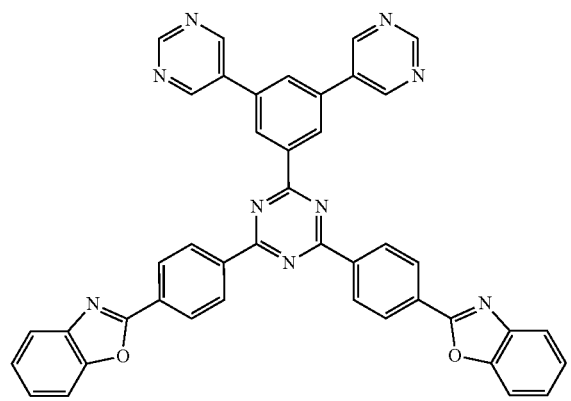
(51)
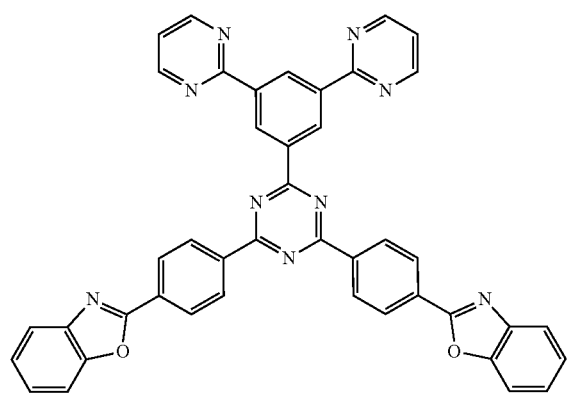
(52)
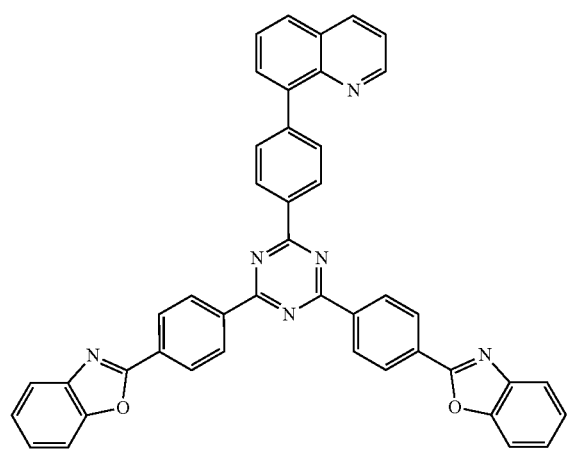

-continued
(53)
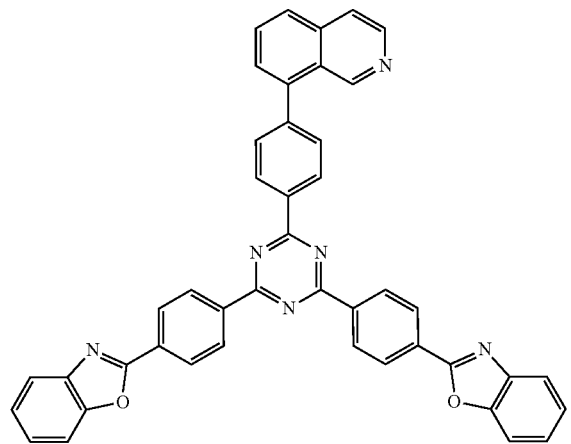
(54)
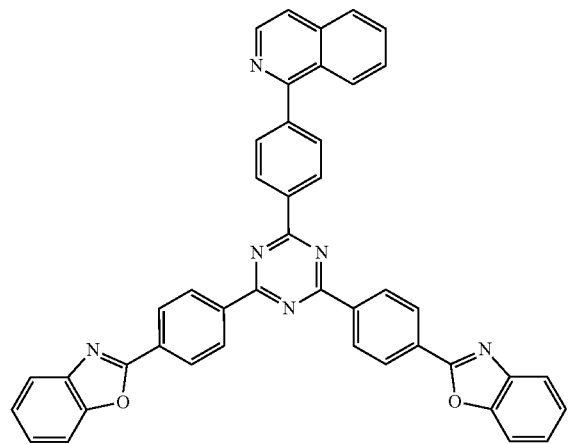
(55)
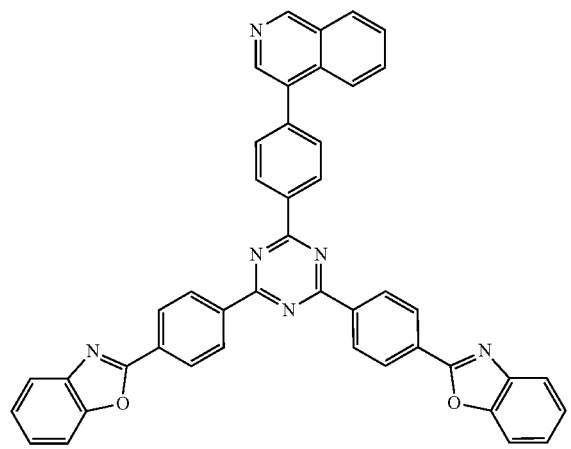
(56)
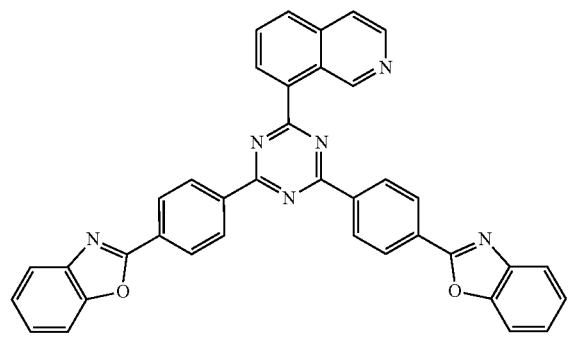
(57)
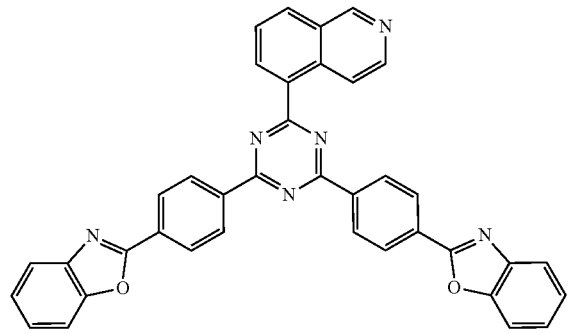
(58)
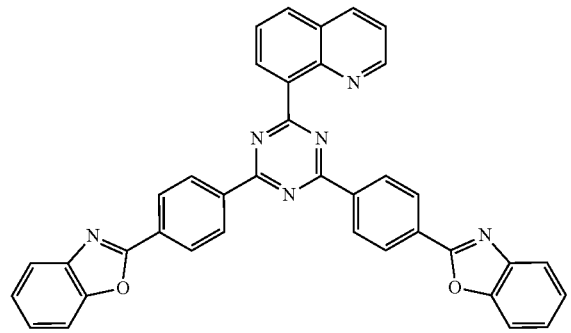

-continued
(59)
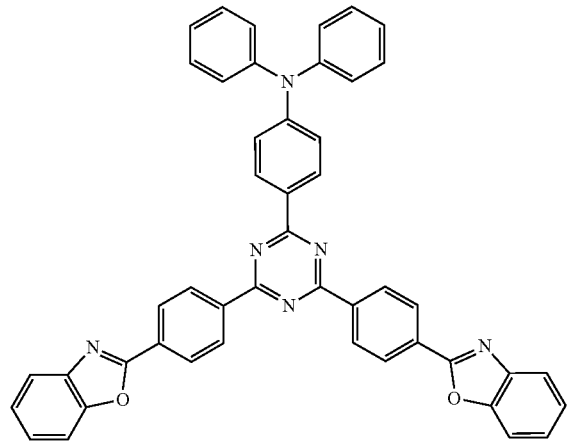
(60)
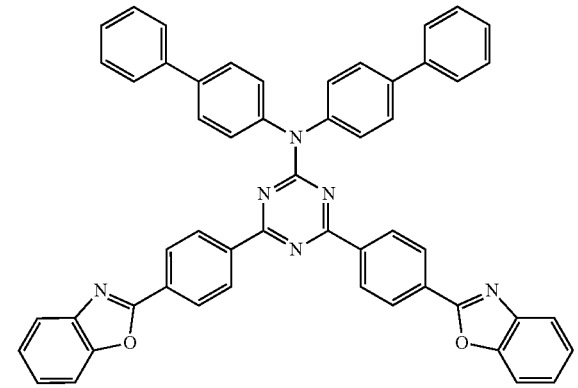
(61)
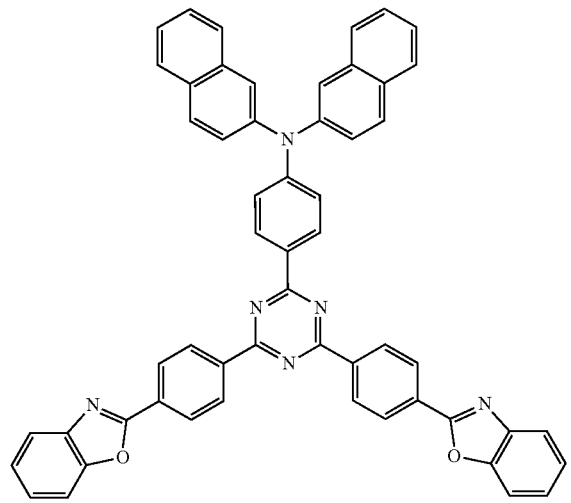
(62)
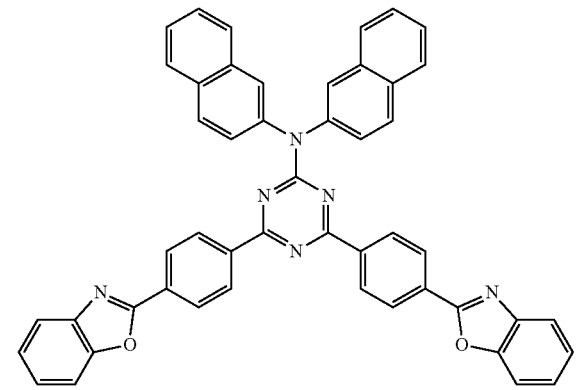
(63)
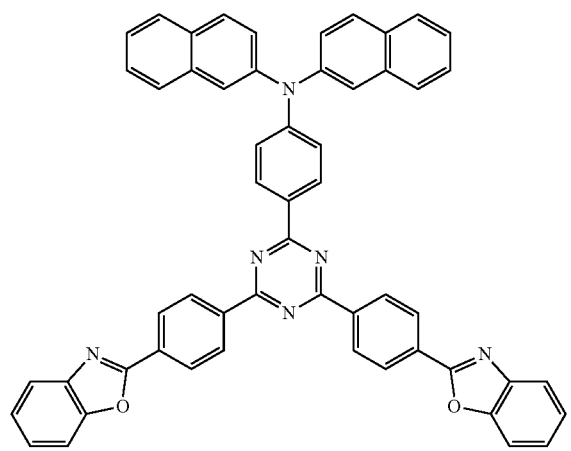
(65)
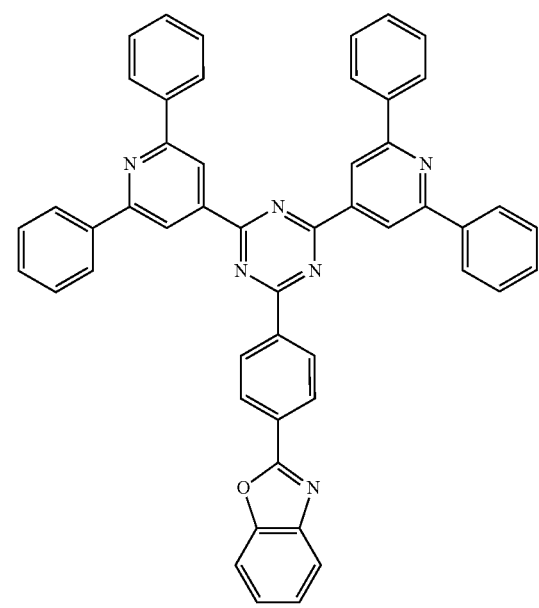

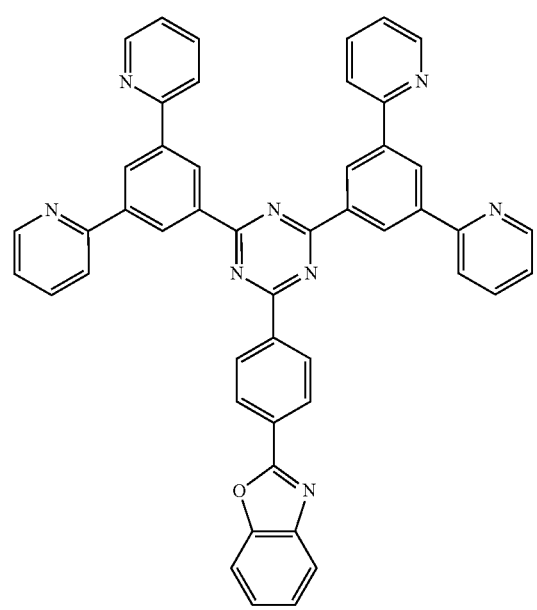
(66)
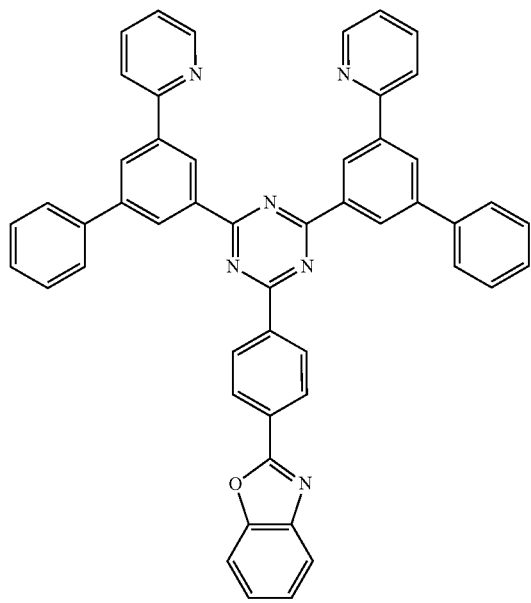
(67)
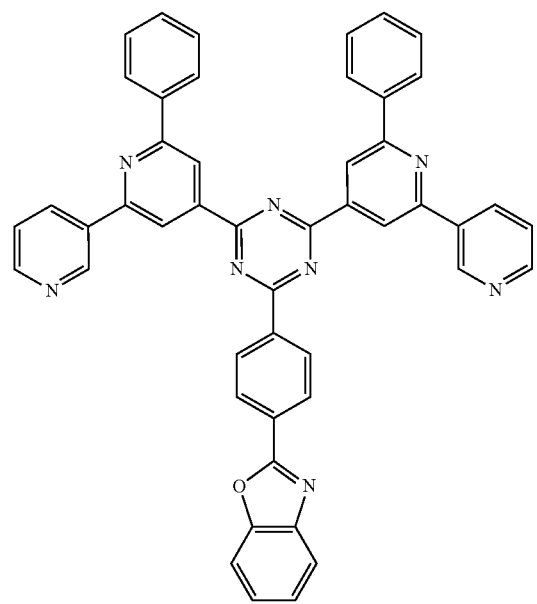
(68)
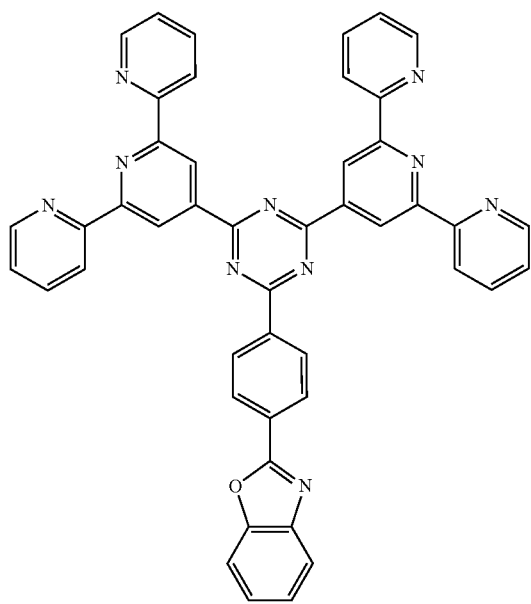
(69)

-continued
(70)
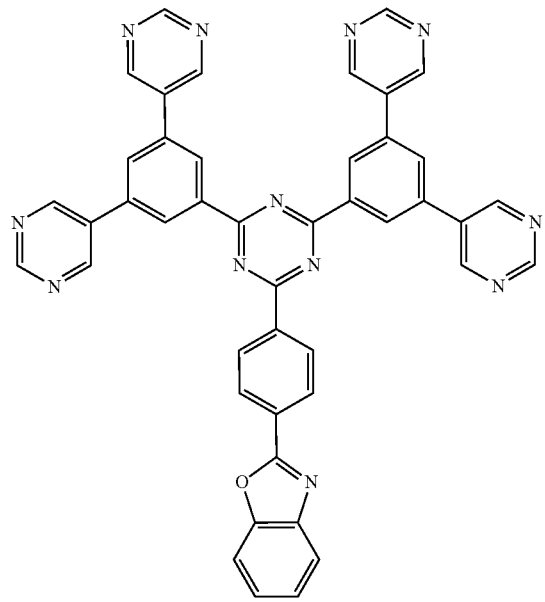
(71)
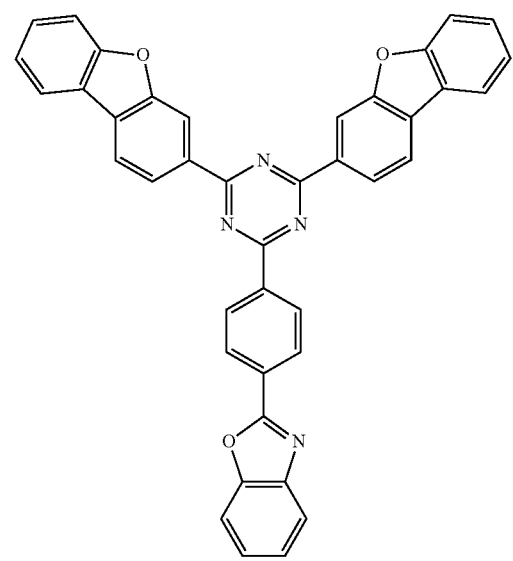
(72)
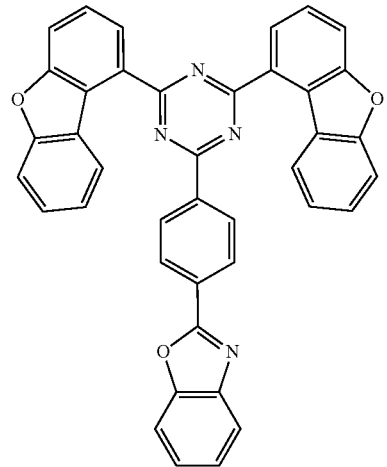
(73)
(74)
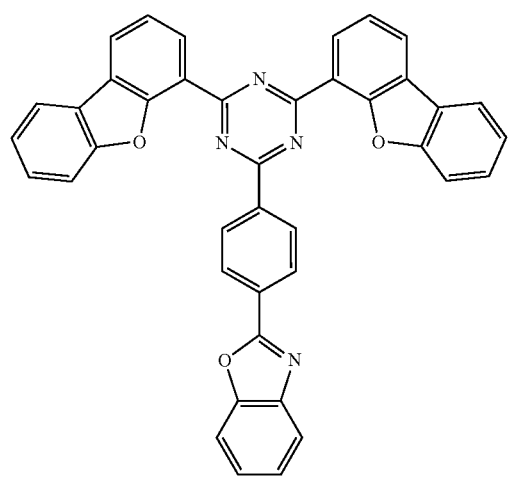
(75)
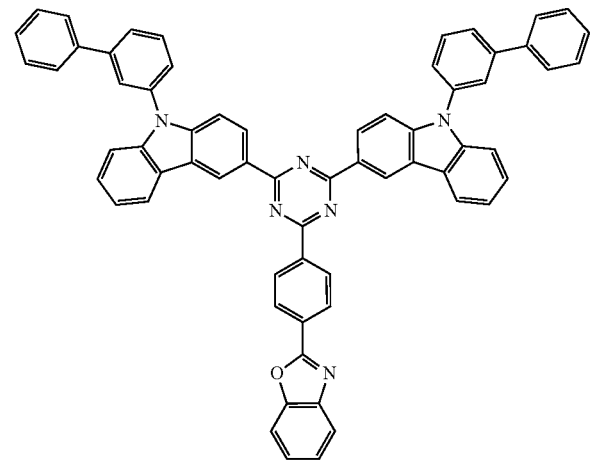

-continued
341
(76)
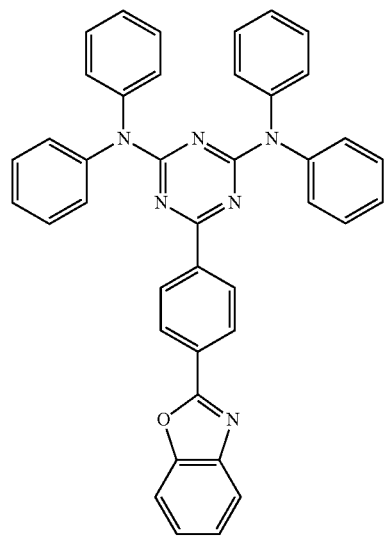
342
(77)
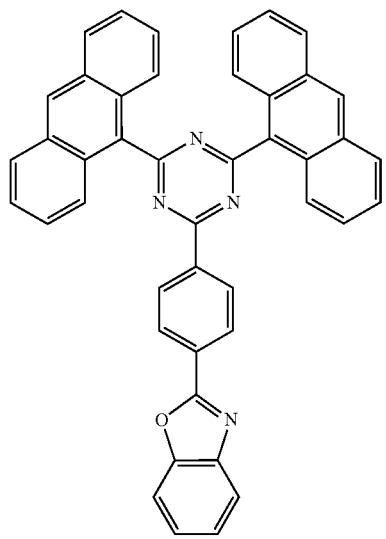
(78)
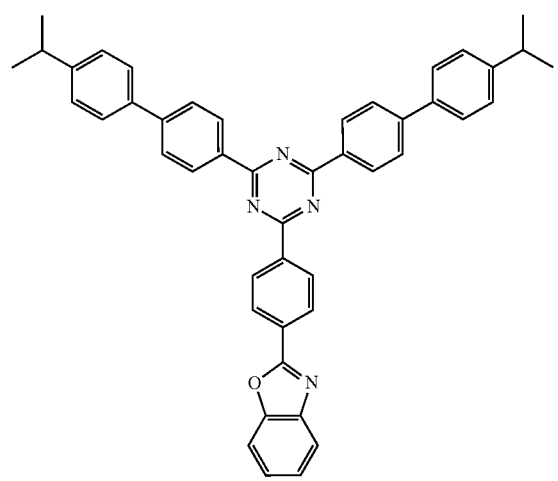
(79)
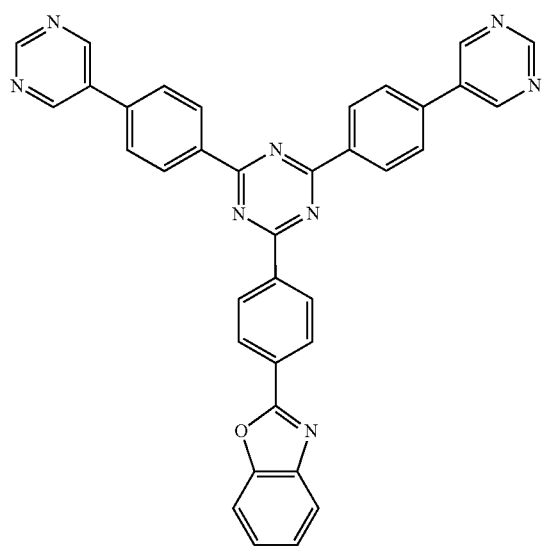
(80)
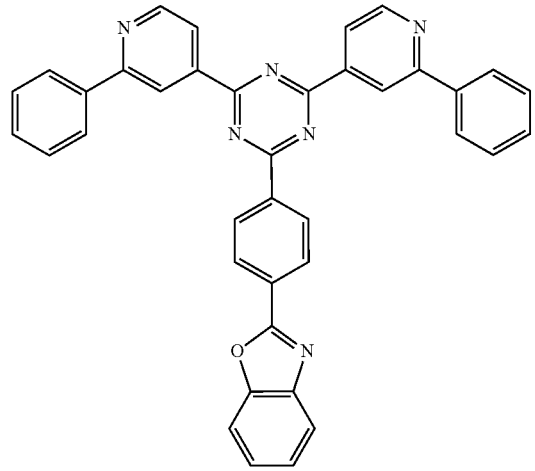
(81)
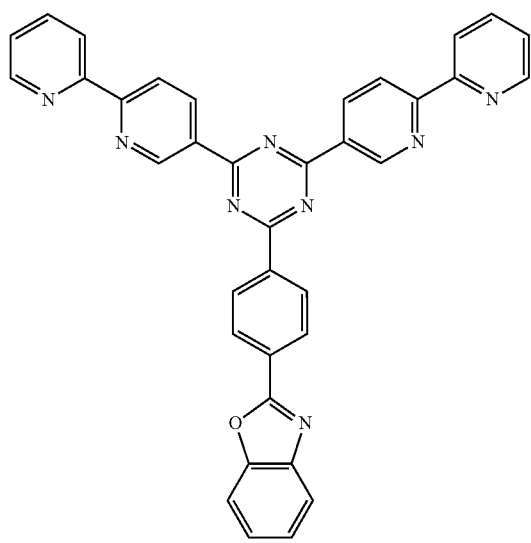

-continued
(82)
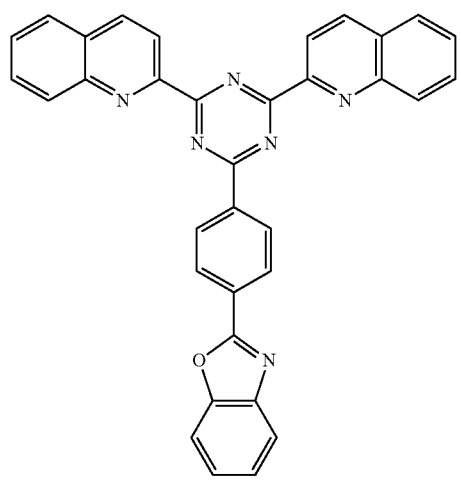
(85)
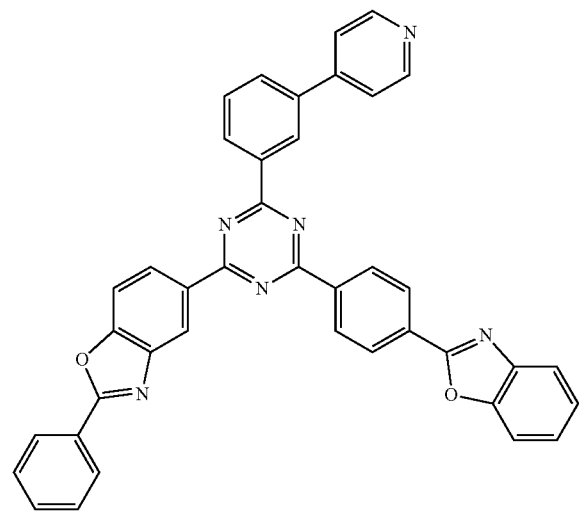
(86)
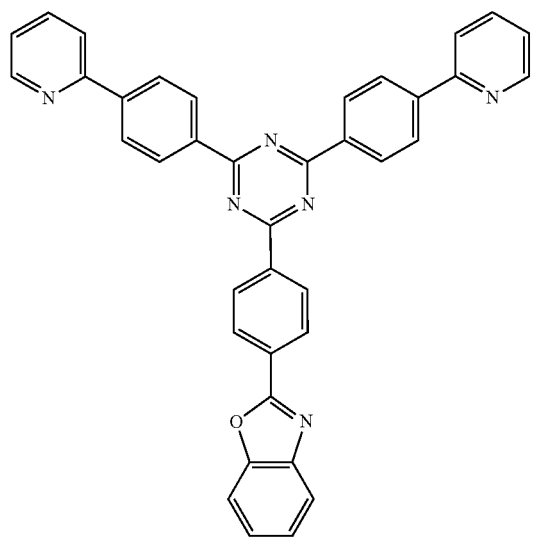
(87)
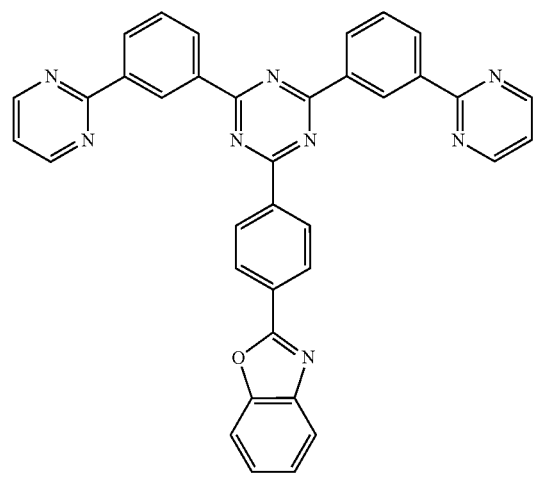
(88)
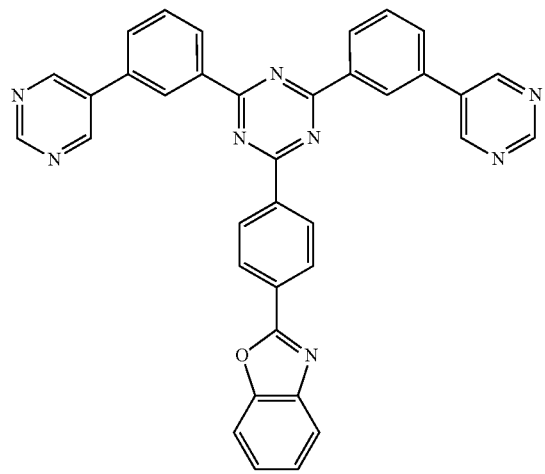
(89)
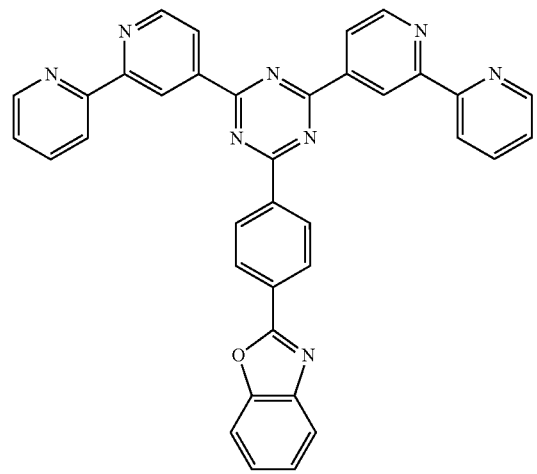

-continued
345
(90)
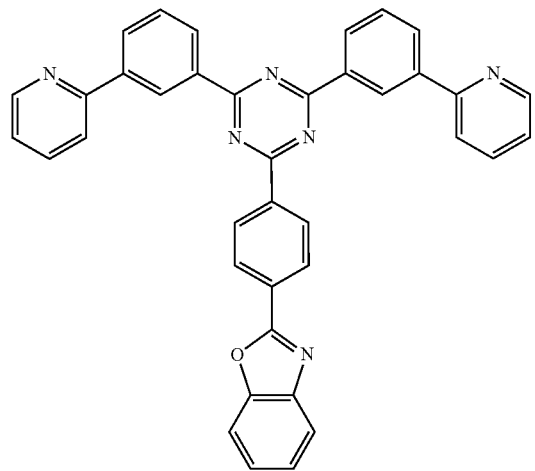
346
(91)
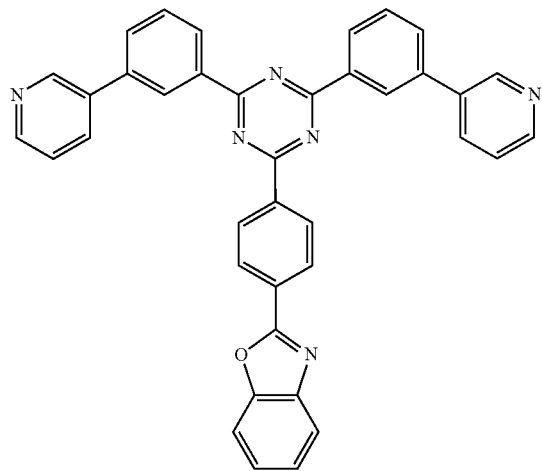
(92)
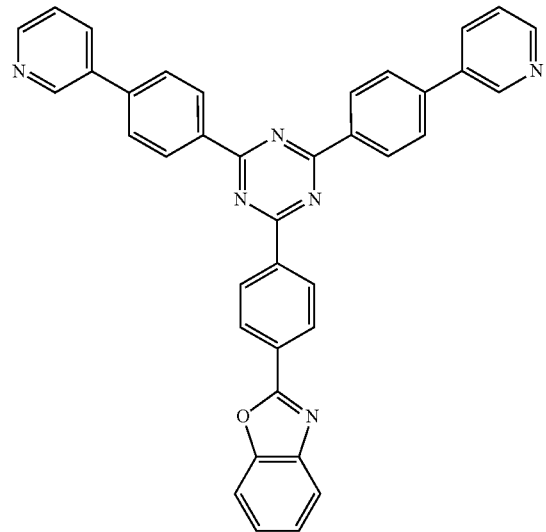
(93)
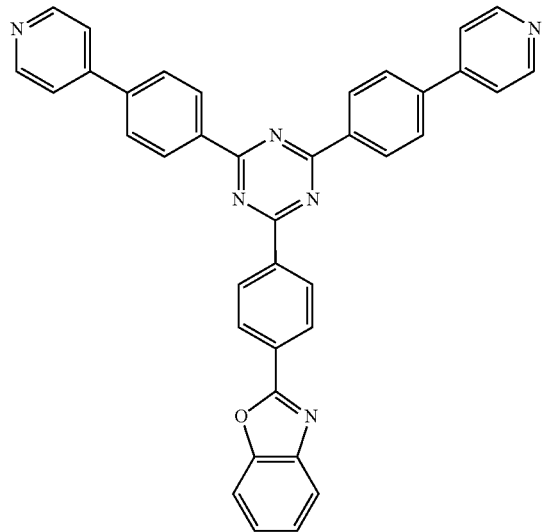
(94)
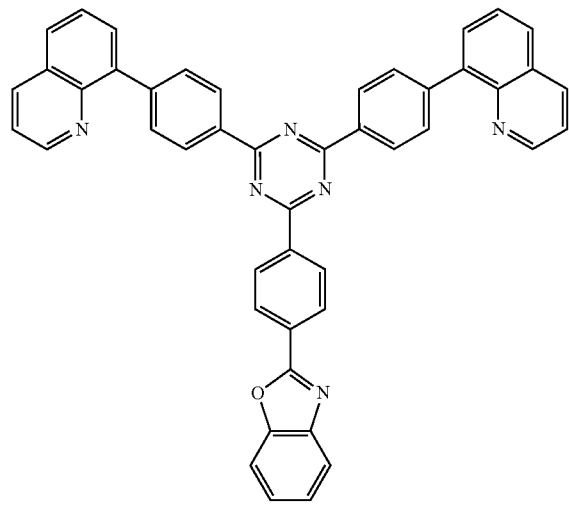
(95)
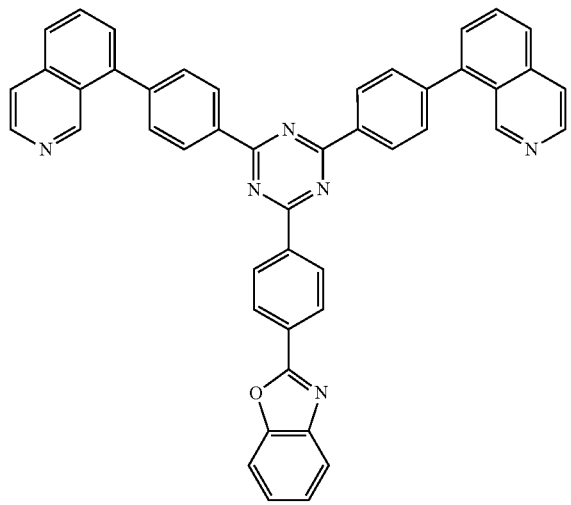

-continued
(96)
(97)
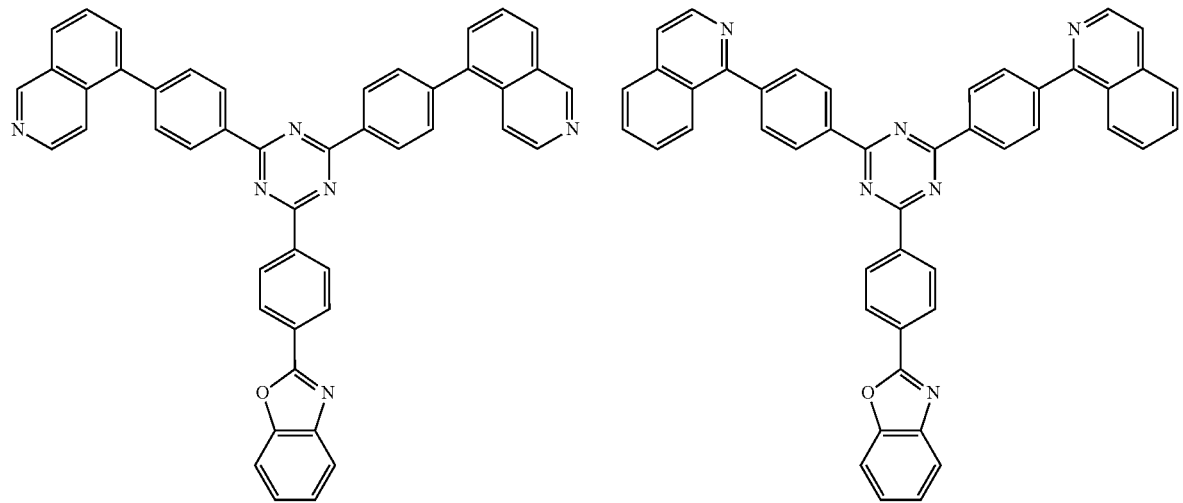
(98)
(99)
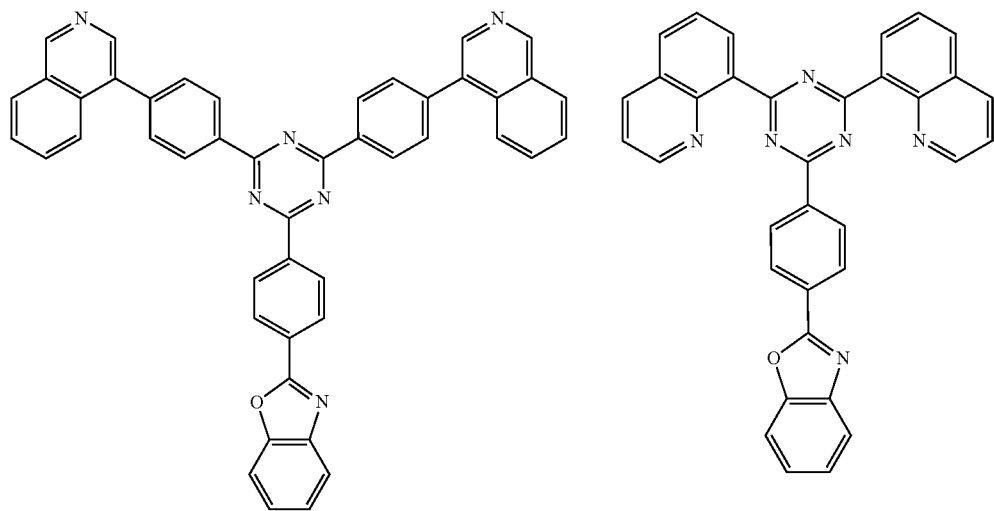
(100)
(101)
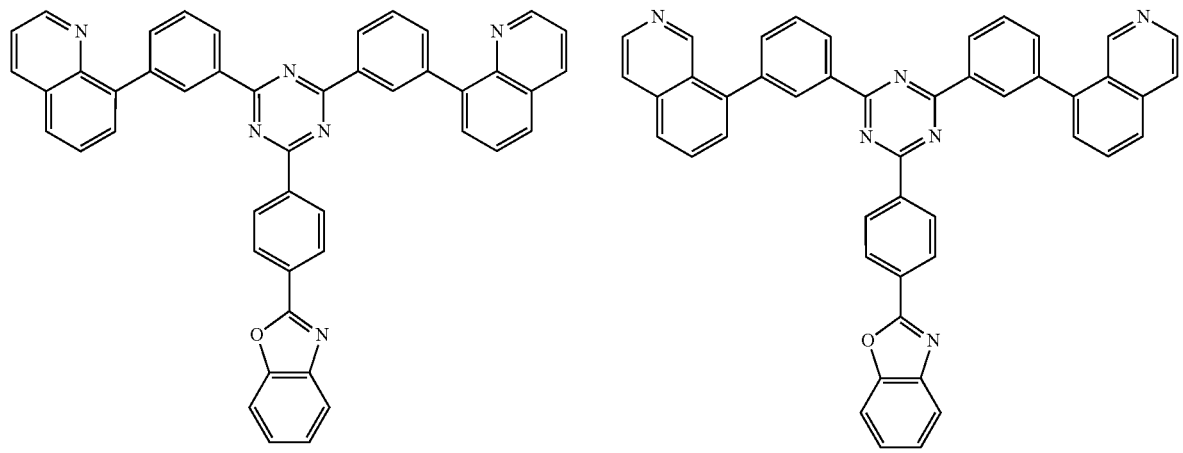

(102)
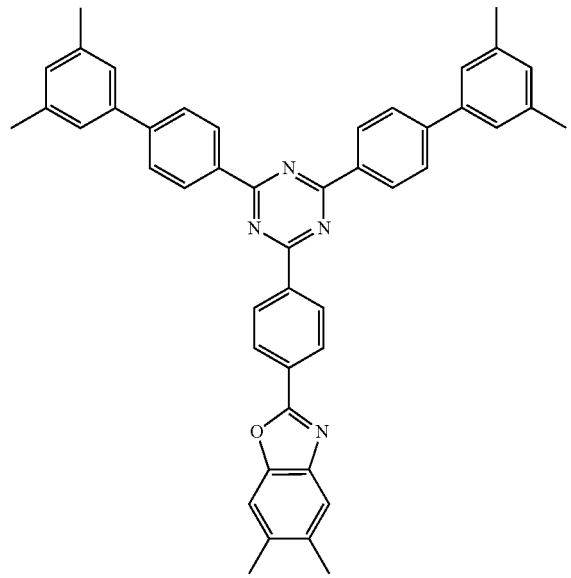
(103)
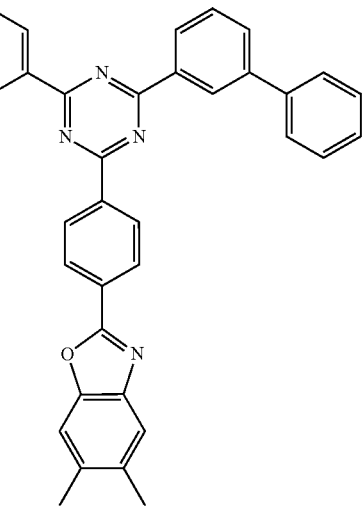
(104)
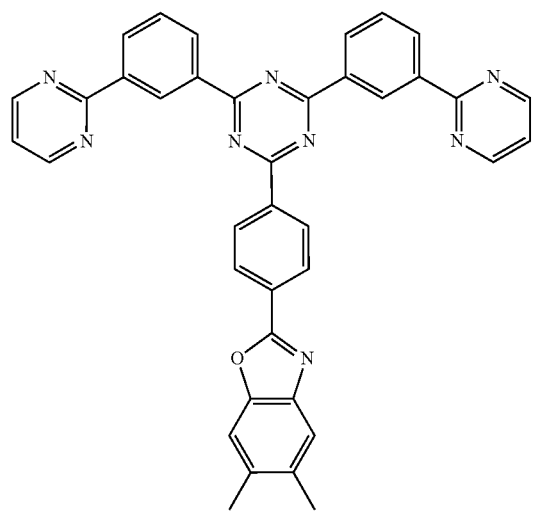
(105)
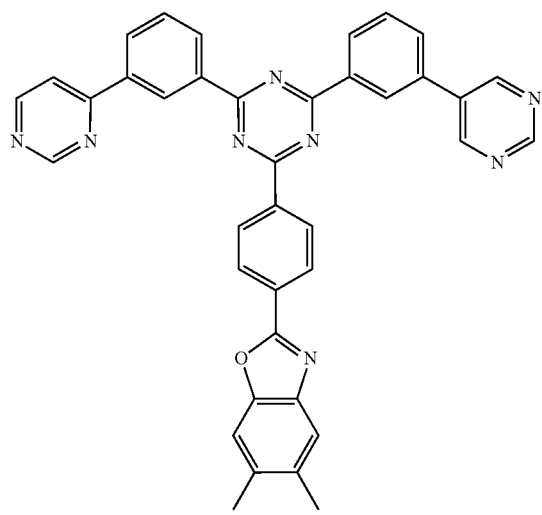

(106)
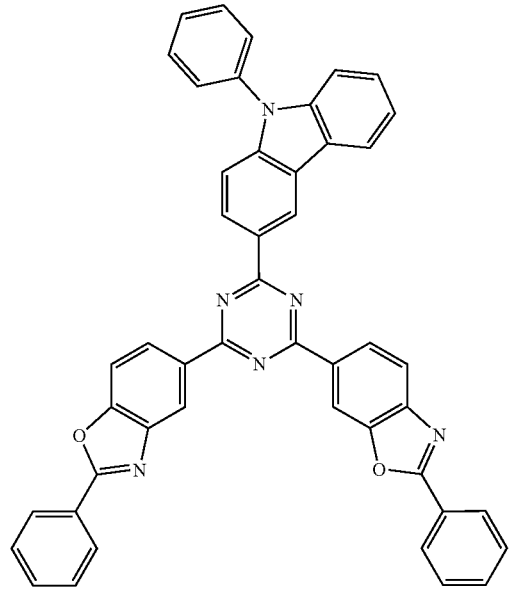
(107)
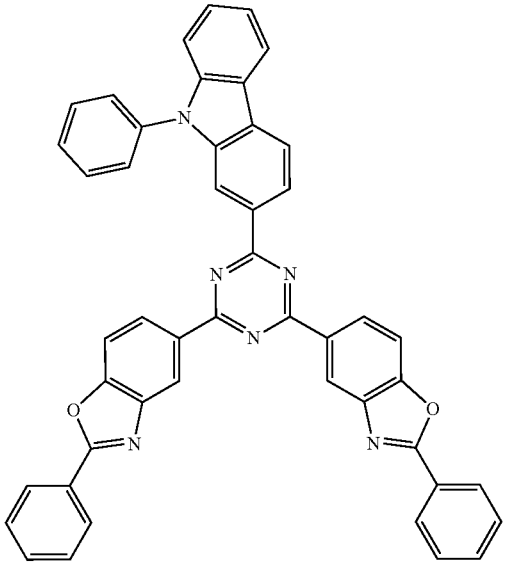
(108)
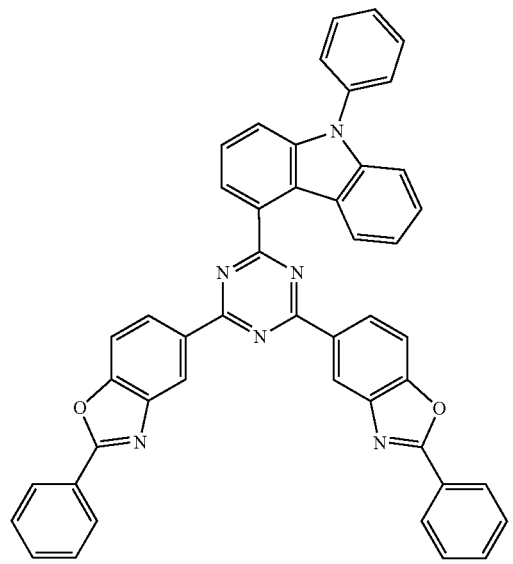
(109)
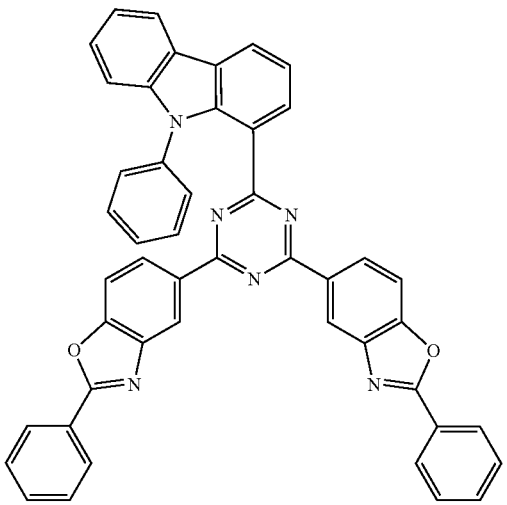

(110)
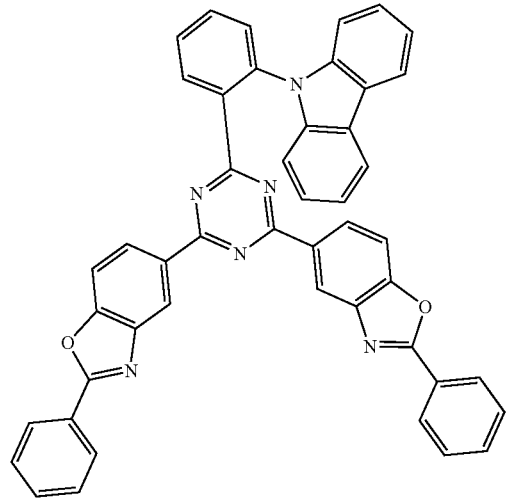
(111)
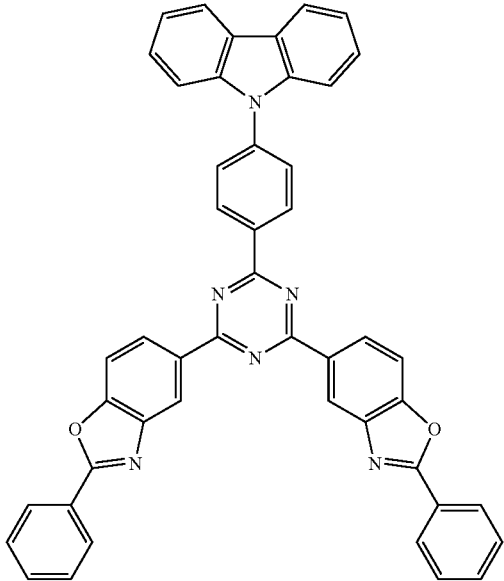
(112)
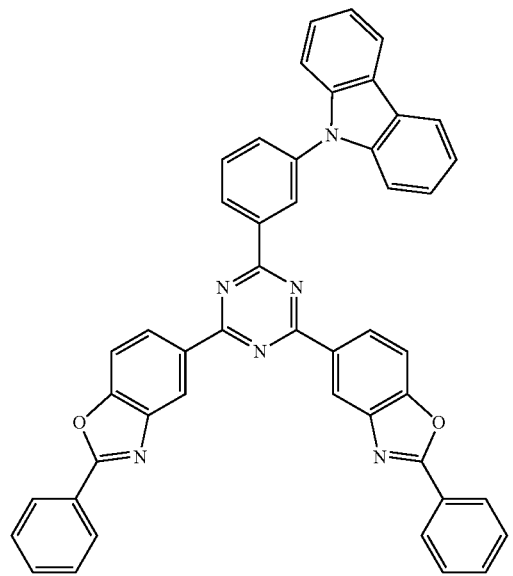
(113)
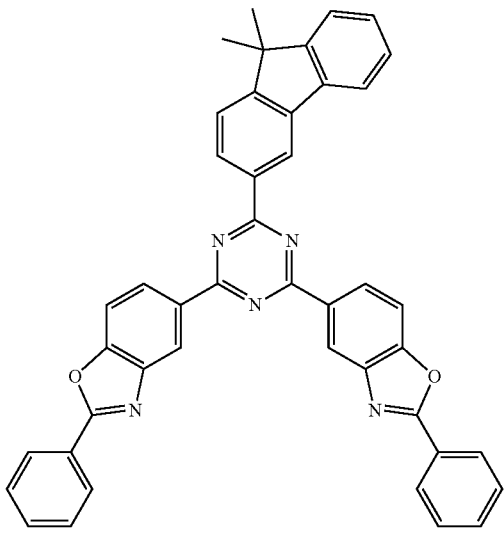

-continued
(114)
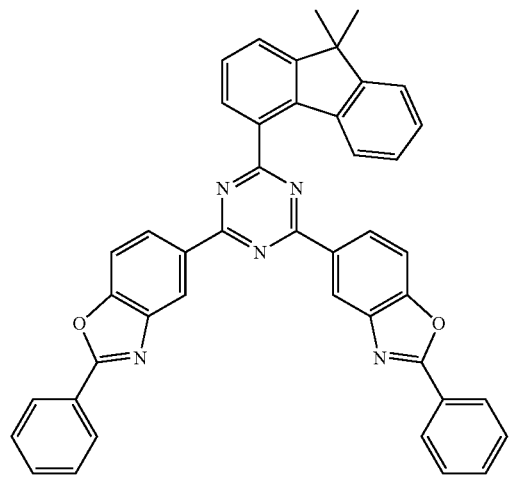
(115)
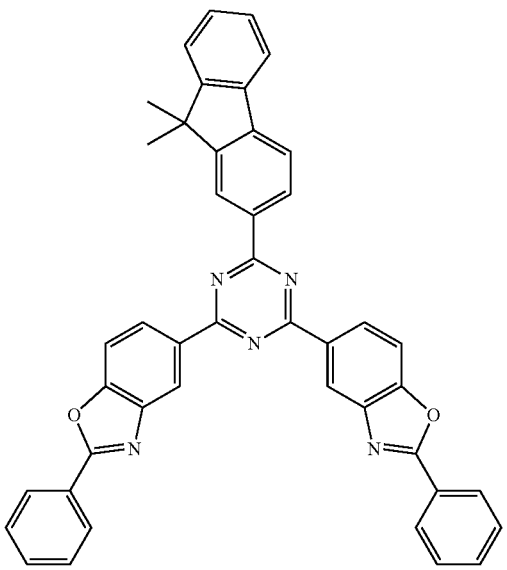
(116)
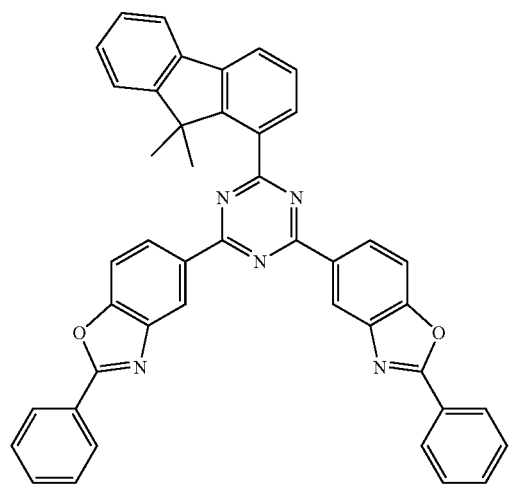
(117)
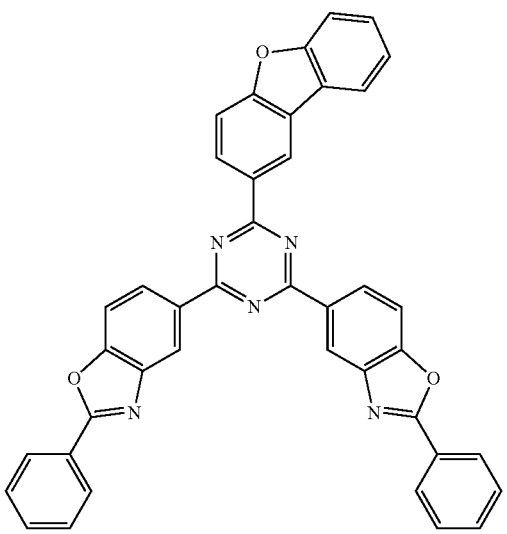
(118)
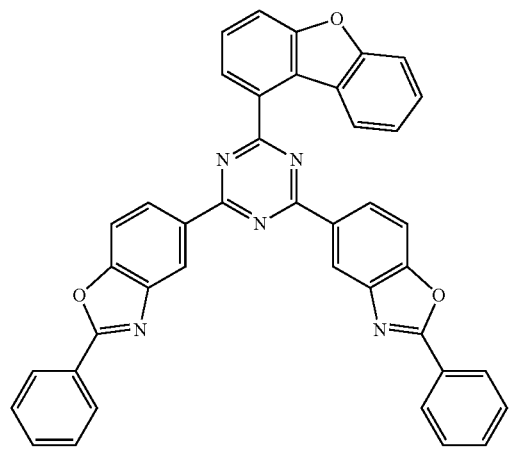
(119)
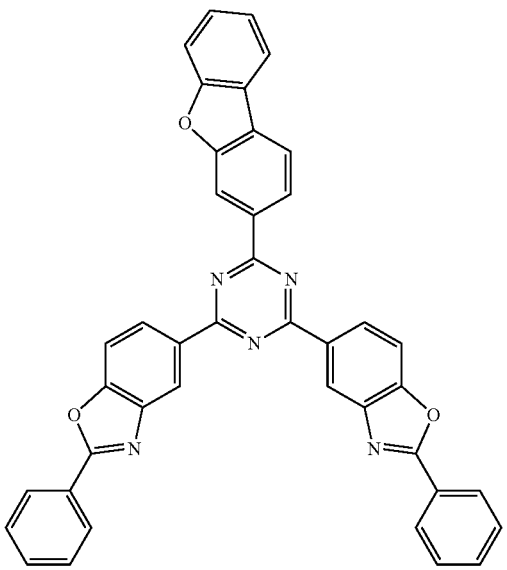

(120)
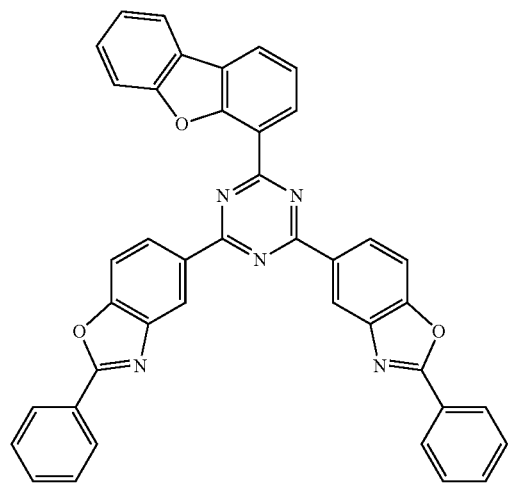
(121)
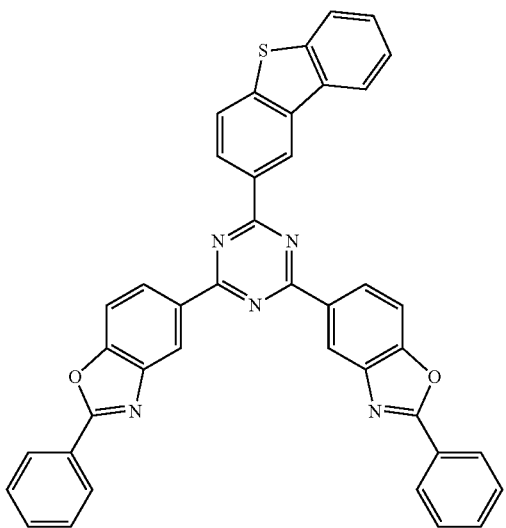
(122)
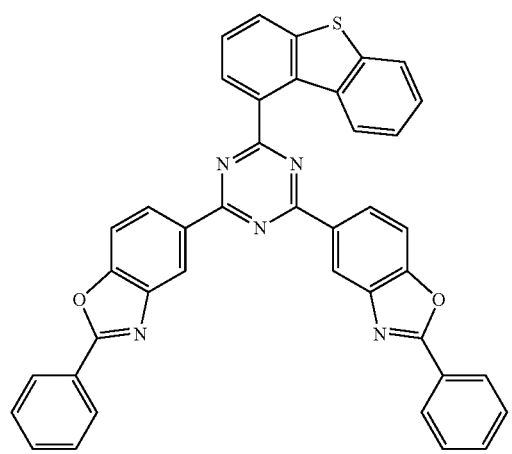
(123)
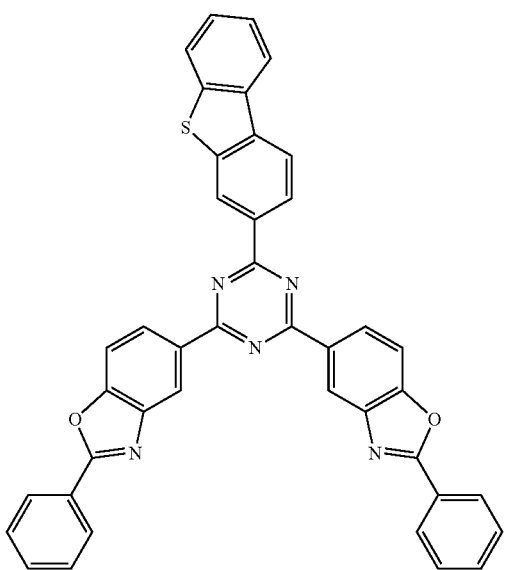

-continued
(124)
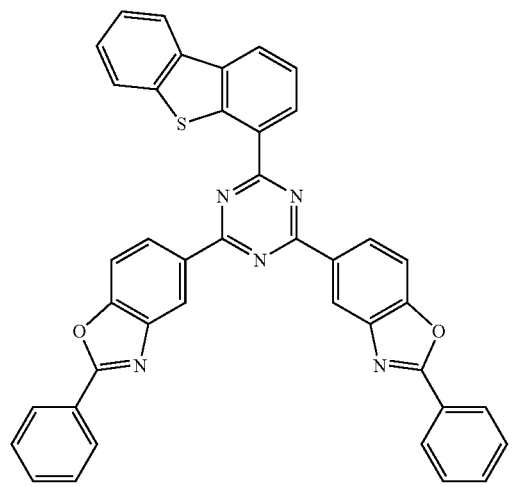
(125)
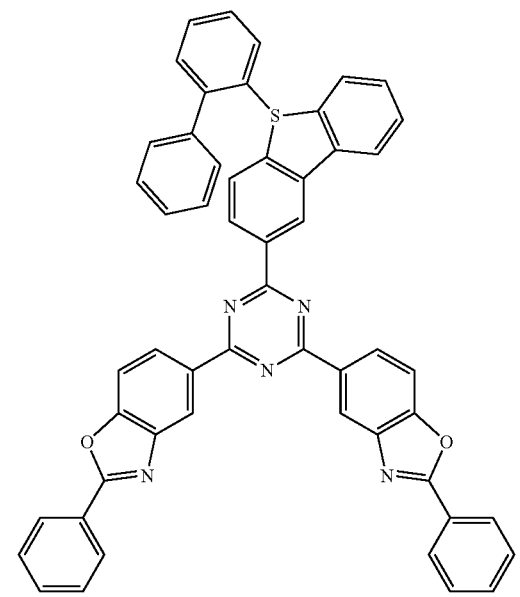
(129)
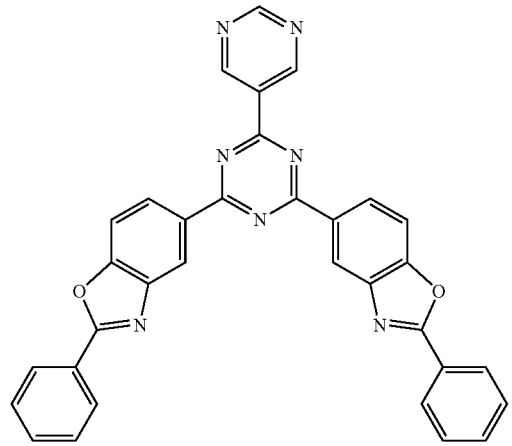
(130)
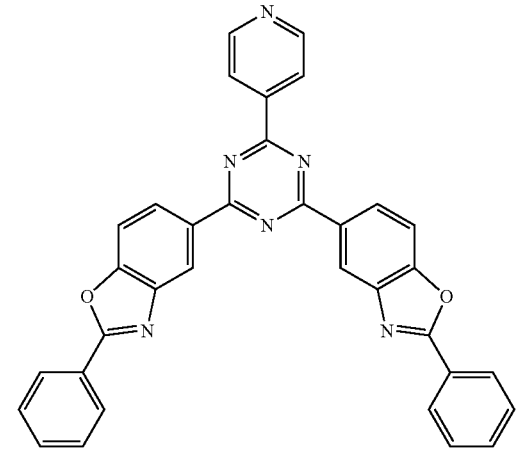
(131)
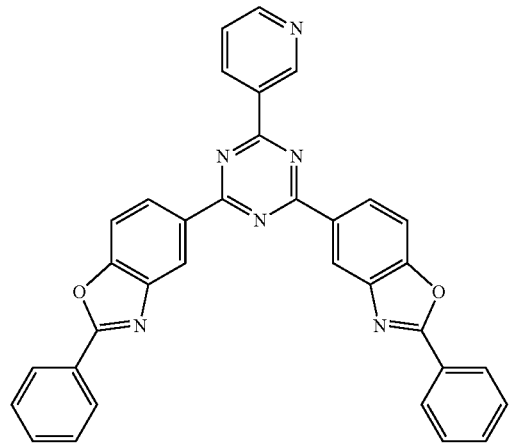
(132)
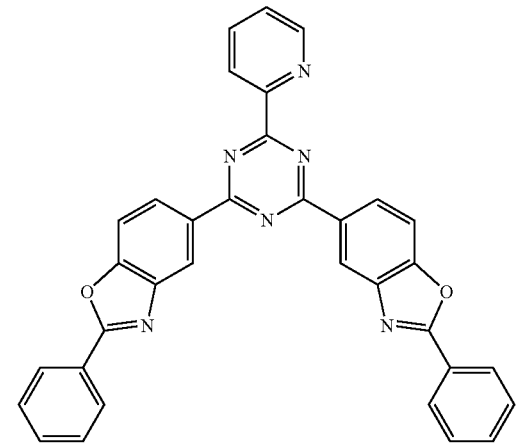

(135)
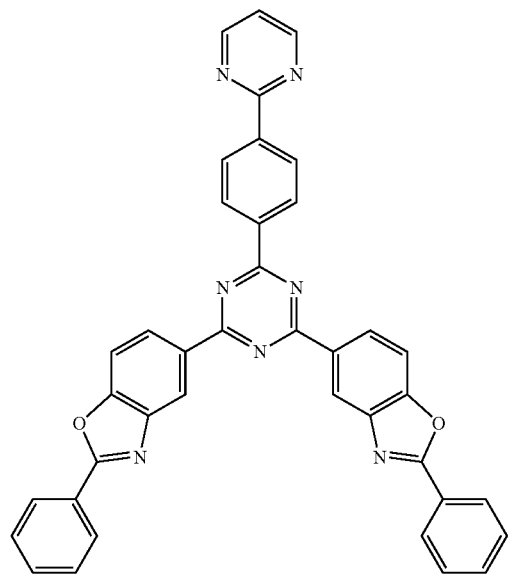
(137)
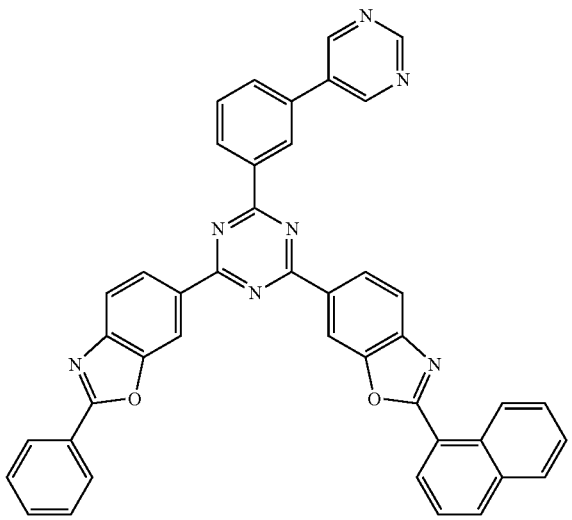
(138)
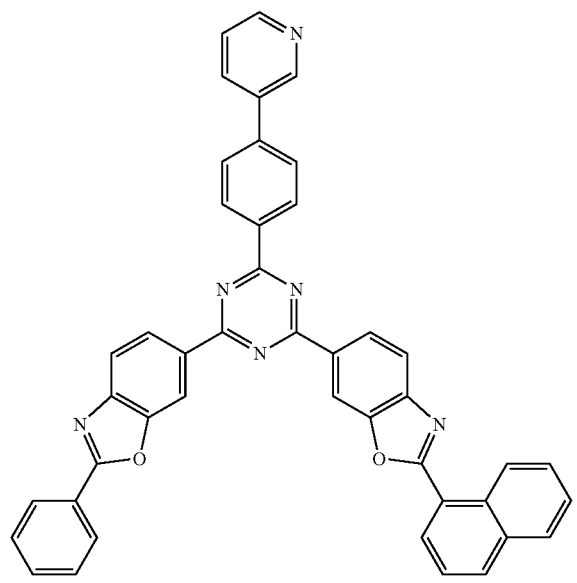
(139)
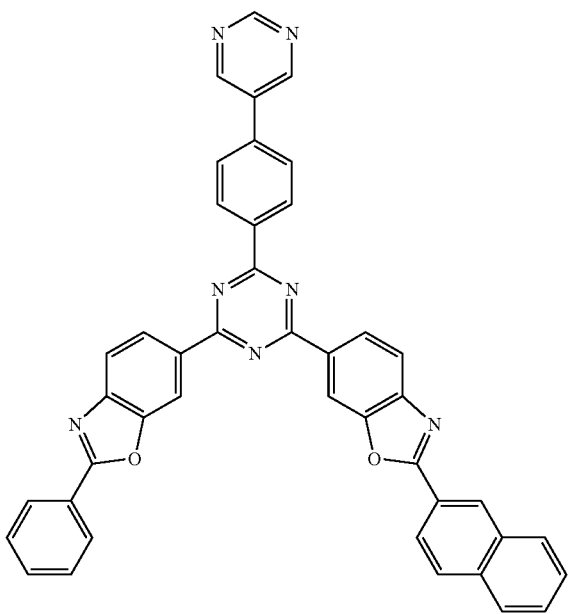

-continued
(140)
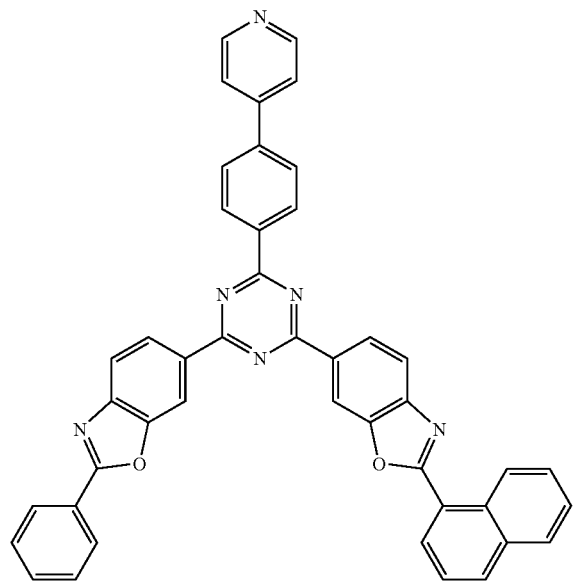
(141)
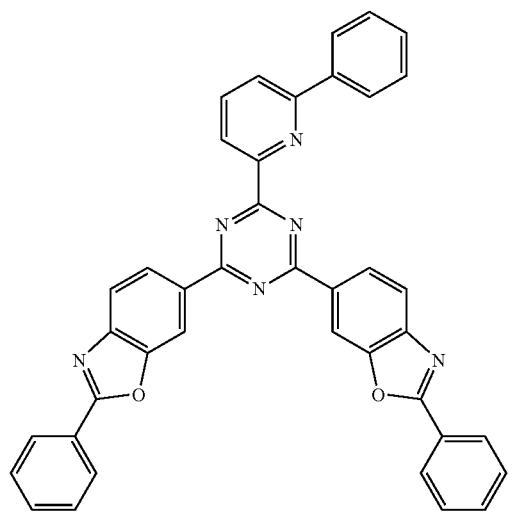
(142)
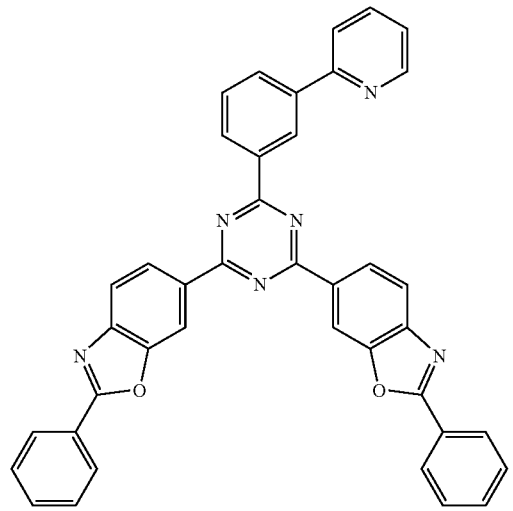
(143)
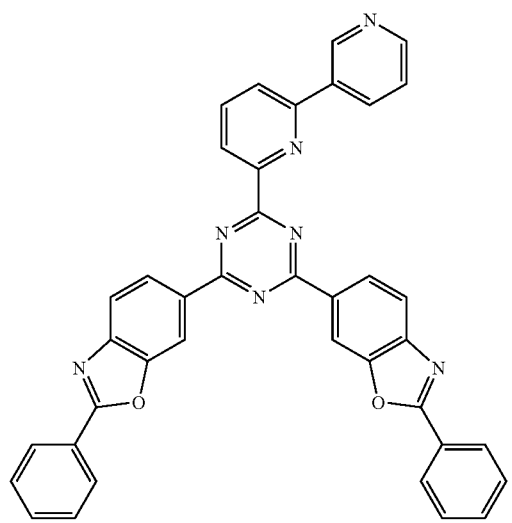
(144)
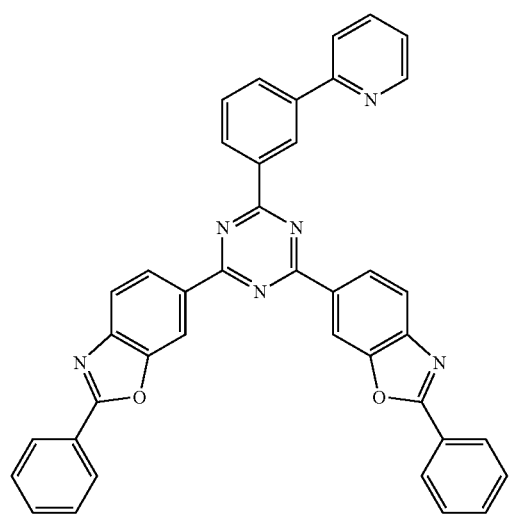
(148)
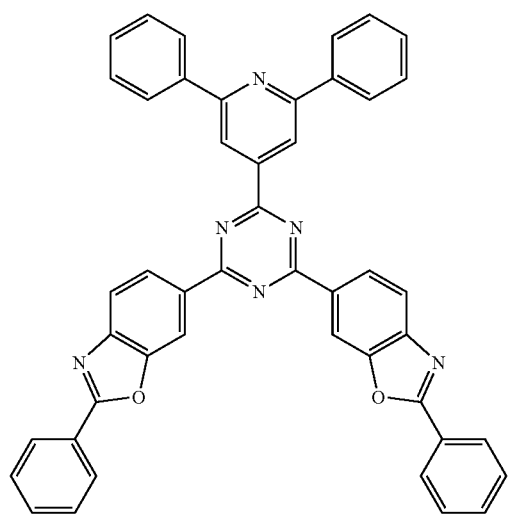

-continued
(149)
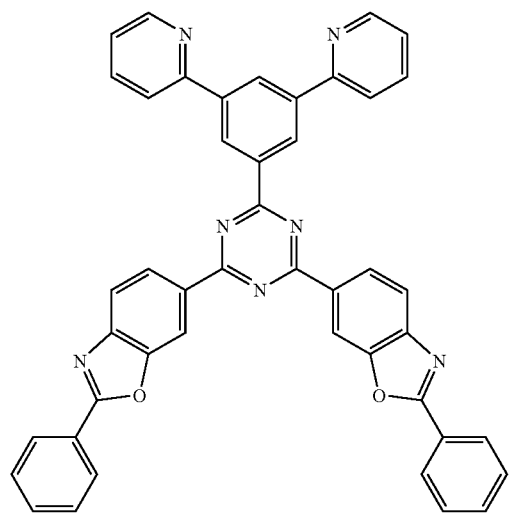
(150)
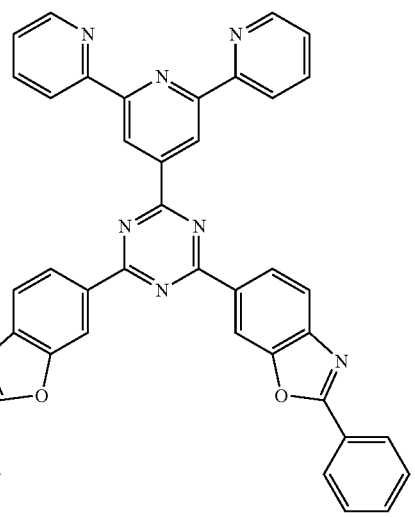
(151)
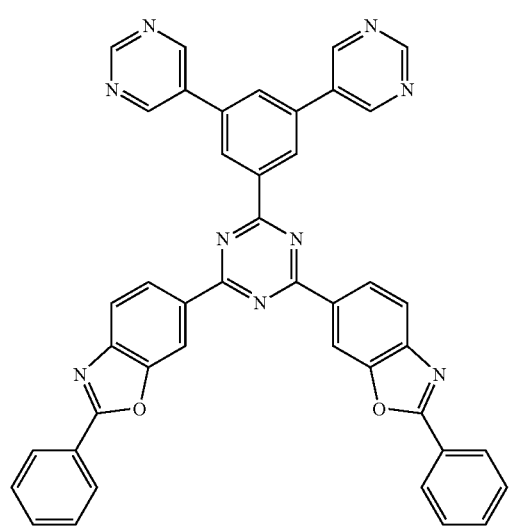
(152)
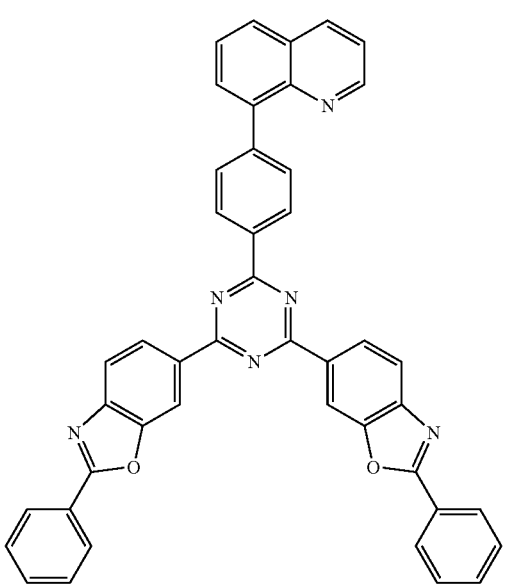
(153)
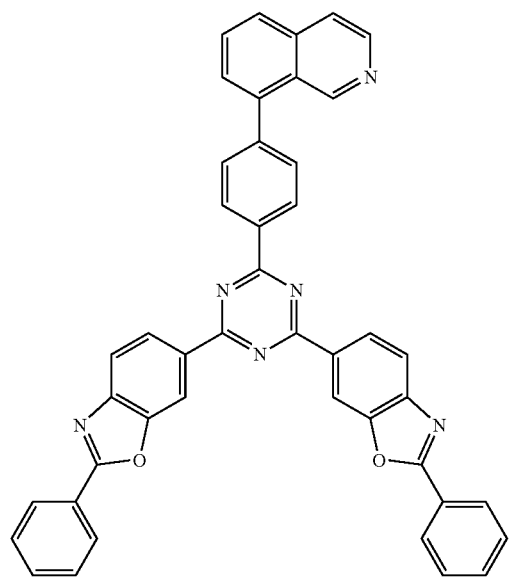
(154)
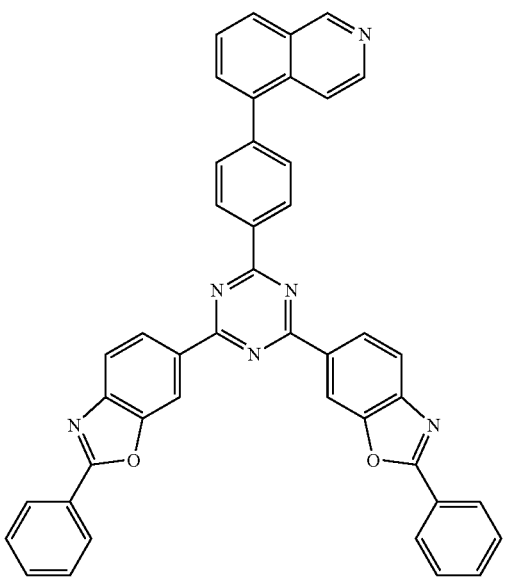

-continued
(155)
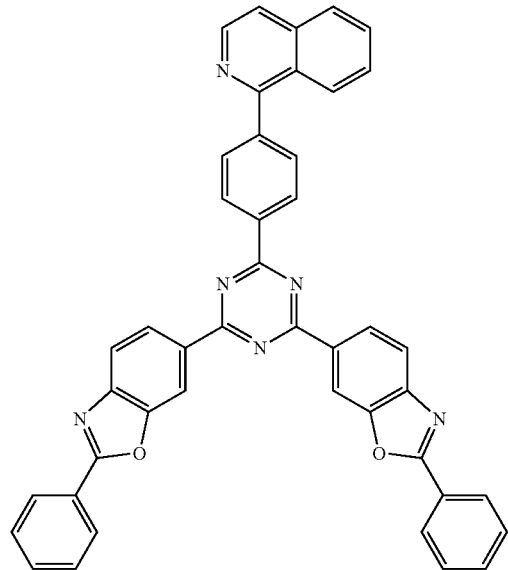
(156)
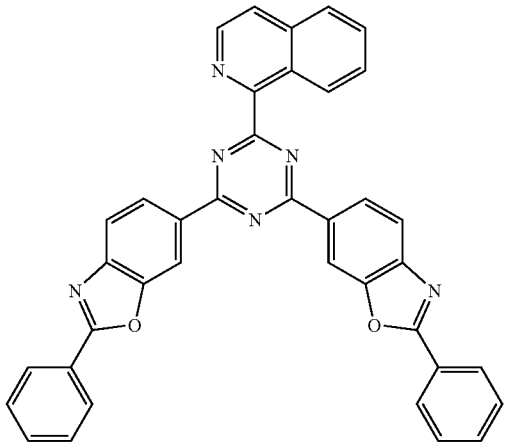
(157)
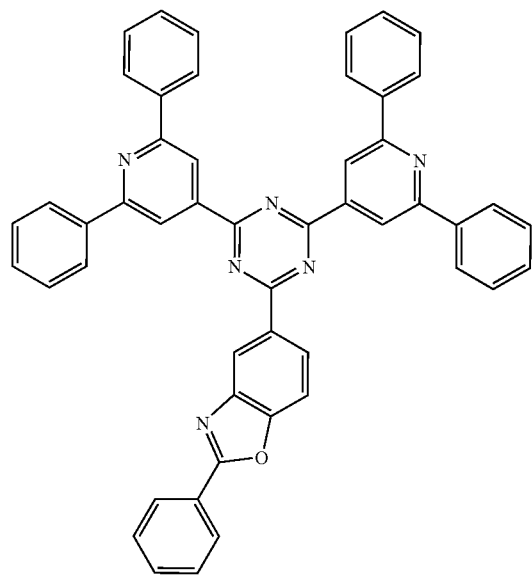
(158)
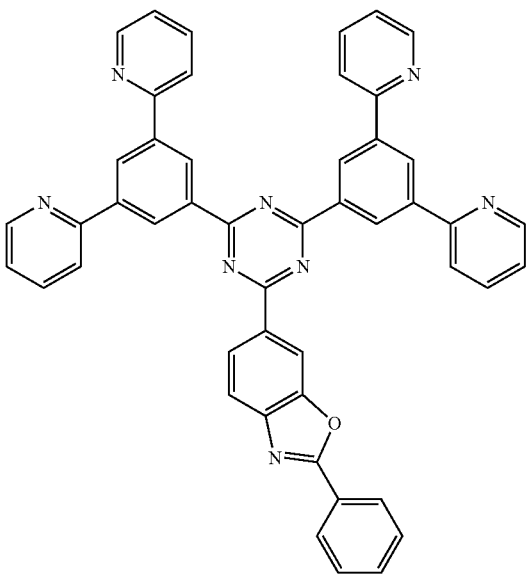

(159)
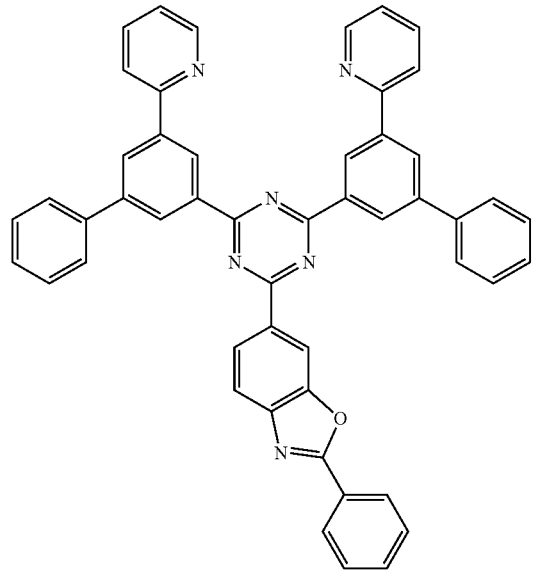
(160)
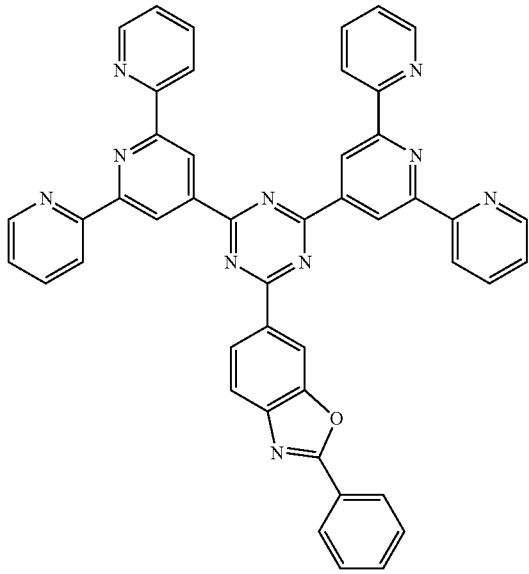
(161)
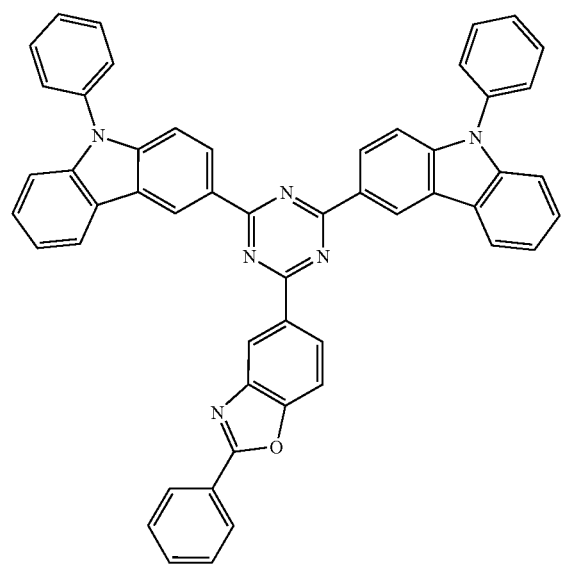
(162)
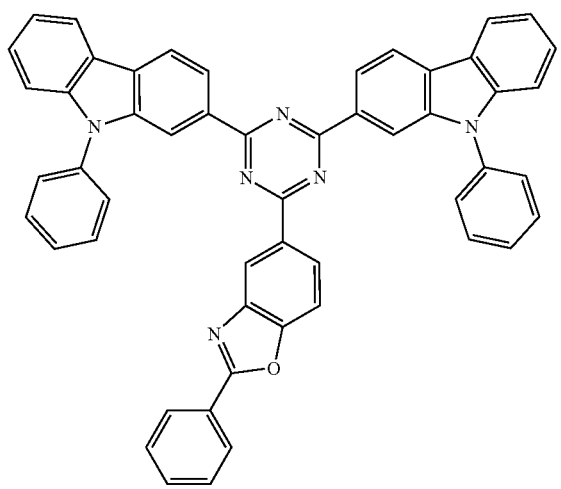

-continued
(163)
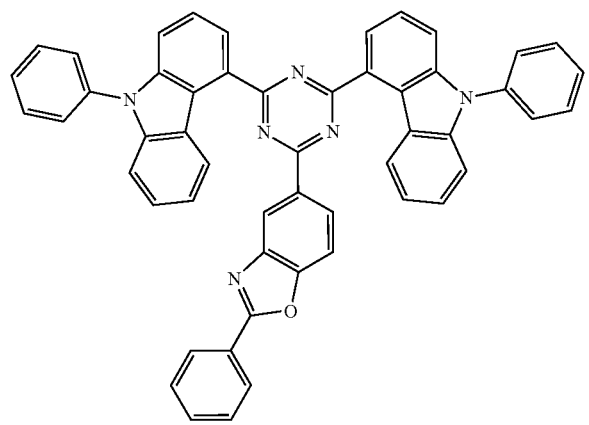
(164)
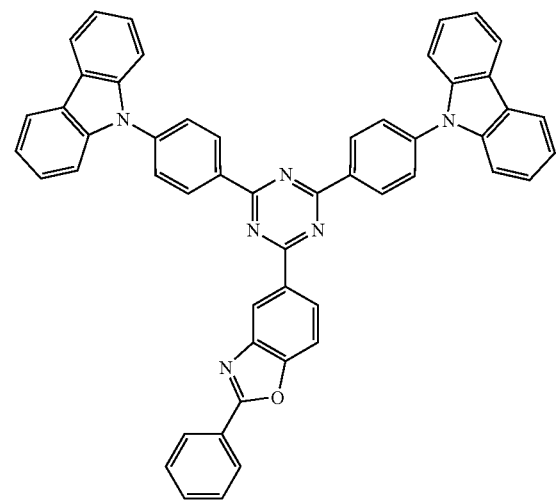
(165)
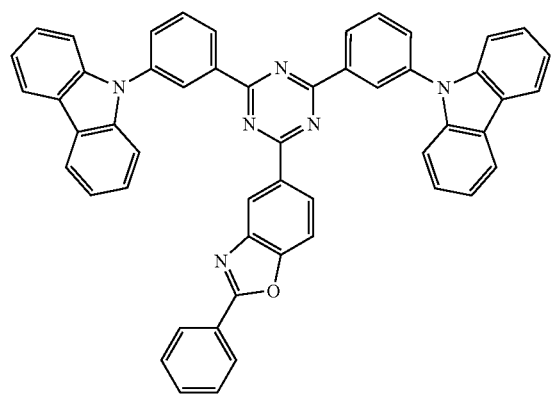
(166)
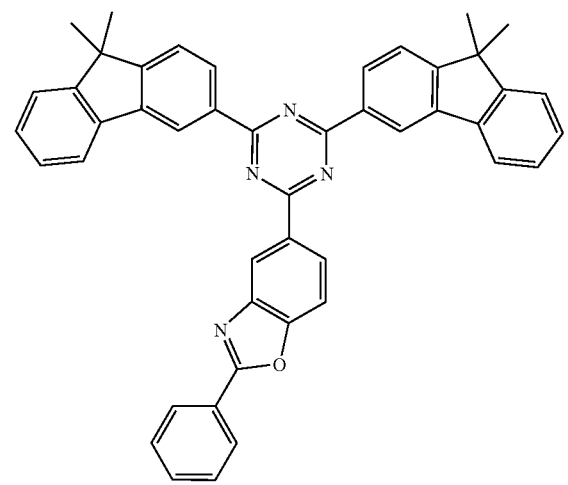
(167)
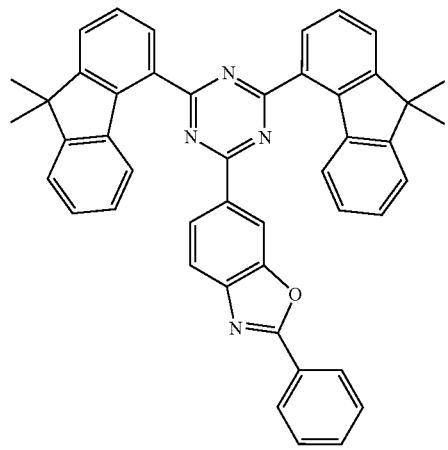
(168)
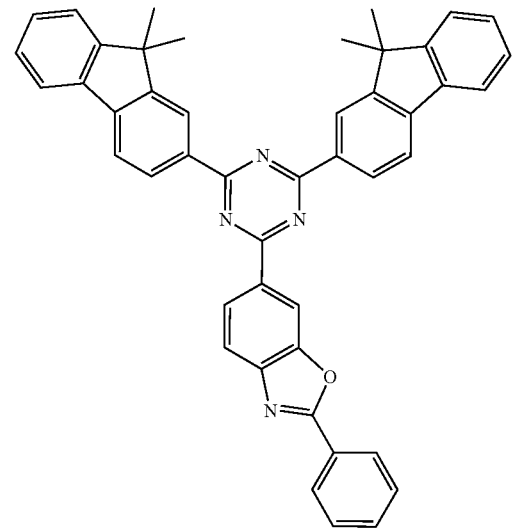

-continued
(169)
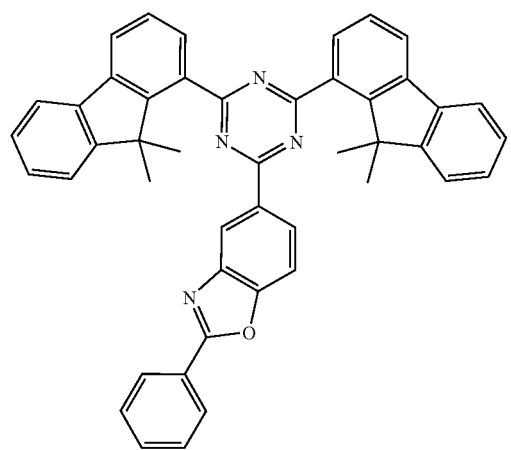
(170)
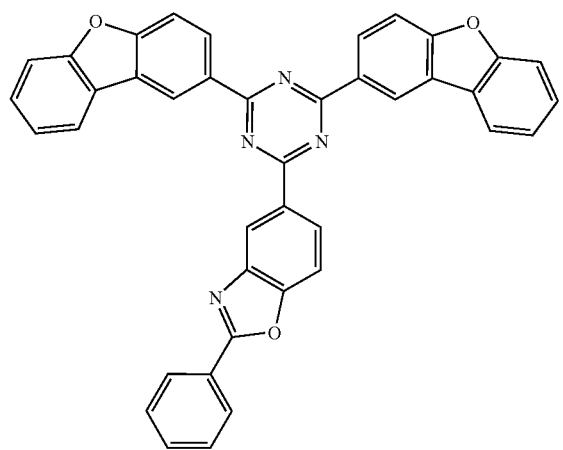
(171)
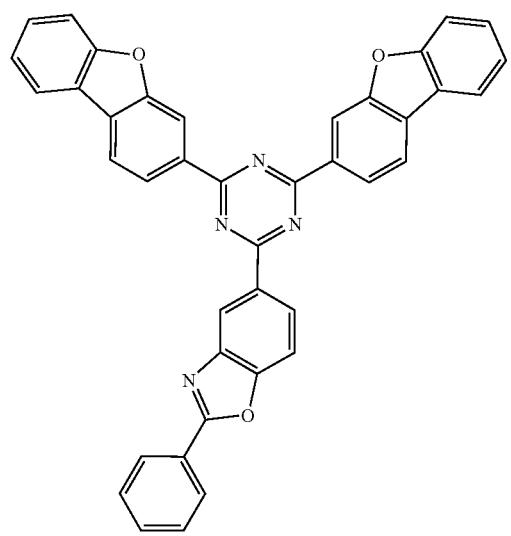
(172)
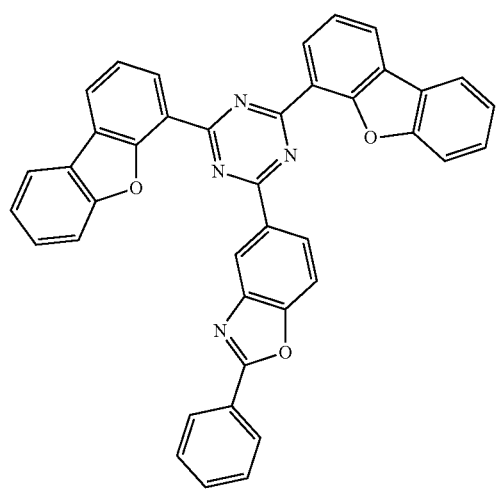
(173)
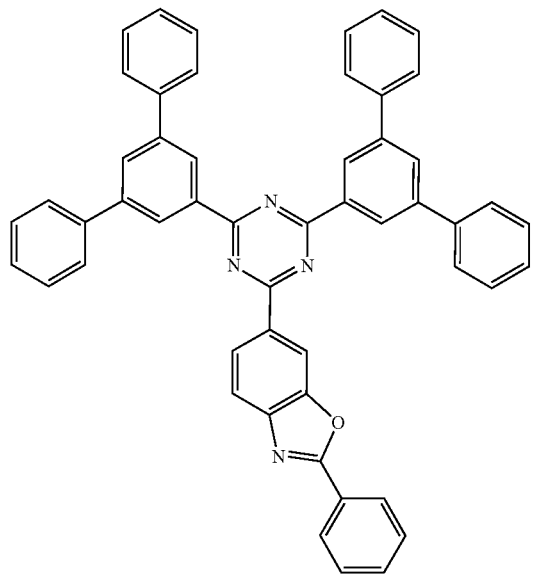
(174)
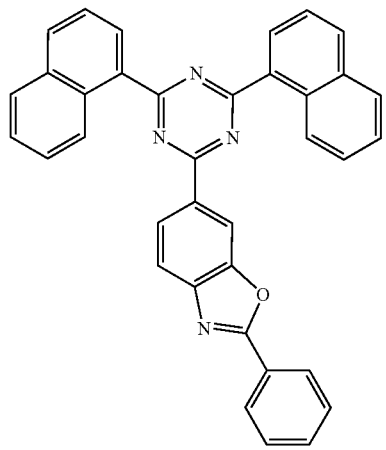

-continued
(175)
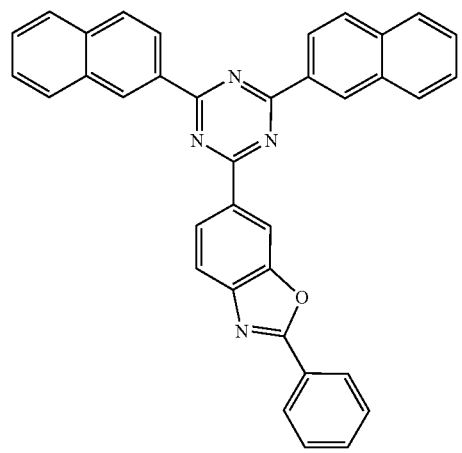
(176)
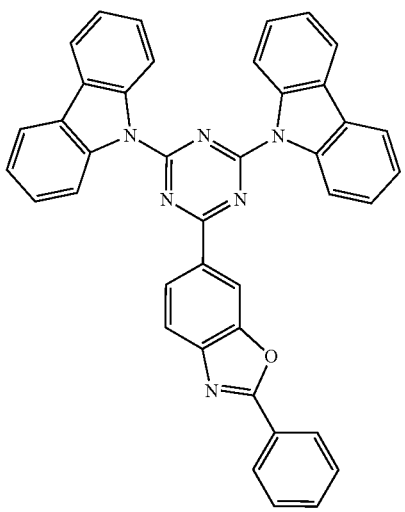
(177)
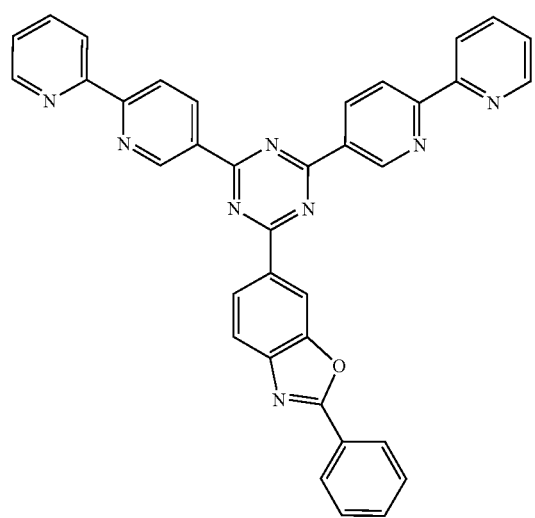
(178)
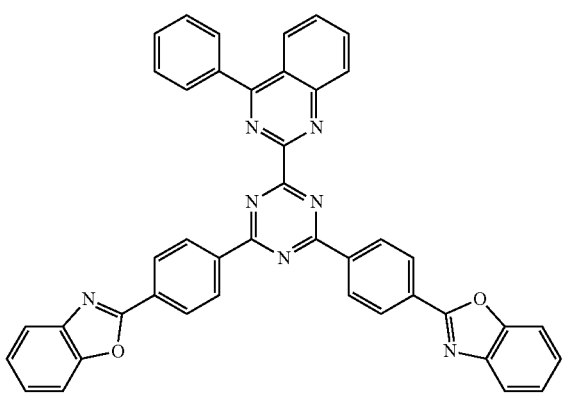
(179)
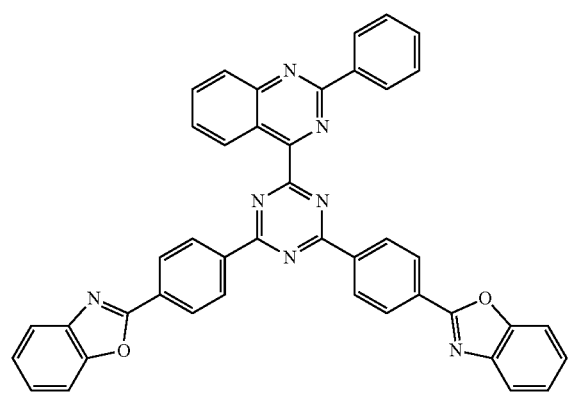
(180)
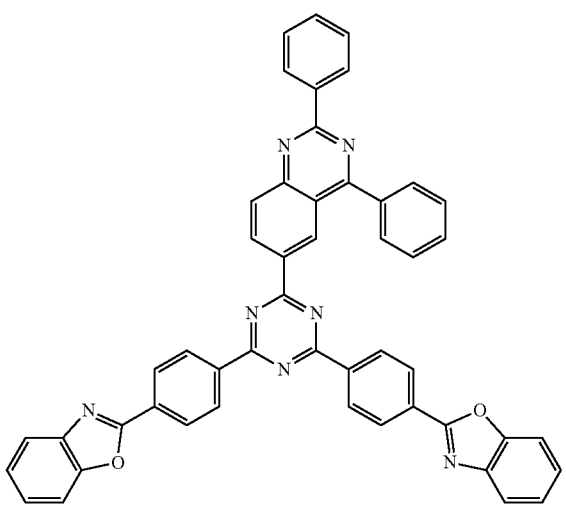

-continued
(181)
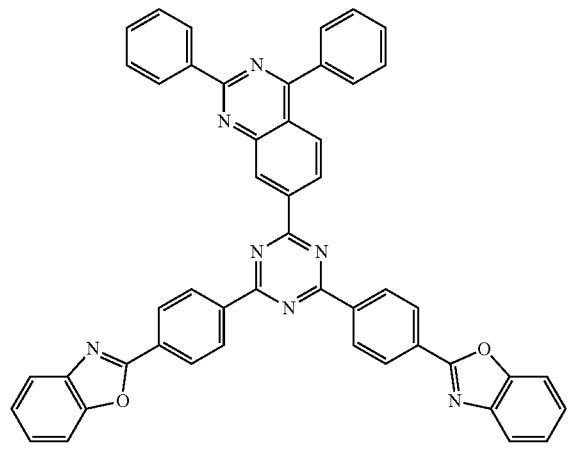
(182)
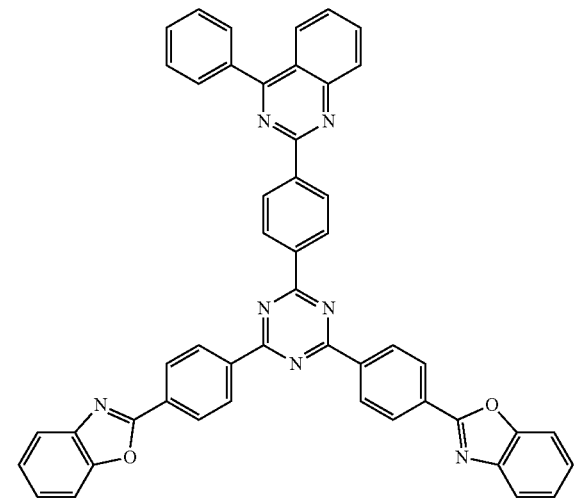
(183)
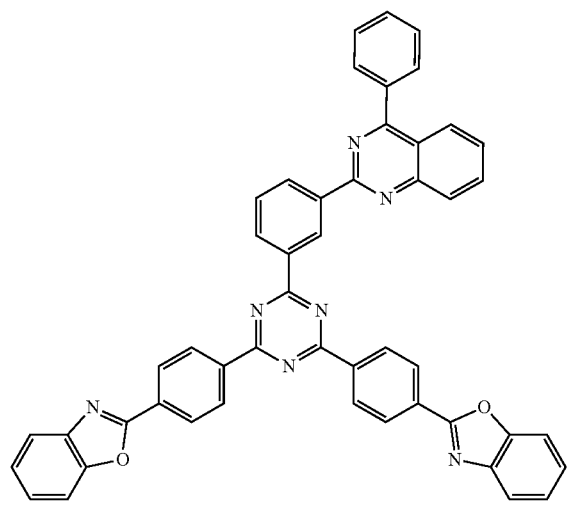
(1184)
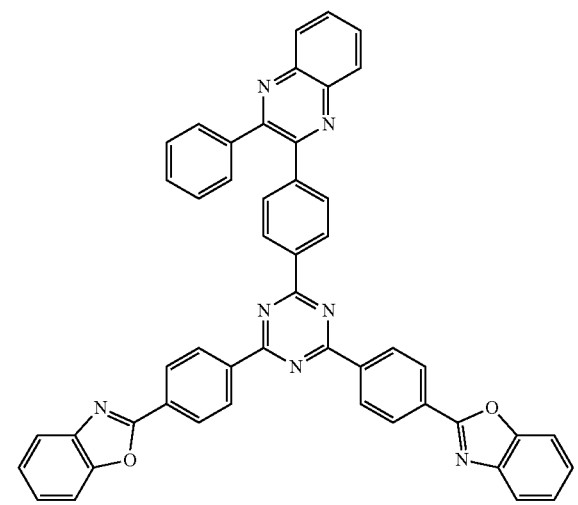
(185)
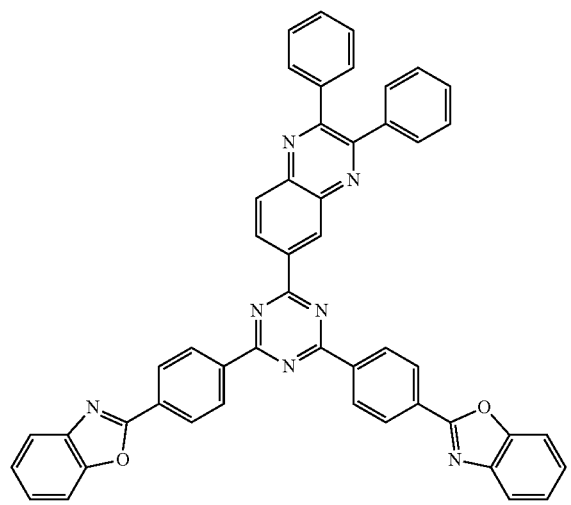
(186)
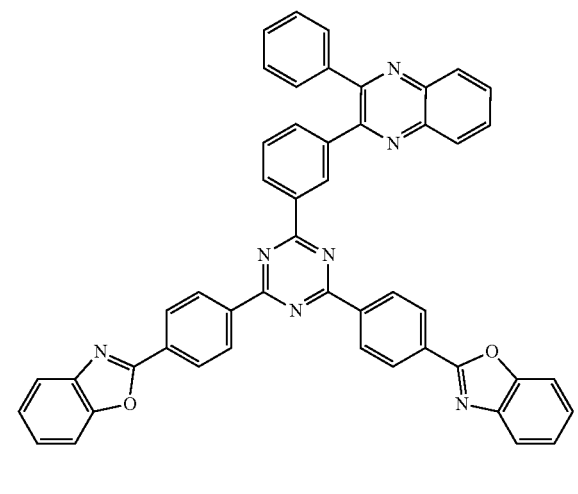

-continued
(187)
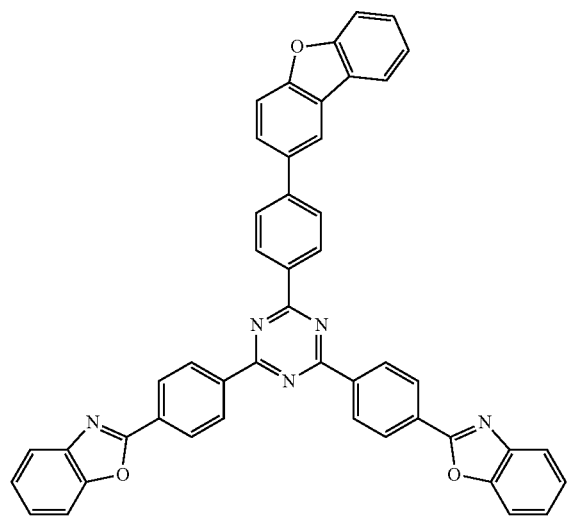
(188)
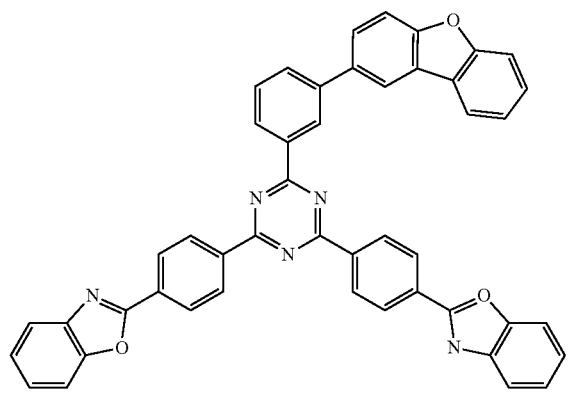
(189)
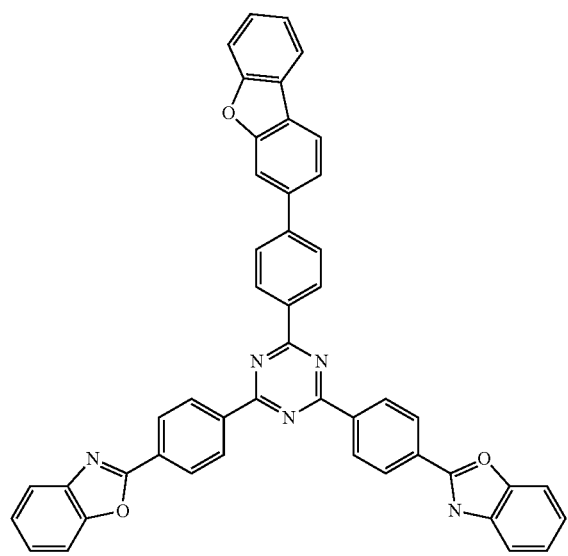
(190)
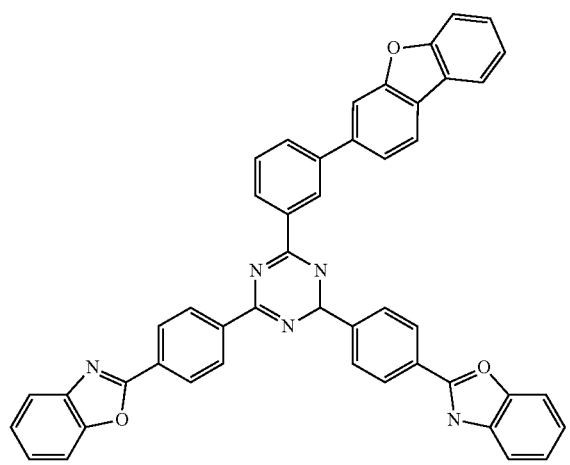
(191)
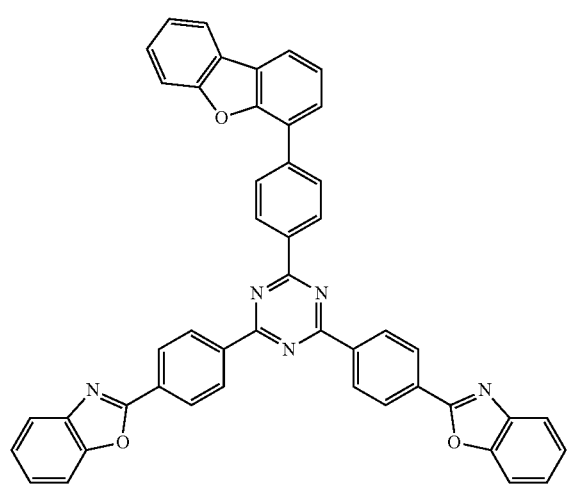
(192)
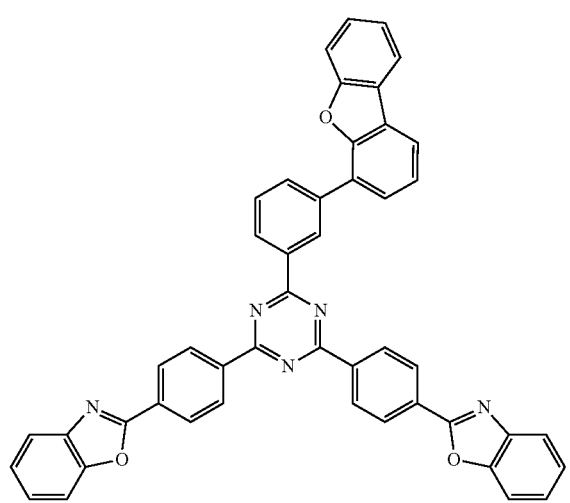

-continued
(193)
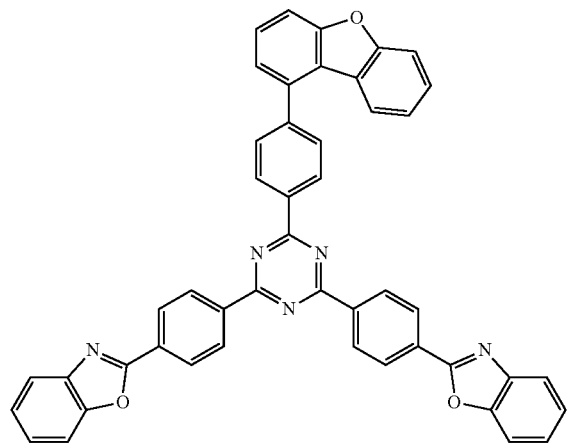
(194)
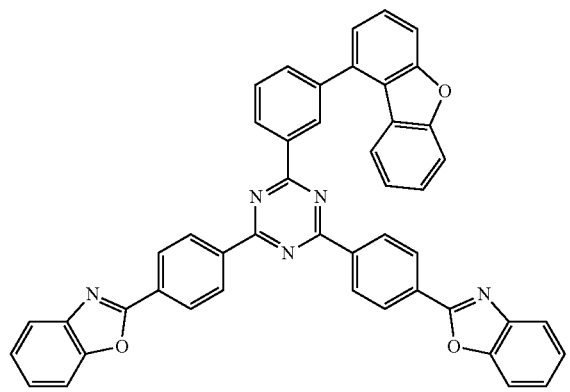
(195)
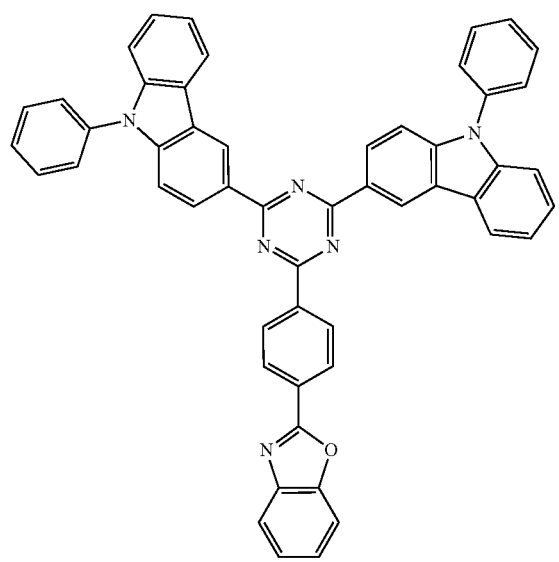
(196)
(197)
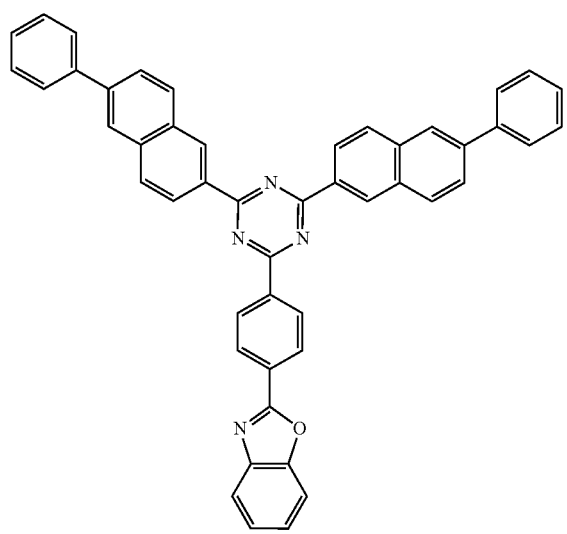
(198)
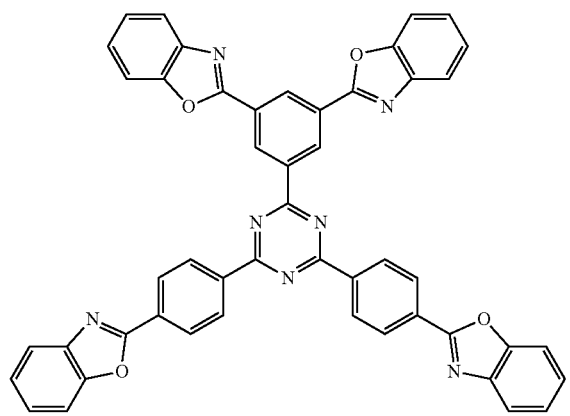

-continued
(199)
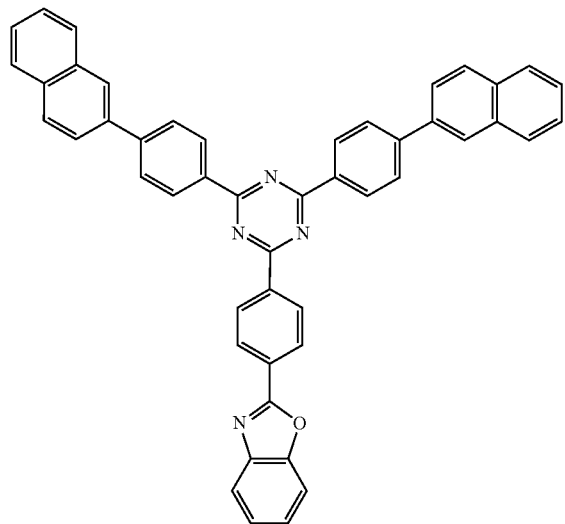
(200)
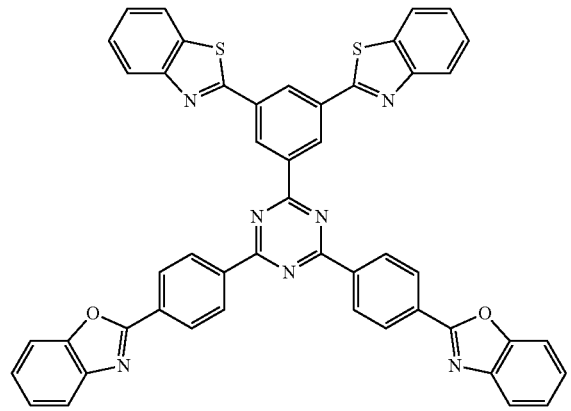
(201)
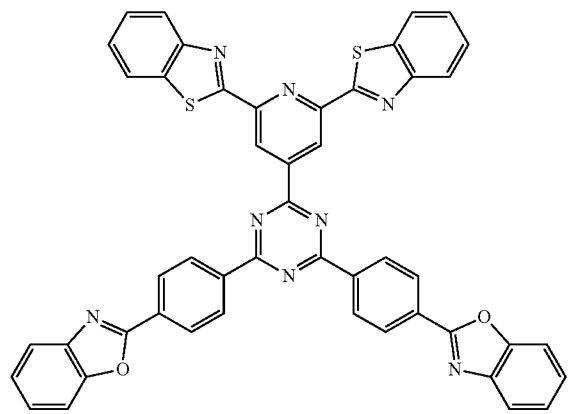
(202)
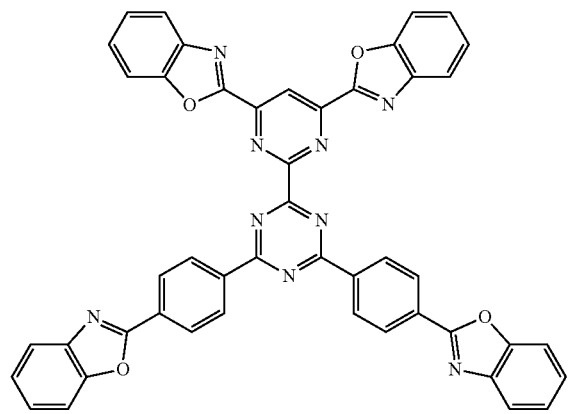
(203)
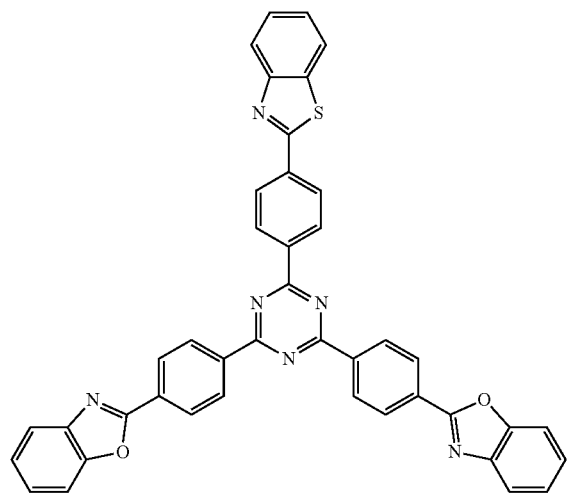
(204)
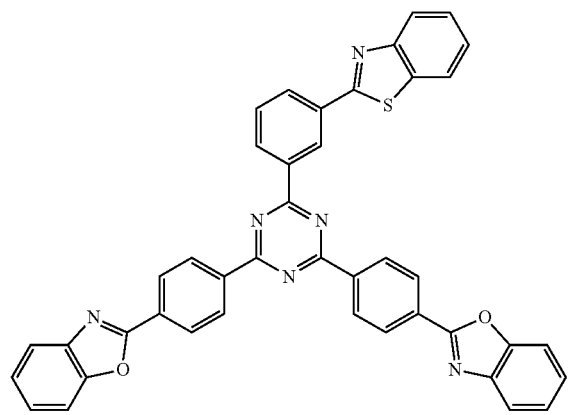

-continued
(205)
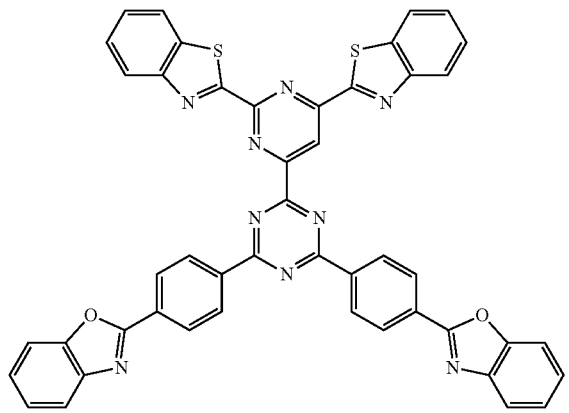
(206)
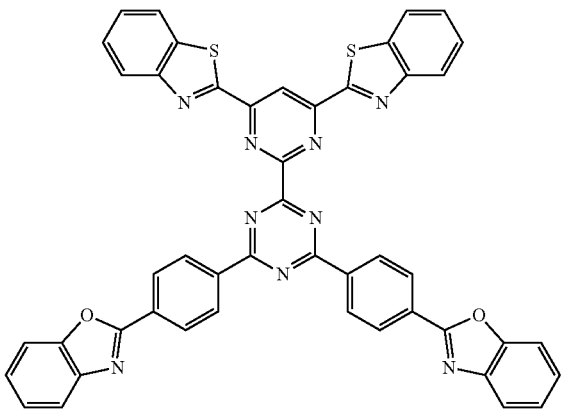
(207)
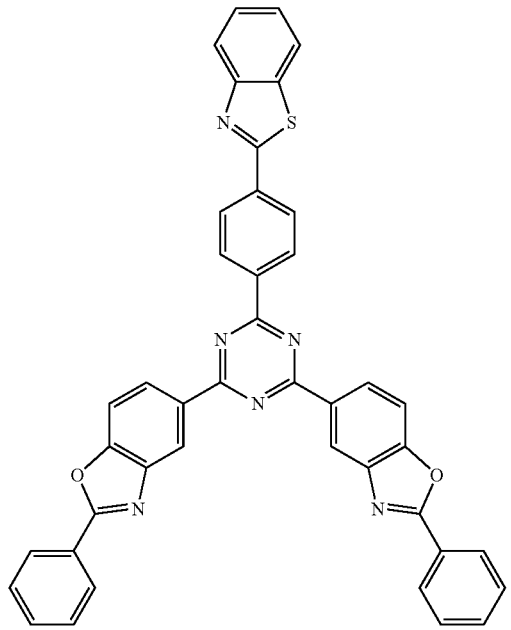
(208)
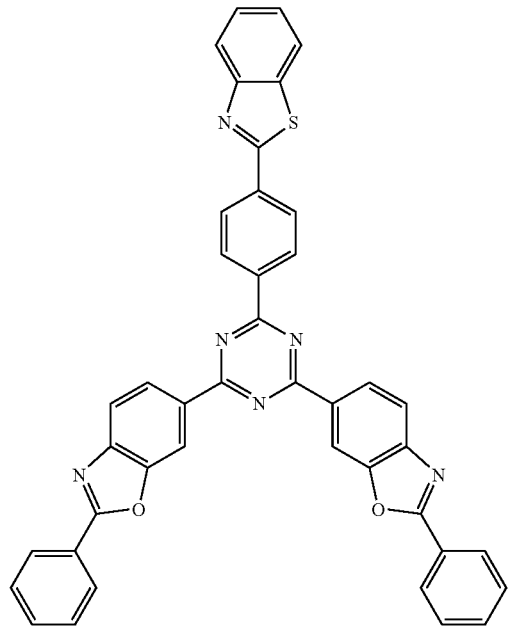
(209)
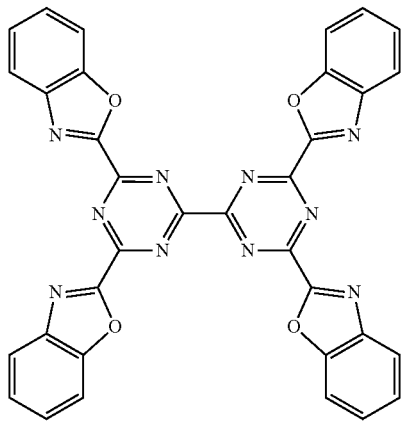
(210)
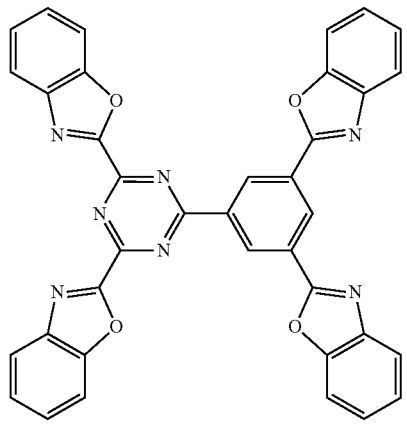

-continued
(211)
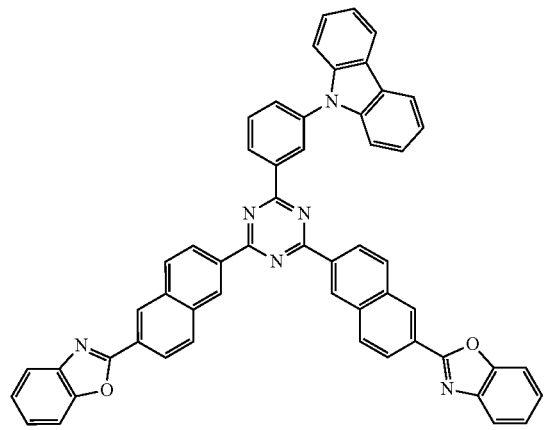
(212)
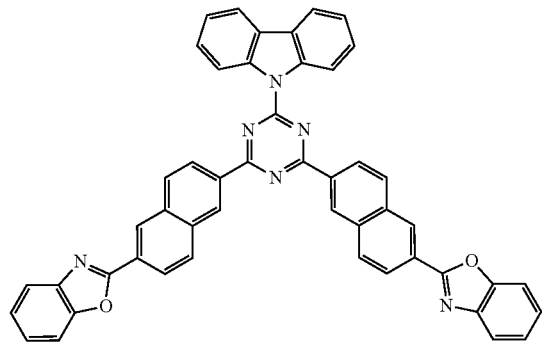
(213)
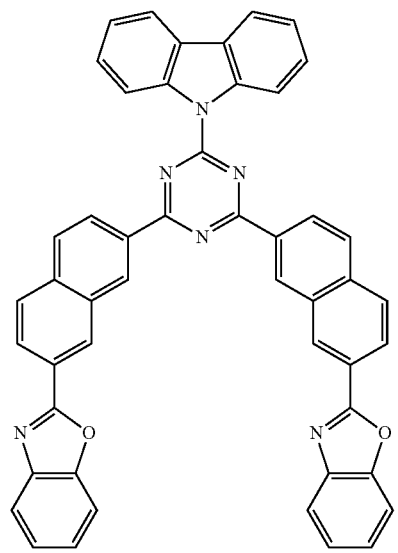
(214)
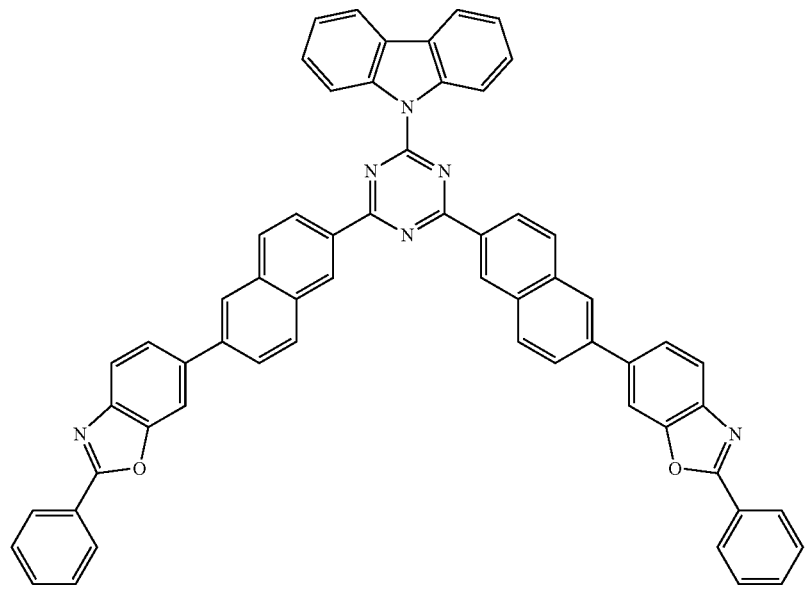

-continued
(215)
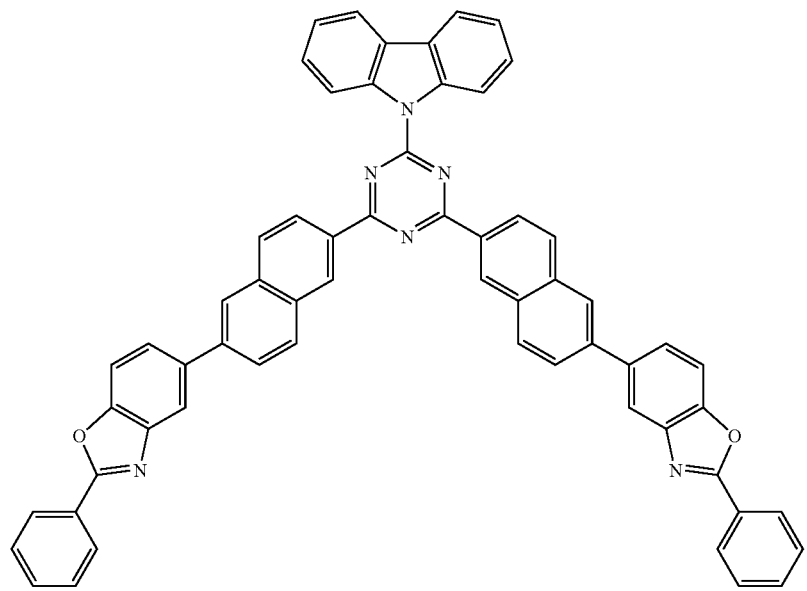
(216)
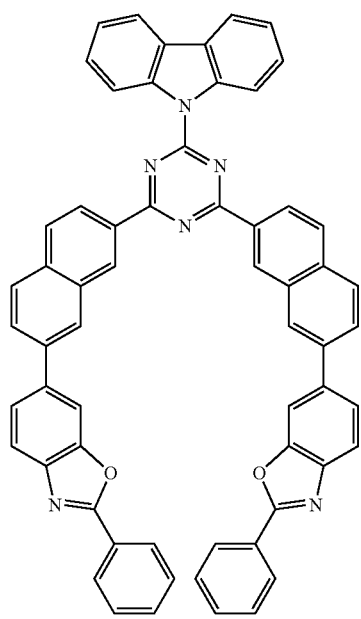
(217)
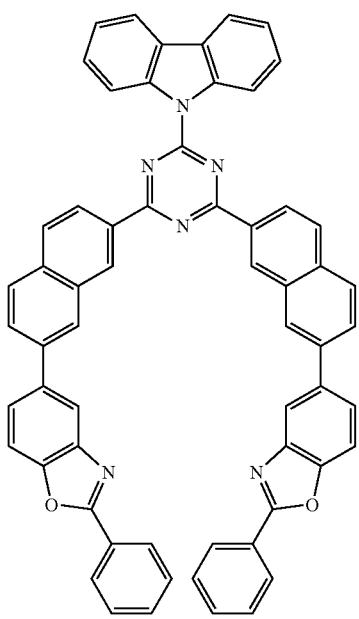
(218)
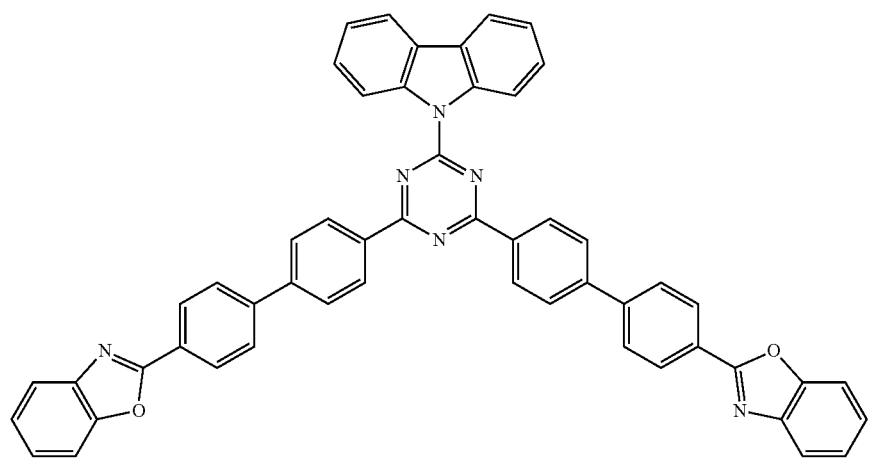

391
392
-continued
(219)
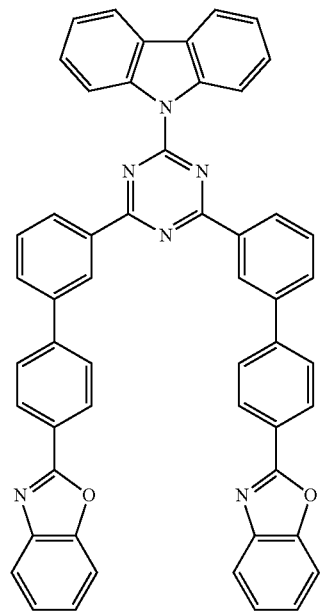
(220)
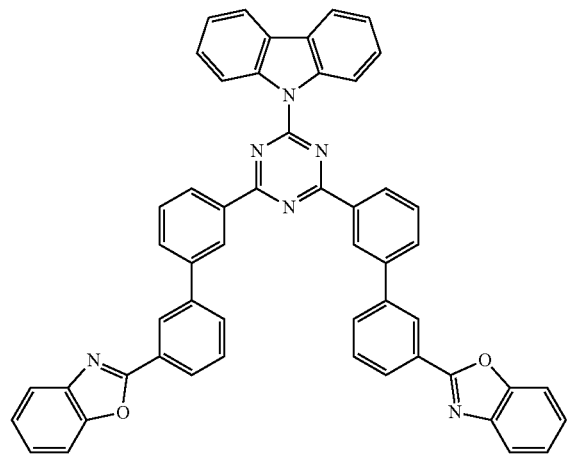
(221)
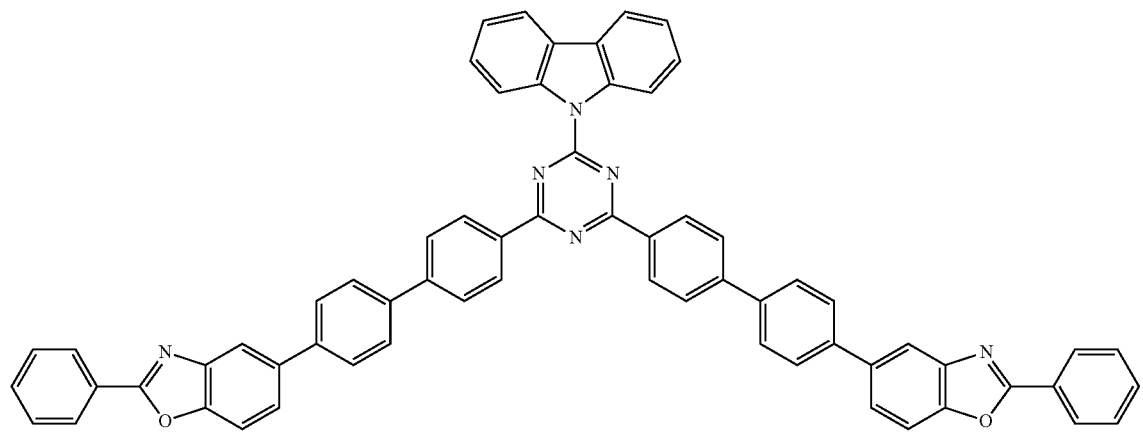
(222)
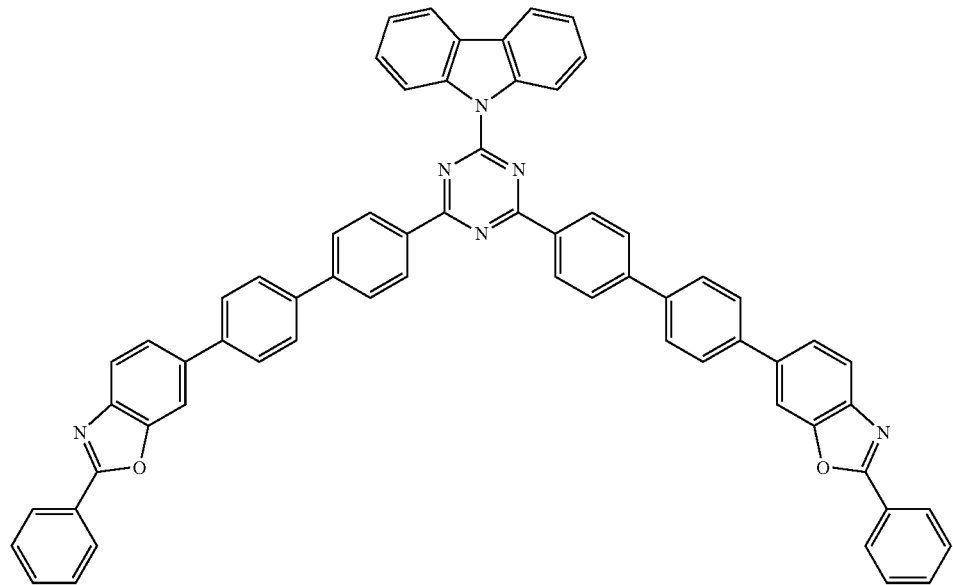

-continued
(223)
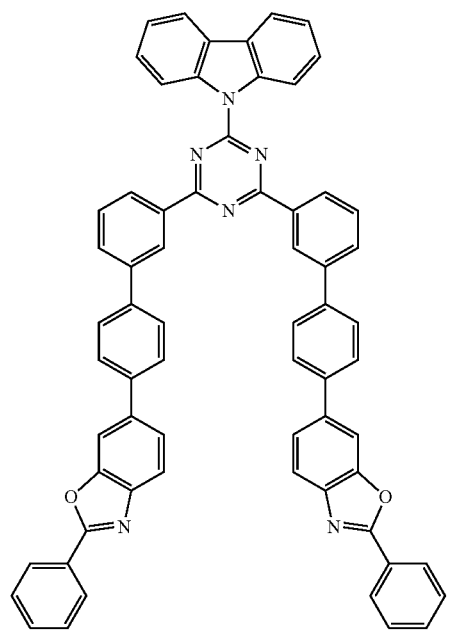
(224)
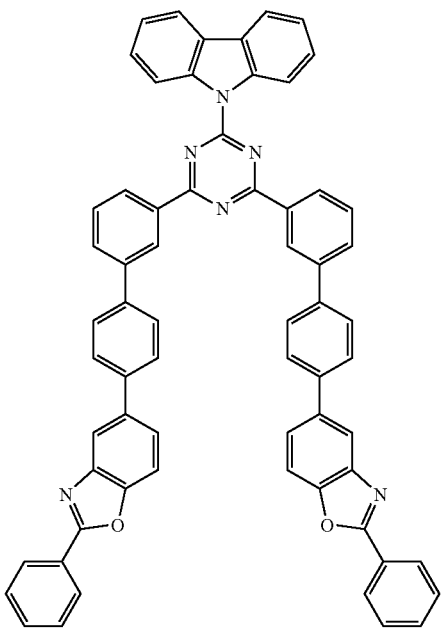
(225)
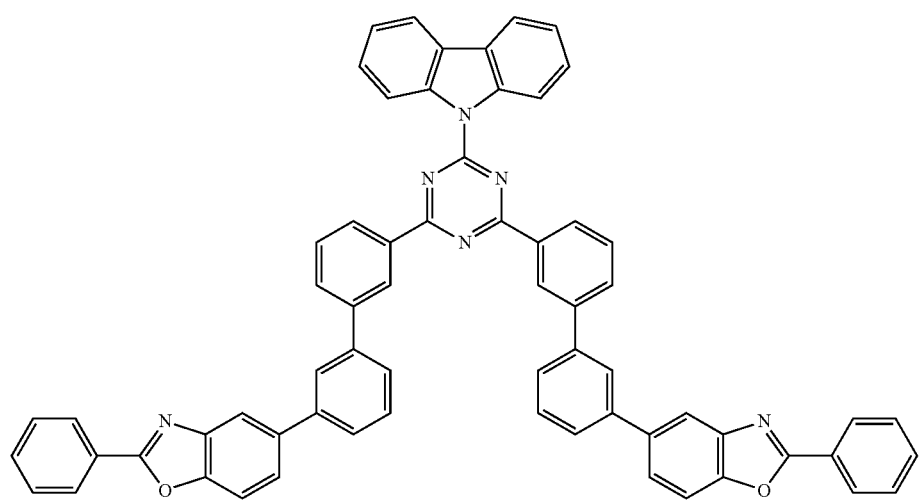
(226)
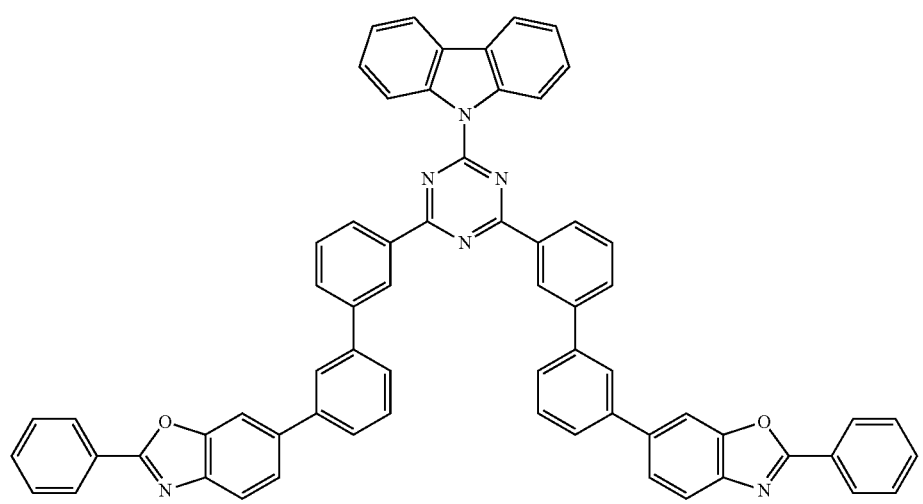

(227)
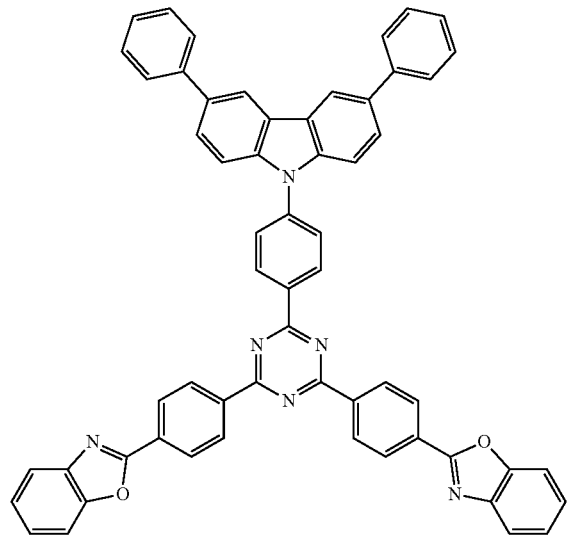
(228)
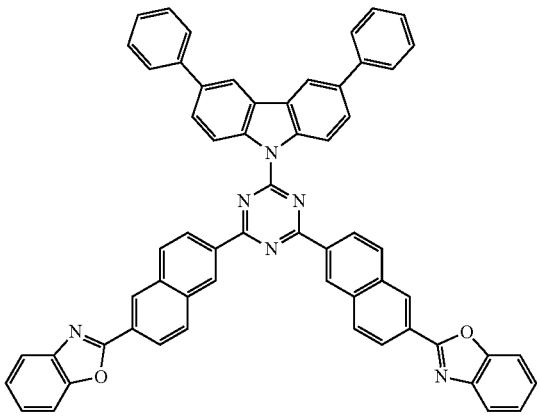
(229)
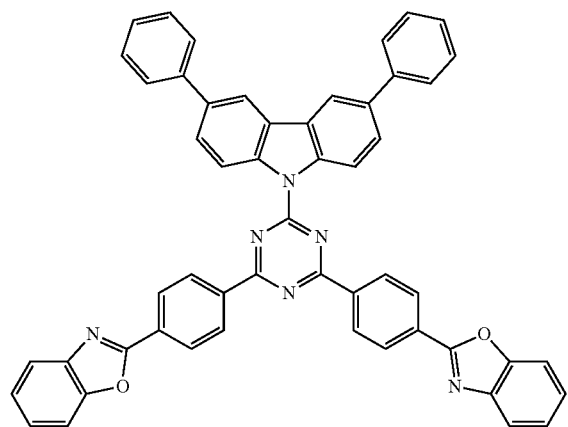
(300)
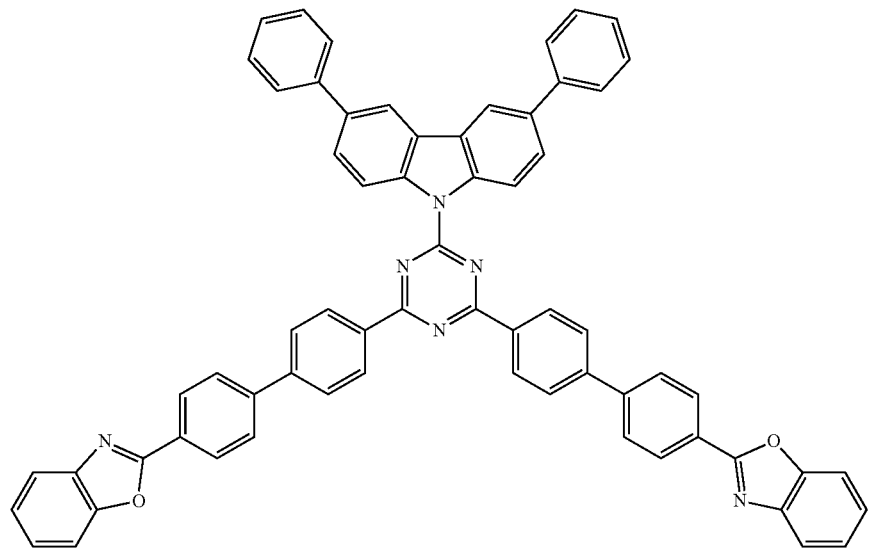

(231)
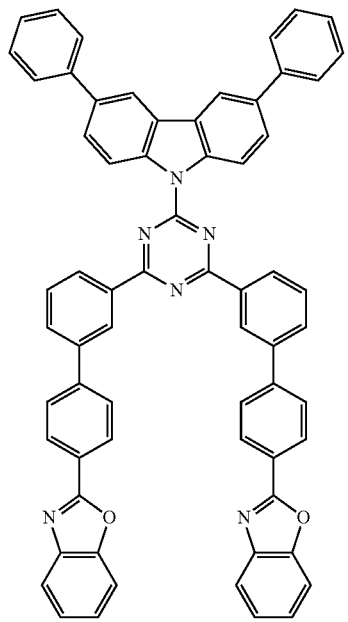
(232)
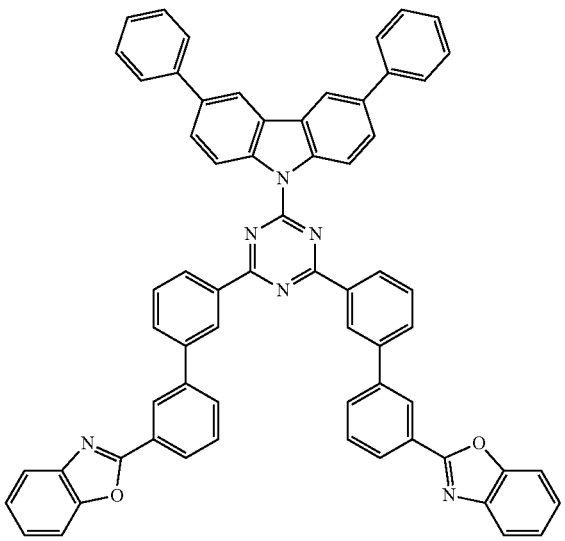
(233)
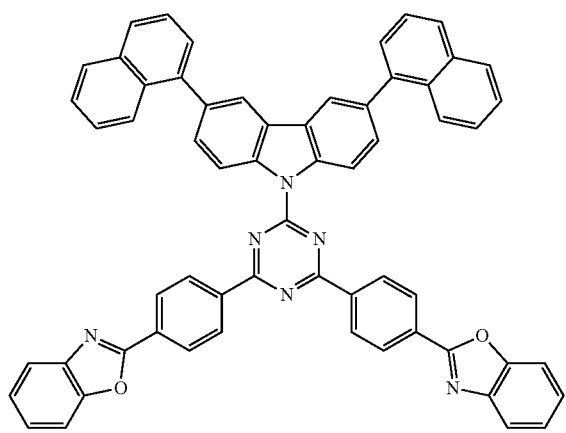
(234)
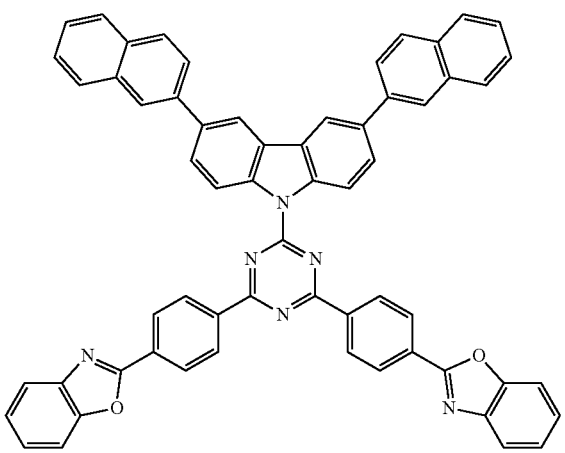
(235)
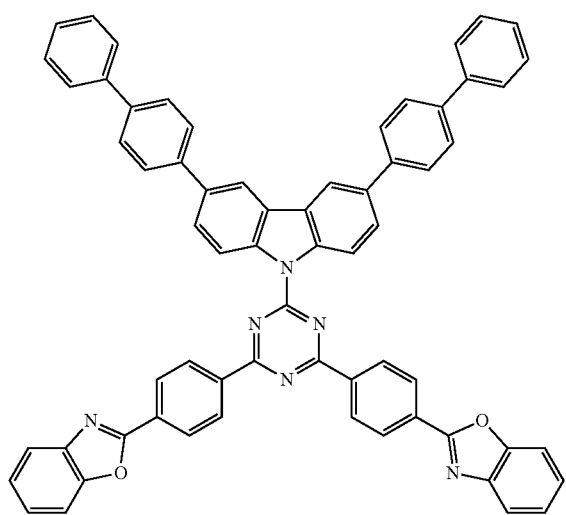
(236)
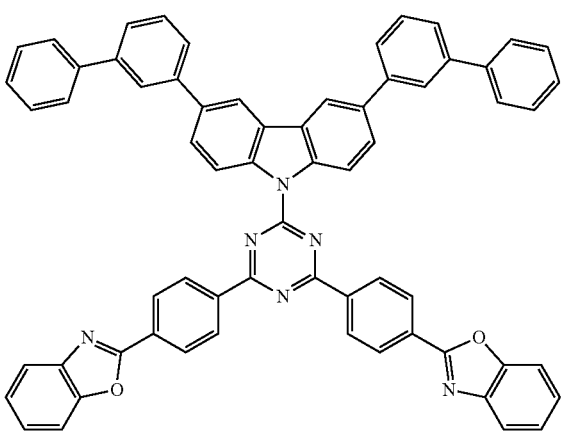

-continued
(237)
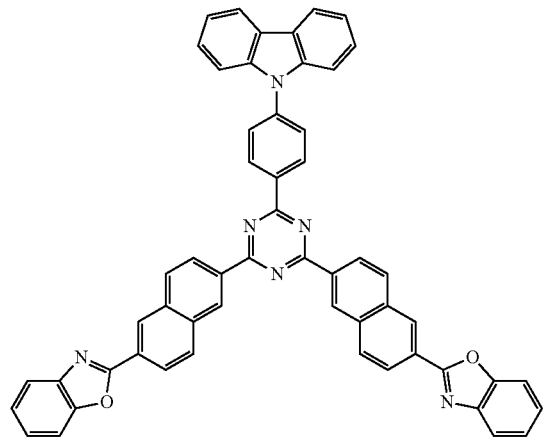
(238)
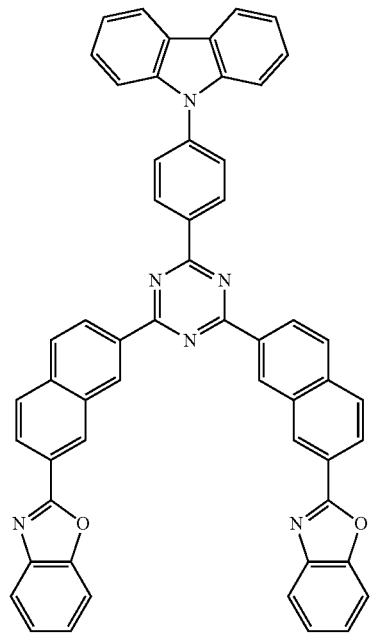
(239)
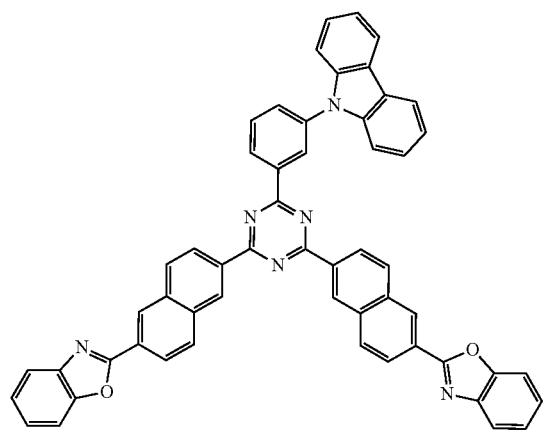
(240)
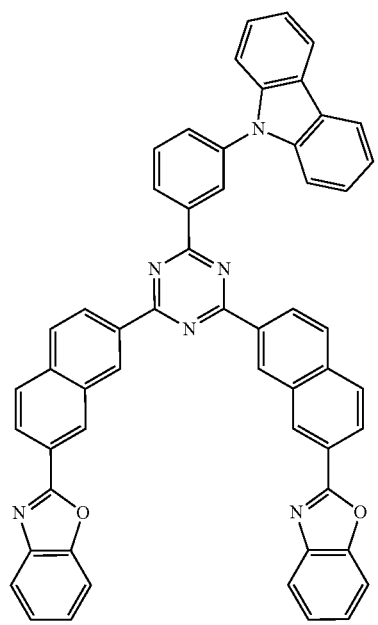

-continued
(241)
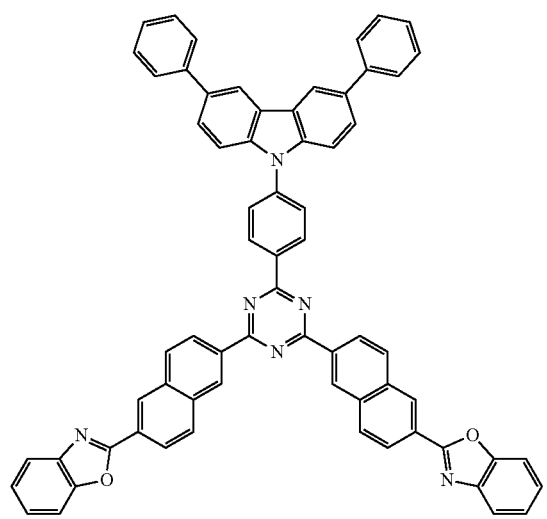
(242)
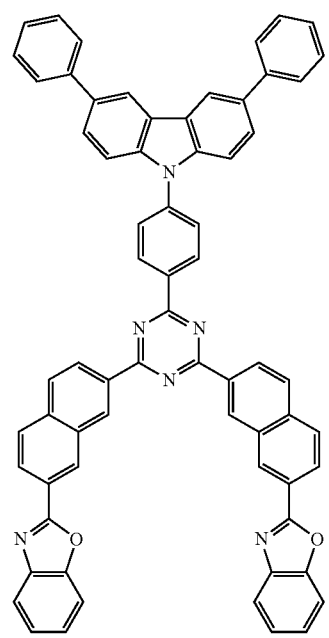
(243)
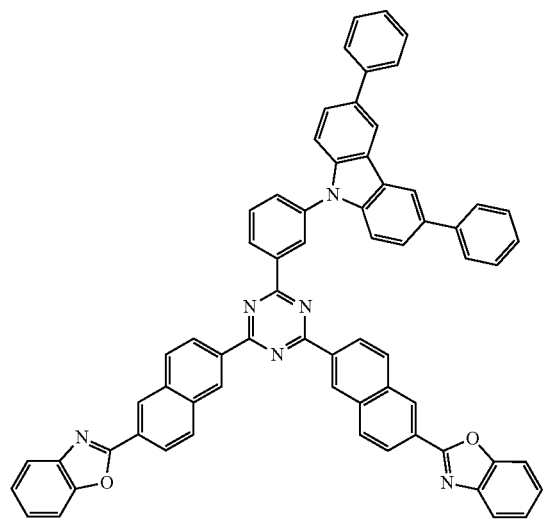
(244)
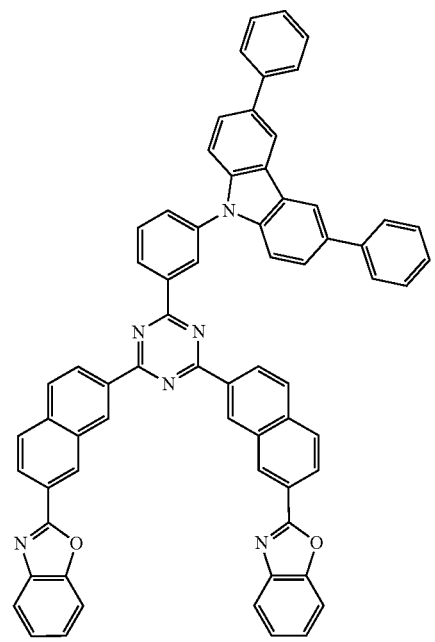

403                                404
(245)
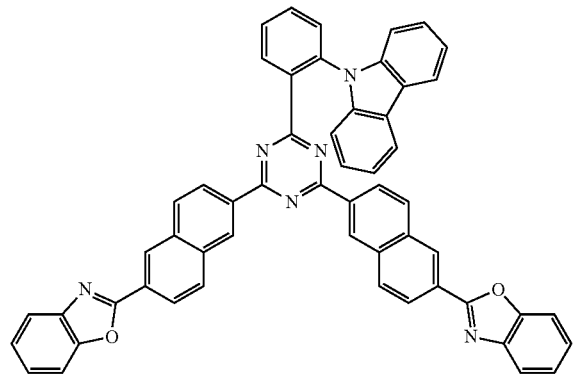
(246)
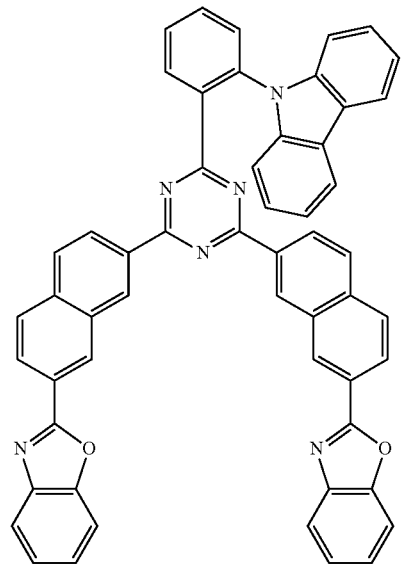
(247)
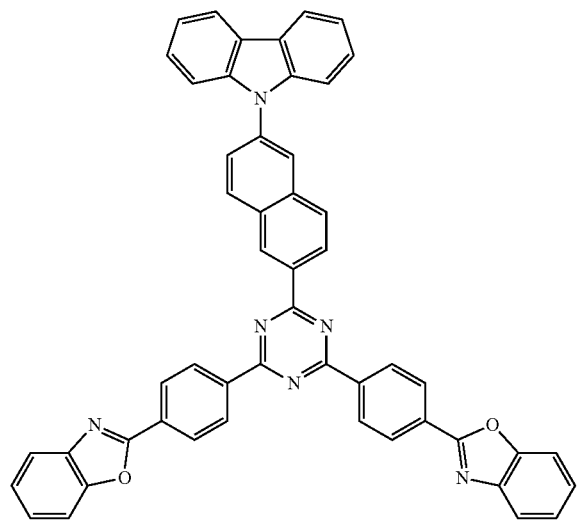
(248)
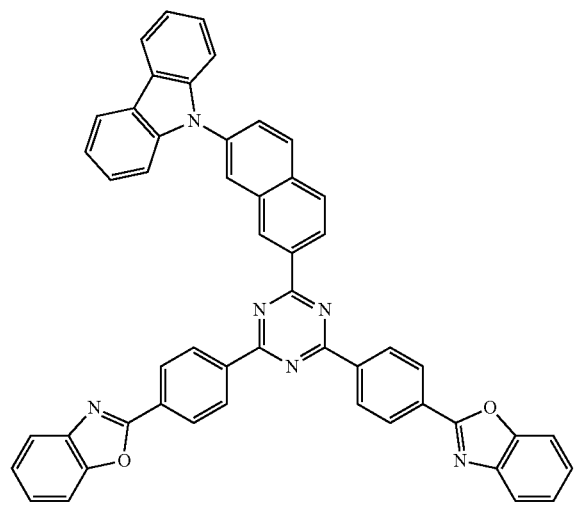
(249)
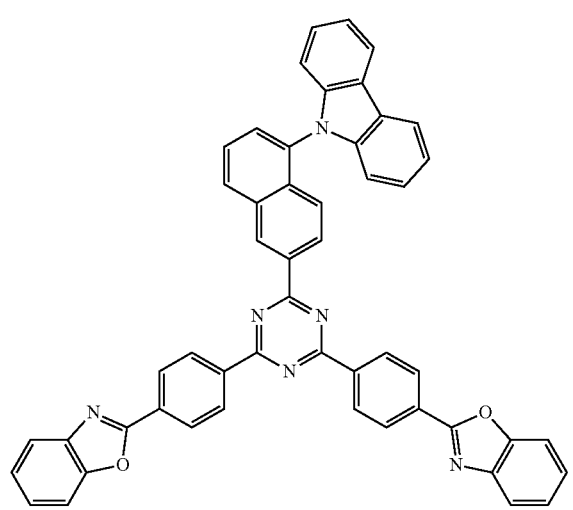
(250)
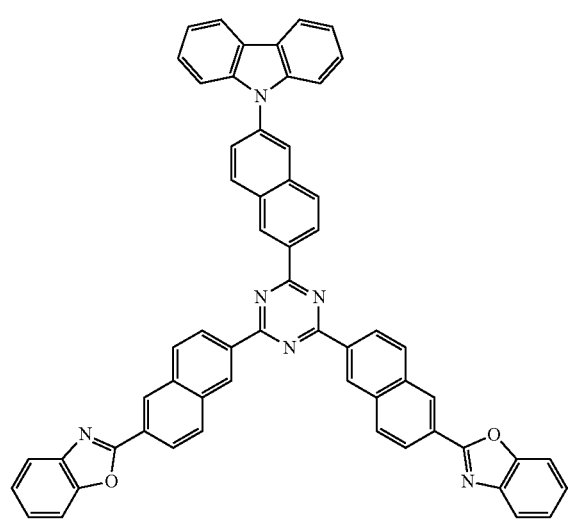

405
406
-continued
(251)
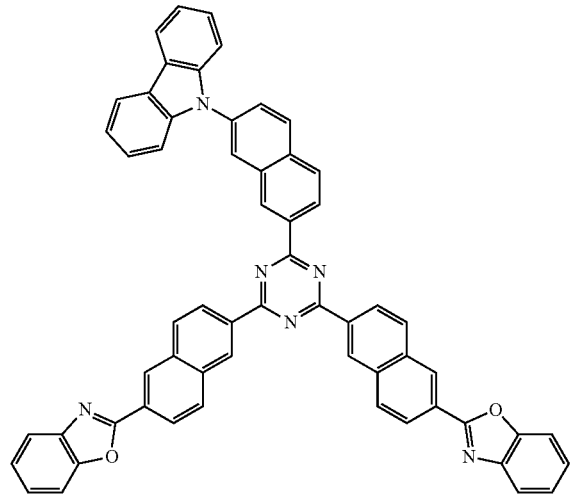
(252)
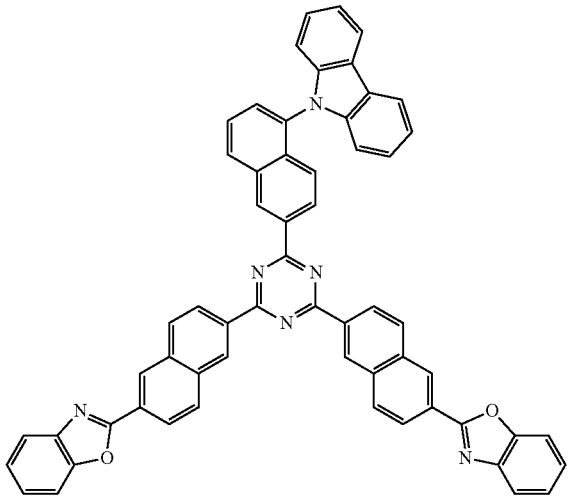
(253)
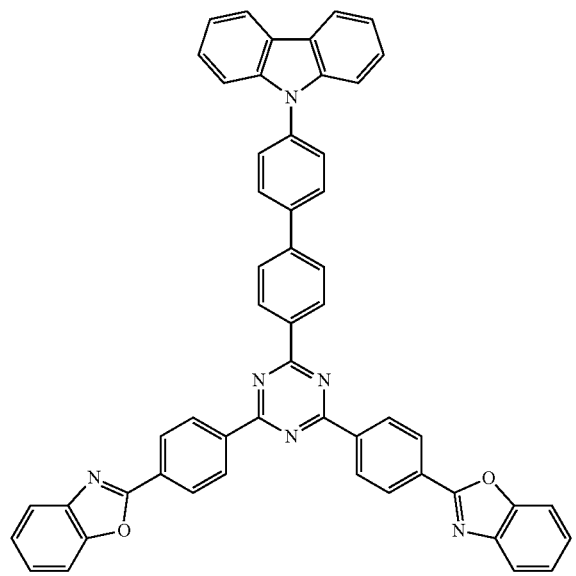
(254)
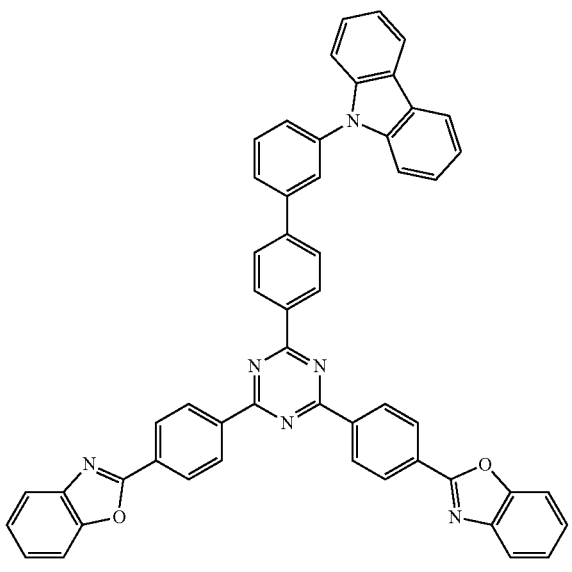

-continued
407 (255)
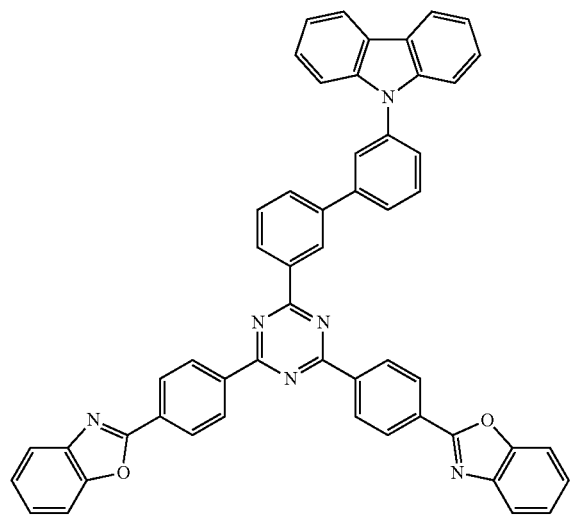
408 (256)
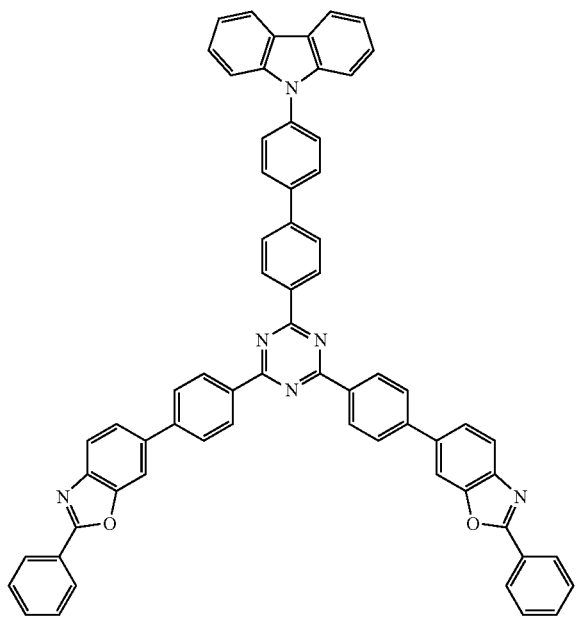
(257)
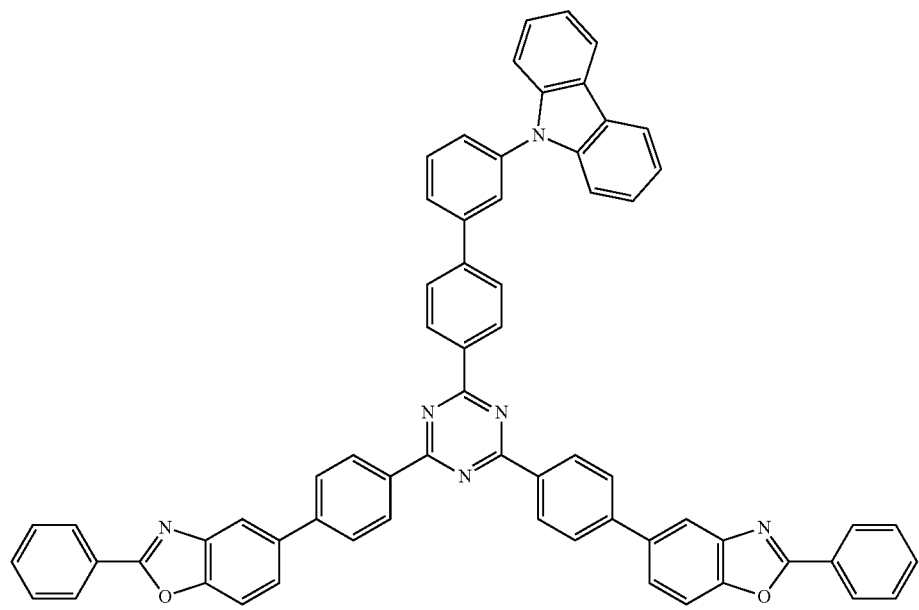

-continued
(258)
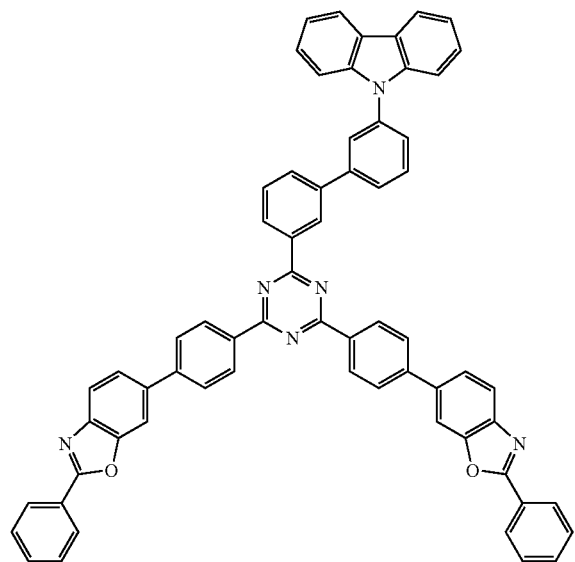
(259)
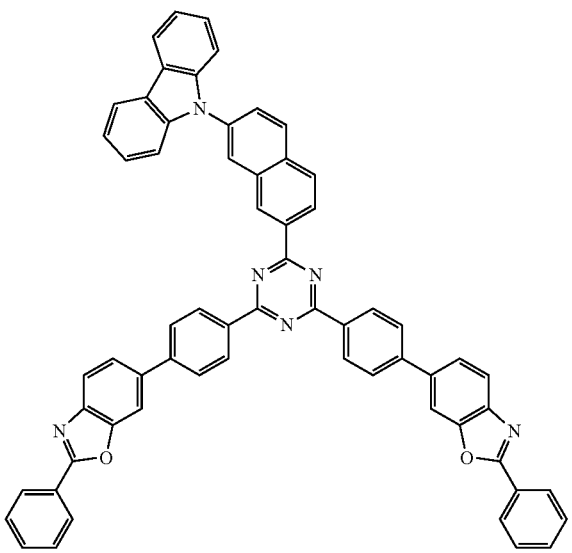
(260)
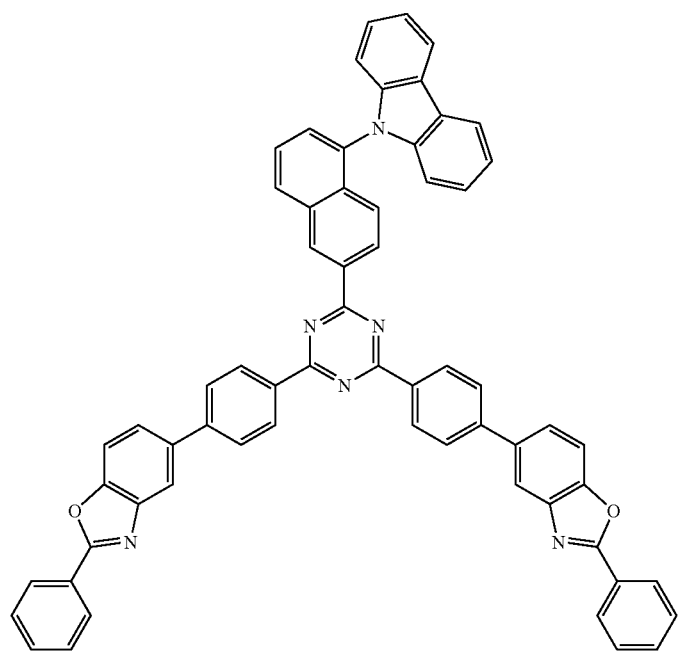

(261)
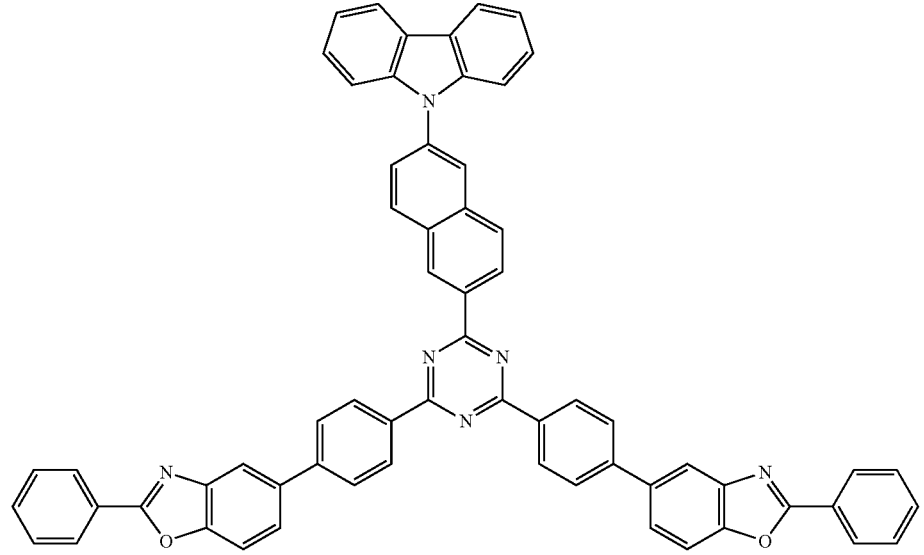
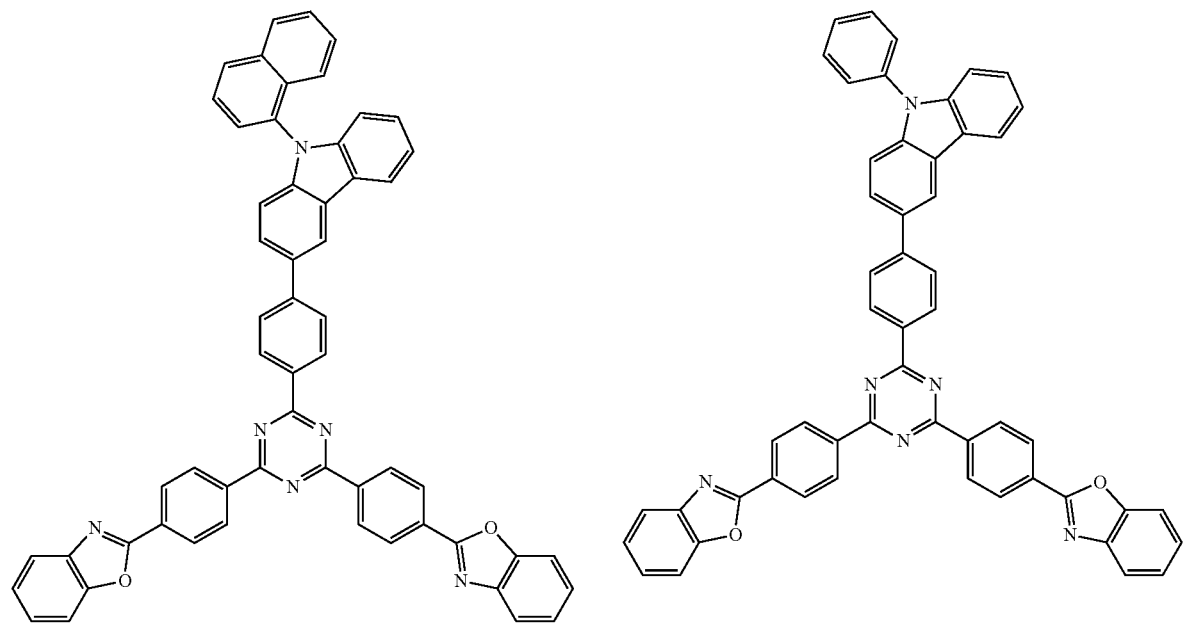
(262)
(263)

413
414
-continued
(264)
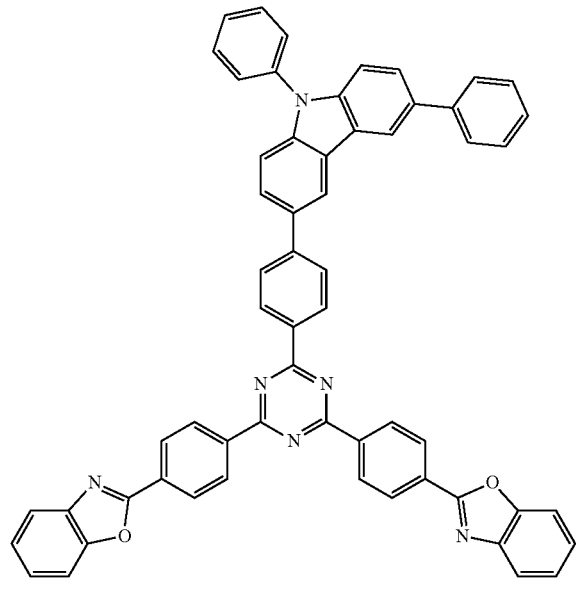
(265)
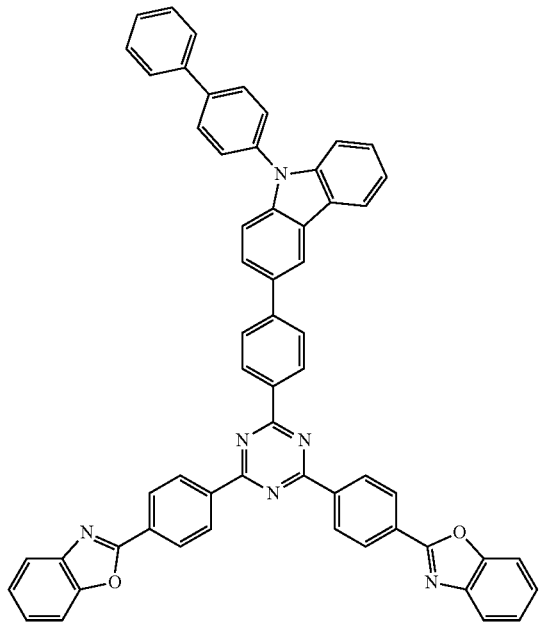
(266)
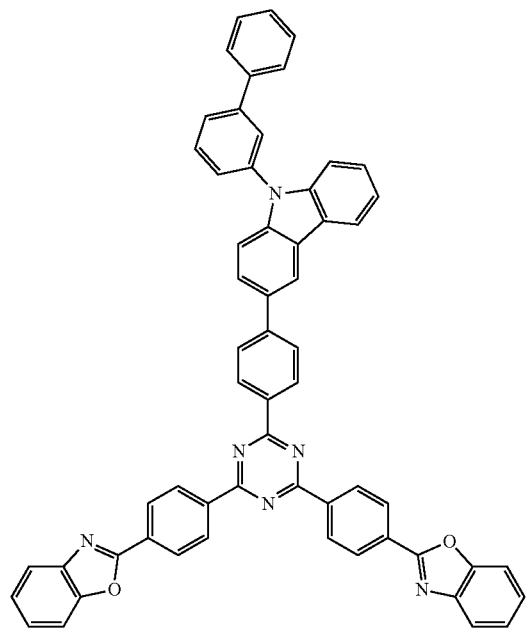

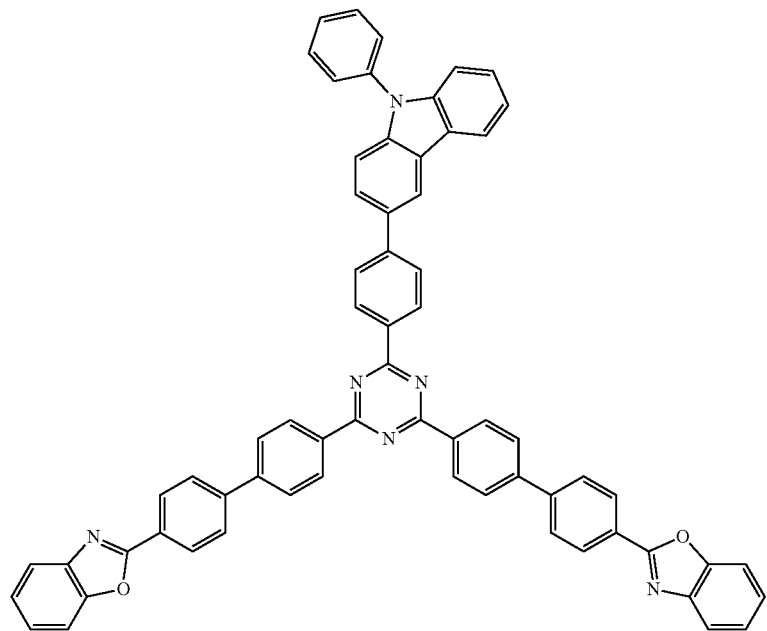
(267)
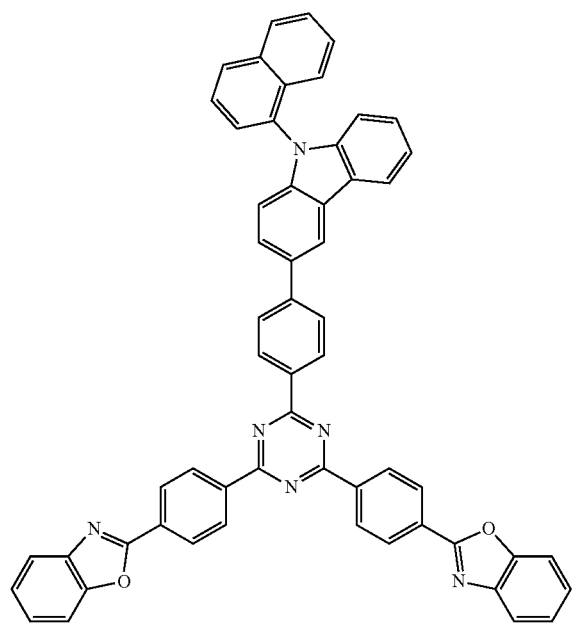
(268)
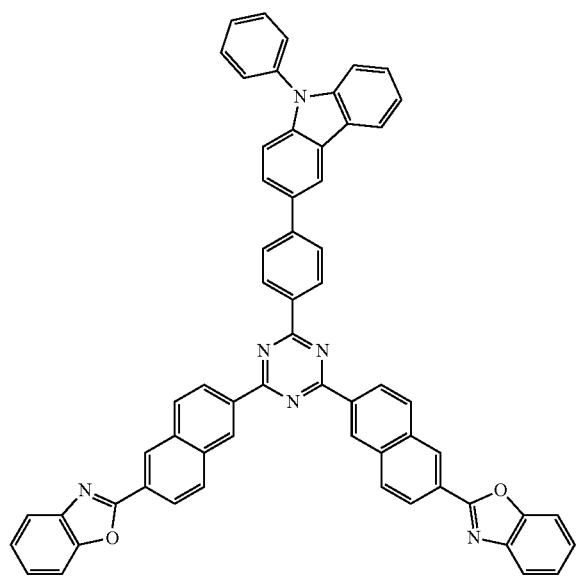
(269)

(270)
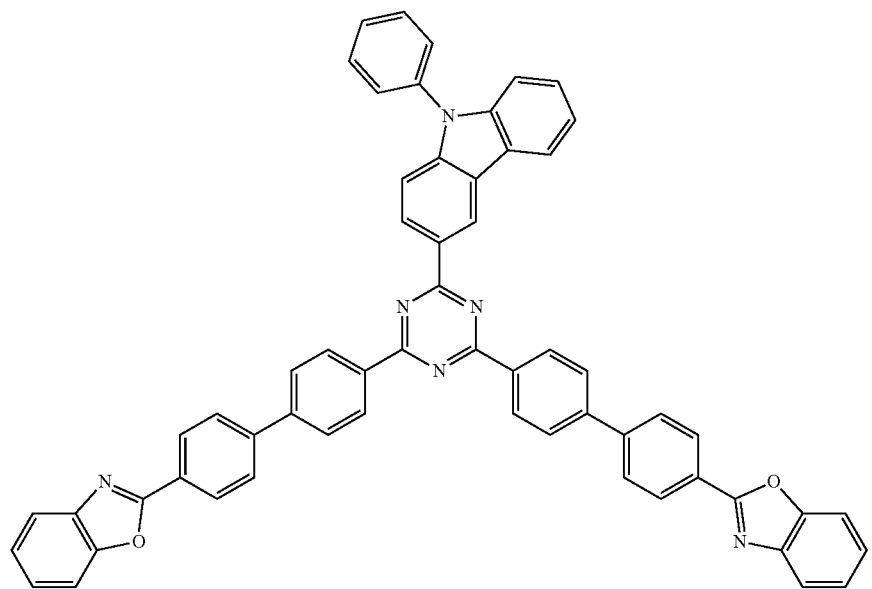
(271)
(272)
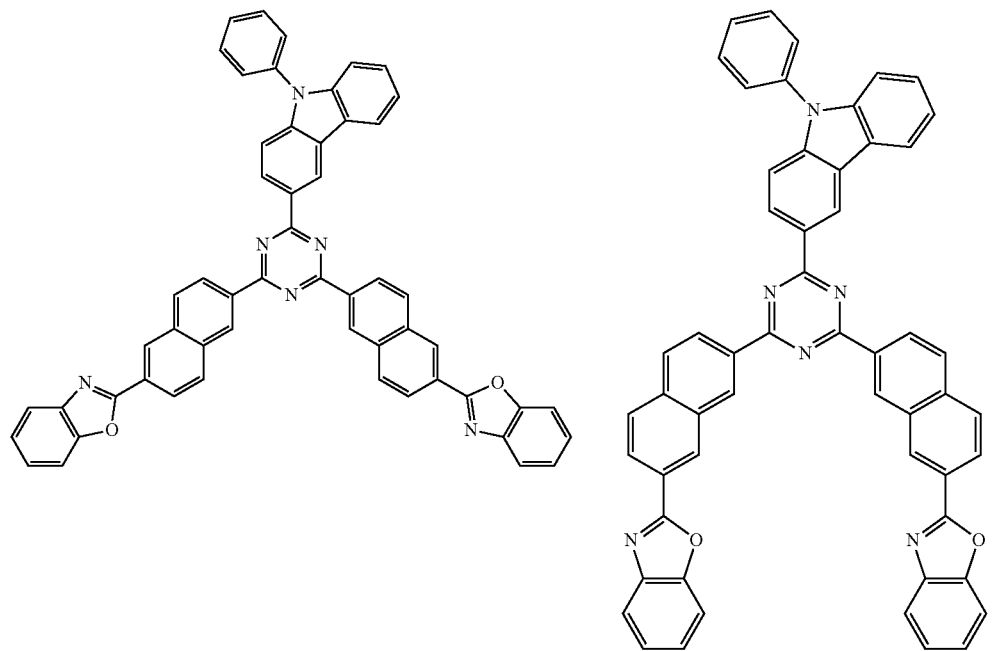

(273)
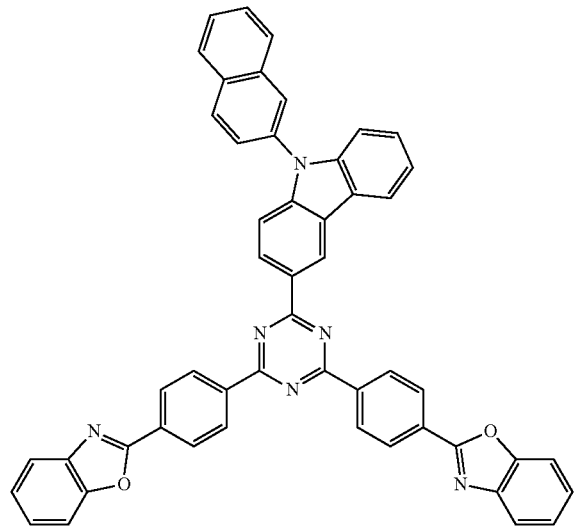
(274)
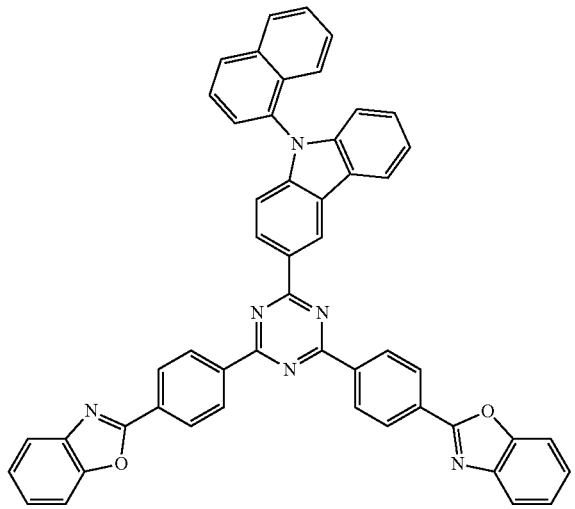
(275)
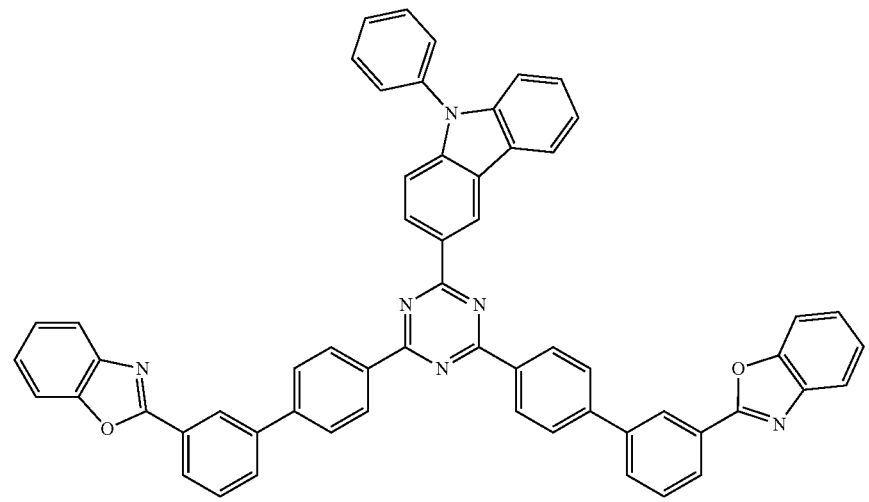

(276)
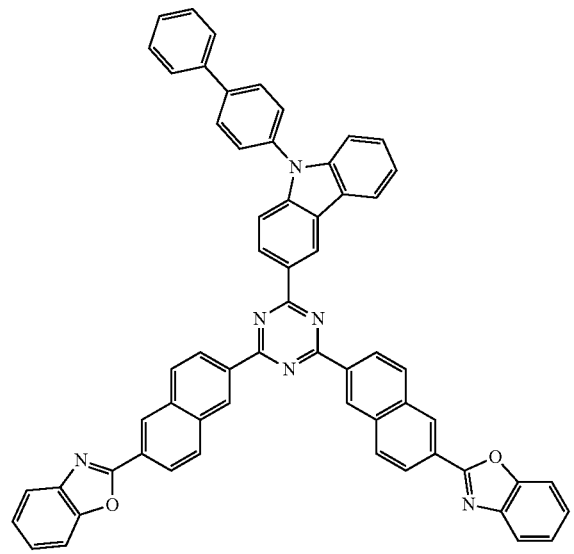
(277)
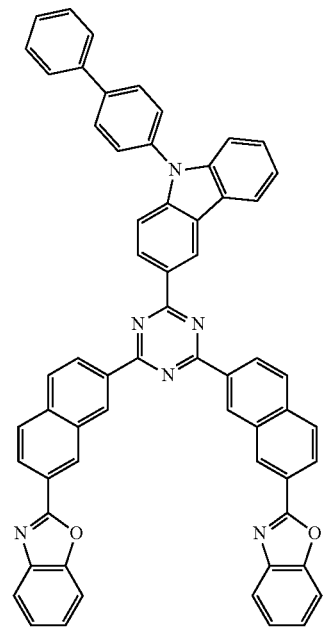
(278)
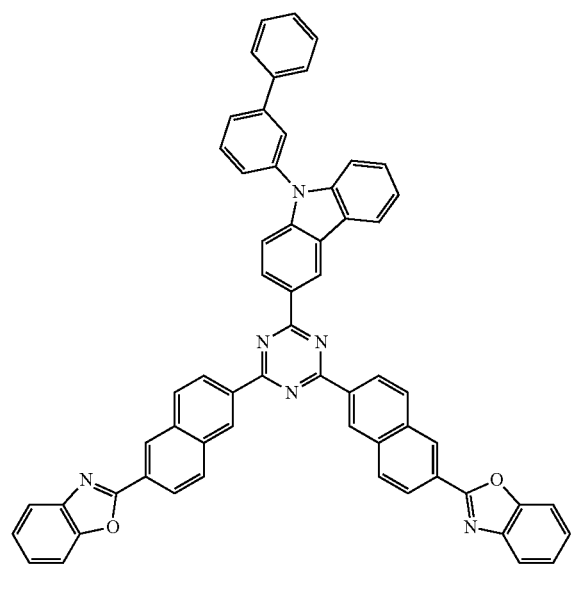
(279)
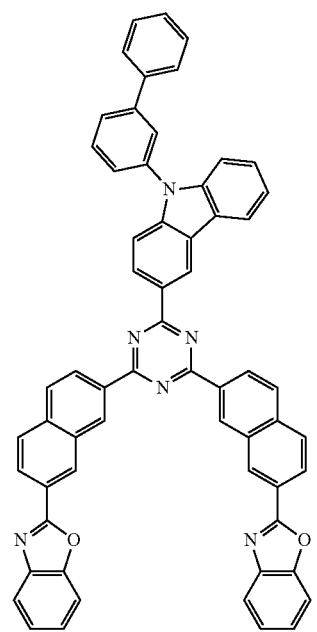

-continued
(280)
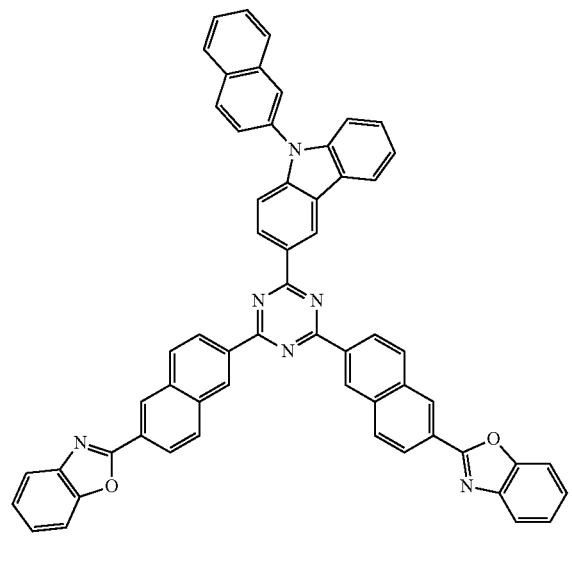
(281)
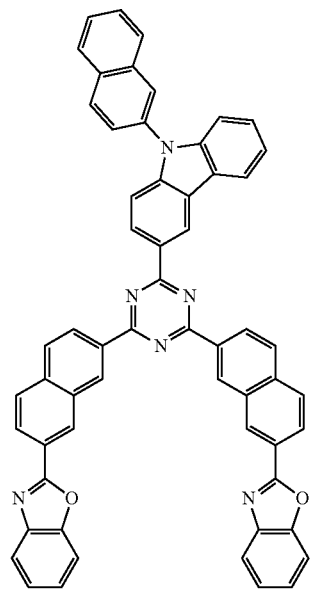
(282)
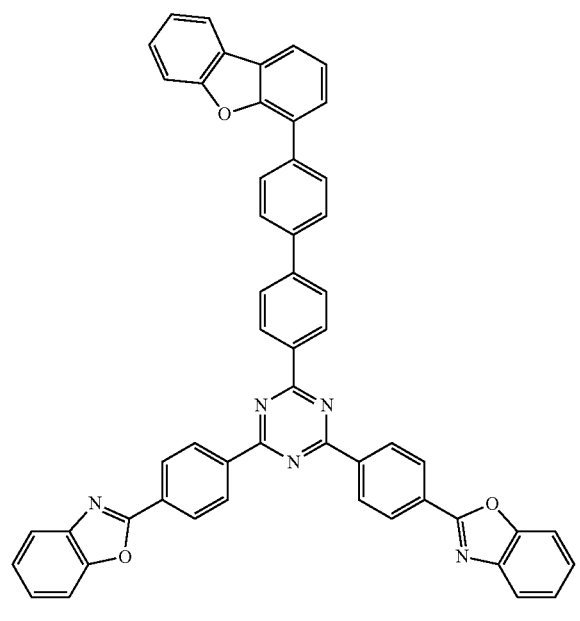
(283)
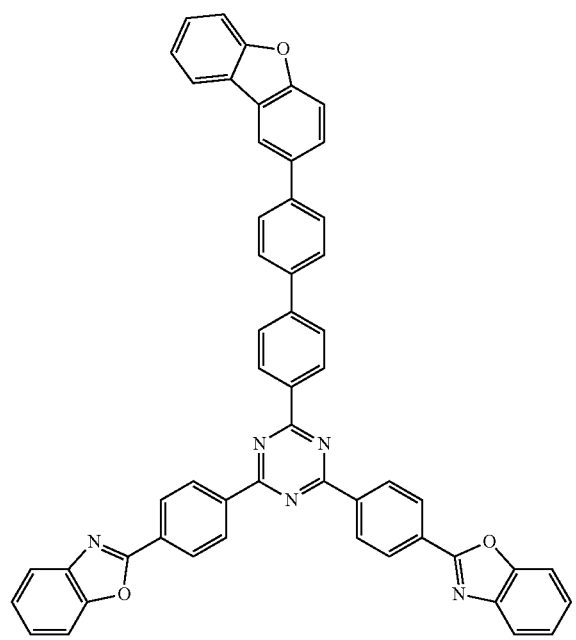

(284)
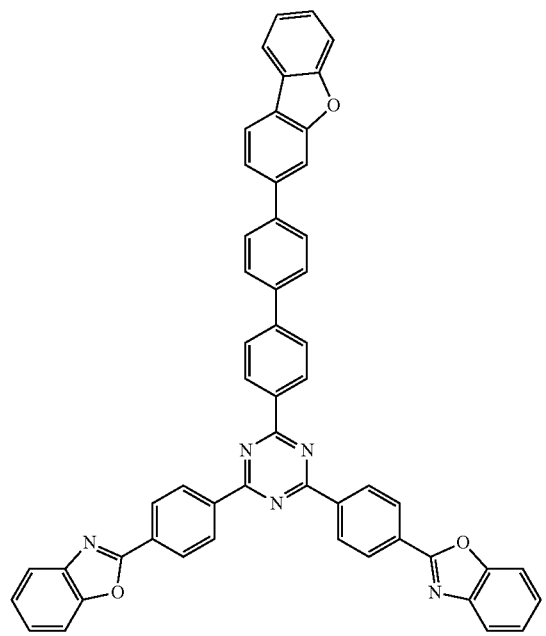
(285)
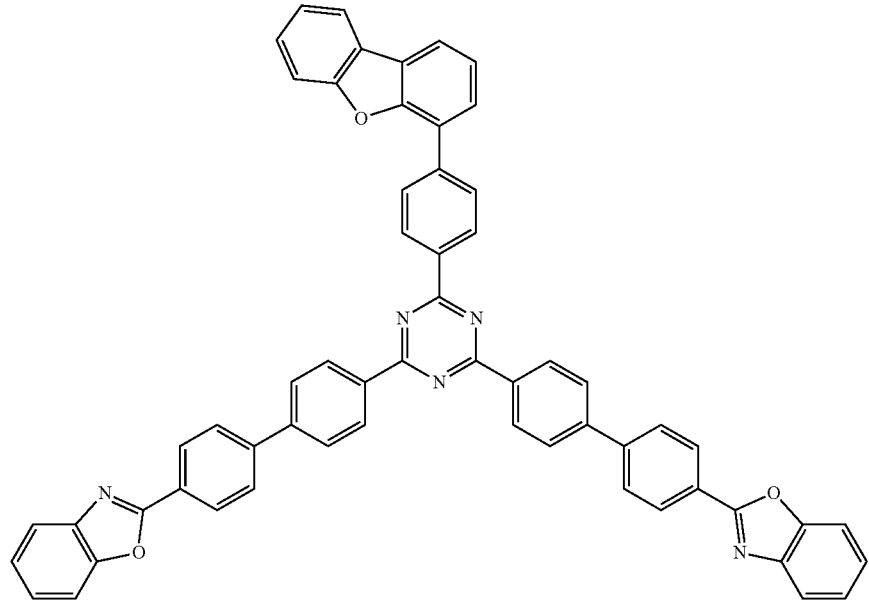

(286)
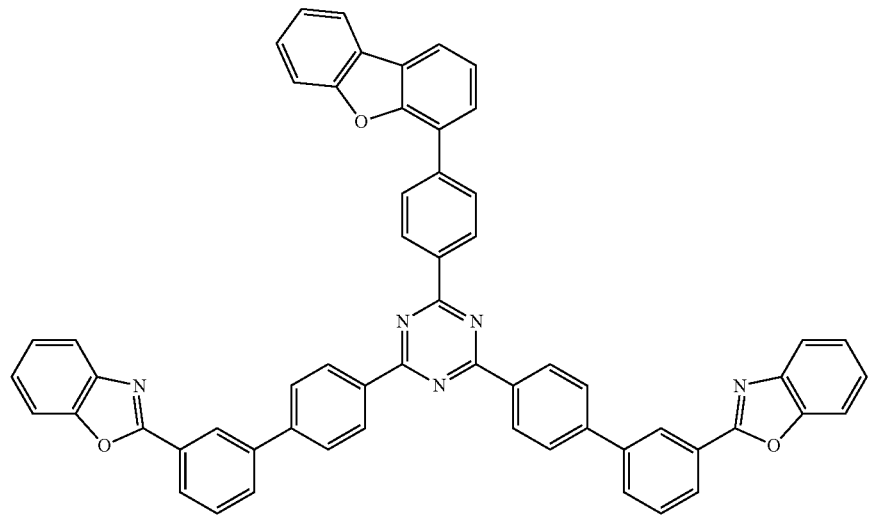
(287)
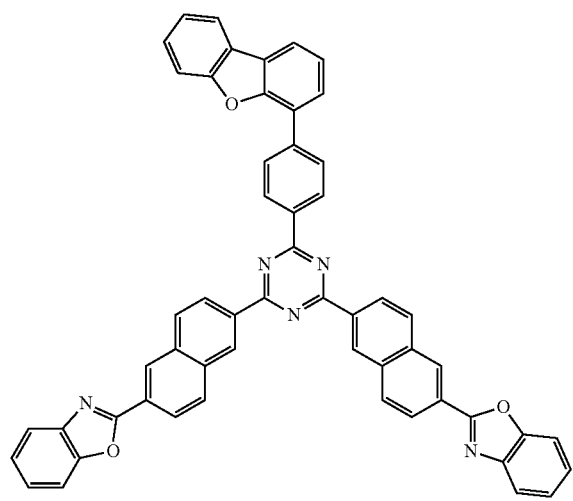
(288)
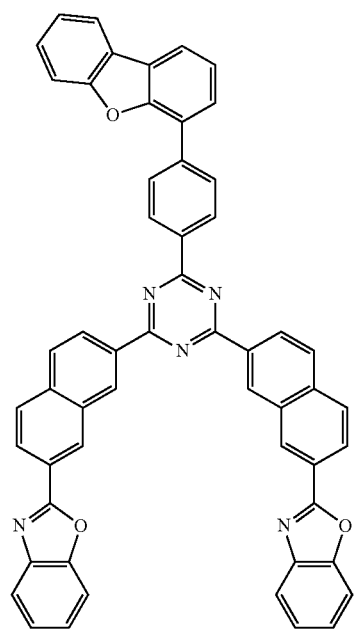

-continued
(289)
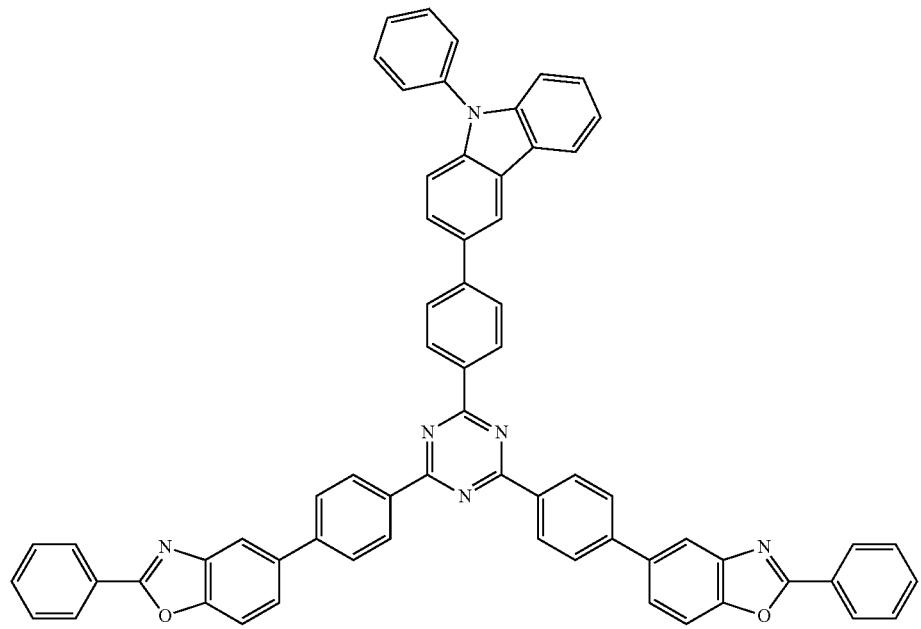
(290)　　(291)
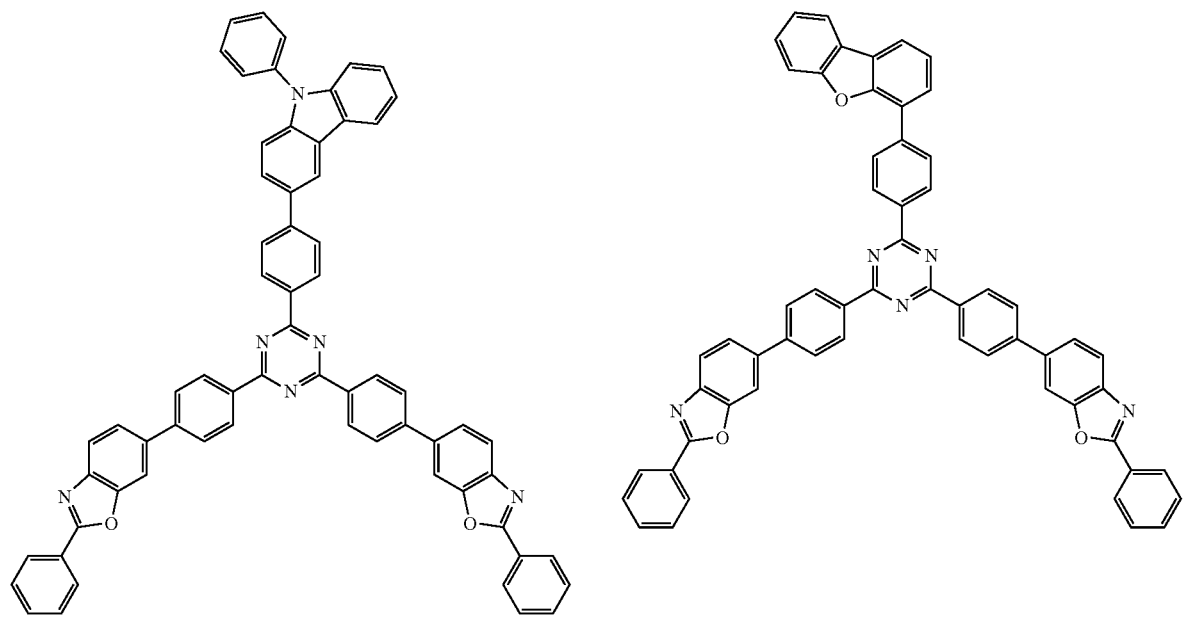

-continued
(292)
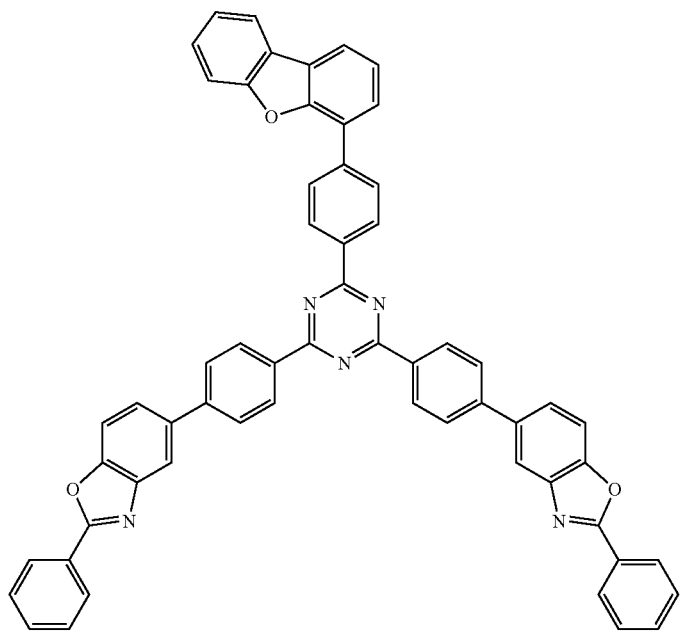
(293)
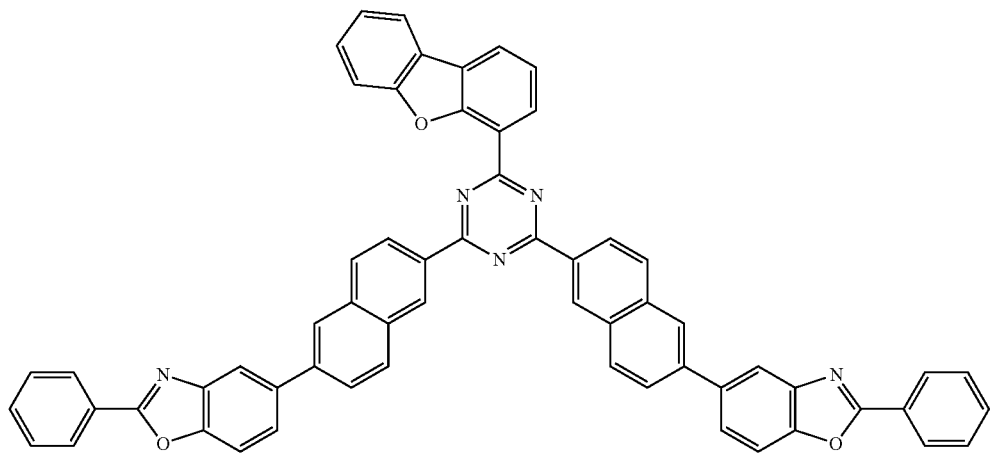
(294)
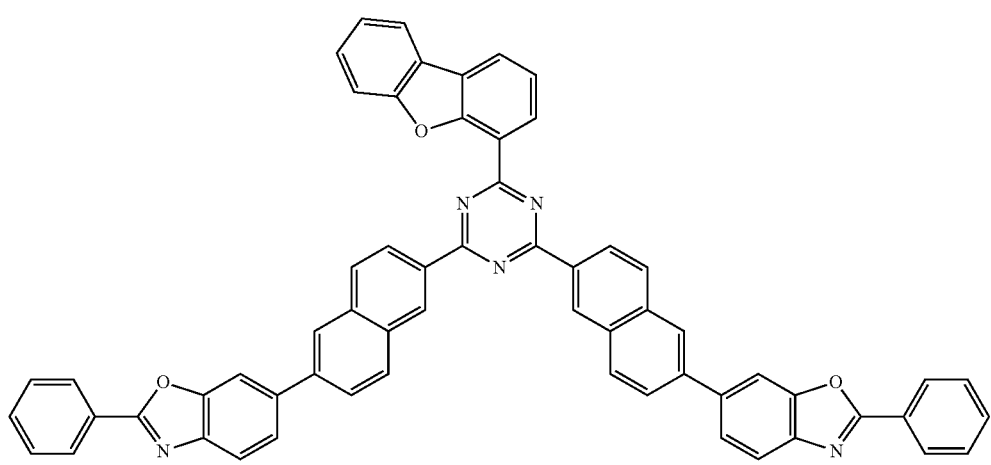

-continued
433
(295)
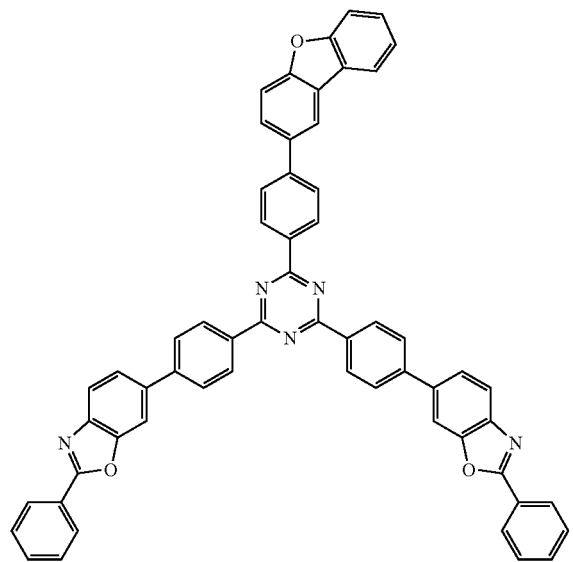
434
(296)
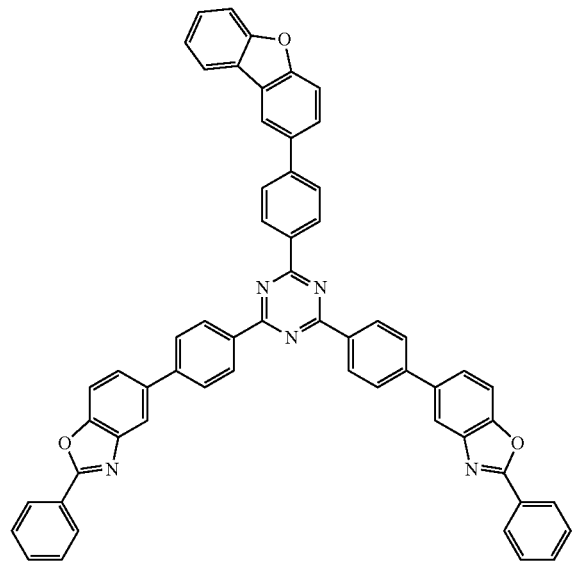
(297)
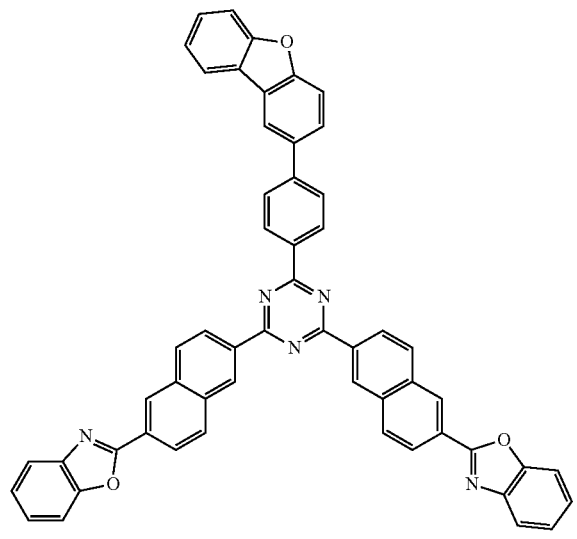
(298)
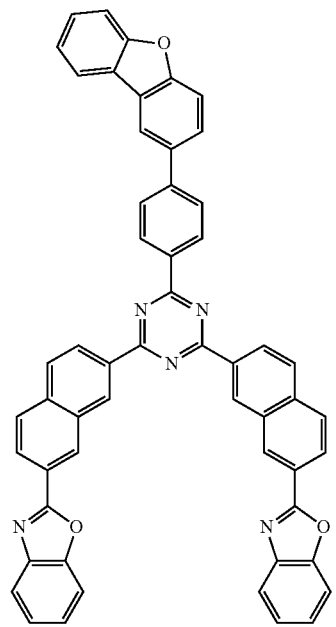

(299)
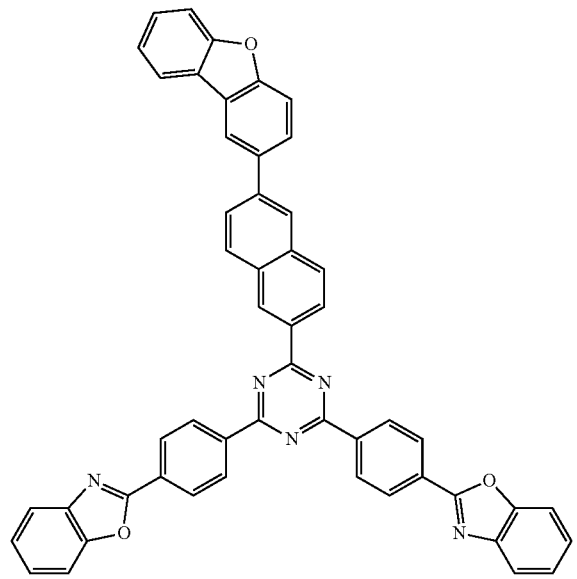
(300)
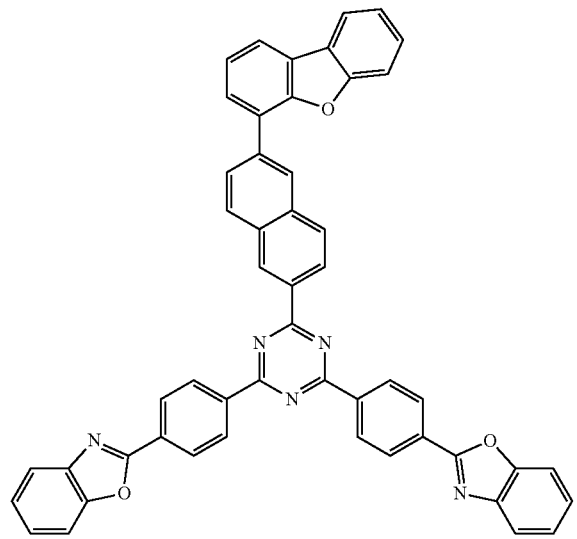
(301)
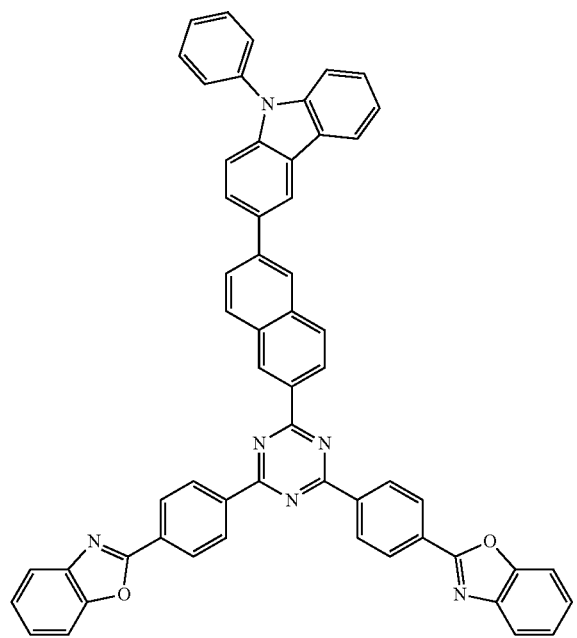
(302)
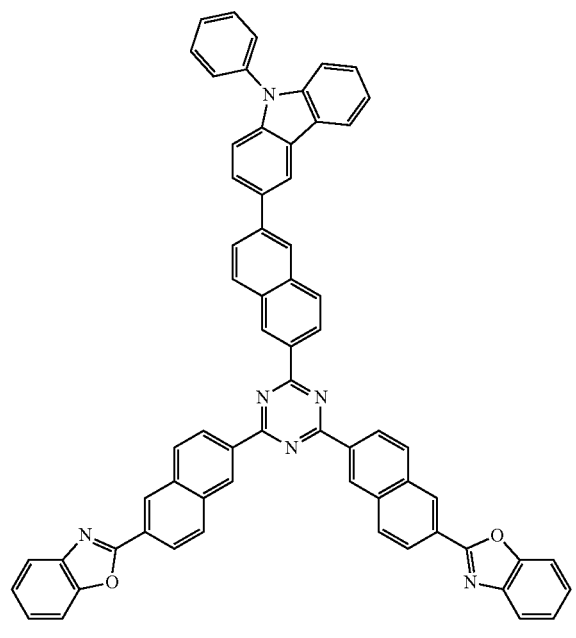

437
-continued
(303)
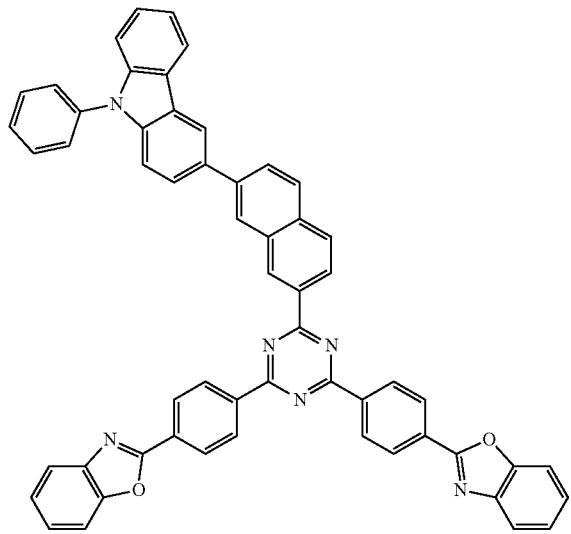
438
(304)
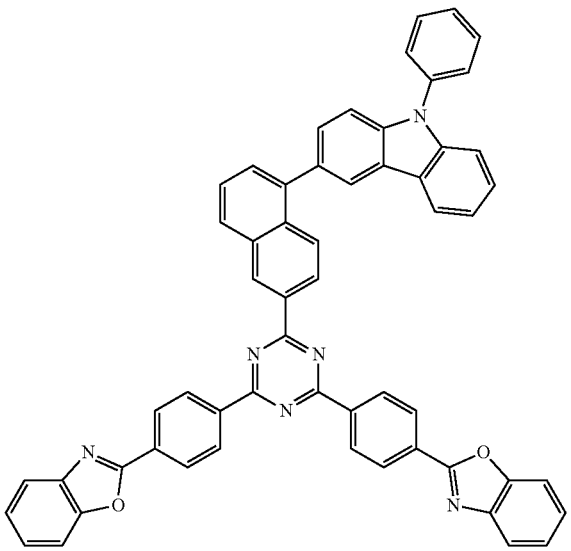
(305)
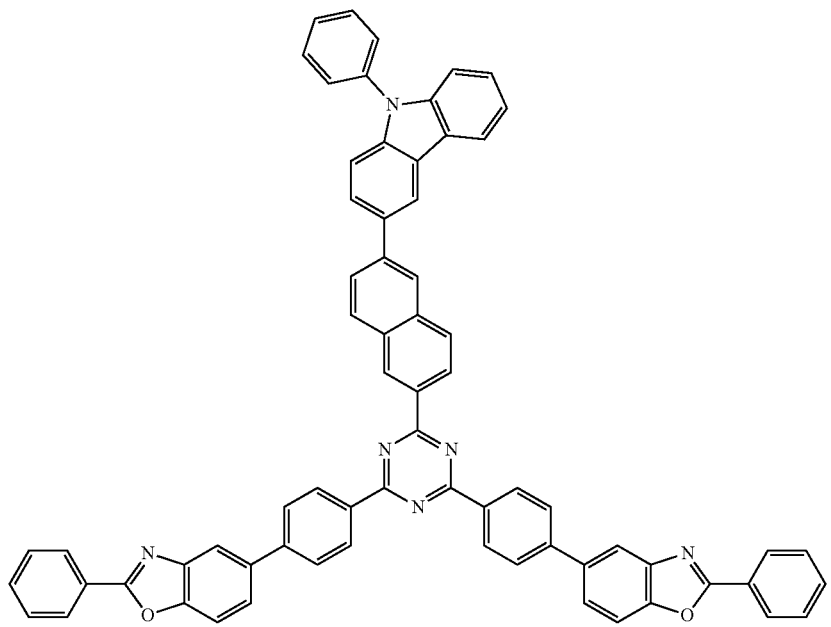
(306)
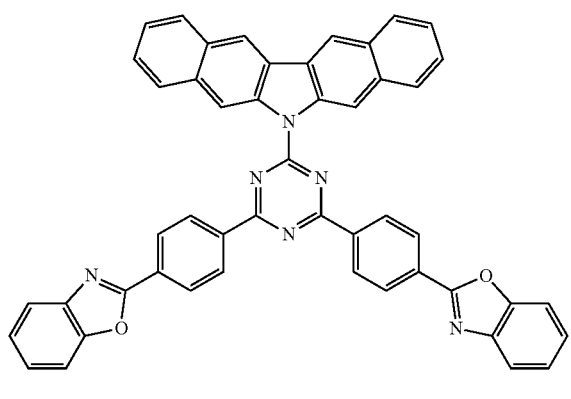
(307)
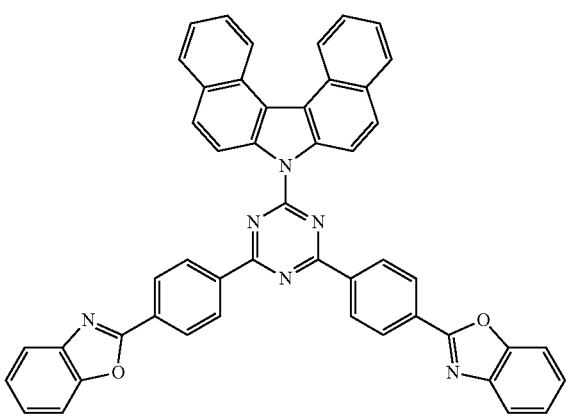

-continued
(308)
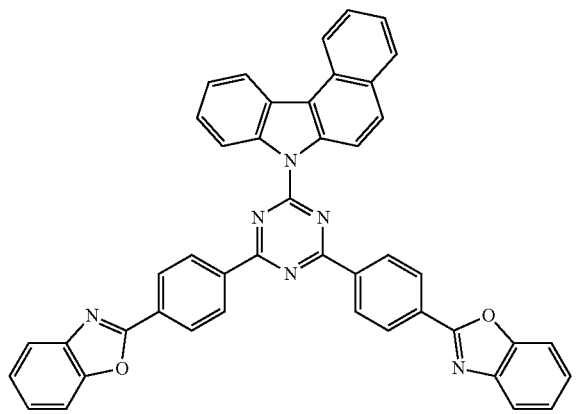
(309)
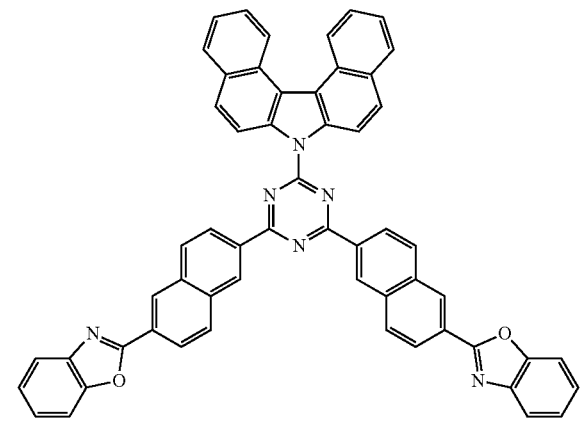
(310)
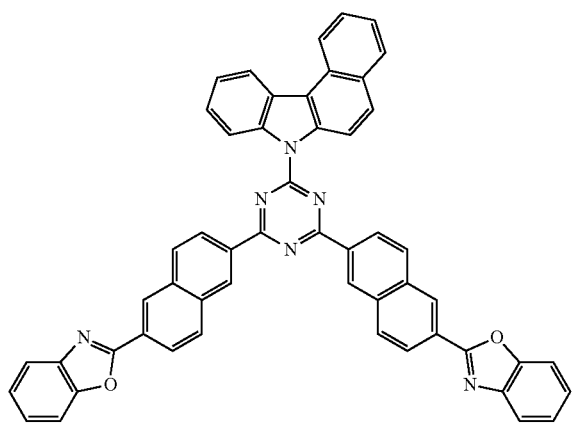
(311)
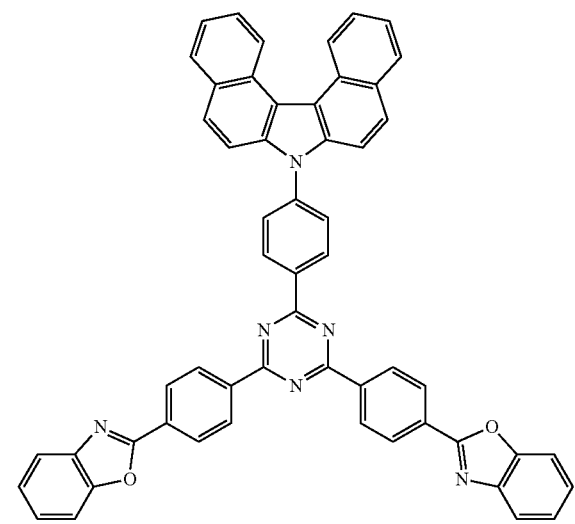
(312)
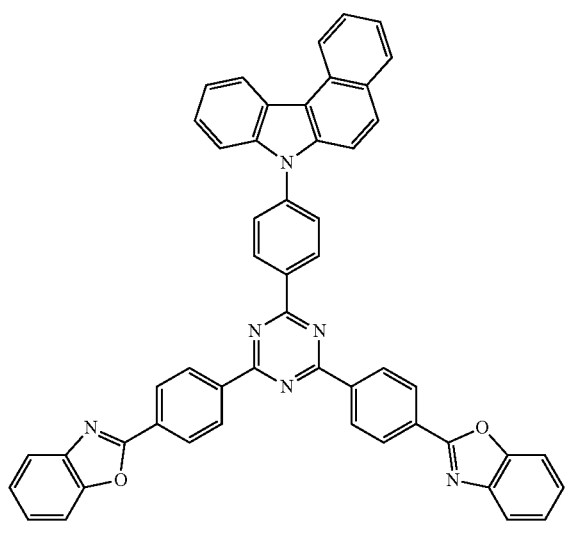
(313)
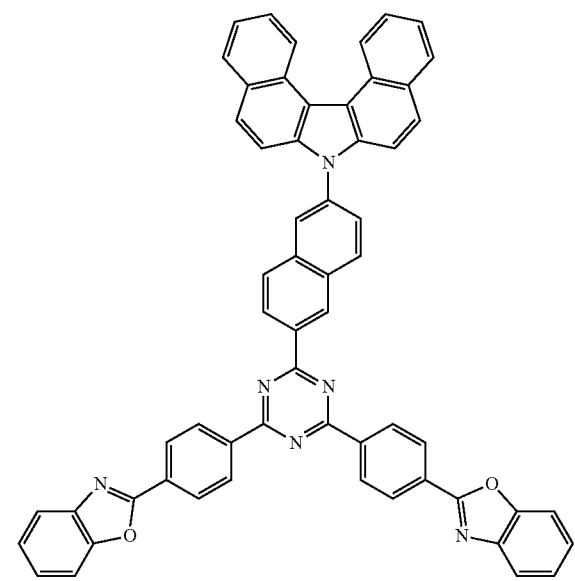

441
(314)
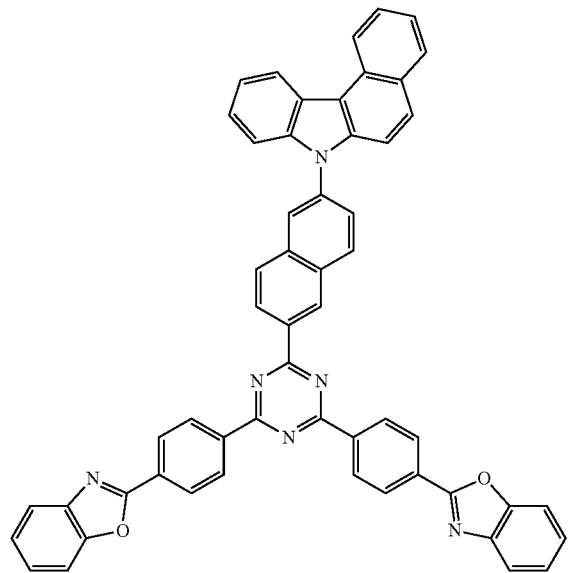
442
(315)
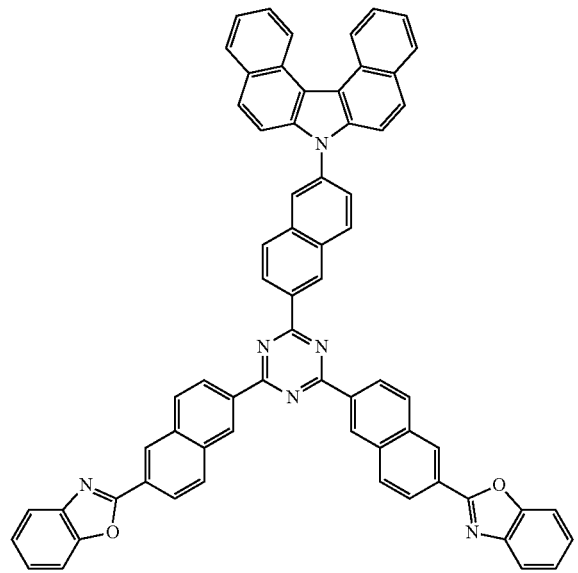
(316)
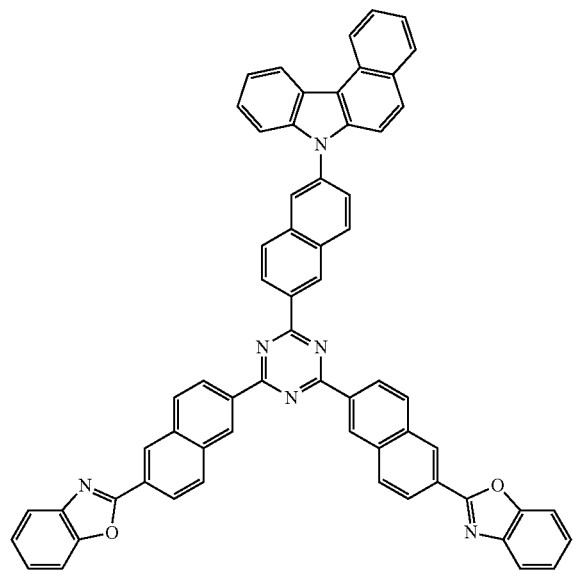
(317)
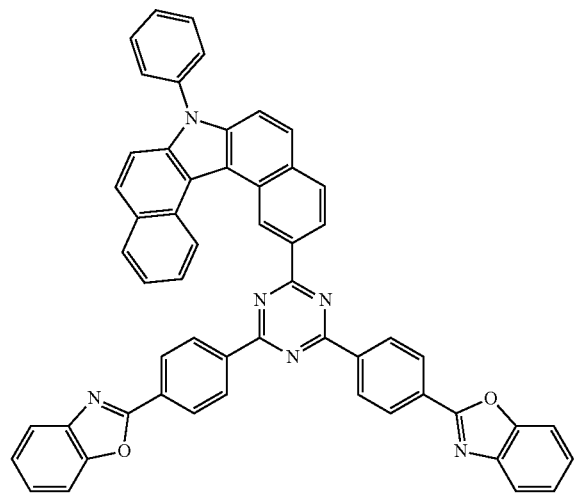

-continued
(318)
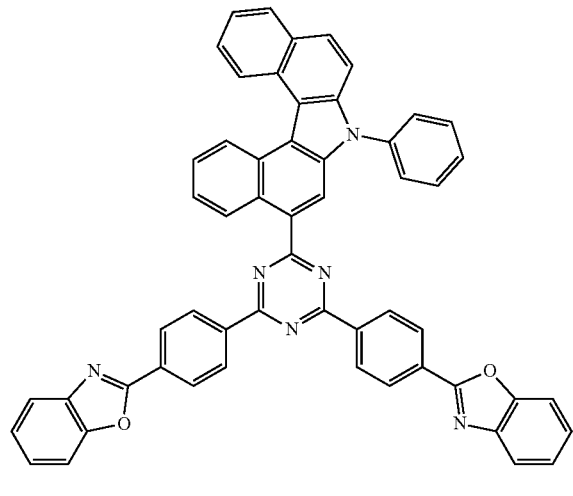
(319)
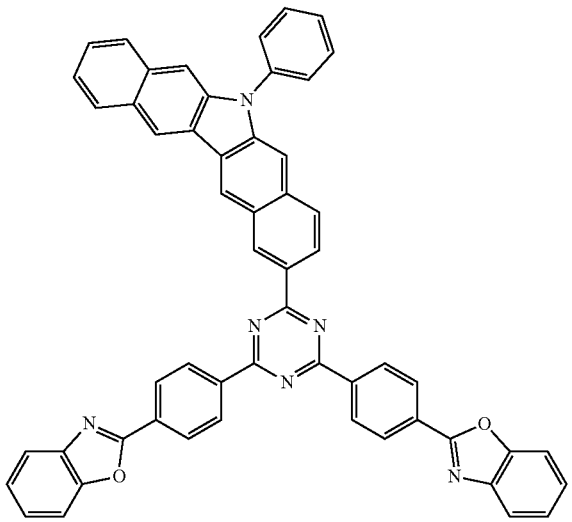
(320)
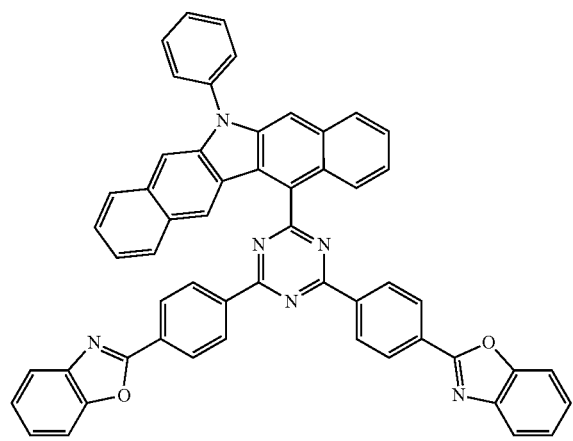
(321)
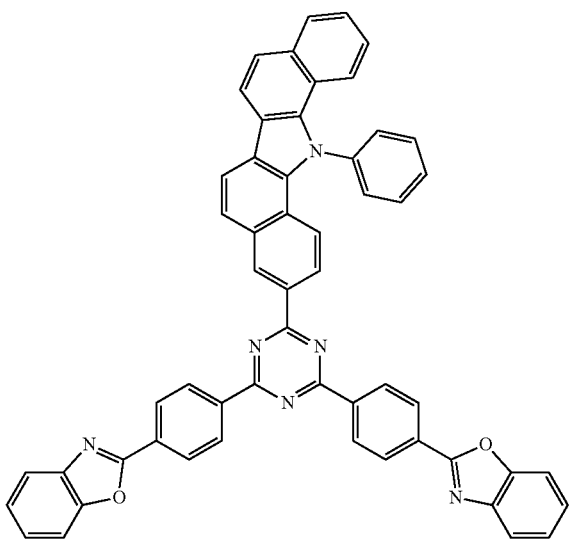

445
(322)
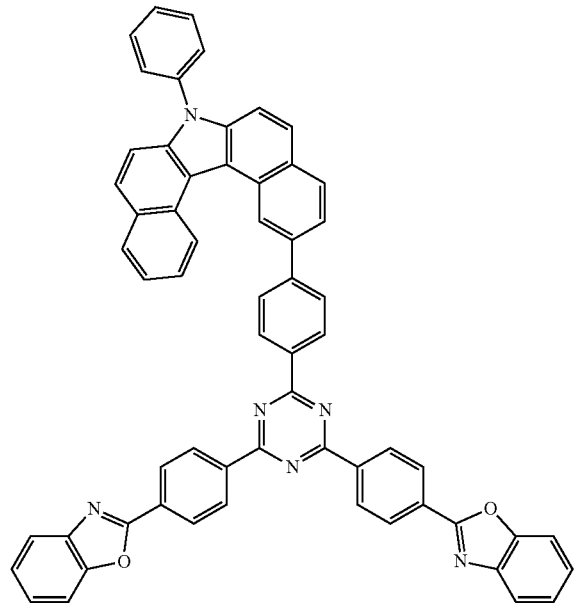
446
(323)
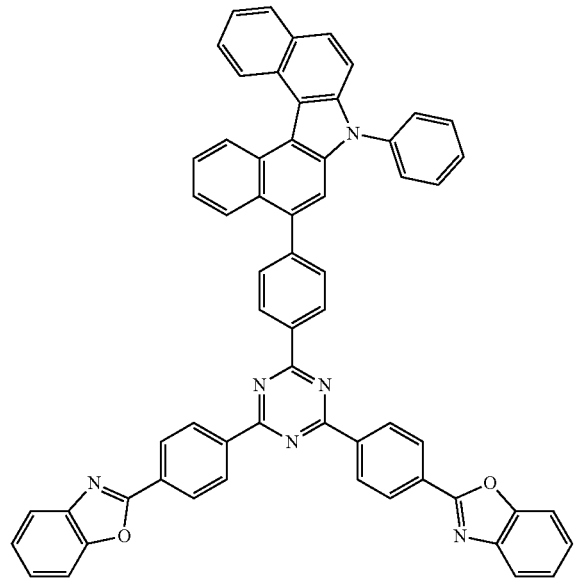
(324)
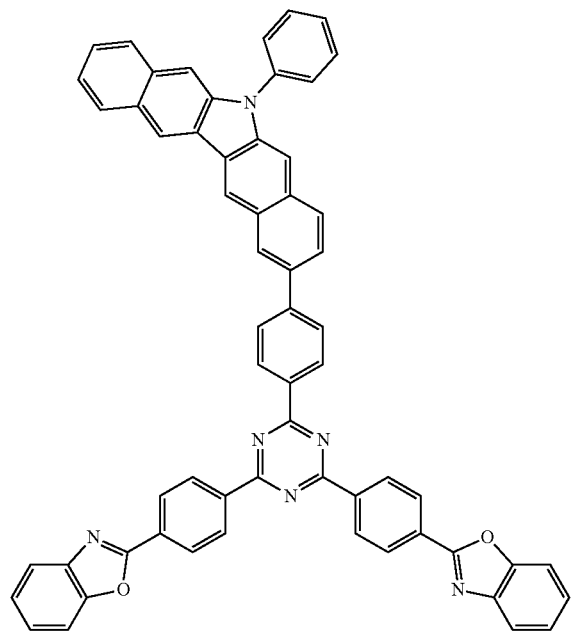
(325)
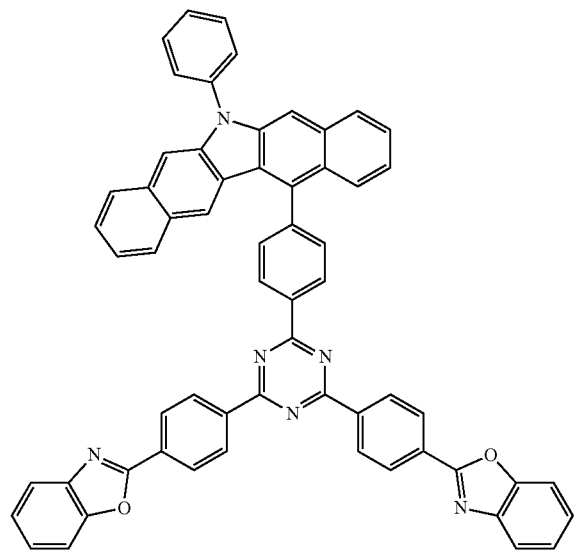

-continued
(326)
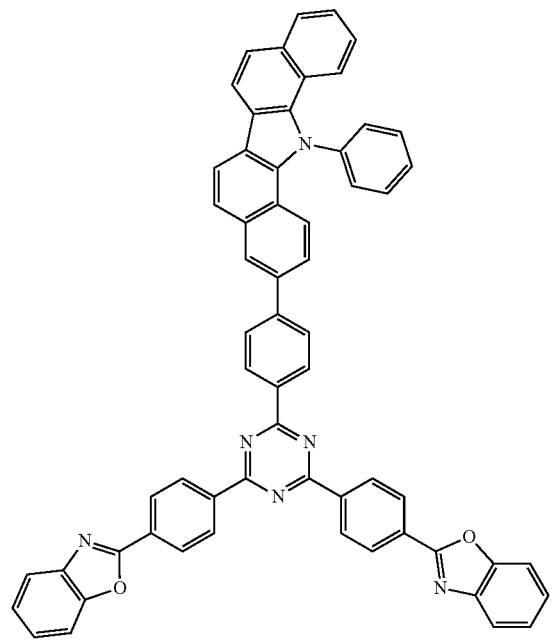
(327)
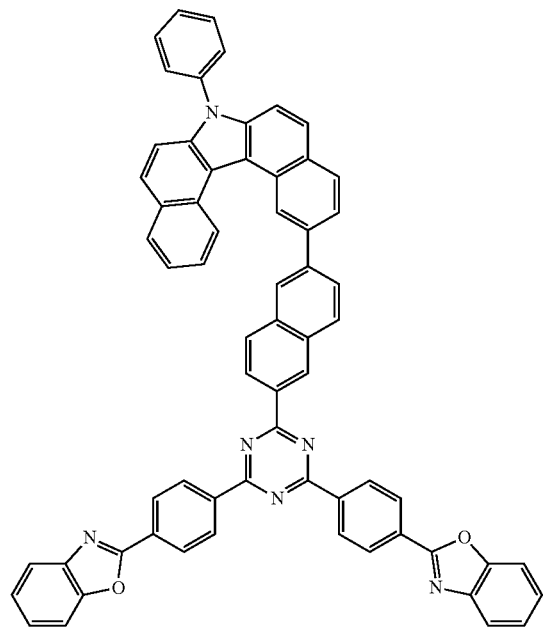
(328)
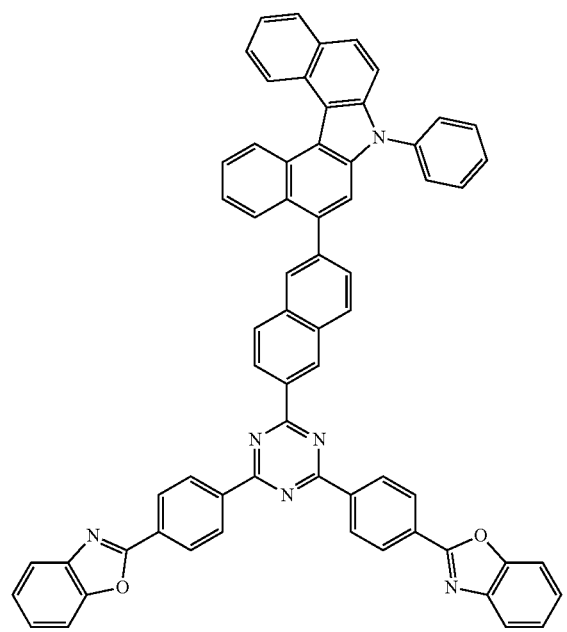
(329)
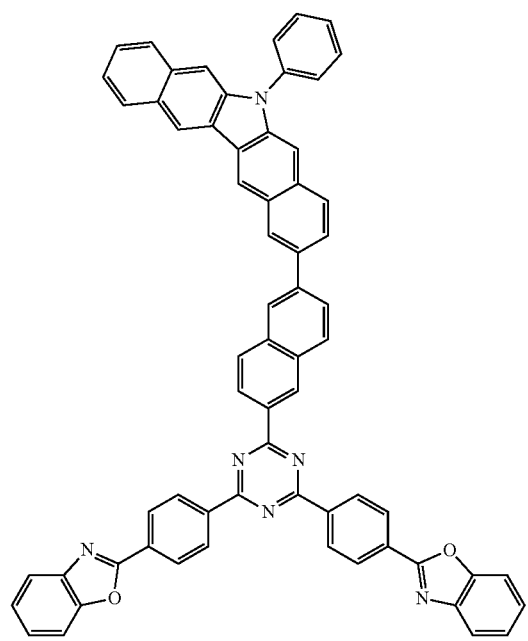

449 450
-continued
(330)
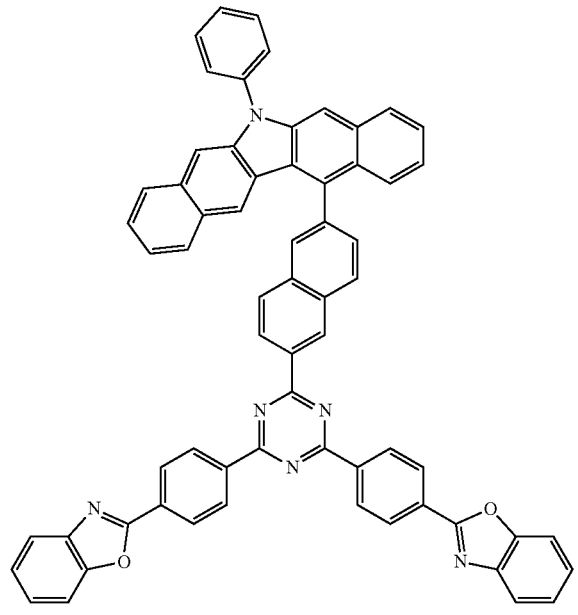
(331)
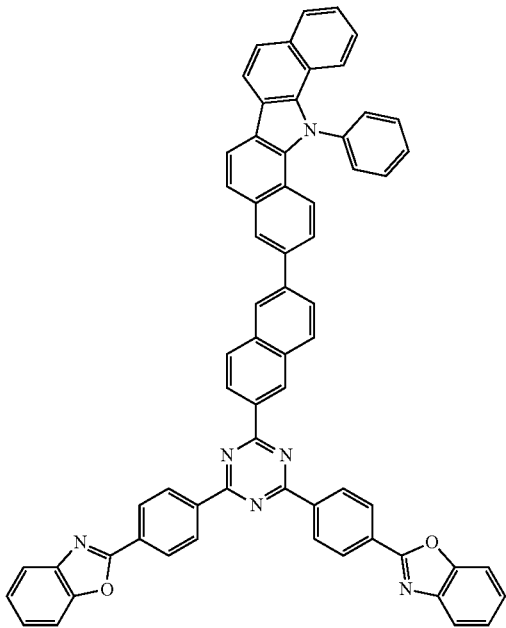
(332)
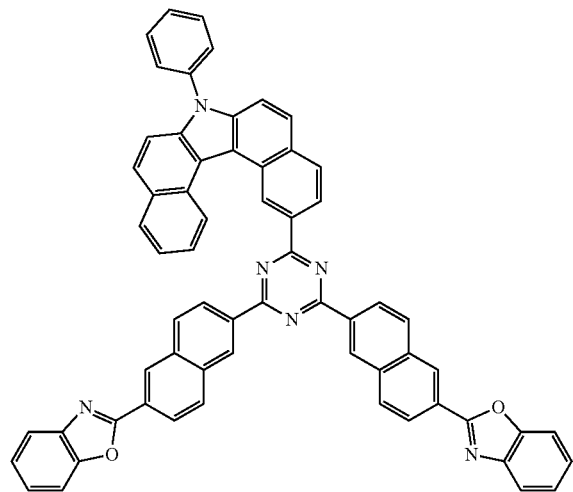
(333)
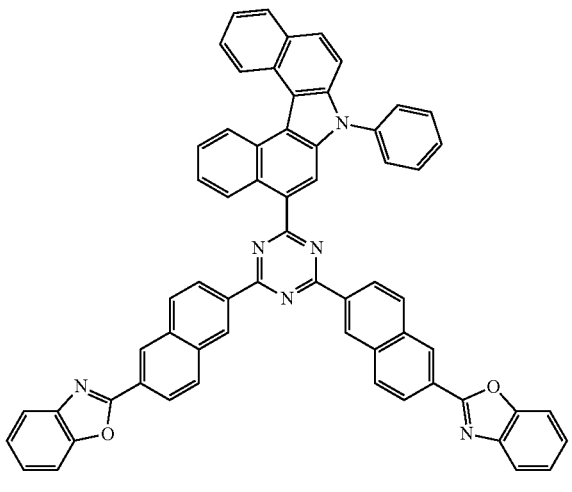

-continued
(334)
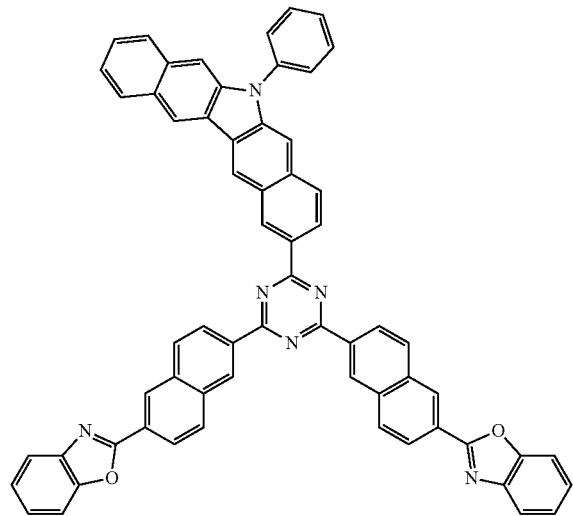
(335)
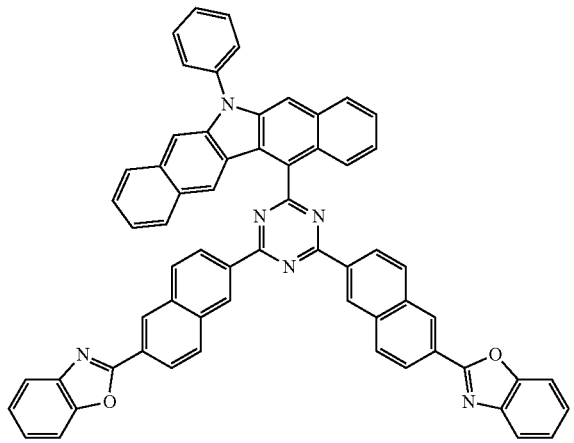
(336)
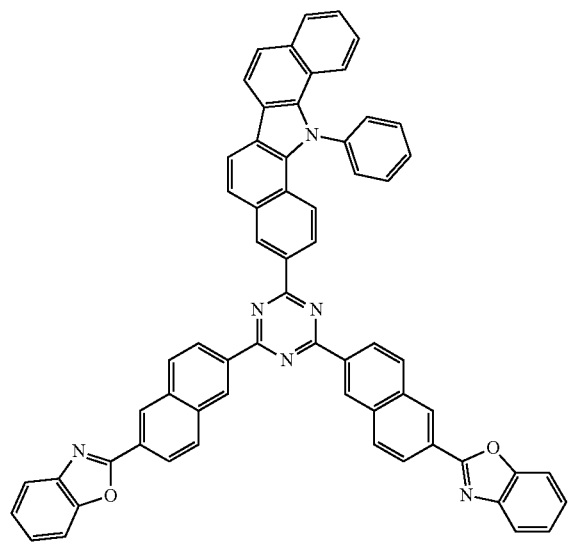
(337)
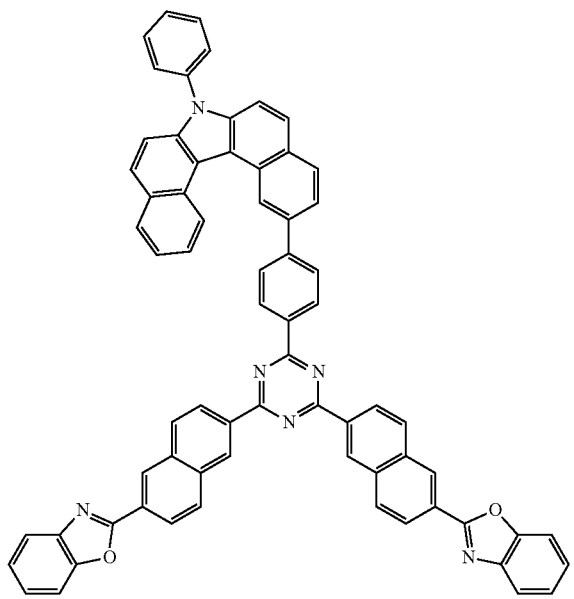

453
(338)
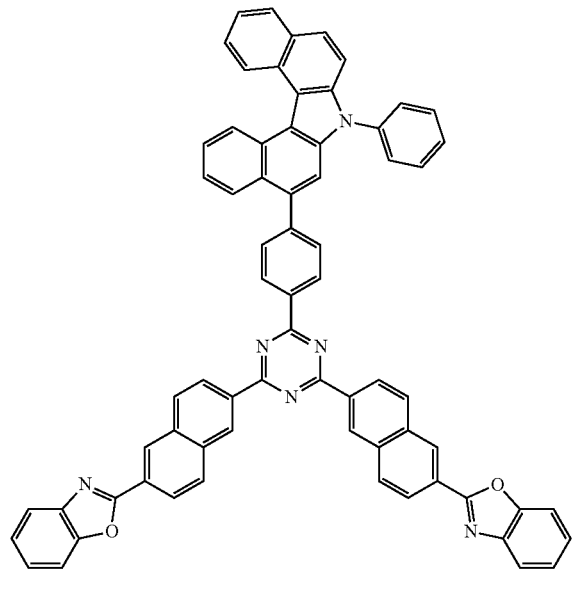
454
(339)
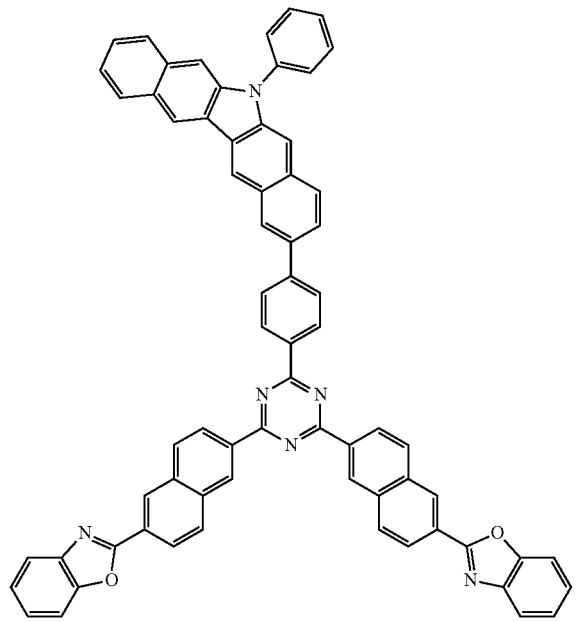
(340)
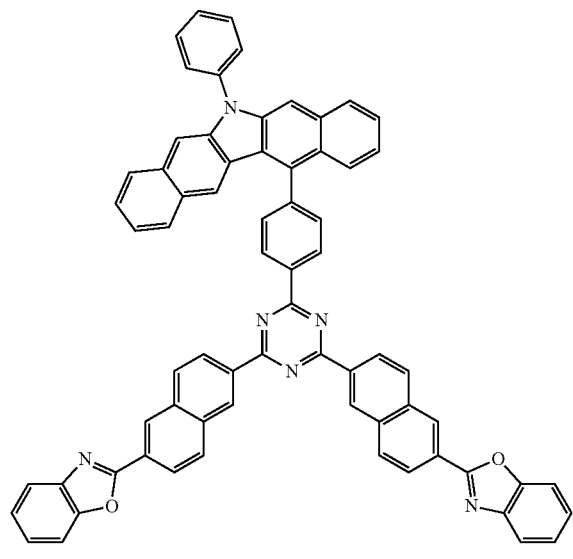
(341)
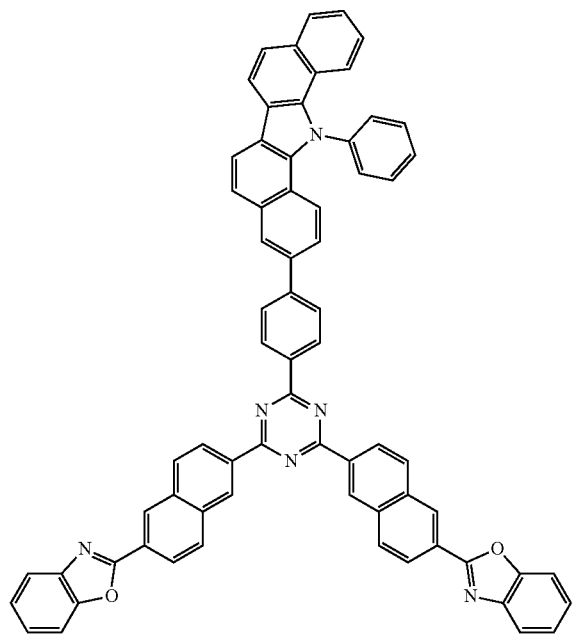

455
-continued
(342)
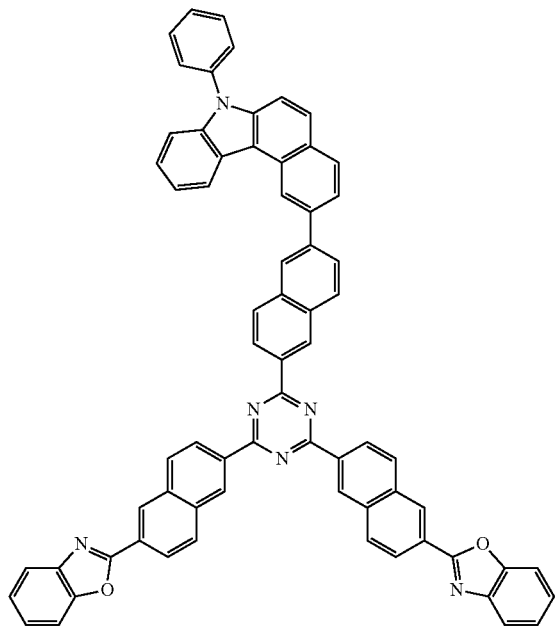
456
(343)
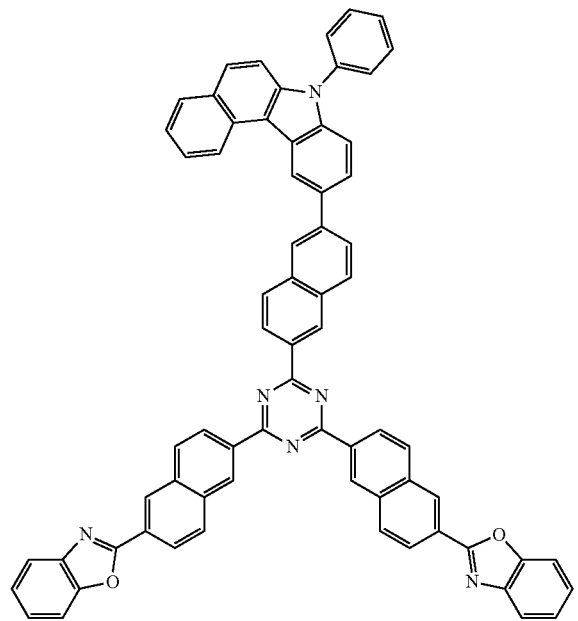
(344)
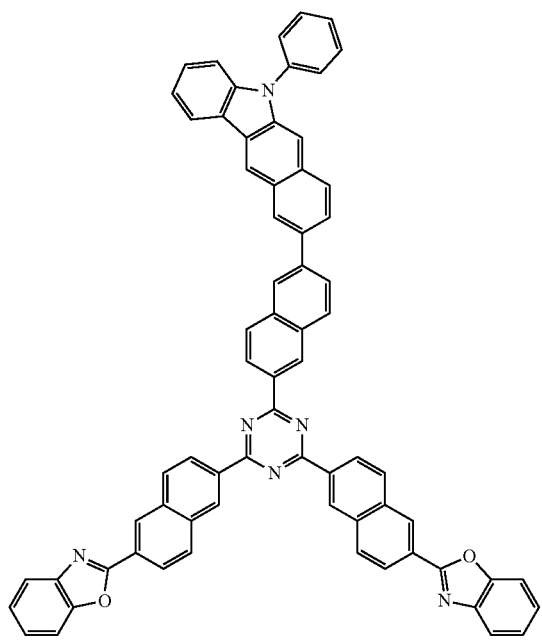
(345)
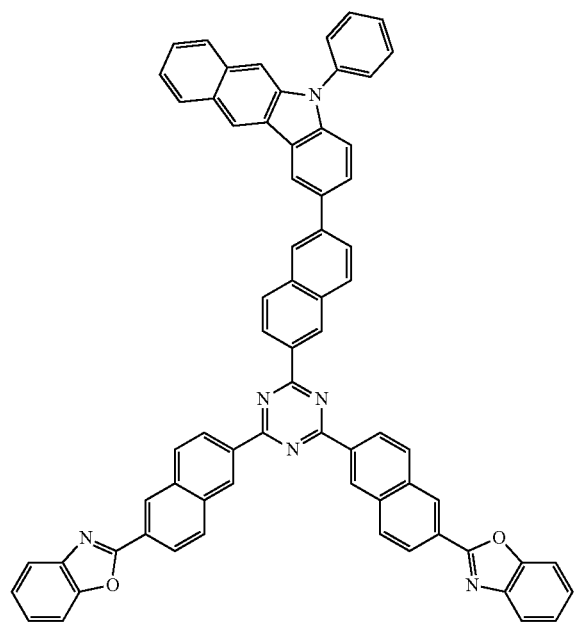

457
458
(346)
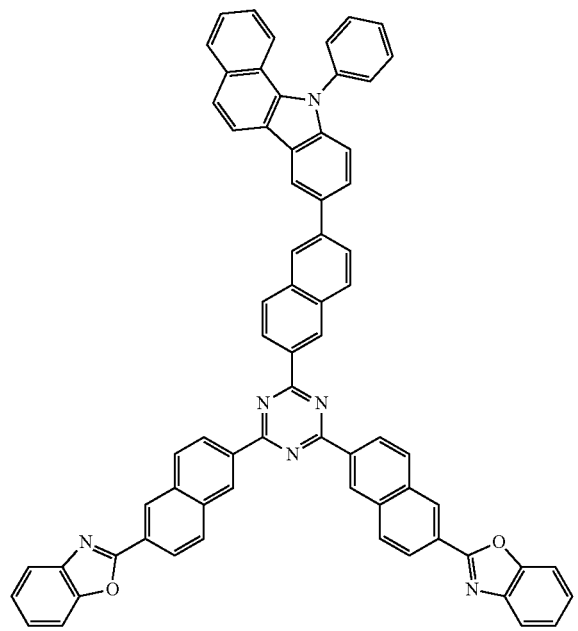
-continued
(347)
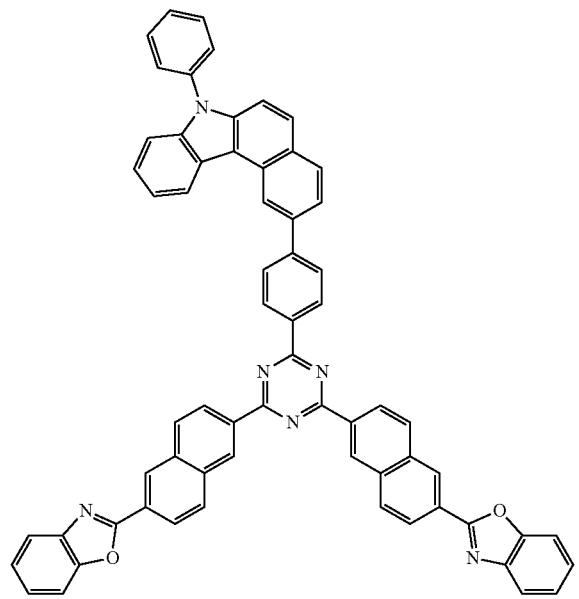
(348)
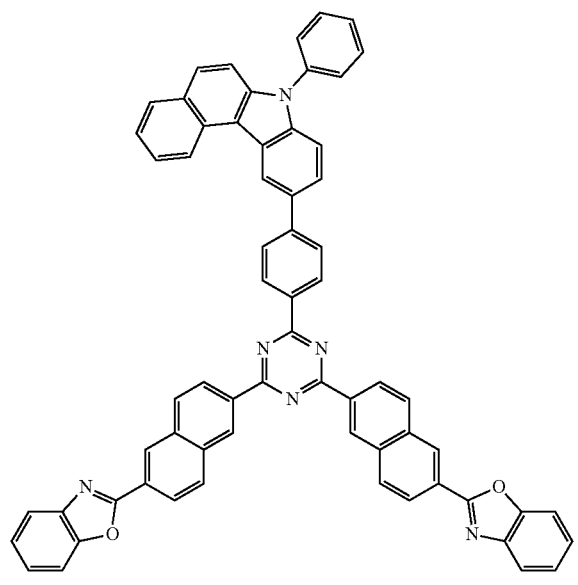
(349)
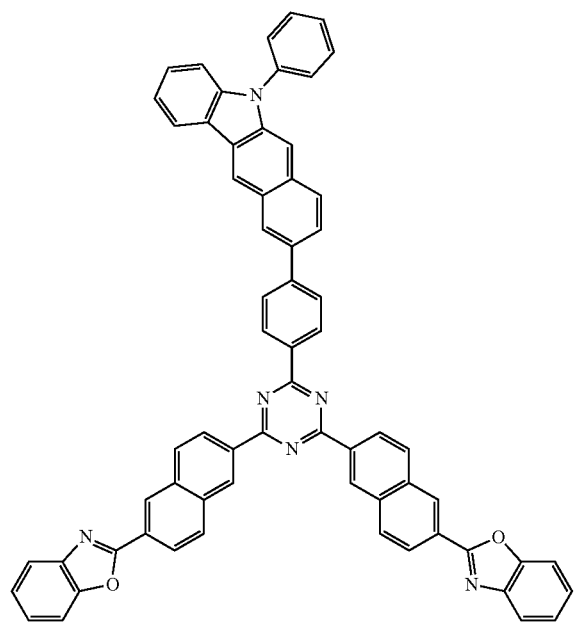

-continued
(350)
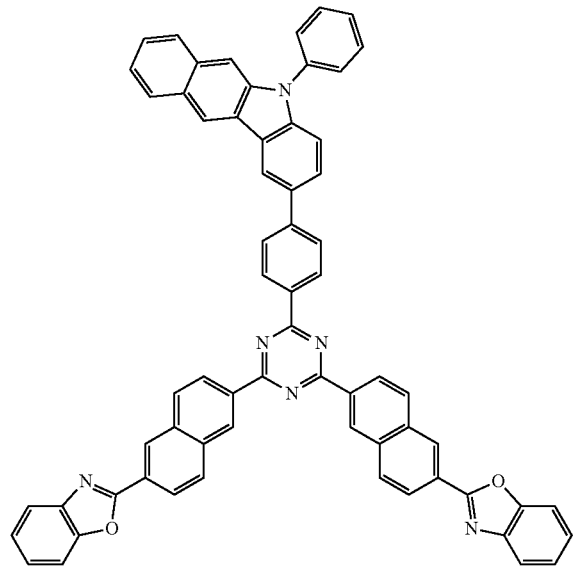
(351)
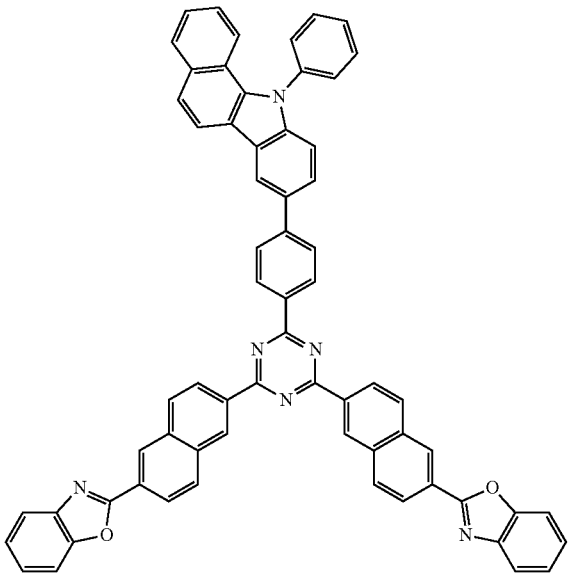
(352)
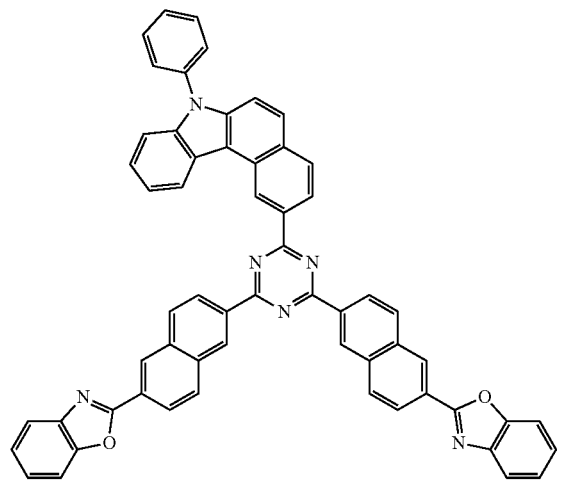
(353)
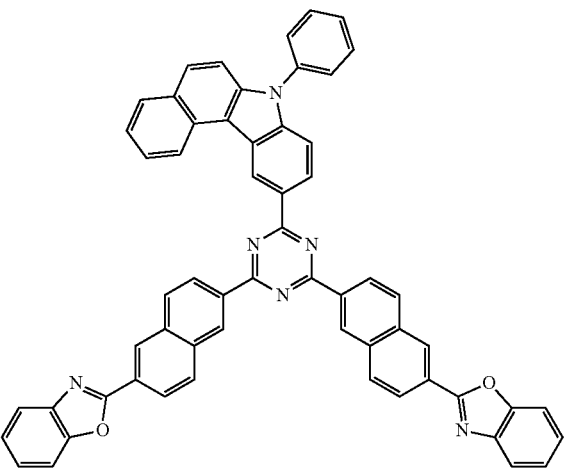
(354)
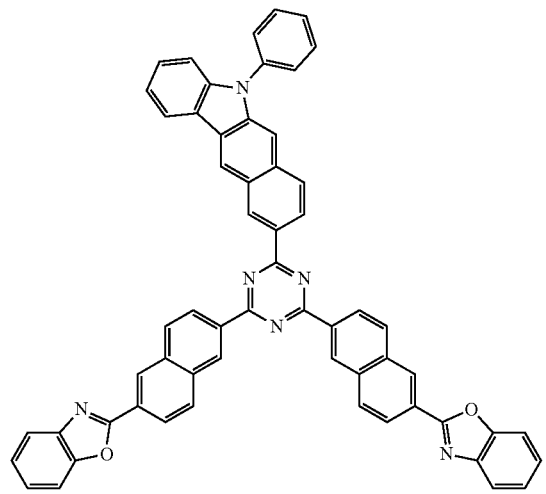
(355)
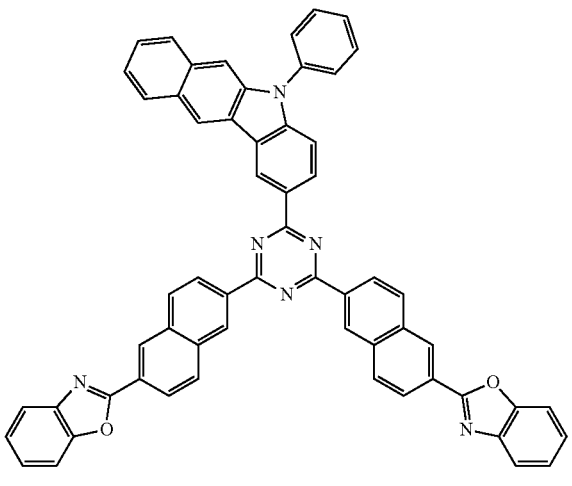

-continued
(356)
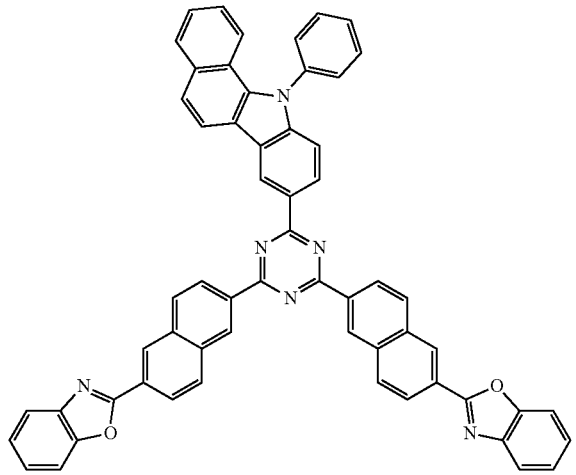
(357)
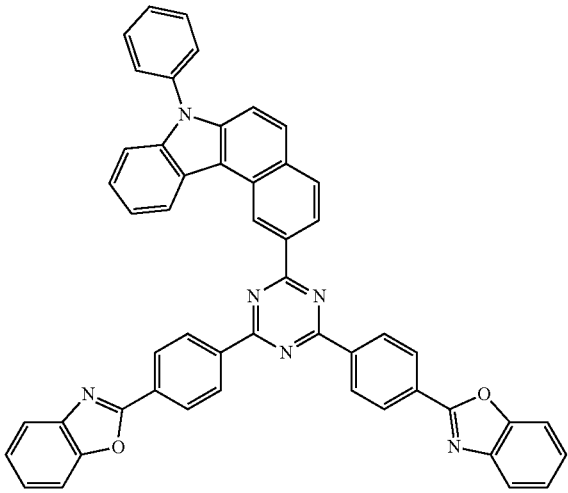
(358)
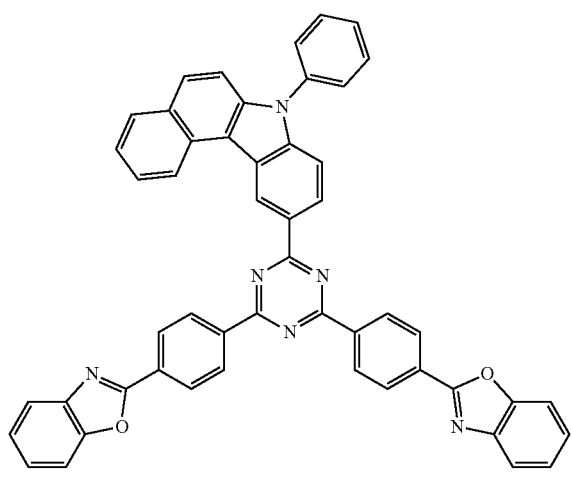
(359)
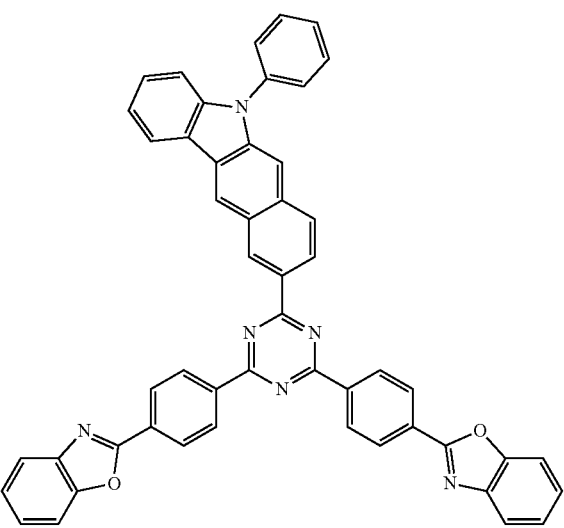
(360)
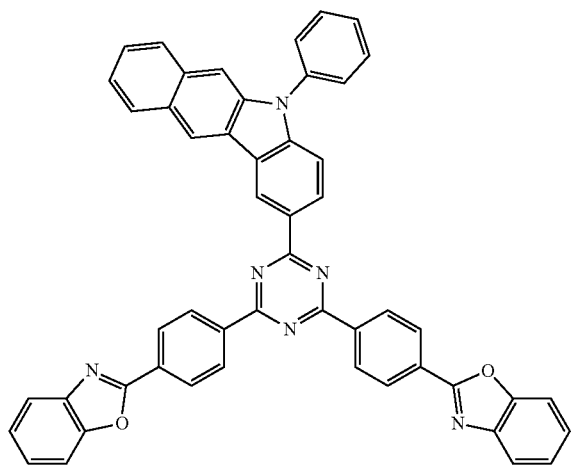
(361)
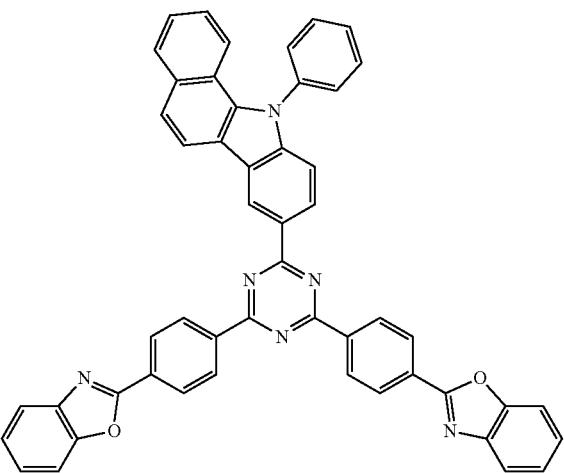

463
464
(362)
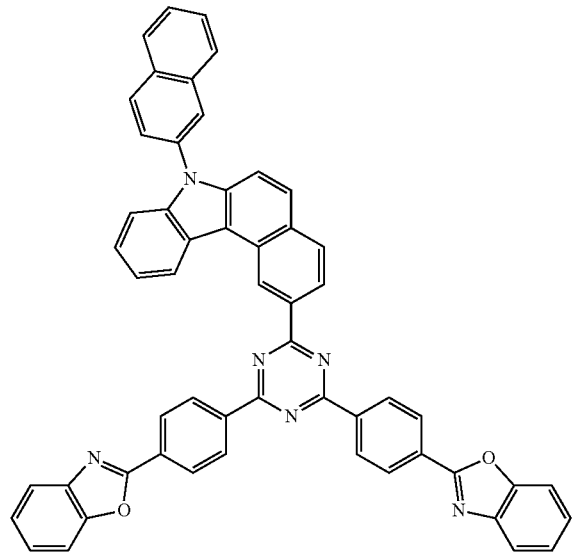
(363)
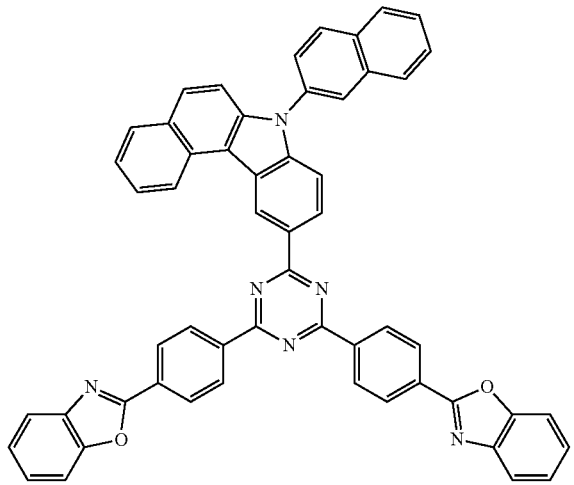
(364)
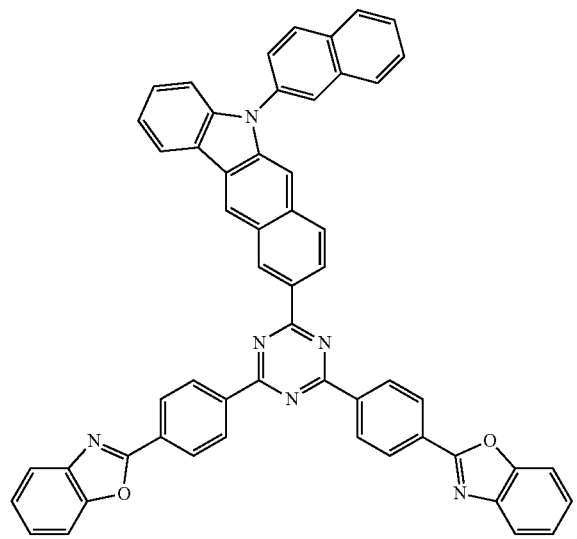
(365)
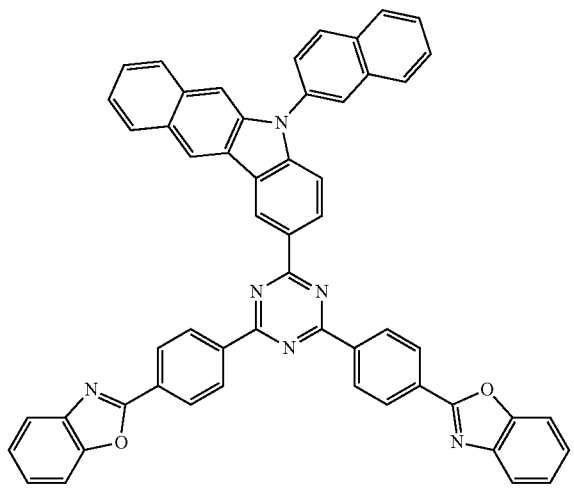

465
466
(366)
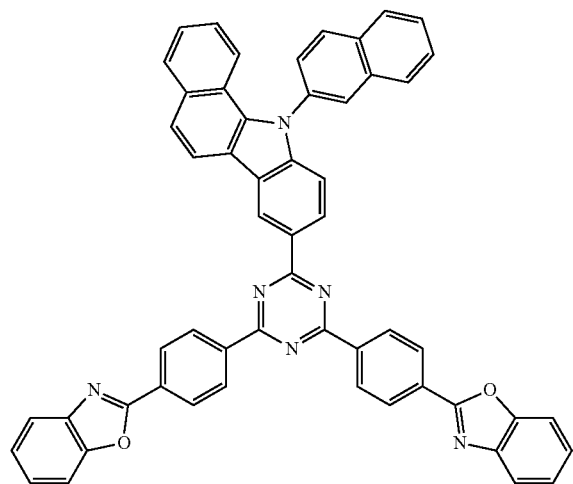
(367)
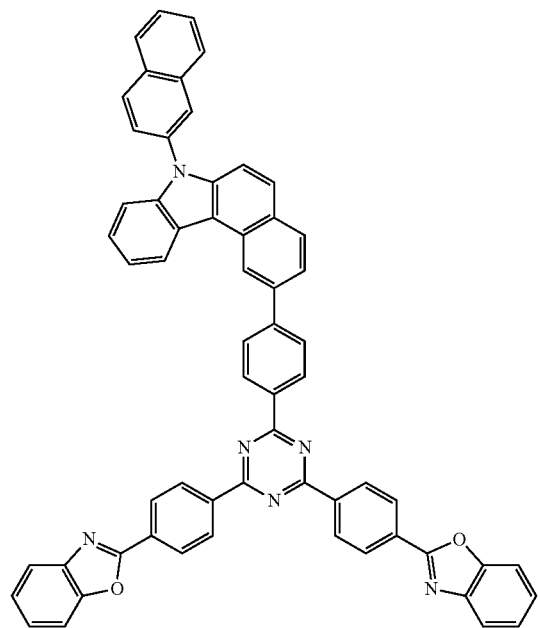
(368)
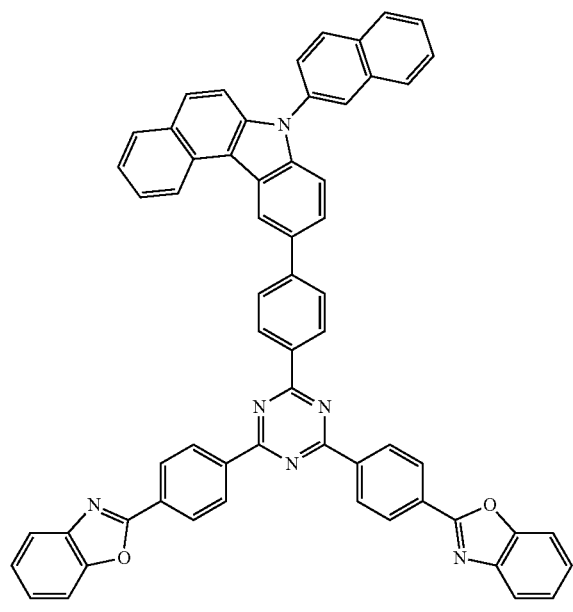
(369)
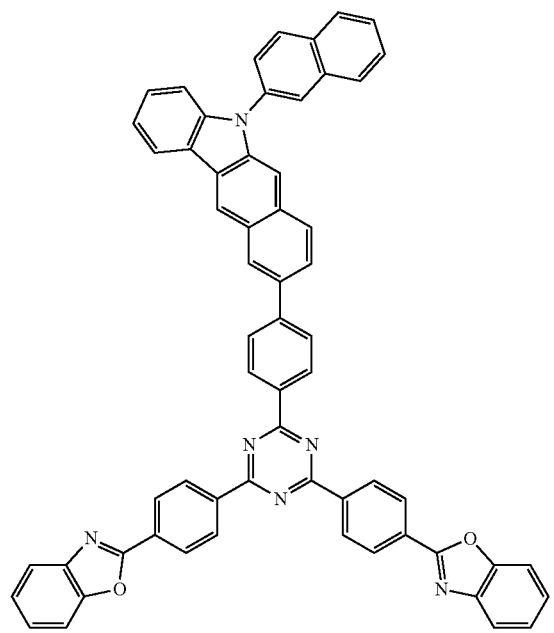

-continued
(370)
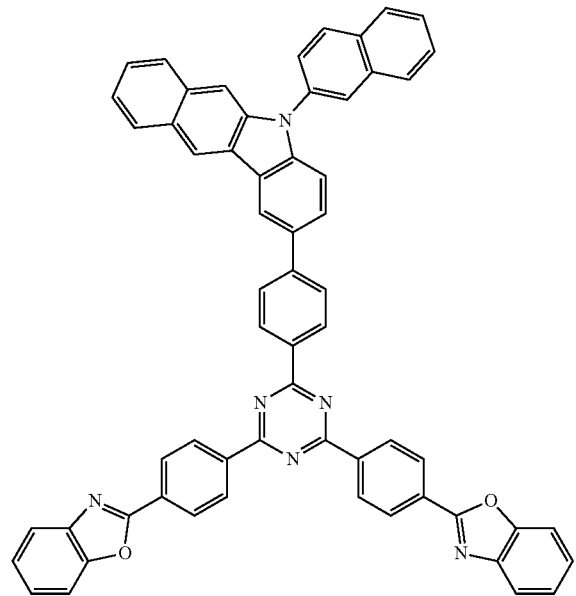
(371)
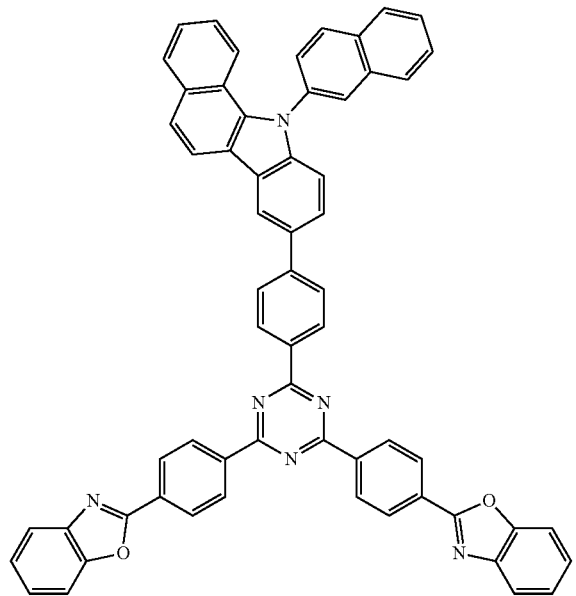
(372)
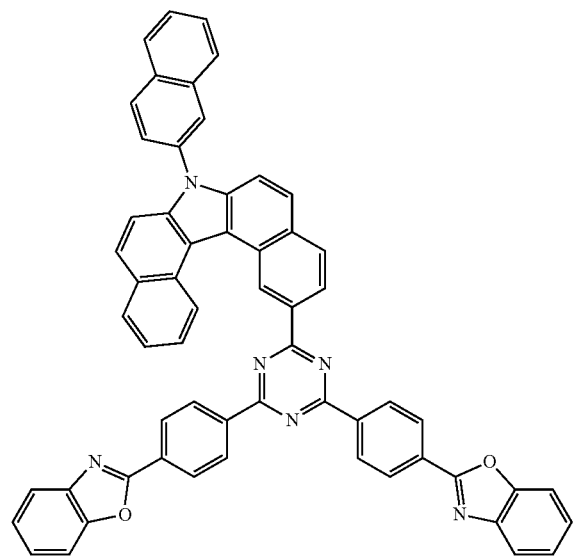
(373)
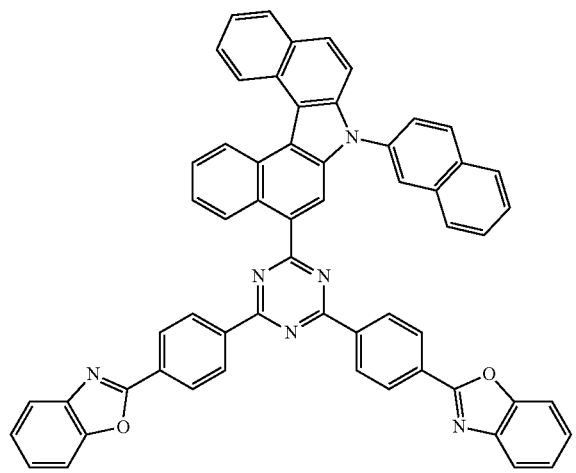

(374)
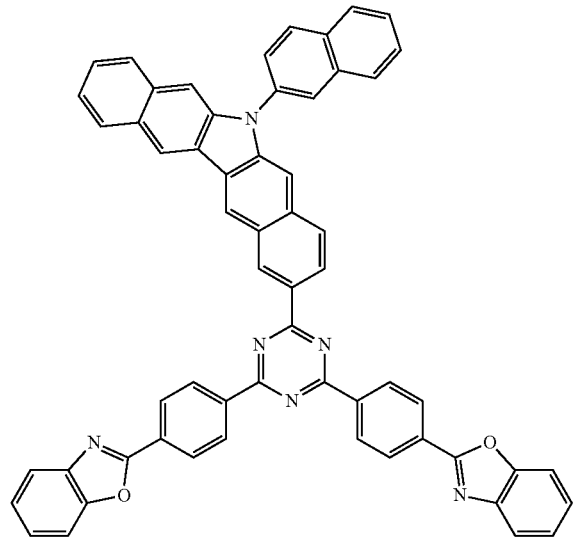
(375)
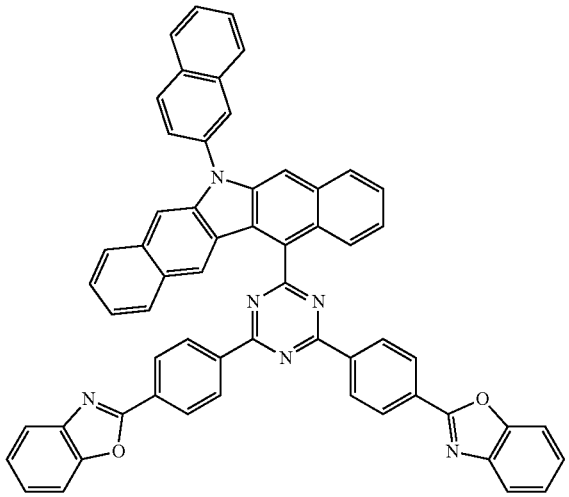
(376)
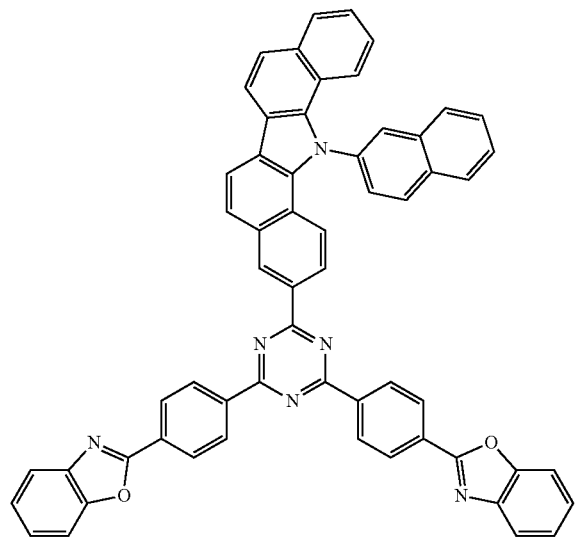
(377)
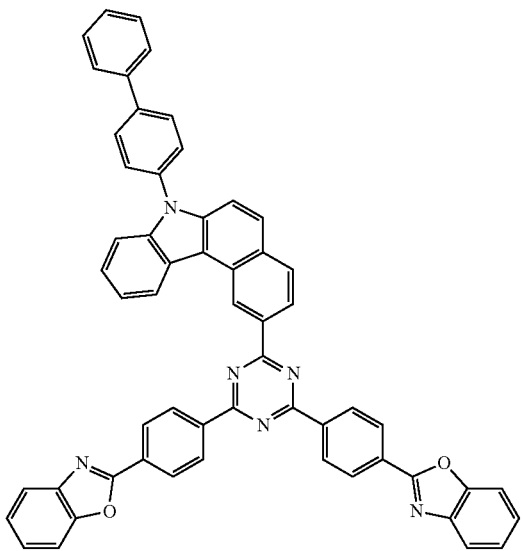

(378)
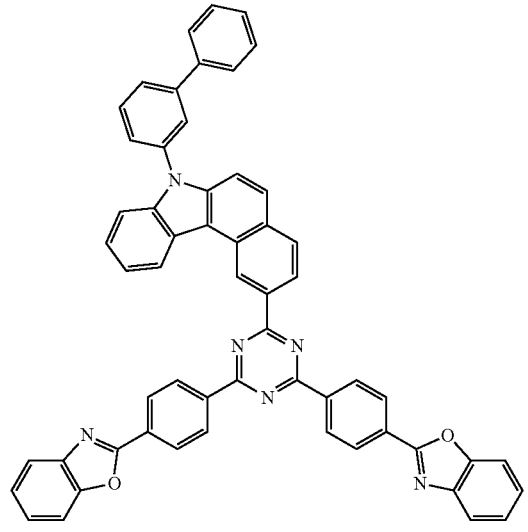
(379)
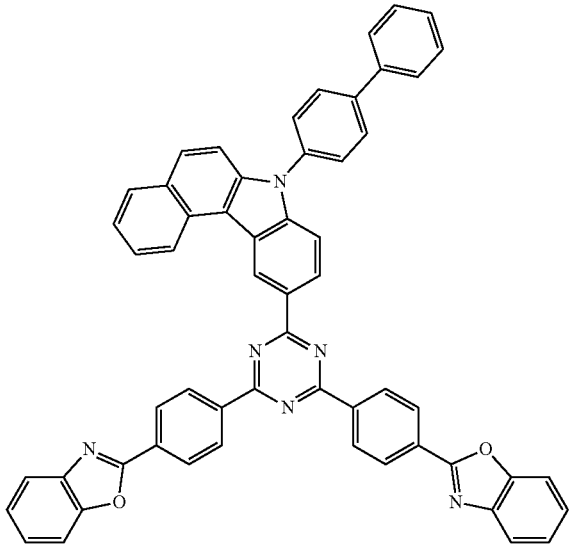
(380)
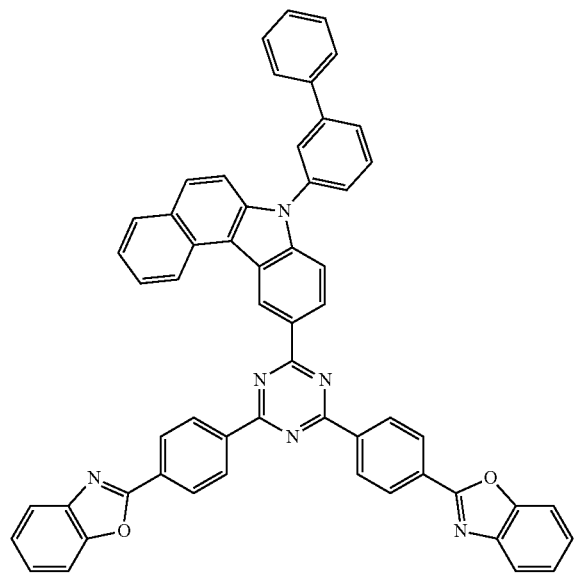
(381)
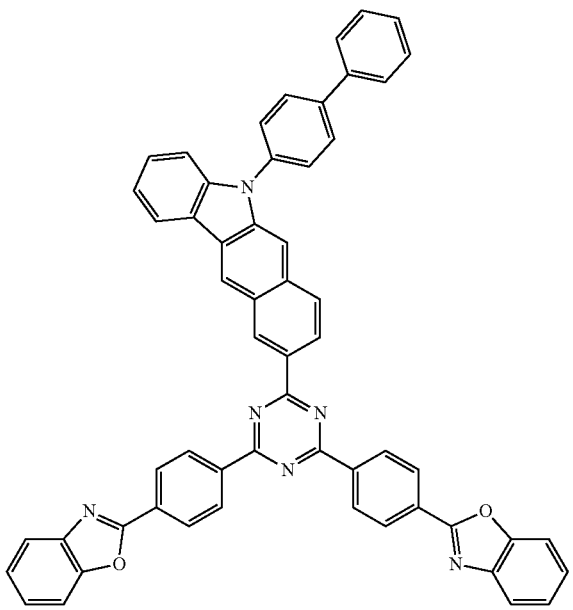

-continued
473
(382)
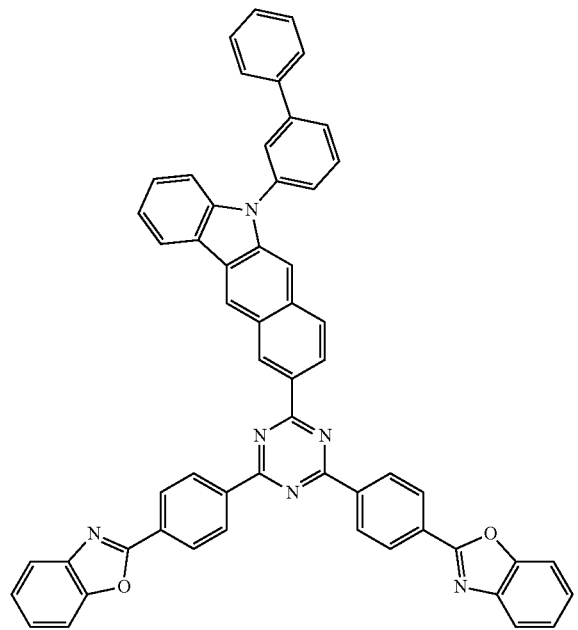
474
(383)
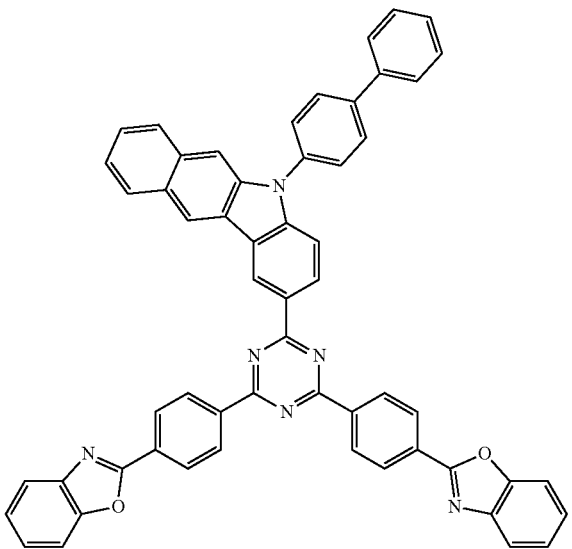
(384)
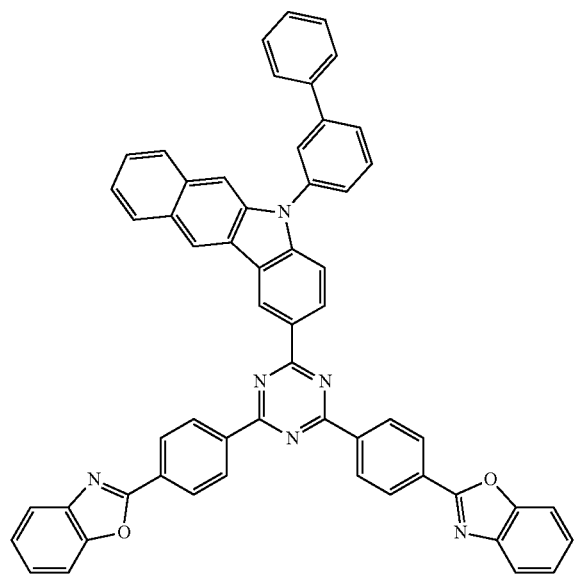
(385)
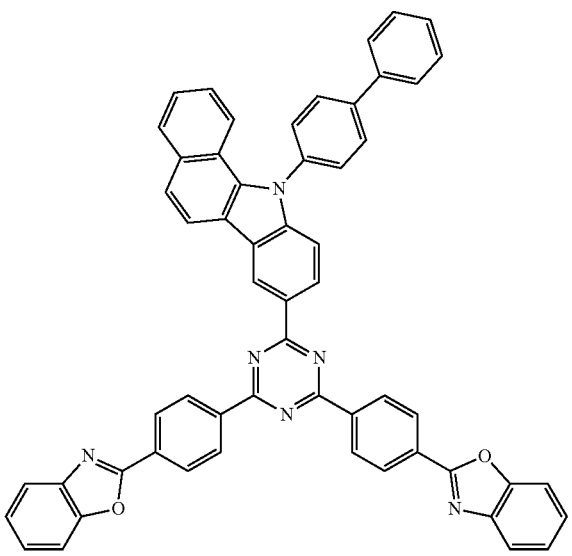

-continued
(386)
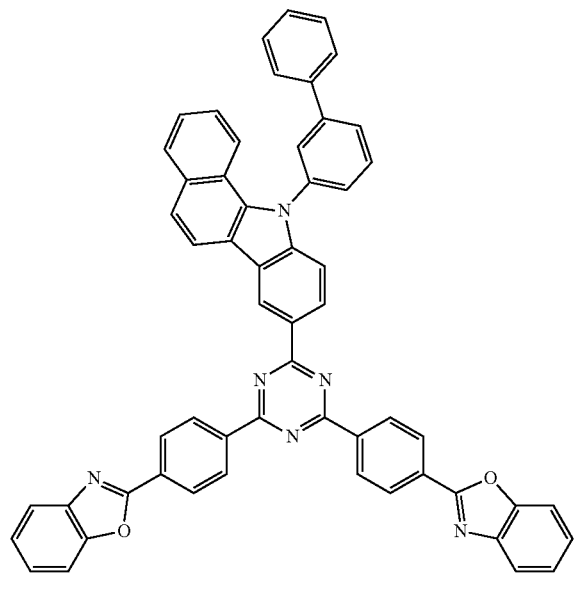
(387)
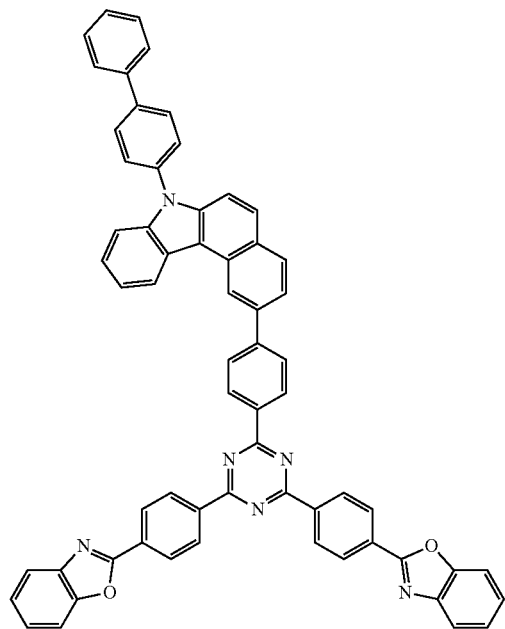
(388)
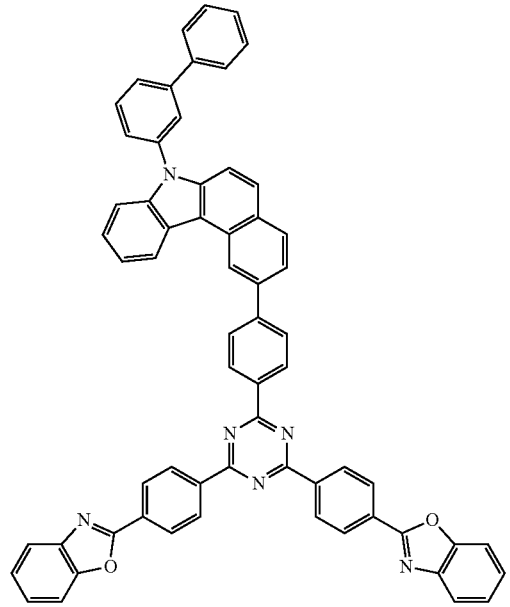
(389)
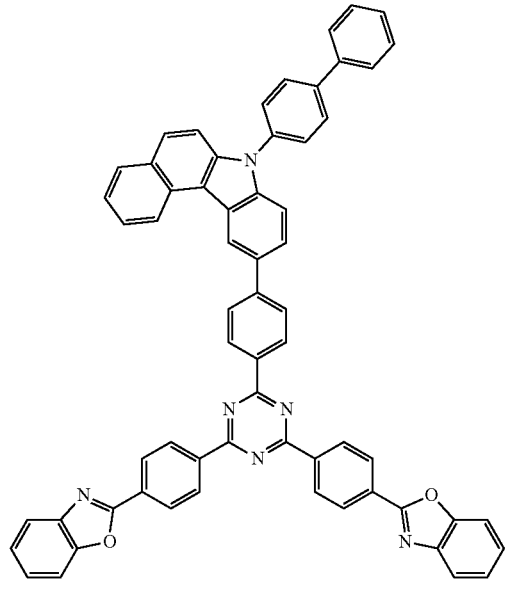

477
478
(390)
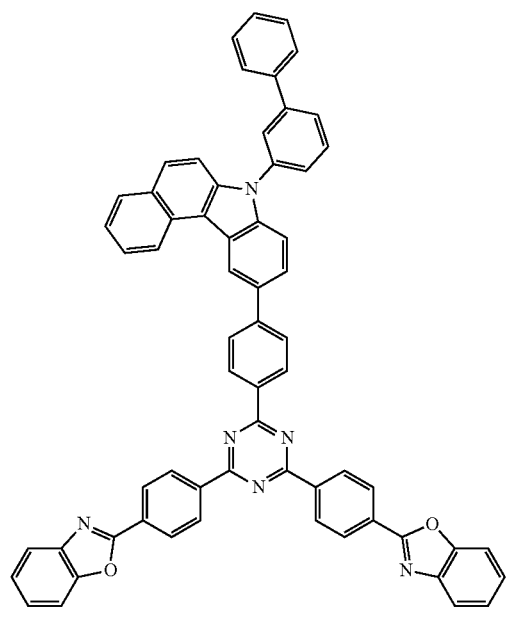
(391)
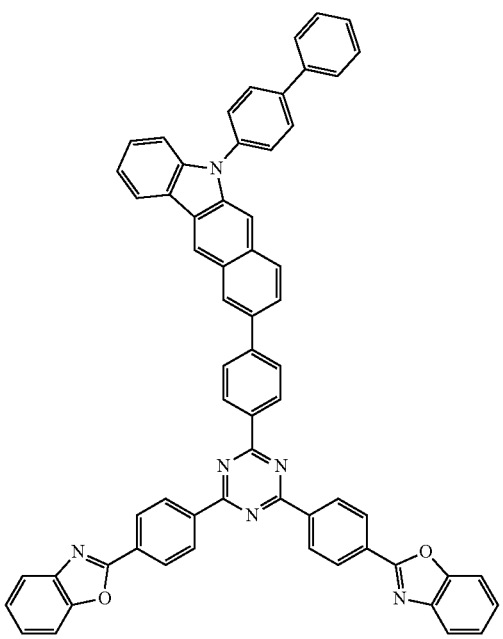
(392)
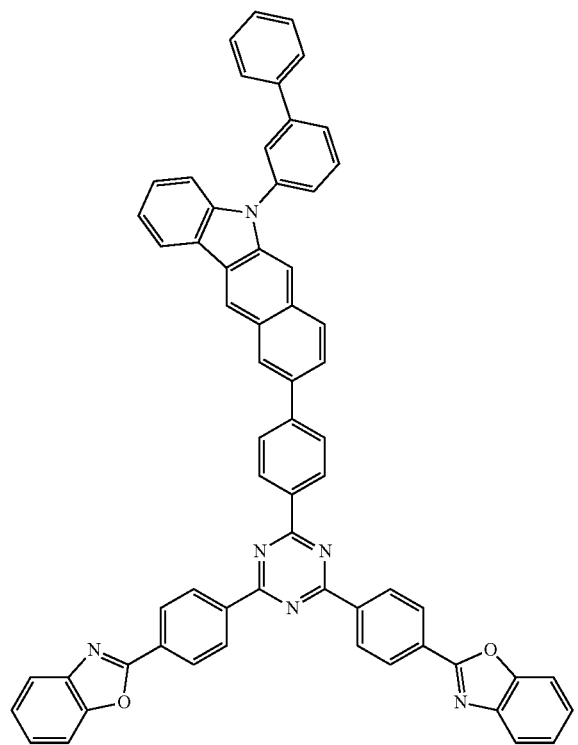
(393)
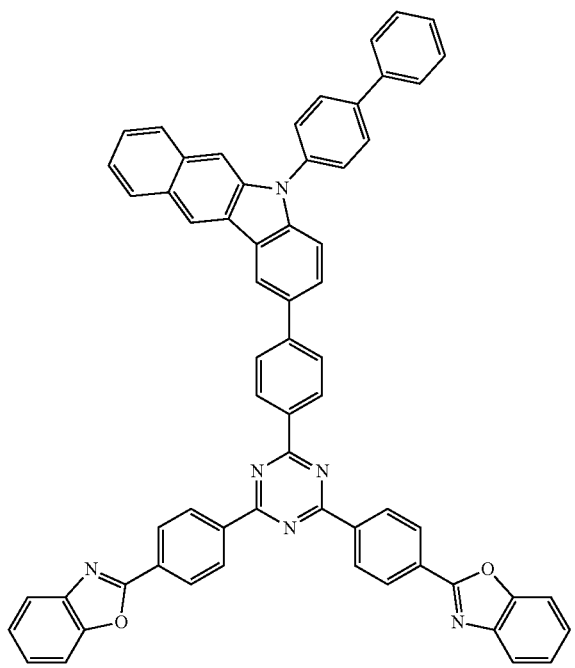

-continued
(394)
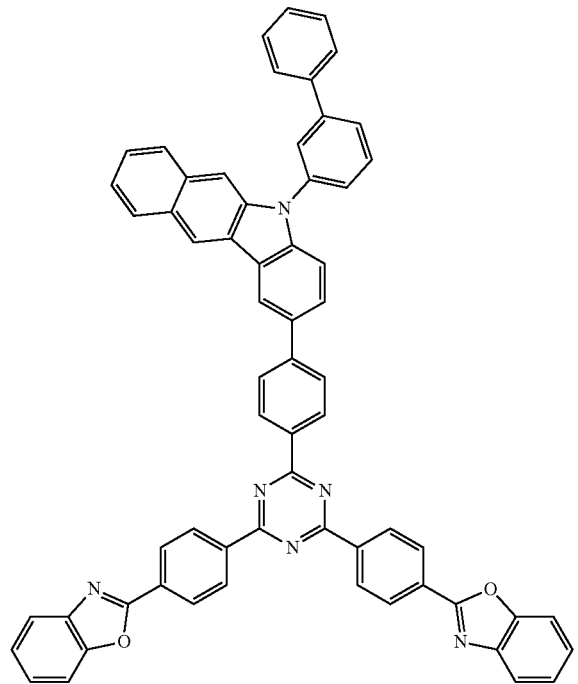
(395)
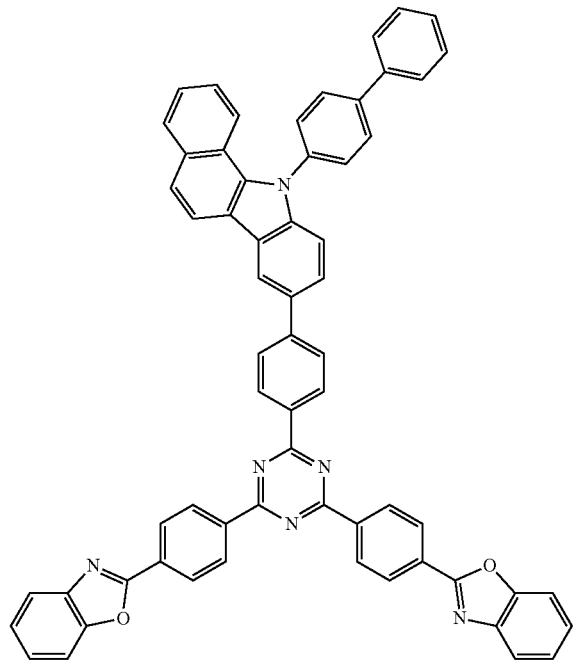
(396)
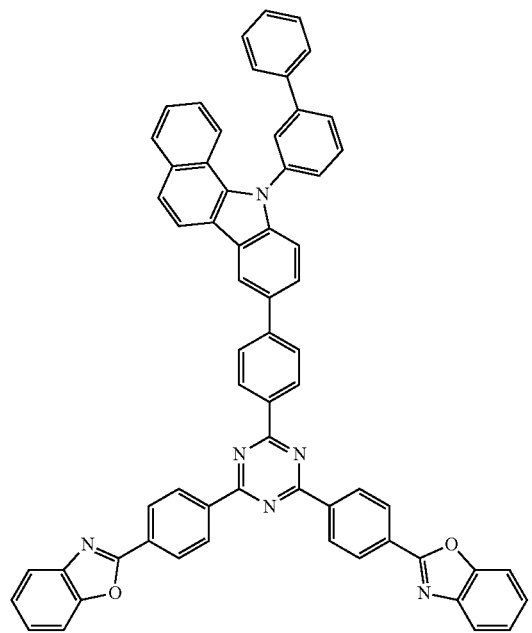
(397)
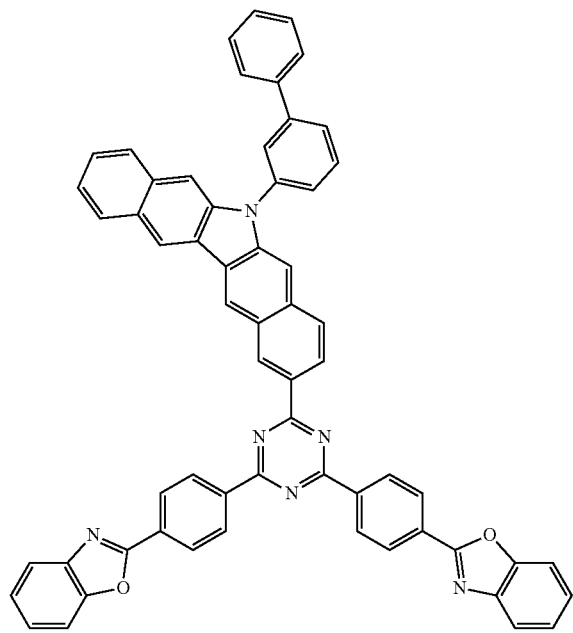

481
482
-continued
(398)
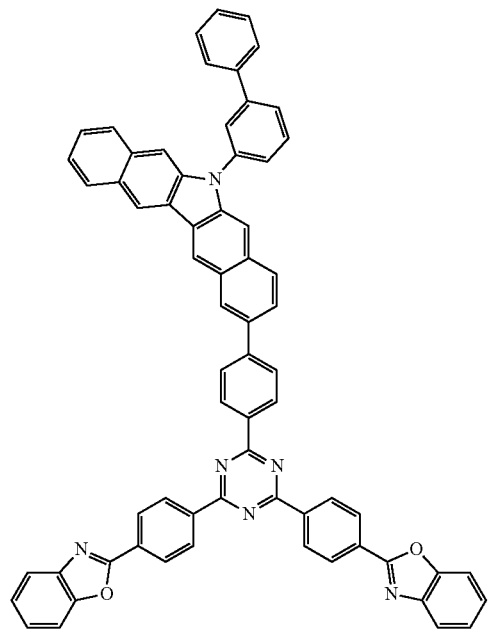
(399)
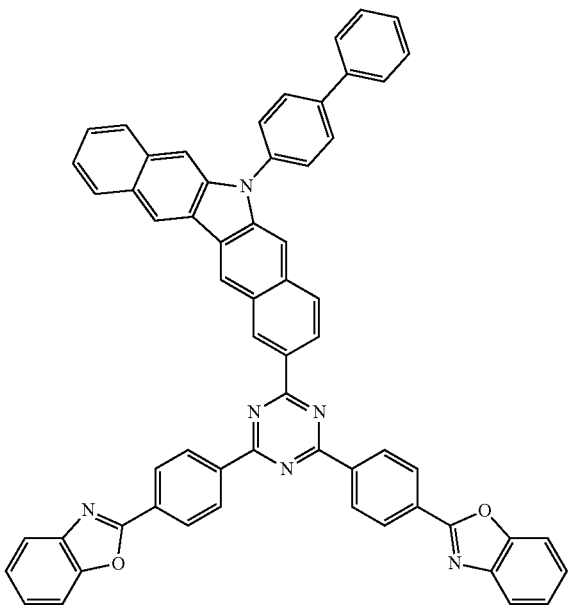
(400)
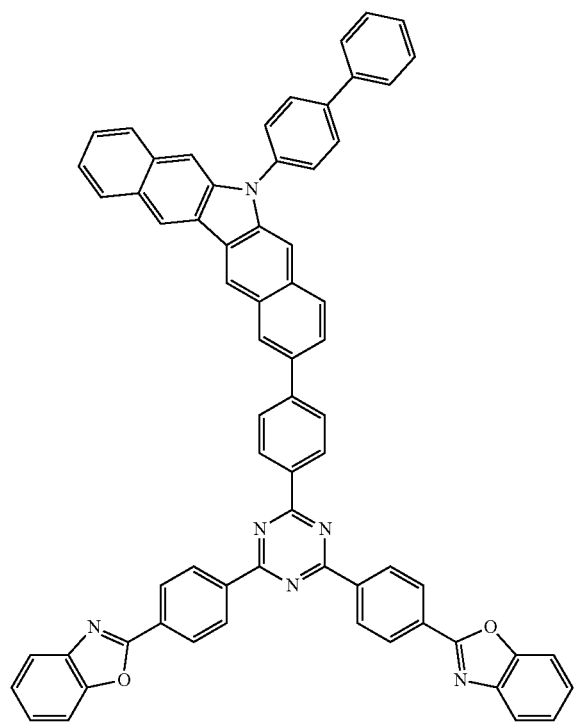
(401)
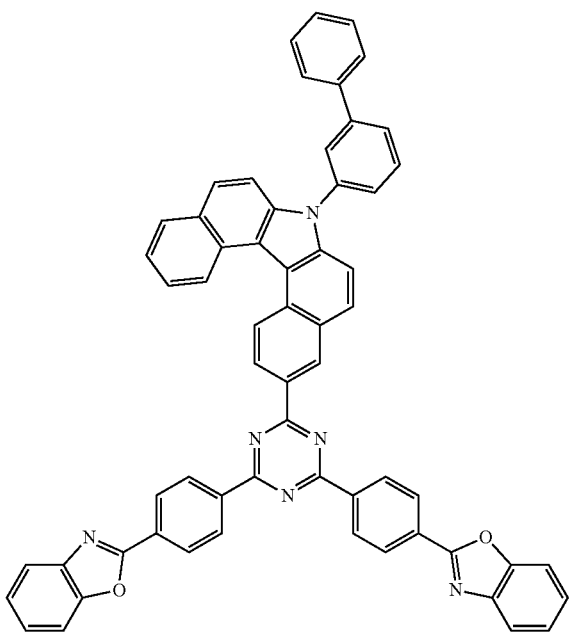

-continued
(402)
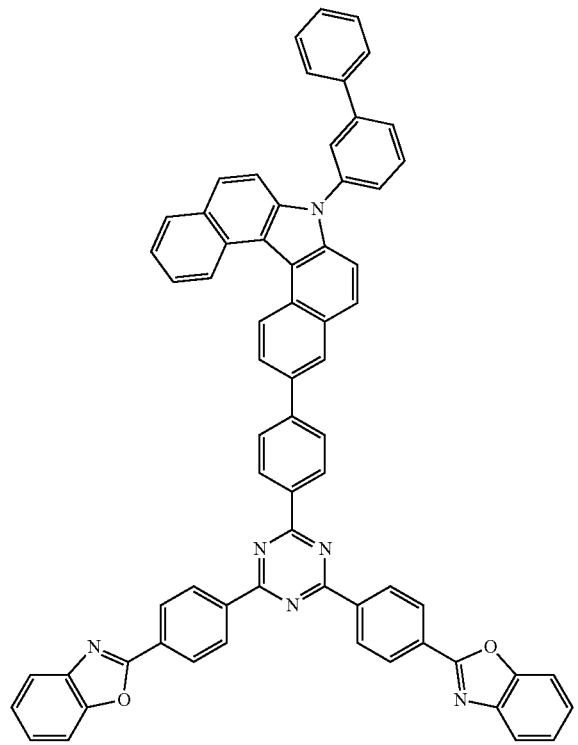
(403)
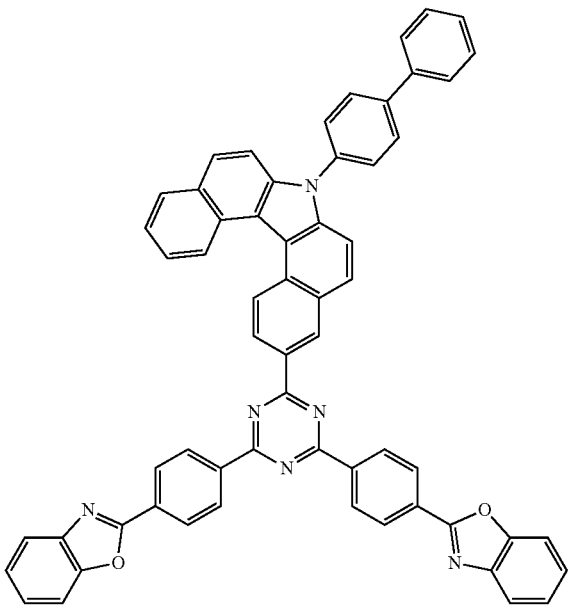
(404)
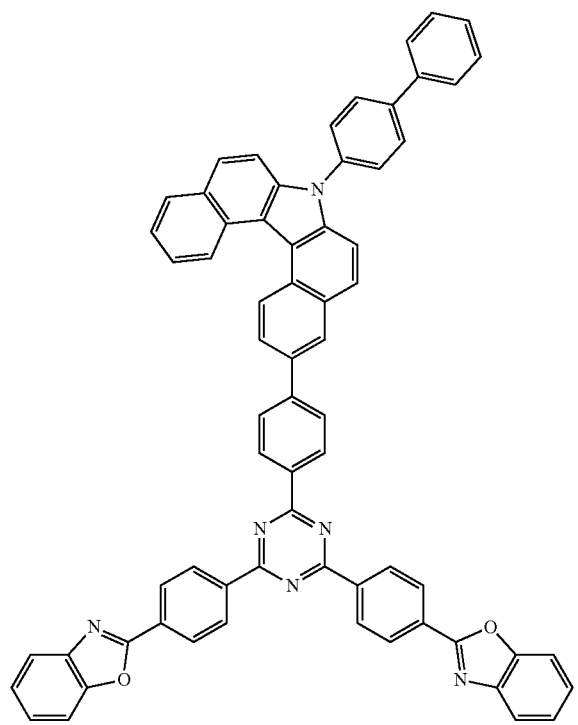
(405)
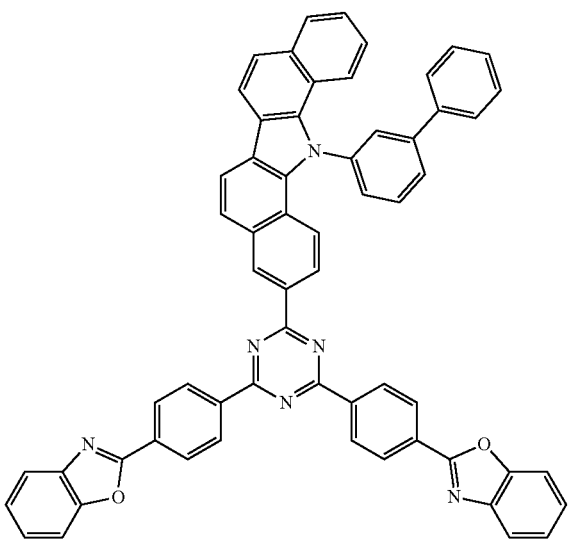

-continued (406)

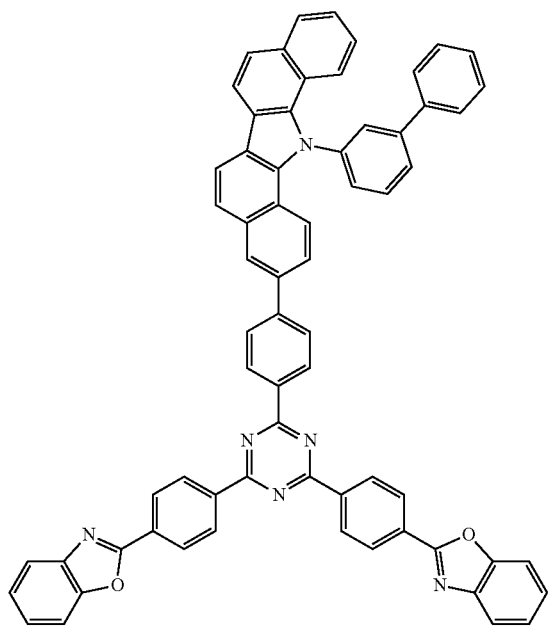

(407)

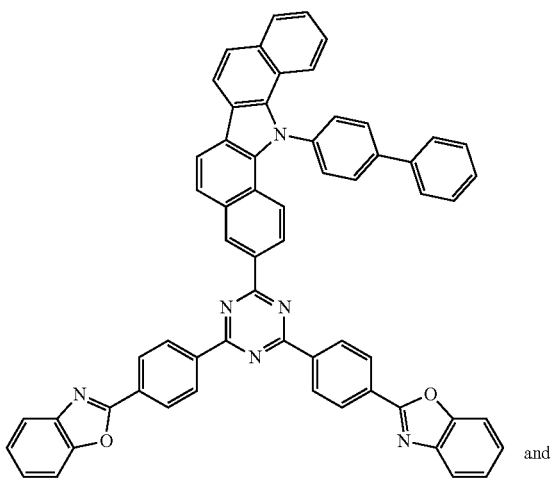

and (408)

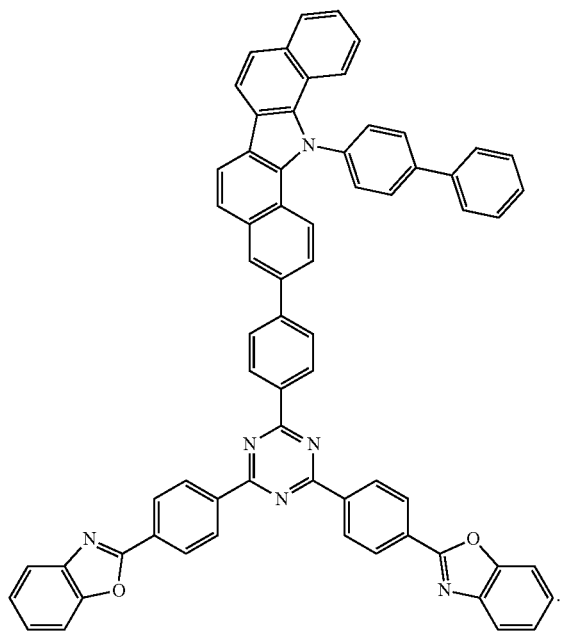

7. The organic electroluminescent device according to claim 1, wherein the organic electroluminescent device comprises at least one functional layer comprising the organic compound based on triazine and benzoxazole.

8. The organic electroluminescent device according to claim 7, wherein the organic electroluminescent device comprises a hole block layer or an electron transport layer comprising the organic compound based on triazine and benzoxazole.

9. The organic electroluminescent device according to claim 7, wherein a particular structural formula of the organic compound is any one of:

487                                              488
(1)
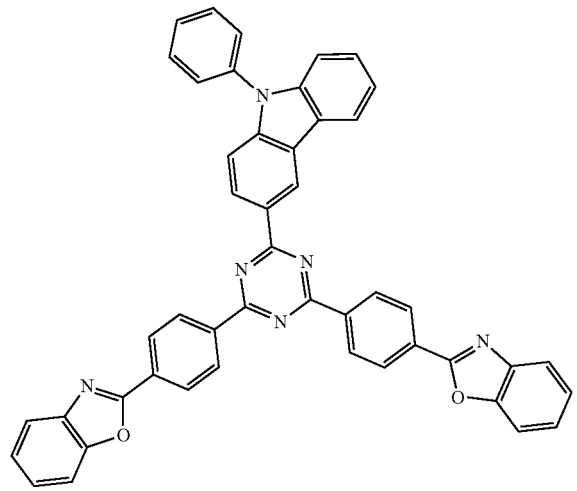
(2)
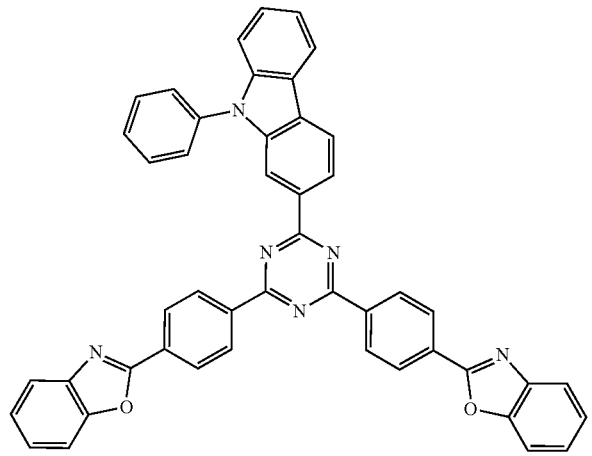
(3)
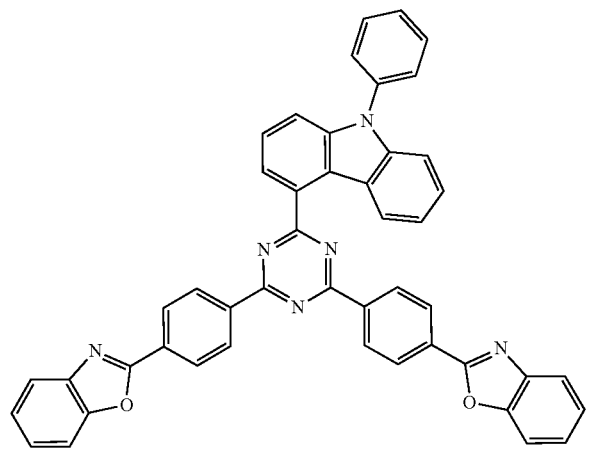
(4)
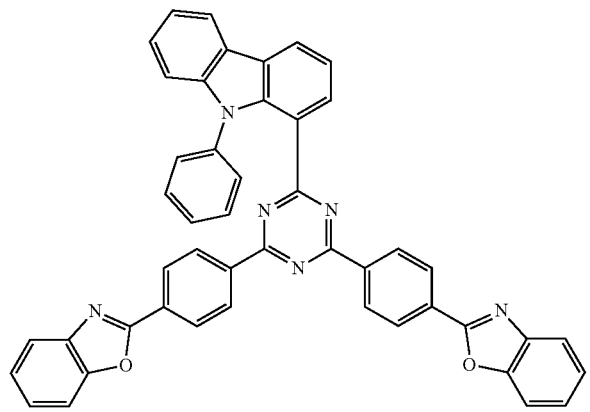
(5)
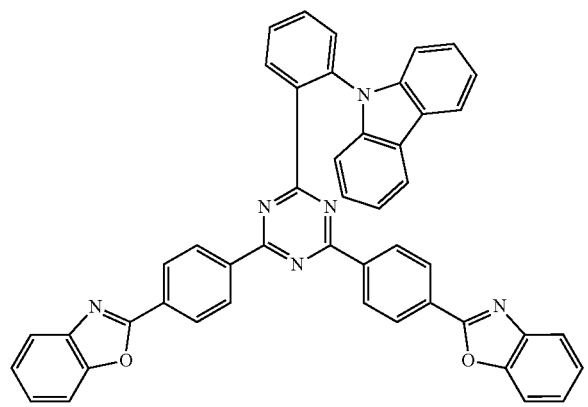
(6)
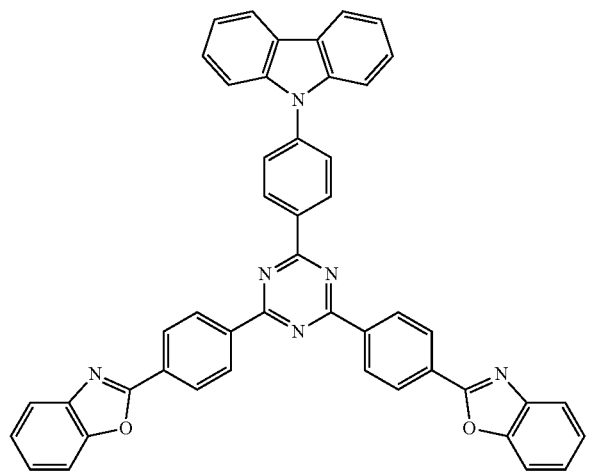

-continued
(7)
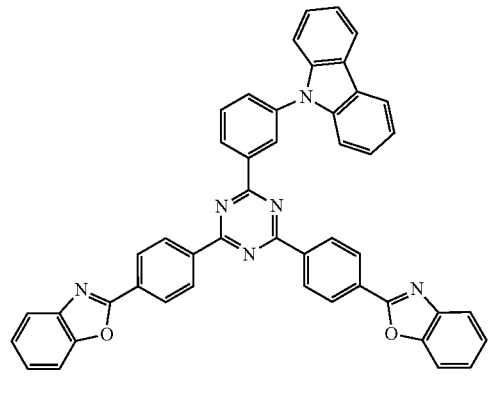
(8)
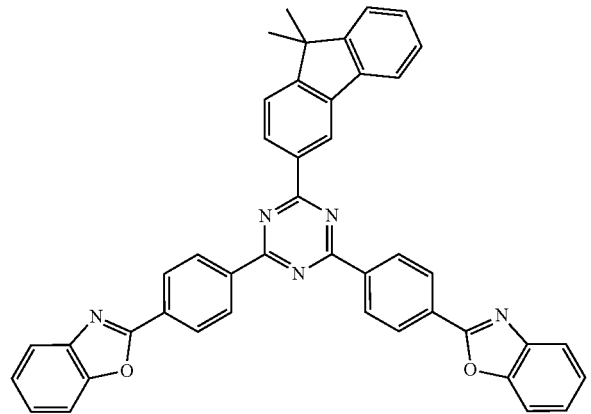
(9)
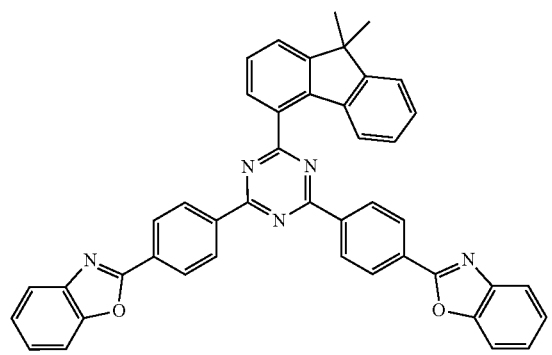
(10)
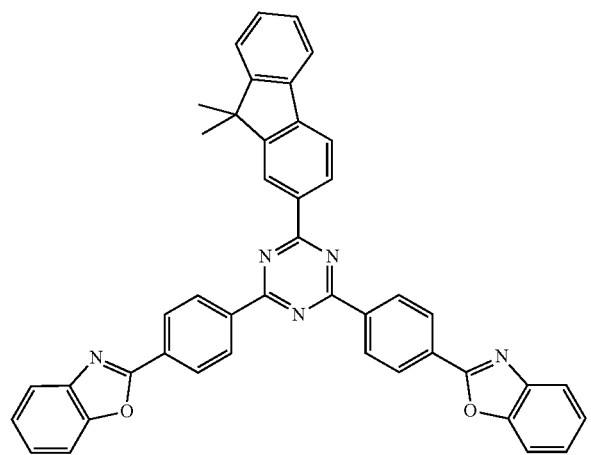
(11)
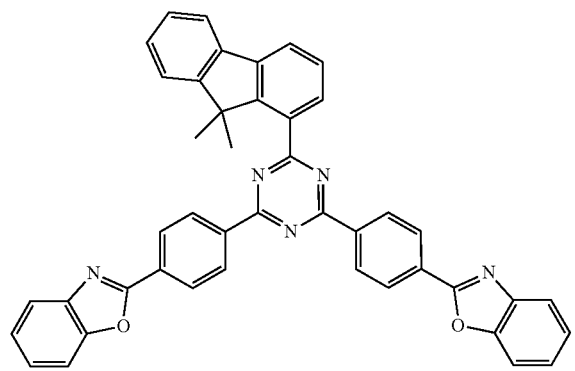
(12)
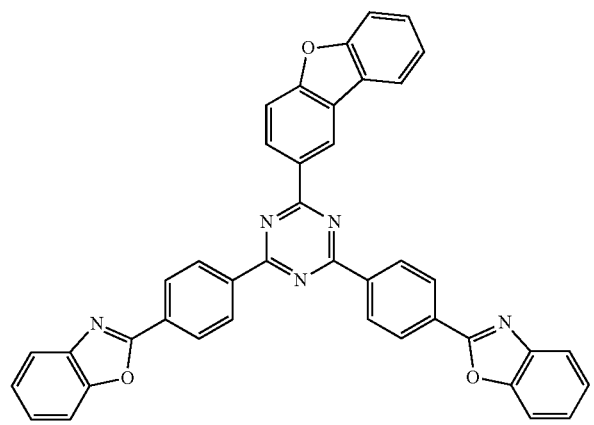

-continued
(13)
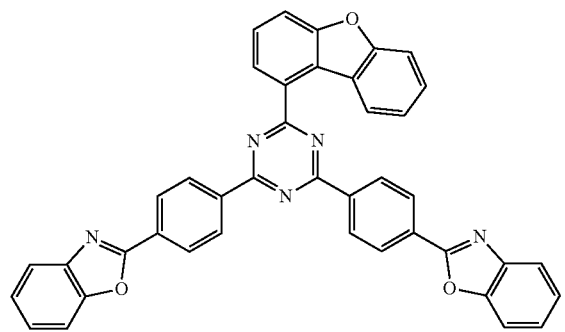
(14)
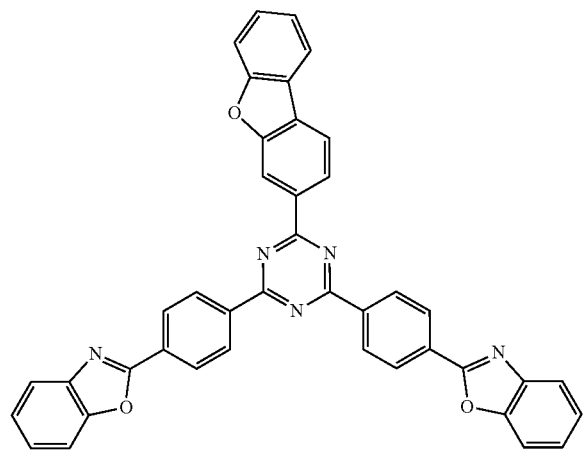
(15)
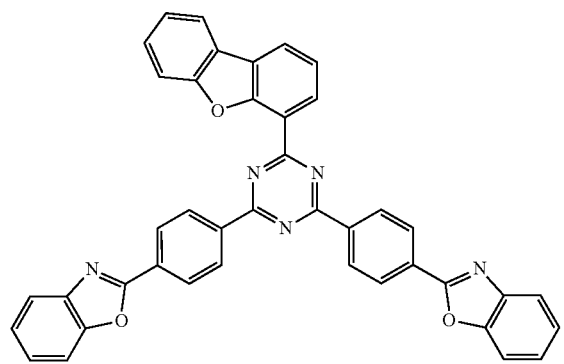
(16)
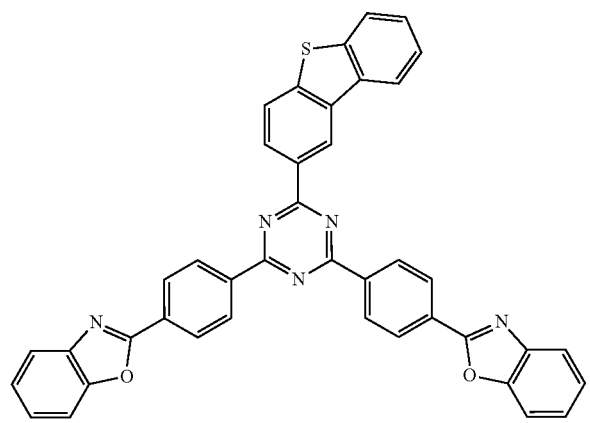
(17)
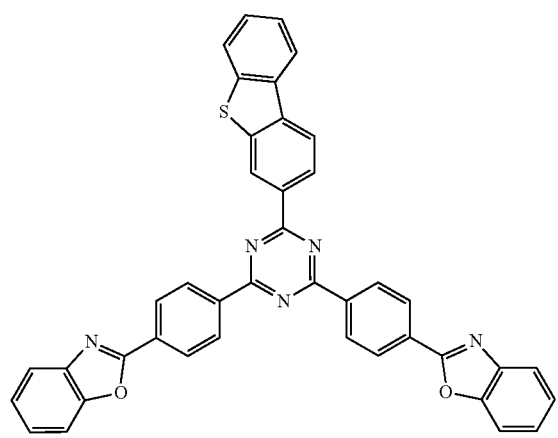
(18)
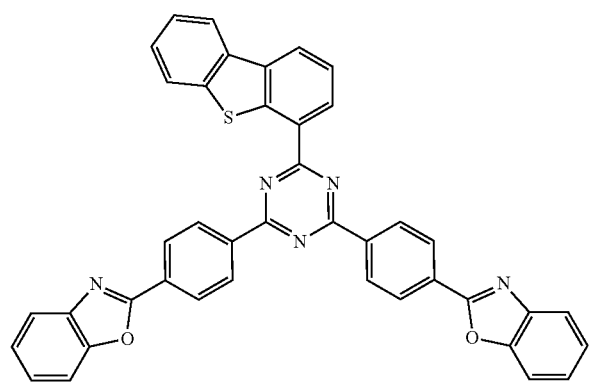

493    494
-continued
(19)
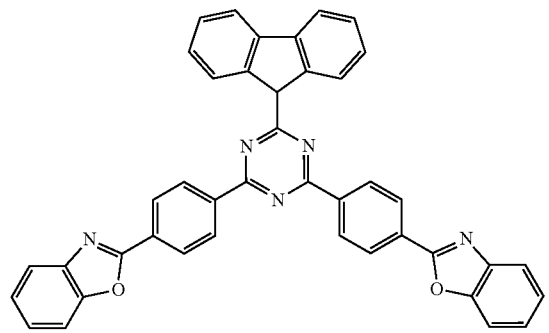
(20)
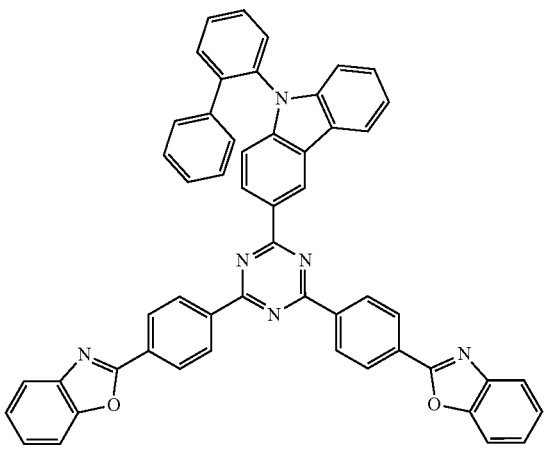
(21)
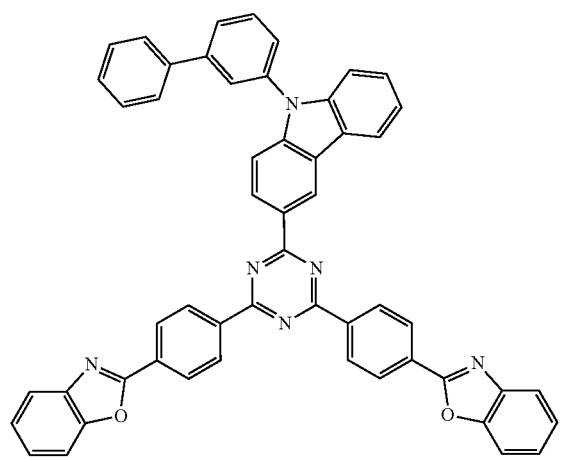
(22)
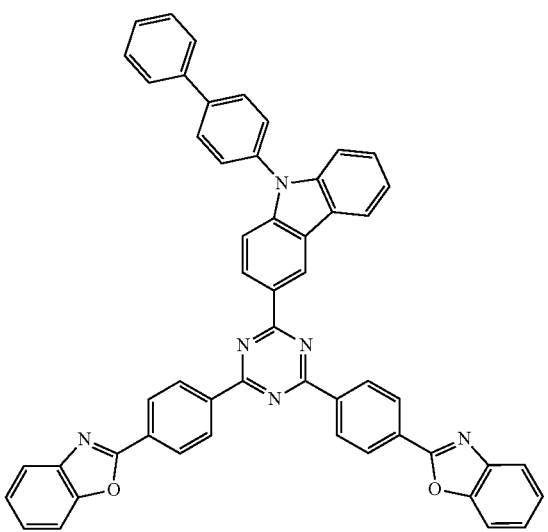
(28)
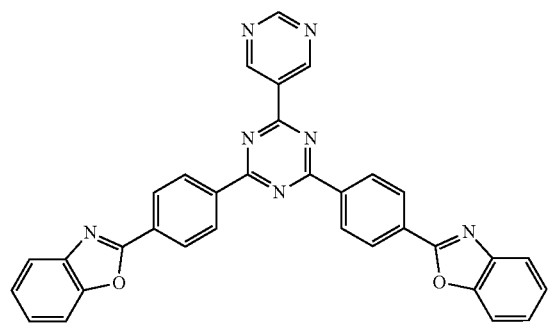
(29)
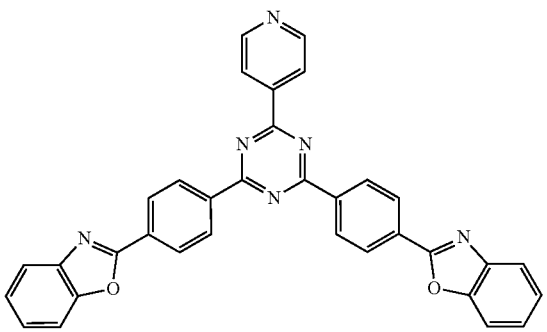
(30)
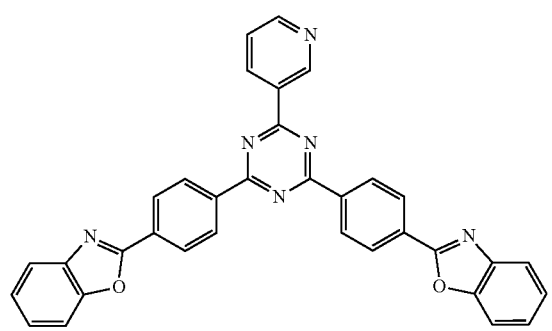
(31)
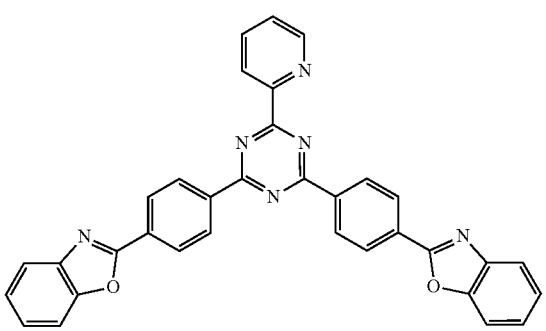

-continued
(35)
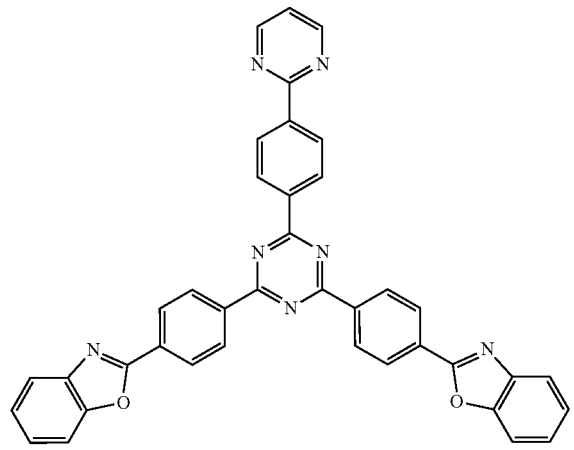
(36)
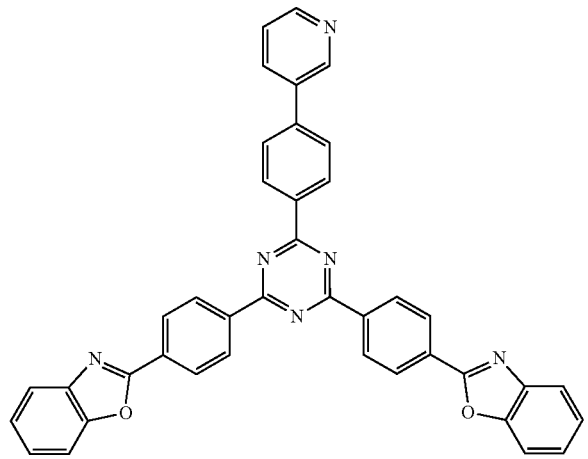
(37)
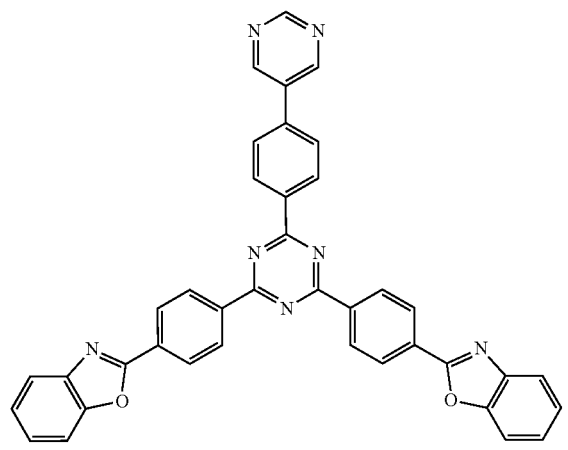
(38)
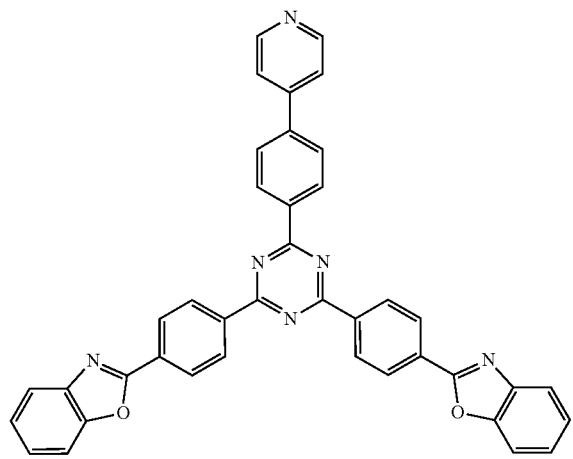
(39)
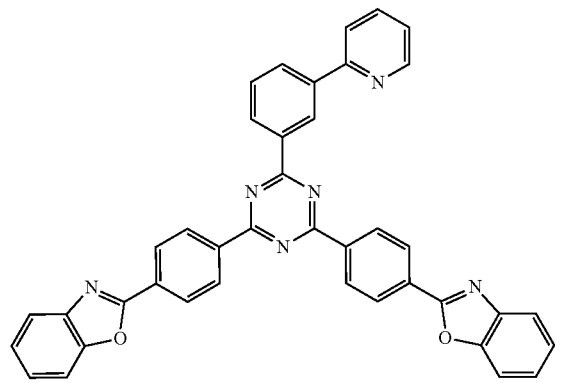
(40)
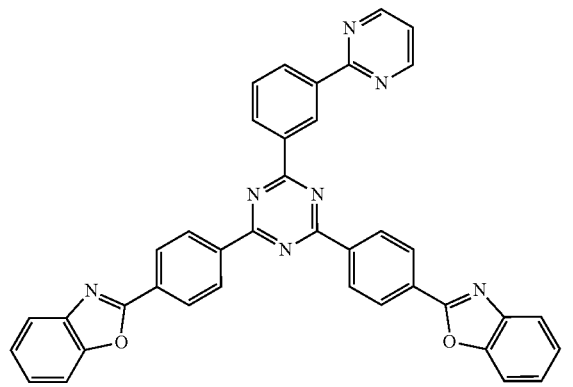

-continued
(41)
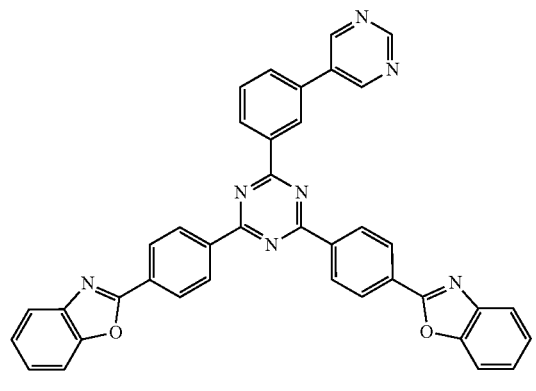
(42)
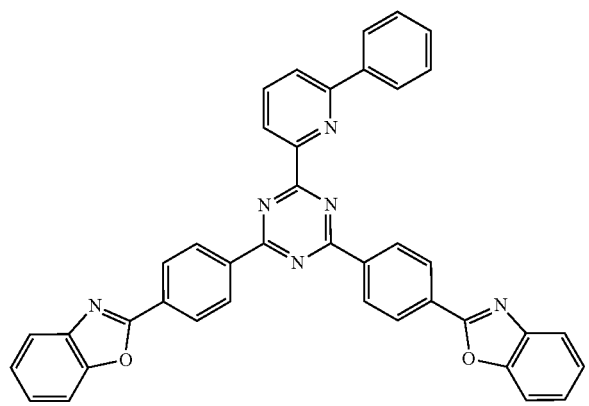
(43)
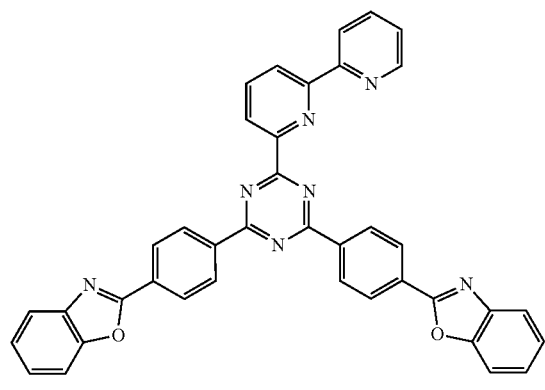
(44)
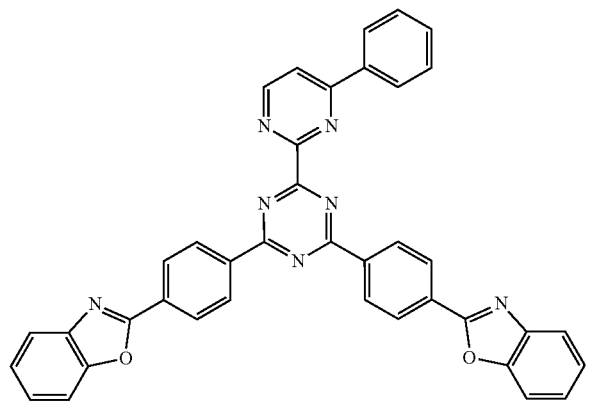
(45)
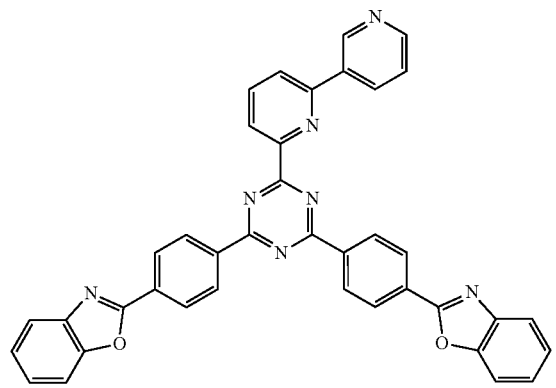
(46)
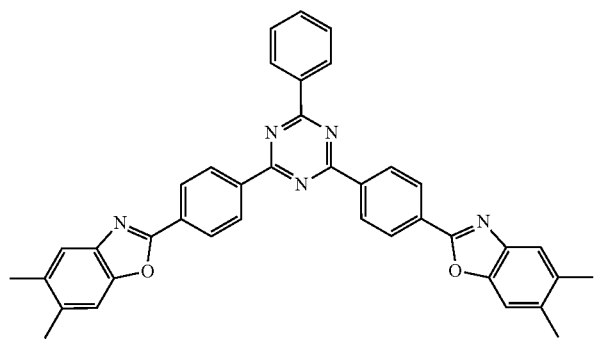

-continued
(47)
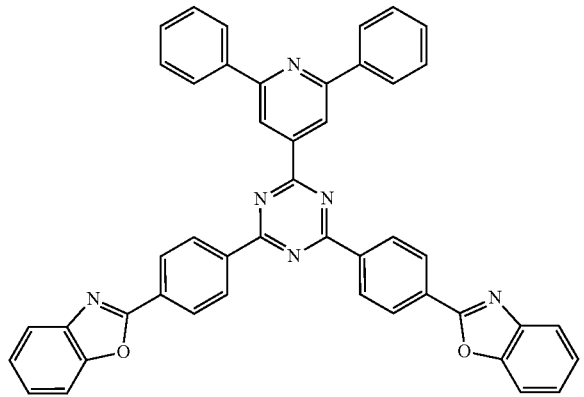
(48)
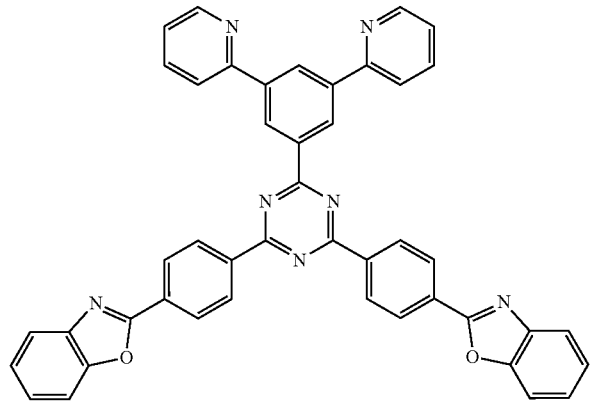
(49)
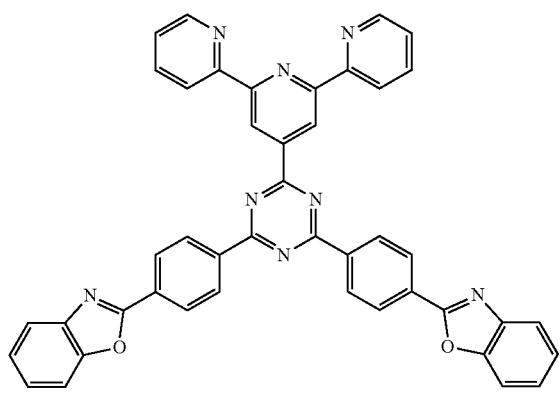
(50)
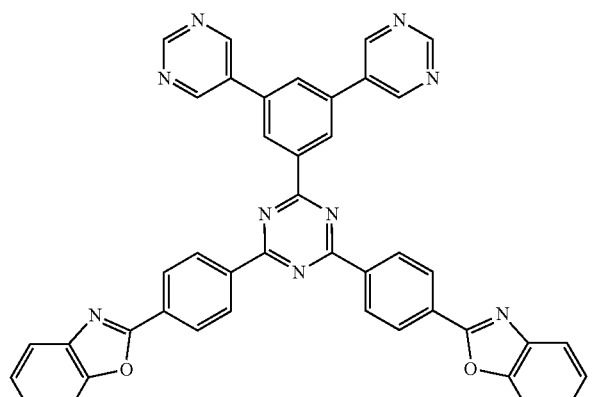
(51)
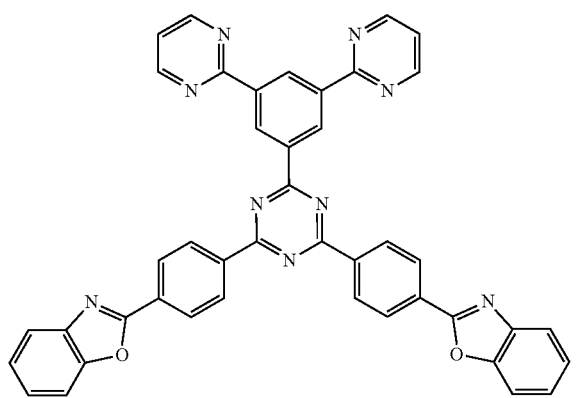
(52)
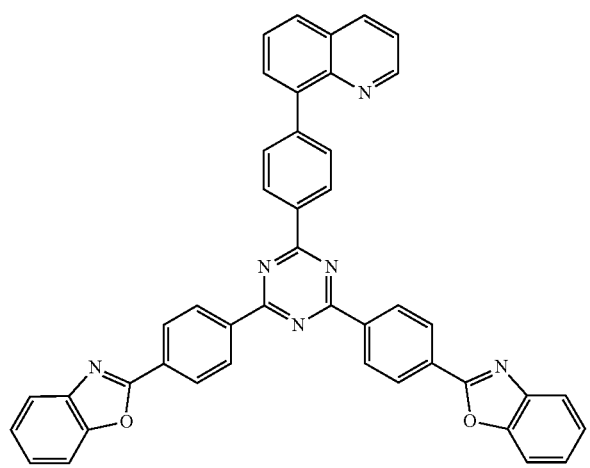

-continued
(53)
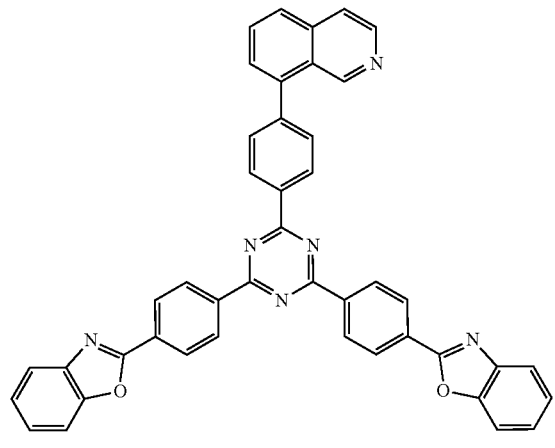
(54)
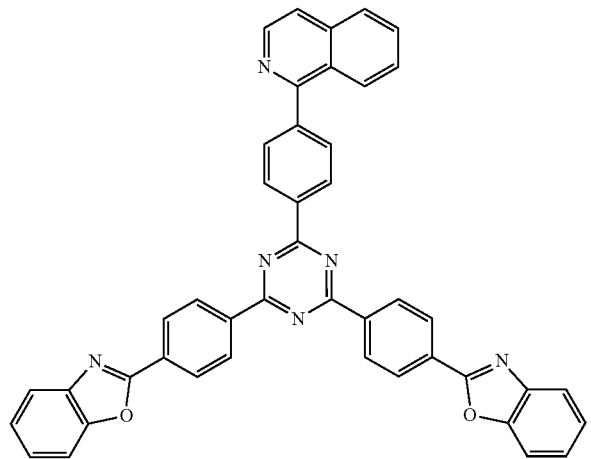
(55)
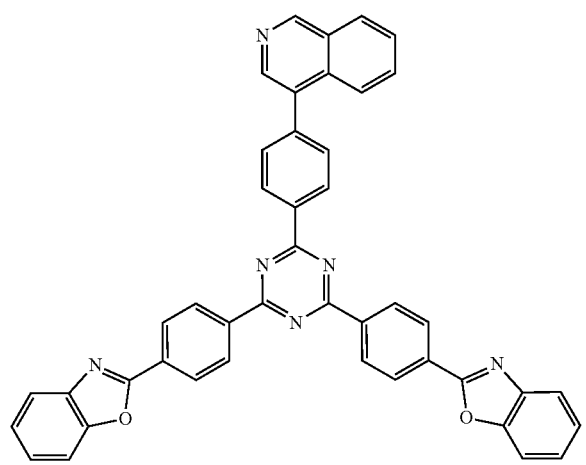
(56)
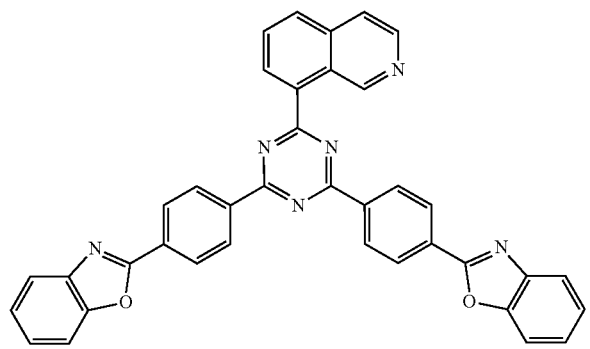
(57)
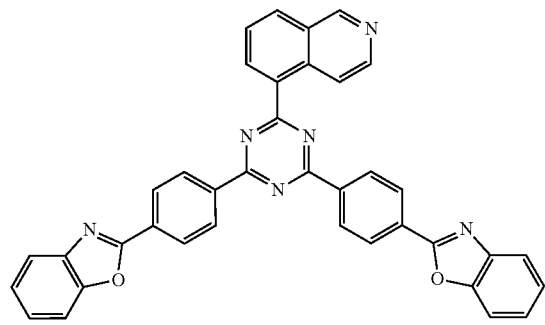
(58)
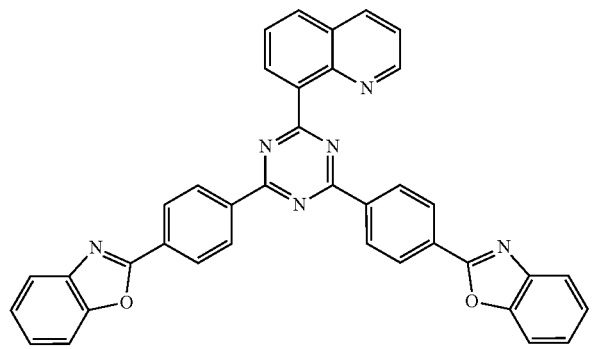

-continued
503
(59)
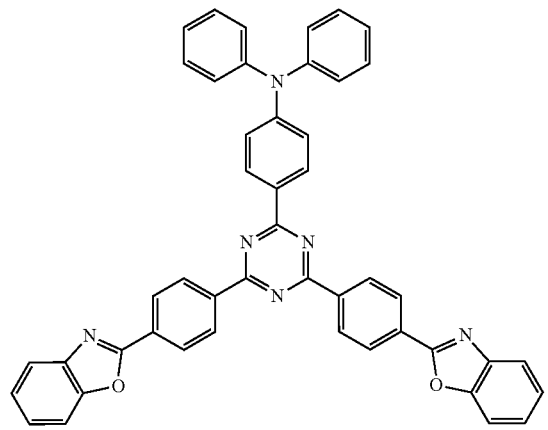
504
(60)
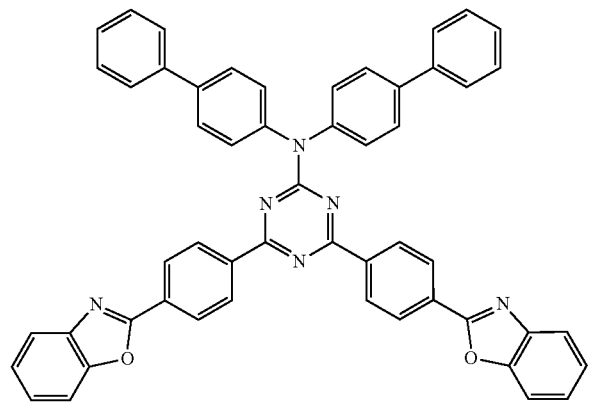
(61)
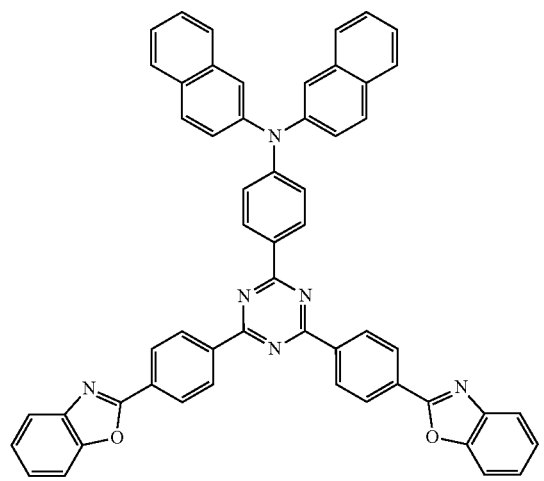
(62)
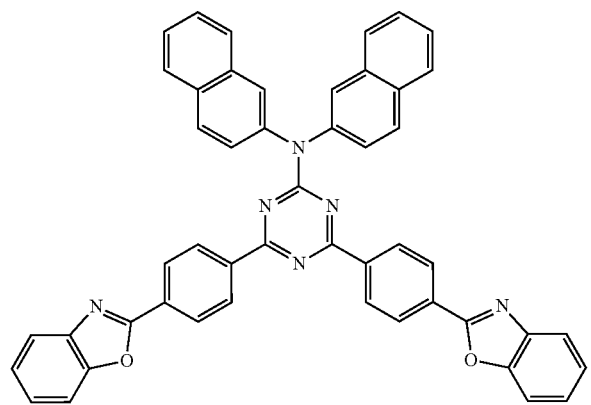
(63)
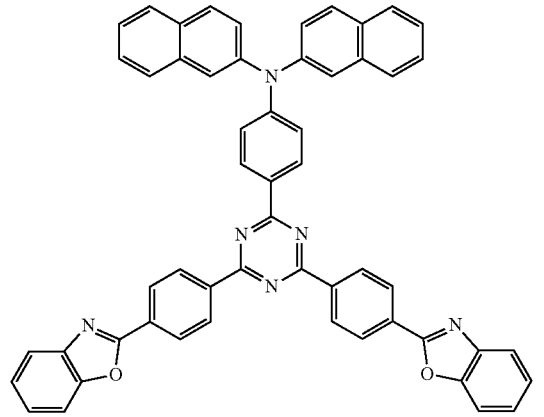
(65)
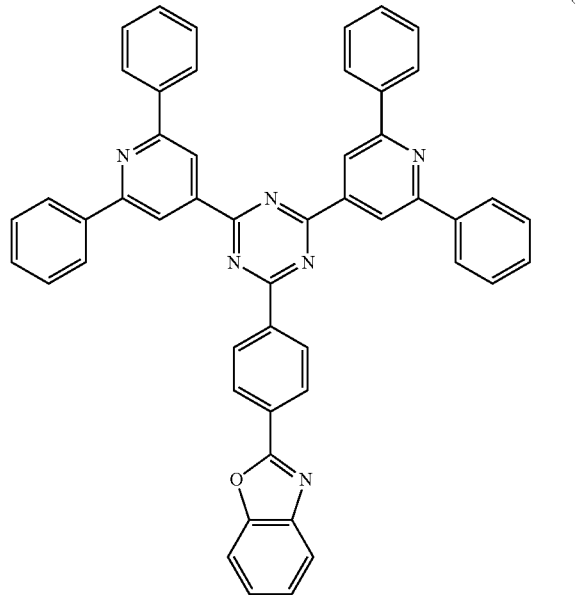

(66)
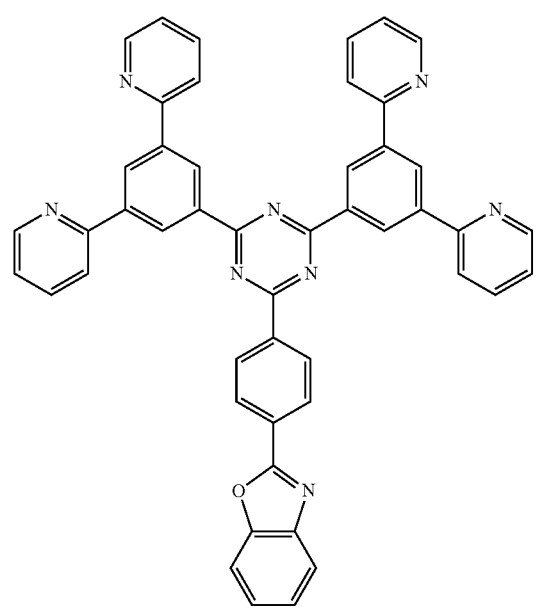
(67)
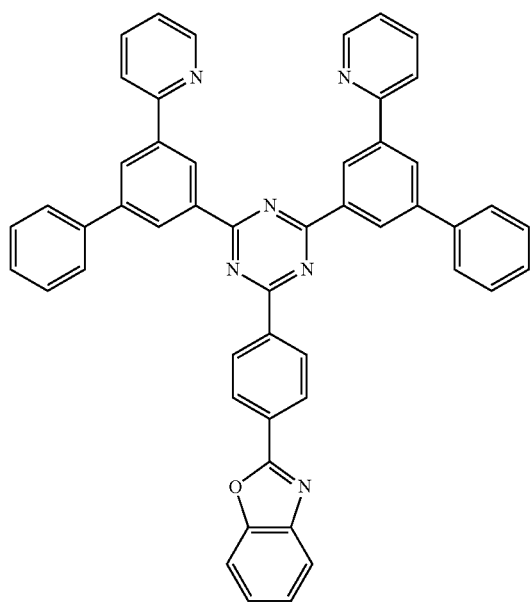
(68)
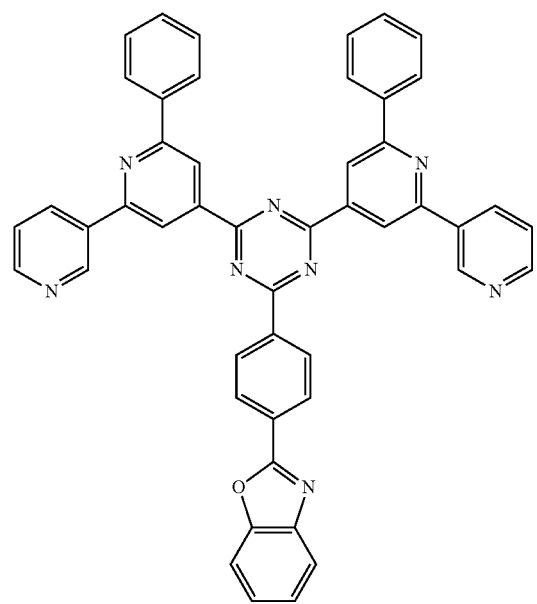
(69)
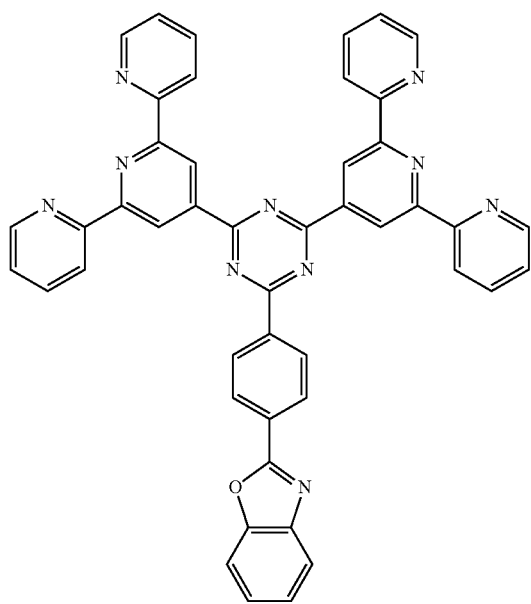

-continued
(70)
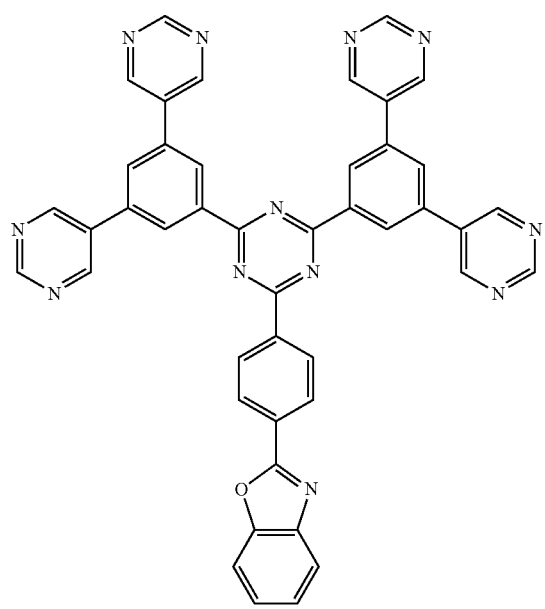
(71)
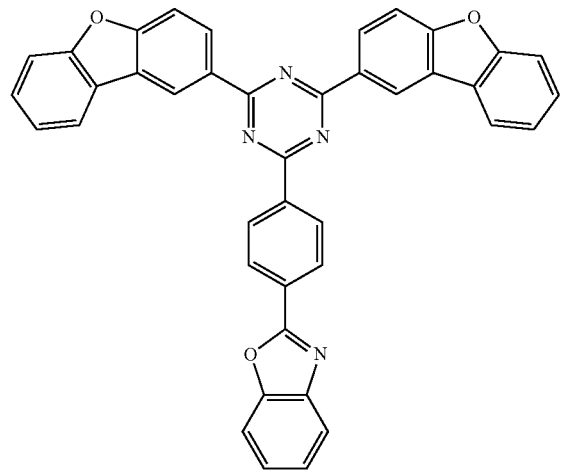
(72)
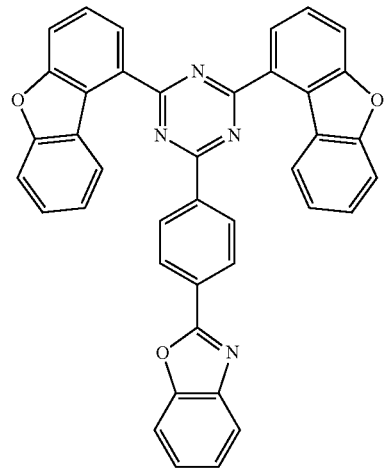
(73)
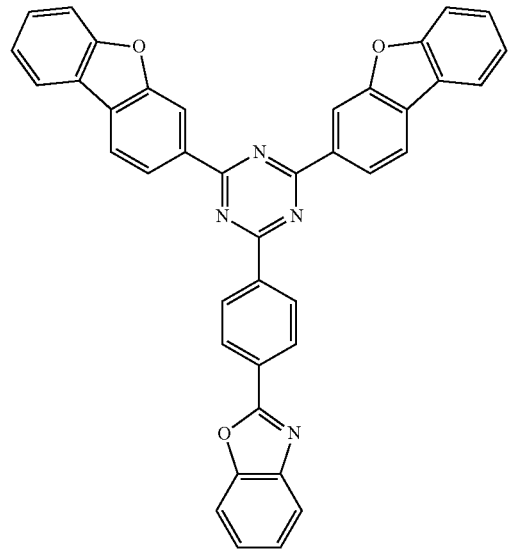
(74)
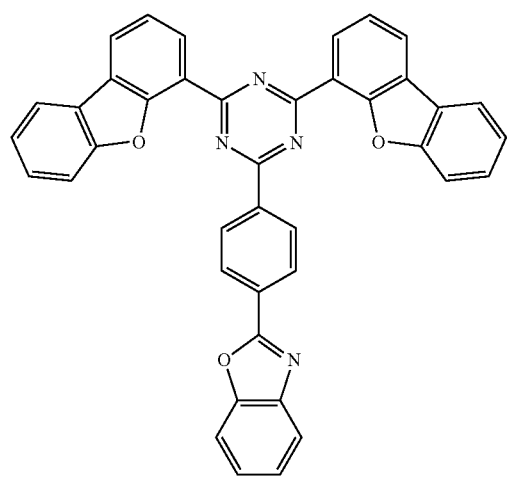
(75)
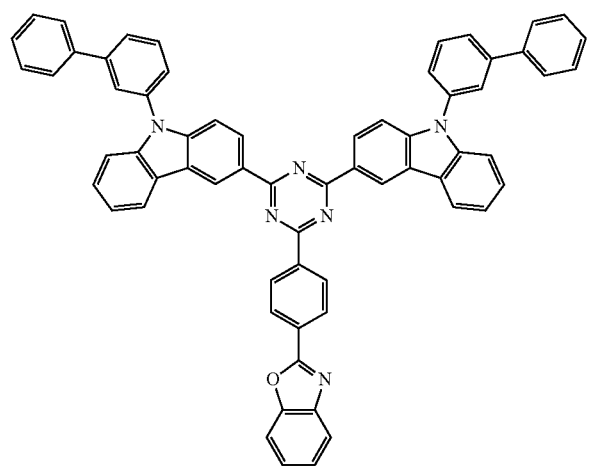

-continued
(76)
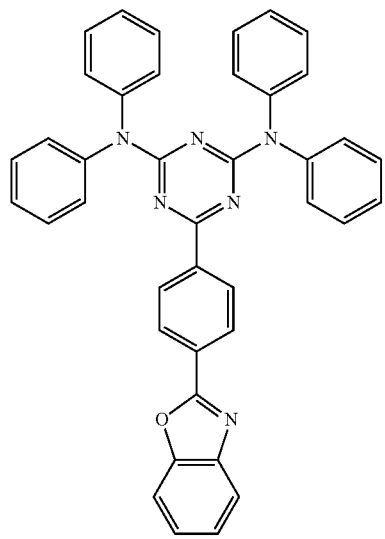
(77)
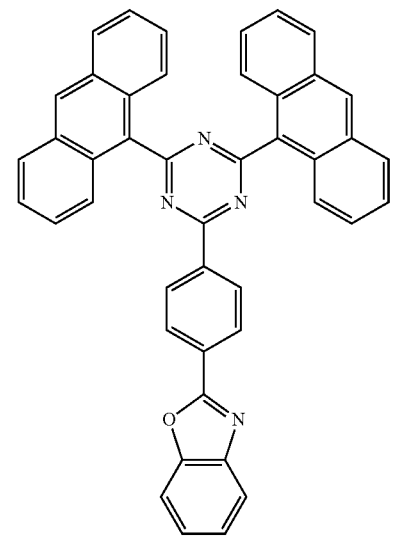
(78)
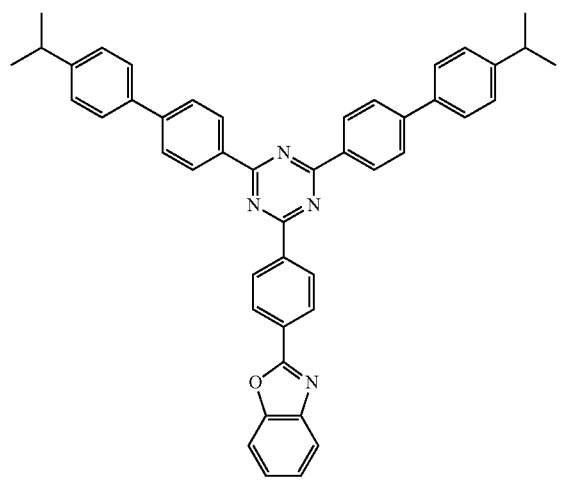
(79)
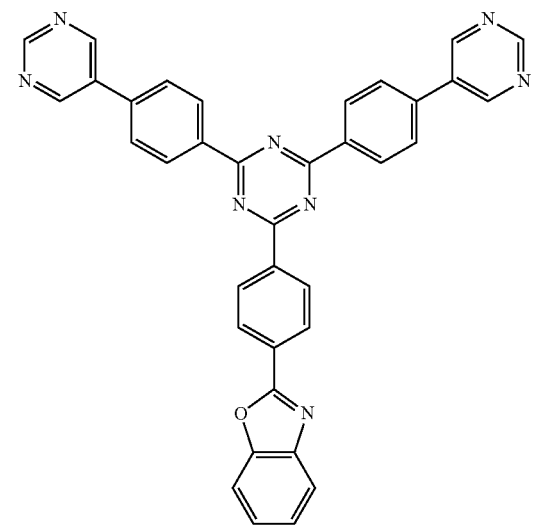
(80)
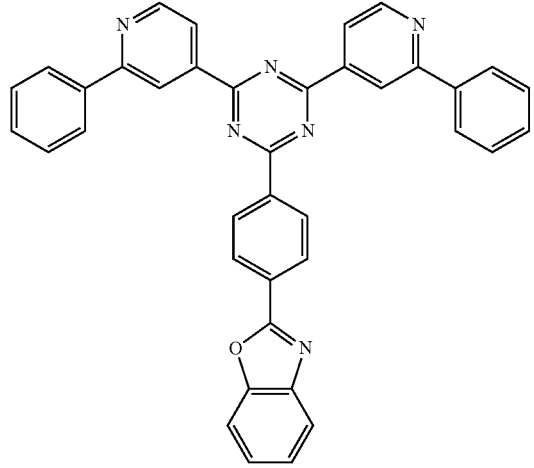
(81)
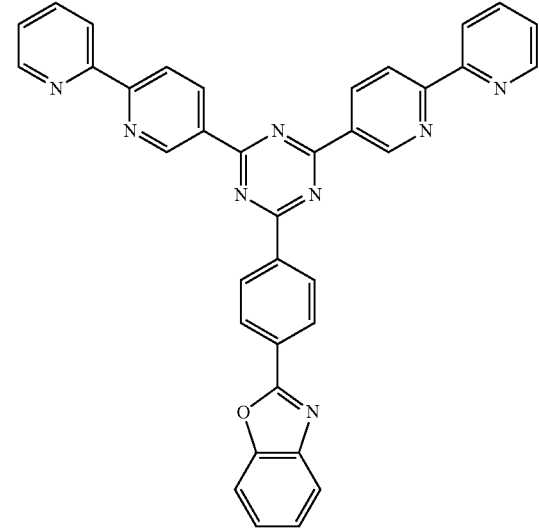

-continued
(82)
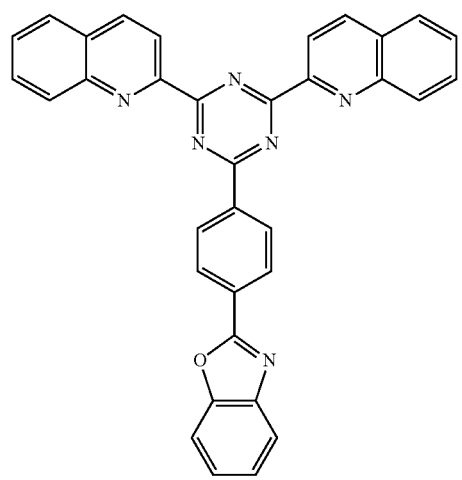
(85)
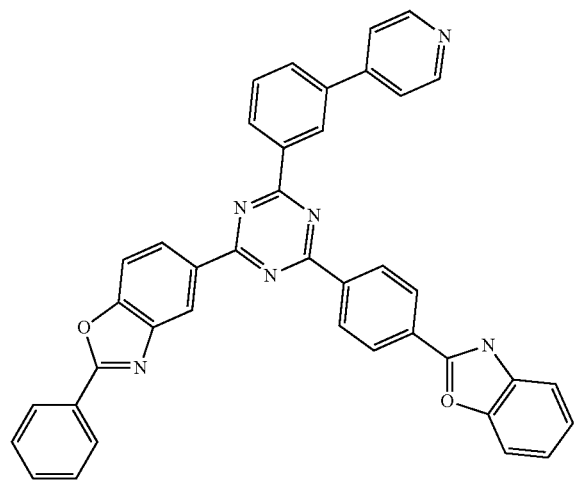
(86)
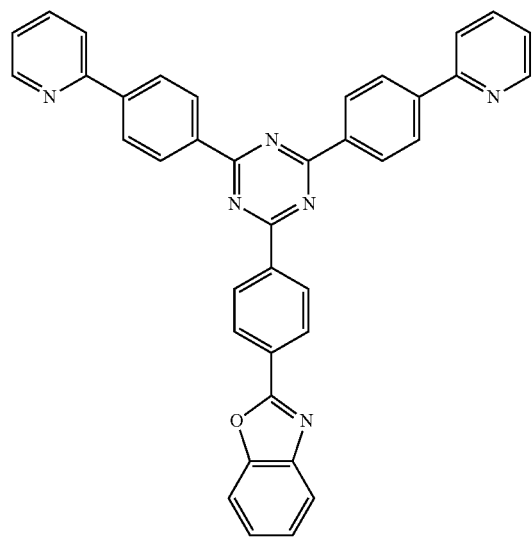
(87)
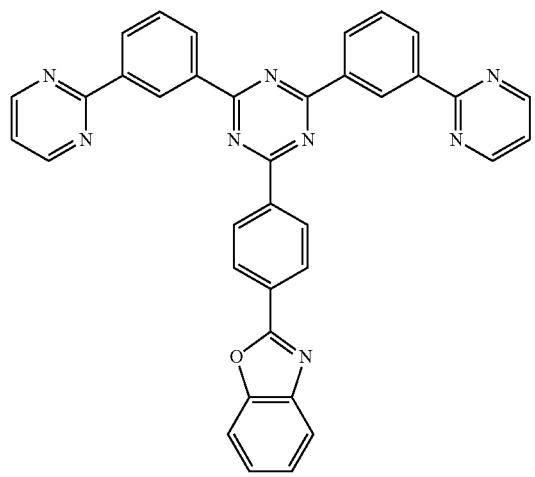
(88)
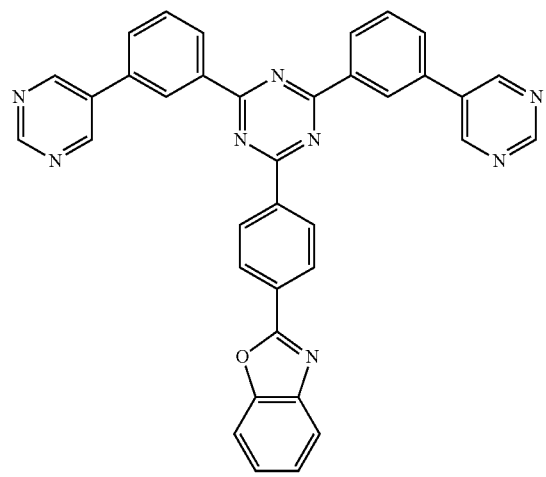
(89)
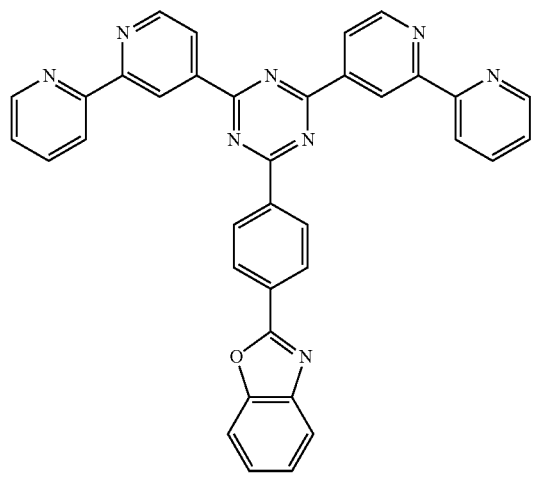

-continued
(90)
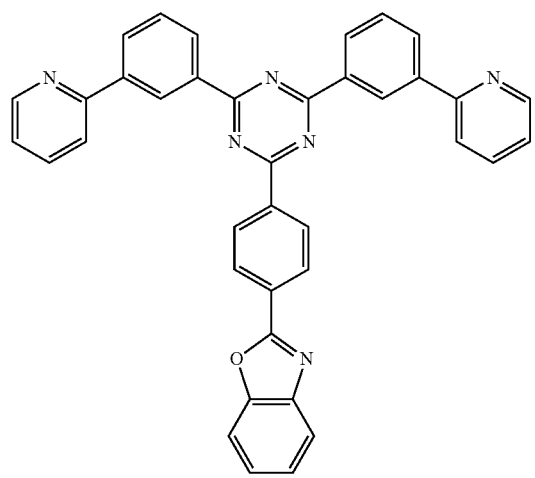
513
(91)
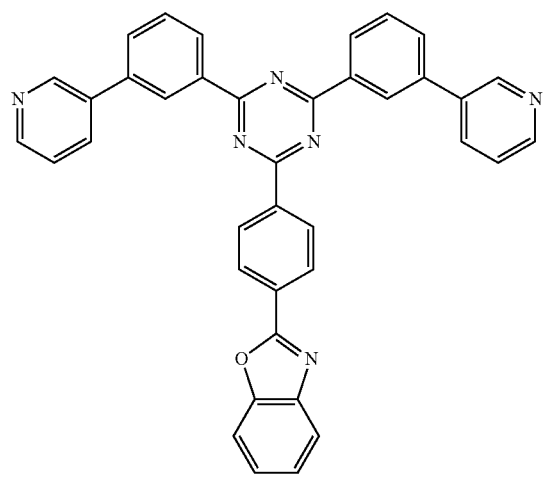
514
(92)
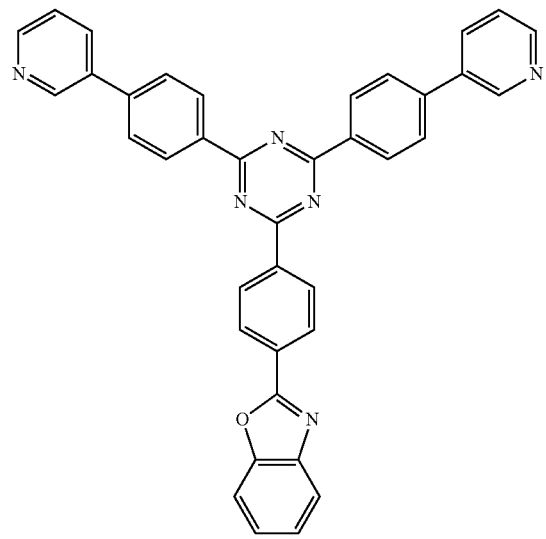
(93)
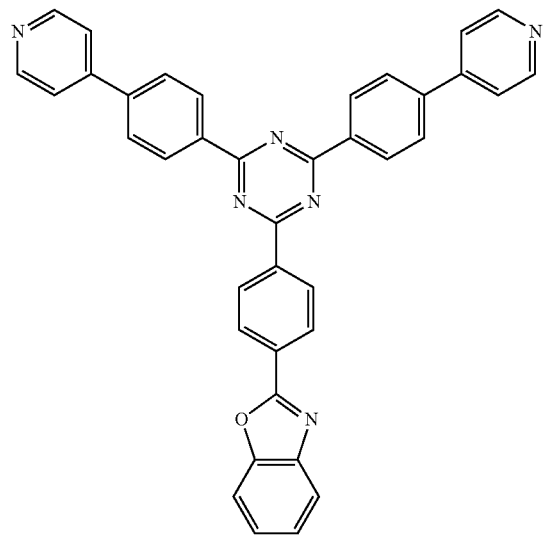
(94)
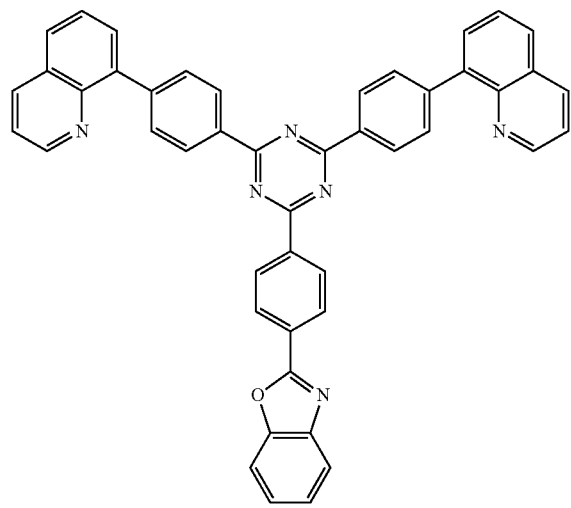
(95)
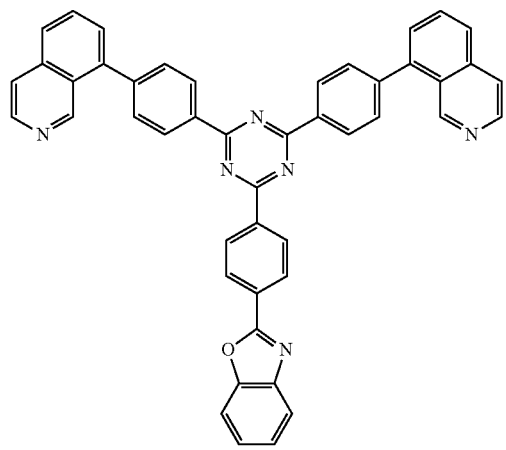

-continued
(96)
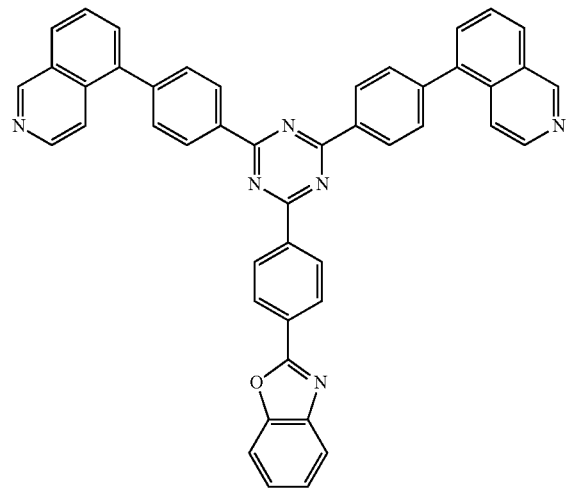
(97)
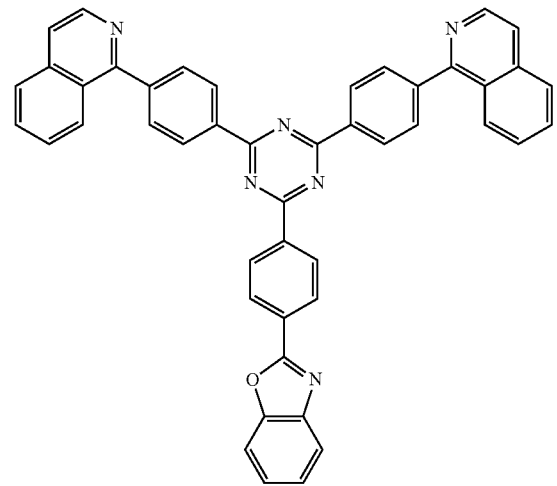
(98)
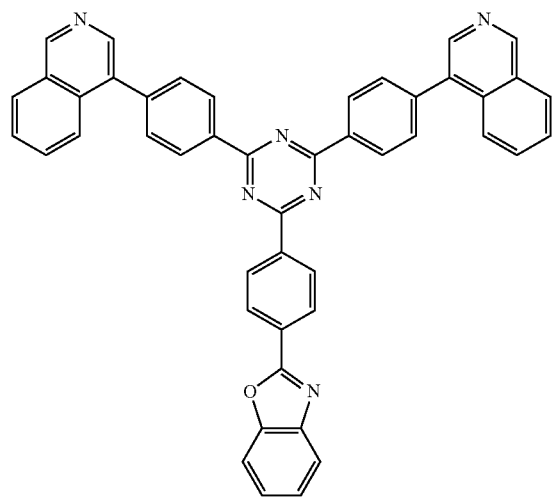
(99)
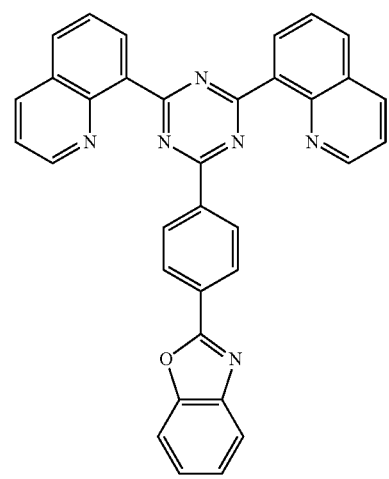
(100)
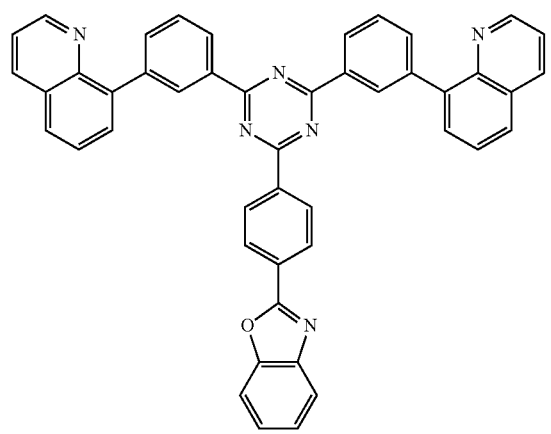
(101)
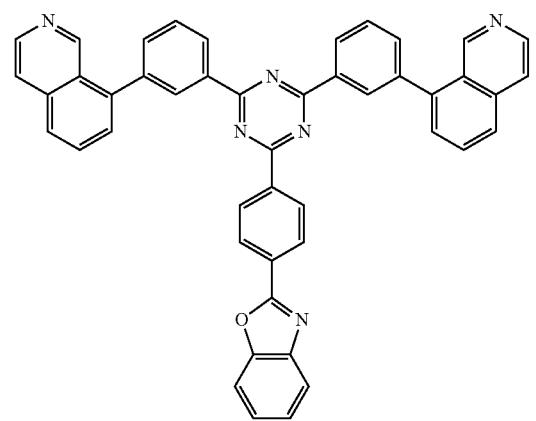

-continued
(102)
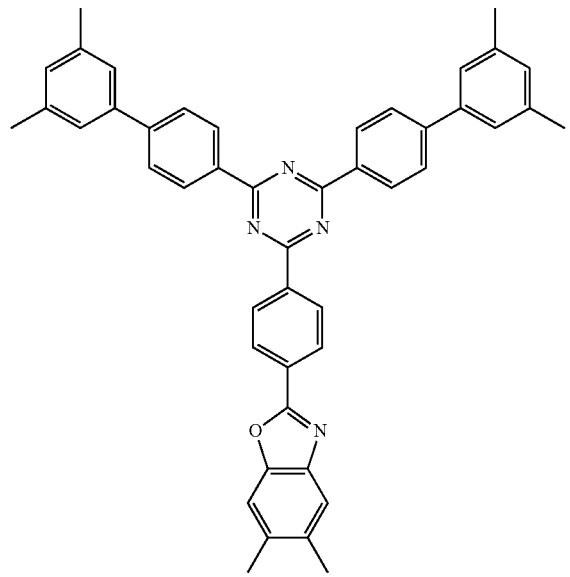
(103)
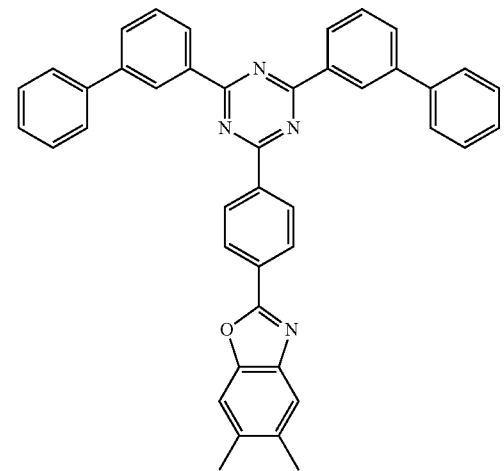
(104)
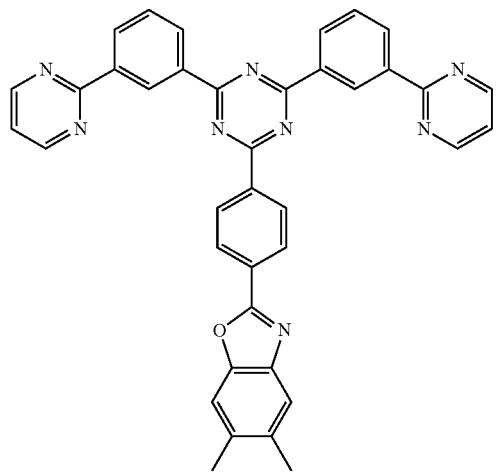
(105)
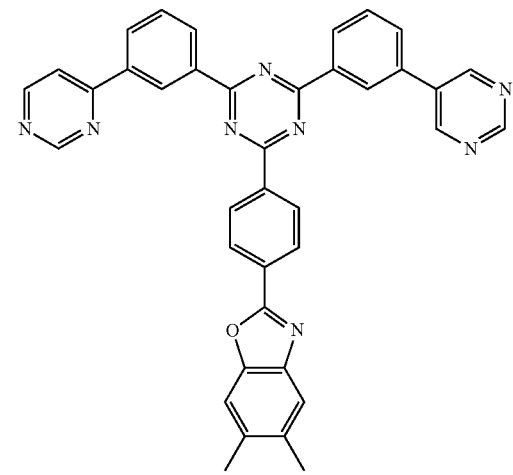
(106)
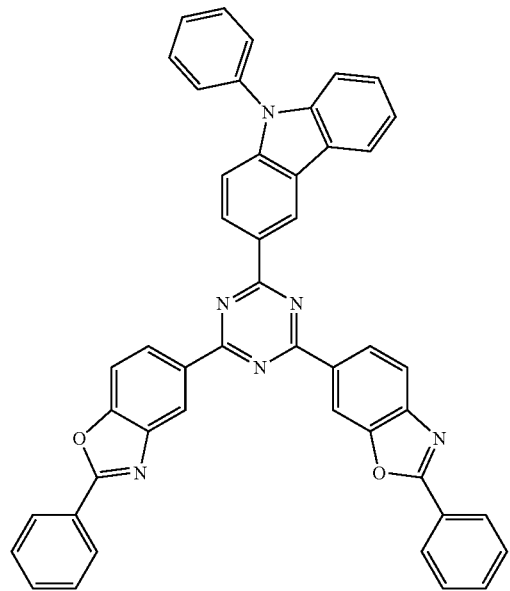
(107)
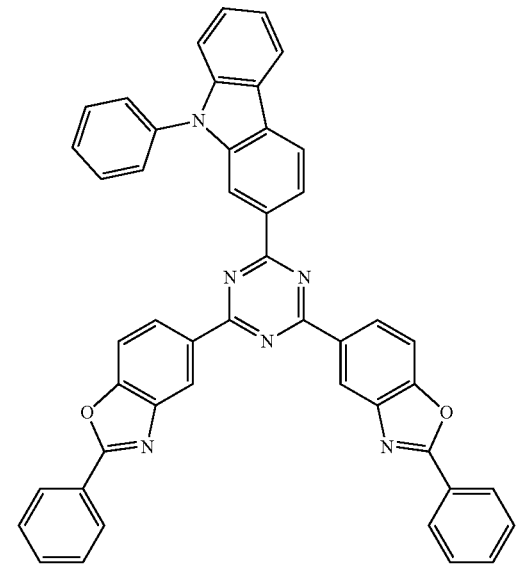

(108)
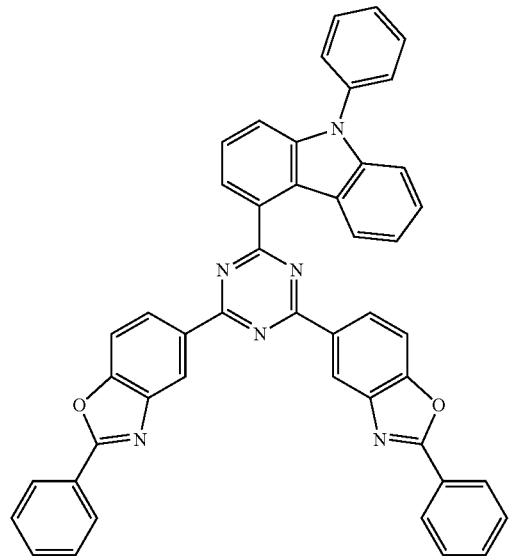
(109)
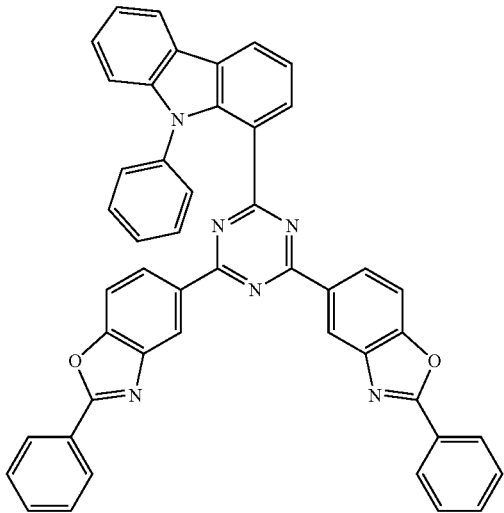
(110)
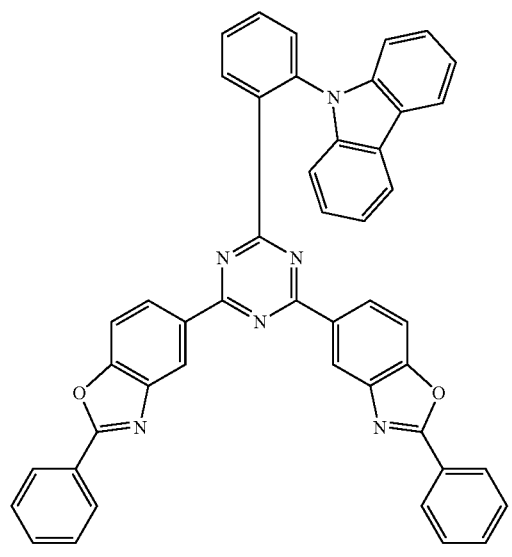
(111)
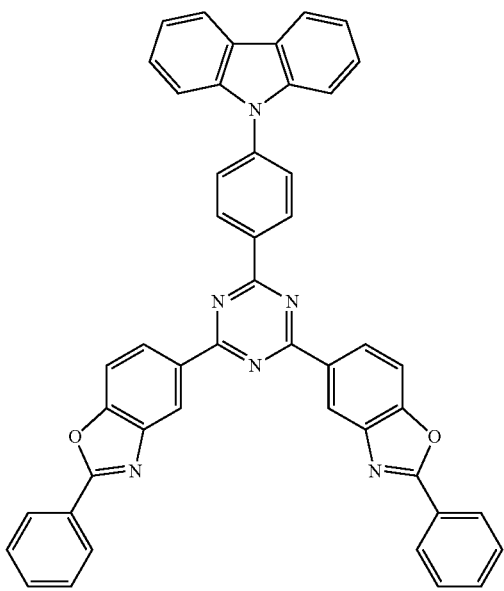

-continued
521
(112)
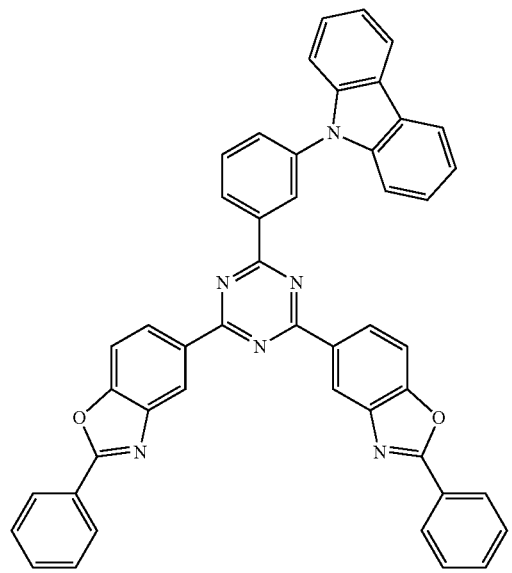
522
(113)
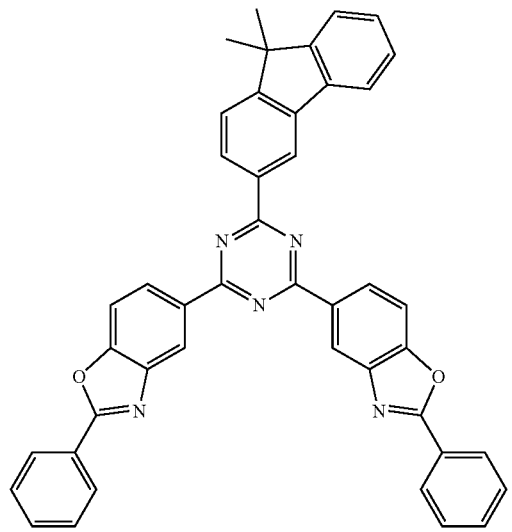
(114)
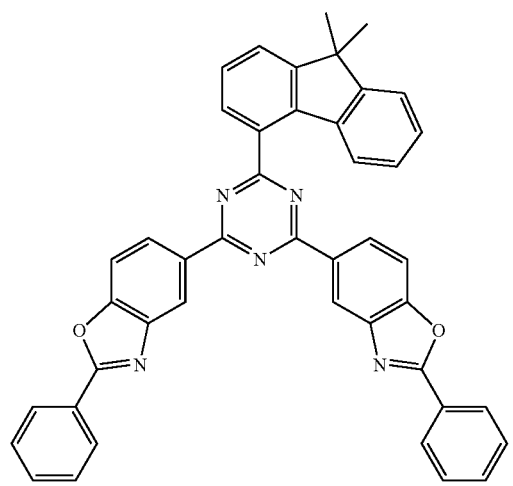
(115)
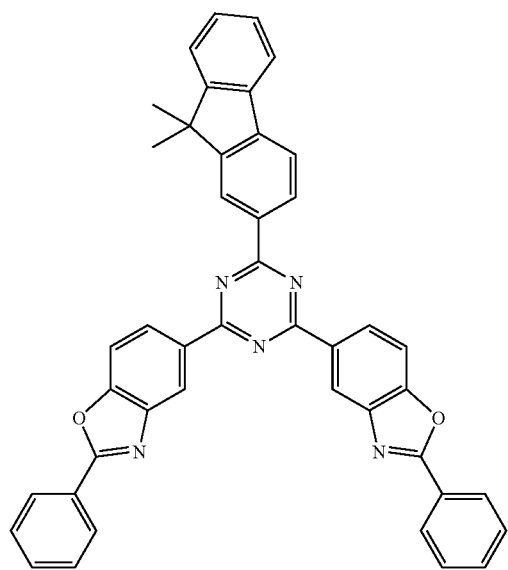
(116)
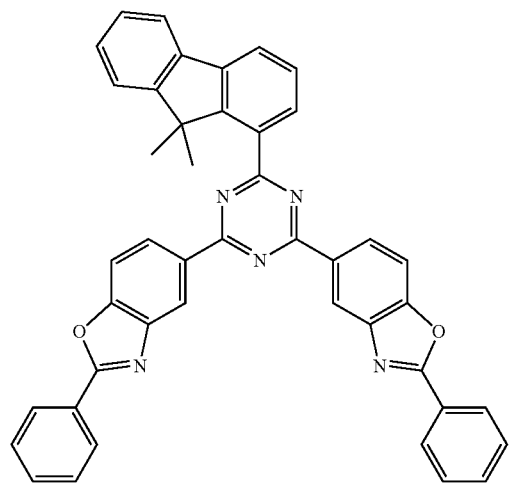
(117)
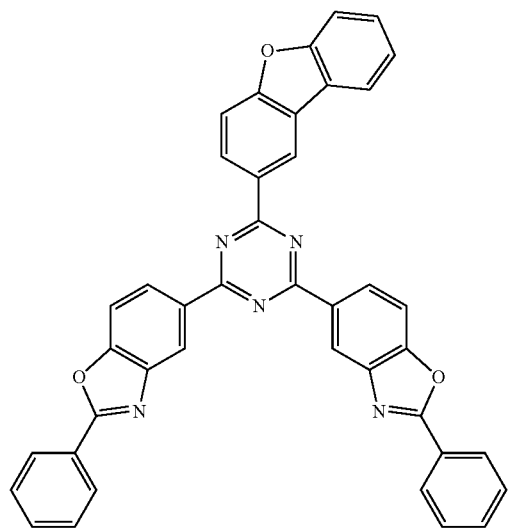

-continued
(118)
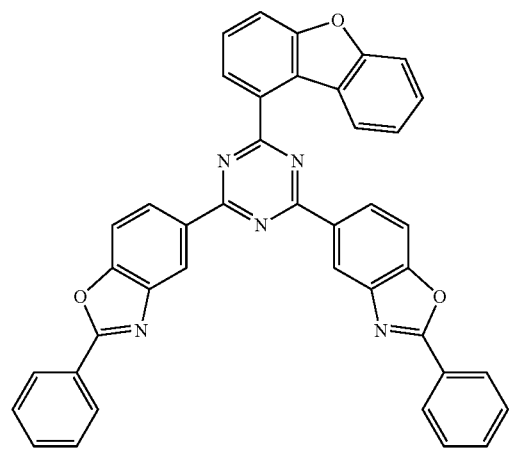
(119)
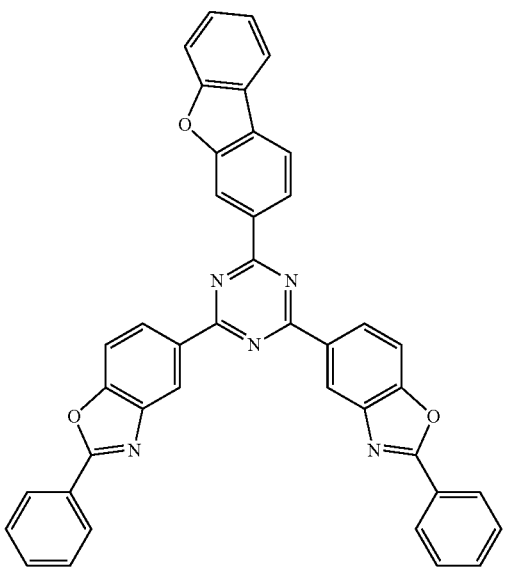
(120)
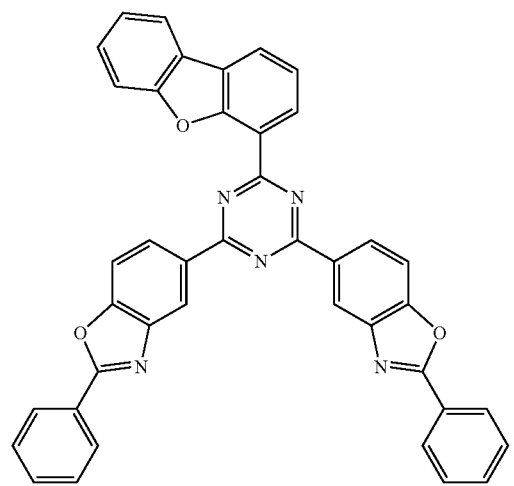
(121)
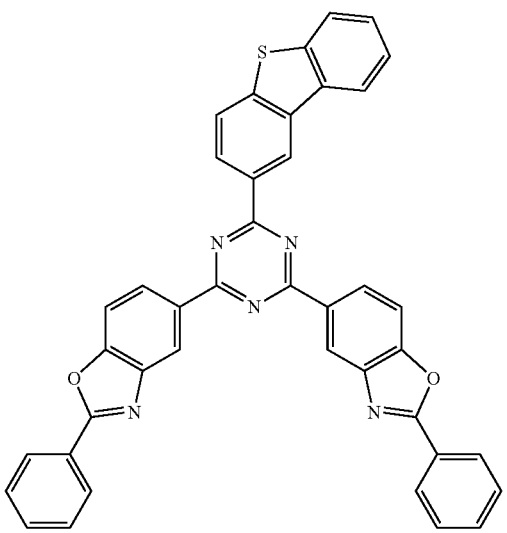
(122)
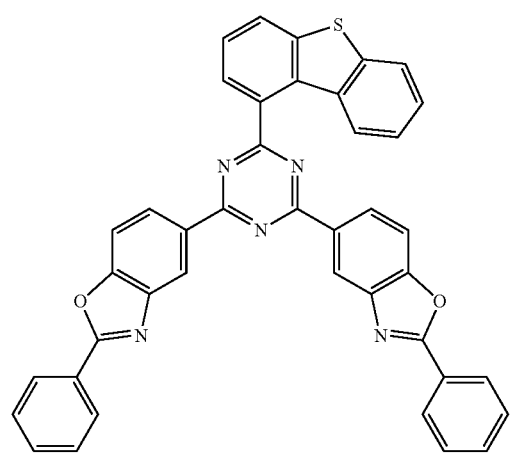
(123)
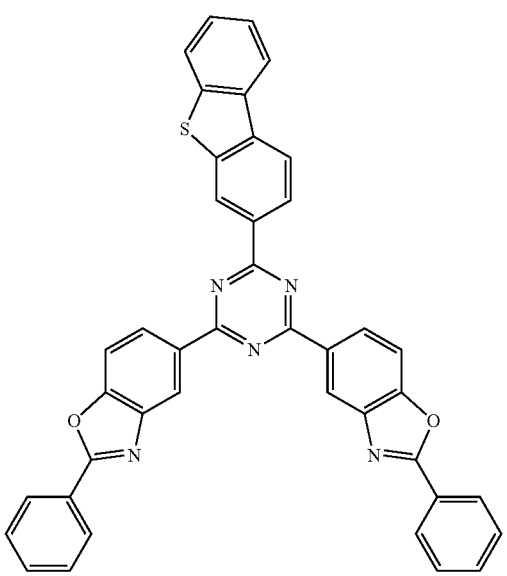

-continued
(124)
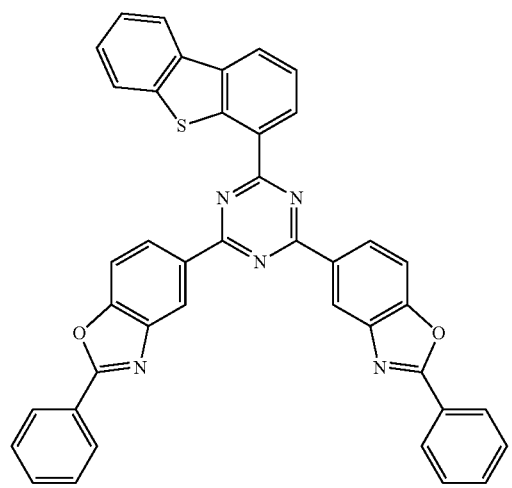
(125)
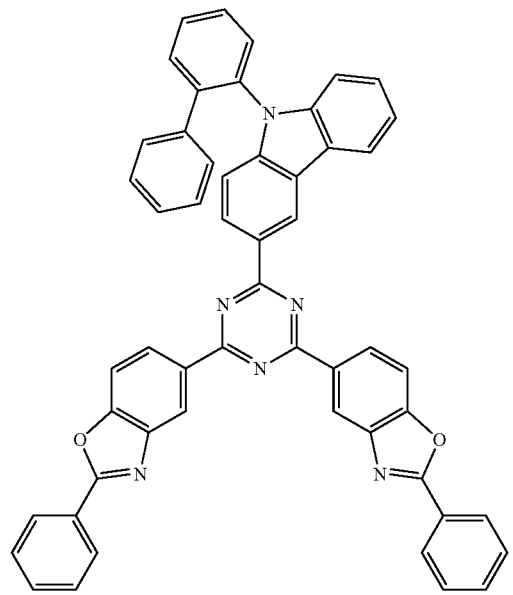
(129)
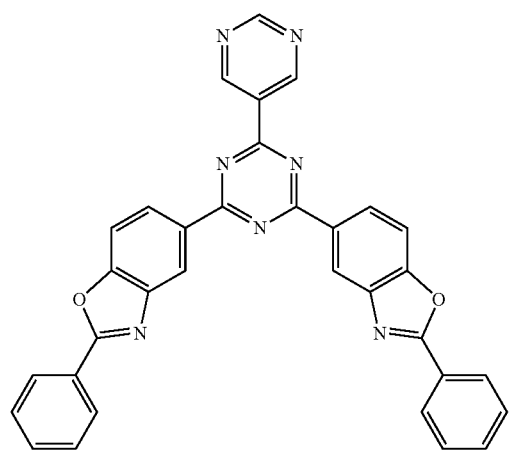
(130)
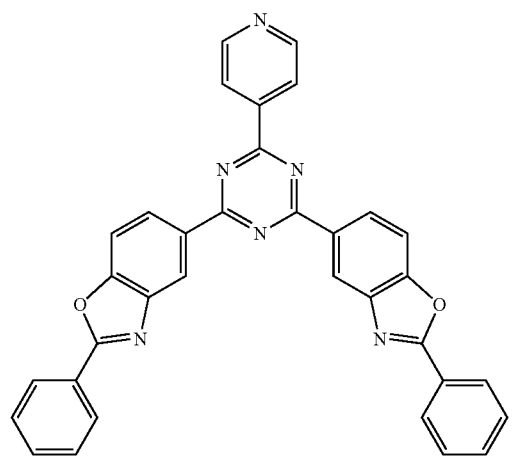
(131)
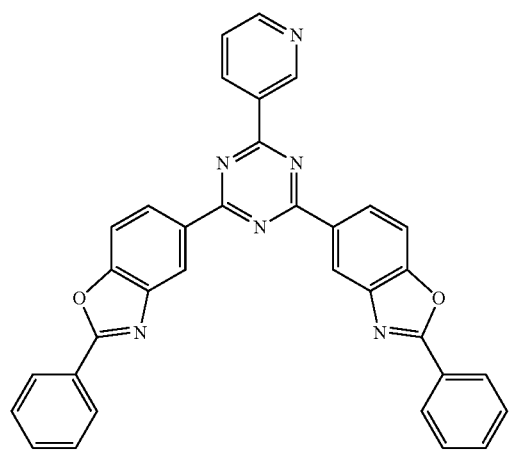
(132)
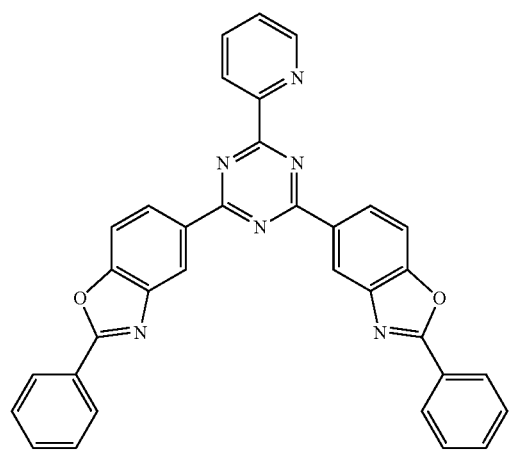

(135)
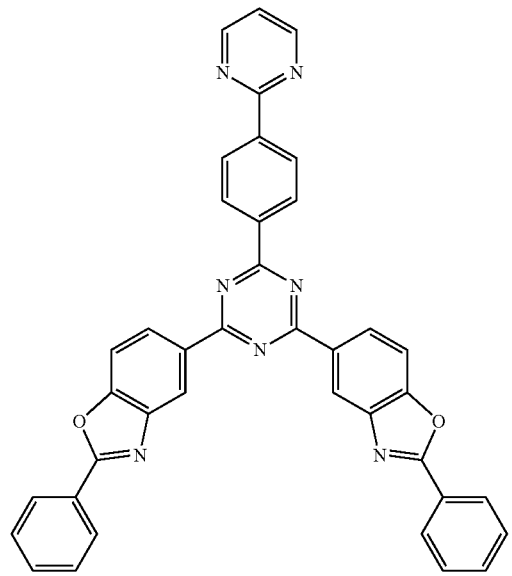
(137)
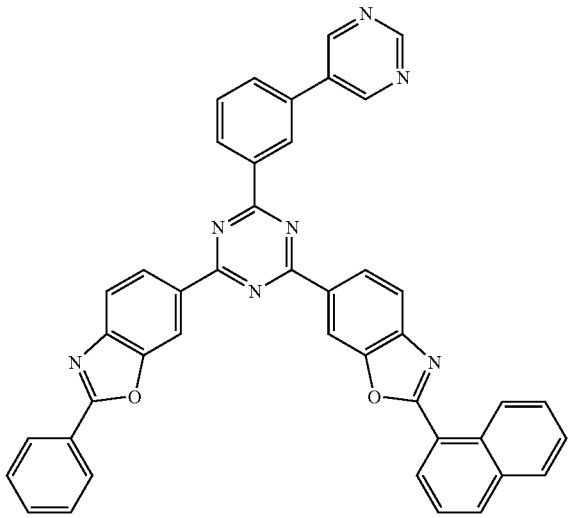
(138)
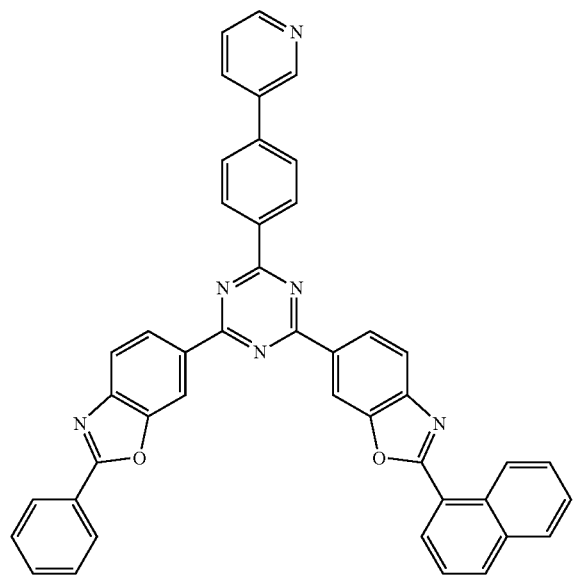
(139)
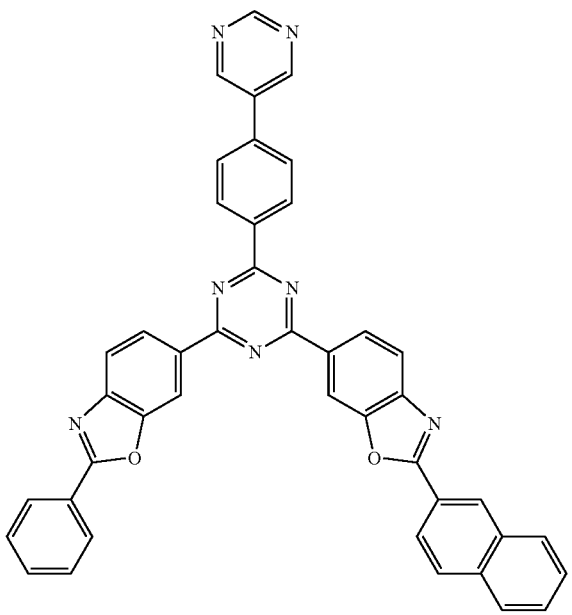

-continued
(140)
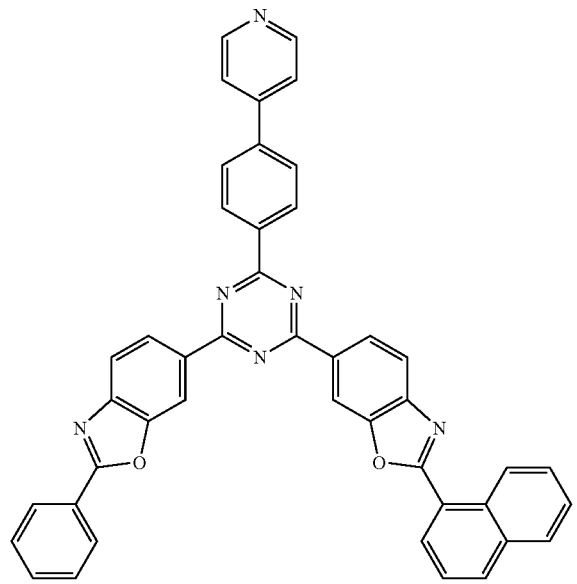
(141)
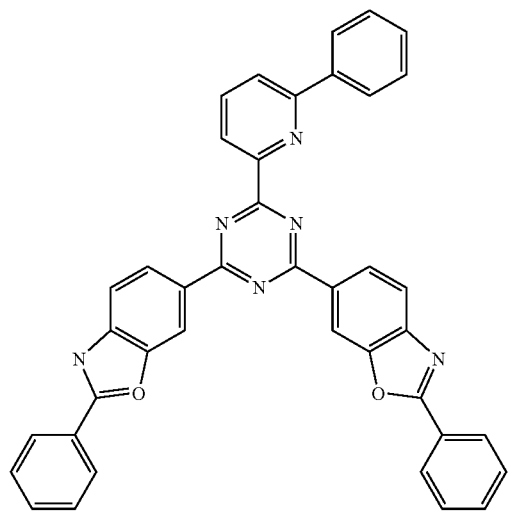
(142)
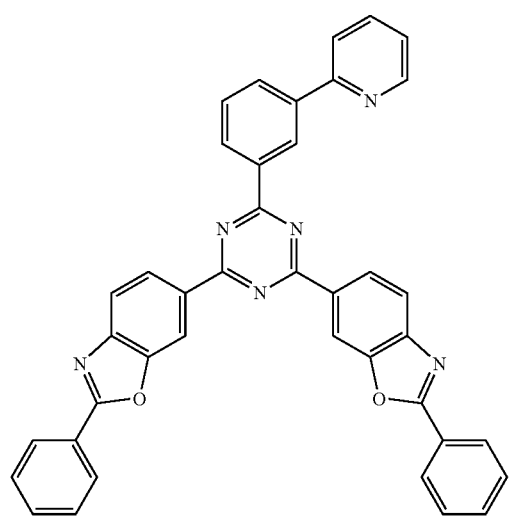
(143)
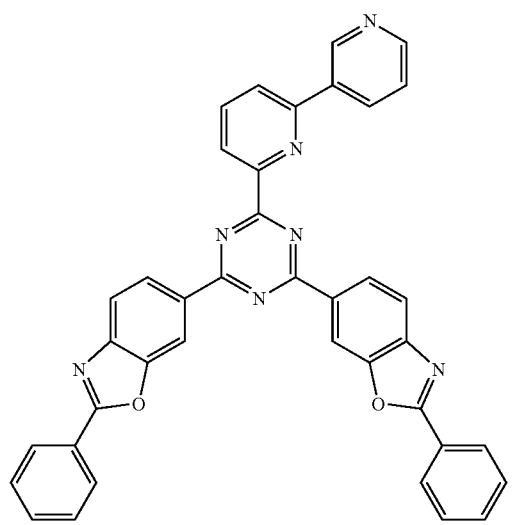
(144)
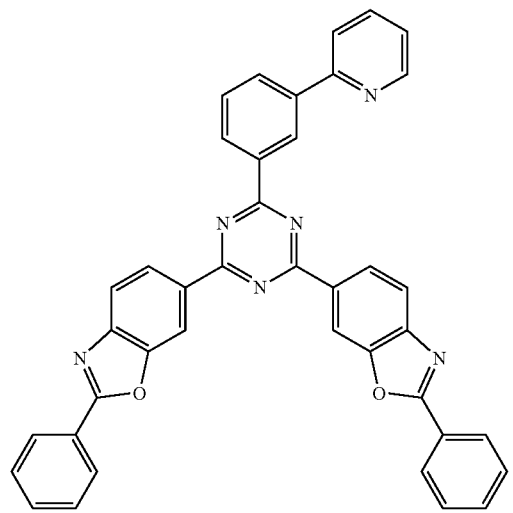
(148)
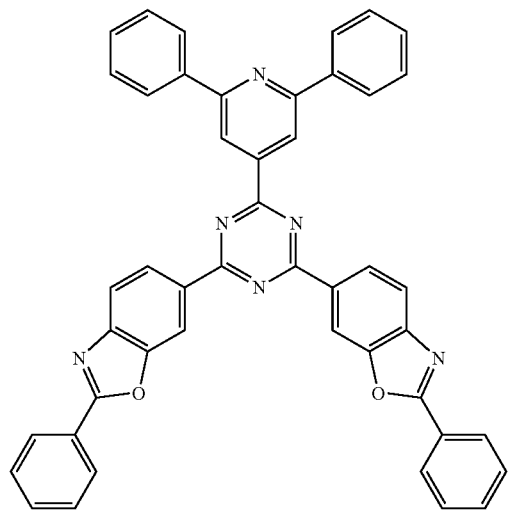

-continued
(149)
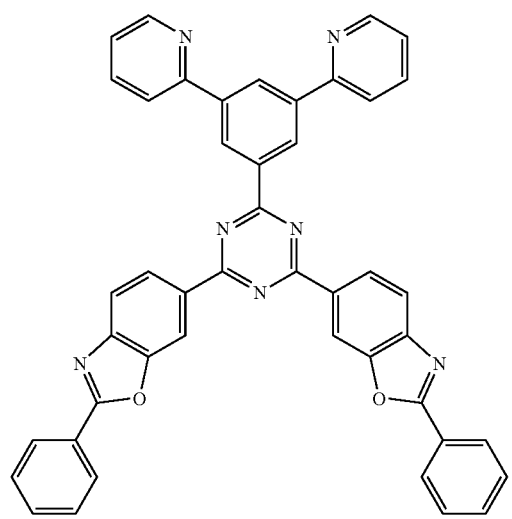
(150)
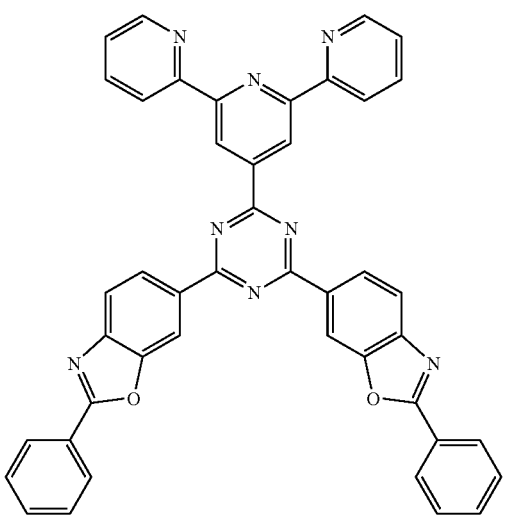
(151)
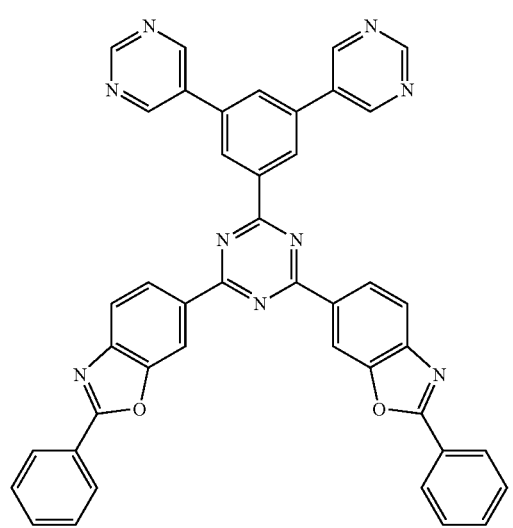
(152)
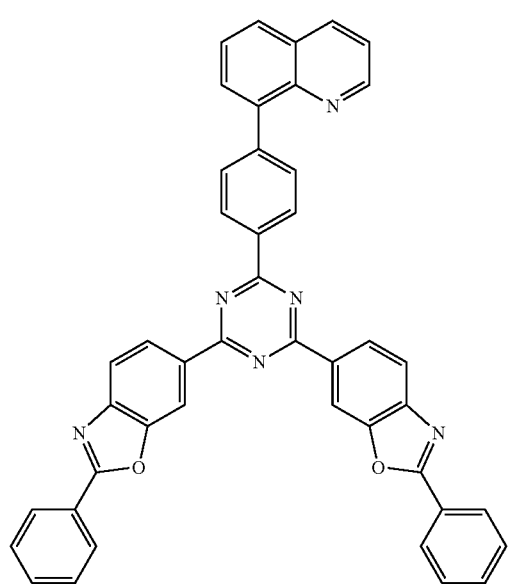
(153)
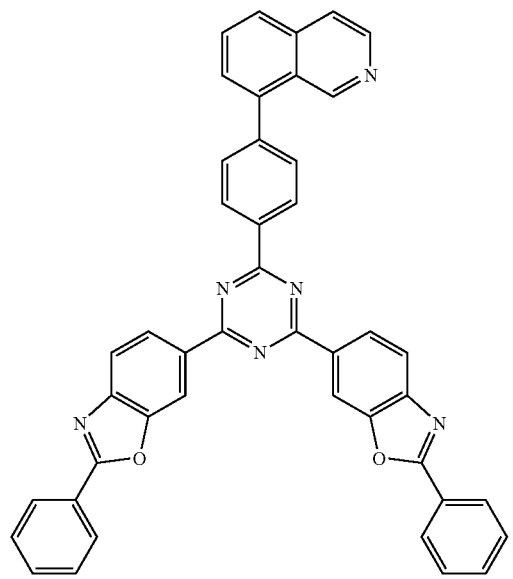
(154)
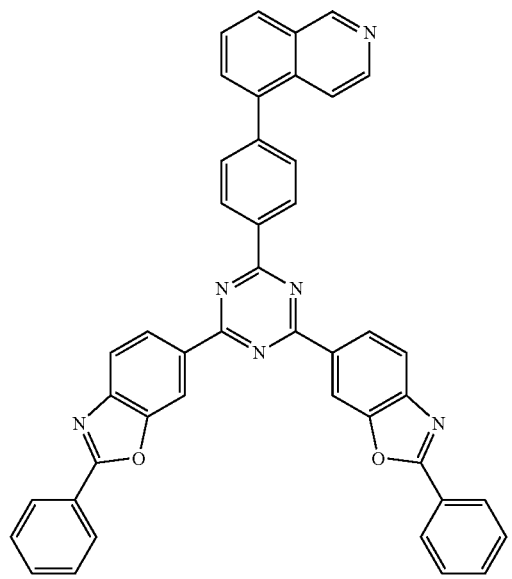

533
534
(155)
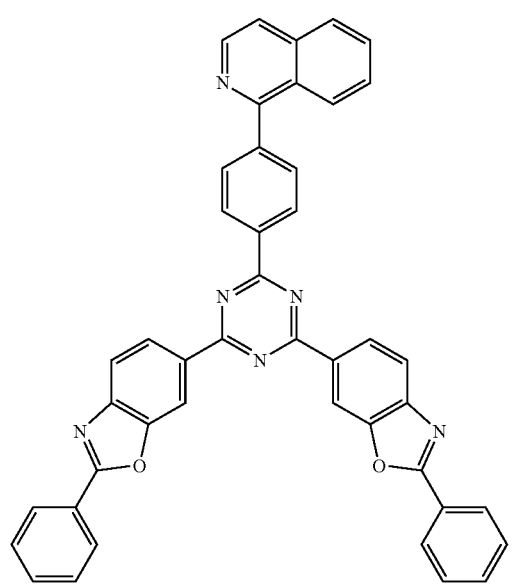
(156)
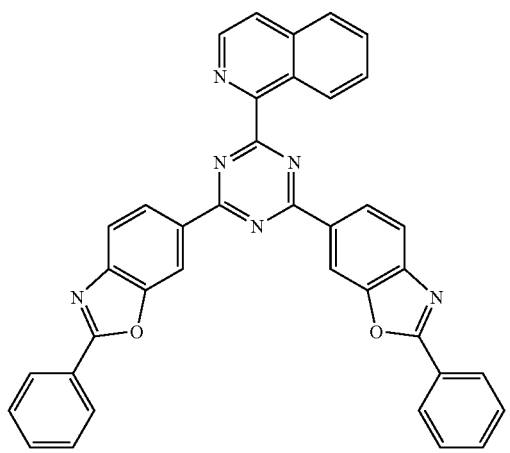
(157)
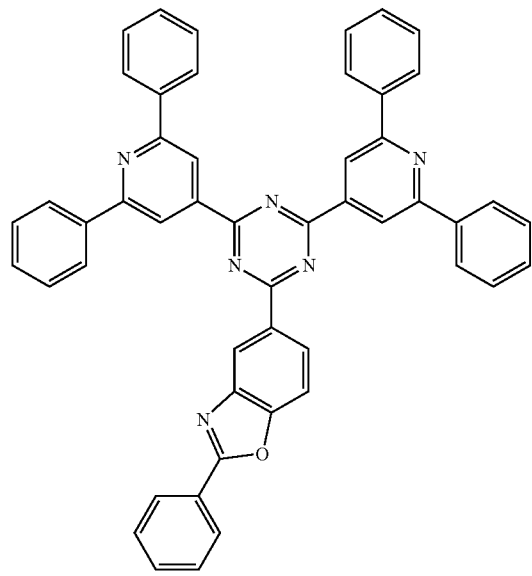
(158)
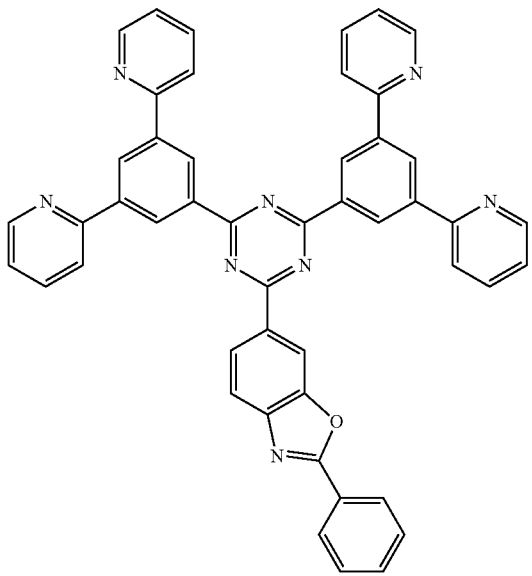

-continued
(159)
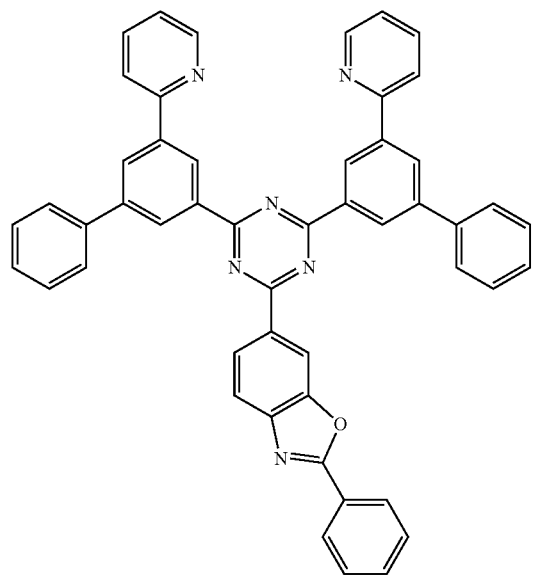
(160)
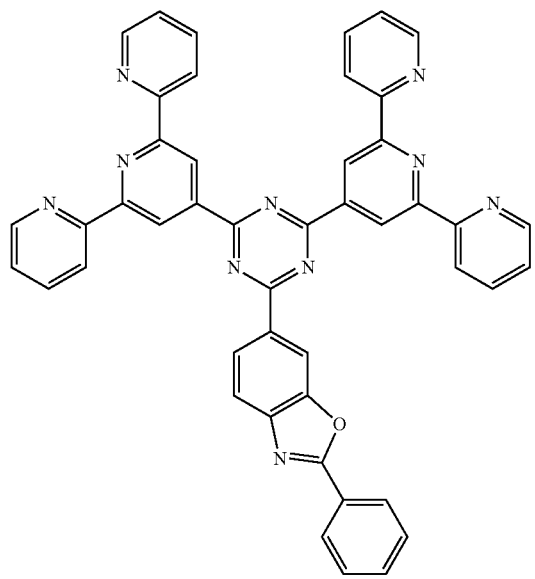
(161)
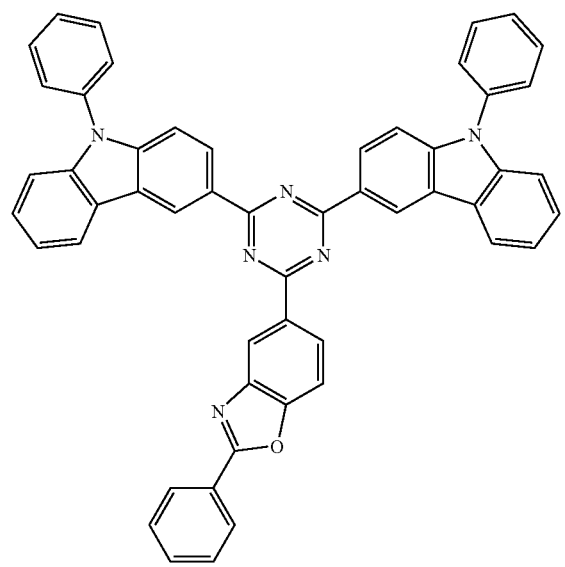
(162)
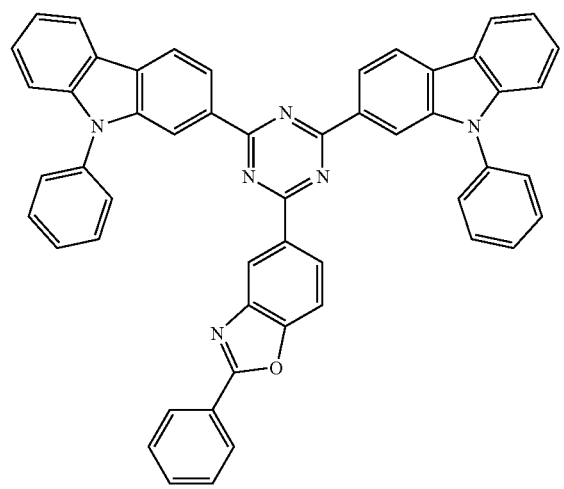
(163)
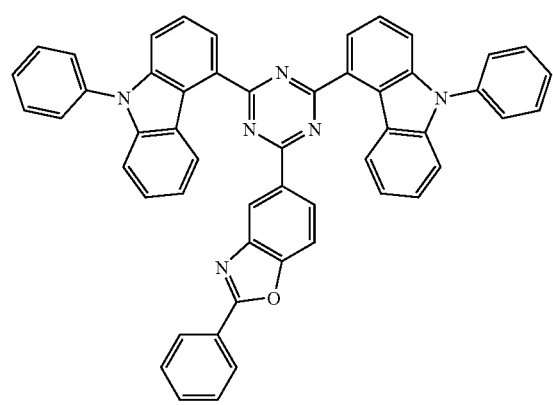
(164)
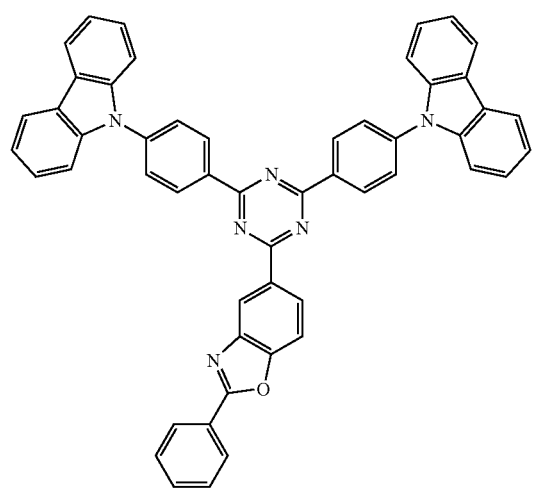

-continued
(165)
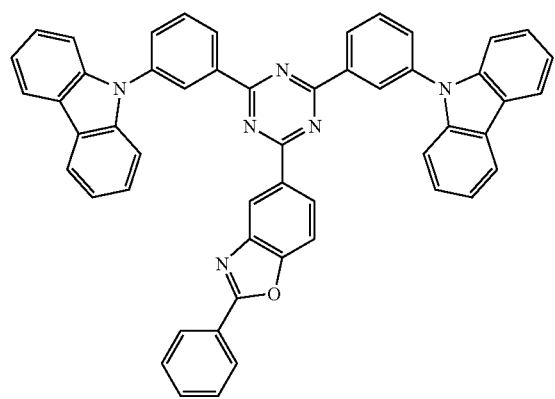
(166)
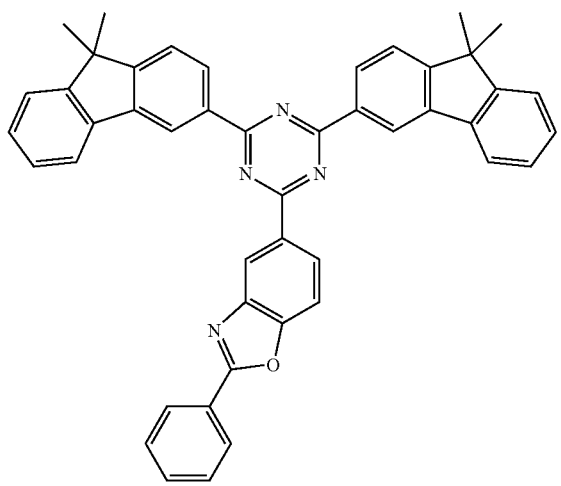
(167)
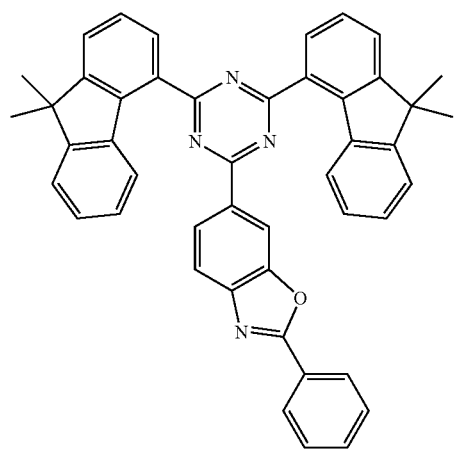
(168)
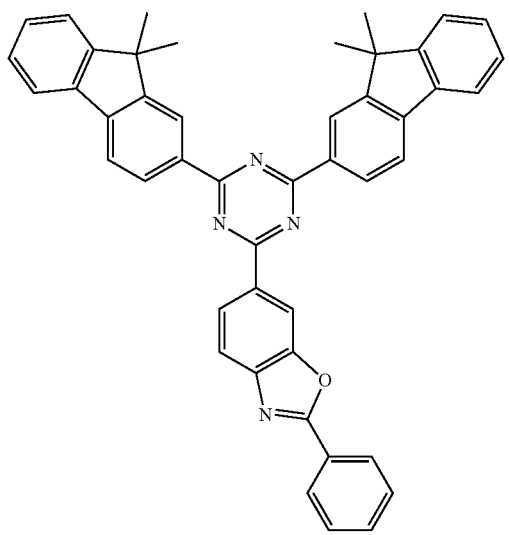
(169)
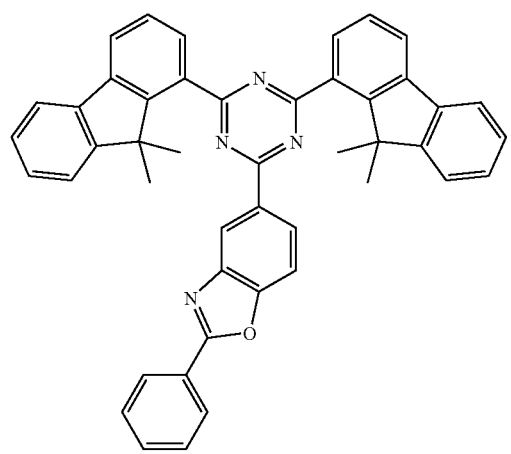
(170)
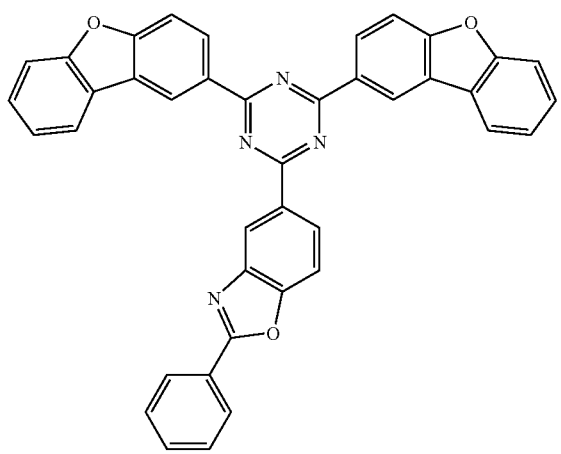

-continued
(171)
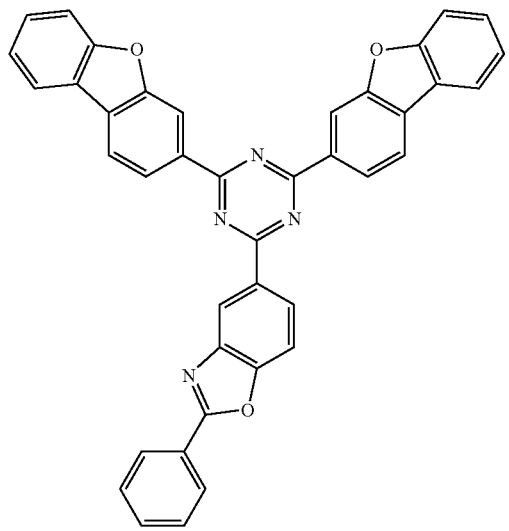
(172)
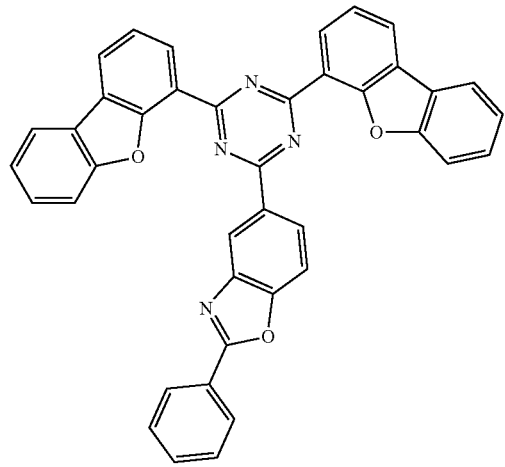
(173)
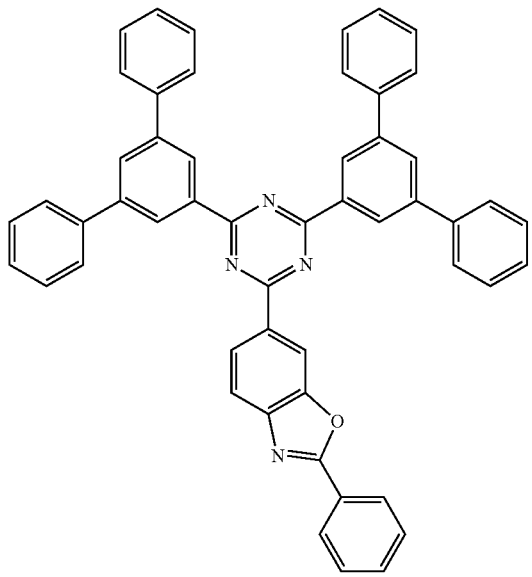
(174)
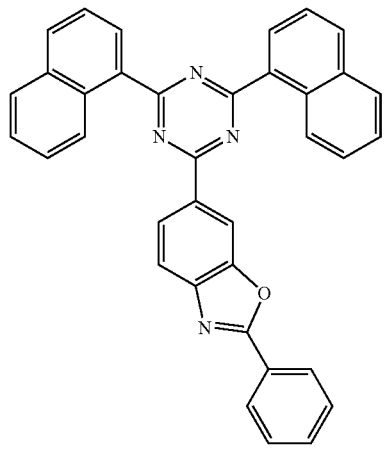
(175)
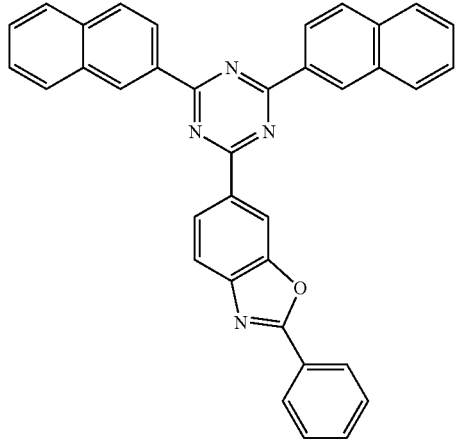
(176)
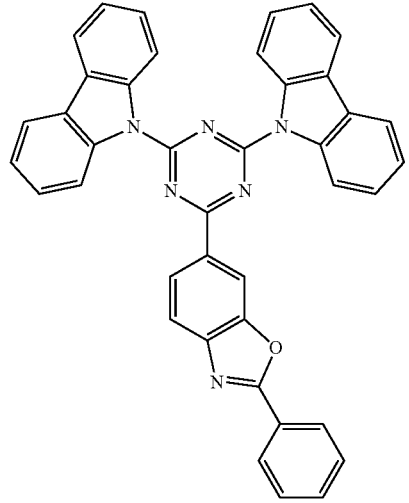

-continued
(177)
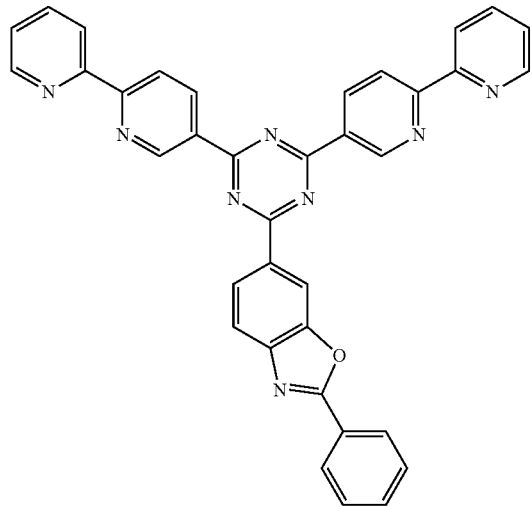
(178)
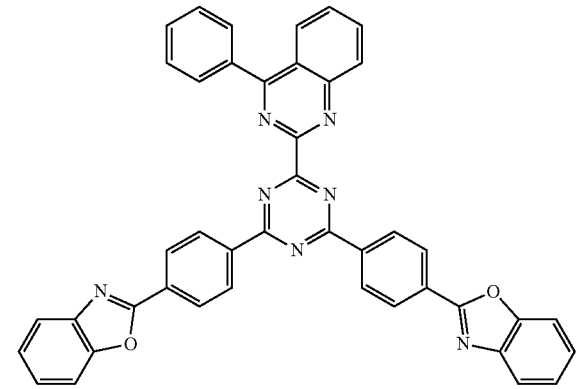
(179)
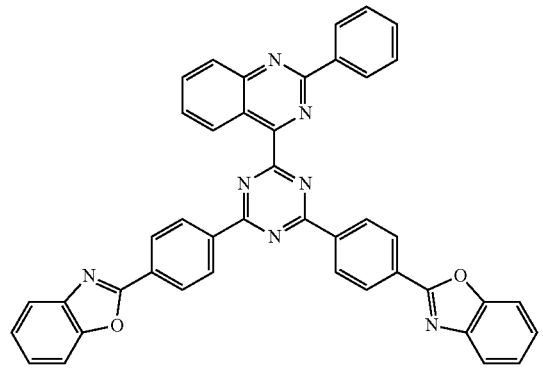
(180)
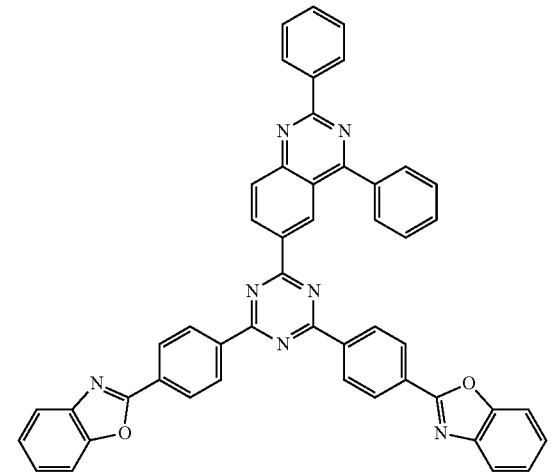
(181)
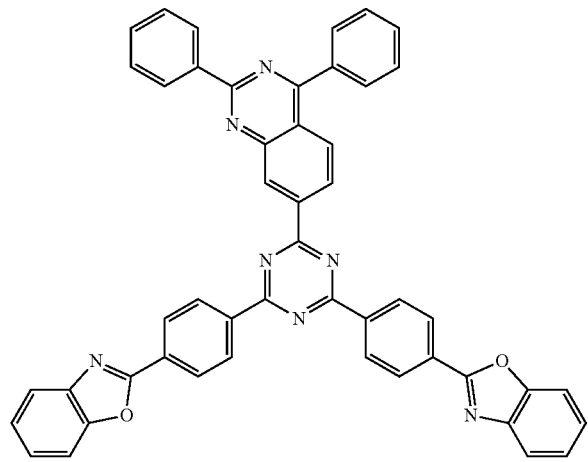
(182)
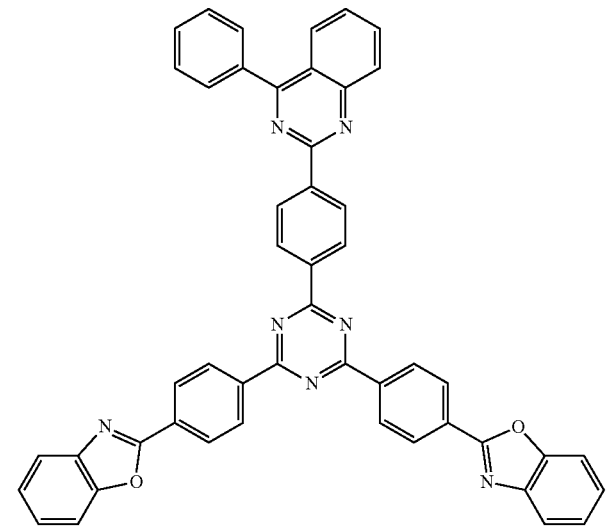

(183)
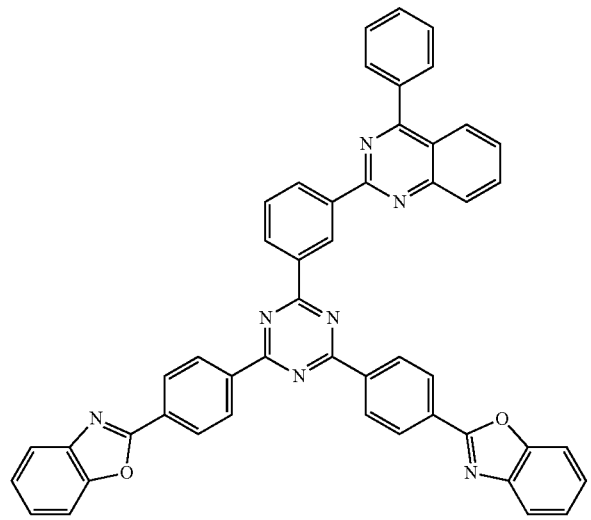
(184)
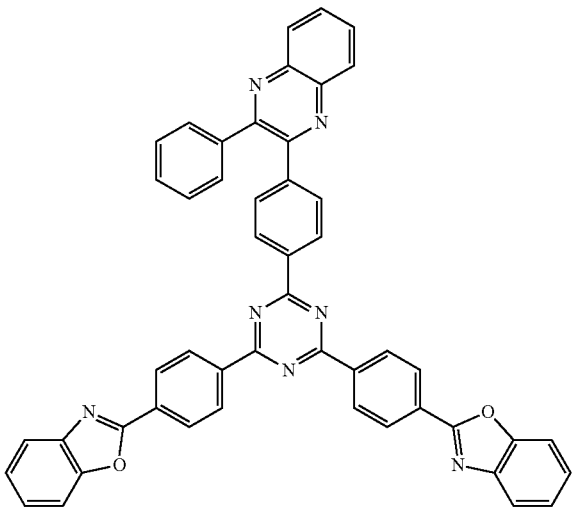
(185)
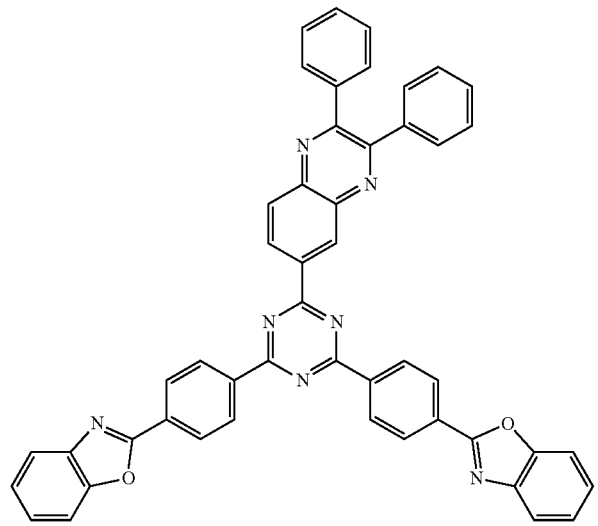
(186)
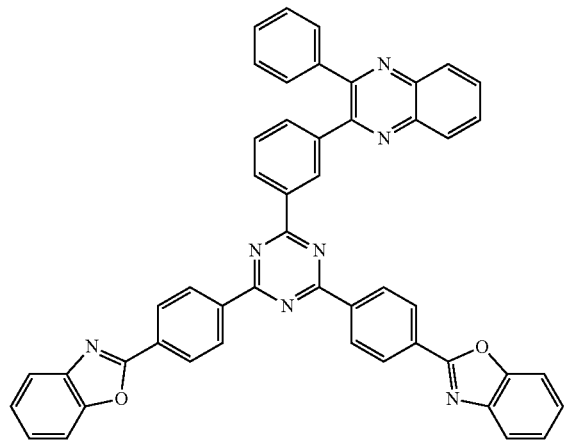
(187)
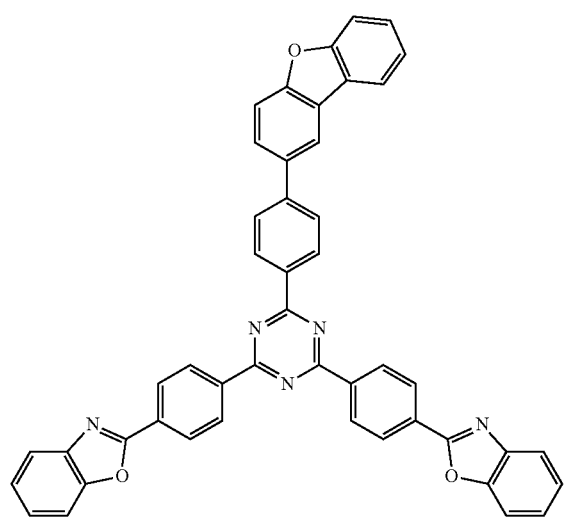
(188)
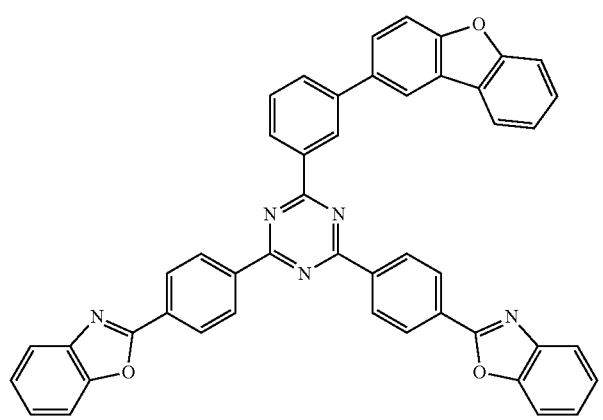

-continued
(189)
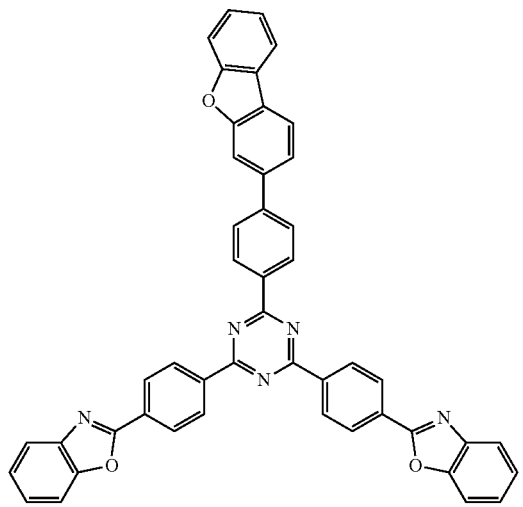
(190)
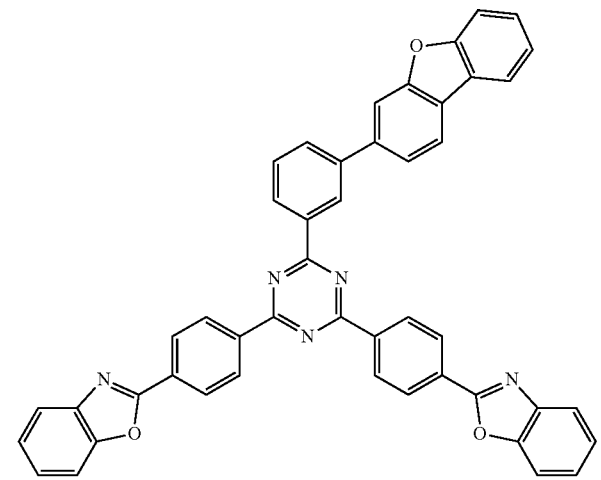
(191)
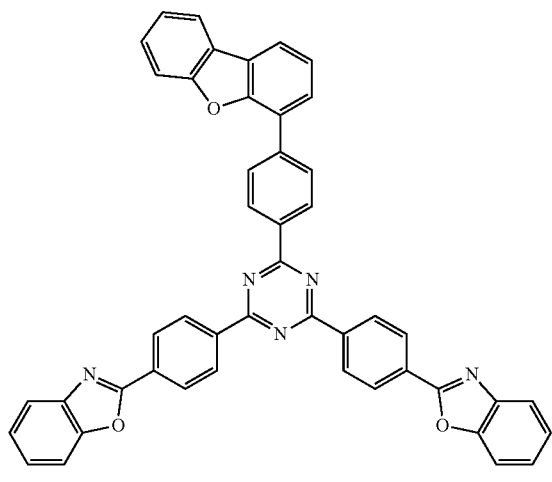
(192)
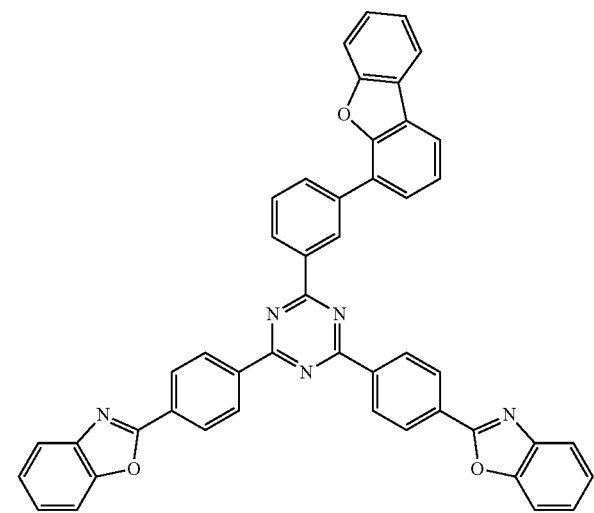
(193)
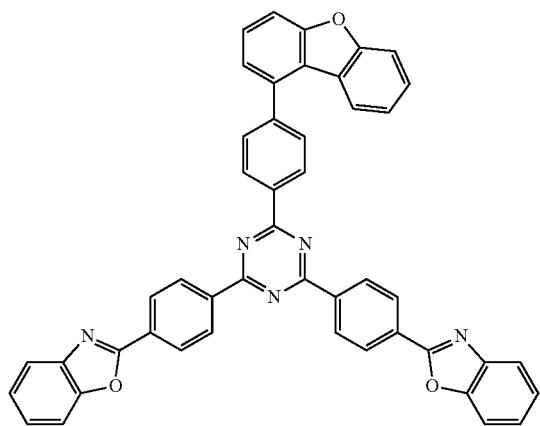
(194)
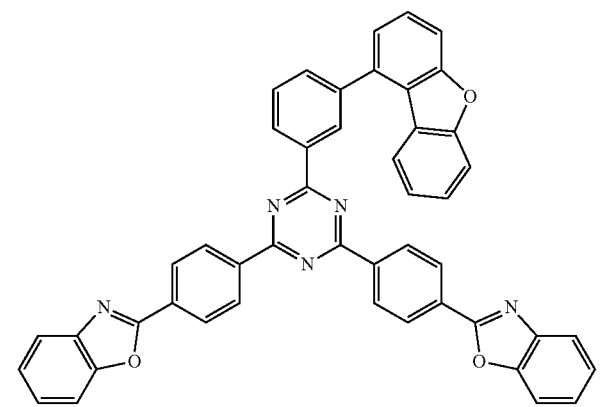

(195)
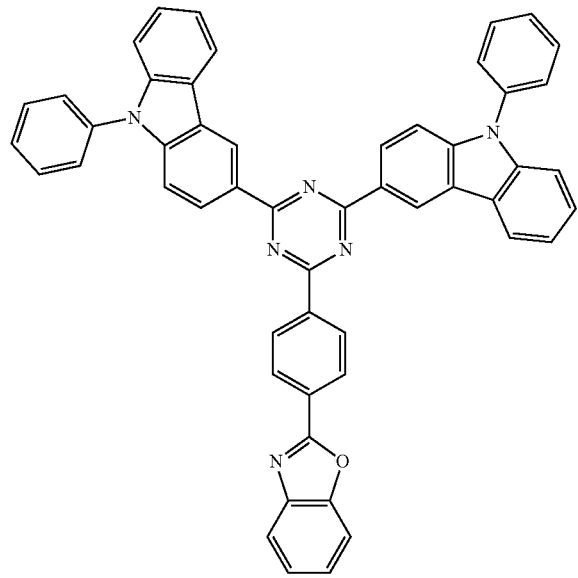
(196)
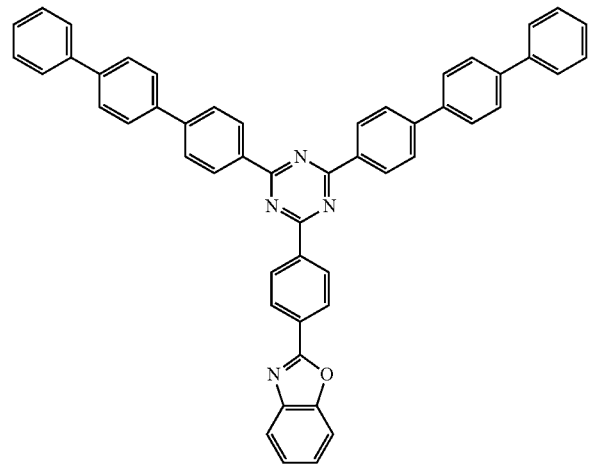
(197)
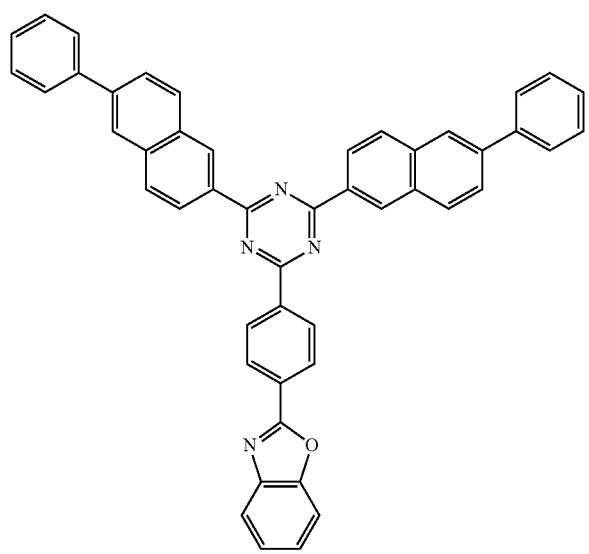
(198)
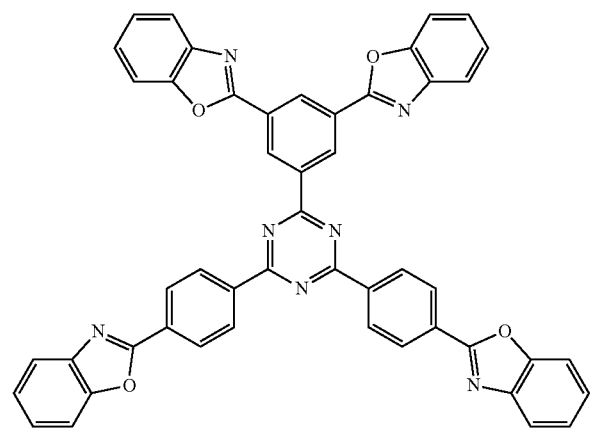

-continued
(199)
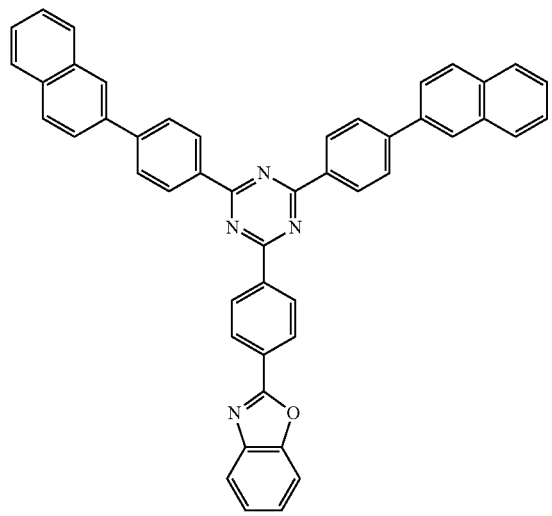
(200)
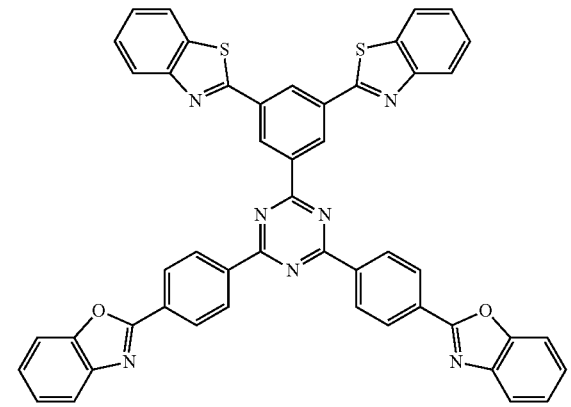
(201)
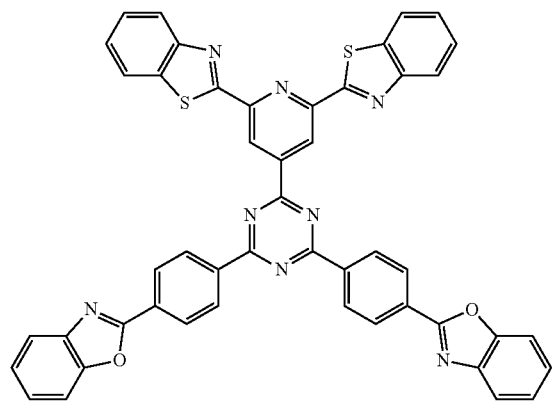
(202)
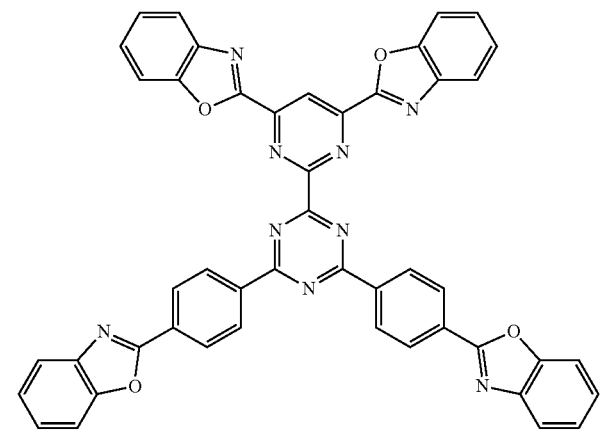
(203)
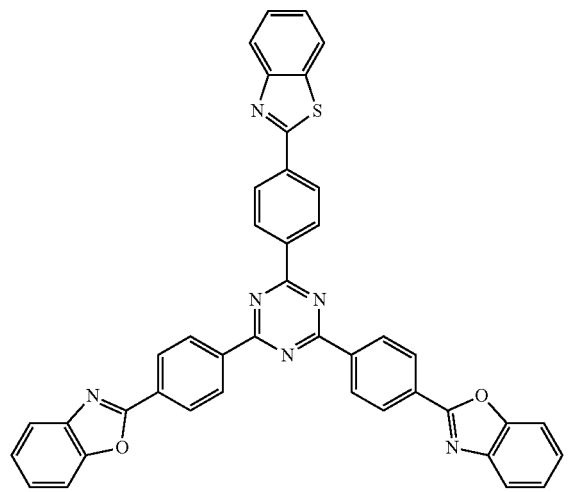
(204)
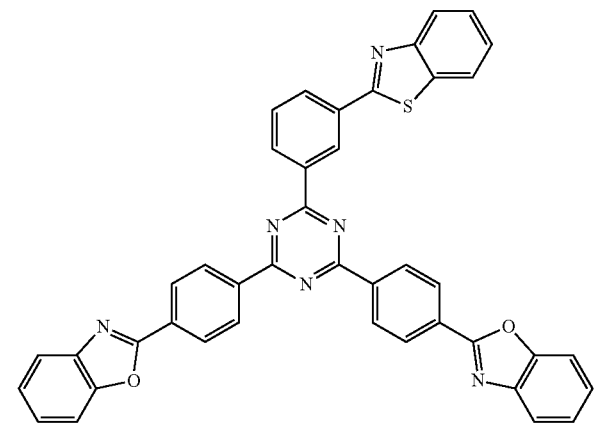

-continued
551
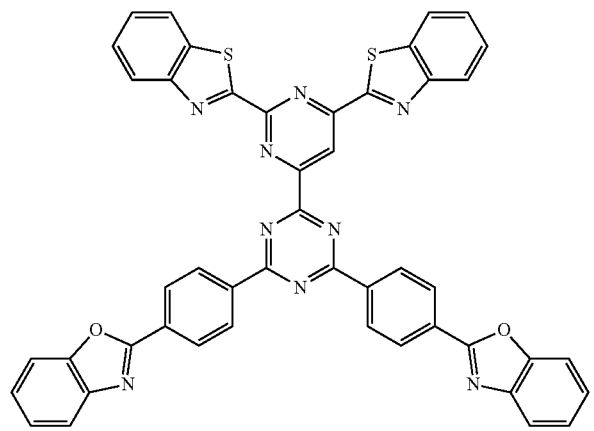
(205)
552
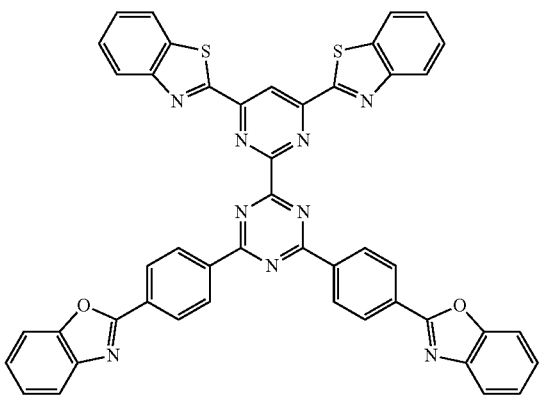
(206)
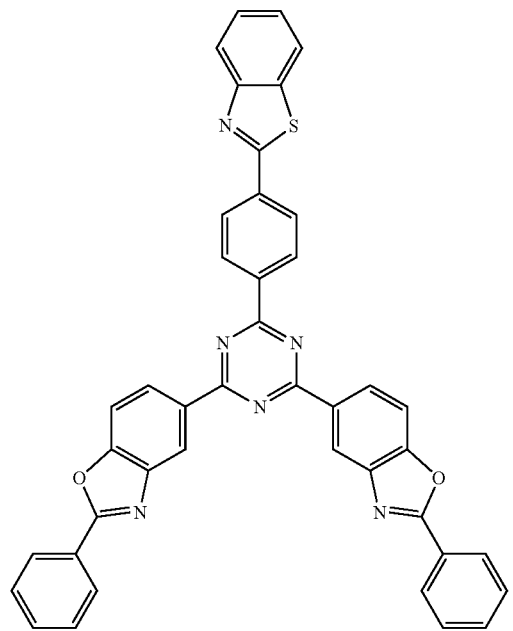
(207)
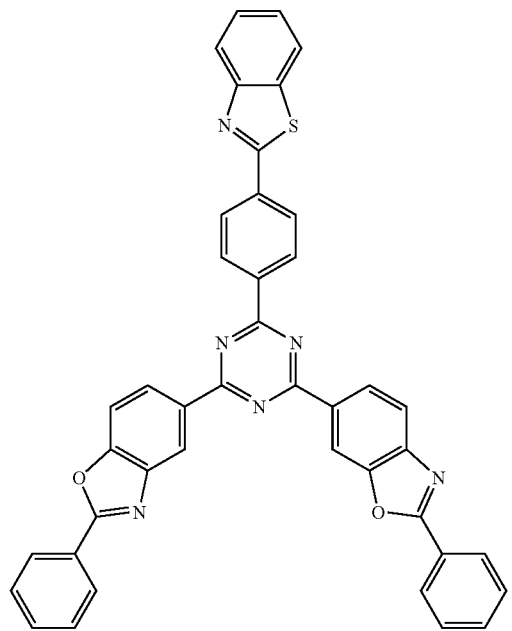
(208)
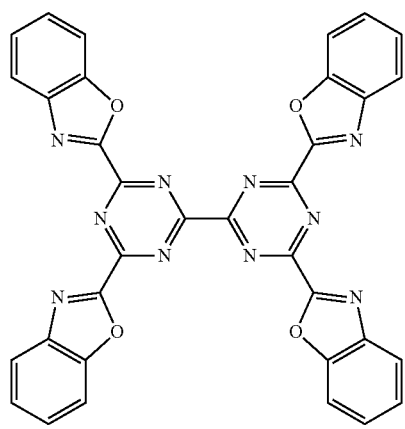
(209)
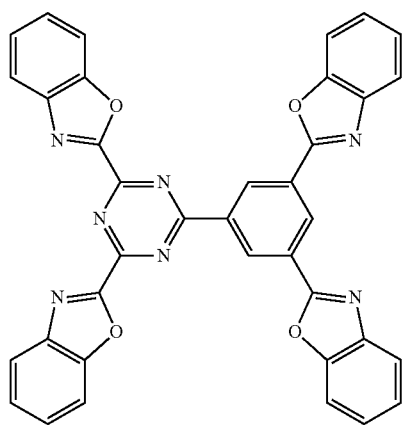
(210)

553 554
-continued
(211)
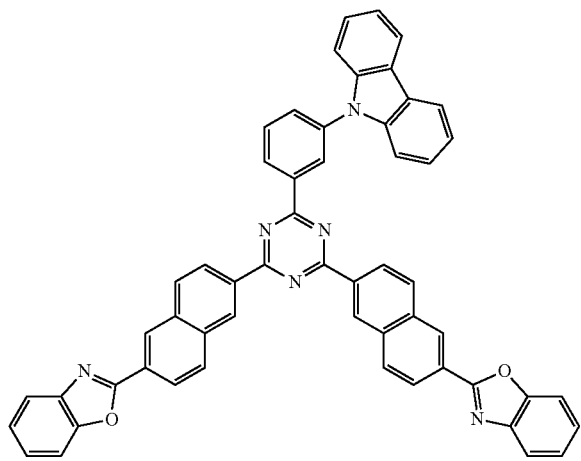
(212)
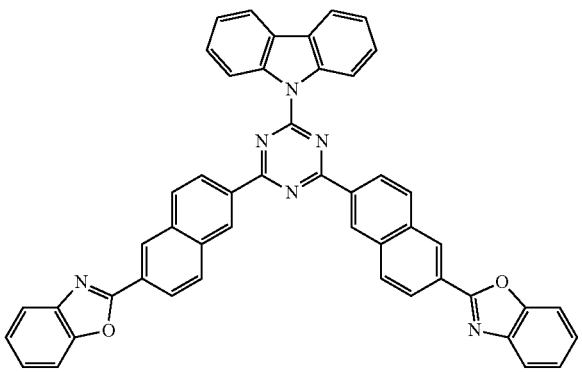
(213)
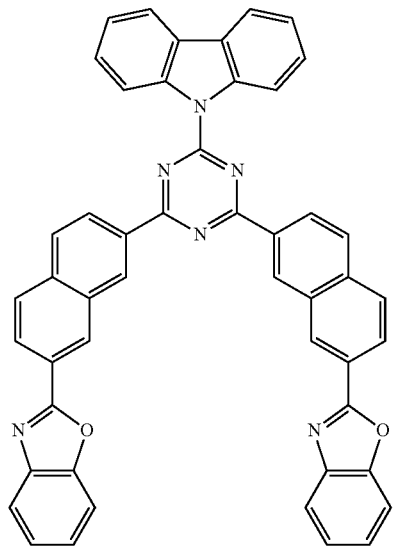
(214)
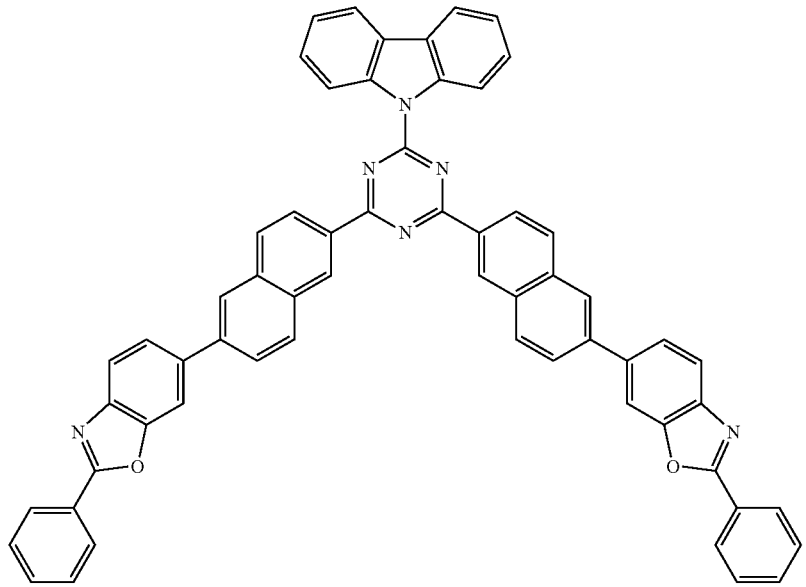

(215)
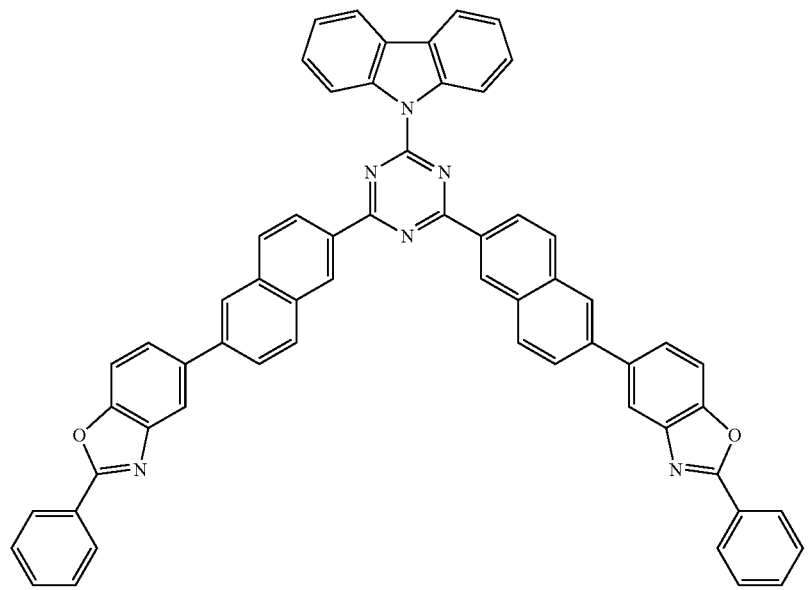
(216)
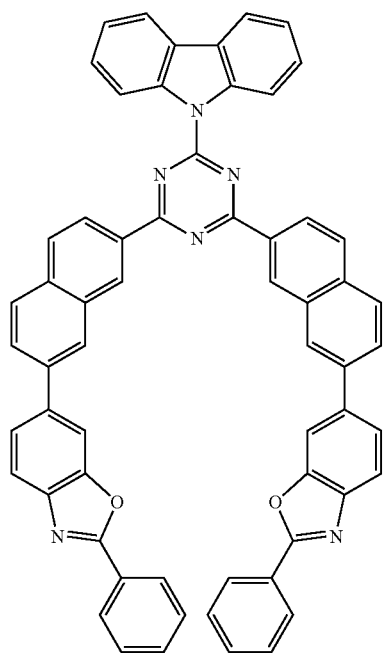
(217)
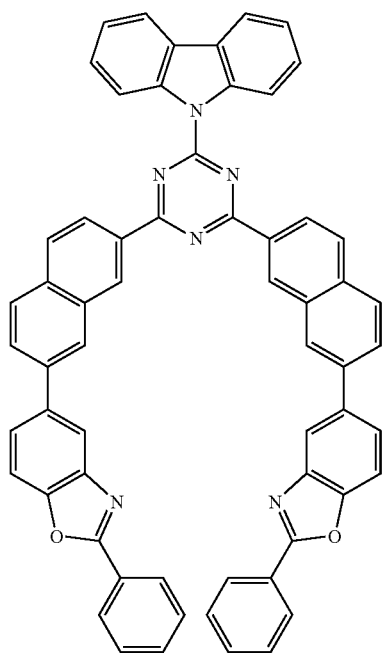

(218)
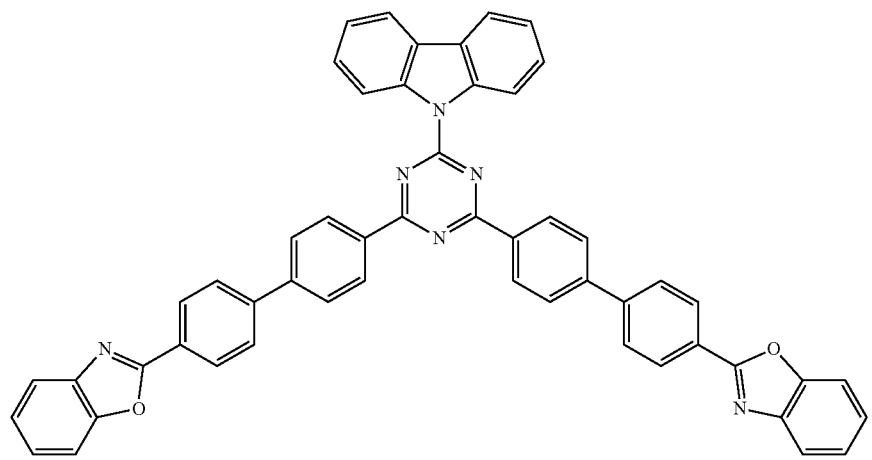
(219)
(220)
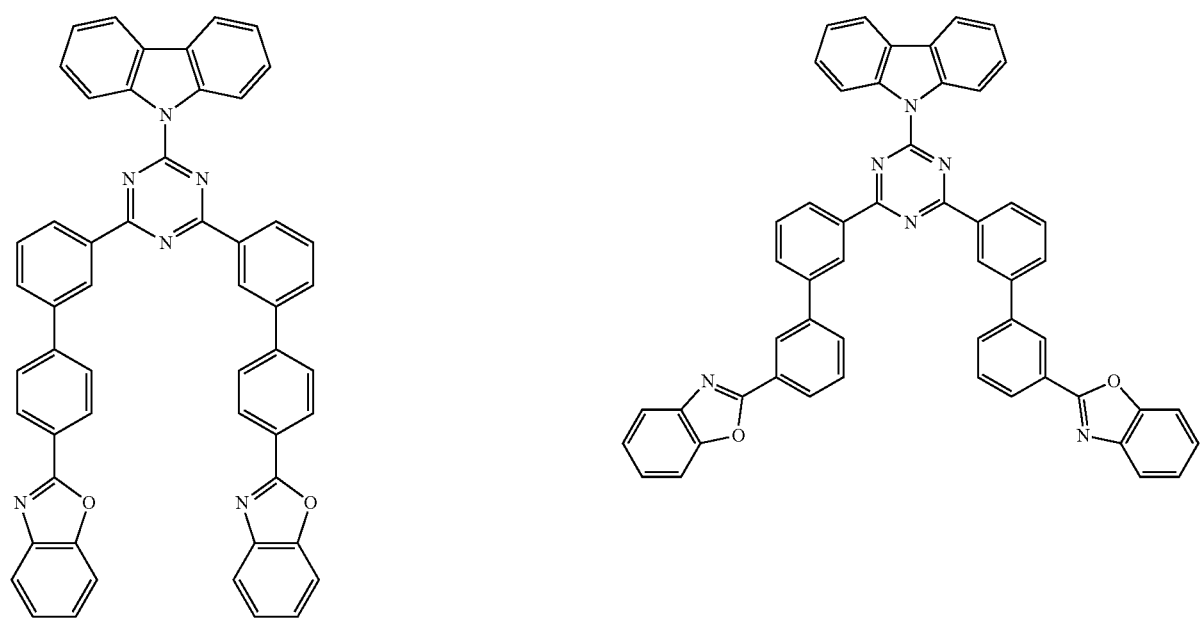
(221)
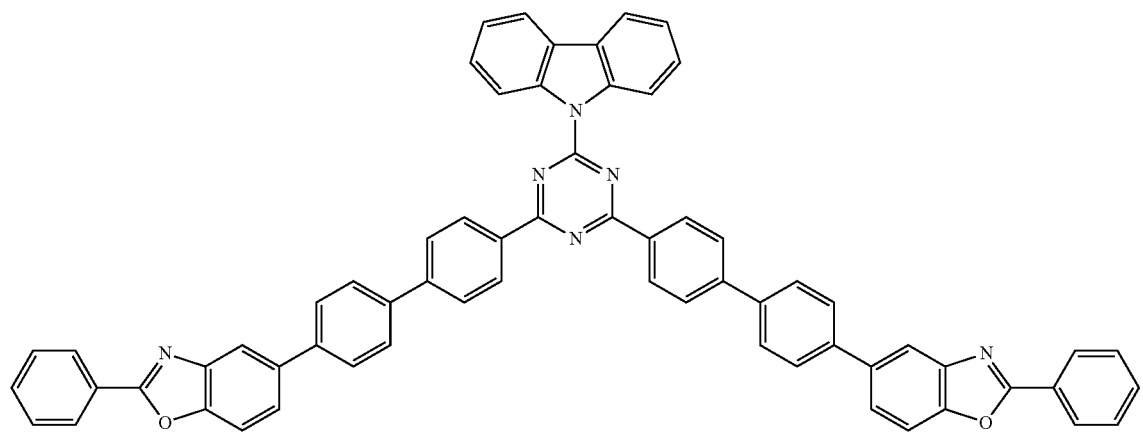

(222)
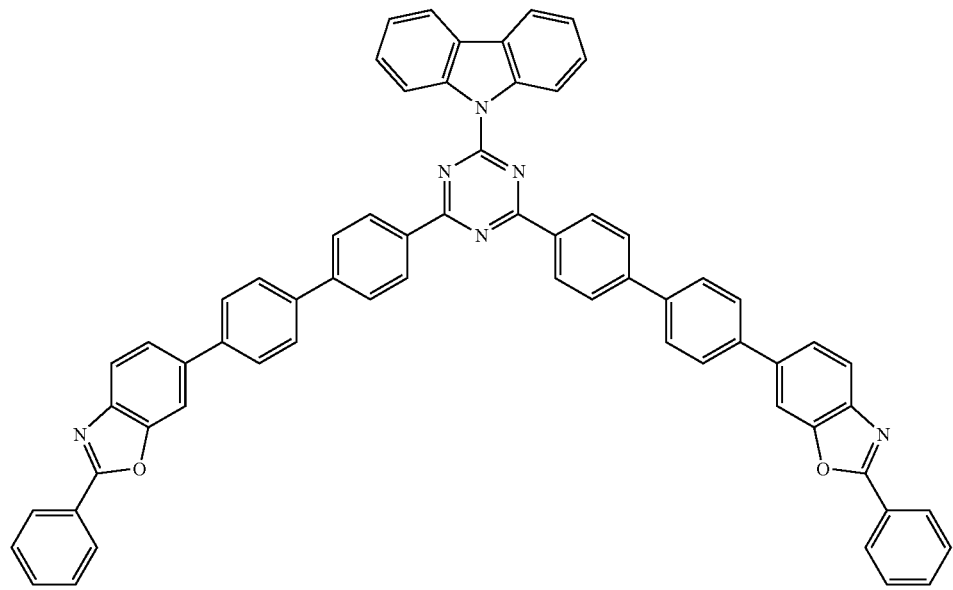
(223)
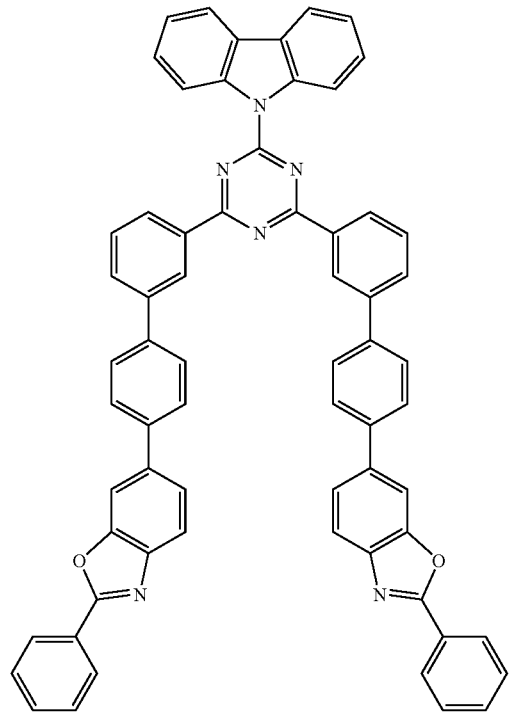
(224)
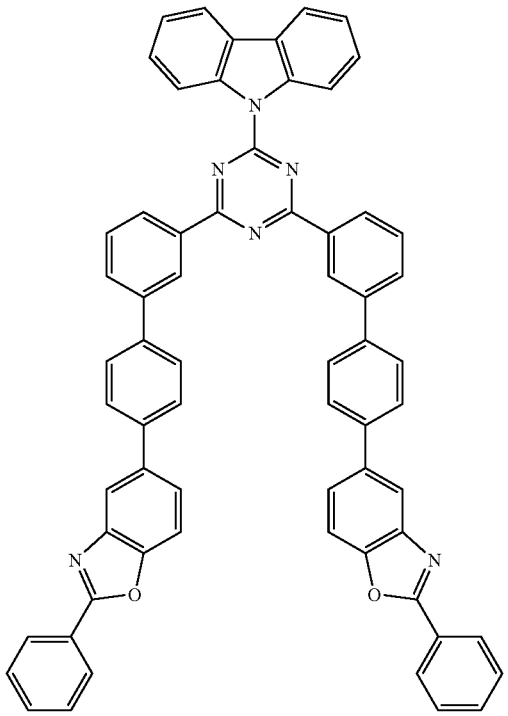

-continued
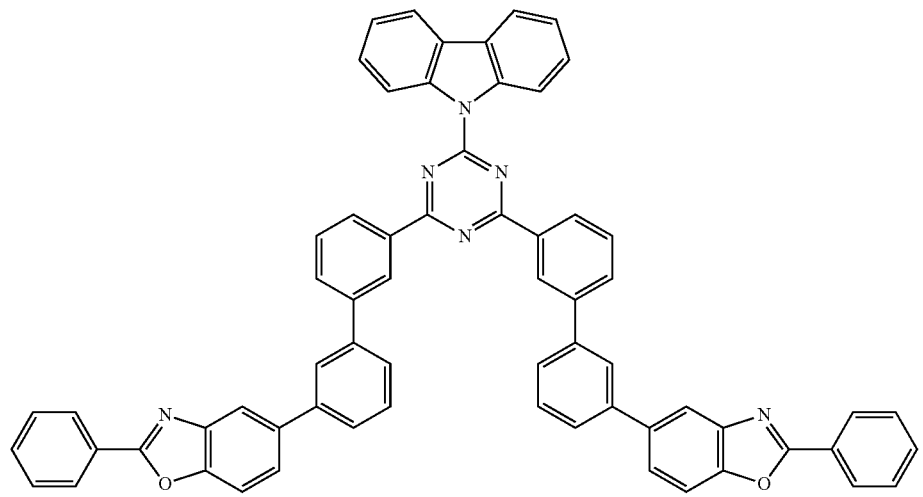
(225)
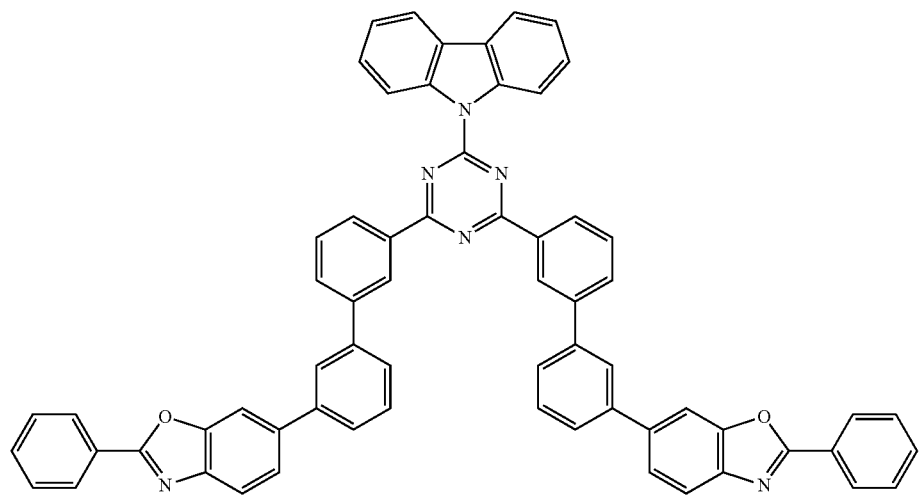
(226)
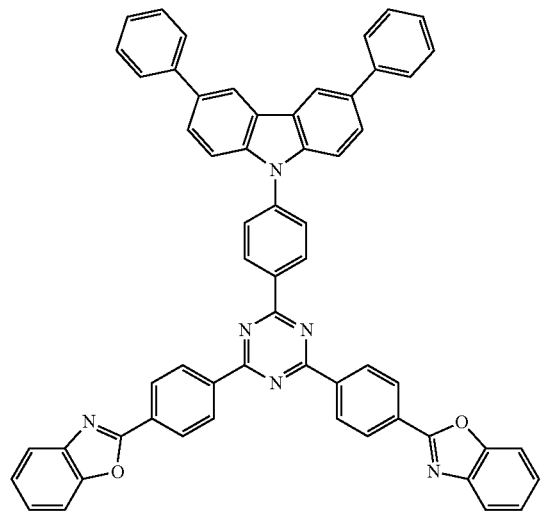
(227)
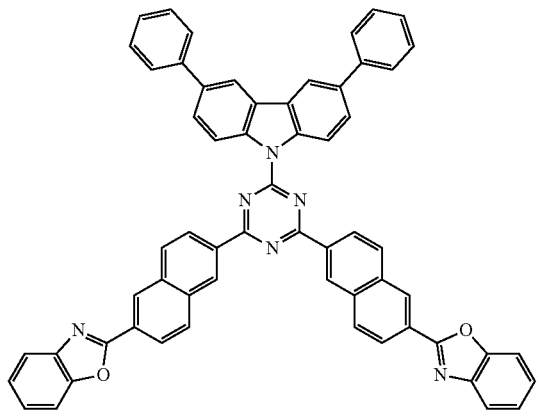
(228)

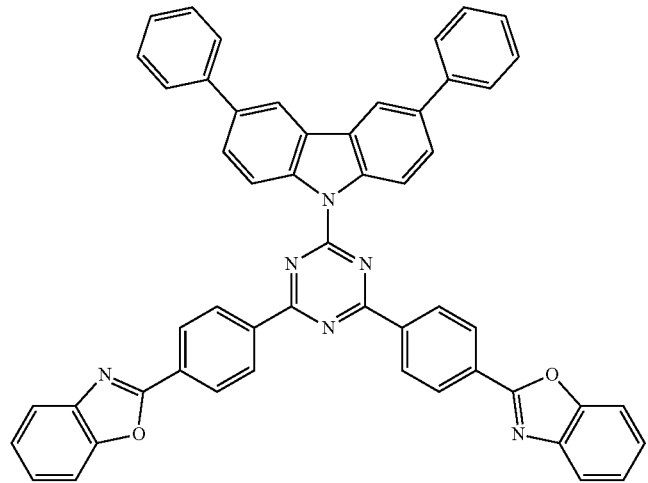
(229)
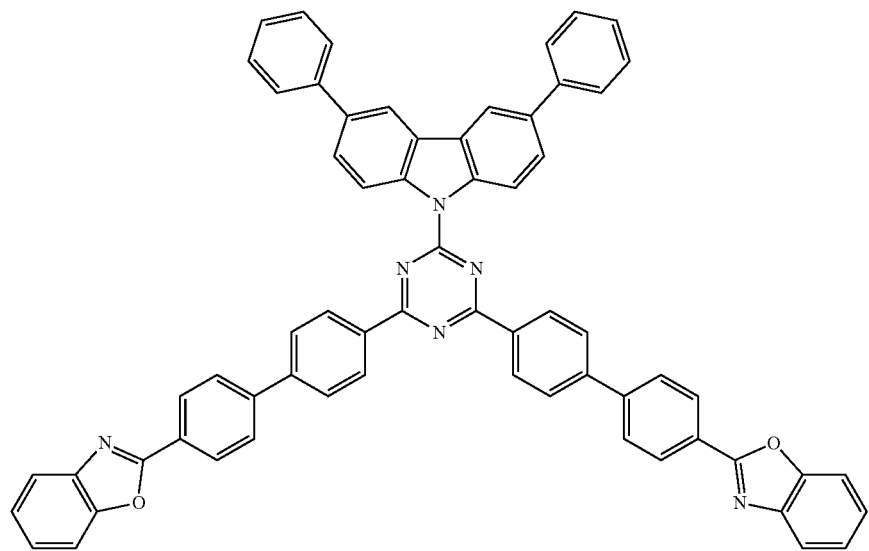
(230)

-continued
(231)
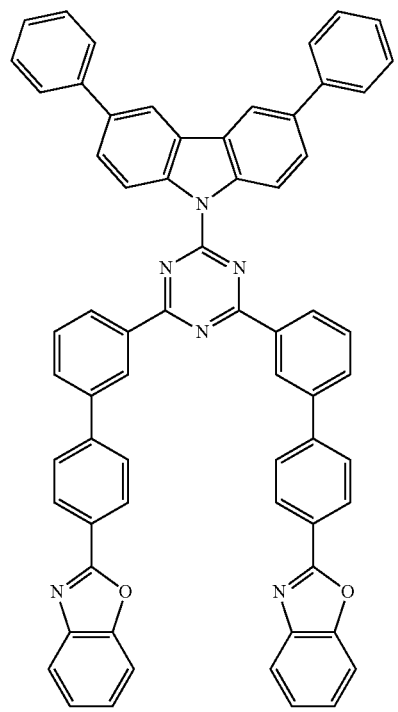
(232)
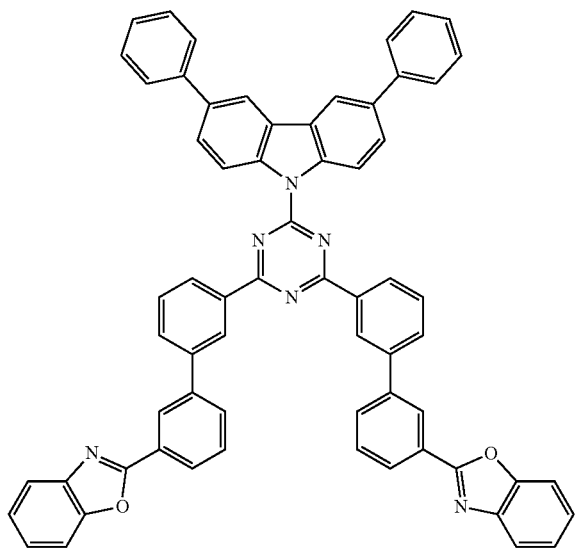
(233)
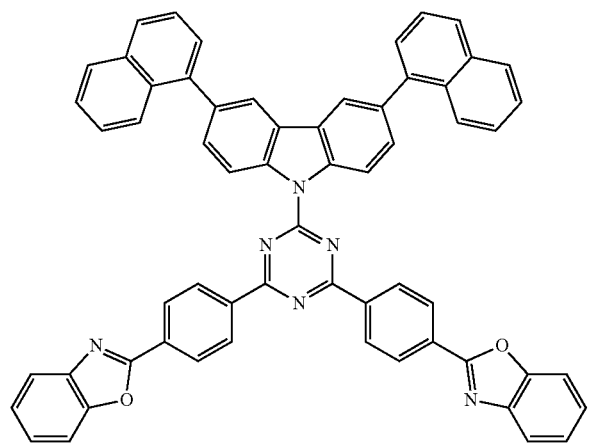
(234)
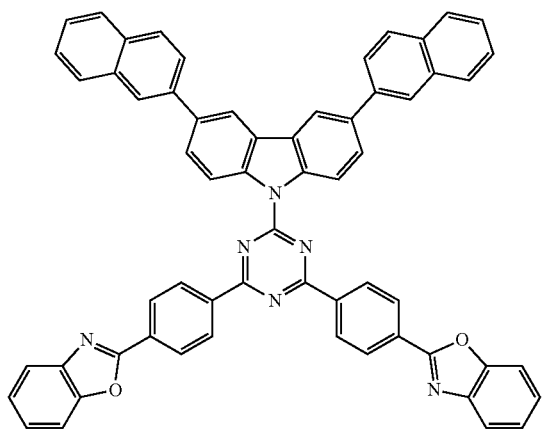

567 568
-continued
(235)
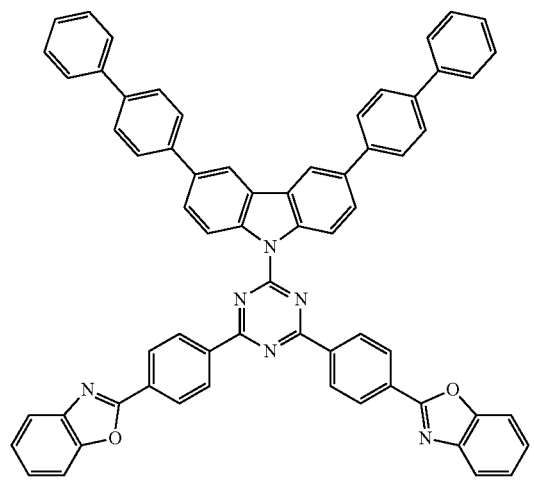
(236)
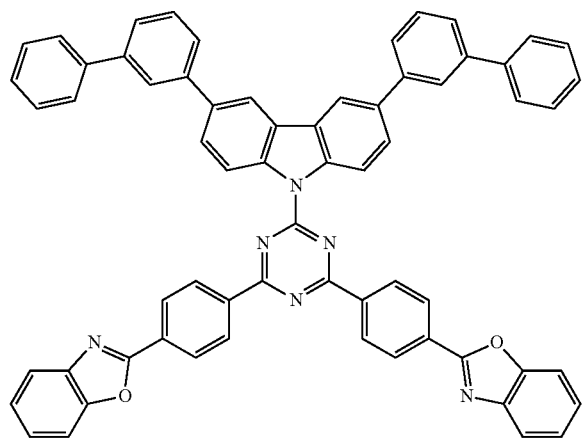
(237)
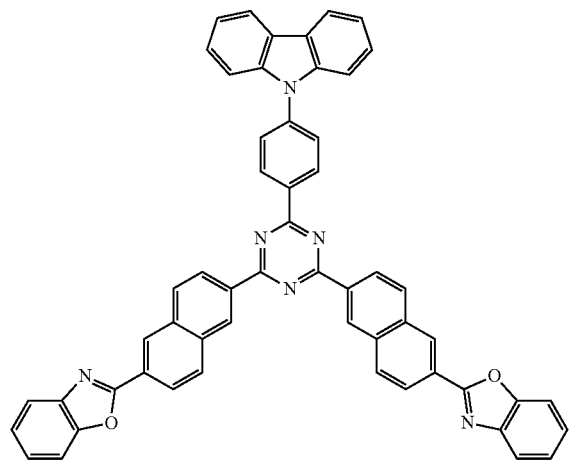
(238)
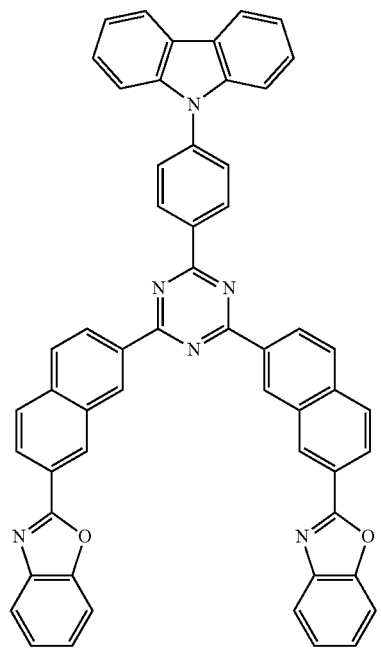

(239)
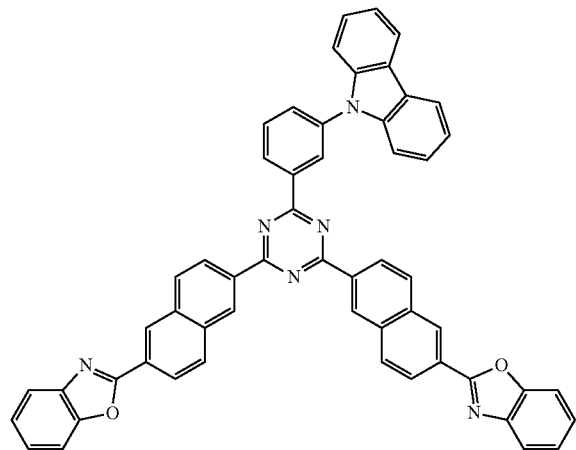
(240)
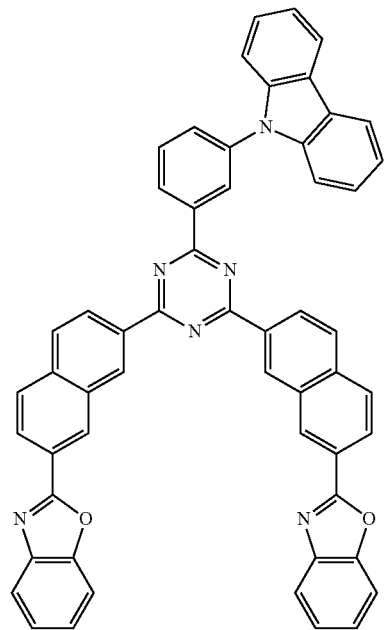
(241)
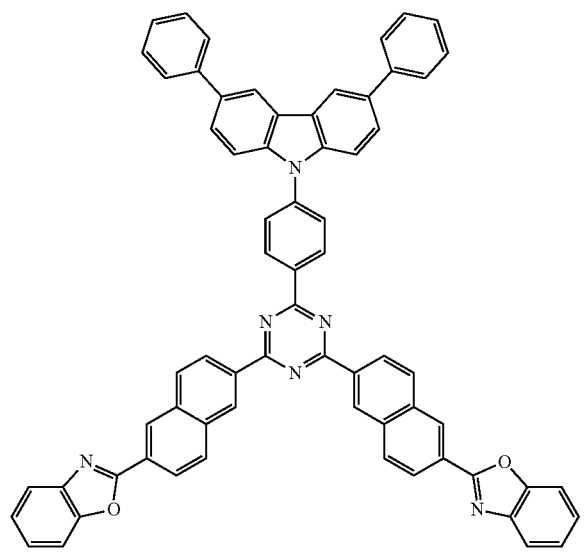
(242)
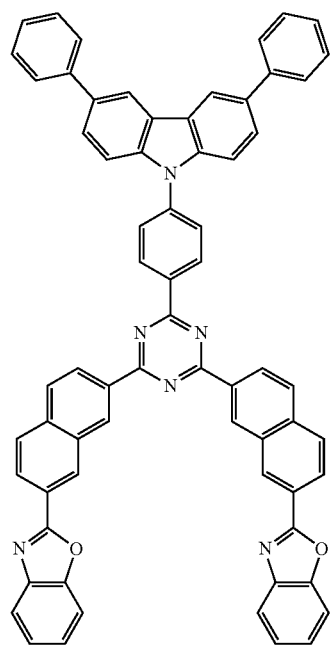

-continued
(243)
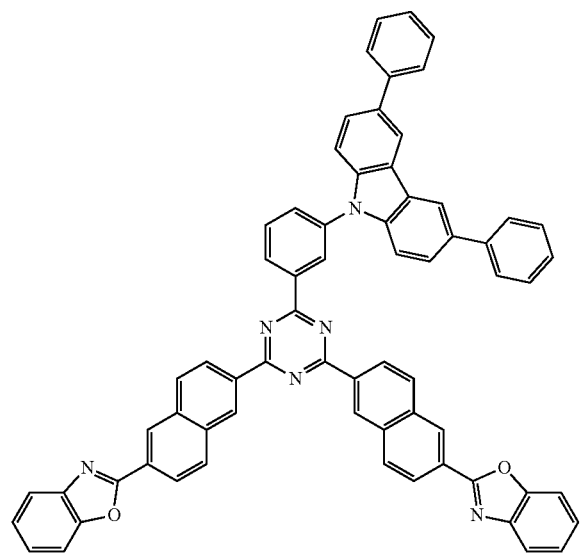
(244)
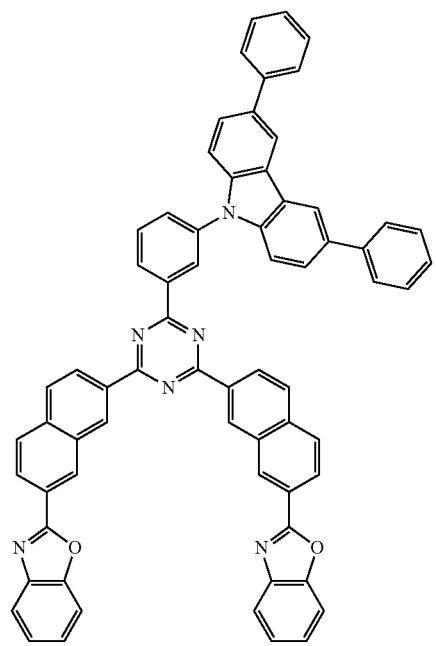
(245)
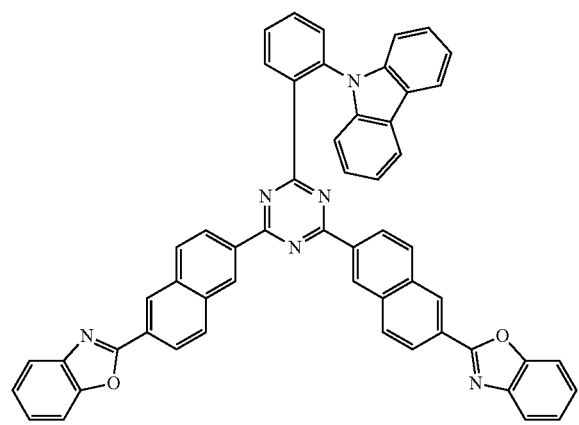
(246)
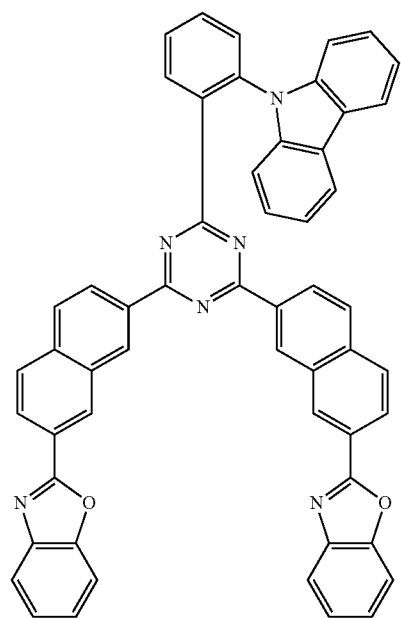

-continued
(247)
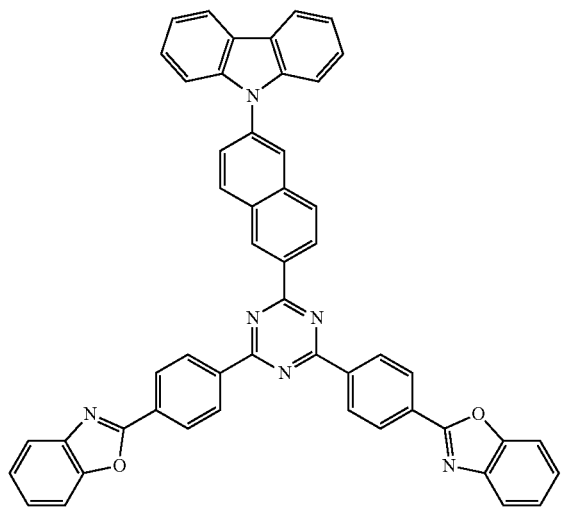
(248)
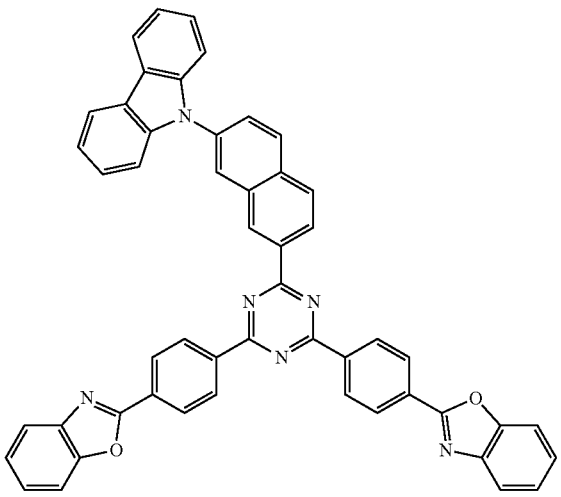
(249)
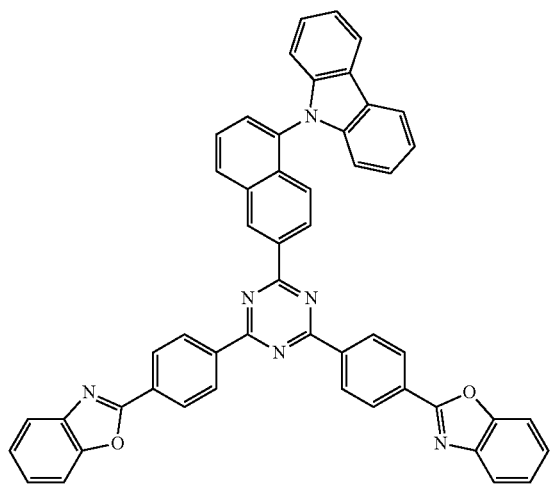
(250)
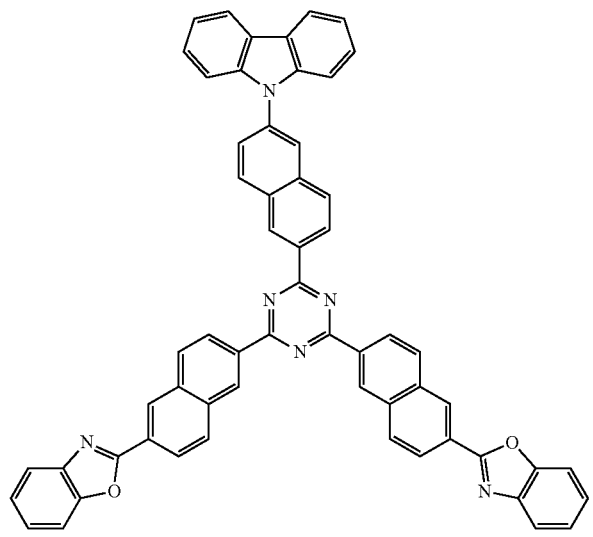
(251)
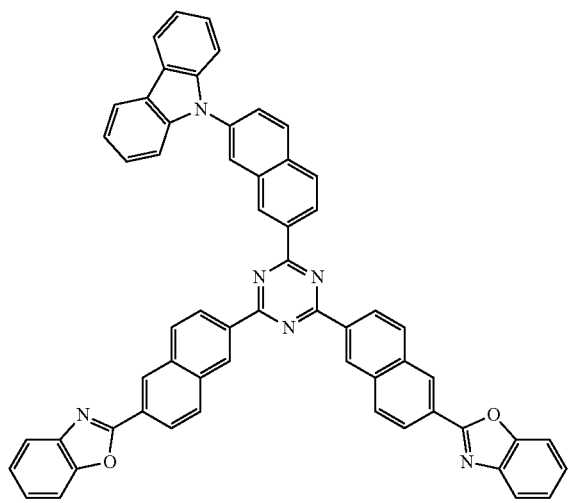
(252)
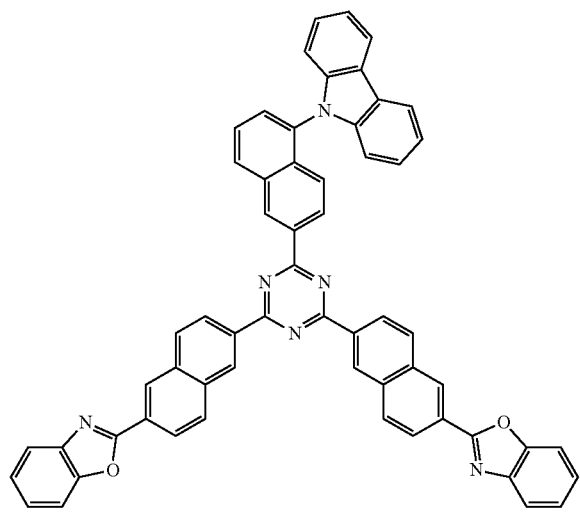

575
-continued
(253)
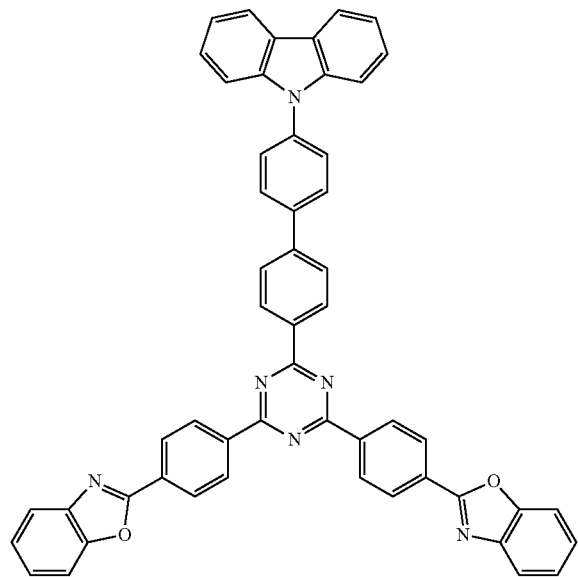
576
(254)
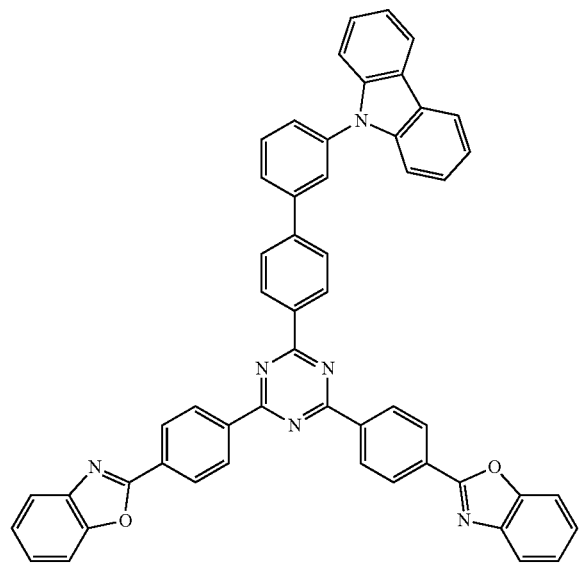
(255)
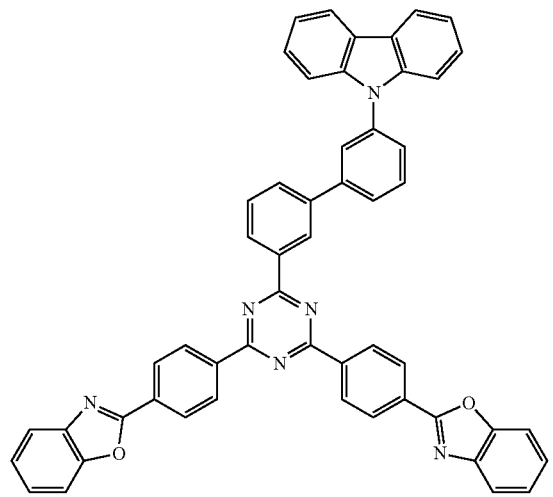
(256)
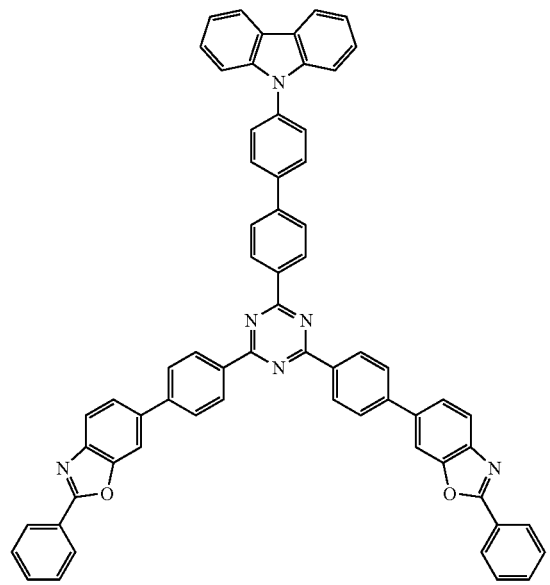

(257)
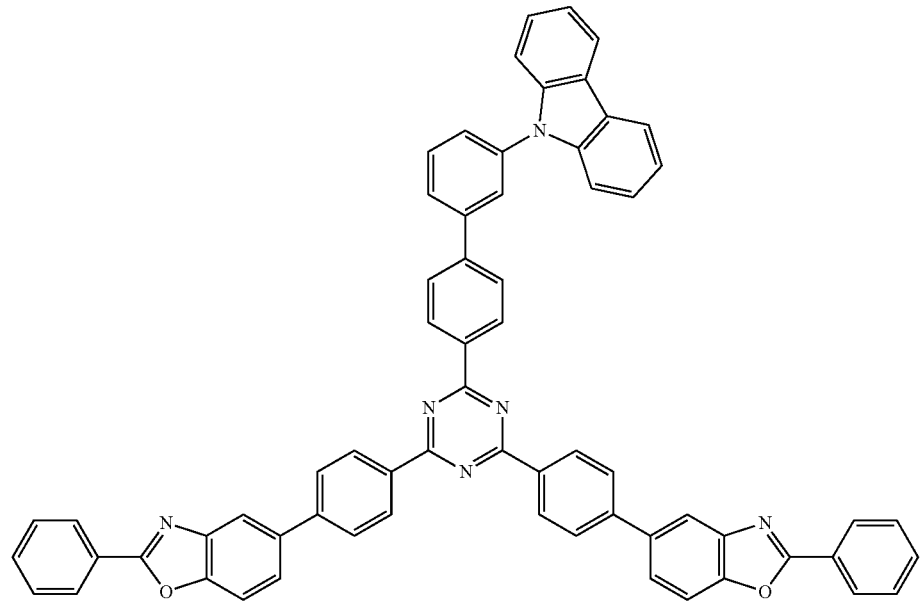
(258)
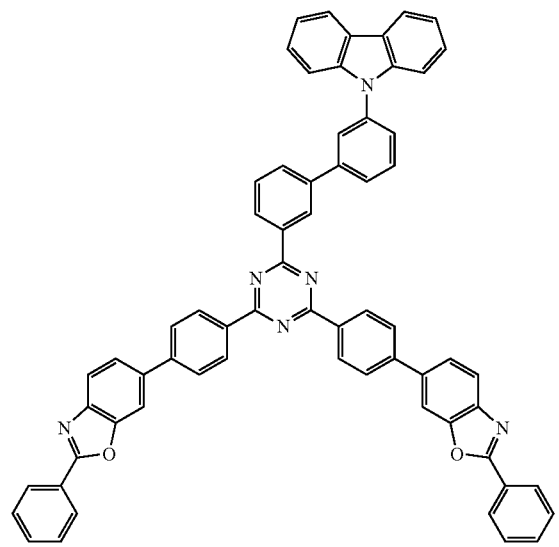
(259)
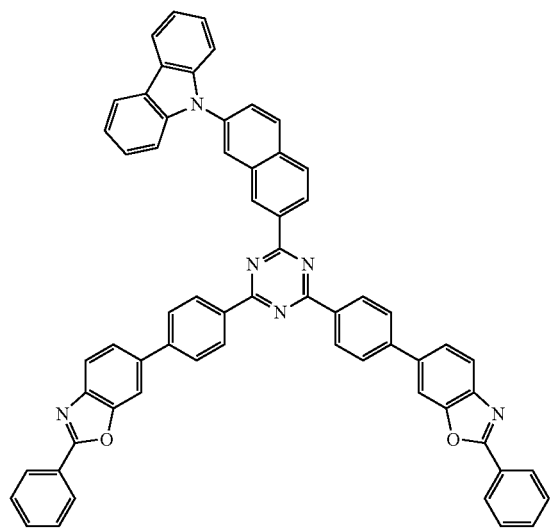

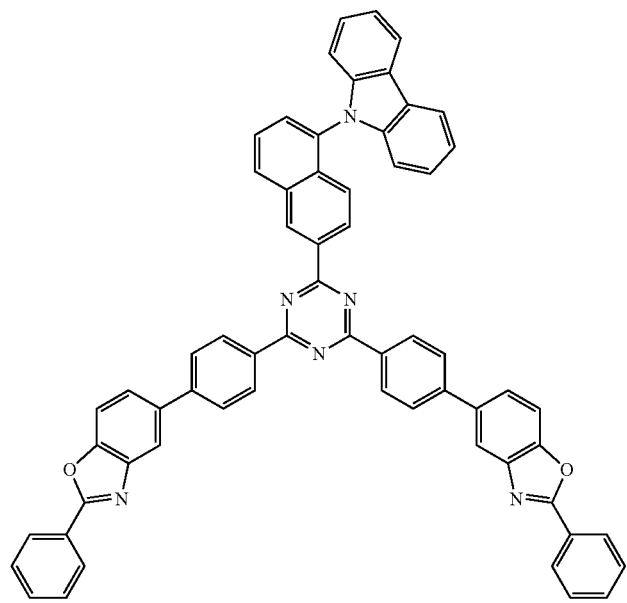
(260)
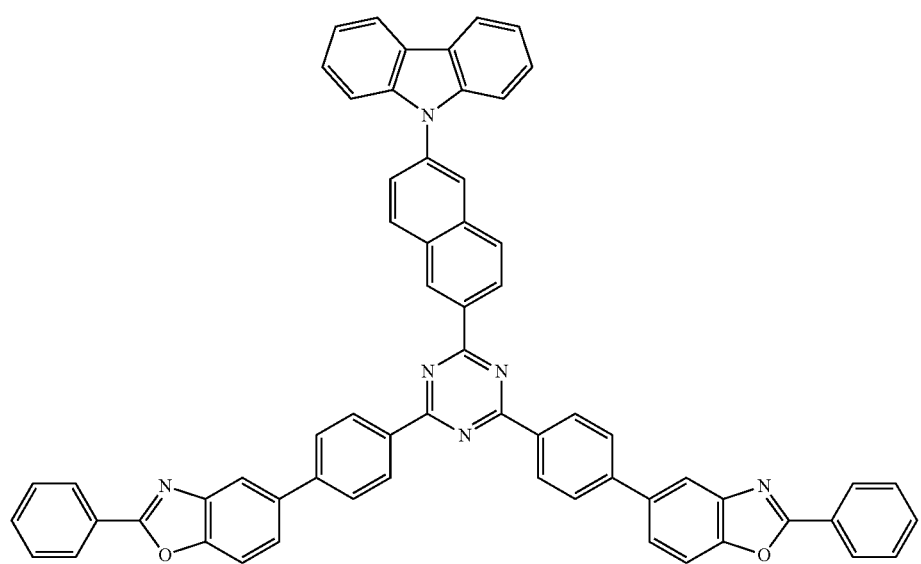
(261)

(262)
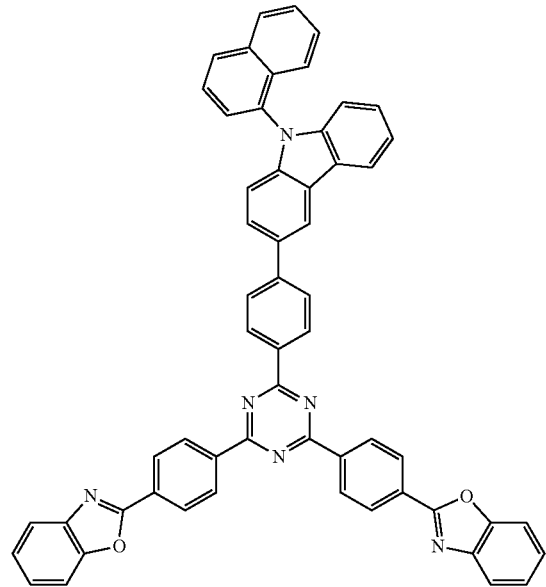
(263)
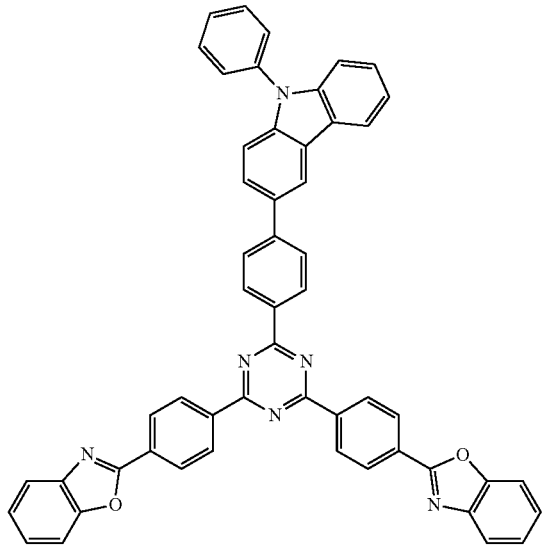
(264)
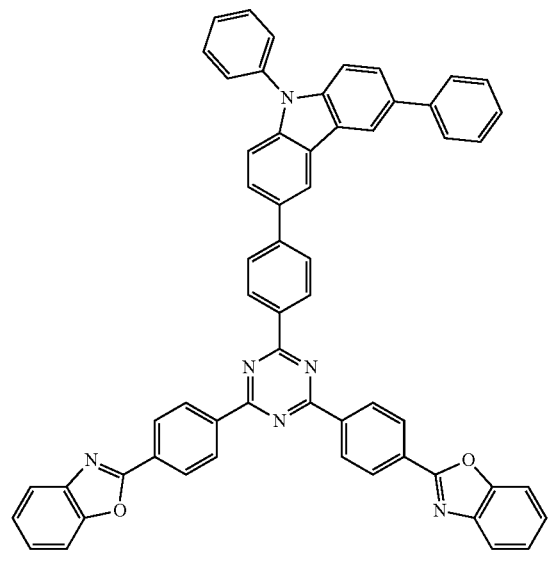
(265)
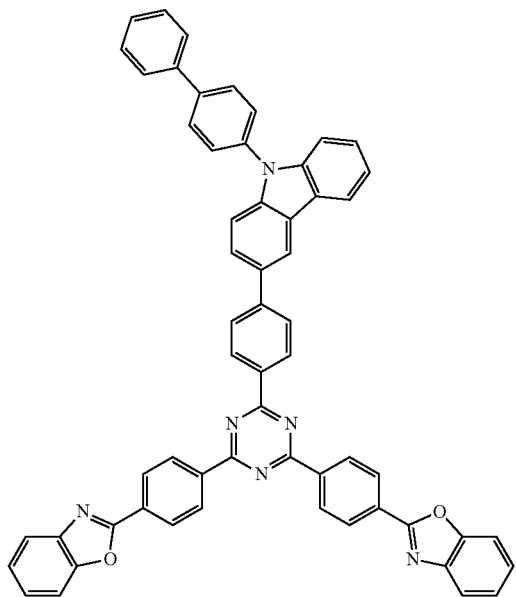

(266)
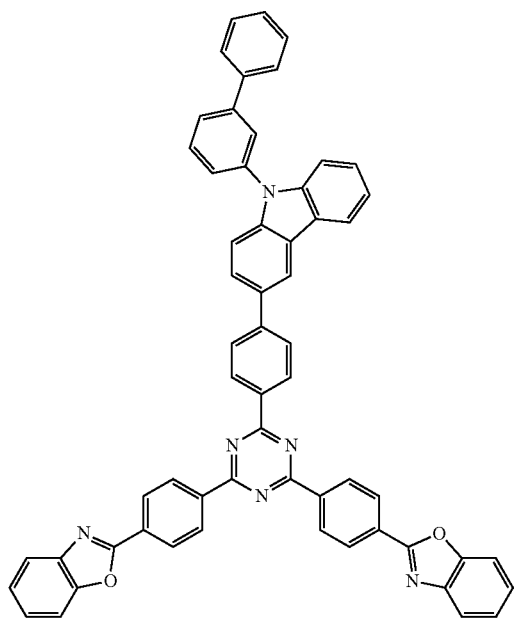
(267)
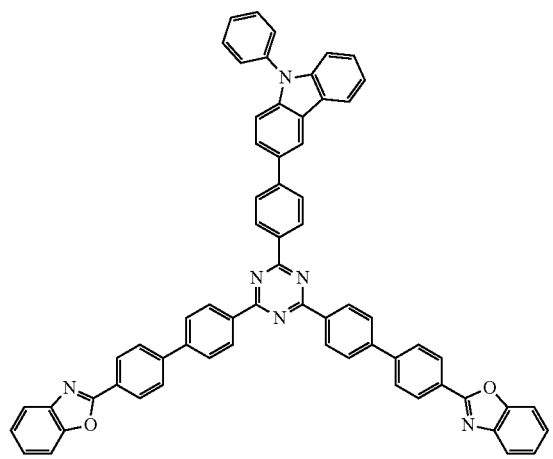
(268)
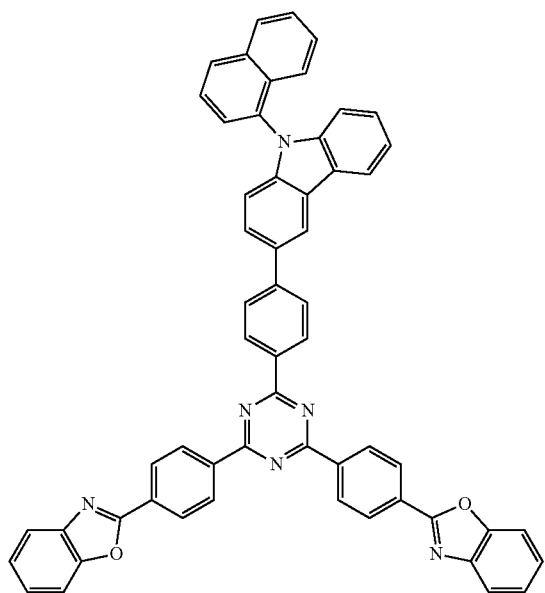
(269)
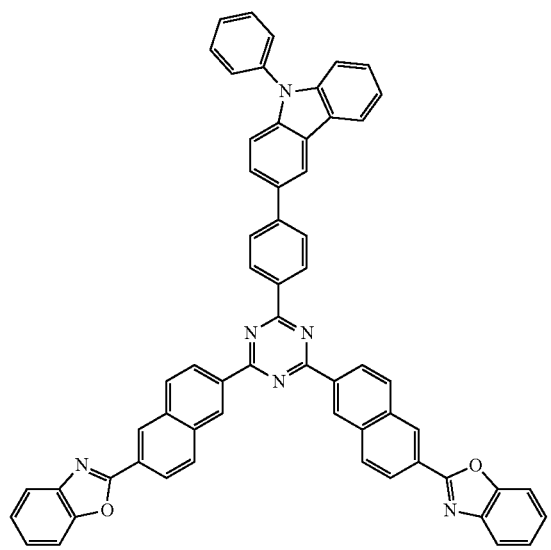

(270)
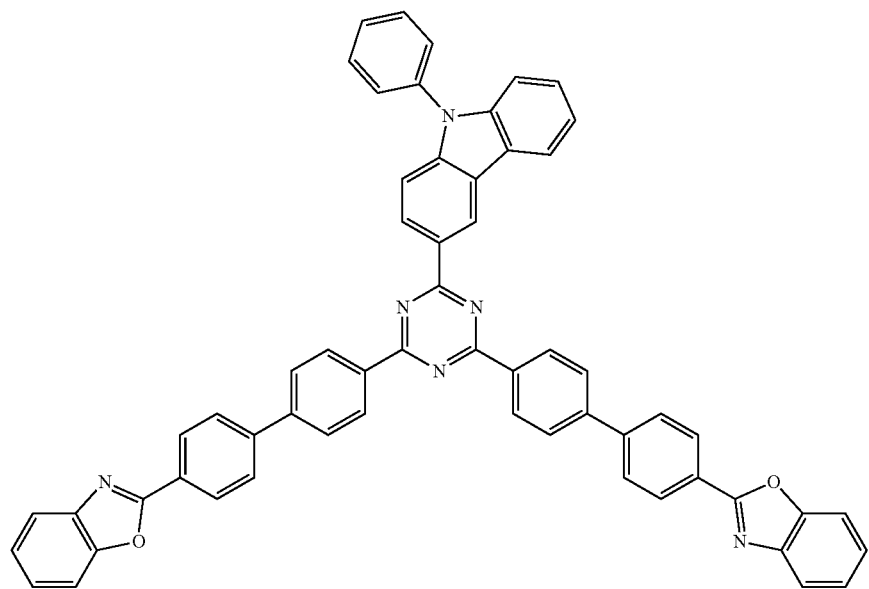
(271)
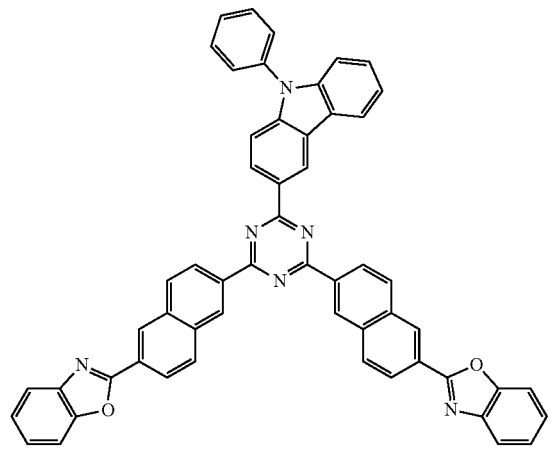
(272)
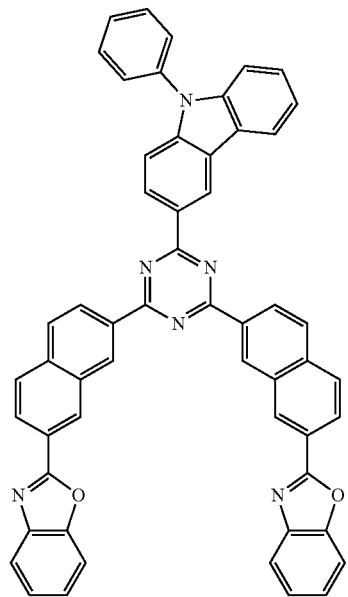

-continued
(273)
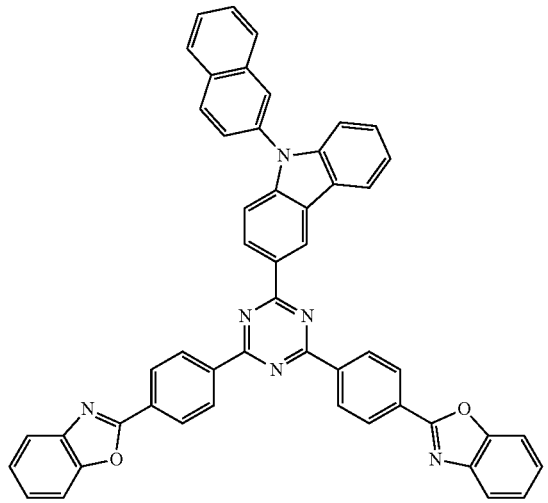
(274)
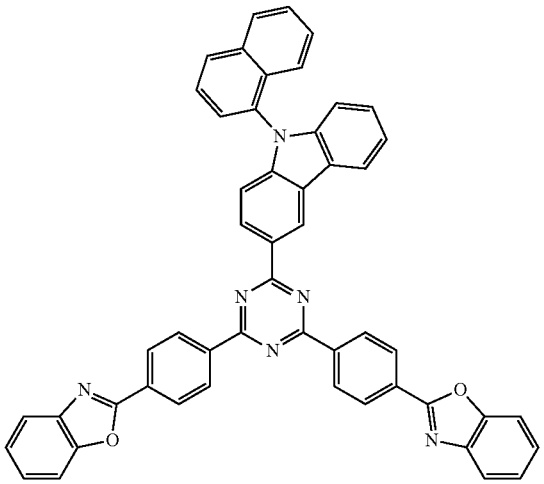
(275)
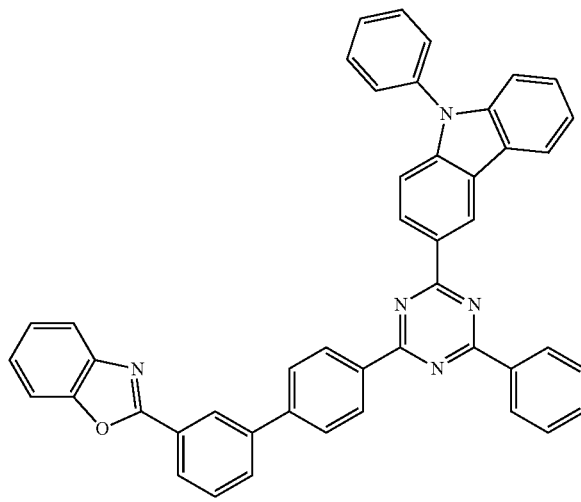
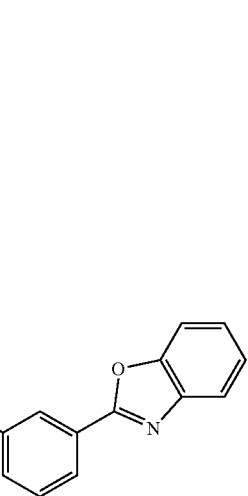
(276)
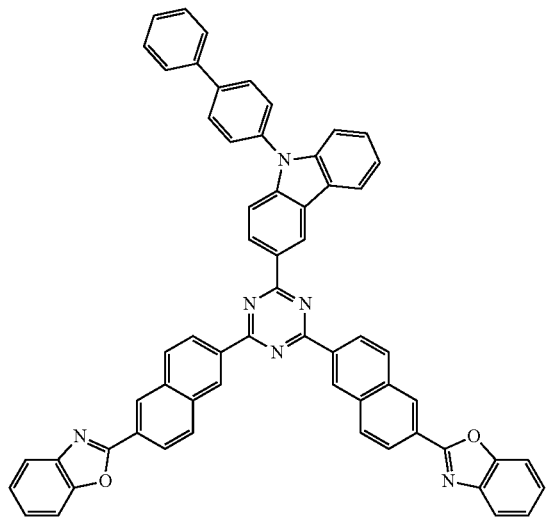
(277)
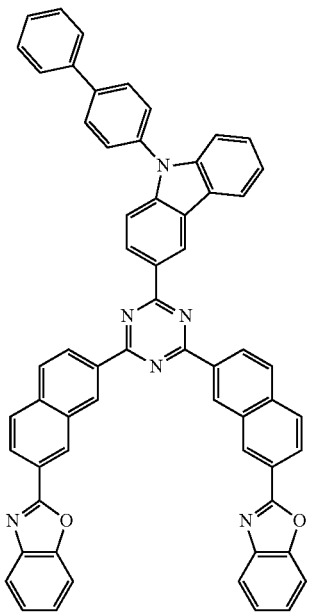

(278)
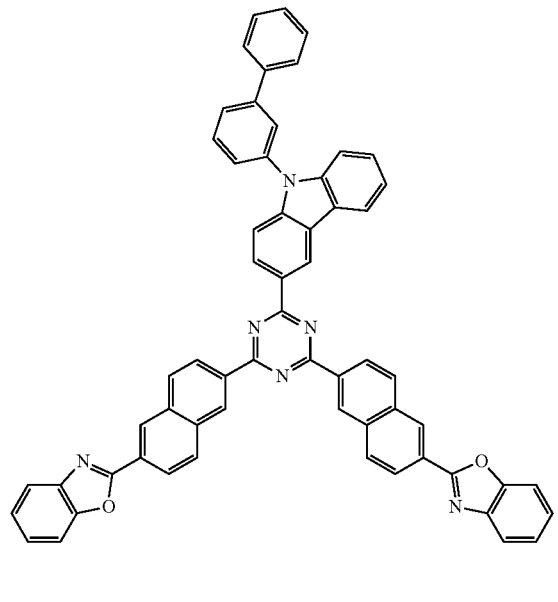
(279)
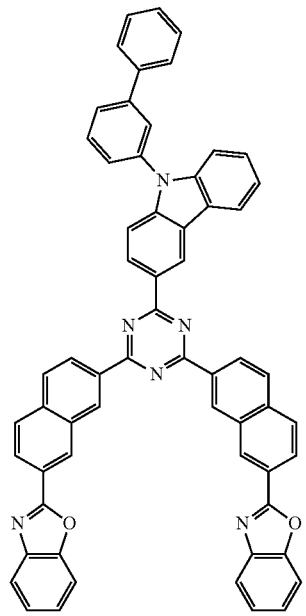
(280)
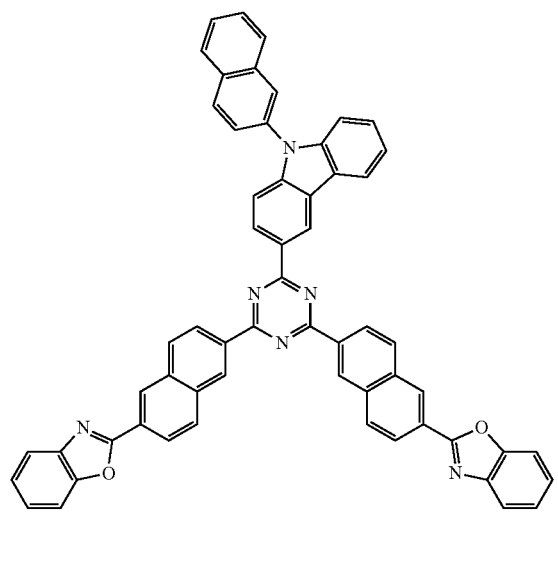
(281)
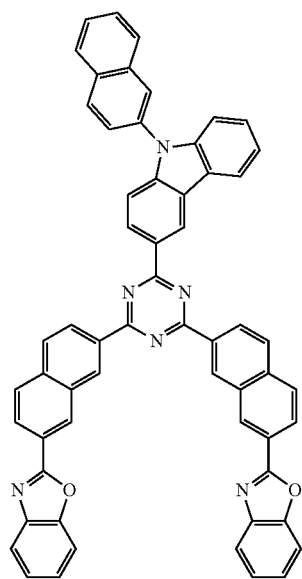

591 592
-continued
(282)
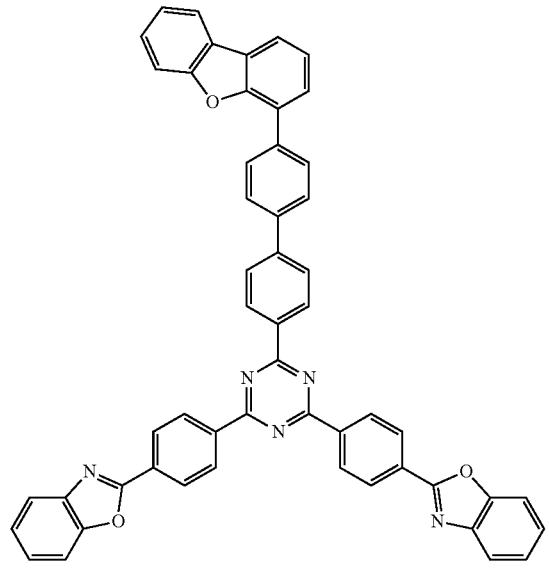
(283)
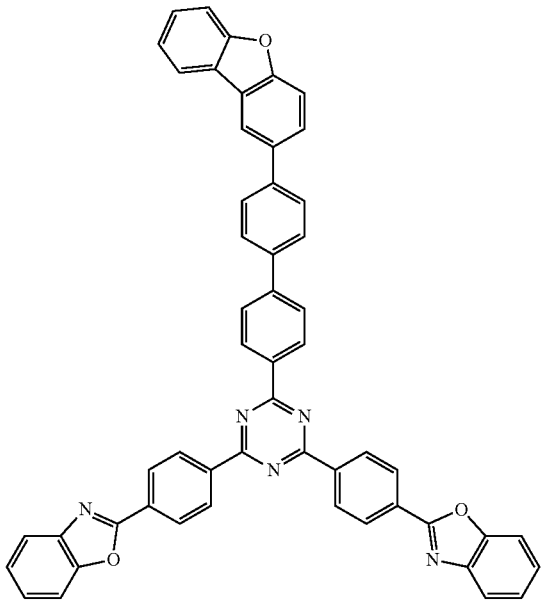
(284)
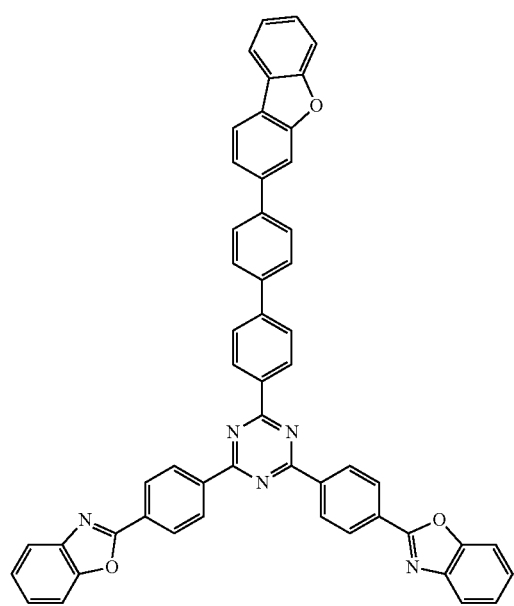

-continued
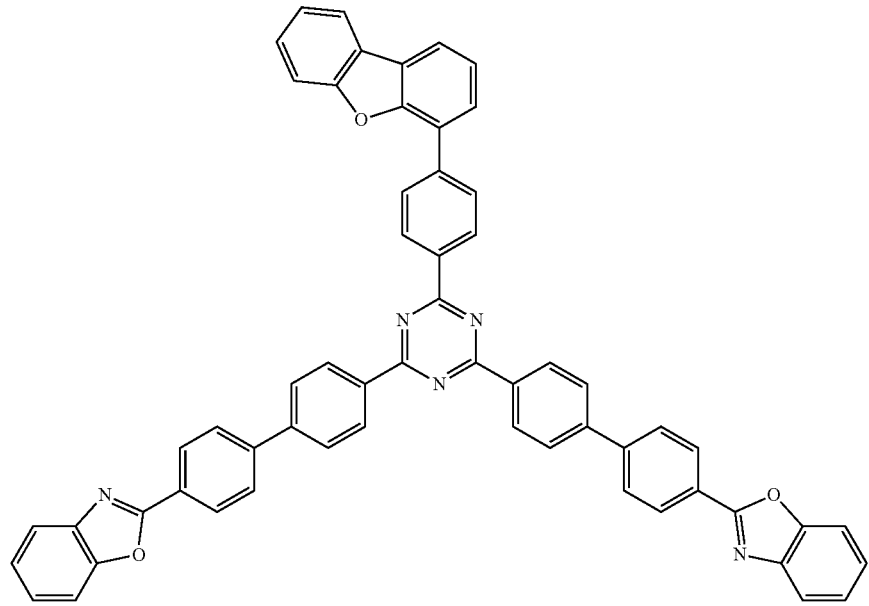
(285)
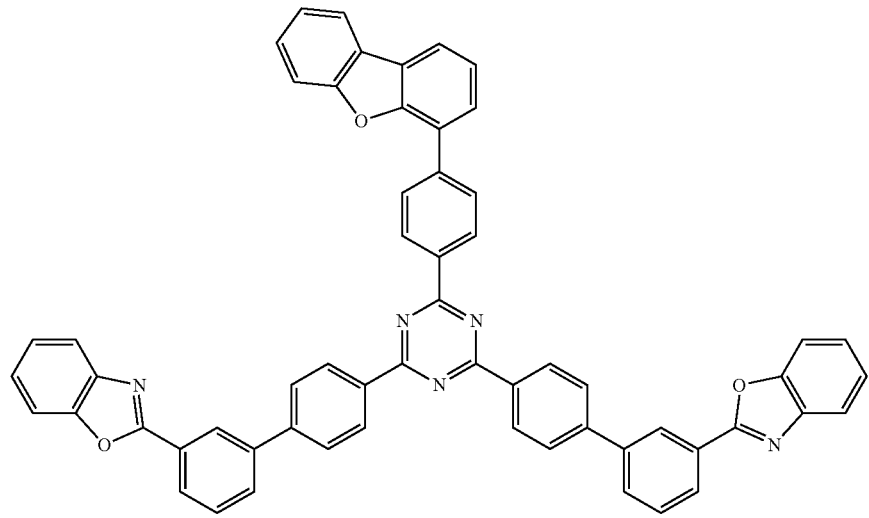
(286)

(287)
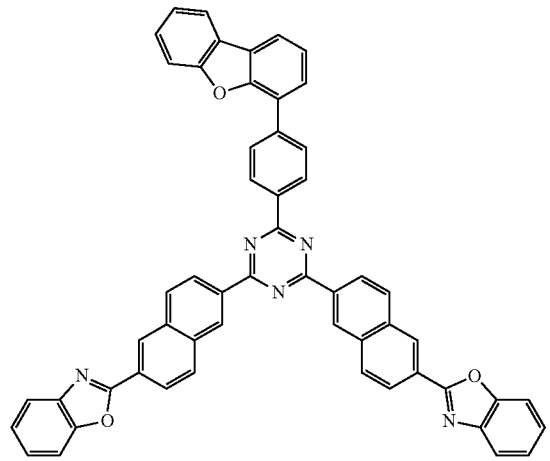
(288)
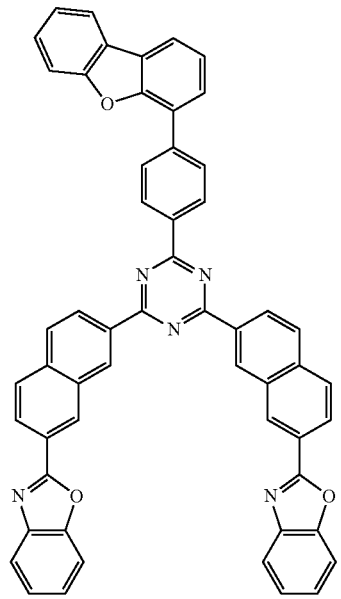
(289)
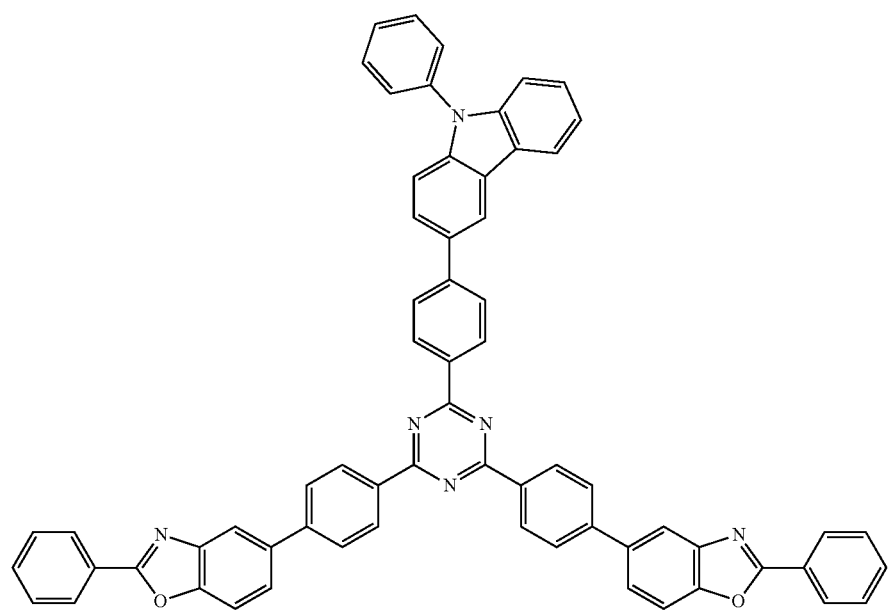

-continued
(290)
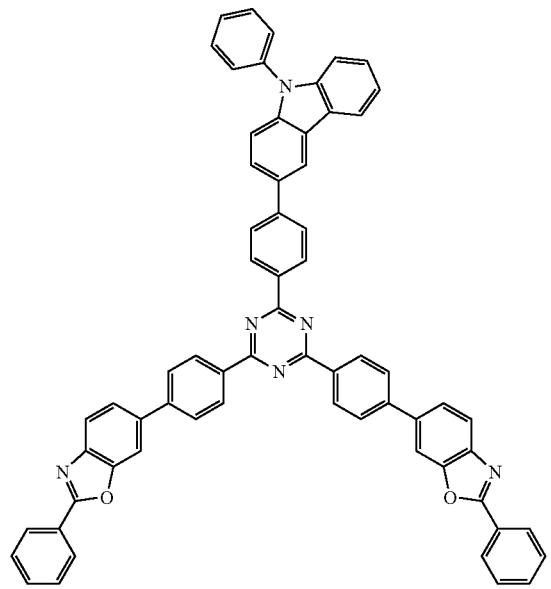
(291)
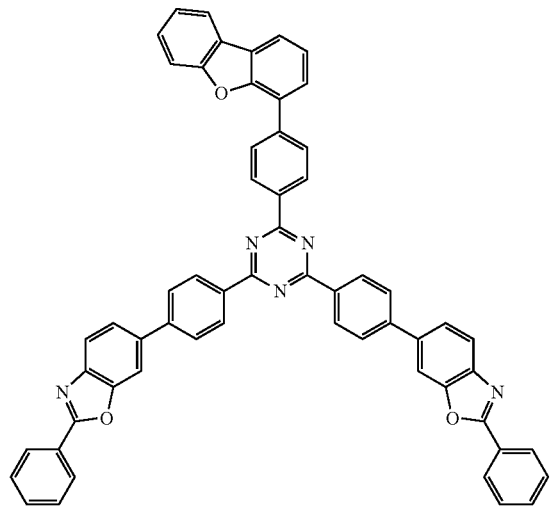
(292)
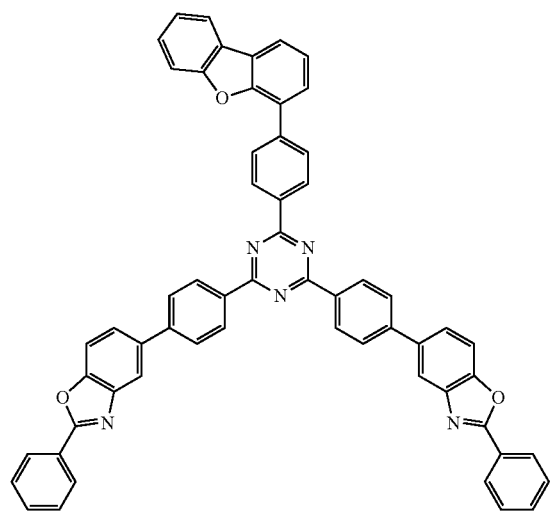
(293)
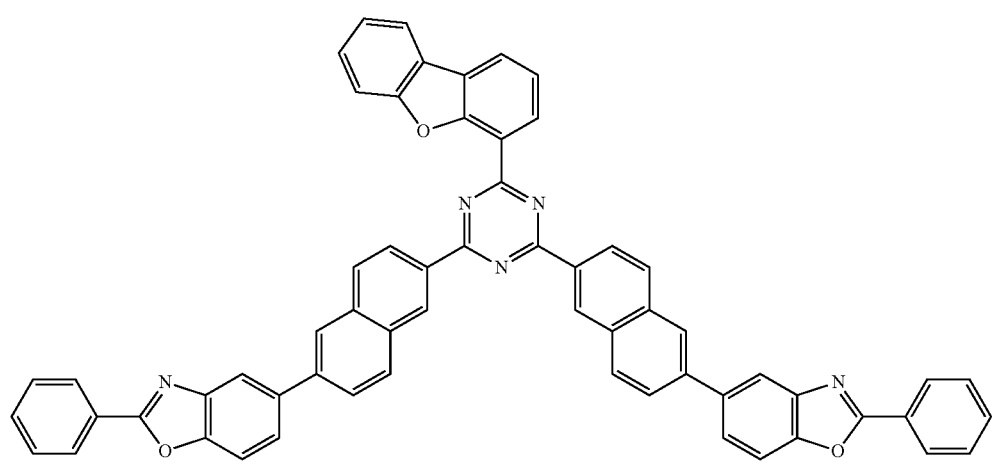

(284)
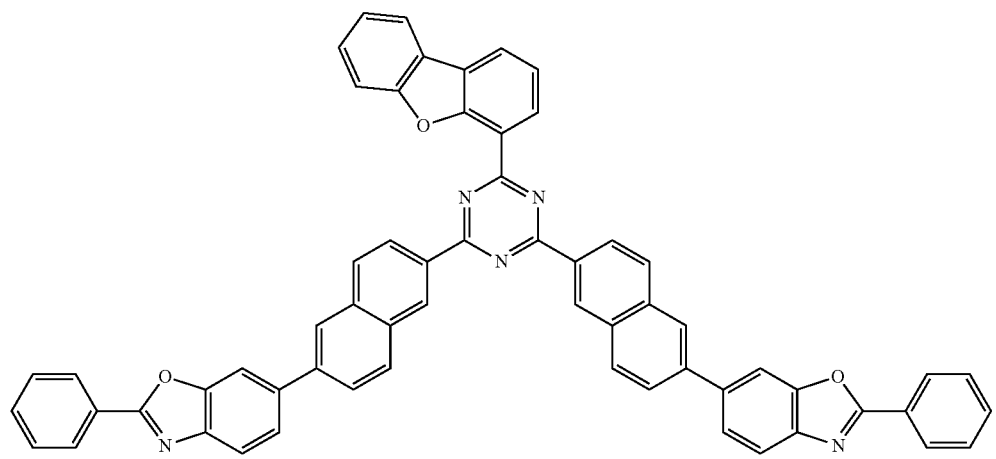
(295)
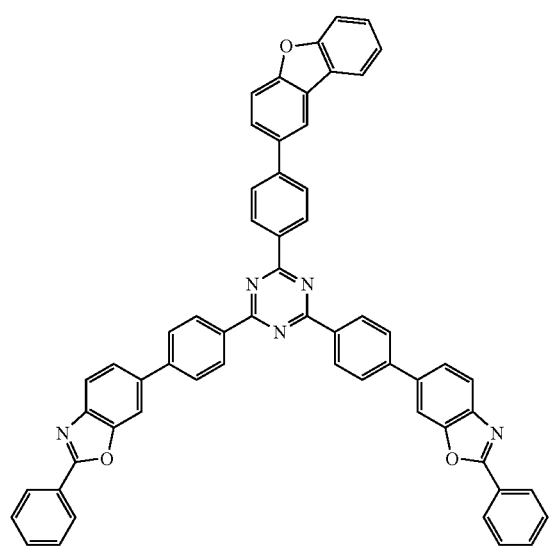
(297)
(296)
(298)

-continued
601
(299)
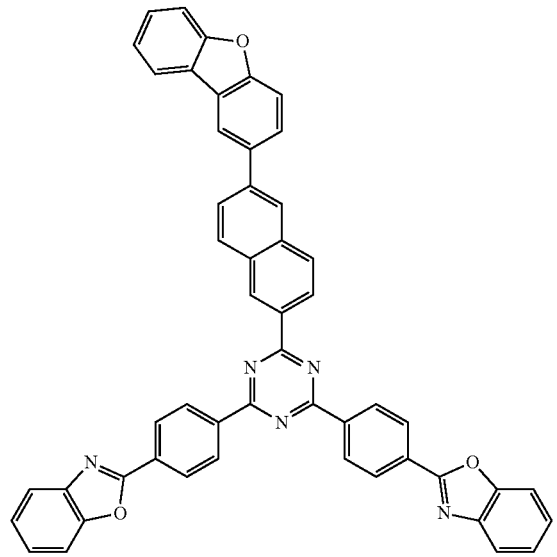
602
(300)
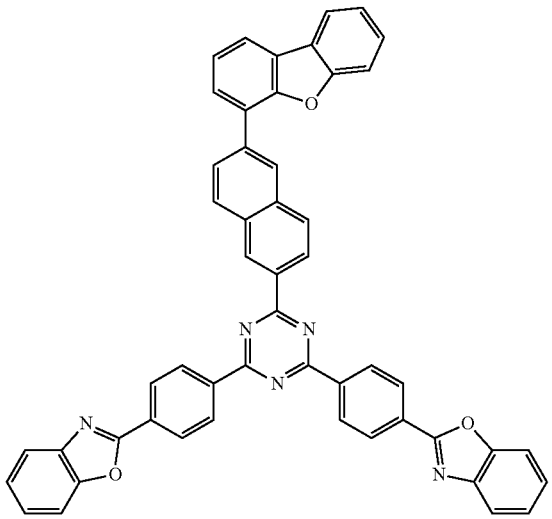
(301)
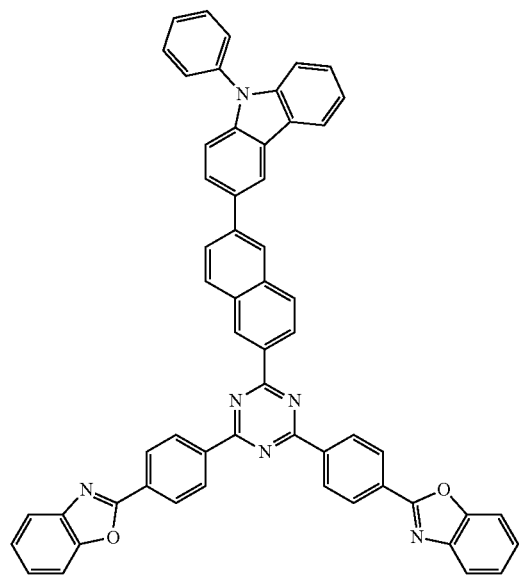
(302)
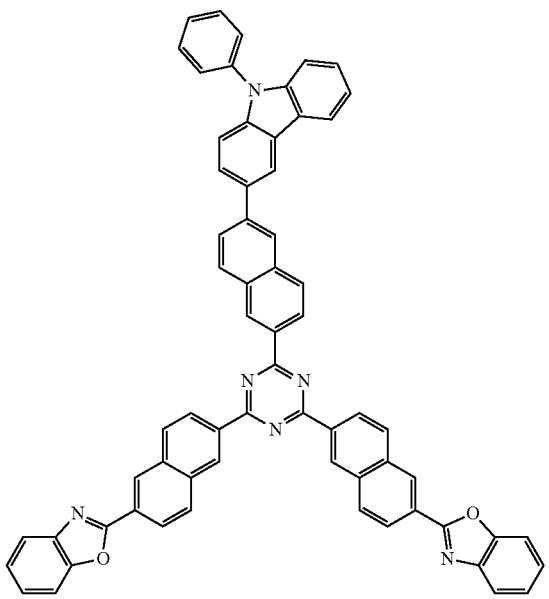

-continued
(303)
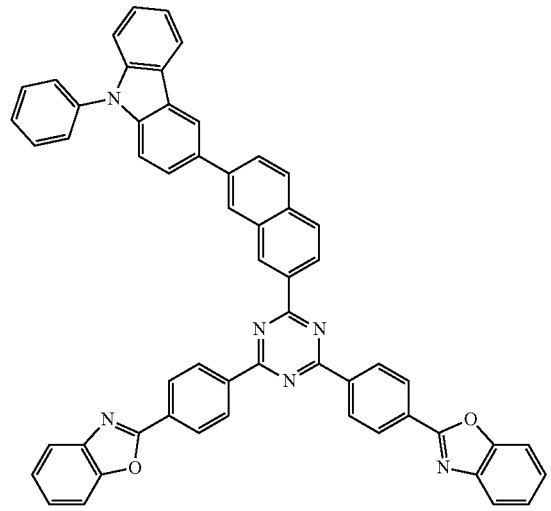
(304)
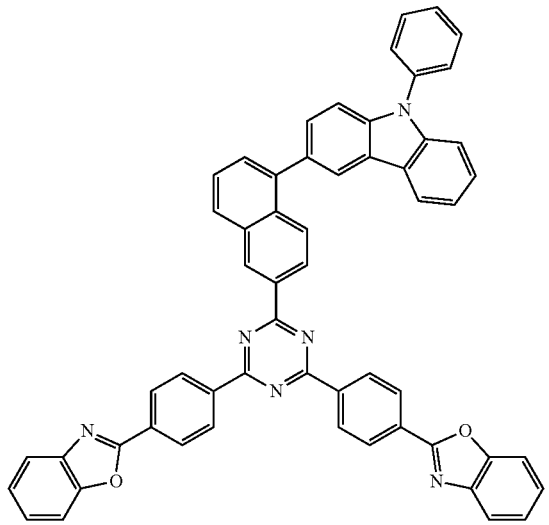
(305)
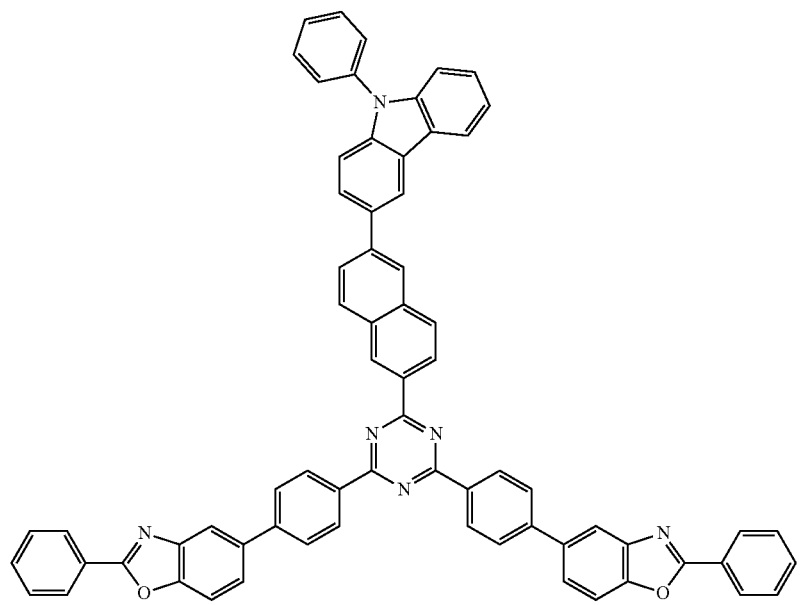
(306)
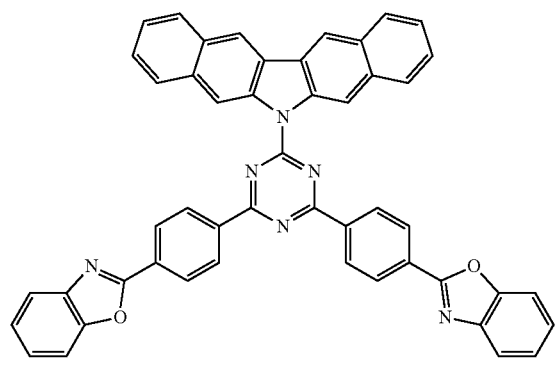
(307)
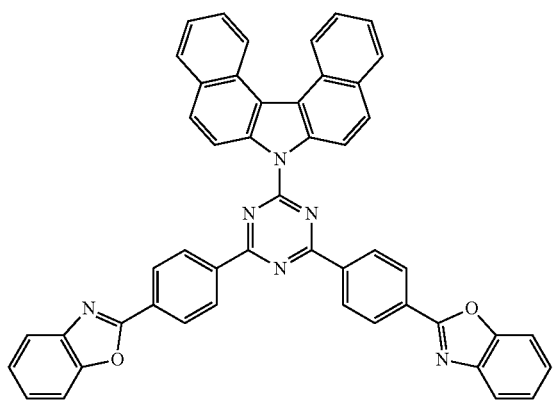

-continued
(308)
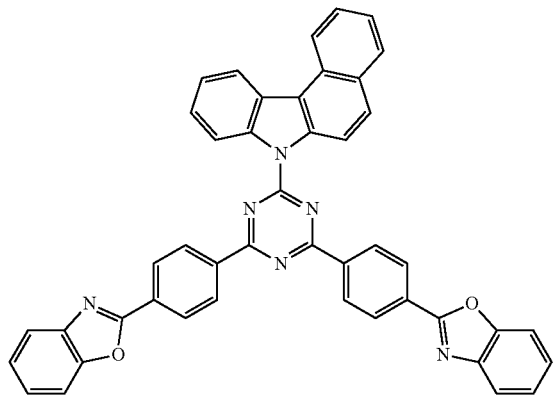
(309)
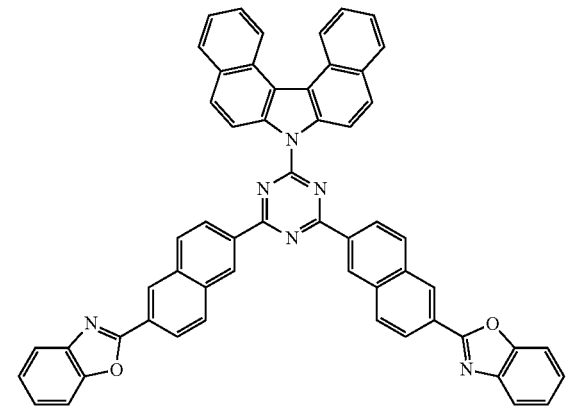
(310)
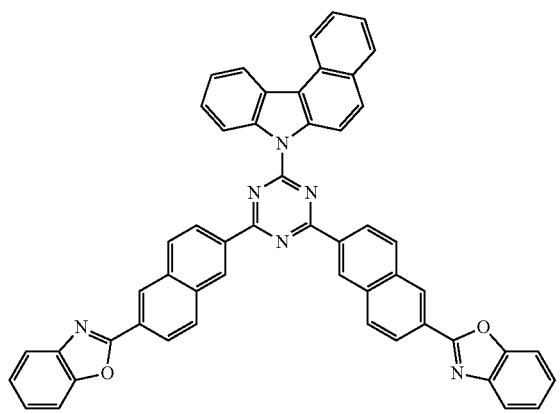
(311)
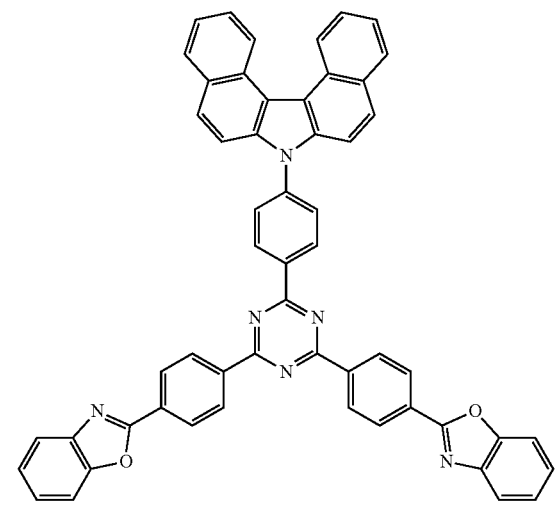
(312)
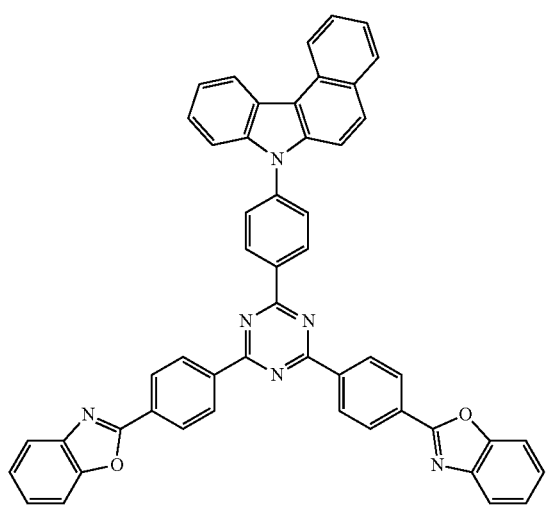
(313)
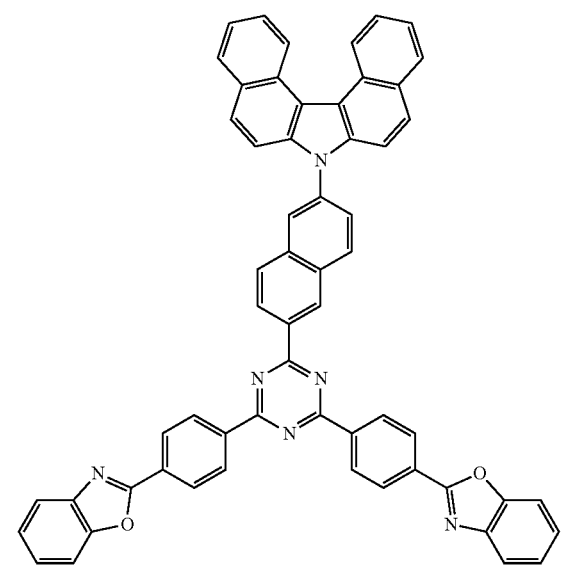

-continued
(314)
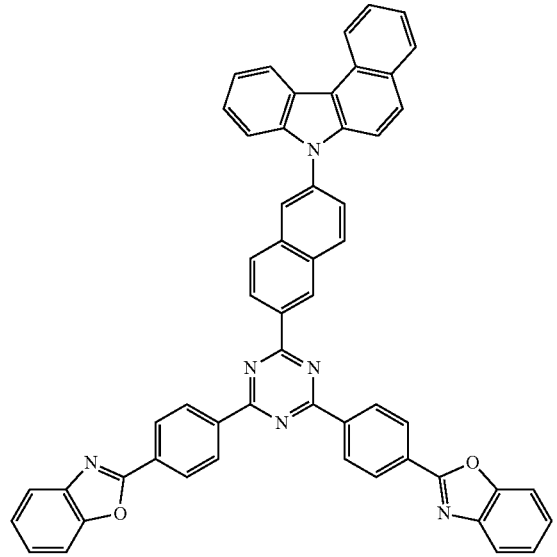
(315)
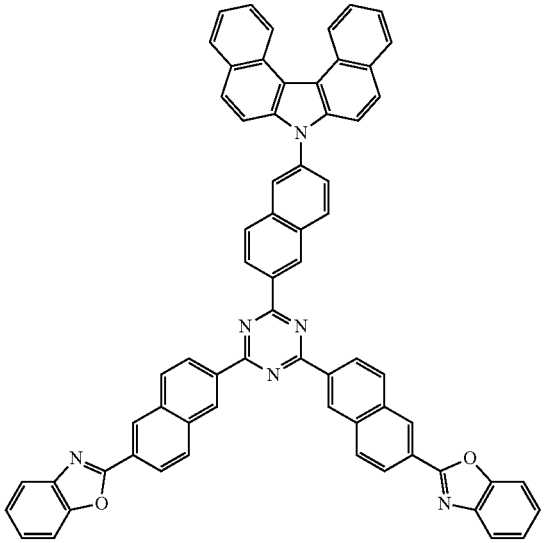
(316)
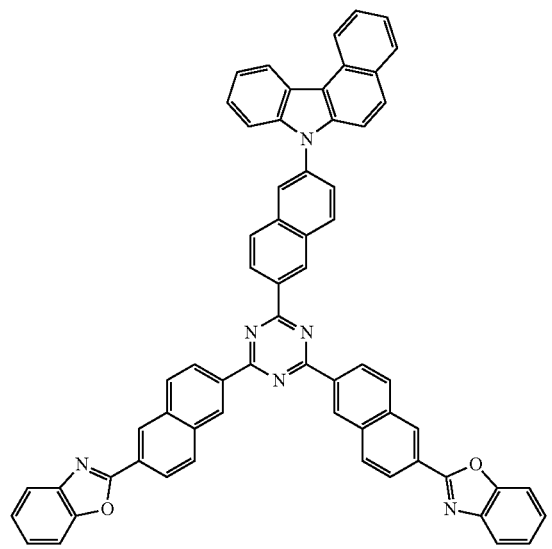
(317)
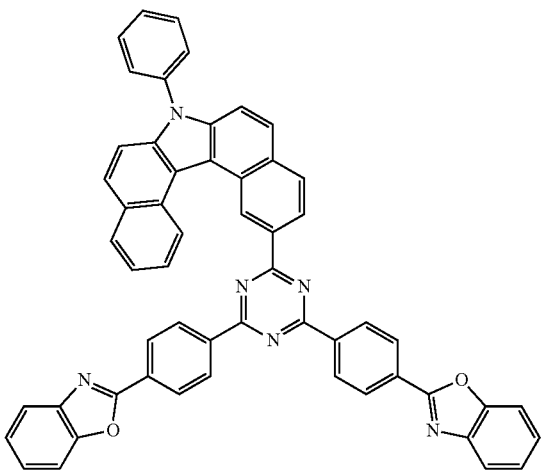
(318)
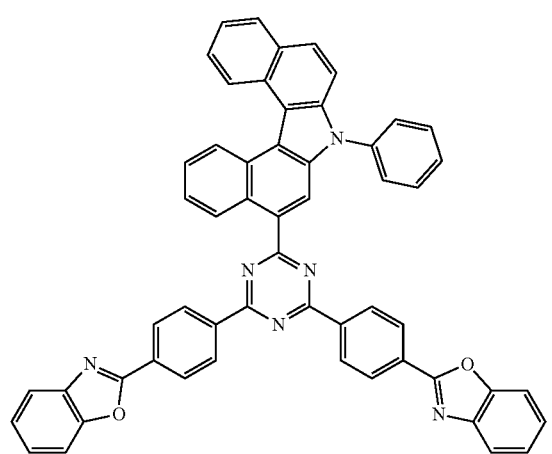
(319)
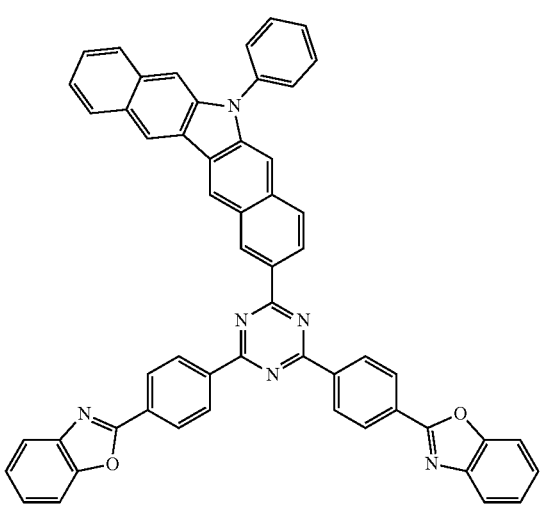

(320)
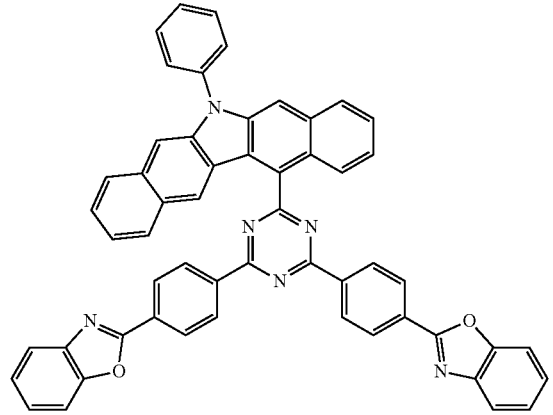
(321)
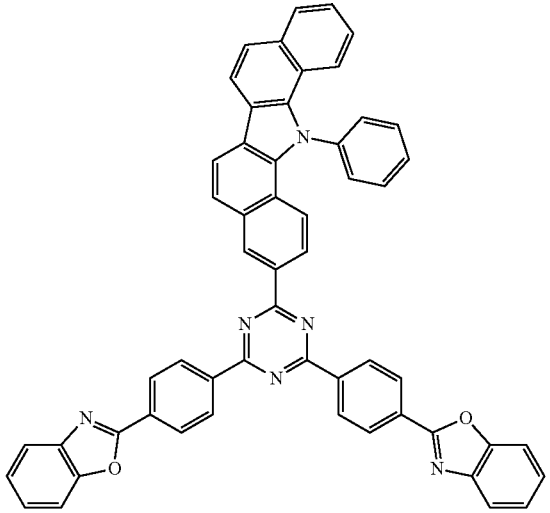
(322)
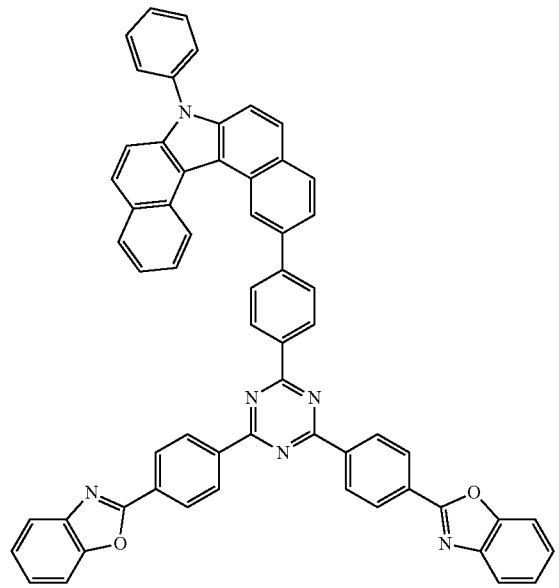
(323)
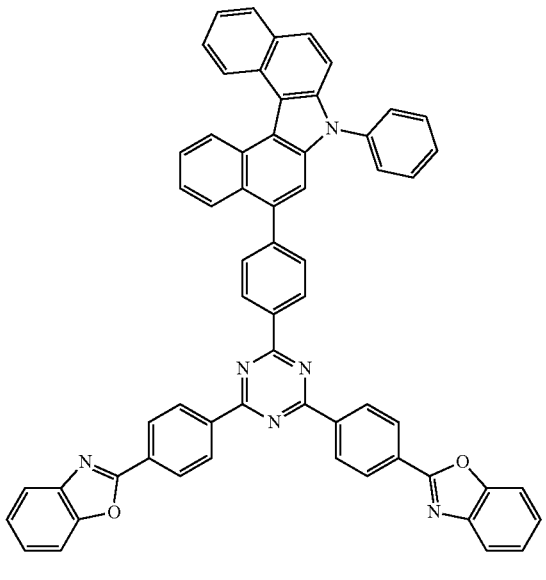

611 612
-continued
(324)
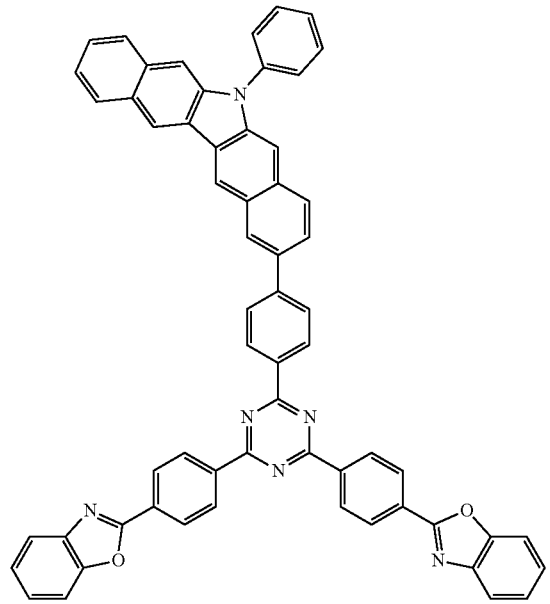
(325)
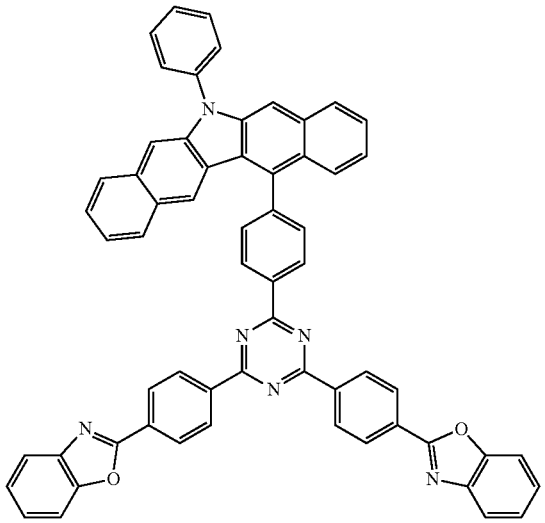
(326)
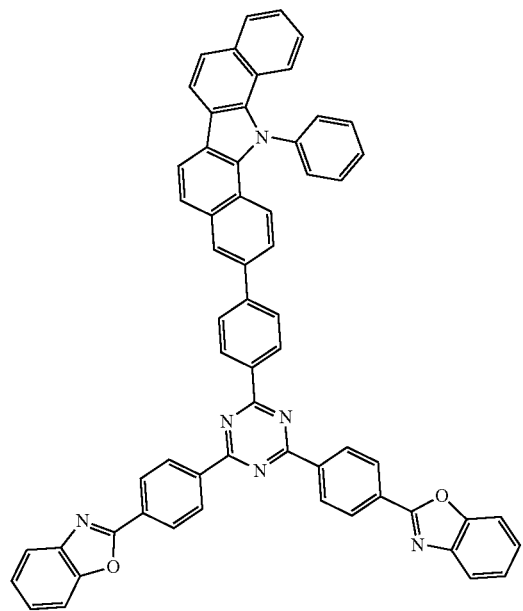
(327)
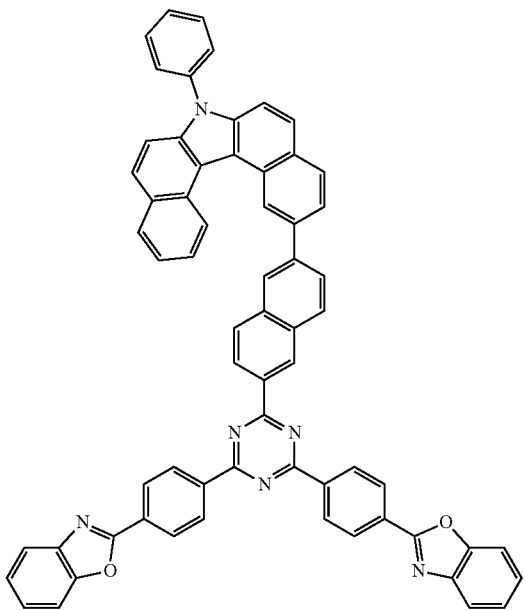

(328)
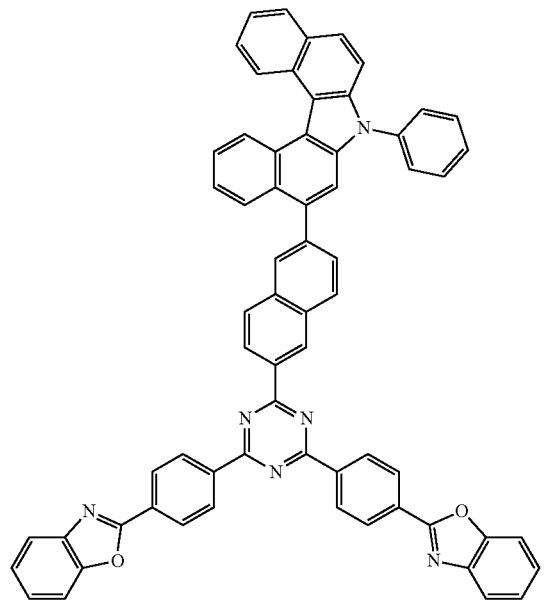
(329)
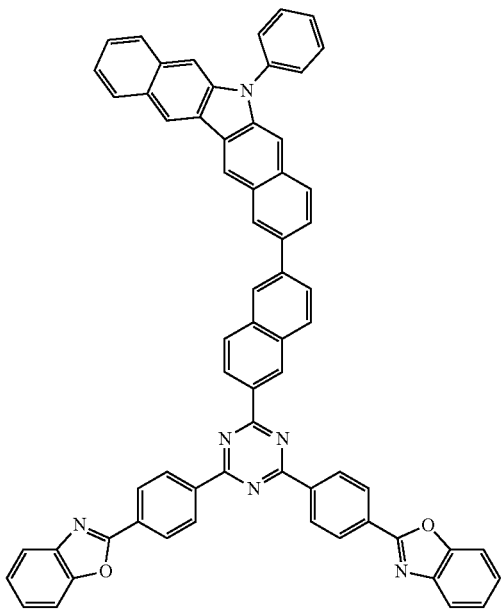
(330)
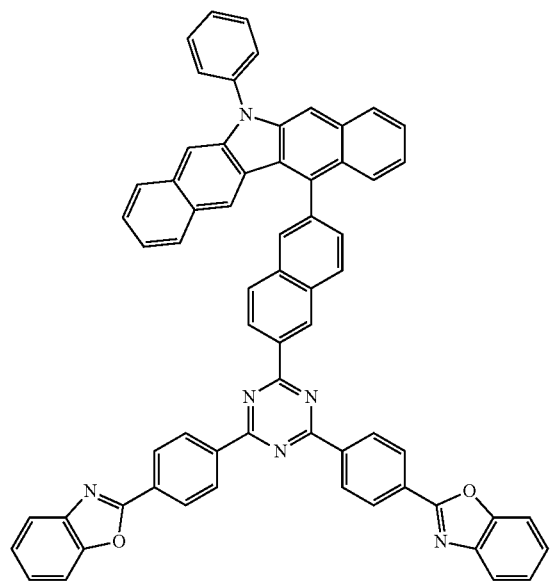
(331)
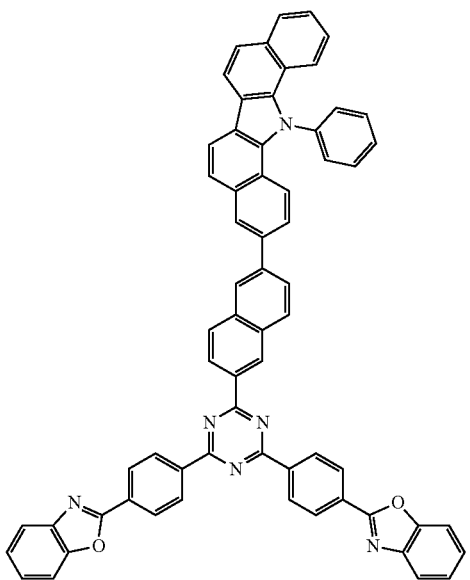

-continued
(332)
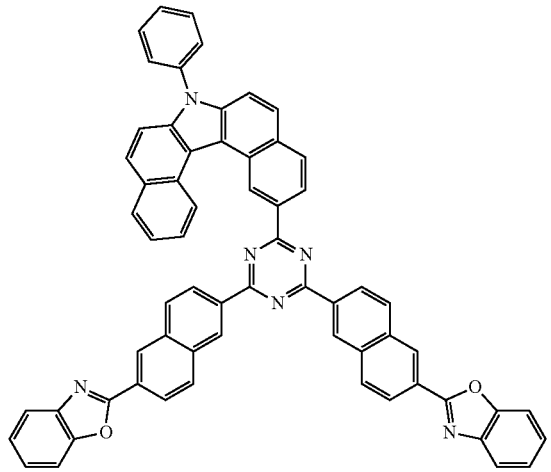
(333)
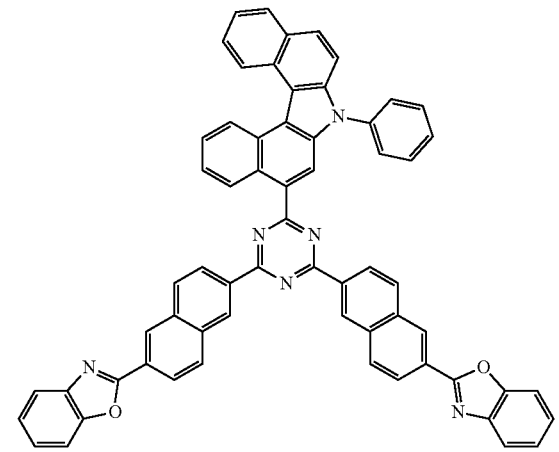
(334)
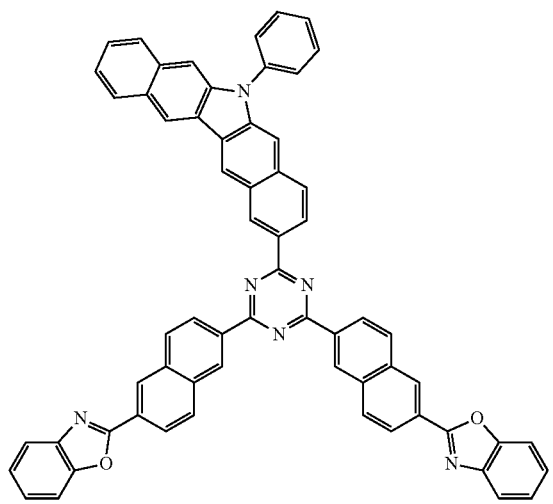
(335)
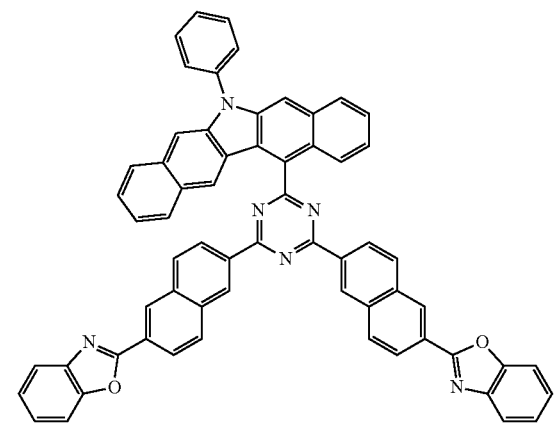
(336)
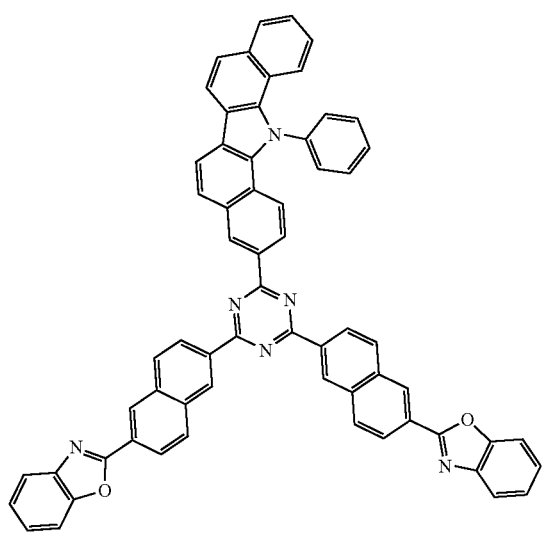
(337)
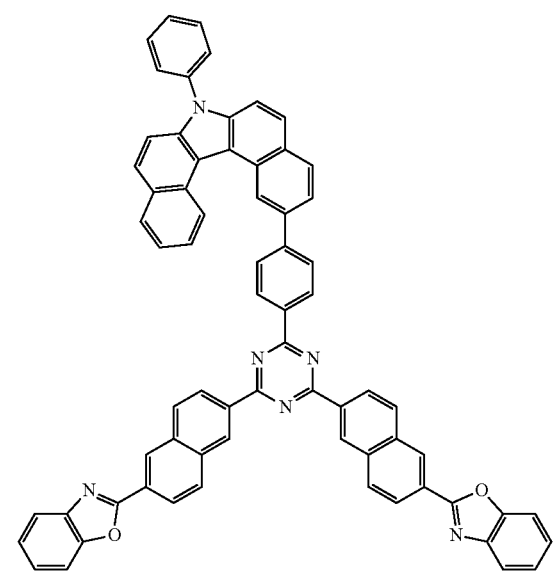

-continued
(338)
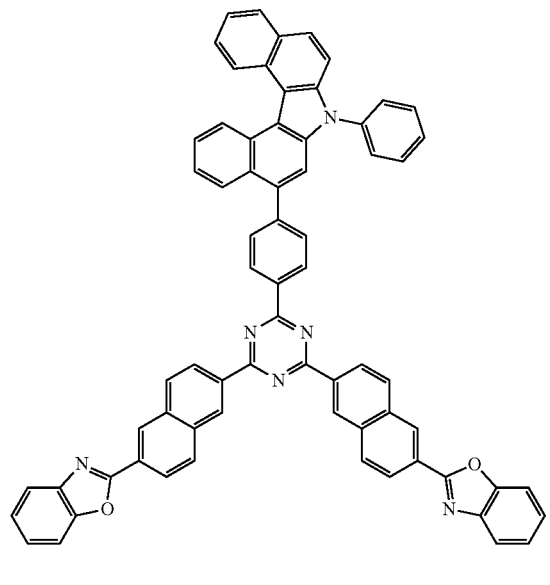
(339)
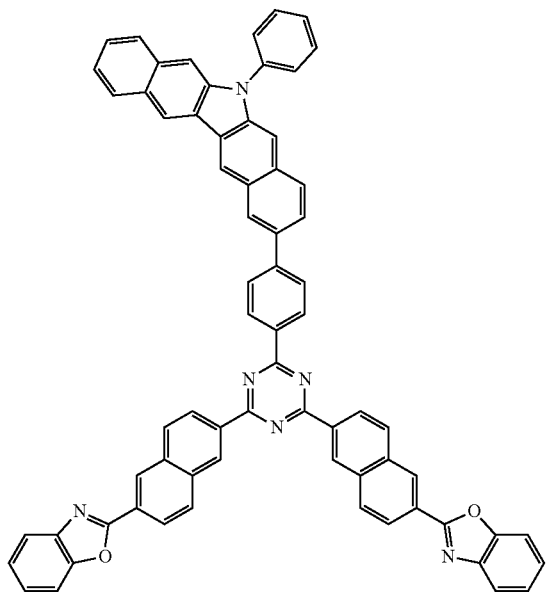
(340)
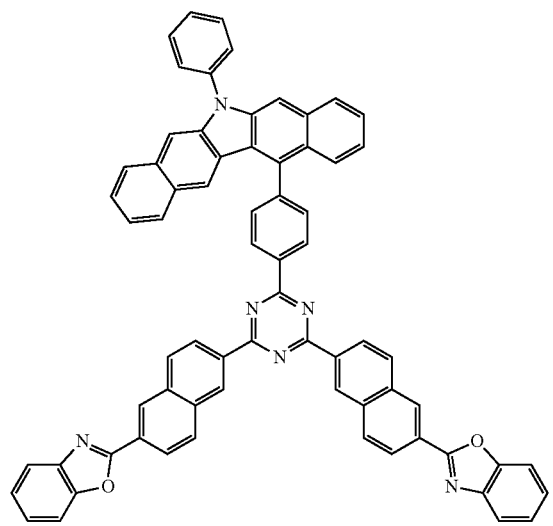
(341)
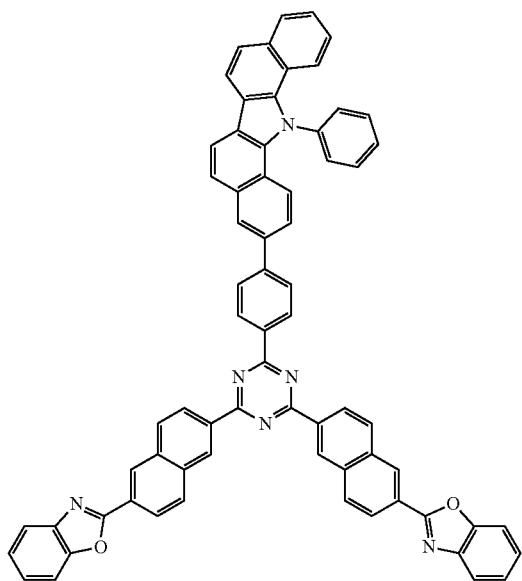

(342)
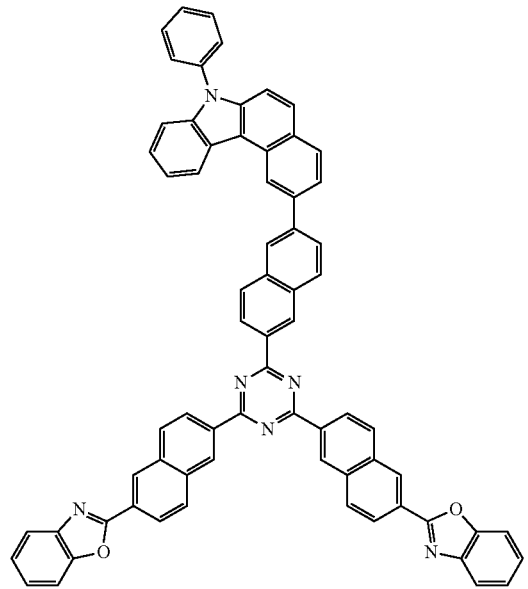
(343)
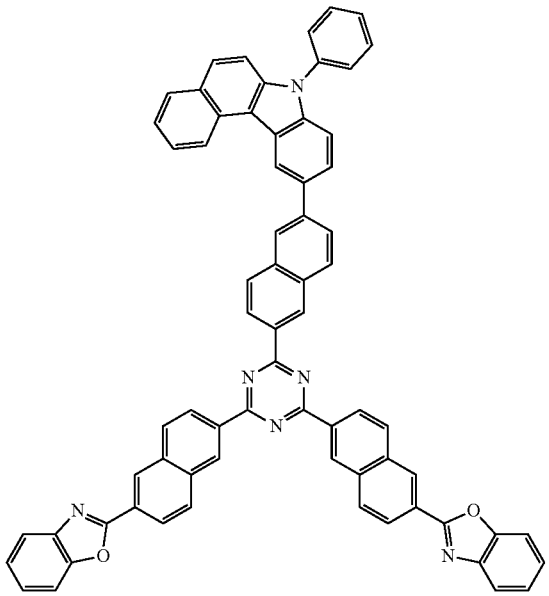
(344)
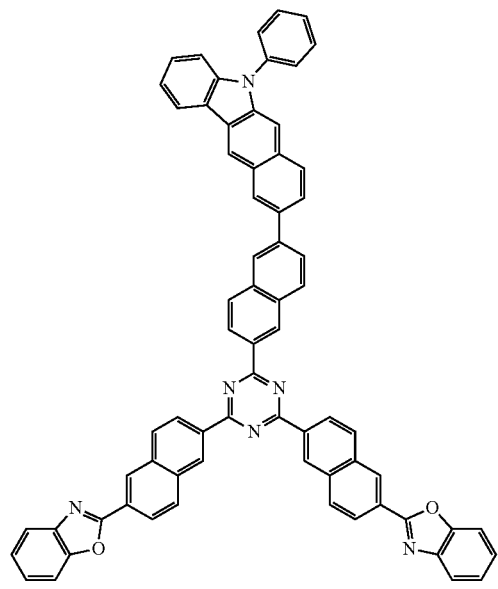
(345)
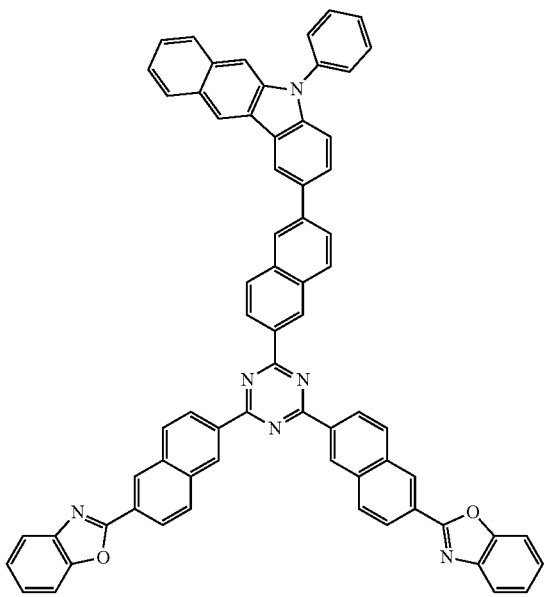

621
622
(346)
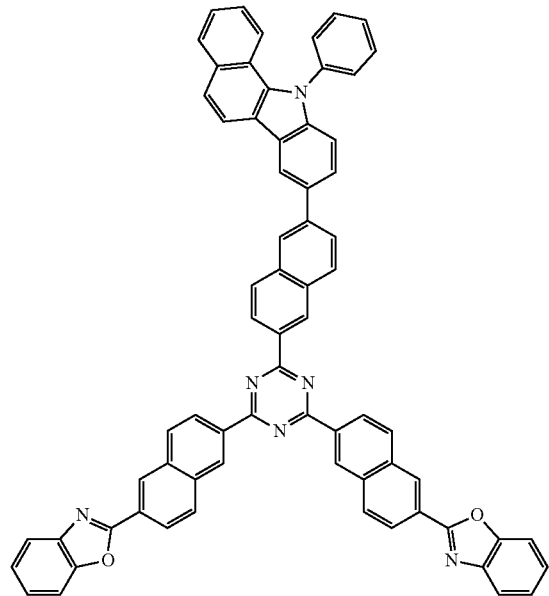
(347)
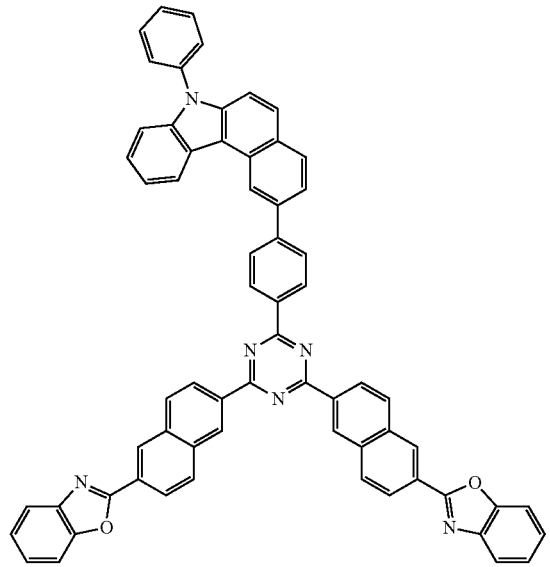
(348)
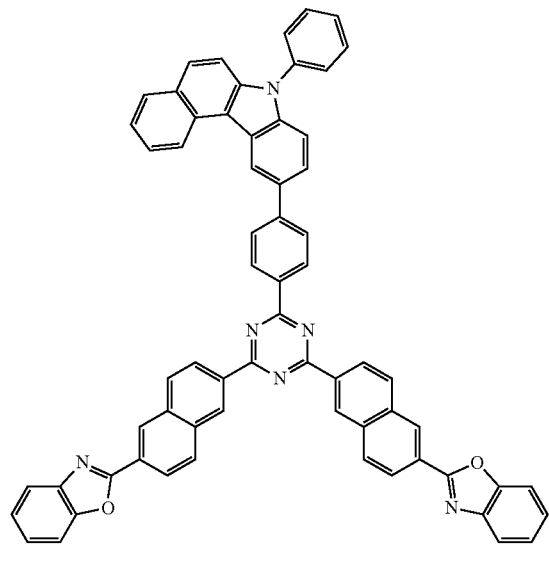
(349)
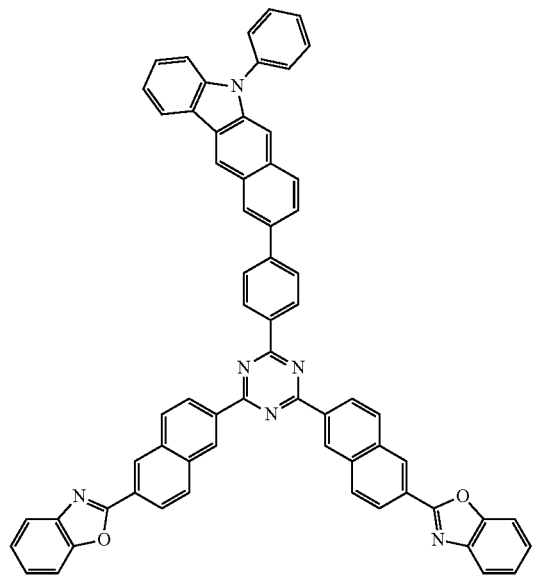

623
624
-continued
(350)
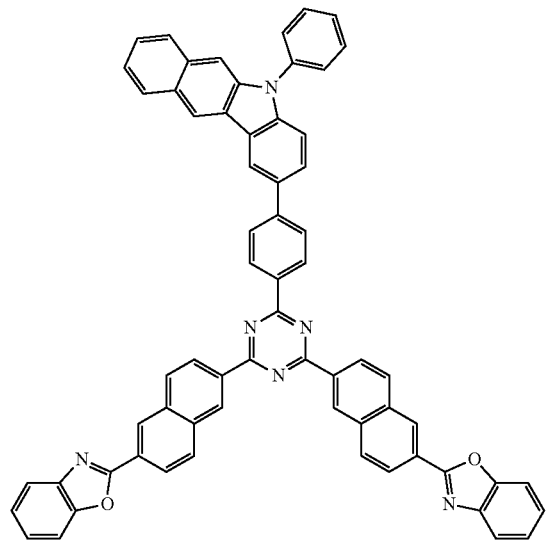
(351)
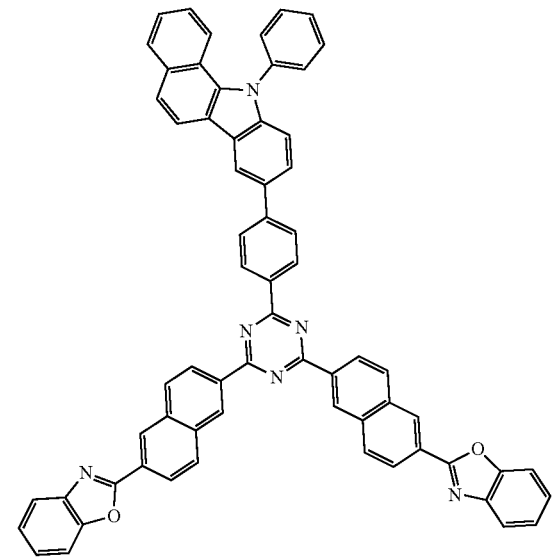
(352)
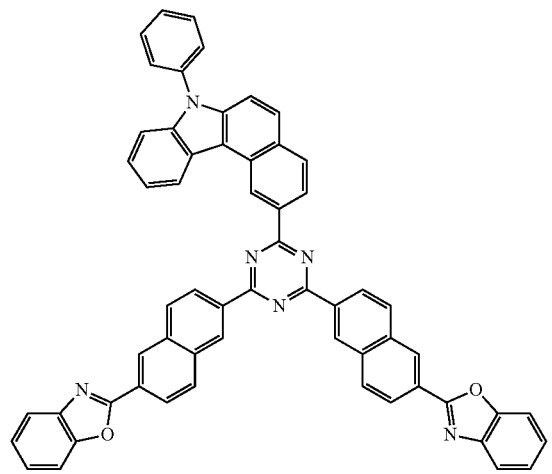
(353)
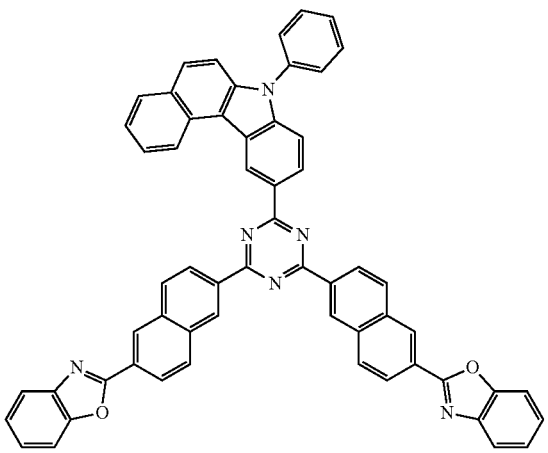
(354)
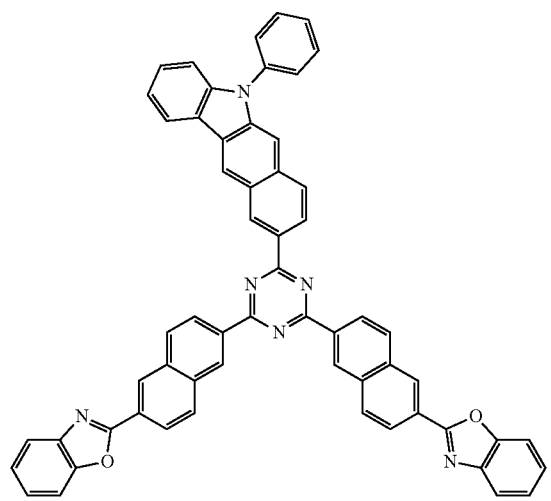
(355)
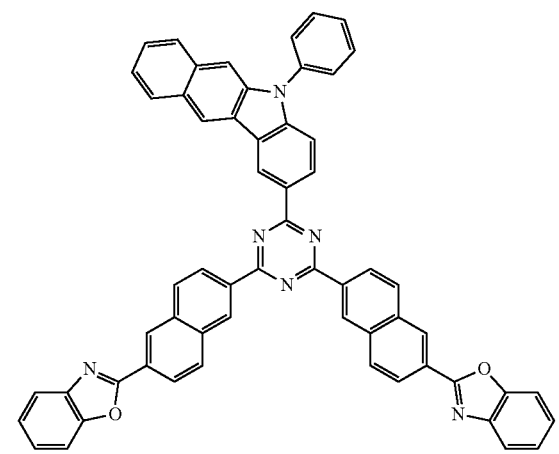

-continued
(356)
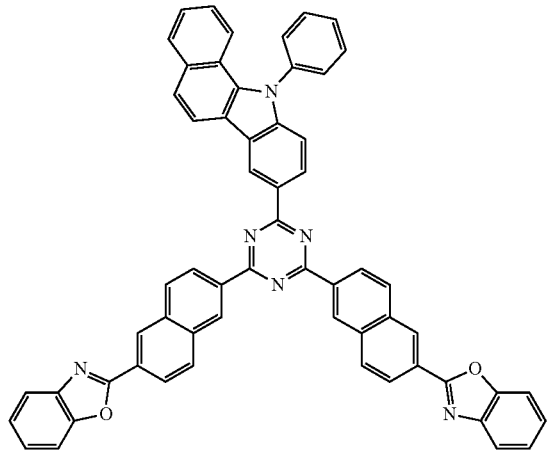
(357)
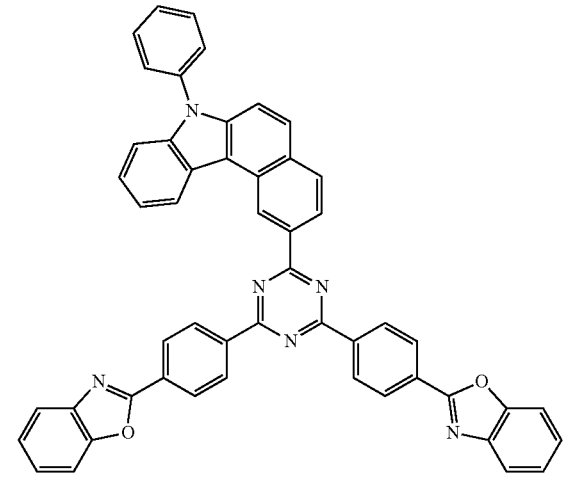
(358)
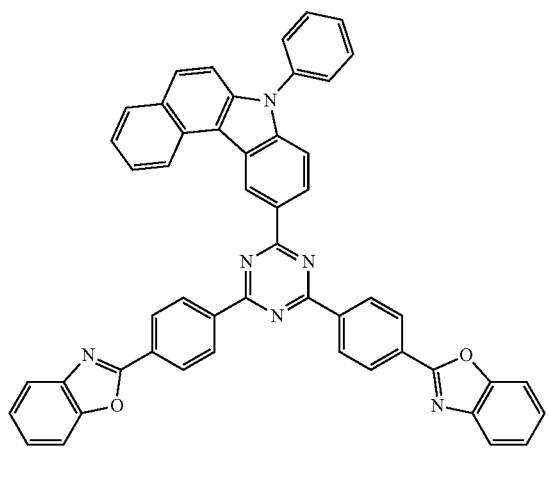
(359)
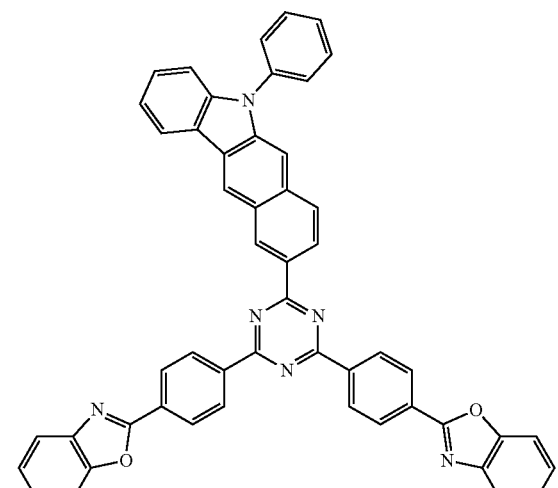
(360)
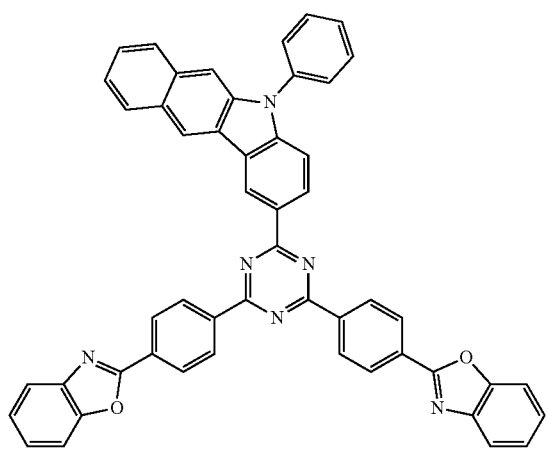
(361)
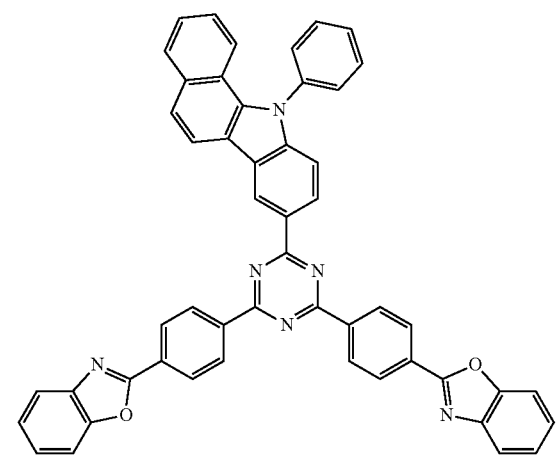

(362)
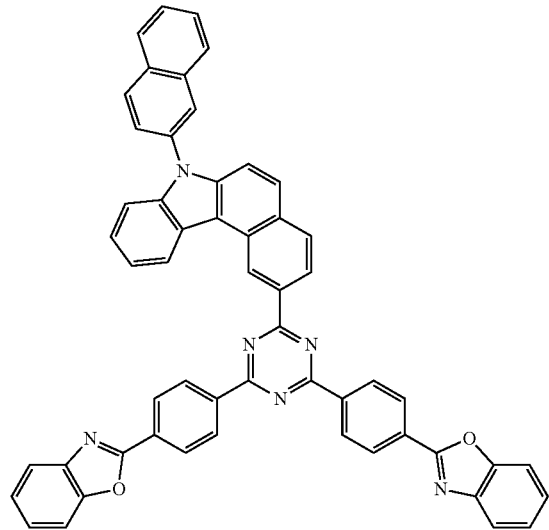
(363)
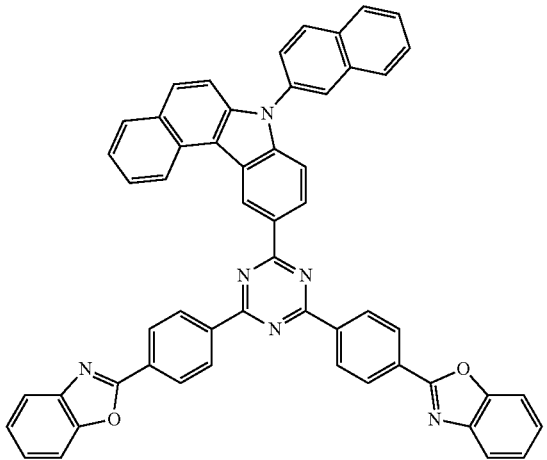
(364)
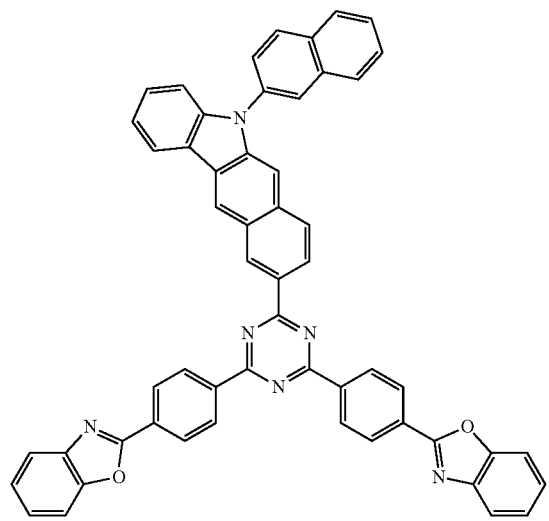
(365)
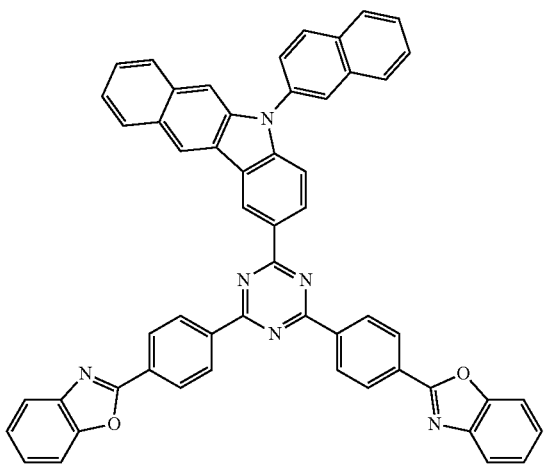

(366)
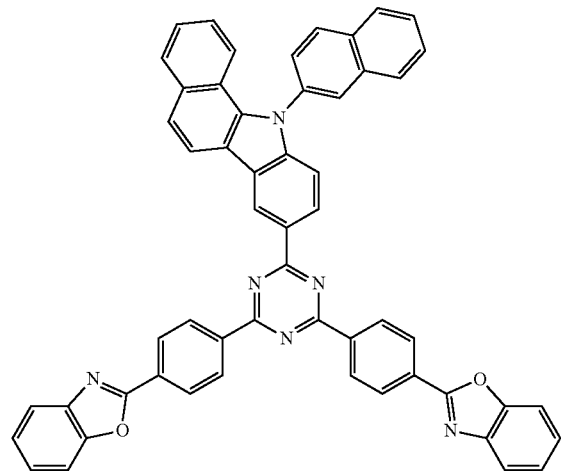
(367)
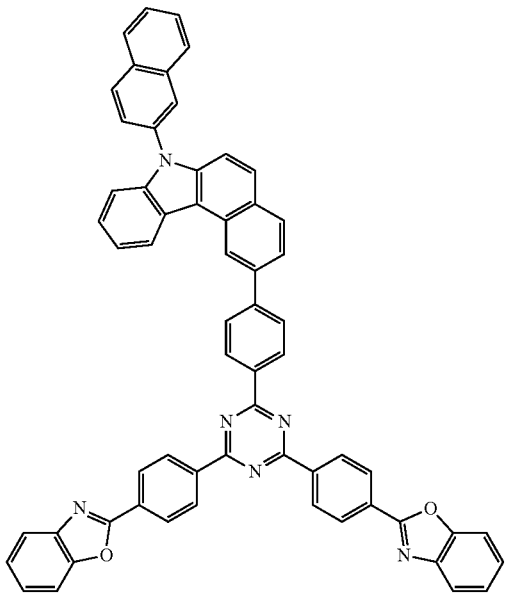
(368)
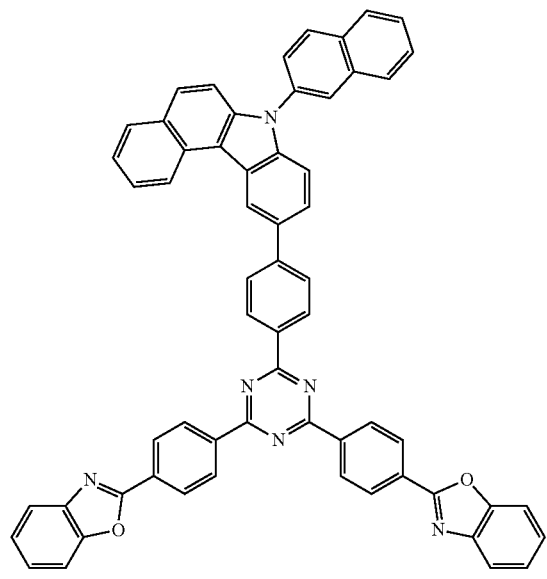
(369)
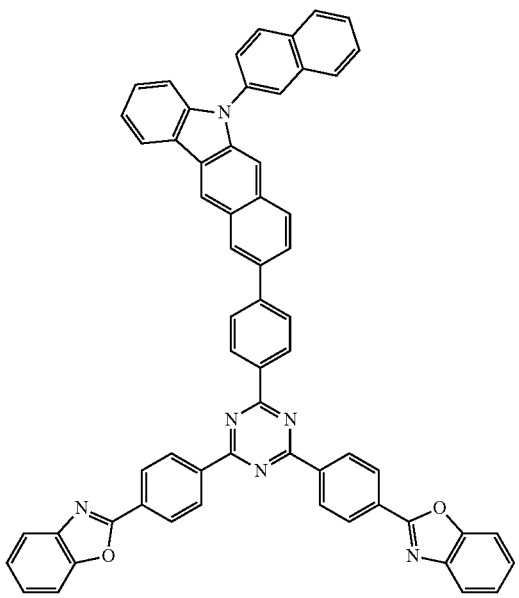

631
632
-continued
(370)
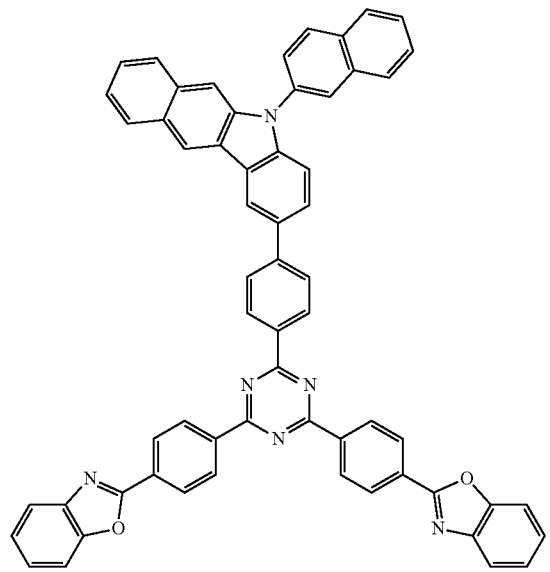
(371)
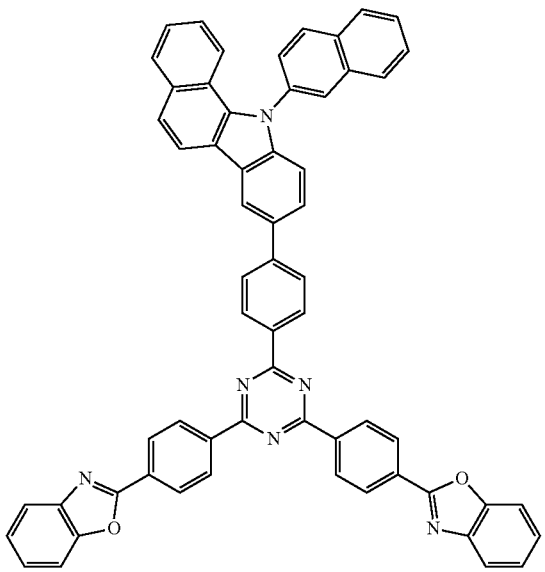
(372)
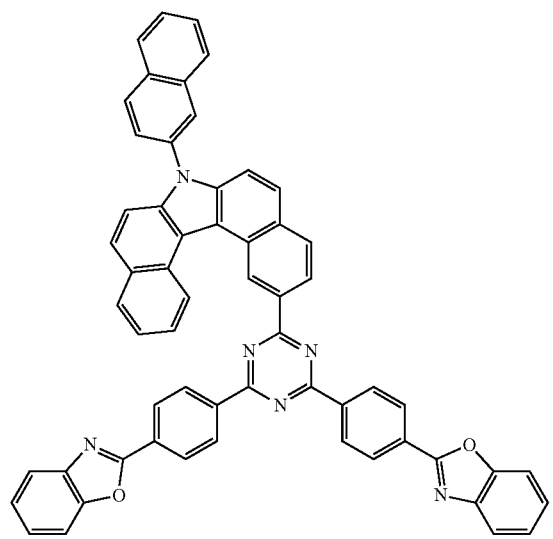
(373)
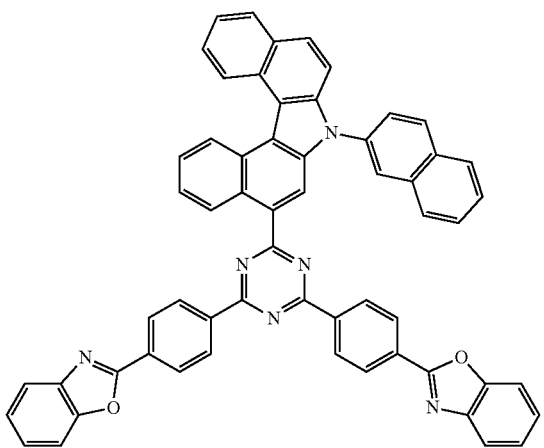

633 634
(374)
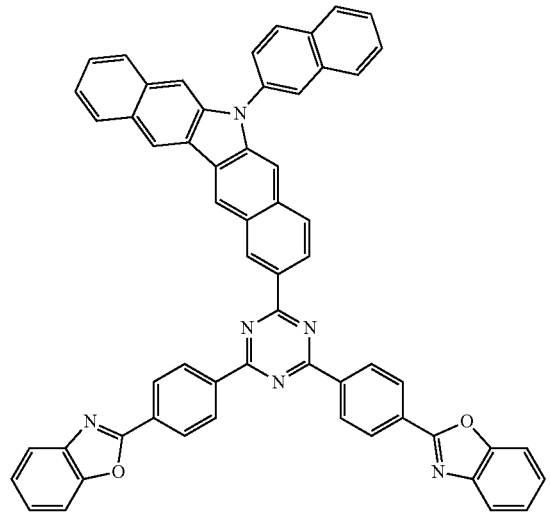
(375)
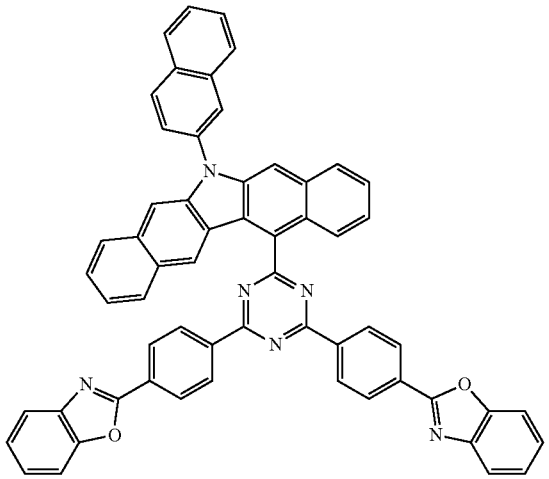
(376)
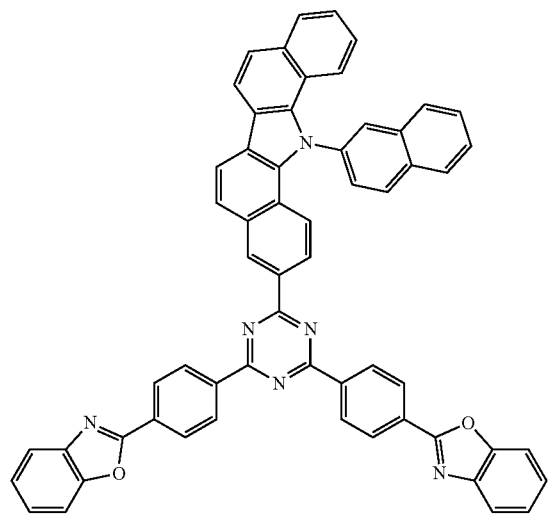
(377)
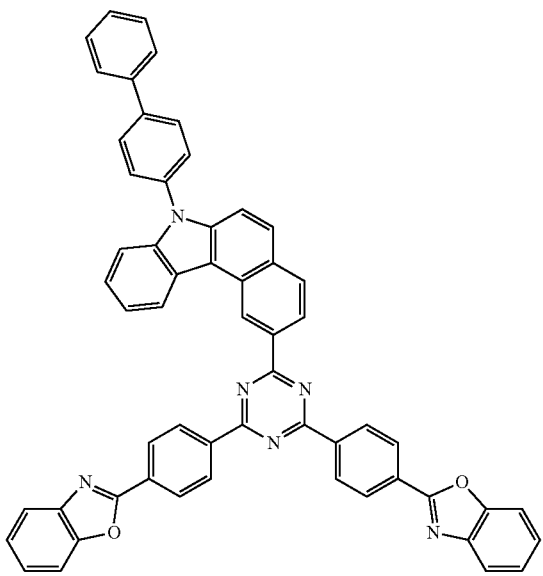

(378)
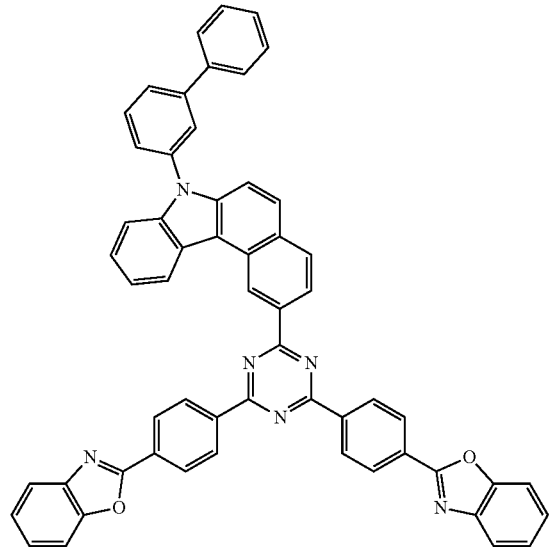
(379)
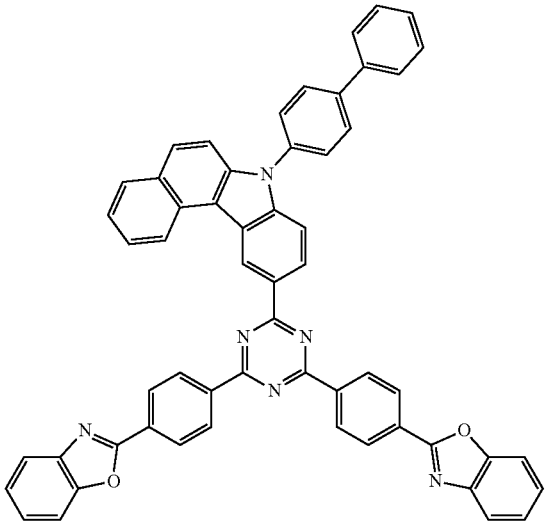
(380)
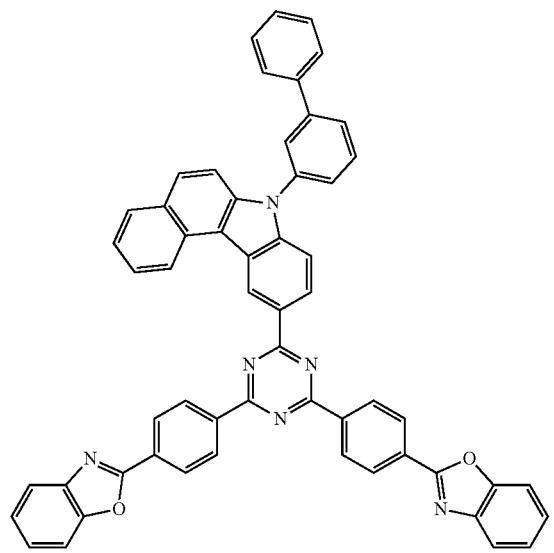
(381)
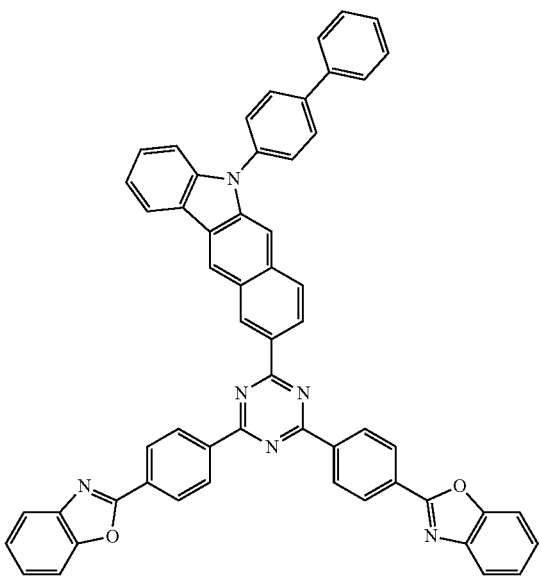

(382)
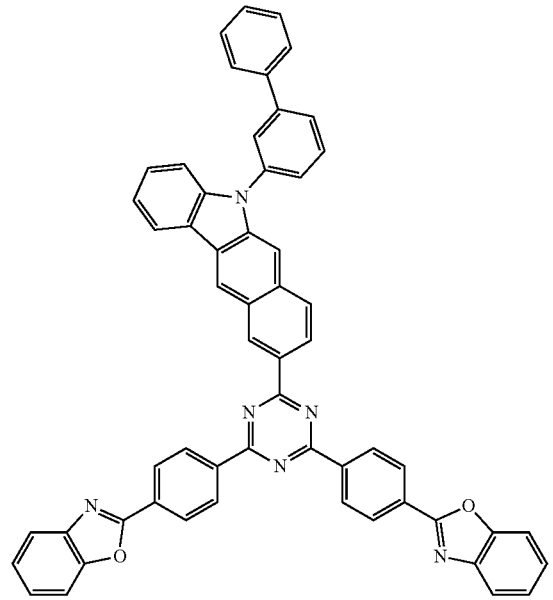
(383)
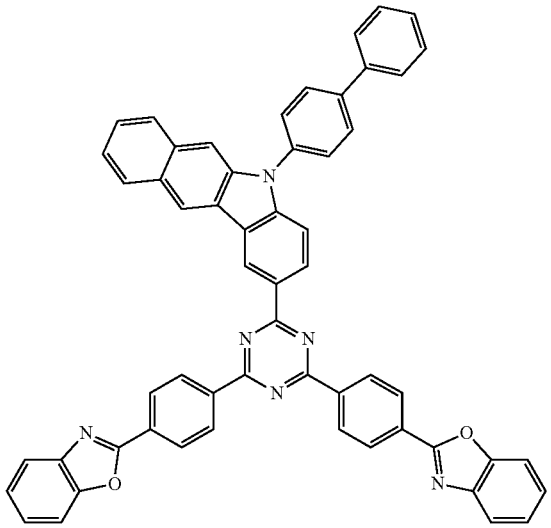
(384)
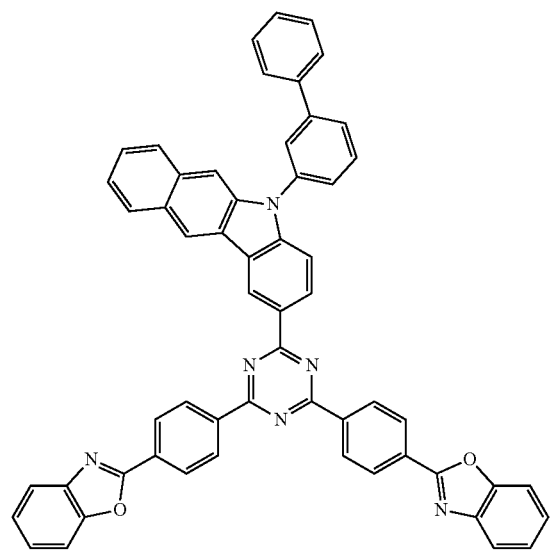
(385)
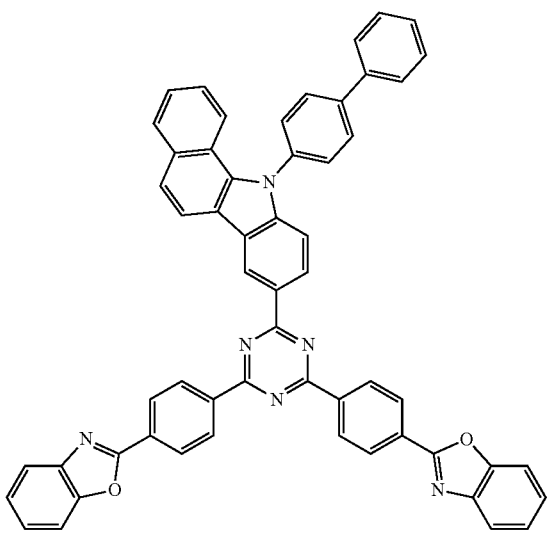

(386)
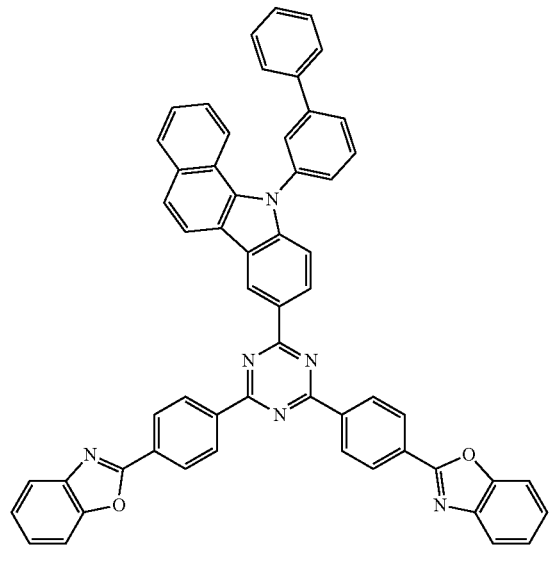
(387)
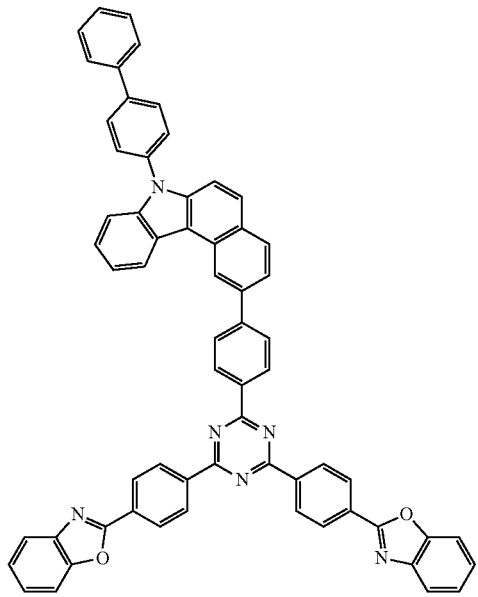
(388)
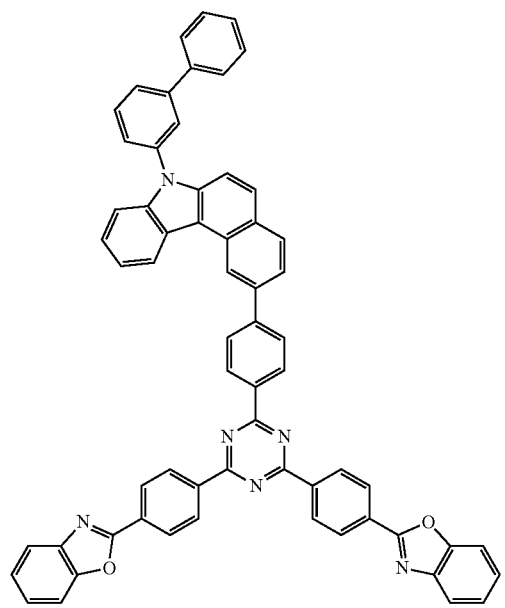
(389)
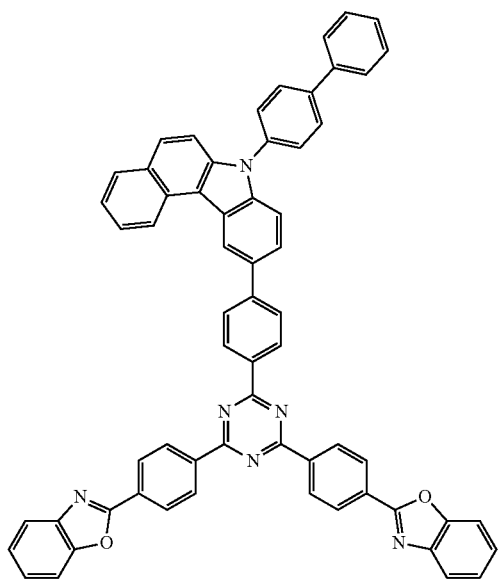

-continued
(390)
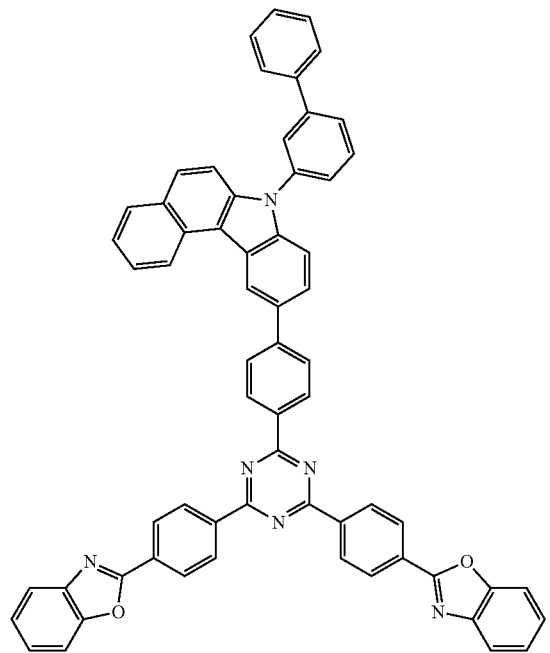
(391)
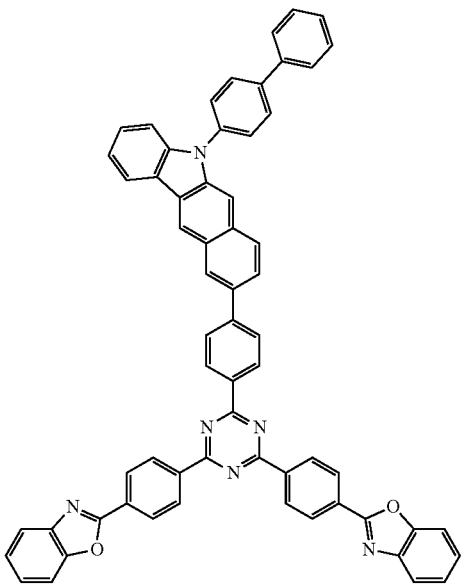
(392)
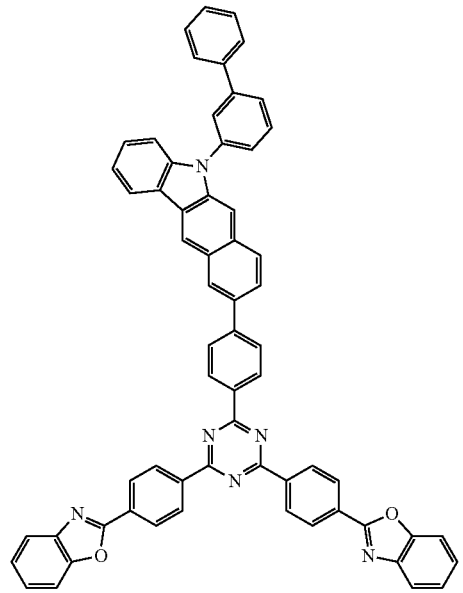
(393)
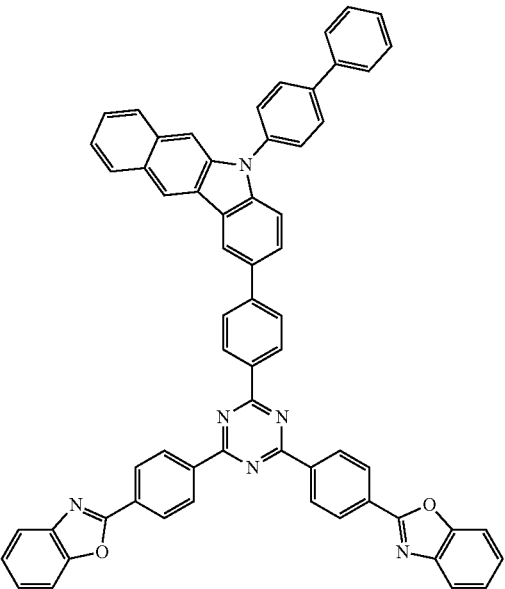

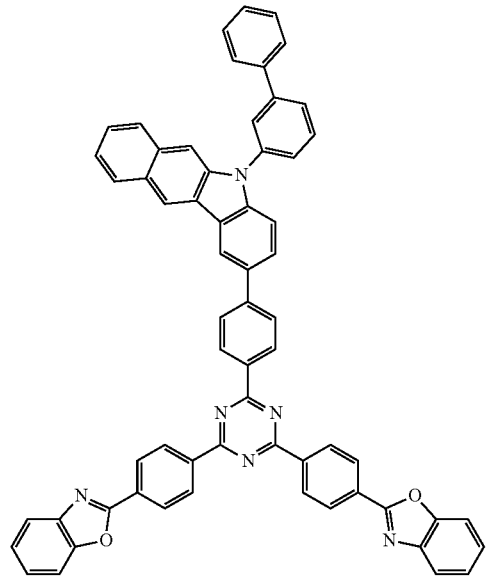
(394)
(395)
(396)
(397)

(398)
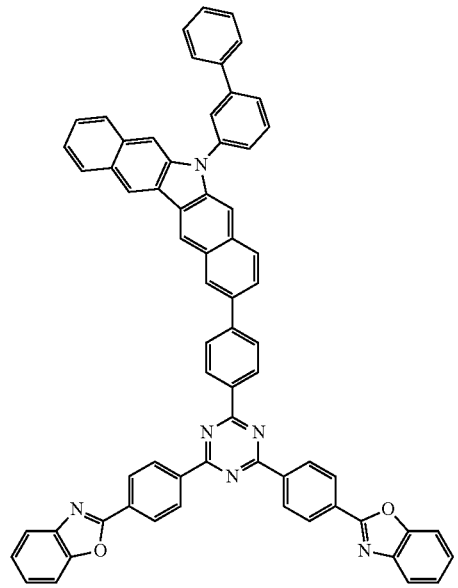
(399)
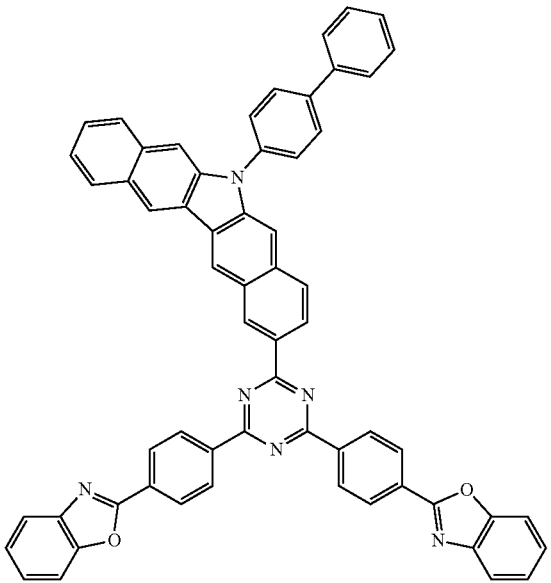
(400)
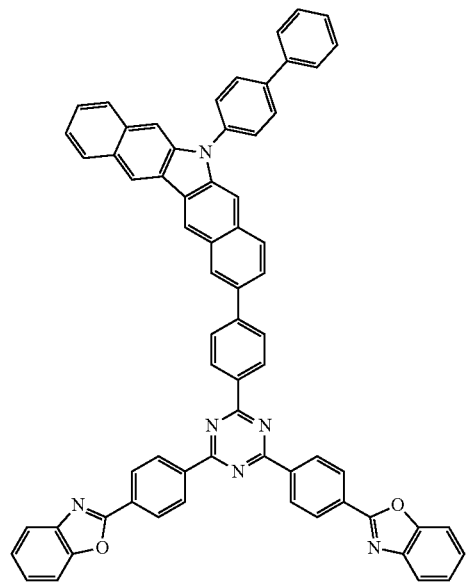
(401)
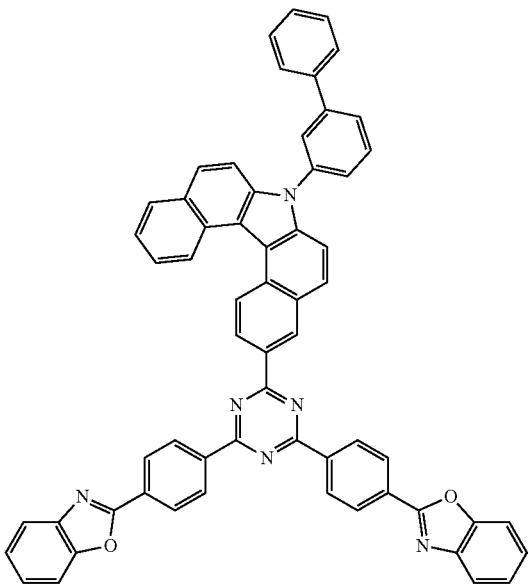

(402)
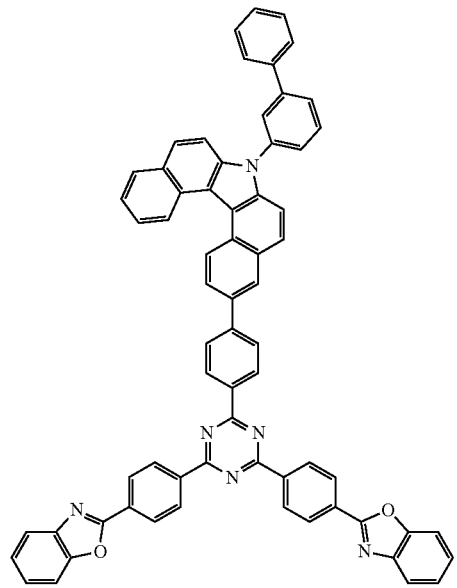
(403)
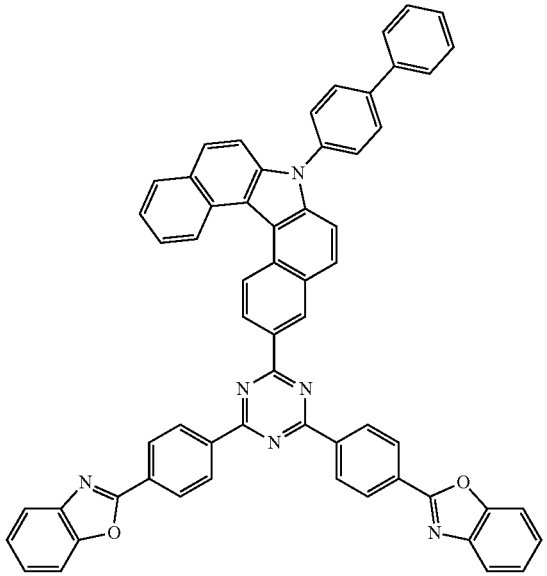
(404)
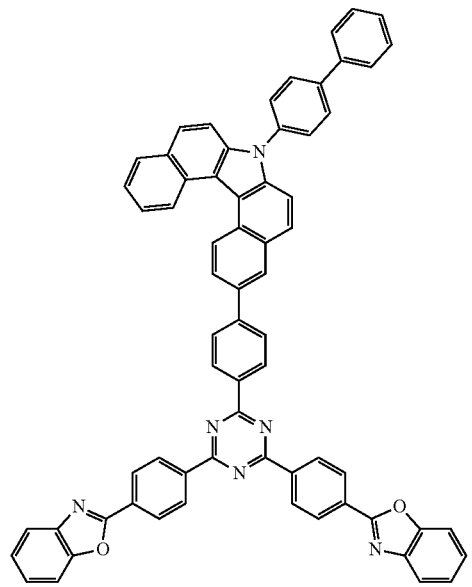
(405)
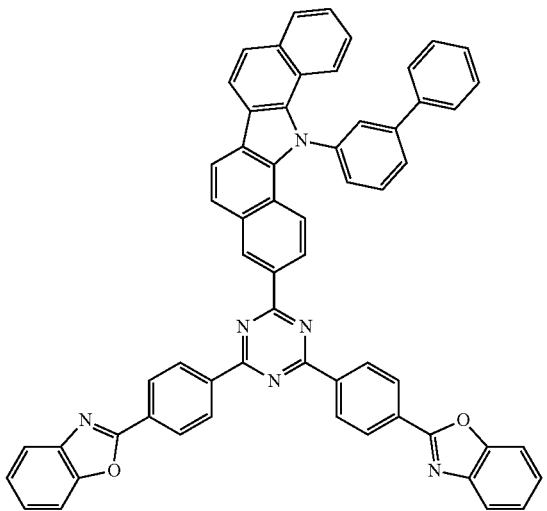

649
(406)
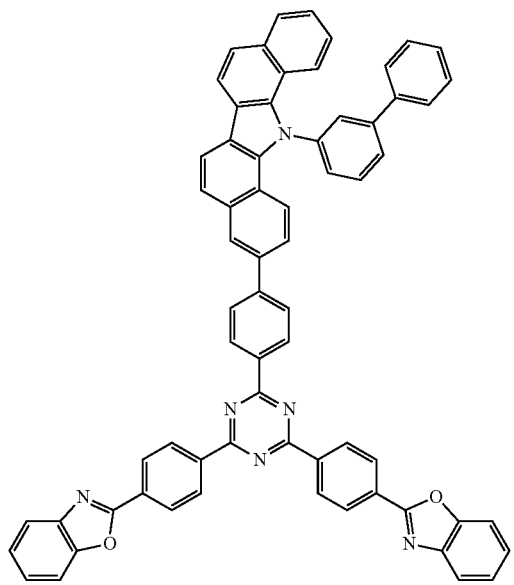
650
-continued
(407)
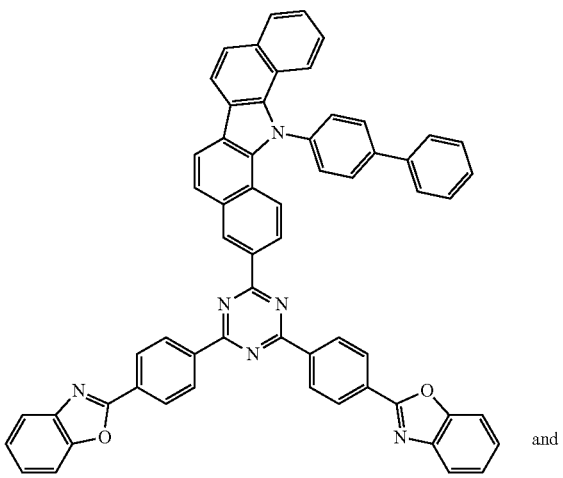 and
(408)
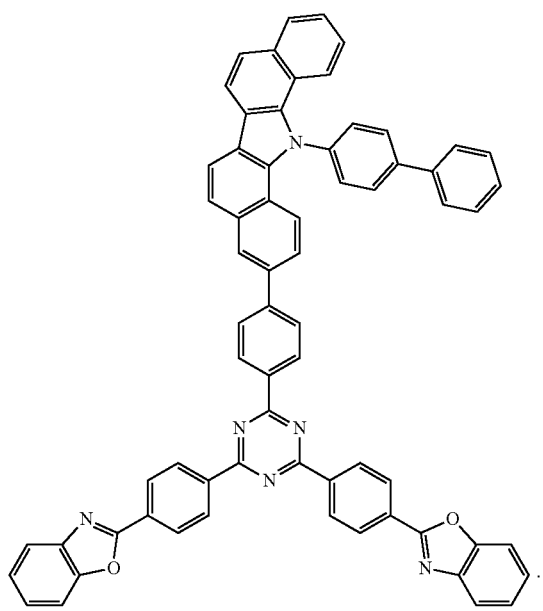
10. The organic electroluminescent device according to claim 9, wherein the organic electroluminescent device comprises a hole block layer or an electron transport layer comprising the organic compound based on triazine and benzoxazole.
* * * * *